(12) United States Patent
Aversa et al.

(10) Patent No.: US 10,377,770 B2
(45) Date of Patent: Aug. 13, 2019

(54) TRICYCLIC COMPOUNDS AND COMPOSITIONS AS KINASE INHIBITORS

(71) Applicant: Novartis AG, Basel (CH)

(72) Inventors: Robert John Aversa, Watertown, MA (US); Matthew T. Burger, Belmont, MA (US); Michael Patrick Dillon, Castro Valley, CA (US); Thomas A. Dineen, Jr., Somerville, MA (US); Rajesh Karki, Quincy, MA (US); Savithri Ramurthy, Arlington, MA (US); Vivek Rauniyar, Cambridge, MA (US); Richard Robinson, Cambridge, MA (US); Patrick James Sarver, Princeton, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 16/062,680

(22) PCT Filed: Dec. 15, 2016

(86) PCT No.: PCT/IB2016/057633
§ 371 (c)(1),
(2) Date: Jun. 15, 2018

(87) PCT Pub. No.: WO2017/103824
PCT Pub. Date: Jun. 22, 2017

(65) Prior Publication Data
US 2018/0362542 A1 Dec. 20, 2018

Related U.S. Application Data

(60) Provisional application No. 62/269,252, filed on Dec. 18, 2015.

(51) Int. Cl.
| | |
|---|---|
| *C07D 487/04* | (2006.01) |
| *C07D 491/04* | (2006.01) |
| *C07D 498/04* | (2006.01) |
| *A61P 35/00* | (2006.01) |
| *C07D 491/044* | (2006.01) |

(52) U.S. Cl.
CPC ............ *C07D 498/04* (2013.01); *A61P 35/00* (2018.01); *C07D 487/04* (2013.01); *C07D 491/044* (2013.01)

(58) Field of Classification Search
None
See application file for complete search history.

(56) References Cited

U.S. PATENT DOCUMENTS

| | | |
|---|---|---|
| 2008/0275022 A1 | 11/2008 | Aquila et al. |
| 2010/0048552 A1 | 2/2010 | Ren et al. |
| 2013/0040949 A1 | 2/2013 | Gray et al. |
| 2015/0157629 A1 | 6/2015 | Gray et al. |
| 2016/0046636 A1 | 2/2016 | Gray et al. |

FOREIGN PATENT DOCUMENTS

| | | |
|---|---|---|
| WO | 2007134259 A2 | 11/2001 |
| WO | 2005123696 A1 | 12/2005 |
| WO | 2011090738 A2 | 7/2011 |

*Primary Examiner* — Nyeemah A Grazier
(74) *Attorney, Agent, or Firm* — Scott W. Reid

(57) ABSTRACT

The present invention provides compounds of Formula (A): (I) as described herein, and salts thereof, and therapeutic uses of these compounds for treatment of disorders associated with Raf kinase activity. The invention further provides pharmaceutical compositions comprising these compounds, and compositions comprising these compounds and a therapeutic co-agent, and methods of using the compositions and combinations to treat conditions including cancers.

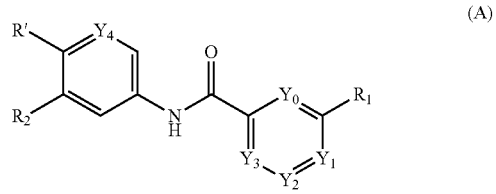

30 Claims, No Drawings

TRICYCLIC COMPOUNDS AND COMPOSITIONS AS KINASE INHIBITORS

CROSS REFERENCE TO RELATED APPLICATIONS

This application is a 371 U.S. national phase application of international application number PCT/IB2016/057633 filed 14 Dec. 2016, which application claims the benefit of priority under 35 U.S.C. § 119(e) to U.S. Provisional Patent Application No. 62/269,252, filed 18 Dec. 2015, the disclosures of which are incorporated herein by reference in their entirety and for all purposes.

FIELD OF THE INVENTION

The invention provides compounds that inhibit Raf kinases, and are accordingly useful for treating certain disorders associated with excessive Raf kinase activity, including cell proliferation disorders such as cancers. The invention further provides pharmaceutical compositions containing these compounds and methods of using these compounds to treat conditions including cancer.

BACKGROUND

Protein Kinases are involved in very complex signaling cascades that regulate most cellular functions, including cell survival and proliferation. These signaling pathways have been heavily studied, particularly in the context of disorders caused by dysregulated cellular function, such as cancer. The mitogen-activated protein kinase (MAPK) cascade has been studied extensively, for example, and kinases in this pathway (e.g., RAS, RAF, MEK, and ERK) have been exploited as target sites for drug discovery. Mutated B-Raf is found in a significant fraction of malignancies (over 30% of all tumors and 40% of melanomas), and several drug candidates that inhibit a common B-Raf mutant (V600E, an activating mutation found in many cancers, particularly in cutaneous malignant melanoma, thyroid cancer, colorectal cancer, and ovarian cancer) have been reported, including GDC-0879, PLX4032, and PLX4720, while other inhibitors targeting C-Raf or B-Raf (or both) include sorafenib, XL281 RAF265, and BAY43-9006. These examples demonstrate that compounds that inhibit B-Raf or C-Raf are useful to treat various cancers.

The MAPK signaling cascade includes RAS, Raf, MEK and ERK kinases, each of which is actually a group of related proteins. These proteins function collectively as a signal transduction cascade where the number of distinct kinases and their varying substrate specificities create a complex and highly branched pathway. Raf, for example, consists of monomers referred to as A-Raf, B-Raf, and C-Raf (also called Raf-1), each of which functions primarily as a dimer. The RAF complex includes heterodimers as well as homodimers of these three species, bringing the total number of dimeric species in the Raf group to six, with each of these having a number of sites where phosphorylation at serine, threonine or tyrosine can cause either activation or inhibition. Due to the complexity of the pathway and its regulation, it has been reported that inhibitors of B-Raf can cause paradoxical activation of the pathway, apparently due to conformational effects on the kinase domain of Raf that affect dimerization, membrane localization, and interaction with RAS-GTP. In particular, ATP-competitive inhibitors can exhibit opposing effects on the signaling pathway, as either inhibitors or activators, depending on the cellular context. As a result, B-Raf inhibitors effective against tumors having the activating B-Raf mutation V600E may not be as effective as expected in tumors having wild-type B-Raf or KRas mutations.

The present invention provides novel inhibitors of Raf kinases, including A-Raf, B-Raf and/or C-Raf, and use of these compounds to treat disorders associated with excessive or undesired levels of Raf activity, such as certain cancers. The compounds of the invention minimize undesired pathway activation effects, and thus can be more efficacious and more predictable in vivo than the B-Raf inhibitors that cause paradoxical pathway activation even when they have similar in vitro potency. The compounds of the invention bind in a DFG-out mode, making them type 2 inhibitors, which have been reported to be less prone to induce paradoxical activation. The compounds are suited for treatment of BRaf wild-type and KRas mutant tumors, as well as B-Raf V600E mutant tumors.

SUMMARY OF THE INVENTION

In one aspect, the invention provides compounds of the formula (A):

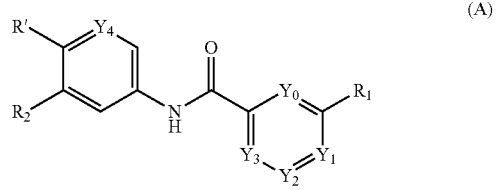

in which:
R' is selected from H and methyl;
$R_1$ is $C_{1-3}$alkyl substituted by CN or by one or more halogens;
$R_2$ is selected from:

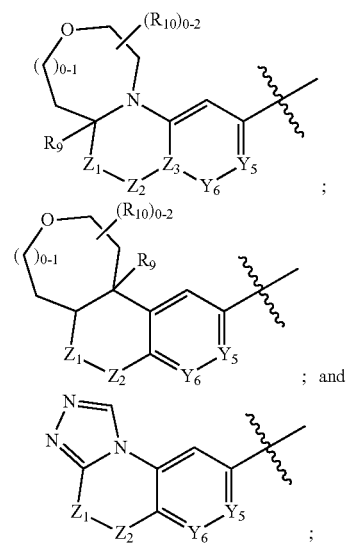

wherein $Z_1$ is $CR_3R_4$, —O—, a bond, or $CR_7$; provided that when $Z_1$ is $CR_7$, $Z_1$ is attached by a double bond to the carbon atom nearing $R_9$ and $R_9$ is absent;
$Z_2$ is $CR_5R_6$, O, —C(O)$NR_8$—[$Y_6$], —$NR_8$C(O)—[$Y_6$], or —$(CR_7)_{0-1}$—C(O)—[$Y_6$], where [$Y_6$] indicates which atom of $Z_2$ is attached to the ring containing $Y_6$; provided $Z_1$ and $Z_2$ are not both simultaneously O;

$Z_3$ is a carbon atom bonded to $Y_6$ by an aromatic bond, or $Z_3$ is a nitrogen atom bonded to $Y_6$ by a single bond;

$R_3$ is selected from hydrogen, $C_{1-3}$alkyl, halo, $C_{1-3}$alkyl-amino-carbonyl, $C_{1-3}$alkyl-S(O)$_{0-2}$—$C_{1-2}$alkyl, carboxyl and hydroxy-substituted-$C_{1-3}$alkyl;

$R_4$ is selected from hydrogen, amino, $C_{1-3}$alkyl, cyano, hydroxy-ethyl and halo; or $R_3$ and $R_4$ together with the carbon atom to which $R_3$ and $R_4$ are attached form a 4 member saturated cyclic ring containing an oxygen molecule;

$R_5$ is selected from hydrogen, halo, amino, $C_{1-3}$alkyl-amino-carbonyl, $C_{1-3}$alkyl-carbonyl, hydroxy and $C_{1-3}$alkoxy;

$R_6$ is selected from hydrogen, $C_{1-3}$alkyl, halo, halo-substituted-$C_{1-3}$alkyl; or $R_4$ and $R_6$ together with the carbon atom to which $R_4$ and $R_6$ are attached form 5-6 member unsaturated ring containing up to 2 heteroatoms selected from O, S and N; wherein said ring is optionally substituted with $C_{1-2}$alkyl;

$R_7$ is selected from hydrogen, hydroxy-carbonyl and $C_{1-3}$alkoxy-carbonyl;

$R_8$ is selected from hydrogen, $C_{1-3}$alkyl-amino-carbonyl, $C_{1-3}$alkyl-carbonyl, $C_{1-3}$alkoxy and hydroxy-substituted-$C_{1-4}$alkoxy, hydroxy-substituted-$C_{1-3}$alkyl, and $C_{1-3}$alkyl;

$R_9$ is independently selected at each occurrence from hydrogen, fluorine, and methyl;

each $R_{10}$ represents an optional substituent selected from $C_{1-3}$ alkyl and $C_{1-3}$ alkoxy, or two $R_{10}$ on non-adjacent ring atoms can be taken together to form a bond or a $(CH_2)_{1-2}$ bridge linking the two non-adjacent ring atoms to form a fused or bridged ring;

$Y_0$ is selected from N, CH and CF;

$Y_1$ is selected from N and CH;

$Y_2$ is selected from N, CH, CF, CCl, C—NH$_2$, and C—C(R$_9$)$_2$NH$_2$;

$Y_3$ is selected from N and CH;

$Y_4$ is selected from N and CH;

$Y_5$ is selected from N and CH; and $Y_6$ is selected from N and CH when $Z_3$ is carbon, and $Y_6$ is C(=O) when $Z_3$ is nitrogen;

or a pharmaceutically acceptable salt thereof.

In a second aspect, the present invention provides a pharmaceutical composition which contains a compound of Formula (A) or a N-oxide derivative, individual isomers and mixture of isomers thereof, including subgenera of Formula (A) described herein; or a pharmaceutically acceptable salt thereof, in admixture with one or more suitable excipients.

In another aspect, the compounds of Formula (A) are inhibitors of Raf kinases as shown by data herein, and are accordingly useful to treat conditions such as melanoma, breast cancer, sarcoma, GI tumors such as gastrointestinal stromal tumors, ovarian cancer, sarcoma, GI tumors such as gastrointestinal stromal tumors, and other malignancies associated with excessive Raf pathway activity, particularly in cancers driven by Ras mutations. In addition, the compounds of the invention exhibit low levels of paradoxical activation of the Raf pathway.

In another aspect, the invention provides pharmaceutical compositions comprising a compound of Formula (A) admixed with at least one pharmaceutically acceptable carrier or excipient, optionally admixed with two or more pharmaceutically acceptable carriers or excipients.

In addition, the invention includes combinations of a compound of Formula (A) with a co-therapeutic agent, optionally including one or more pharmaceutically acceptable carriers, and methods of treatment using a compound of Formula (A) or Formula (I) or any of the sub-formula thereof described herein in combination with a co-therapeutic agent. Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like.

In another aspect, the invention provides a method to treat a condition characterized by excessive or undesired levels of activity of Raf, especially B-Raf and/or C-Raf, which comprises administering to a subject in need of such treatment an effective amount of a compound of Formula (A) or any subgenus thereof as described herein, or a pharmaceutical composition comprising such compound. The subject can be a mammal, and is preferably a human. Conditions treatable by the compounds and methods described herein include various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. The invention thus includes compounds of Formula (A) or (I) and the subgenera thereof that are disclosed herein, including each species disclosed herein, for use in therapy, particularly for use to treat cancers such as melanoma, breast cancer, lung cancer, liver cancer, sarcoma, GI tumors such as gastrointestinal stromal tumors, sarcoma, GI tumors such as gastrointestinal stromal tumors, ovarian cancer, colorectal cancer, thyroid cancer, and pancreatic cancer. The invention also includes use of such compounds for manufacture of a medicament for treating these conditions.

The invention includes compounds of Formula (A) and the subgenera of Formula (A) described herein, and all stereoisomers (including diastereoisomers and enantiomers), tautomers and isotopically enriched versions thereof (including deuterium substitutions), as well as pharmaceutically acceptable salts of these compounds. In particular, where a heteroaryl ring containing N as a ring atom is optionally substituted with hydroxyl, e.g., a 2-hydroxypyridine ring, tautomers where the hydroxyl is depicted as a carbonyl (e.g., 2-pyridone) are included. Compounds of the present invention also comprise polymorphs of compounds of formula (A) (or sub-formulae thereof) and salts thereof.

DETAILED DESCRIPTION

The following definitions apply unless otherwise expressly provided.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "hetero atoms" refers to nitrogen (N), oxygen (O) or sulfur (S) atoms, in particular nitrogen or oxygen, unless otherwise provided.

As used herein, the term "alkyl" refers to a fully saturated branched or unbranched hydrocarbon moiety having up to 20 carbon atoms. Unless otherwise provided, alkyl refers to hydrocarbon moieties having 1 to 10 carbon atoms, 1 to 6 carbon atoms, or 1 to 4 carbon atoms. Typically, alkyl groups have 1-6 carbon atoms. "Lower alkyl" refers to alkyl groups having 1-4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like.

A substituted alkyl is an alkyl group containing one or more substituents in place of hydrogen, such as one, two or three substituents, or 1-4 substituents, up to the number of hydrogens present on the unsubstituted alkyl group. Suitable substituents for alkyl groups, if not otherwise specified, may be selected from halogen, CN, oxo, hydroxy, substituted or unsubstituted $C_{1-4}$ alkoxy, substituted or unsubstituted $C_{3-6}$ cycloalkyl, substituted or unsubstituted $C_{3-6}$ heterocycloalkyl, substituted or unsubstituted phenyl, amino, $(C_{1-4}$ alkyl)amino, di$(C_{1-4}$alkyl)amino, $C_{1-4}$ alkylthio, $C_{1-4}$ alkylsulfonyl, —C(=O)—$C_{1-4}$ alkyl, COOH, COO($C_{1-4}$ alkyl), —O(C=O)—$C_{1-4}$ alkyl, —NHC(=O)$C_{1-4}$ alkyl and —NHC(=O)O$C_{1-4}$ alkyl groups; wherein the substituents for substituted $C_{1-4}$ alkoxy, substituted $C_{3-6}$ cycloalkyl, $C_{3-6}$ heterocycloalkyl, and substituted phenyl are up to three groups selected from halo, $C_{1-4}$ alkyl, $C_{1-4}$ haloalkyl, $C_{1-4}$ alkoxy, amino, hydroxy, and CN. Preferred substituents for alkyl groups include halogen, CN, oxo, hydroxy, $C_{1-4}$ alkoxy, $C_{3-6}$ cycloalkyl, phenyl, amino, $(C_{1-4}$ alkyl)amino, di$(C_{1-4}$ alkyl)amino, $C_{1-4}$ alkylthio, $C_{1-4}$ alkylsulfonyl, —C(=O)—$C_{1-4}$ alkyl, COOH, —COO($C_{1-4}$ alkyl), —O(C=O)—$C_{1-4}$ alkyl, —NHC(=O)$C_{1-4}$ alkyl and —NHC(=O)O$C_{1-4}$ alkyl groups.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like. A substituted alkylene is an alkylene group containing one or more, such as one, two or three substituents; unless otherwise specified, suitable and preferred substituents are selected from the substituents described as suitable and preferred for alkyl groups.

As used herein, the term "haloalkyl" refers to an alkyl as defined herein, which is substituted by one or more halo groups as defined herein. The haloalkyl can be monohaloalkyl, dihaloalkyl, trihaloalkyl, or polyhaloalkyl including perhaloalkyl. A monohaloalkyl can have one iodo, bromo, chloro or fluoro within the alkyl group. Chloro and fluoro are preferred on alkyl or cycloalkyl groups; fluoro, chloro and bromo are often preferred on aryl or heteroaryl groups. Dihaloalkyl and polyhaloalkyl groups can have two or more of the same halo atoms or a combination of different halo groups within the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms, e.g, trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-10, or 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable and preferred substituents are selected from the substituents listed above for alkyl groups, except that hydroxyl and amino are not normally present on the carbon that is directly attached to the oxygen of the substituted 'alkyl-O' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are selected from the suitable or preferred substituents named above for alkyl groups unless otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

Description of Embodiments

The present invention provides compounds, compositions and methods for the treatment of kinase related disease, particularly Raf kinase related diseases; for example: various forms of cancer, such as solid tumors, melanoma, breast cancer, lung cancer (e.g., non-small cell lung cancer), sarcoma, GI tumors such as gastrointestinal stromal tumors, ovarian cancer, colorectal cancer, thyroid cancer, and pancreatic cancer. Various embodiments of the invention are described herein. It will be recognized that features specified in each embodiment may be combined with other specified features to provide further embodiments of the present invention. The following embodiments are representative of the invention.

1. A compound of formula (A):

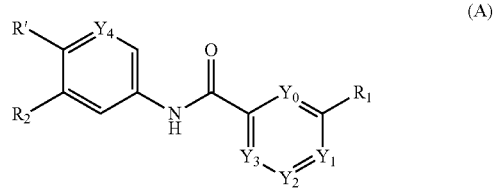

in which:

R' is selected from H and methyl;

$R_1$ is $C_{1-3}$alkyl substituted by CN or by one or more halogens;

$R_2$ is selected from:

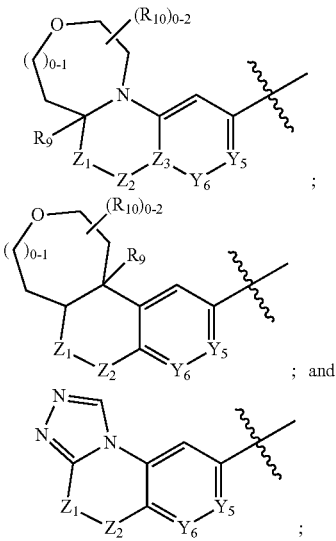

wherein $Z_1$ is $CR_3R_4$, —O—, a bond, or $CR_7$; provided that when $Z_1$ is $CR_7$, $Z_1$ is attached to the carbon atom bonded to $R_9$ by a double bond and $R_9$ is absent;

$Z_2$ is $CR_5R_6$, O, —C(O)$NR_8$—[$Y_6$], —$NR_8$C(O)—[$Y_6$], or —($CR_7$)$_{0-1}$—C(O)—[$Y_6$], where [$Y_6$] indicates which atom of $Z_2$ is attached to the ring containing $Y_6$; provided $Z_1$ and $Z_2$ are not both simultaneously O;

$Z_3$ is a carbon atom bonded to $Y_6$ by an aromatic bond, or $Z_3$ is a nitrogen atom bonded to $Y_6$ by a single bond;

$R_3$ is selected from hydrogen, $C_{1-3}$alkyl, halo, $C_{1-3}$alkyl-amino-carbonyl, $C_{1-3}$alkyl-S(O)$_{0-2}$—$C_{1-2}$alkyl, carboxyl and hydroxy-substituted-$C_{1-3}$alkyl;

$R_4$ is selected from hydrogen, amino, $C_{1-3}$alkyl, cyano, hydroxy-ethyl and halo; or $R_3$ and $R_4$ together with the carbon atom to which $R_3$ and $R_4$ are attached form a 4 member saturated cyclic ring containing an oxygen molecule;

$R_5$ is selected from hydrogen, halo, amino, $C_{1-3}$alkyl-amino-carbonyl, $C_{1-3}$alkyl-carbonyl, hydroxy and $C_{1-3}$alkoxy;

$R_6$ is selected from hydrogen, $C_{1-3}$alkyl, halo, halo-substituted-$C_{1-3}$alkyl; or $R_4$ and $R_6$ together with the carbon atom to which $R_4$ and $R_6$ are attached form 5-6 member unsaturated ring containing up to 2 heteroatoms selected from O, S and N; wherein said ring is optionally substituted with $C_{1-2}$alkyl;

$R_7$ is selected from hydrogen, hydroxy-carbonyl and $C_{1-3}$alkoxy-carbonyl;

$R_8$ is selected from hydrogen, $C_{1-3}$alkyl-amino-carbonyl, $C_{1-3}$alkyl-carbonyl, $C_{1-3}$alkoxy and hydroxy-substituted-$C_{1-4}$alkoxy, hydroxy-substituted-$C_{1-3}$alkyl, and $C_{1-3}$alkyl;

$R_9$ is independently selected at each occurrence from hydrogen, fluorine, and methyl;

each $R_{10}$ represents an optional substituent selected from $C_{1-3}$ alkyl and $C_{1-3}$ alkoxy, or two $R_{10}$ on non-adjacent ring atoms can be taken together to form a bond or a ($CH_2$)$_{1-2}$ bridge linking the two non-adjacent ring atoms to form a fused or bridged ring;

$Y_0$ is selected from N, CH and CF;

$Y_1$ is selected from N and CH;

$Y_2$ is selected from N, CH, CF, CCl, C—$NH_2$, and C—C($R_9$)$_2$$NH_2$;

$Y_3$ is selected from N and CH;

$Y_4$ is selected from N and CH;

$Y_5$ is selected from N and CH; and $Y_6$ is selected from N and CH when $Z_3$ is carbon, and $Y_6$ is C(=O) when $Z_3$ is nitrogen;

or a pharmaceutically acceptable salt thereof.

2. The compound of embodiment 1, wherein R' is methyl.

3. The compound of embodiment 1 or 2, wherein $Y_4$ is CH.

4. The compound of embodiment 1 or 2, wherein $Y_4$ is N.

5. The compound of any of the preceding embodiments, wherein $Y_0$ is CH.

6. The compound of any of the preceding embodiments, wherein $Y_1$ is N.

7. The compound of any of the preceding embodiments, wherein $Y_2$ is CH.

8. The compound of any of the preceding embodiments, wherein $Y_3$ is CH

9. The compound of any of the preceding embodiments, wherein $Y_5$ is CH.

10. The compound of any of the preceding embodiments, wherein $Y_6$ is CH.

11. The compound of any of the preceding embodiments, wherein $R_9$ is H.

12. The compound of any of the preceding embodiments, wherein $Z_1$ is $CH_2$ or a bond.

13. The compound of any of the preceding embodiments, wherein $R_2$ is selected from:

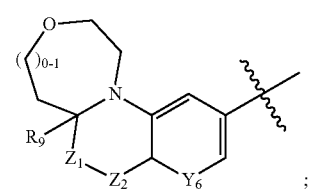

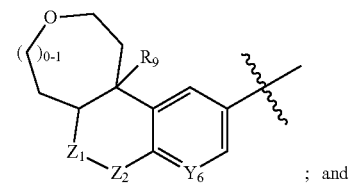

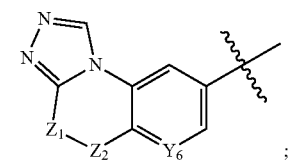

wherein $Y_6$ is selected from N and CH;

$Z_1$ is $CR_3R_4$ or a bond; and $Z_2$ is $CR_5R_6$, —C(O)$NR_8$—[$Y_6$] or —$NR_8$C(O)—[$Y_6$], where [$Y_6$] indicates which atom of $Z_2$ is attached to the ring containing $Y_6$.

14. The compound of embodiment 1, which is of the formula (I):

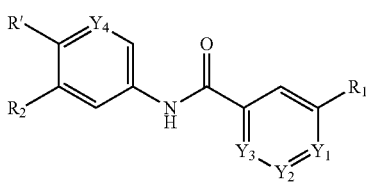

in which:

R' is selected from H and methyl;
$R_1$ is selected from halo-substituted $C_{1-3}$alkyl;
$R_2$ is selected from:

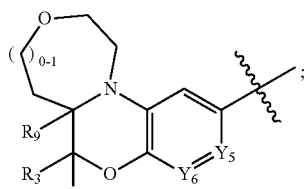

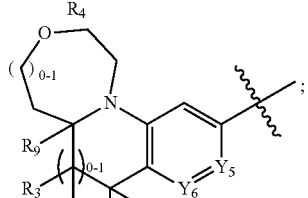

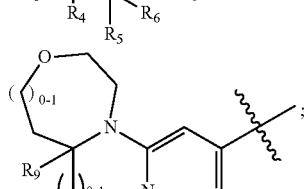


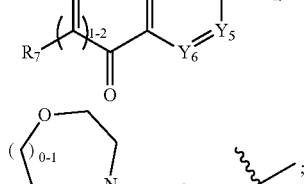

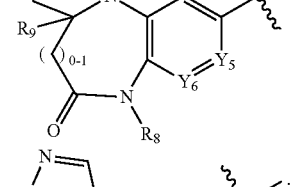

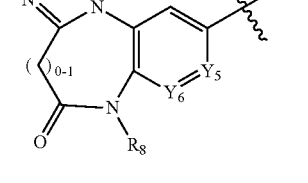

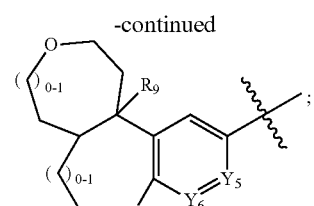

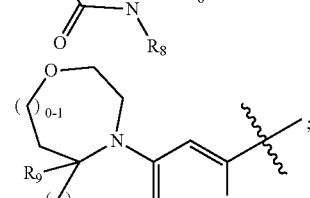

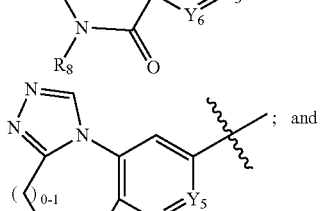

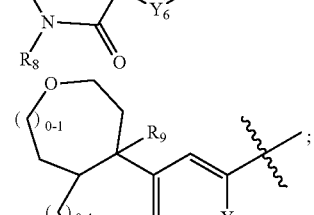

; and and optionally also

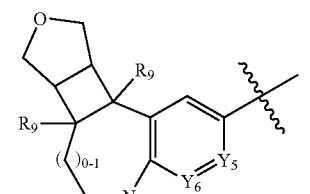

;

$R_3$ is selected from hydrogen, $C_{1-3}$alkyl, halo, $C_{1-3}$alkyl-amino-carbonyl, $C_{1-3}$alkyl-S(O)$_{0-2}$—$C_{1-2}$alkyl, carboxyl and hydroxy-substituted-$C_{1-3}$alkyl;

$R_4$ is selected from hydrogen, amino, $C_{1-3}$alkyl, cyano, hydroxy-ethyl and halo; or $R_3$ and $R_4$ together with the carbon atom to which $R_3$ and $R_4$ are attached form a 4 member saturated cyclic ring containing an oxygen molecule;

$R_5$ is selected from hydrogen, halo, amino, $C_{1-3}$alkyl-amino-carbonyl, $C_{1-3}$alkyl-carbonyl, hydroxy and $C_{1-3}$alkoxy;

$R_6$ is selected from hydrogen, $C_{1-3}$alkyl, halo, halo-substituted-$C_{1-3}$alkyl; or $R_4$ and $R_6$ together with the carbon atom to which $R_4$ and $R_6$ are attached form 5-6 member unsaturated ring containing up to 2 heteroatoms selected from O, S and N; wherein said ring is optionally substituted with $C_{1-2}$alkyl; each $R_7$ is selected from hydrogen, hydroxy-carbonyl and $C_{1-3}$alkoxy-carbonyl;

$R_8$ is selected from hydrogen, $C_{1-3}$alkyl-amino-carbonyl, $C_{1-3}$alkyl-carbonyl, $C_{1-3}$alkoxy and hydroxy-substituted-$C_{1-4}$alkoxy and $C_{1-3}$alkyl;

$R_9$ is selected from hydrogen and methyl;

$Y_1$ is selected from N and CH;

$Y_2$ is selected from N and CH;

$Y_3$ is selected from N and CH;

$Y_4$ is selected from N and CH;

$Y_5$ is selected from N and CH; and $Y_6$ is selected from N and CH; or the pharmaceutically acceptable salt thereof.

In a 15th embodiment, with reference to compounds of formula I, are compounds of formula (Ia):

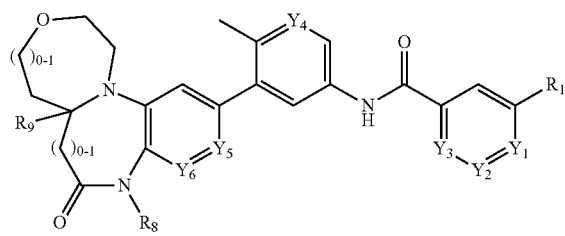

(Ia)

in which:

$R_1$ is selected from halo-substituted $C_{1-3}$alkyl; $R_8$ is selected from hydrogen and $C_{1-3}$alkyl; $R_9$ is selected from hydrogen and methyl; $Y_1$ is selected from N and CH; $Y_2$ is CH; $Y_3$ is CH; $Y_4$ is selected from N and CH; $Y_5$ is selected from N and CH; and $Y_6$ is selected from N and CH; or the pharmaceutically acceptable salt thereof.

In a 16th embodiment, $R_1$ is selected from trifluoromethyl, 2-fluoropropan-2-yl, 2-cyanopropan-2-yl and 1,1-difluoroethyl; $R_8$ is selected from hydrogen and ethyl; $Y_1$ is selected from N and CH; $Y_4$ is selected from N and CH; $Y_5$ is selected from N and CH; and $Y_6$ is selected from N and CH; or the pharmaceutically acceptable salt thereof. Specific compounds of this embodiment are selected from the following compounds and their pharmaceutically acceptable salts:

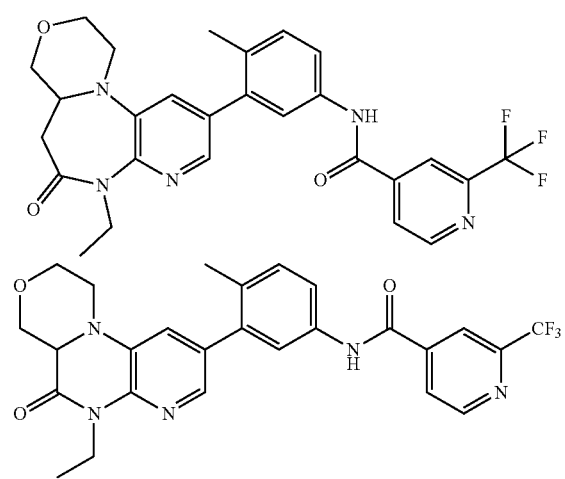

-continued

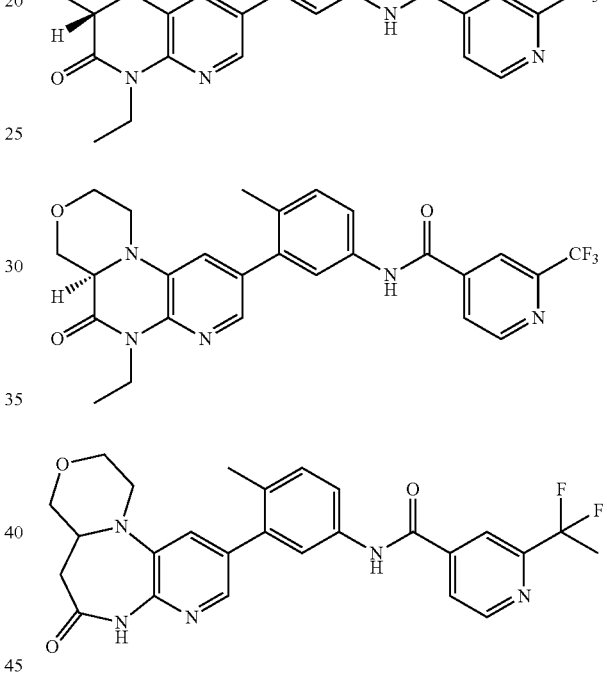

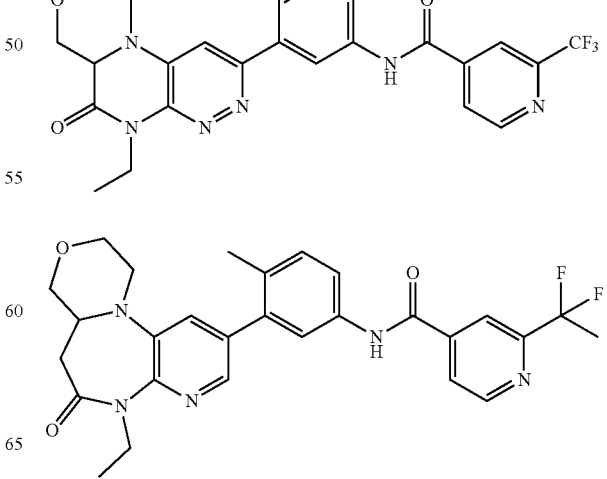

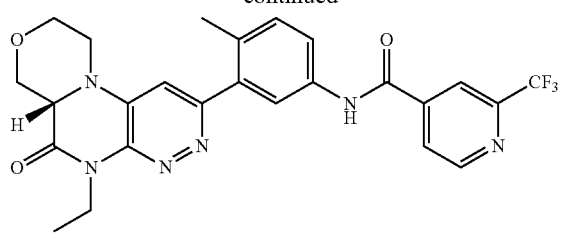

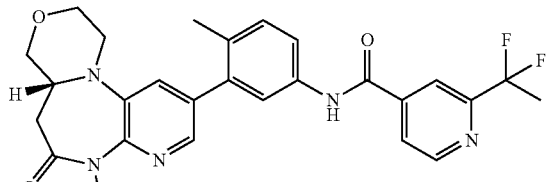

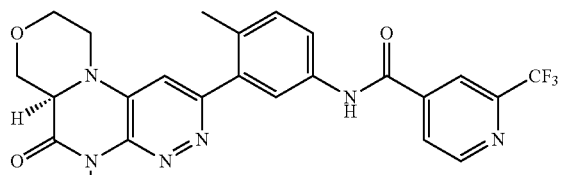

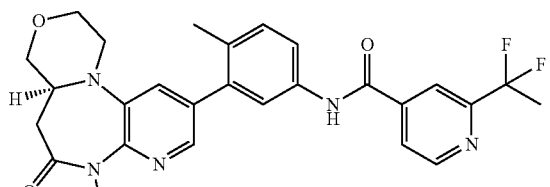

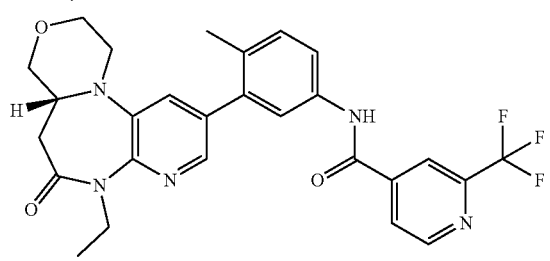

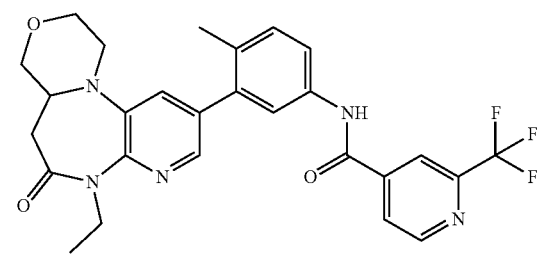

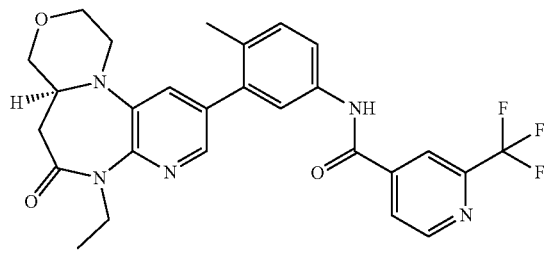

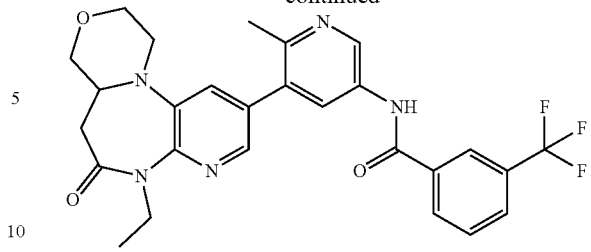

In a 17th embodiment, with reference to compounds of formula I, are compounds of formula (Ib):

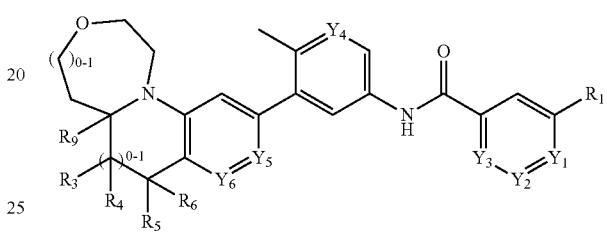

(Ib)

in which: $R_1$ is selected from halo-substituted $C_{1-3}$alkyl; $R_3$ is selected from hydrogen, $C_{1-3}$alkyl, halo, $C_{1-3}$alkyl-amino-carbonyl, $C_{1-3}$alkyl-$S(O)_{0-2}$—$C_{1-2}$alkyl, carboxyl and hydroxy-substituted-$C_{1-3}$alkyl; $R_4$ is selected from hydrogen, amino, $C_{1-3}$alkyl, cyano, hydroxy-ethyl and halo; or $R_3$ and $R_4$ together with the carbon atom to which $R_3$ and $R_4$ are attached form a 4 member saturated cyclic ring containing an oxygen molecule; $R_5$ is selected from hydrogen, halo, amino, $C_{1-3}$alkyl-amino-carbonyl, hydroxy and $C_{1-3}$alkoxy; $R_6$ is selected from hydrogen, $C_{1-3}$alkyl, halo, halo-substituted-$C_{1-3}$alkyl; or $R_4$ and $R_6$ together with the carbon atom to which $R_4$ and $R_6$ are attached form 5-6 member unsaturated ring containing up to 2 heteroatoms selected from O, S and N; wherein said ring is optionally substituted with $C_{1-3}$alkyl; $R_9$ is selected from hydrogen and methyl; $Y_1$ is selected from N and CH; $Y_2$ is selected from N and CH; $Y_3$ is selected from N and CH; $Y_4$ is selected from N and CH; $Y_5$ is selected from N and CH; and $Y_6$ is selected from N and CH; or the pharmaceutically acceptable salt thereof.

In an 18th embodiment, $R_1$ is selected from trifluoromethyl, 2-fluoropropan-2-yl, 2-cyanopropan-2-yl and 1,1-difluoroethyl; $R_3$ is selected from hydrogen and methyl, fluoro, methyl-amino-carbonyl, ethyl-amino-carbonyl, methyl-sulfonyl-methyl, carboxyl and hydroxy-ethyl; $R_4$ is selected from hydrogen, methyl, cyano, amino, hydroxy-ethyl and fluoro; or $R_3$ and $R_4$ together with the carbon atom to which $R_3$ and $R_4$ are attached form oxetan-3-yl; $R_5$ is selected from hydrogen, fluoro, amino, methyl-carbonyl-amino, ethyl-carbonyl-amino, hydroxy and methoxy; $R_6$ is selected from hydrogen, methyl, fluoro and trifluoromethyl; or $R_4$ and $R_6$ together with the carbon atom to which $R_4$ and $R_6$ are attached form pyrazolyl optionally substituted with methyl; $R_9$ is selected from hydrogen and methyl; $Y_1$ is selected from N and CH; $Y_2$ is CH; $Y_3$ is CH; $Y_4$ is selected from N and CH; $Y_5$ is selected from N and CH; and $Y_6$ is selected from N and CH; or the pharmaceutically acceptable salt thereof.

Particular examples of this embodiment are compounds, or the pharmaceutically acceptable salt thereof, selected from:

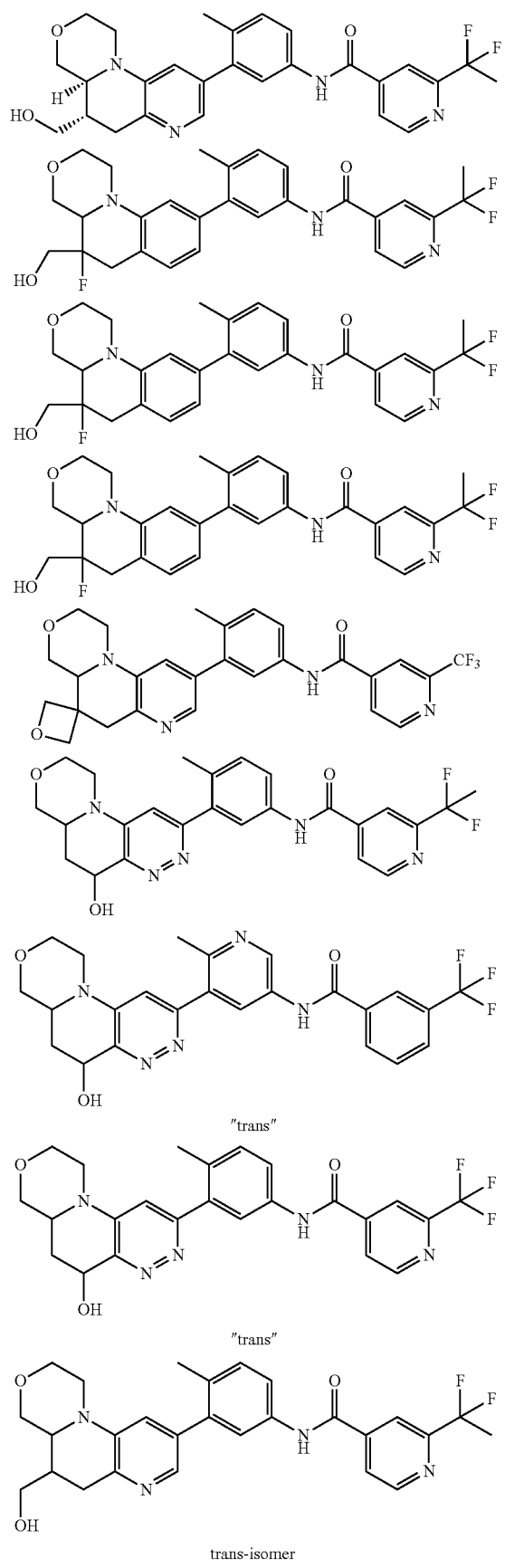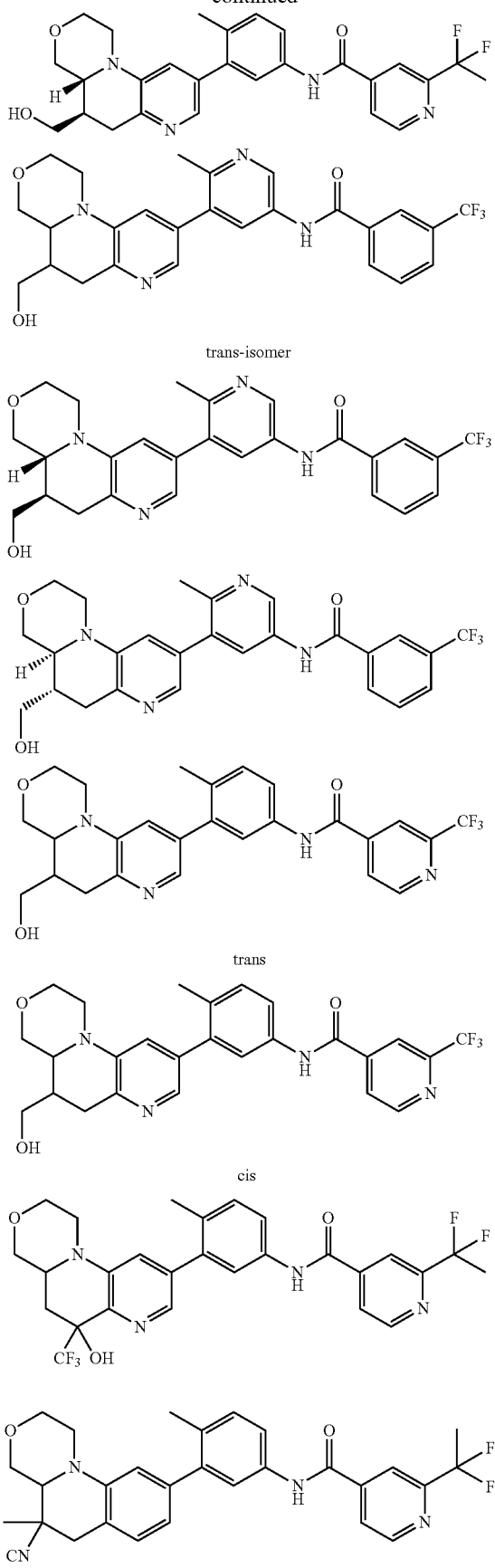

-continued
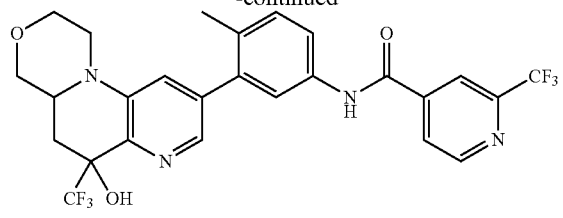
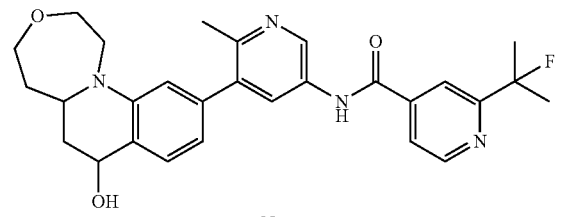
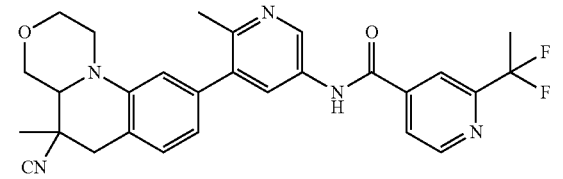
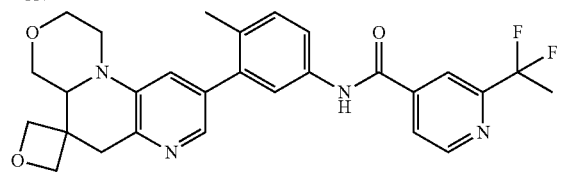
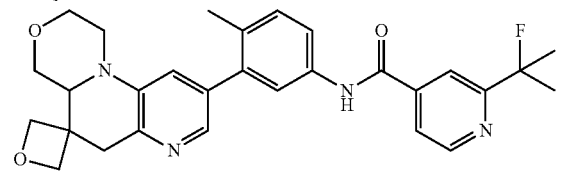
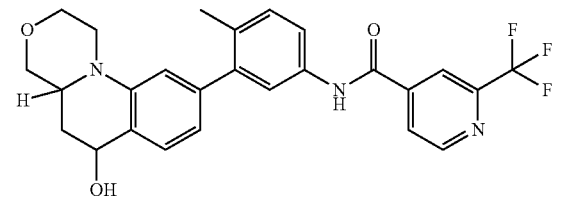
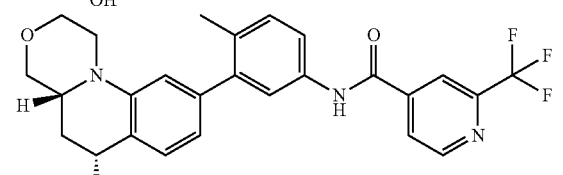
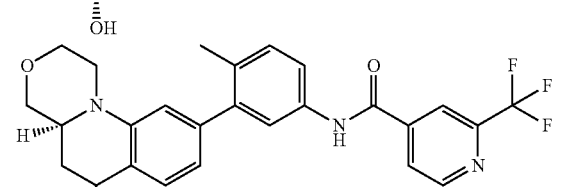
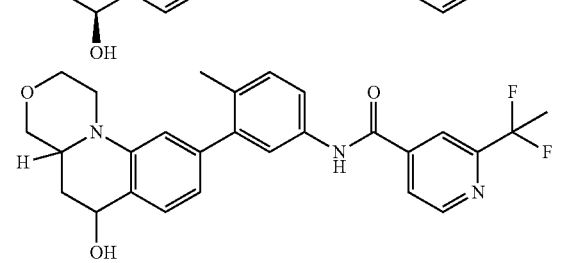
-continued
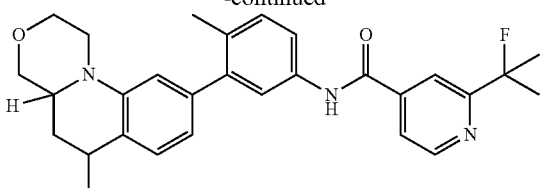
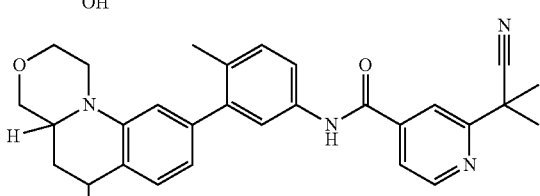
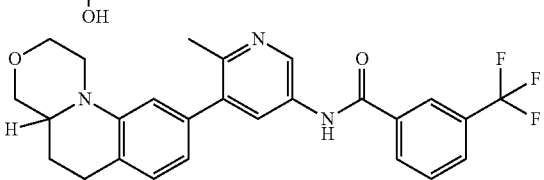
"trans"
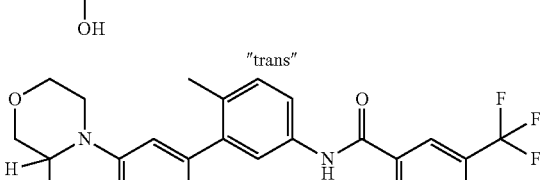
"trans"
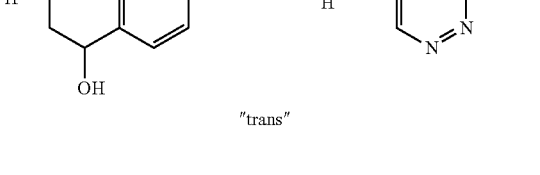
"trans"
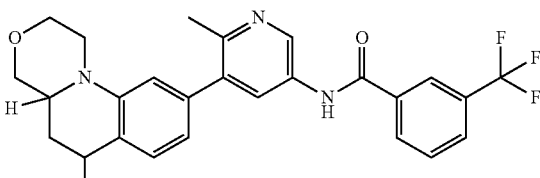
"trans"
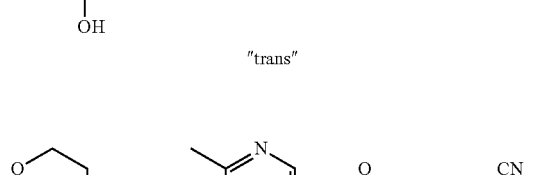

-continued
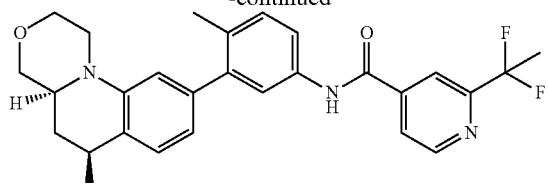
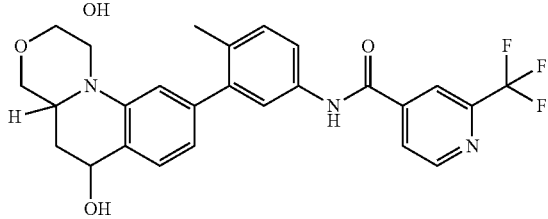
"cis"
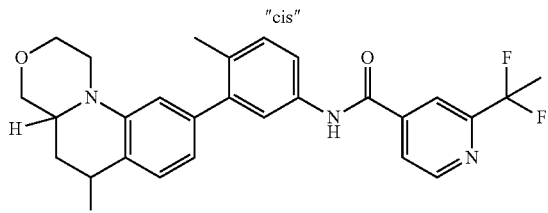
"cis"
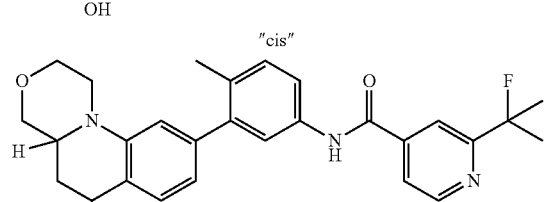
"cis"
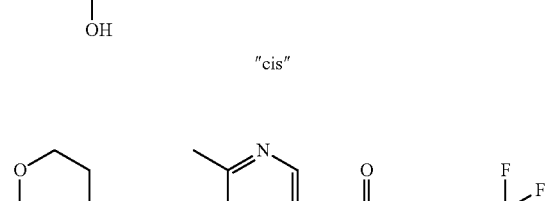
"cis"
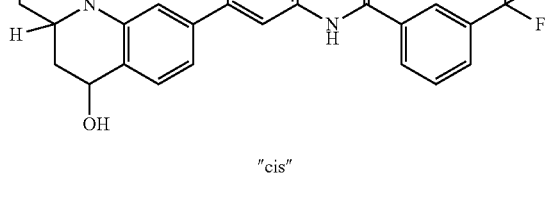
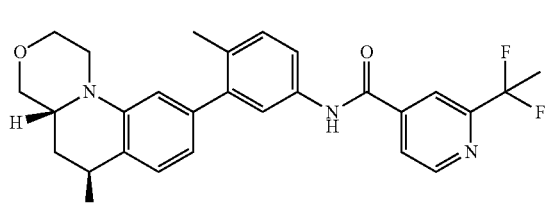
-continued
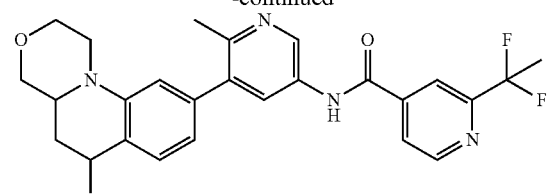
"trans"
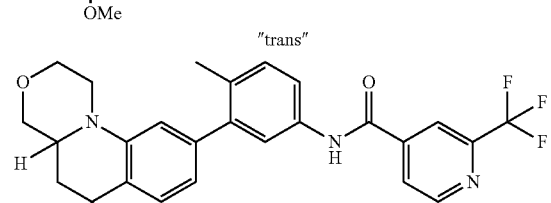
"trans-hydroxy"
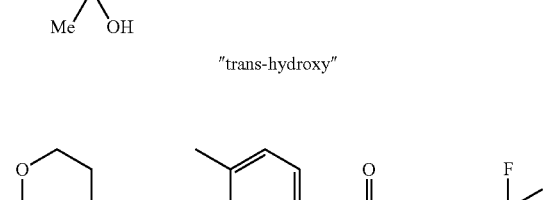
"trans-hydroxy"
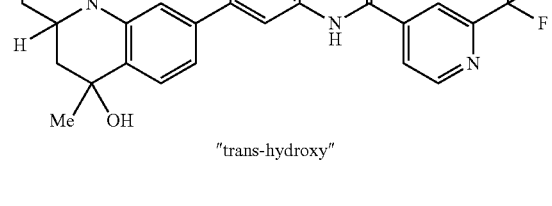
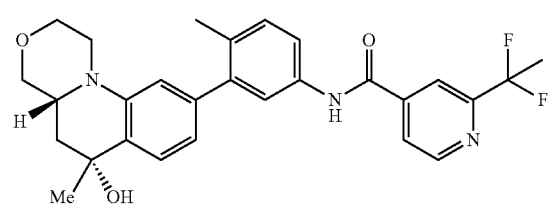
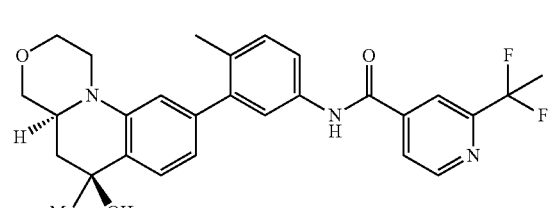
"trans"
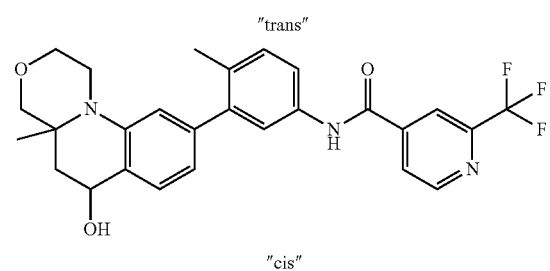
"cis"

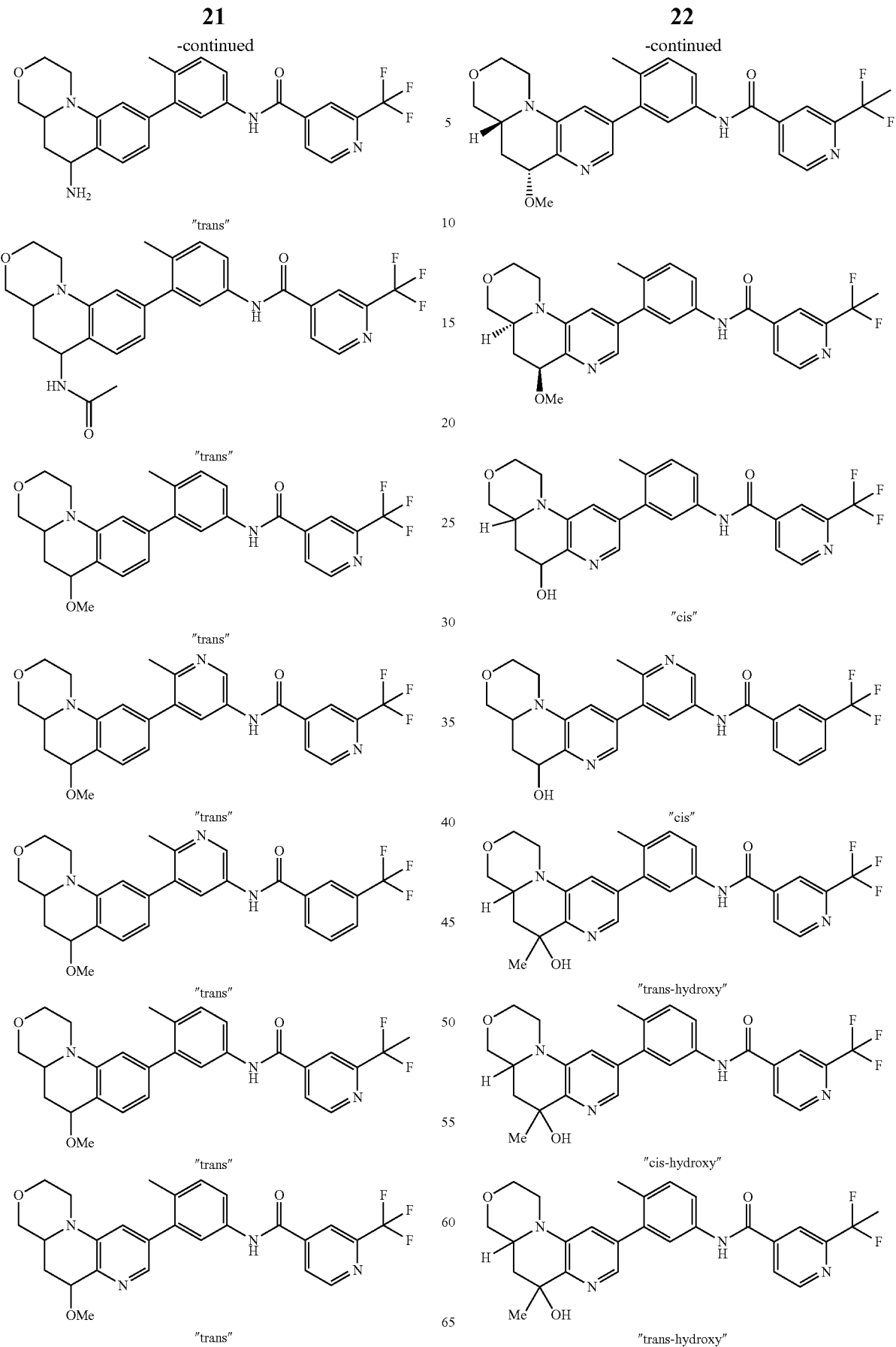

-continued
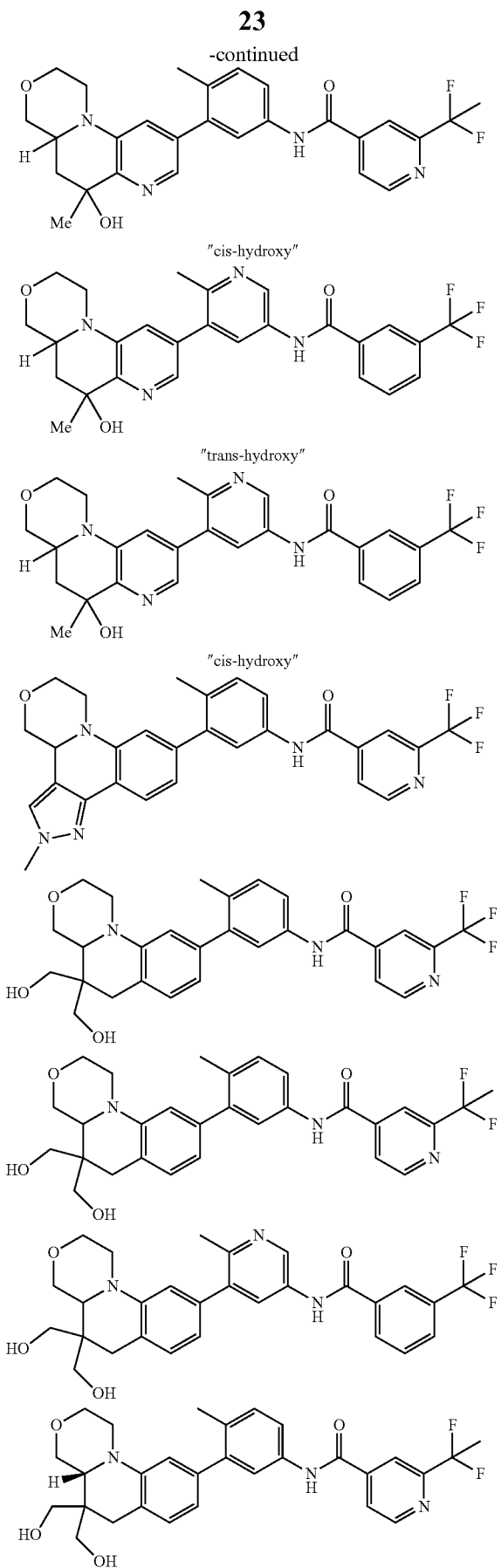
-continued
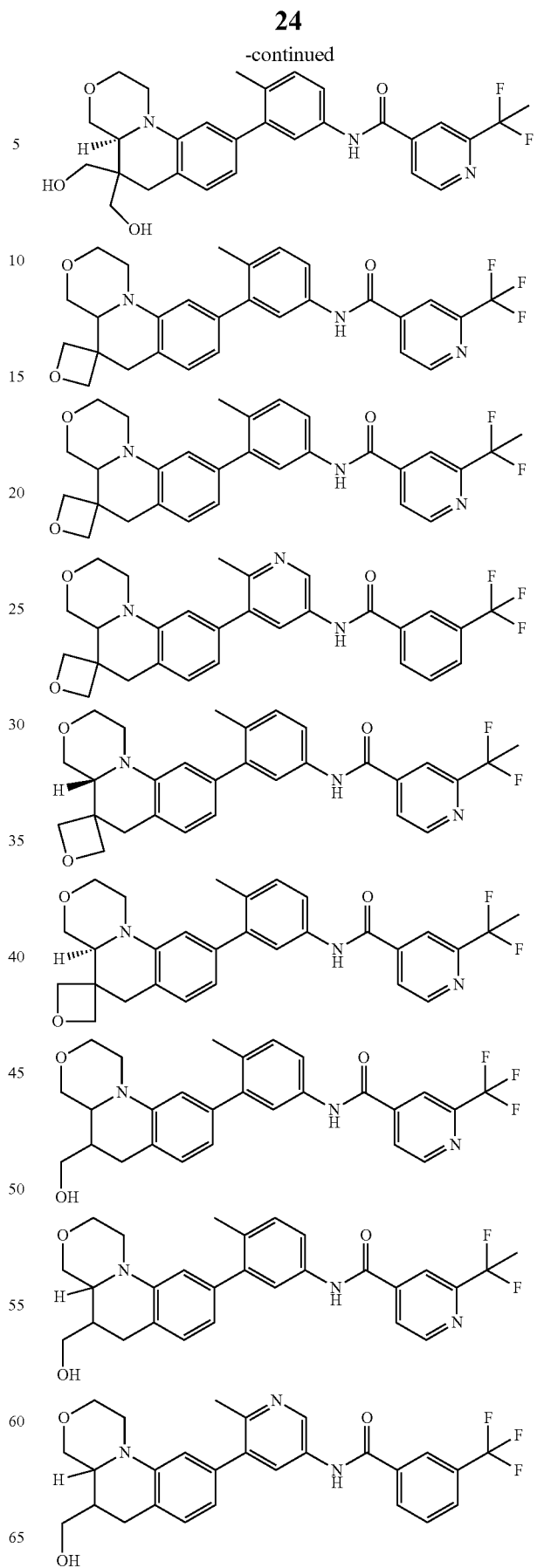

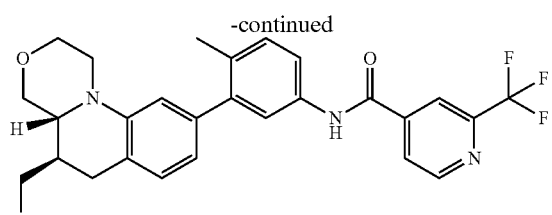
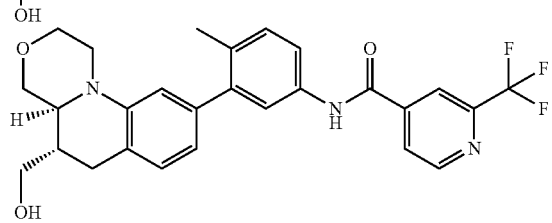
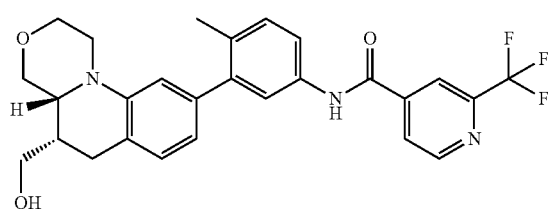
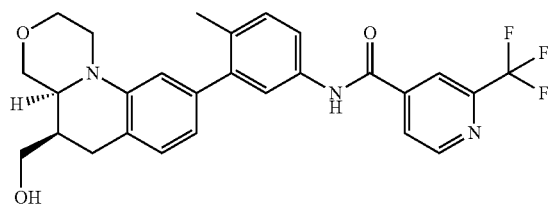
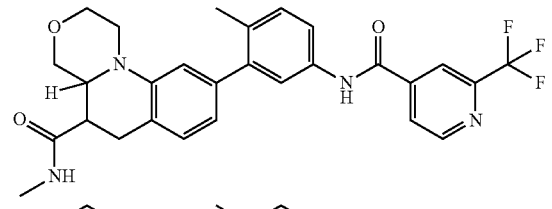
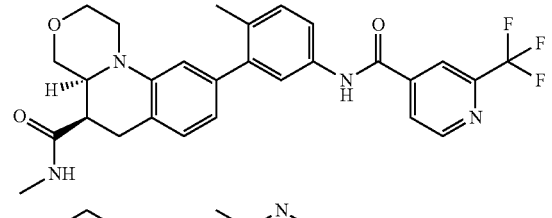
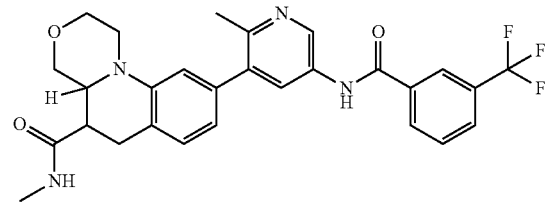
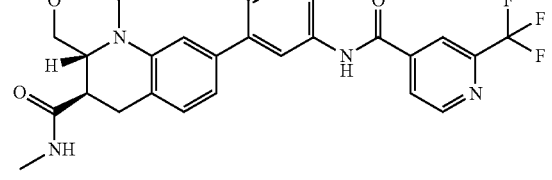
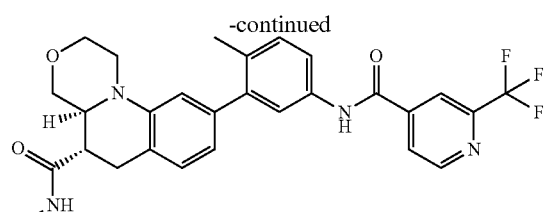
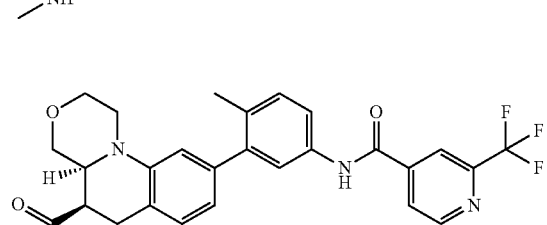
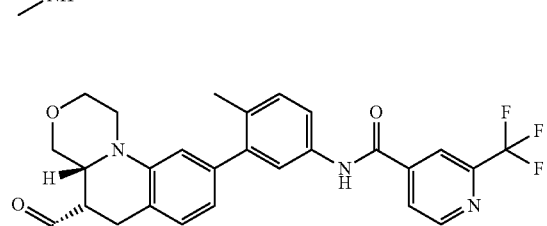

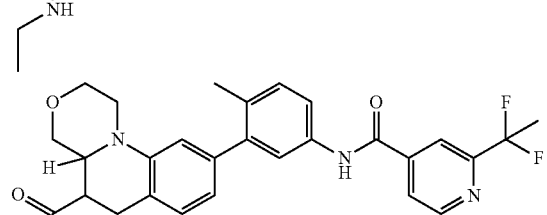
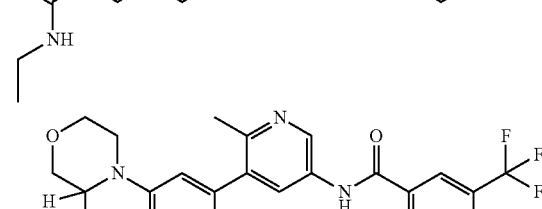
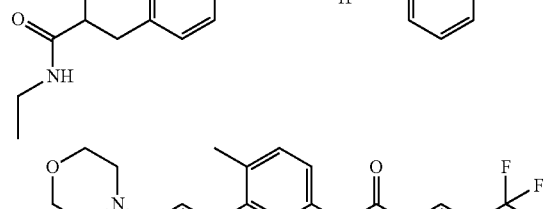
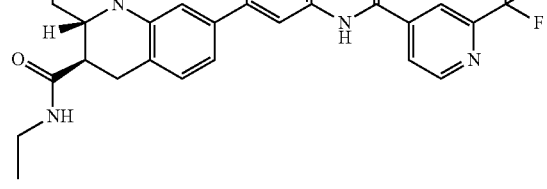

27
-continued
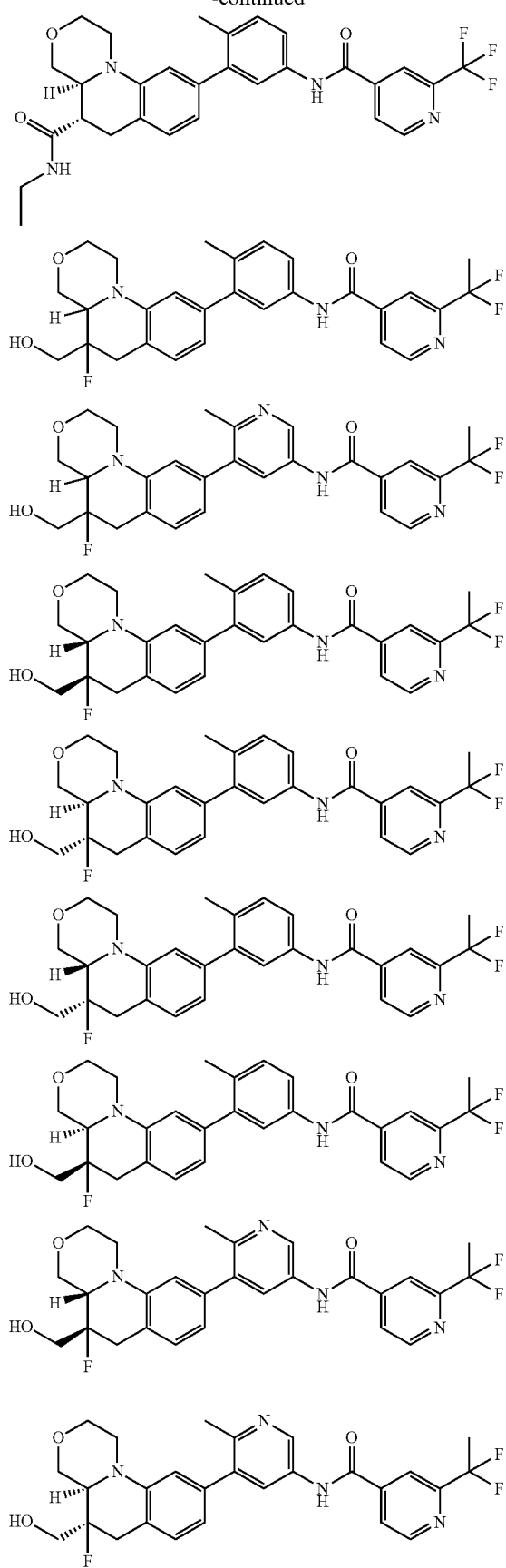
28
-continued
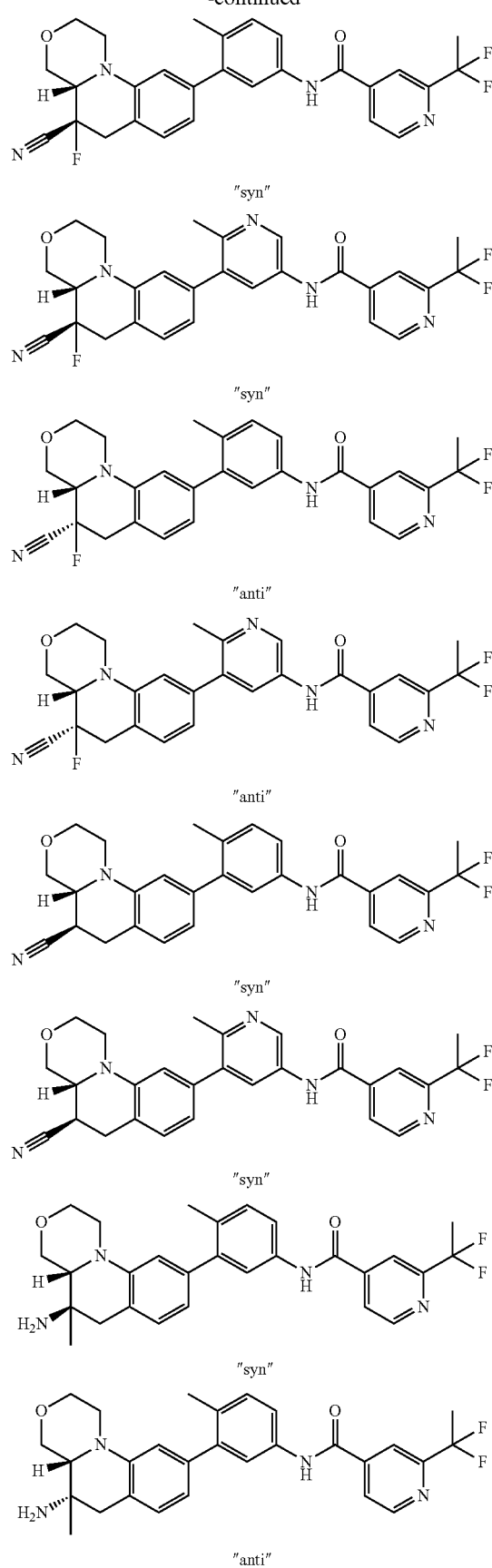

-continued
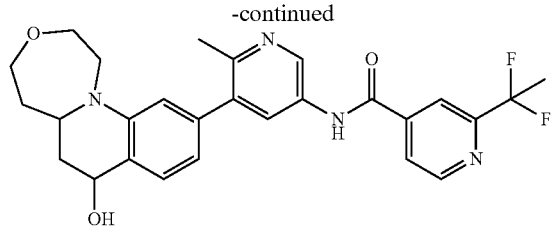
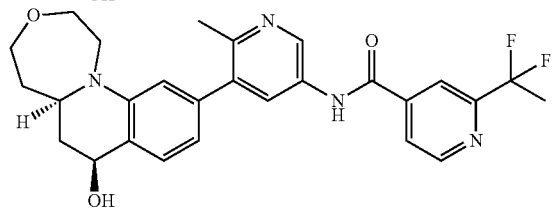
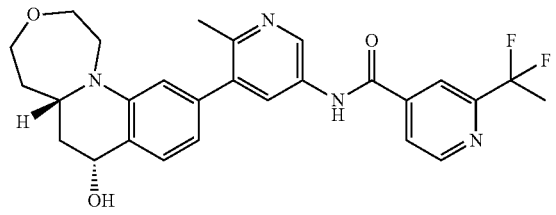
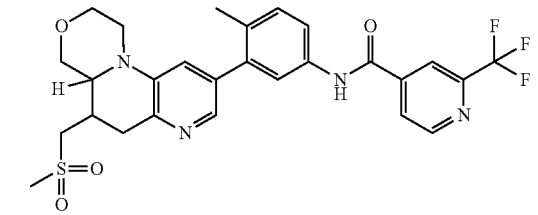
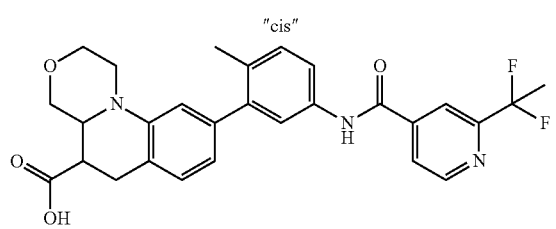

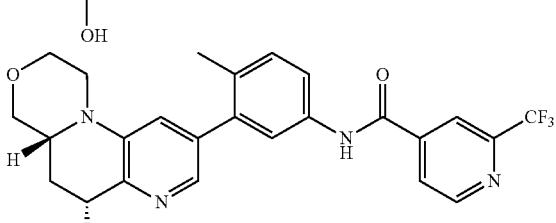
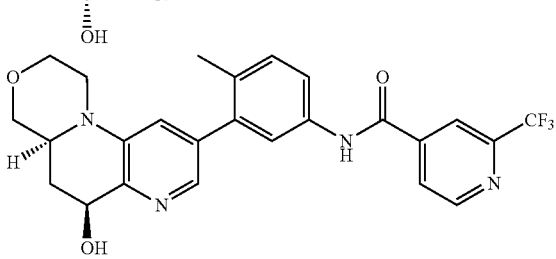
-continued
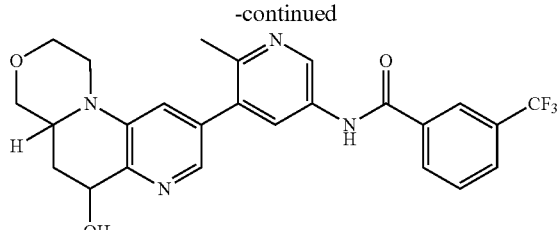
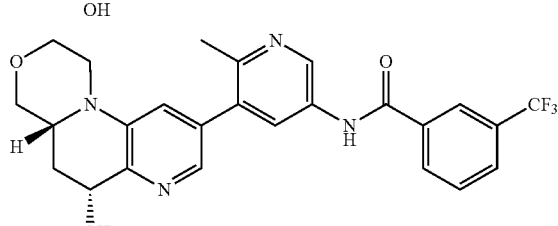
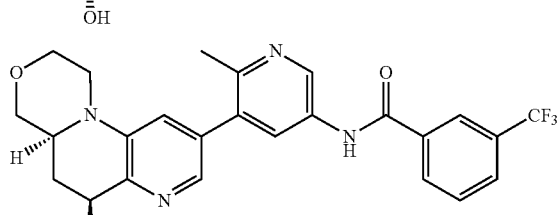
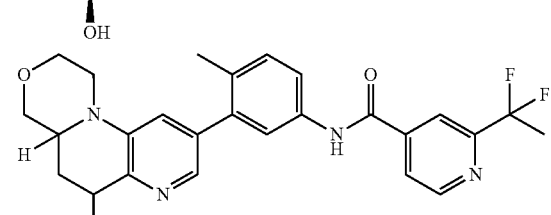
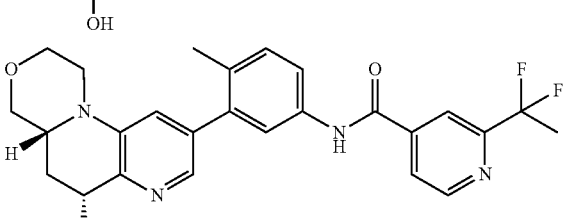
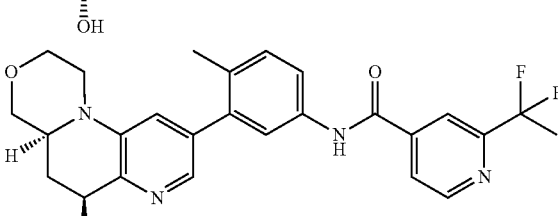
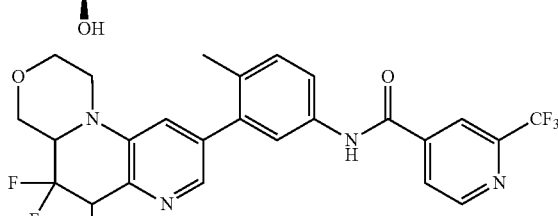
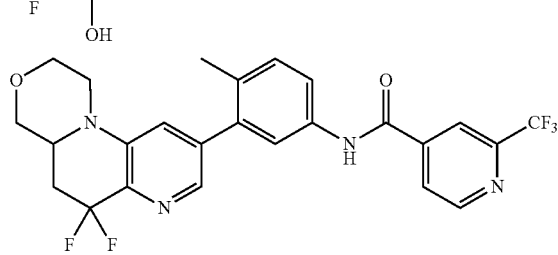

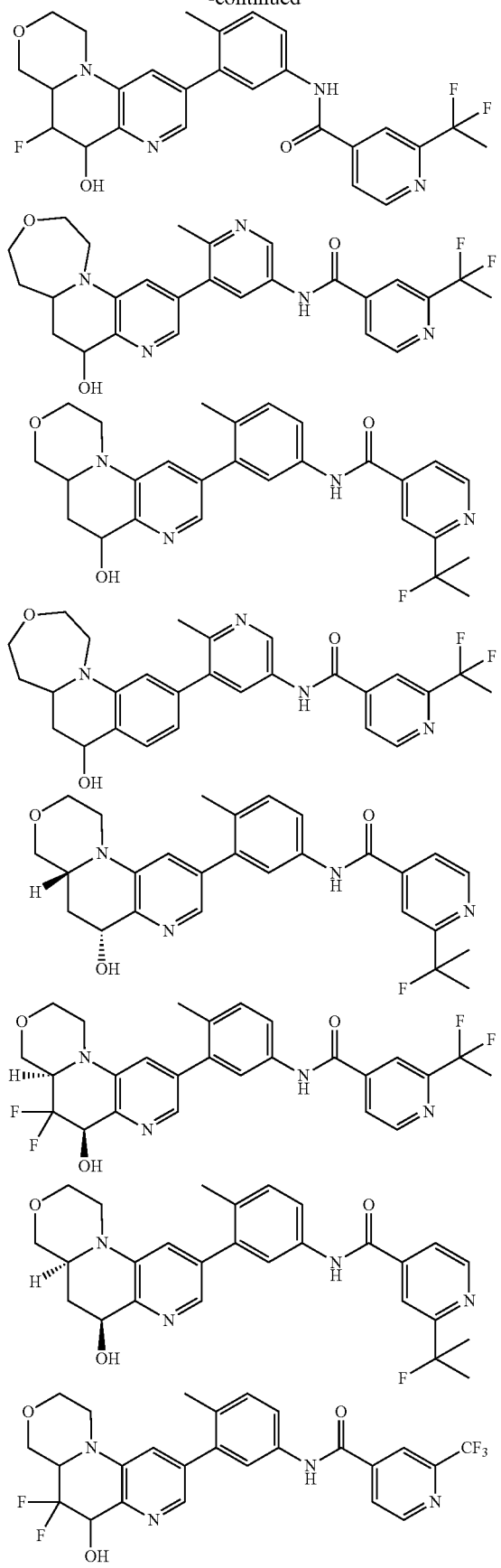
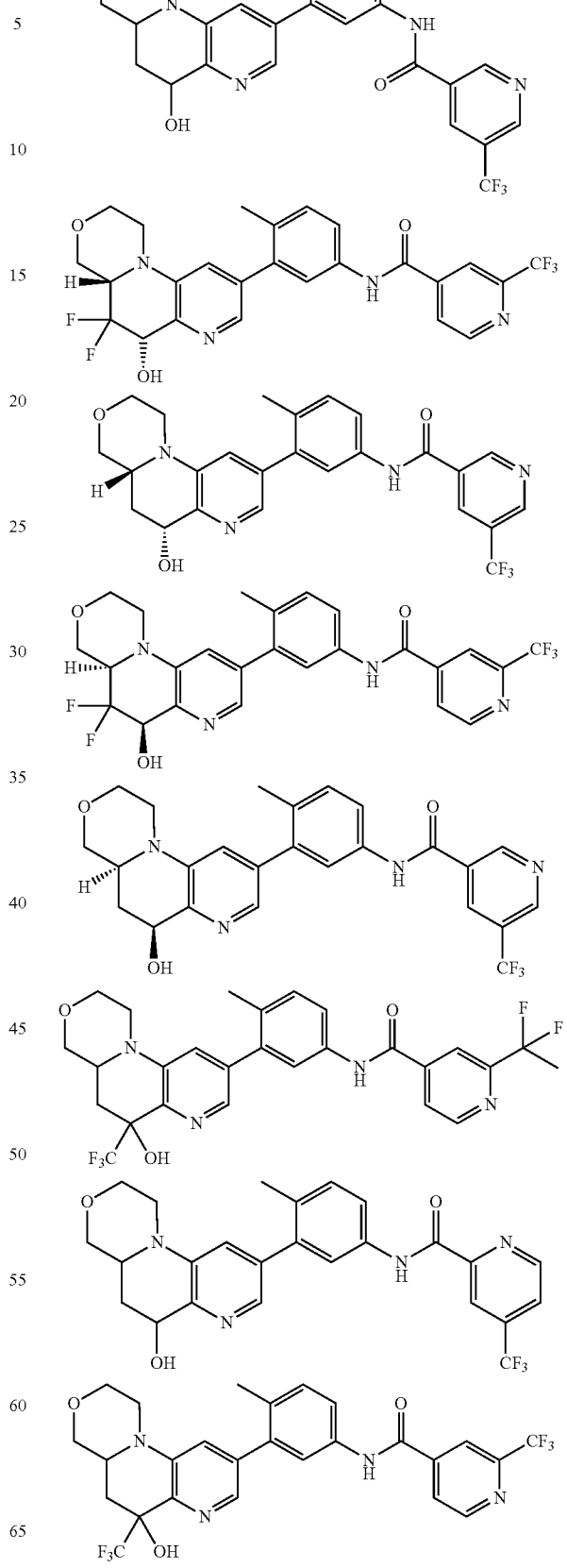

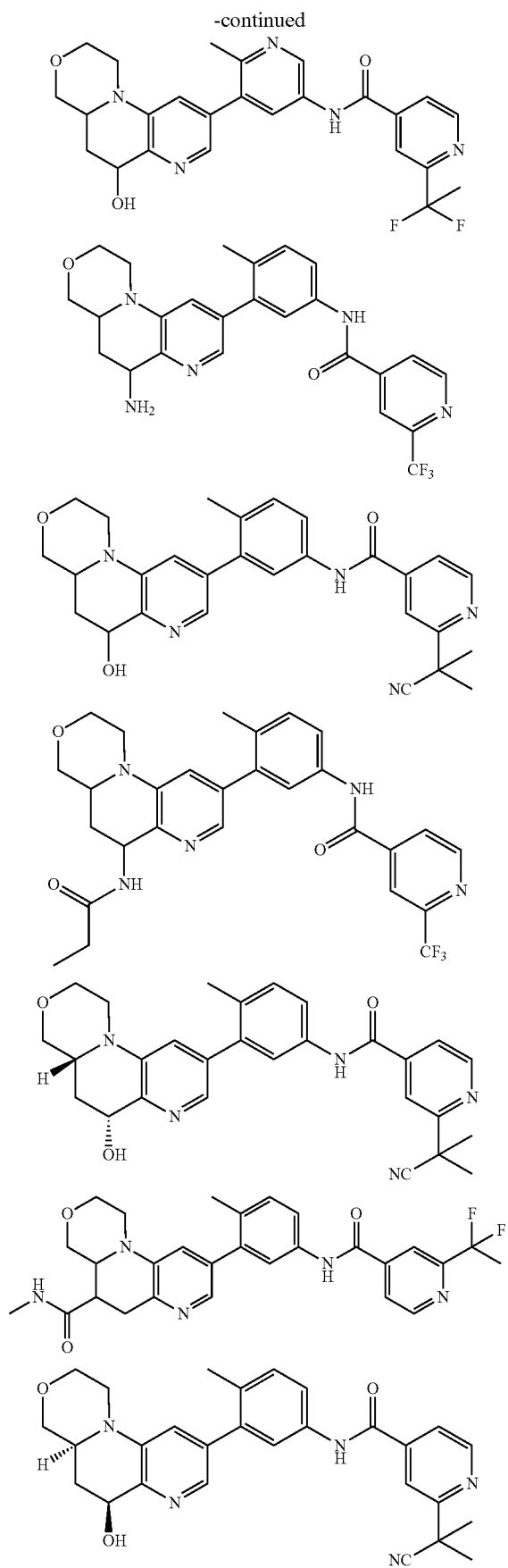
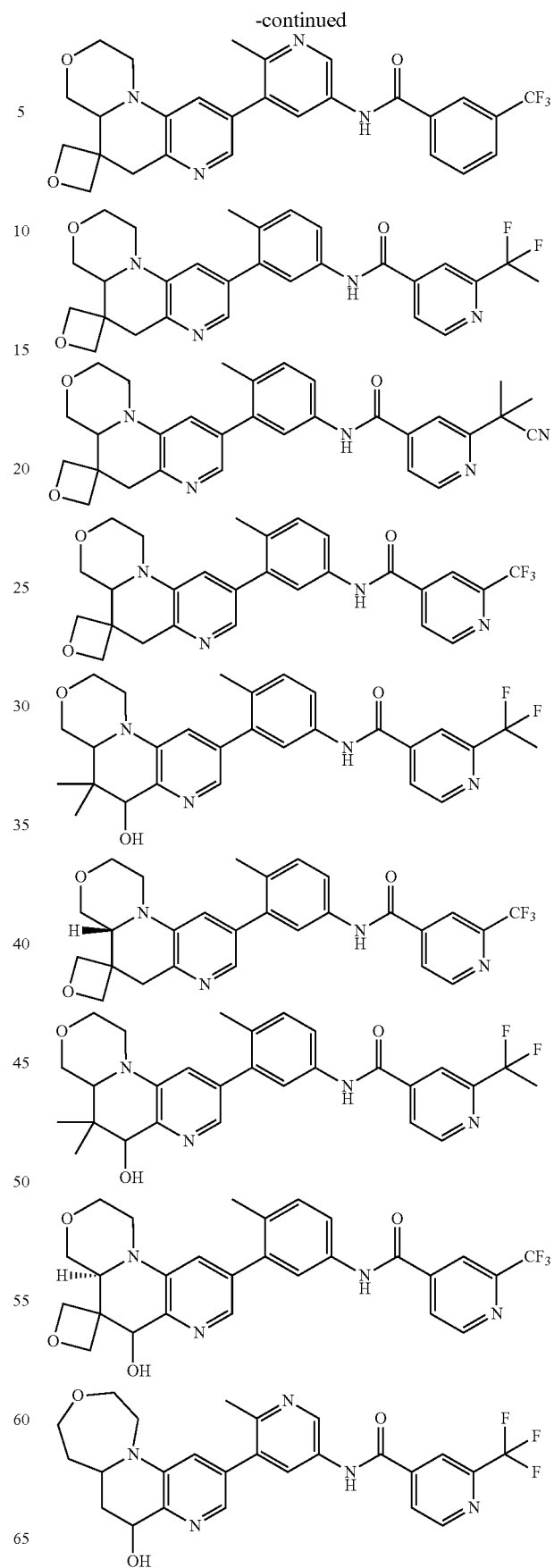

-continued

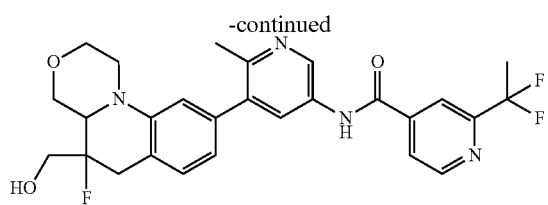

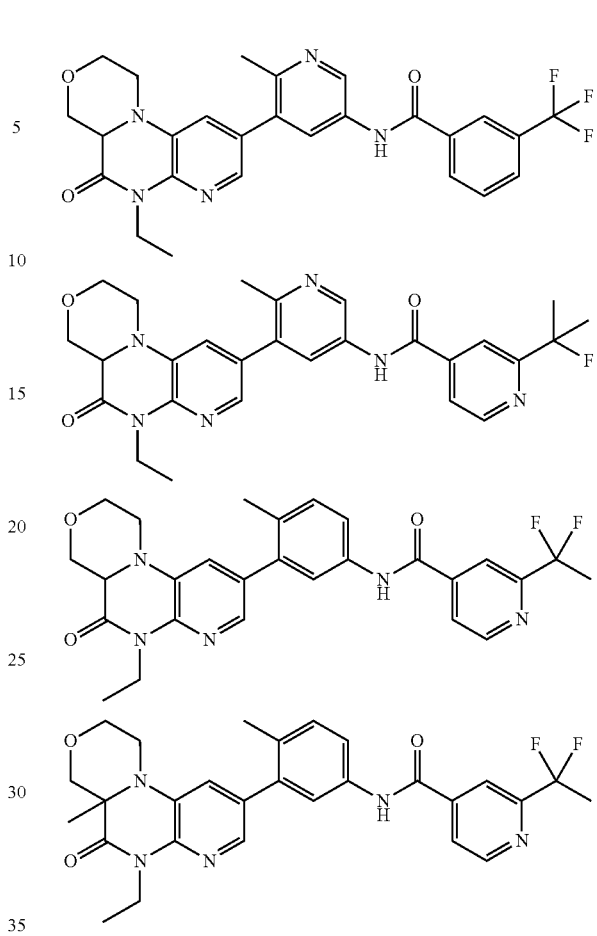

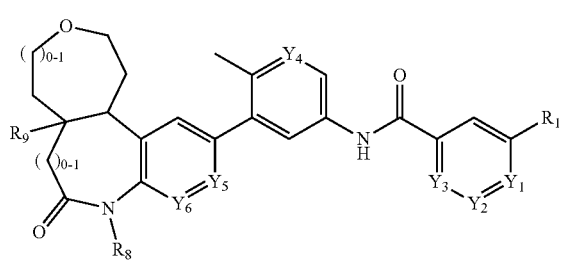

In a 19th embodiment, with reference to compounds of formula (I), are compounds of formula (Ic):

(Ic)

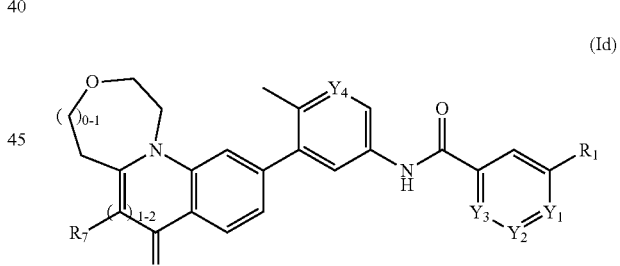

in which: $R_1$ is selected from halo-substituted $C_{1-3}$alkyl; $R_8$ is selected from hydrogen and $C_{1-3}$alkyl; $R_9$ is selected from hydrogen and methyl; $Y_1$ is selected from N and CH; $Y_2$ is selected from N and CH; $Y_3$ is selected from N and CH; $Y_4$ is selected from N and CH; $Y_5$ is selected from N and CH; and $Y_6$ is selected from N and CH; or the pharmaceutically acceptable salt thereof.

In a subset of this embodiment, $R_1$ is selected from trifluoromethyl, 2-fluoropropan-2-yl, 2-cyanopropan-2-yl and 1,1-difluoroethyl; $R_8$ is selected from hydrogen and ethyl; $R_9$ is selected from hydrogen and methyl; $Y_1$ is selected from N and CH; $Y_2$ is CH; $Y_3$ is CH; $Y_4$ is selected from N and CH; $Y_5$ is selected from N and CH; and $Y_6$ is selected from N and CH; or the pharmaceutically acceptable salt thereof.

In particular examples of this embodiment are compounds, or the pharmaceutically acceptable salt thereof, selected from:

In a 21st embodiment, with reference to compounds of formula (I), are compounds of formula (Id):

(Id)

in which: $R_1$ is selected from halo-substituted $C_{1-3}$alkyl; each $R_7$ is selected from hydrogen, $C_{1-2}$alkoxy-carbonyl and hydroxy-carbonyl; $Y_1$ is selected from N and CH; $Y_2$ is CH; $Y_3$ is CH; and $Y_4$ is selected from N and CH; or the pharmaceutically acceptable salt thereof.

In a 22nd embodiment, $R_1$ is selected from trifluoromethyl, 2-fluoropropan-2-yl, 2-cyanopropan-2-yl and 1,1-difluoroethyl; each $R_7$ is selected from hydrogen, ethoxycarbonyl and hydroxy-carbonyl; $Y_1$ is selected from N and CH; $Y_2$ is CH; $Y_3$ is CH; and $Y_4$ is selected from N and CH; or the pharmaceutically acceptable salt thereof.

In particular examples of this embodiment are compounds, or the pharmaceutically acceptable salt thereof, selected from:

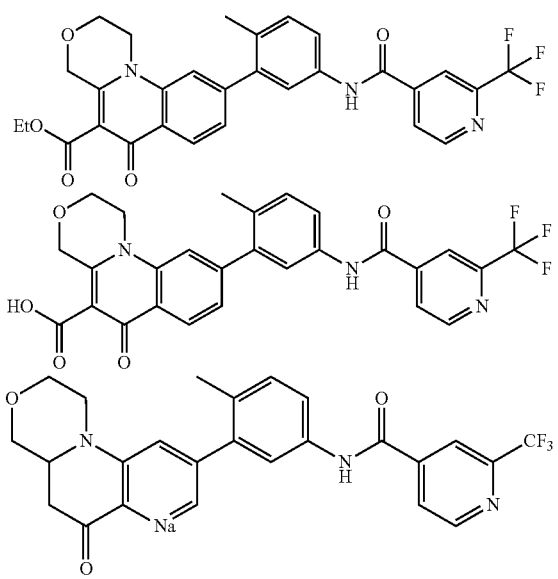

In a 23rd embodiment, with reference to compounds of formula (I), are compounds of formula (Ie):

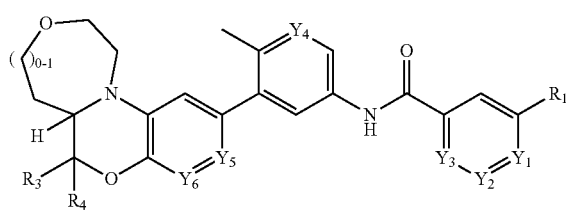

in which: $R_1$ is selected from halo-substituted $C_{1-3}$alkyl; $R_3$ is selected from hydrogen and $C_{1-3}$alkyl; $R_4$ is selected from hydrogen and $C_{1-3}$alkyl; $Y_1$ is selected from N and CH; $Y_2$ is selected from N and CH; $Y_3$ is selected from N and CH; $Y_4$ is selected from N and CH; $Y_5$ is selected from N and CH; and $Y_6$ is selected from N and CH; or the pharmaceutically acceptable salt thereof.

In a subset of this embodiment, $R_1$ is selected from trifluoromethyl, 2-fluoropropan-2-yl, 2-cyanopropan-2-yl and 1,1-difluoroethyl; $R_3$ is selected from hydrogen, methyl and ethyl; $R_4$ is selected from hydrogen, methyl and ethyl; $Y_1$ is N; $Y_2$ is CH; $Y_3$ is CH; $Y_4$ is CH; $Y_5$ is N; and $Y_6$ is N; or the pharmaceutically acceptable salt thereof.

In particular examples of this embodiment are compounds, or the pharmaceutically acceptable salt thereof, selected from:

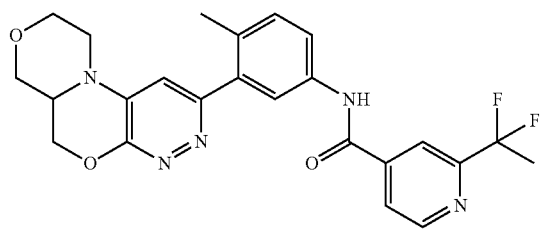

-continued

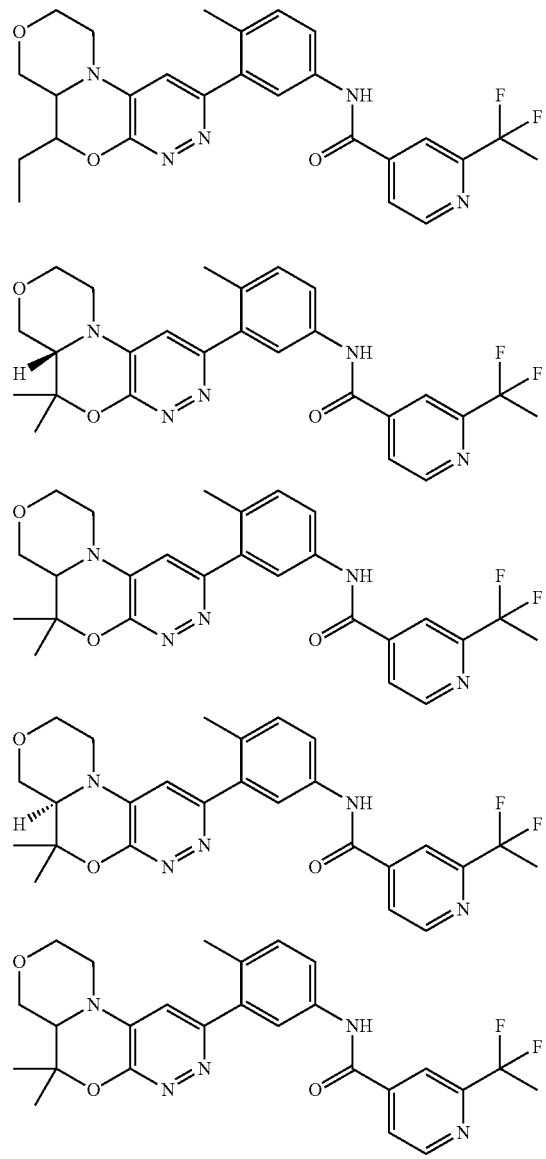

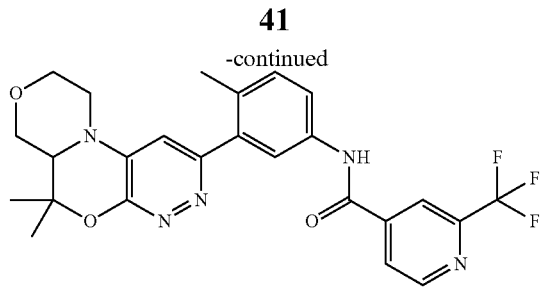

In a 25th embodiment, with reference to compounds of formula (I), are compounds of formula (If):

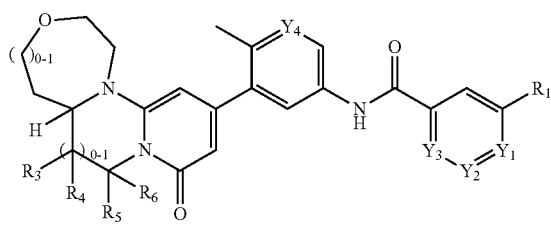

in which: $R_1$ is selected from trifluoromethyl, 2-fluoropropan-2-yl, 2-cyanopropan-2-yl and 1,1-difluoroethyl; $R_3$ is selected from hydrogen and $C_{1-3}$alkyl; $R_4$ is selected from hydrogen and $C_{1-3}$alkyl; $R_5$ is selected from hydrogen, halo, amino, $C_{1-3}$alkyl-amino-carbonyl, hydroxy and $C_{1-3}$alkoxy; $R_6$ is selected from hydrogen, $C_{1-3}$alkyl, halo and halo-substituted-$C_{1-3}$alkyl; $Y_1$ is selected from N and CH; $Y_2$ is selected from N and CH; $Y_3$ is selected from N and CH; and $Y_4$ is selected from N and CH; or the pharmaceutically acceptable salt thereof.

Included in this embodiment are compounds, or the pharmaceutically acceptable salt thereof, selected from:

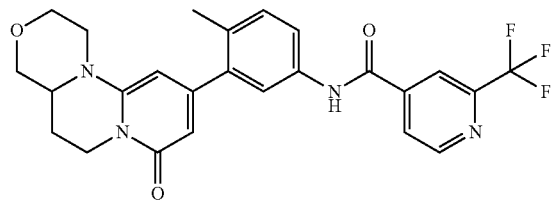

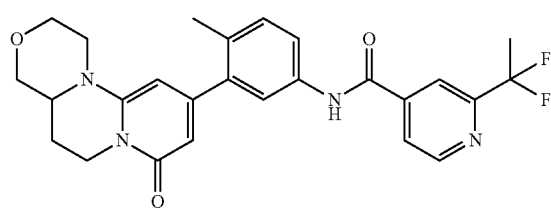

In a 26th embodiment, with reference to compounds of formula (I), are compounds of formula (Ig):

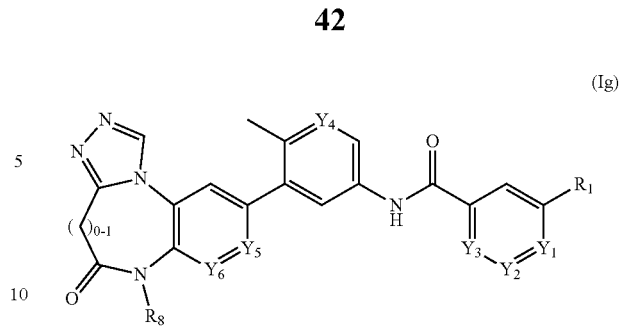

in which: $R_1$ is selected from trifluoromethyl, 2-fluoropropan-2-yl, 2-cyanopropan-2-yl and 1,1-difluoroethyl; $R_8$ is selected from hydrogen and $C_{1-3}$alkyl; $Y_1$ is selected from N and CH; $Y_2$ is selected from N and CH; $Y_3$ is selected from N and CH; $Y_4$ is selected from N and CH; $Y_5$ is selected from N and CH; and $Y_6$ is selected from N and CH; or the pharmaceutically acceptable salt thereof.

In certain examples of this embodiment are compounds, or the pharmaceutically acceptable salt thereof, selected from:

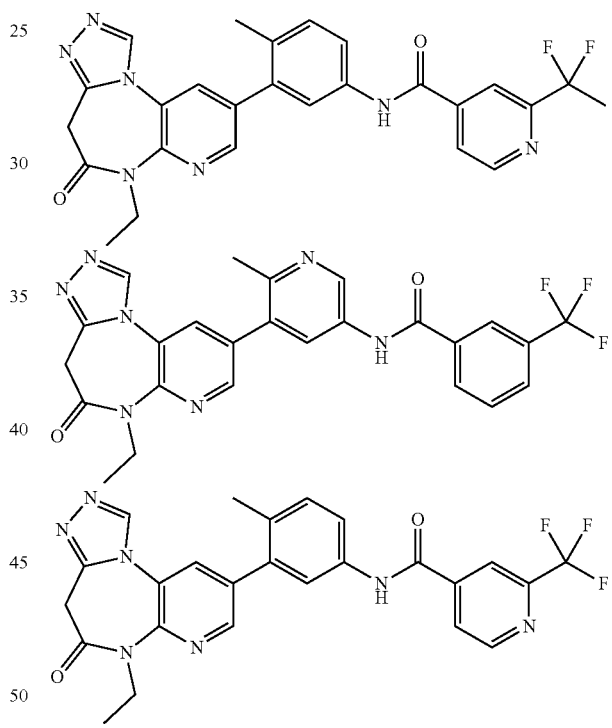

27. The compound of embodiment 1 or embodiment 14, or a pharmaceutically acceptable salt thereof, selected from the compound of any of Examples 1-534.

28. A pharmaceutical composition comprising a compound of embodiment 1 or embodiment 14, or a pharmaceutically acceptable salt thereof, and one or more pharmaceutically acceptable carriers.

29. A combination comprising a therapeutically effective amount of a compound according to embodiment 1 embodiment claim 14, or a pharmaceutically acceptable salt thereof, and one or more therapeutically active co-agents.

30. A method of treating a cancer, comprising administering to a subject in need thereof a therapeutically effective amount of a compound of embodiment 1 or embodiment 14, or a pharmaceutically acceptable salt thereof.

31. The method of embodiment 30, wherein the cancer is selected from melanoma, breast cancer, non-small cell lung cancer, lung adenocarcinoma, sarcoma, gastrointestinal stromal tumors, ovarian cancer, colorectal cancer, thyroid cancer and pancreatic cancer.

Each of the Example compounds has a measured IC-50 (c-Raf) shown in the Bioactivity Table below. Thus the use of any one of these compounds for treatment of a condition selected from melanoma, breast cancer, lung cancer (e.g., non-small cell lung cancer, lung adenocarcinoma), sarcoma, GI tumors such as gastrointestinal stromal tumors, ovarian cancer, colorectal cancer, thyroid cancer, and pancreatic cancer is an embodiment of the invention.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those in which radioactive isotopes, such as $^3$H and $^{14}$C, or those in which non-radioactive isotopes, such as $^2$H and $^{13}$C, are present at levels significantly above the natural abundance for these isotopes. These isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (A) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (A). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (A) that contain groups capable of acting as donors and/or acceptors for hydrogen bonds may be capable of forming co-crystals with suitable co-crystal formers. These co-crystals may be prepared from compounds of formula (A) by known co-crystal forming procedures. Such procedures include grinding, heating, co-subliming, co-melting, or contacting in solution compounds of formula (A) with the co-crystal former under crystallization conditions and isolating co-crystals thereby formed. Suitable co-crystal formers include those described in WO 2004/078163. Hence the invention further provides co-crystals comprising a compound of formula (A).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease mediated by a Raf kinase such as B-Raf or C-Raf, or associated with activity of a kinase such as B-Raf or C-Raf, or (2) reduce or inhibit the activity of a kinase such as B-Raf or C-Raf in vivo.

In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of a kinase such as B-Raf or C-Raf, or at least partially reduce or alleviate a symptom or a condition associated with excessive Raf kinase activity.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

In another aspect, the present invention provides a pharmaceutical composition comprising a compound of the present invention, or a pharmaceutically acceptable salt thereof, and at least one pharmaceutically acceptable carrier. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions for compounds of Formula (A) are tablets or gelatin capsules comprising an active ingredient of Formula (A) together with at least one of the following pharmaceutically acceptable excipients:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula (A) in free form or in salt form, exhibit valuable pharmacological activities, e.g. they modulate or inhibit activity of A-Raf, B-Raf and/or C-Raf, as indicated by test data provided in the next sections, and are therefore indicated for therapy or for use as research chemicals, e.g. as tool compounds. These compounds are especially useful for treatment of cancers driven by mutations in the Raf/Raf/MEK/ERK pathway, including cancers characterized by an activating Raf mutation such as Raf V600E, including but not limited to melanoma (e.g., malignant melanoma), breast cancer, lung cancer (e.g., non-small cell lung cancer), sarcoma, GI tumors such as gastrointestinal stromal tumors, ovarian cancer, colorectal cancer, thyroid cancer, and pancreatic cancer.

Thus, as a further embodiment, the present invention provides the use of a compound of formula (A) or any of the embodiments within the scope of Formula (A) as described herein, in therapy. In a further embodiment, the therapy is for a disease which may be treated by inhibition of A-Raf, B-Raf or C-Raf. In another embodiment, the compounds of the invention are useful to treat cancers, including but not limited to melanoma, breast cancer, lung cancer, sarcoma, GI tumors such as gastrointestinal stromal tumors, ovarian cancer, colorectal cancer, thyroid cancer, and pancreatic cancer.

In another embodiment, the invention provides a method of treating a disease which is treatable by inhibition of A-Raf, B-Raf or C-Raf, or a combination thereof, comprising administration of a therapeutically effective amount of a compound of formula (A) or any of the embodiments within the scope of Formula (A) as described herein. In a further embodiment, the disease is selected from the afore-mentioned list, suitably melanoma, breast cancer, lung cancer, sarcoma, GI tumors such as gastrointestinal stromal tumors, ovarian cancer, colorectal cancer, thyroid cancer, and pancreatic cancer. The method typically comprises administering an effective amount of a compound as described herein or a pharmaceutical composition comprising such compound to a subject in need of such treatment. The compound may be administered by any suitable method such as those described herein, and the administration may be repeated at intervals selected by a treating physician.

Thus, as a further embodiment, the present invention provides the use of a compound of formula (A) or any of the embodiments of such compounds described herein for the manufacture of a medicament. In a further embodiment, the medicament is for treatment of a disease which may be treated by inhibition of A-Raf, B-Raf or C-Raf. In another embodiment, the disease is a cancer, e.g., a cancer selected from the afore-mentioned list, including melanoma, breast cancer, lung cancer, sarcoma, GI tumors such as gastrointestinal stromal tumors, ovarian cancer, colorectal cancer, thyroid cancer, and pancreatic cancer.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more therapeutic co-agent(s) (co-therapeutic agents). Suitable co-therapeutic agents for use in the invention include, for example, cancer chemotherapeutics including but not limited to inhibitors of PI3K, other inhibitors of the Raf pathway, paclitaxel, docetaxel, temozolomide, platins, doxorubicins, vinblastins, cyclophosphamide, topotecan, gemcitabine, ifosfamide, etoposide, irinotecan, and the like. The compound of the present invention may be administered separately, by the same or different route of administration, or together in the same pharmaceutical composition as the co-agent(s).

In one embodiment, the invention provides a product comprising a compound of formula (A) and at least one other therapeutic co-agent as a combined preparation for simultaneous, separate or sequential use in therapy. In one embodiment, the therapy is the treatment of a disease or condition mediated by B-Raf or C-Raf, such as cancer. Products provided as a combined preparation include a composition comprising the compound of formula (A) and the other therapeutic co-agent(s) together in the same pharmaceutical composition, or the compound of formula (A) and the other therapeutic co-agent(s) in separate form, e.g. in the form of a kit.

In one embodiment, the invention provides a pharmaceutical composition comprising a compound of formula (A) and another therapeutic co-agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (A). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic co-agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (A) for treating a disease or condition mediated by B-Raf or C-Raf, wherein the medicament is prepared for administration with another therapeutic agent. The invention also provides the use of another therapeutic co-agent for treating a disease or condition, wherein the medicament is administered with a compound of formula (A).

The invention also provides a compound of formula (A) for use in a method of treating a disease or condition mediated by B-Raf or C-Raf, wherein the compound of formula (A) is prepared for administration with another therapeutic agent. The invention also provides another therapeutic co-agent for use in a method of treating a disease or condition mediated by B-Raf or C-Raf, wherein the other therapeutic co-agent is prepared for administration with a compound of formula (A). The invention also provides a compound of formula (A) for use in a method of treating a disease or condition mediated by B-Raf or C-Raf, wherein the compound of formula (A) is administered with another therapeutic co-agent. The invention also provides another therapeutic co-agent for use in a method of treating a disease or condition mediated by B-Raf or C-Raf, wherein the other therapeutic co-agent is administered with a compound of formula (A).

The invention also provides the use of a compound of formula (A) for treating a disease or condition mediated by B-Raf or C-Raf, wherein the patient has previously (e.g. within 24 hours) been treated with another therapeutic agent. The invention also provides the use of another therapeutic agent for treating a disease or condition mediated by B-Raf or C-Raf, wherein the patient has previously (e.g. within 24 hours) been treated with a compound of formula (A).

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula (A) can be prepared by proceeding as in the following Reaction Scheme I:

Reaction Scheme I

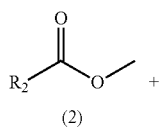

(2)

-continued

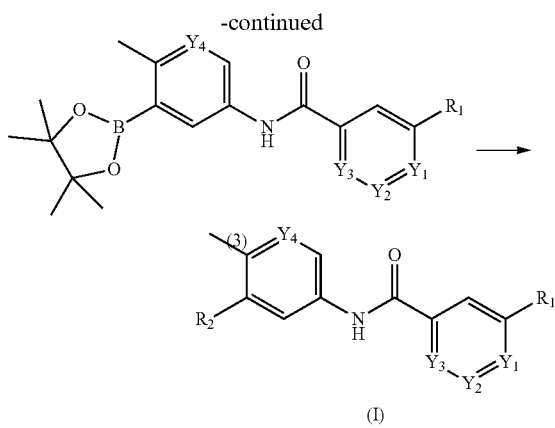

(I)

in which $R_1$, $R_2$, $Y_1$, $Y_2$, $Y_3$ and $Y_4$ are as described in the Summary of the Invention. Compounds of formula (A) can be prepared by reacting a compound of formula 2 with a compound of formula 3 in the presence of a suitable catalyst (for example, $PdCl_2(dppf) \cdot CH_2Cl_2$ adduct, and the like), a suitable solvent (for example dioxane and DMF, or the like) and a suitable buffer (for example, $Na_2CO_3$, or the like). The reaction proceeds at a temperature of about 90° C. to about 140° C. and can take up to about 1 hour to complete.

Compounds of Formula (A) can also be prepared by proceeding as in the following Reaction Scheme II:

Reaction Scheme II

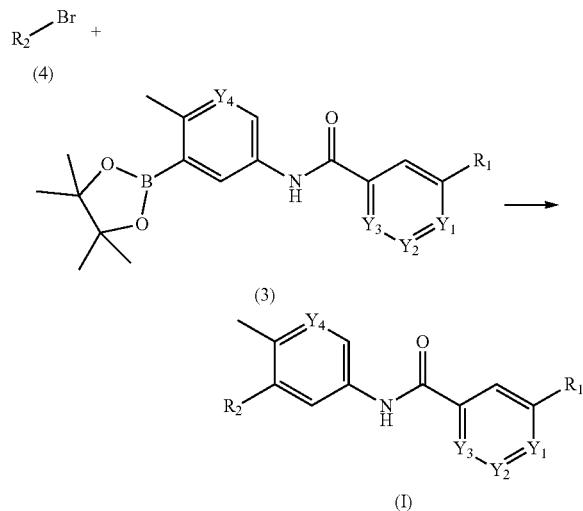

(I)

in which $R_1$, $R_2$, $Y_1$, $Y_2$, $Y_3$ and $Y_4$ are as described in the Summary of the Invention. Compounds of formula (A) can be prepared by reacting a compound of formula 4 with a compound of formula 3 in the presence of a suitable catalyst (for example, $PdCl_2(dppf) \cdot CH_2Cl_2$ adduct, and the like), a suitable solvent (for example dioxane and DMF, or the like) and a suitable buffer (for example, $Na_2CO_3$, or the like). The reaction proceeds at a temperature of about 90° C. to about 140° C. and can take up to about 1 hour to complete. Descriptions of the synthesis of specific examples are described, below.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", 3$^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula (A) can be made by a process, which involves:

(a) that of reaction schemes I and II; and
(b) optionally converting a compound of the invention into a pharmaceutically acceptable salt;
(c) optionally converting a salt form of a compound of the invention to a non-salt form;
(d) optionally converting an unoxidized form of a compound of the invention into a pharmaceutically acceptable N-oxide;
(e) optionally converting an N-oxide form of a compound of the invention to its unoxidized form;
(f) optionally resolving an individual isomer, for example stereoisomer, of a compound of the invention from a mixture of isomers;
(g) optionally converting a non-derivatized compound of the invention into a pharmaceutically acceptable prodrug derivative; and
(h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well-known methods can similarly be used.

EXAMPLES

The present invention is further exemplified, but not limited, by the following intermediates and examples that illustrate the preparation of compounds of Formula (A) according to the invention.

The following abbreviations may be used herein:

| | |
|---|---|
| DAST | (diethylamino)sulfurtrifluoride |
| DCM | Dichloromethane |
| DIAD | diisopropylazodicarboxylate |
| DIEA | diisopropylethylamine |
| DMA | Dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-Dimethylaminopropyl)-3-ethylcarbodiimide hydrochloride |
| EtOAc | ethyl acetate |
| EtOH | Ethanol |
| HOAT | Hydroxyazabenzotriazole |
| HOBt | Hydroxybenzotriazole |
| $K_2CO_3$ | Potassium carbonate |
| MeCN | Acetonitrile |
| $MgSO_4$ | Magnesium sulfate |
| MeOH | Methanol |
| $Na_2CO_3$ | sodium carbonate |
| NaCl | Sodium chloride |
| $NaHCO_3$ | sodium bicarbonate |
| NBS | N-bromosuccinimide |
| NMP | N-methyl-2-pyrrolidone |
| $Pd_2(dba)_3$ | Tris(dibenzylideneacetone)dipalladium(0) |
| $Pd(PPh_3)_4$ | Tetrakis(triphenylphospine)palladium(0) |
| $Pd(dppf)Cl_2$- | Dichloro-(1,2-bis(diphenylphosphino)ethan)-Palladium(II)- |
| DCM | dichloromothethane adduct |
| RT or rt | room temperature |
| TBDMSCl | tert-butyldimethylsilylchloride |
| TEA | Triethylamine |
| THF | tetrahydrofuran |

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

Mass spectrometric analysis was performed on LCMS instruments: Waters System (Acuity UPLC and a Micromass ZQ mass spectrometer; Column: Acuity HSS C18 1.8-micron, 2.1×50 mm; gradient: 5-95% acetonitrile in water with 0.05 TFA over a 1.8 min period; flow rate 1.2 mL/min; molecular weight range 200-1500; cone Voltage 20 V; column temperature 50° C.). All masses were reported as those of the protonated parent ions.

Nuclear magnetic resonance (NMR) analysis was performed on some of the compounds with a Varian 400 MHz NMR (Palo Alto, Calif.). The spectral reference was either TMS or the known chemical shift of the solvent.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

INTERMEDIATES

Synthesis of cis-9-bromo-1,2,4,4a,5,6-hexahydro-[1,4]oxazino[4,3-a][1,5]naphthyridin-6-ol

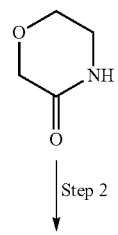

Step 2

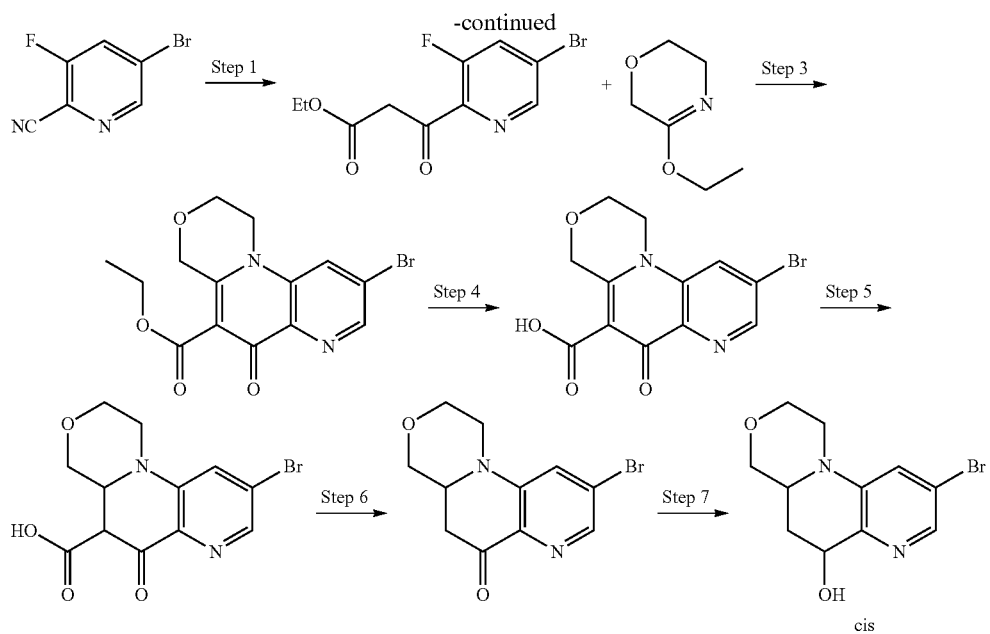

Step 1:

A suspension of zinc (5 equiv) in THF (1 M) was treated with trimethylsilylchloride (0.25 equiv). The mixture was heated in a 50° C. heating bath (reflux condenser) for 10 min, then ethyl bromoacetate (2.5 equiv) was added dropwise. After 25 min, the mixture was cooled to room temperature, and the solid was allowed to settle. The supernatant was transferred via syringe to a flask containing the supernatant as possible was transferred via syringe to a round-bottom flask containing 5-bromo-3-fluoropicolinonitrile (1 equiv), and the resulting mixture was stirred for 9 h. The reaction mixture diluted with 10% aq. citric acid solution (2 volumes) and EtOAc (1 volume) and stirred overnight. In the morning, the mixture filtered through celite with the aid of EtOAc and water. The layers were separated, and the aq. layer was extracted with EtOAc. The combined organic layers were dried over sodium sulfate, filtered, and concentrated. The residue was wet so it was diluted with water and extracted with DCM (3×). The combined organic extracts were dried over sodium sulfate, filtered, and concentrated. The residue was purified by silica gel chromatography (0-30% EtOAc/heptane) to give ethyl 3-(5-bromo-3-fluoro-pyridin-2-yl)-3-oxopropanoate (35.7% yield) as a yellow oil. $^1$H NMR (400 MHz, CHLOROFORM-d) δ ppm 8.56 (dd, J=1.71, 0.98 Hz, 1H) 7.78 (dd, J=9.66, 1.83 Hz, 1H) 4.15-4.25 (m, 2H) 4.12 (s, 2H) 1.19-1.30 (m, 3H). LCMS (m/z) (M+H)=289.9, Rt=1.32 min.

Step 2:

Into a round-bottom flask were charged morpholin-3-one (1 equiv) and DCM (0.65 M). To the mixture at room temperature under nitrogen was added triethyloxonium tetrafluoroborate (1.1 equiv). The mixture was agitated at room temperature overnight. The next morning, the reaction mixture was quenched by the addition of saturated aq. sodium carbonate solution. The organic layer was separated, dried over sodium sulfate, filtered, and concentrated in vacuo (35° C., 250 mmHg) to afford the crude 5-ethoxy-3,6-dihydro-2H-1,4-oxazine (65.3% yield) as a 50% solution in DCM. $^1$H NMR (400 MHz, CHLOROFORM-d) δ ppm 8.34 (d, J=8.56 Hz, 1H) 7.69 (d, J=1.59 Hz, 1H) 7.56 (dd, J=8.56, 1.71 Hz, 1H) 5.00 (s, 2H) 4.42 (q, J=7.09 Hz, 2H) 4.18-4.27 (m, 2H) 4.02-4.11 (m, 2H) 1.41 (t, J=7.15 Hz, 3H).

Step 3:

A vial was charged with ethyl 3-(5-bromo-3-fluoropyridin-2-yl)-3-oxopropanoate (1 equiv) and 5-ethoxy-3,6-dihydro-2H-1,4-oxazine (1.1 equiv), sealed, and heated to 115° C. After 3 h, an additional portion of 5-ethoxy-3,6-dihydro-2H-1,4-oxazine (1.1 equiv) was added, and the mixture was heated overnight. In the morning, the mixture was cooled and concentrated. The residue was concentrated from EtOH, then taken up in EtOH and heated to boiling for 1 min. The mixture was cooled to room temperature then filtered. The collected solid was washed with EtOH (2×), then dried under a flow of $N_2$ (g) to give ethyl 9-bromo-6-oxo-1,2,4,6-tetrahydro-[1,4]oxazino[4,3-a][1,5]naphthyridine-5-carboxylate (59% yield) as a tan solid. $^1$H NMR (400 MHz, DMSO-$d_6$) δ ppm 8.84 (d, J=1.83 Hz, 1H) 8.62 (d, J=1.83 Hz, 1H) 4.83 (s, 2H) 4.26 (q, J=7.09 Hz, 2H) 4.07-4.21 (m, 4H) 1.27 (t, J=7.15 Hz, 3H). LCMS (m/z) (M+H)=352.9, Rt=0.86 min.

Step 4:

A vial was charged with ethyl 9-bromo-6-oxo-1,2,4,6-tetrahydro-[1,4]oxazino[4,3-a][1,5]naphthyridine-5-carboxylate (1 equiv) a 1.4:1 water/AcOH mixture (0.2 M). Sulfuric acid (6.5 equiv) was added, resulting in a solution. The vial was heated to 110° C. for 2 h. After cooling to room temperature, the mixture was filtered, and the collected solid was washed with water (2×), then dried under a flow of $N_2$ (g) overnight to give 9-bromo-6-oxo-1,2,4,6-tetrahydro-[1,4]oxazino[4,3-a][1,5]naphthyridine-5-carboxylic acid as an off-white solid. LCMS (m/z) (M+H)=324.9, Rt=0.76 min.

Step 5:

9-bromo-6-oxo-1,2,4,6-tetrahydro-[1,4]oxazino[4,3-a][1,5]naphthyridine-5-carboxylic acid (1 equiv) was suspended in MeOH (0.07 M), and sodium borohydride (4 equiv) was carefully added in 3 portions. After stirring for 5 min, p-toluenesulfonic acid monohydrate (0.1 equiv) was added. The mixture was heated to 65° C. for 2 h, then cooled to room temperature, diluted with acetone, and concentrated. The residue was taken up in sat. aq. sodium bicarbonate solution and extracted with EtOAc (3×). The combined organic extracts were dried over sodium sulfate, filtered, and concentrated to give 9-bromo-1,2,4a,5-tetrahydro-[1,4]oxazino[4,3-a][1,5]naphthyridin-6(4H)-one (88% yield) as a yellow solid. LCMS (m/z) (M+H)=284.9, Rt=0.90 min.

Step 6:

9-bromo-1,2,4a,5-tetrahydro-[1,4]oxazino[4,3-a][1,5]naphthyridin-6(4H)-one (1 equiv) was suspended in 3:2 MeOH/THF (0.1 M). The suspension was cooled to 0° C. and then sodium borohydride (2 equiv) was added in one portion. After 10 min, the cooling bath was removed. The mixture was stirred at room temperature for 1.5 h, then saturated. aq. ammonium chloride solution was added. The volatiles were removed in vacuo. The resulting mixture was diluted with water and extracted EtOAc (3×). The combined organic extracts were dried over sodium sulfate, filtered, and concentrated. The residue was purified by chromatography on silica gel (0-50% EtOAc/heptane) to give racemic cis-9-bromo-1,2,4,4a,5,6-hexahydro-[1,4]oxazino[4,3-a][1,5]naphthyridin-6-ol (71% yield, 90% purity) as a white solid. LCMS (m/z) (M+H)=286.9, Rt=0.65 min.

Synthesis of diethyl 9-chloro-1,2,4,4a-tetrahydro-[1,4]oxazino[4,3-a][1,5]naphthyridine-5,5(6H)-dicarboxylate

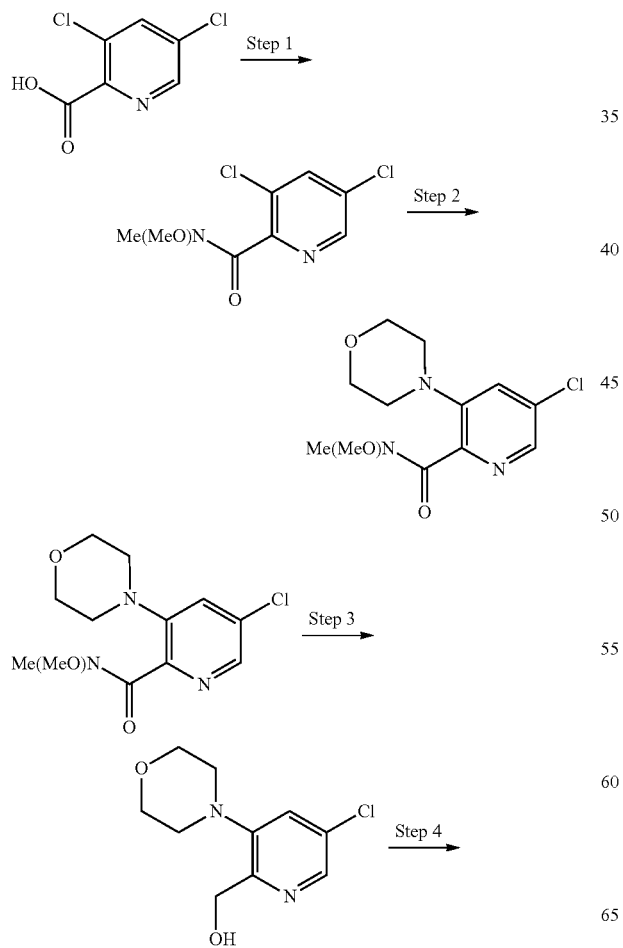

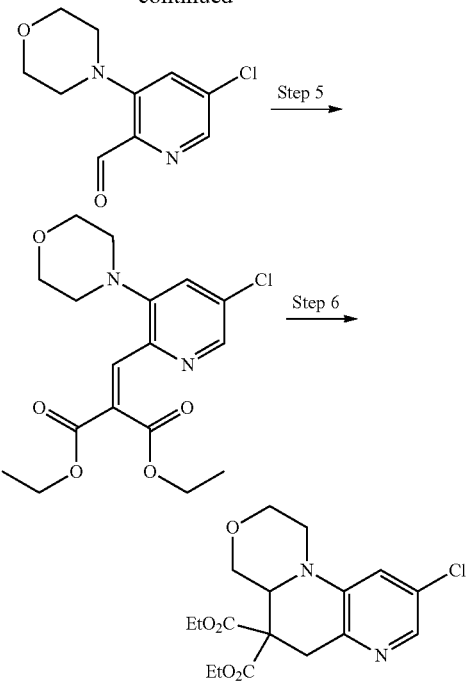

Step 1:

A suspension of 3,5-dichloropicolinic acid (1 equiv) in DCM (0.3 M) containing catalytic DMF (5 drops) was treated dropwise with oxalyl chloride (1.3 equiv). After 3 h, the mixture was concentrated. The residue was concentrated from DCM (1×), then taken up in DCM (0.35 M). The resulting solution was cooled in an ice-water bath for 5 min, then N,O-dimethylhydroxylamine hydrochloride (1.2 equiv) was added. Triethylamine (2.5 equiv) was added dropwise and a thick mixture formed. The cooling bath was removed, and an additional portion of DCM (0.35 M) was added. After stirring overnight, the mixture was washed with water, washed with 1N aq. HCl, washed with brine, dried over sodium sulfate, filtered, and concentrated. The residual solid was taken up in heptane (some residue remained on the flask), then filtered, washed with heptane, dried under a flow of $N_2$ (g), then dried under vacuum to give 3,5-dichloro-N-methoxy-N-methylpicolinamide (88% yield) as a white solid. $^1$H NMR (400 MHz, CHLOROFORM-d) δ ppm 8.49 (d, J=1.96 Hz, 1H) 7.80 (d, J=1.96 Hz, 1H) 3.58 (s, 3H) 3.41 (s, 3H). LCMS (m/z) (M+H)=253.2, Rt=1.03 min.

Step 2:

A vial was charged with 3,5-dichloro-N-methoxy-N-methylpicolinamide (1 equiv) and morpholine (6 equiv). The vial was sealed and heated to 140° C. for 8 h. After the mixture was cooled to room temperature, it was diluted with ether and filtered with the aid of ether. The filtrate was washed with 1N aq. HCl (300 mL), and the aq. layer was extracted with ether (2×150 mL). The combined ethereal extracts were dried over magnesium sulfate, filtered, and concentrated. The residue was purified by chromatography on silica gel (20-70% EtOAc/heptane) to give 5-chloro-N-methoxy-N-methyl-3-morpholinopicolinamide (74.4% yield) as an oily white solid. $^1$H NMR (400 MHz, CHLOROFORM-d) δ ppm 8.24 (d, J=1.96 Hz, 1H) 7.36 (d, J=1.59 Hz, 1H) 3.75-3.94 (m, 4H) 3.59 (s, 3H) 3.37 (s, 3H) 3.08 (br s, 4H). LCMS (m/z) (M+H)=286.0, Rt=0.92.

Step 3:

5-chloro-N-methoxy-N-methyl-3-morpholinopicolinamide (1 equiv) was charged in a round-bottom flask, then concentrated from toluene (1×). The residue was dissolved in THF (0.2 M), and the resulting solution was cooled in an ice-water bath for 10 min. A solution of DIBAL-H (1 M in THF, 2 equiv) was added dropwise over 5 min. After 10 min of stirring, the reaction was quenched by the addition of EtOAc (20 equiv). The mixture was then diluted with 1N aq. HCl, resulting in some bubbling. The mixture was stirred for 5 min, then extracted with EtOAc (3×). The aq. layer was neutralized with sat. bicarb solution and extracted with DCM (2×). An emulsion formed, so more DCM was added, and the whole mixture was stirred vigorously with sat. aq. Rochelle's salt solution overnight. The next morning, the mixture was extracted with DCM (3×). The combined organic extracts were dried over sodium sulfate, filtered, and concentrated to give (5-chloro-3-morpholinopyridin-2-yl)methanol (90% yield) as a light red solid. LCMS (m/z) (M+H)=229.1, Rt=0.71 min.

Step 4:

A solution of (5-chloro-3-morpholinopyridin-2-yl)methanol (1 equiv) in DCM (0.2 M) cooled in an ice-water bath was treated with Dess-Martin periodinane (1.1 equiv). After 30 min of stirring, an additional portion of Dess-Martin periodinane (0.3 equiv) was added, and the cooling bath was removed. After stirring at room temperature for 3 h, the mixture was recooled in an ice-water bath for 5 min, then an additional portion of Dess-Martin (0.15 equiv) was added. After another 10 min, a sat. aq. sodium bicarbonate solution was carefully added. The mixture was stirred for 1 h, then was further diluted with sat. aq. sodium thiosulfate solution and extracted with DCM (5×). The combined organic extracts were dried over sodium sulfate, filtered, and concentrated. The residue was purified by chromatography on silica gel (0-50% EtOAc/heptane) to give 5-chloro-3-morpholinopicolinaldehyde (84% yield) as a yellow oil: $^1$H NMR (400 MHz, CHLOROFORM-d) δ ppm 10.09 (d, J=0.73 Hz, 1H) 8.35 (d, J=1.96 Hz, 1H) 7.39 (d, J=1.96 Hz, 1H) 3.91-4.00 (m, 4H) 3.14-3.22 (m, 4H). LCMS (m/z) (M+H)=227.0, Rt=1.03 min.

Step 5:

A flask was charged with 5-chloro-3-morpholinopicolinaldehyde (1 equiv), toluene (0.2 M), diethyl malonate (1.1 equiv), and acetic anhydride (1.2 equiv) to give a solution. Indium(III) chloride (0.065 equiv) was added, and the flask was heated to 80° C. for 5 h. The mixture was cooled, then partitioned between saturated aq. sodium bicarbonate solution and EtOAc. The aq. layer was extracted with EtOAc (2×), and the combined organic extracts were washed with brine, dried over sodium sulfate, filtered, and concentrated. The residue was purified by chromatography on silica gel (25-75% EtOAc/heptane) to give diethyl 2-((5-chloro-3-morpholinopyridin-2-yl)methylene)malonate (90% yield) as a yellow oil. $^1$H NMR (400 MHz, CHLOROFORM-d) δ ppm 8.24 (d, J=1.96 Hz, 1H) 7.94 (s, 1H) 7.34 (d, J=2.20 Hz, 1H) 4.36 (dq, J=14.21, 7.16 Hz, 4H) 3.86-3.99 (m, 4H) 2.96-3.10 (m, 4H) 2.07 (s, 1H) 1.28-1.40 (m, 2H) 1.36 (d, J=7.83 Hz, 4H). LCMS (m/z) (M+H)=369.0, Rt=1.49 min.

Step 6:

A solution of diethyl 2-((5-chloro-3-morpholinopyridin-2-yl)methylene)malonate (1 equiv) in acetonitrile (0.1 M) was treated with gadolinium(III) trifluoromethanesulfonate (0.1 equiv). The mixture was heated to reflux for 6 h, then was cooled to room temperature. The mixture was concentrated, and the residue was dissolved in toluene (0.1 M). Zinc chloride (2 equiv) was added, and the resulting mixture was heated to reflux overnight. The mixture was then cooled, diluted with saturated aq. bicarbonate solution, EtOAc, and water. The layers were separated, and the aq. layer was extracted with EtOAc (2×). The combined organic layers were washed with brine, dried over sodium sulfate, filtered, and concentrated. The residue was purified by chromatography on silica gel (25-75% EtOAc/heptane) to give diethyl 9-chloro-1,2,4,4a-tetrahydro-[1,4]oxazino[4,3-a][1,5]naphthyridine-5,5(6H)-dicarboxylate (89% yield) as a light-yellow oil. LCMS (m/z) (M+H)=369.1, Rt=1.32 min.

Synthesis of trans- and cis-ethyl 9-chloro-1,2,4,4a, 5,6-hexahydro-[1,4]oxazino[4,3-a][1,5]naphthyridine-5-carboxylate

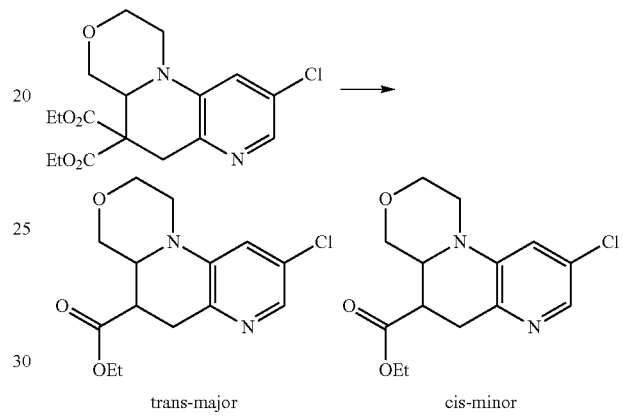

trans-major      cis-minor

A round-bottom flask was charged with diethyl 9-chloro-1,2,4,4a-tetrahydro-[1,4]oxazino[4,3-a][1,5]naphthyridine-5,5(6H)-dicarboxylate (1 equiv), LiCl (2 equiv), DMSO (0.5 M), and water (2 equiv). The flask was fitted with a reflux condenser and heated to 180° C. for 6 h, and the mixture was cooled to room temperature overnight. In the morning, the mixture was diluted with water and a small amount of brine, then extracted with EtOAc (3×). The combined organic extracts were dried over sodium sulfate, filtered, and concentrated. The residue was purified by chromatography on silica gel (0-50% EtOAc/heptane). The first eluting spot was collected to give trans-ethyl 9-chloro-1,2,4,4a,5,6-hexahydro-[1,4]oxazino[4,3-a][1,5]naphthyridine-5-carboxylate (69.0% yield); LCMS (m/z) (M+H) 297.0; Rt.=1.08 min. The second eluting spot was collected to give cis-ethyl 9-chloro-1,2,4,4a,5,6-hexahydro-[1,4]oxazino[4,3-a][1,5] naphthyridine-5-carboxylate (15.91% yield). LCMS (m/z) (M+H) 297.0; Rt.=0.93 min.

Synthesis of trans-(9-chloro-1,2,4,4a,5,6-hexahydro-[1,4]oxazino[4,3-a][1,5]naphthyridin-5-yl)methanol

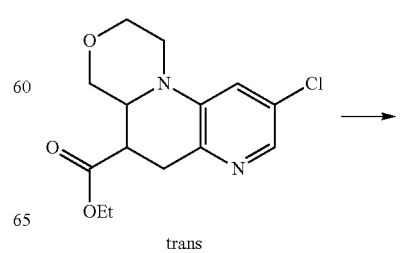

trans

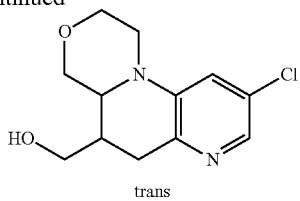

trans

A flask was charged with trans-ethyl 9-chloro-1,2,4,4a,5,6-hexahydro-[1,4]oxazino[4,3-a][1,5]naphthyridine-5-carboxylate (1 equiv) and THF (0.2 M) to give a clear, yellow solution. The flask was cooled in an ice-water bath for 5 min, then lithium aluminum hydride (1M in THF, 1.1 equiv) was added dropwise. After 15 min, sodium sulfate decahydrate (2 equiv) was added in a single portion, then the cooling bath was removed. After stirring for 20 min at room temperature, the mixture was diluted with EtOAc and filtered. The filter pad was washed with EtOAc (2×) and DCM (1×). The filtrate was concentrated to give trans-(9-chloro-1,2,4,4a,5,6-hexahydro-[1,4]oxazino[4,3-a][1,5]naphthyridin-5-yl)methanol (96% yield) as an off-white solid. LCMS (m/z) (M+H)=255.0, Rt.=0.64 min.

Synthesis of 1:1 trans-(9-chloro-1,2,4,4a,5,6-hexahydro-[1,4]oxazino[4,3-a][1,5]naphthyridin-5-yl)methanol and cis-(9-chloro-1,2,4,4a,5,6-hexahydro-[1,4]oxazino[4,3-a][1,5]naphthyridin-5-yl)methanol

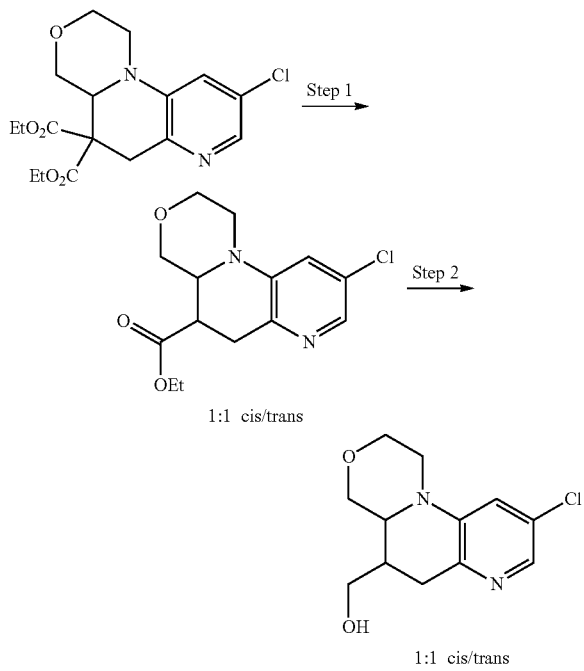

Step 1:
A vial was charged with diethyl 9-chloro-1,2,4,4a-tetrahydro-[1,4]oxazino[4,3-a][1,5]naphthyridine-5,5(6H)-dicarboxylate (1 equiv) and 1.4:1 water-AcOH. Sulfuric acid (6.5 equiv) was added, resulting in a solution. The vial was heated to 110° C. for 3 h, then an additional portion of sulfuric acid (6.5 equiv) was added. The vial was heated to 130° C. for 4 h, then cooled to room temperature. The mixture was diluted with water (1 volume), extracted with DCM (4×). The aq. layer was then concentrated in vacuo. The residue was taken up in methanol, and the mixture was filtered. The collected solid was washed with MeOH (4×). The filtrate was concentrated. The residue was treated with a small amount of MeOH, then diluted with DCM. The mixture was filtered, and the filtrate was again concentrated to give 9-chloro-1,2,4,4a,5,6-hexahydro-[1,4]oxazino[4,3-a][1,5]naphthyridine-5-carboxylic acid (96% yield, 80% purity) as a 1:1 mixture of cis and trans diastereomers. The material was used directly in the next step.

Step 2:
9-chloro-1,2,4,4a,5,6-hexahydro-[1,4]oxazino[4,3-a][1,5]naphthyridine-5-carboxylic acid (1:1 cis/trans, 1 equiv) was suspended in THF (4.5 mL), then lithium aluminum hydride (1M in THF, 3 equiv) was added dropwise. The resulting mixture was stirred overnight. In the morning, the mixture was quenched by the slow addition of sodium sulfate decahydrate (3 equiv). After stirring for 40 min, the mixture was filtered through celite with the aid of THF. The filtrate was concentrated, and the residue was purified by chromatography on silica gel (0-10% MeOH/DCM, then 20% MeOH/DCM) to give (9-chloro-1,2,4,4a,5,6-hexahydro-[1,4]oxazino[4,3-a][1,5]naphthyridin-5-yl)methanol (44% yield) as a 1:1 mixture of cis and trans diastereomers. LCMS (m/z) (M+H) 255.0; Rt.=0.58, 0.64 mins.

Synthesis of 9-bromo-1,2,4,4a-tetrahydropyrido[2',3':5,6]pyrazino[2,1-c][1,4]oxazin-5(6H)-one

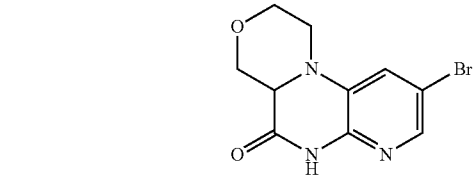

Step 1:

Carbonyldiimidazole (1.5 equiv) was added to a solution of 4-(tert-butoxycarbonyl)morpholine-3-carboxylic acid (1 equiv) in 3:1 DCM/DMF (0.8 M) resulting in bubbling. The resulting mixture was stirred overnight. In the morning, DMF (ca. 1 volume), 3,5-dibromopyridin-2-amine (2 equiv), N,N-diisopropylethylamine (2 equiv), and 1,8-diazabicyclo[5.4.0]undec-7-ene (1 equiv) were added. A reflux condenser was attached, and the flask was heated to 90° C. for 1 h. The mixture was then cooled, diluted with water, and extracted with EtOAc (3×). The combined organic extracts were dried over sodium sulfate, filtered, and concentrated. The residue was purified by chromatography on silica gel (0-40% EtOAc/heptane) to give tert-butyl 3-((3,5-dibromopyridin-2-yl)carbamoyl)morpholine-4-carboxylate (79% yield) as an off-white foam. LCMS (m/z) (M+H)=465.9, Rt=1.33 min.

Step 2:

A flask was charged with tert-butyl 3-((3,5-dibromopyridin-2-yl)carbamoyl)morpholine-4-carboxylate (1 equiv), 2:1 DCM/TFA (0.12 M) (2 pm). The mixture was stirred for 30 min, then concentrated. The residue was concentrated from ether. The residue was diluted with saturated aq. sodium bicarbonate solution and extracted with DCM (3×). The combined organic extracts were dried over sodium sulfate, filtered, and concentrated to give N-(3,5-dibromopyridin-2-yl)morpholine-3-carboxamide (75% yield) as a white solid. LCMS (m/z) (M+H)=365.8, Rt=0.67 min.

Step 3:

A vial was charged with xantphos (0.3 equiv), palladium acetate (0.1 equiv), 1,4-dioxane (0.07 M relative to starting material), and water (0.4 equiv). The vial was sealed and heated to 110° C. for 5 min to give a dark maroon solution. To the cooled solution was then added to a vial containing N-(3,5-dibromopyridin-2-yl)morpholine-3-carboxamide (1 equiv), potassium phosphate (3 equiv, freshly ground), 4-A molecular sieves (50 mg/mL). The vial was sealed and heated to 140° C. for 2 h in a microwave reactor. The mixture was cooled to room temperature, then filtered through celite with the aid of THF. The filtrate was concentrated, and the residue was taken up in 10% MeOH/DCM to give a suspension. The suspension was filtered, and the collected solid was washed with DCM (2×), then dried under a flow of N$_2$ (g) to give 9-bromo-1,2,4,4a-tetrahydropyrido[2',3':5,6]pyrazino[2,1-c][1,4]oxazin-5(6H)-one (13%) of an off-white solid that was 90% pure as assessed by LCMS. LCMS (m/z) (M+H)=283.9, Rt=1.03 min.

Synthesis of 9-bromo-6-ethyl-1,2,4,4a-tetrahydropyrido[2',3':5,6]pyrazino[2,1-c][1,4]oxazin-5(6H)-one

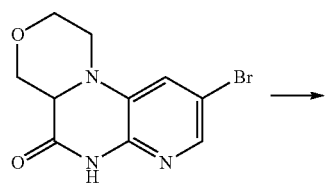

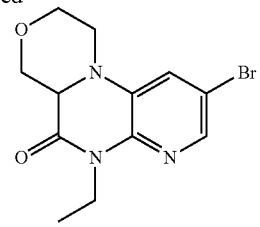

A flask was charged with sodium hydride (60% in mineral oil) (2 equiv) and DMF (0.1 M). 9-Bromo-1,2,4,4a-tetrahydropyrido[2',3':5,6]pyrazino[2,1-c][1,4]oxazin-5(6H)-one (1 equiv) was added. After 25 min, iodoethane (3 equiv) was added. After another 10 min of stirring, the mixture was quenched with saturated aq. ammonium chloride solution and water, then extracted with EtOAc (3×). The combined organic extracts were dried over sodium sulfate, filtered, and concentrated. The residue was purified by chromatography on silica gel (0-30% EtOAc/heptane) to give 9-bromo-6-ethyl-1,2,4,4a-tetrahydropyrido[2',3':5,6]pyrazino[2,1-c][1,4]oxazin-5(6H)-one (89% yield) as a white solid. LCMS (m/z) (M+H) 313.9, Rt=1.42 min.

Synthesis of 2-chloro-6a,7,9,10-tetrahydropyridazino[3',4':5,6]pyrazino[2,1-c][1,4]oxazin-6(5H)-one

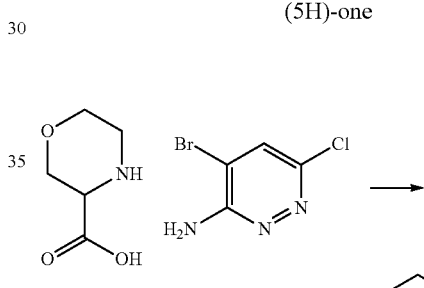

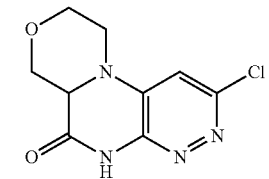

A vial was charged with 4-bromo-6-chloropyridazin-3-amine (1 equiv), morpholine-3-carboxylic acid (1.3 equiv), copper(I) iodide (0.1 equiv), and cesium carbonate (2 equiv). The vial was flushed with N$_2$ (g), then DMSO (0.65 M) was added. The vial was sealed and heated to 130° C. for 3 h. The mixture was cooled, diluted with saturated aq. ammonium chloride solution, extracted with EtOAc (3×), and extracted with DCM (3×). The combined organic extracts were dried over sodium sulfate, filtered, and concentrated. The residue was concentrated from DCM, then taken up in DCM and filtered. The collected solid was washed with DCM (3×) then dried under vacuum to give 2-chloro-6a,7,9,10-tetrahydropyridazino[3',4':5,6]pyrazino[2,1-c][1,4]oxazin-6(5H)-one (23.22% yield) as an off-white solid, with 92% purity as assessed by LCMS and NMR. $^1$H NMR (400 MHz, DMSO-d6) δ ppm 11.69 (s, 1H) 6.99-7.05 (m, 1H) 4.12-4.25 (m, 2H) 3.93 (dd, J=11.62, 3.55 Hz, 1H) 3.75 (dd, J=12.96, 1.96 Hz, 1H) 3.36-3.58 (m, 2H) 2.93-3.02 (m, 1H). LCMS (m/z) (M+H)=214.0, Rt=0.66 min (basic polar method).

Synthesis of 2-chloro-5-ethyl-6a,7,9,10-tetrahydro-pyridazino[3',4':5,6]pyrazino[2,1-c][1,4]oxazin-6(5H)-one and 2-chloro-5,6a-diethyl-6a,7,9,10-tetrahydropyridazino[3',4':5,6]pyrazino[2,1-c][1,4]oxazin-6(5H)-one

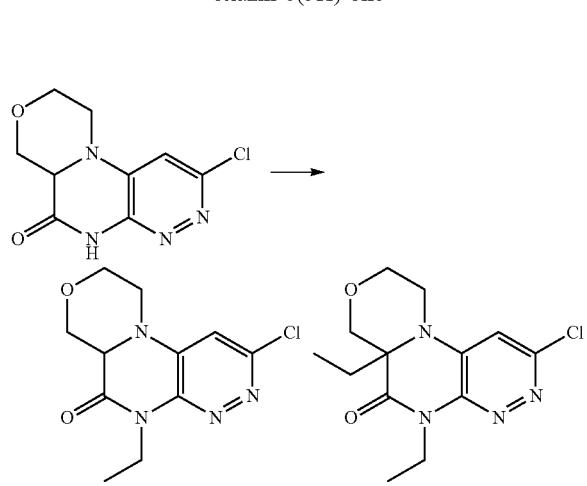

To an opaque mixture of 2-chloro-6a,7,9,10-tetrahydropyridazino[3',4':5,6]pyrazino[2,1-c][1,4]oxazin-6(5H)-one (1 equiv) and DMF (0.2 M) was added sodium hydride (60% in mineral oil, 2 equiv) in one portion. The mixture was stirred for 50 min, then iodoethane (3 equiv) was added dropwise. The mixture was stirred 30 min, quenched with saturated aq. ammonium chloride solution and water, and extracted with EtOAc (3×). The combined organic extracts were dried over sodium sulfate, filtered, and concentrated. The residue was purified by chromatography on silica gel (0-50% EtOAc/heptane) to give 2-chloro-5,6a-diethyl-6a,7,9,10-tetrahydropyridazino[3',4':5,6]pyrazino[2,1-c][1,4]oxazin-6(5H)-one (first eluting peak, 28.2% yield), LCMS (m/z) (M+H)=297.0, Rt=1.15 min and 2-chloro-5-ethyl-6a,7,9,10-tetrahydropyridazino[3',4':5,6]pyrazino[2,1-c][1,4]oxazin-6(5H)-one (second eluting peak, 31.7% yield), LCMS (m/z) (M+H)=269.0, Rt=0.97 min.

Synthesis of 5-chloro-3-fluoro-2-nitropyridine

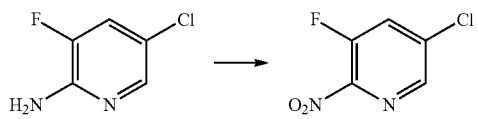 [SMILES: Nc1ncc(Cl)cc1F ; O=[N+]([O-])c1ncc(Cl)cc1F]

A round-bottom flask was charged with 3,5-dichloropyridin-2-amine (1 equiv), sulfuric acid (0.5 M) to give a solution. Potassium persulfate (5 equiv) was added in two portions over 10 min. After stirring for 20 min, a substantial exotherm and gas evolution was observed. The resulting mixture was stirred overnight. The next morning the mixture was poured into crushed ice with the aid of water, then the aq. mixture was treated with solid sodium carbonate until it reached pH 8-10. The aq. mixture was extracted with DCM (3×), and the combined organic extracts were dried over sodium sulfate, filtered, and concentrated. The residue was purified by chromatography on silica gel (0-50% EtOAc/heptane) to give 5-chloro-3-fluoro-2-nitropyridine (31.6% yield) as an off-white solid. LCMS (m/z) (M+H)=176.9, Rt=1.03 min.

Synthesis of 10-chloro-1,2,4a,5-tetrahydro-4H-[1,4]oxazino[4,3-d]pyrido[2,3-b][1,4]diazepin-6(7H)-one

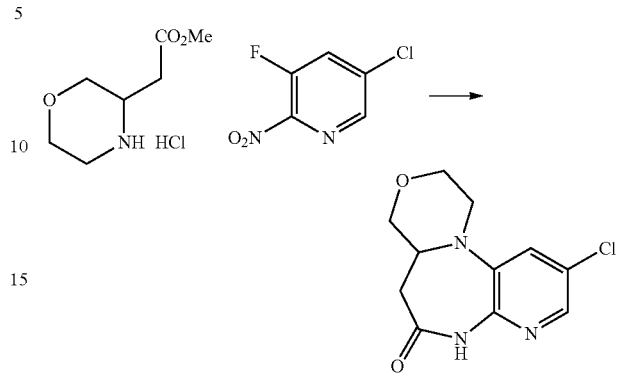

A vial was charged with 5-chloro-3-fluoro-2-nitropyridine (1 equiv), methyl 2-(morpholin-3-yl)acetate hydrochloride (1.1 equiv), DMF (0.4 M), and triethylamine (3 equiv). The vial was sealed and heated to 80° C. for 7 h. The mixture was cooled, then diluted with 1N aq. HCl and extracted with EtOAc (3×). The combined organic extracts were dried over sodium sulfate, filtered, and concentrated. The residue was dissolved in acetic acid (0.2 M). Iron (10 equiv) was added, and the resulting mixture was heated to 110° C. overnight. The mixture was cooled to room temperature, diluted with EtOAc and filtered through celite. The filter pad was washed successively with EtOAc, DCM, and 20% MeOH/DCM. The combined filtrate was concentrated. The residue was suspended between sat. aq. sodium bicarbonate and EtOAc. The layers were separated, and the aq. layer was extracted with EtOAc (4×). The combined organic extracts were dried over sodium sulfate, filtered, and concentrated. The residue was purified by chromatography on silica gel (40-90% EtOAc/heptane) to give 10-chloro-4,4a,5,7-tetrahydro-1H-[1,4]oxazino[4,3-d]pyrido[2,3-b][1,4]diazepin-6(2H)-one (54% yield) as a white solid. $^1$H NMR (400 MHz, DMSO-d6) δ ppm 10.12 (s, 1H) 8.05 (d, J=2.20 Hz, 1H) 7.57 (d, J=2.20 Hz, 1H) 3.75-3.88 (m, 2H) 3.36-3.53 (m, 3H) 3.16-3.29 (m, 1H) 2.96 (br d, J=11.13 Hz, 1H) 2.60-2.69 (m, 1H) 2.02 (d, J=13.69 Hz, 1H). LCMS (m/z) (M+H)=254.0, Rt=0.89 min.

Synthesis of 10-chloro-7-ethyl-1,2,4a,5-tetrahydro-4H-[1,4]oxazino[4,3-d]pyrido[2,3-b][1,4]diazepin-6(7H)-one

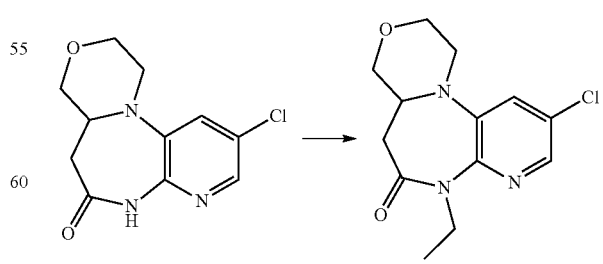

A round-bottom flask was charged with 10-chloro-4,4a,5,7-tetrahydro-1H-[1,4]oxazino[4,3-d]pyrido[2,3-b][1,4]diazepin-6(2H)-one (1 equiv) and DMF (0.15 M) to give a clear, colorless solution. Sodium hydride (60% in mineral oil, 1.3 equiv) was added in one portion. The mixture was stirred for 35 min, then iodoethane (1.2 equiv) was added. The mixture was stirred for an additional 20 min, quenched with sat. aq. ammonium chloride solution, and extracted with EtOAc (3×). The combined organic extracts were concentrated. The residue was purified by chromatography on silica gel (0-40% EtOAc/heptane) to give 10-chloro-7-ethyl-4,4a,5,7-tetrahydro-1H-[1,4]oxazino[4,3-d]pyrido[2,3-b][1,4]diazepin-6(2H)-one (quantitative yield) as an off-white solid. LCMS (m/z) (M+H)=282.1, Rt=1.19 min.

Synthesis of (4-(3,6-dichloropyridazin-4-yl)morpholin-3-yl)methanol

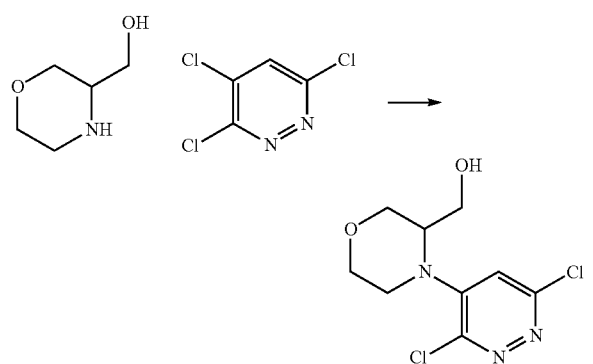

A vial was charged with 2,3,5-trichloropyridine (1 equiv), morpholin-3-ylmethanol (1 equiv), DMF (1 M), and triethylamine (3 equiv). The resulting solution was heated to 90° C. for 8 h, then was cooled to room temperature. The cooled mixture was diluted with saturated. aq. ammonium chloride solution and water, then extracted with EtOAc (4×). The combined organic extracts were washed with brine, dried over sodium sulfate, filtered, and concentrated. The residue was taken up in ether and stirred overnight. In the morning, the mixture was filtered, and the collected solid was washed with ether (2×), then dried under a flow of $N_2$ (g) to give (4-(3,6-dichloropyridazin-4-yl)morpholin-3-yl)methanol (51.9% yield) as a tan solid. $^1$H NMR (400 MHz, DMSO-d6) δ ppm 7.32 (s, 1H) 4.53-4.91 (m, 1H) 4.04-4.24 (m, 1H) 3.73-3.92 (m, 3H) 3.44-3.70 (m, 4H) 3.16 (br d, J=11.49 Hz, 1H). LCMS (m/z) (M+H)=264.2, Rt=0.79 min.

Synthesis of 2-chloro-6a,7,9,10-tetrahydro-6H-[1,4]oxazino[4,3-d]pyridazino[3,4-b][1,4]oxazine

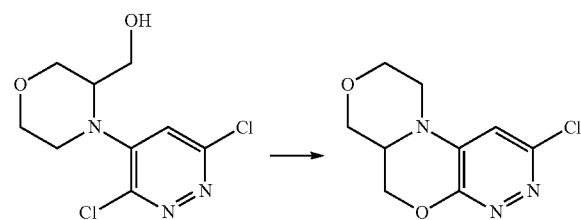 [SMILES: OCC1COCCN1c1cc(Cl)nnc1Cl ; Clc1cc2c(nn1)OCC1COCCN21]

Sodium hydride (60% in mineral oil, 1.5 equiv) was added to a solution of (4-(3,6-dichloropyridazin-4-yl)morpholin-3-yl)methanol (1 equiv) in DMF (0.125 M). The resulting mixture was stirred for 20 min, diluted with saturated. aq. ammonium chloride solution and water, and extracted with EtOAc (3×). The combined organic extracts were dried over sodium sulfate, filtered and concentrated to give 2-chloro-6a,7,9,10-tetrahydro-6H-[1,4]oxazino[4,3-d]pyridazino[3,4-b][1,4]oxazine (quantitative yield) as an oil containing ca. 45 wt % of DMF. The material was used directly. LCMS (m/z) (M+H)=228.1, Rt=0.66 min.

Synthesis of 2-chloro-6,6-dimethyl-6a,7,9,10-tetrahydro-6H-[1,4]oxazino[4,3-d]pyridazino[3,4-b][1,4]oxazine

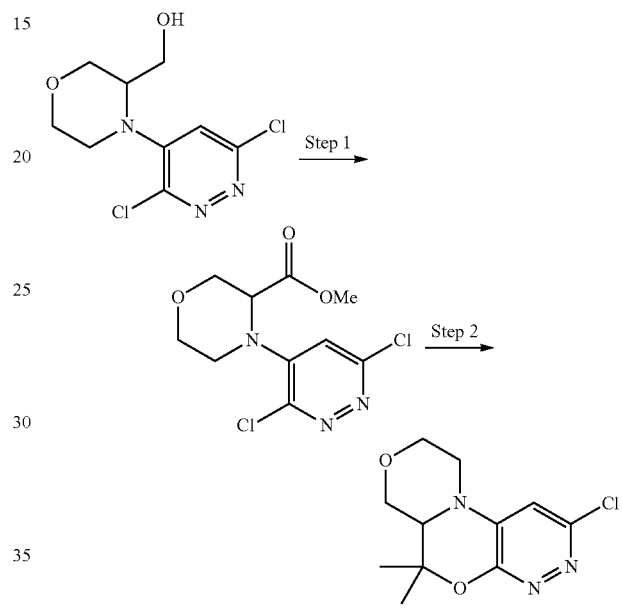

Step 1:

A suspension of (4-(3,6-dichloropyridazin-4-yl)morpholin-3-yl)methanol (1 equiv) in a 3:2:2 mixture of water:acetonitrile:ethyl acetate was treated in sequence with sodium periodate (4 equiv) and ruthenium(III) chloride hydrate (0.1 equiv) were added in sequence, and the resulting mixture was stirred vigorously for 2 h. The reaction mixture was quenched by the addition of EtOH, stirred for 5 min, then diluted with water and extracted with EtOAc (4×). The combined organic extracts were dried over sodium sulfate, filtered, and concentrated. The residue was taken up in 1:1 MeOH/toluene (3 mL). The resulting solution was treated dropwise with TMS-diazomethane (2M in hexanes, 2 equiv). After 2 h, the reaction was quenched with acetic acid and concentrated. The residue was purified by chromatography on silica gel (0-50% EtOAc/heptane) to give methyl 4-(3,6-dichloropyridazin-4-yl)morpholine-3-carboxylate (82.1 mg, 0.281 mmol, 52.1% yield) as a light-yellow oil. LCMS (m/z) (M+H)=292.0, Rt=1.05 min.

Step 2:

A vial charged with methyl 4-(3,6-dichloropyridazin-4-yl)morpholine-3-carboxylate (1 equiv) and THF (0.1 M) to give a solution. Methylmagnesium bromide (3M in ether, 10 equiv) was added dropwise. The mixture was stirred for 30 min, then was quenched by the careful addition of saturated aq. ammonium chloride solution. The mixture was diluted with water and extracted with EtOAc (3×). The combined organic extracts were dried over sodium sulfate, filtered, and concentrated to give crude 2-(4-(3,6-dichloropyridazin-4-yl)

morpholin-3-yl)propan-2-ol as a brown oil. This material was dissolved in DMF (0.1 M) and treated with sodium hydride (60% in mineral oil, 1.5 equiv) in one portion. The mixture was stirred for 4 h at room temperature, then was diluted with saturated aq. ammonium chloride and water and extracted with EtOAc (3×). The combined organic extracts were dried over sodium sulfate, filtered, and concentrated. The residue was purified by chromatography on silica gel (50-100% EtOAc/heptane) to give 2-chloro-6,6-dimethyl-6a,7,9,10-tetrahydro-6H-[1,4]oxazino[4,3-d]pyridazino[3,4-b][1,4]oxazine (82% yield) as a yellow oil. LCMS (m/z) (M+H)=256.0, Rt=0.85 min.

Synthesis of 9-chloro-5-fluoro-1,2,4,4a,5,6-hexahydro-[1,4]oxazino[4,3-a][1,5]naphthyridin-6-ol

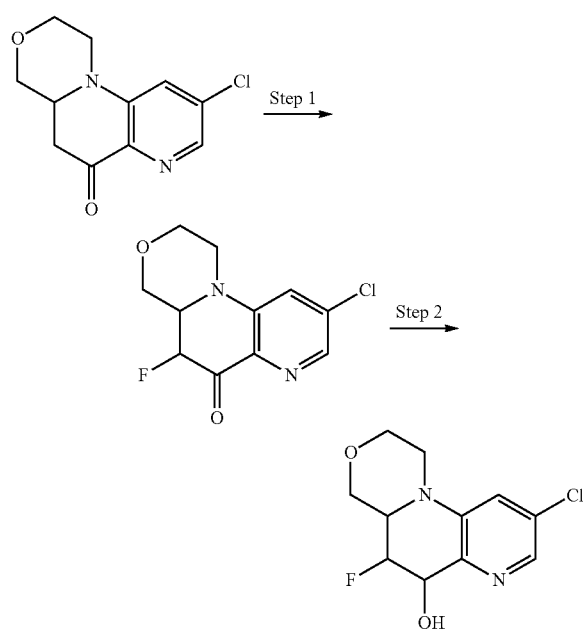

Step 1:
9-chloro-1,2,4a,5-tetrahydro-[1,4]oxazino[4,3-a][1,5]naphthyridin-6(4H)-one (1 equiv) was dissolved in THF (0.2 M) and the partial solution was cooled in a dry ice-acetone bath. Lithium diisopropylamide (2M in THF/heptane/ethylbenzene, 1.1 equiv) was added dropwise. The flask was transferred to an ice-water bath for 40 min, then re-cooled in a dry ice-acetone bath. A solution of N-fluorobenzenesulfonimide (1.3 equiv) in THF was added dropwise. The mixture was stirred for 2 h, then the flask was warmed to −40° C. for 30 min, then warmed to room temperature. The reaction mixture was diluted with saturated aq. sodium bicarbonate solution and extracted with EtOAc (3×). The combined organic extracts were dried over sodium sulfate, filtered, and concentrated. The residue was purified by chromatography on silica gel (10-60% EtOAc/heptane) to give 9-chloro-5-fluoro-1,2,4a,5-tetrahydro-[1,4]oxazino[4,3-a][1,5]naphthyridin-6(4H)-one (14.73% yield) as a yellow solid. LCMS indicated an 8:1 mixture of diastereomers. LCMS (m/z) (M+H)=257.3, Rt=0.88 min.

Step 2:
9-chloro-5-fluoro-1,2,4a,5-tetrahydro-[1,4]oxazino[4,3-a][1,5]naphthyridin-6(4H)-one (1 equiv) was dissolved in MeOH (0.1 M). The resulting solution was cooled in an ice-water bath and NaBH₄ (6.49 mg, 0.171 mmol) was added. The resulting mixture was stirred for 45 min, then the reaction was quenched by the addition of acetone and saturated aq. ammonium chloride solution. The mixture was partitioned between EtOAc and water, and the aqueous phase was separated and washed with EtOAc (2×). The combined organics were dried over sodium sulfate, filtered and concentrated to give 9-chloro-5-fluoro-1,2,4,4a,5,6-hexahydro-[1,4]oxazino[4,3-a][1,5]naphthyridin-6-ol as a light yellow solid. LCMS (m/z) (M+H)=259.2, Rt=0.85 min.

Synthesis of 9-bromo-6,6-difluoro-1,2,4,4a,5,6-hexahydro-[1,4]oxazino[4,3-a][1,5]naphthyridine

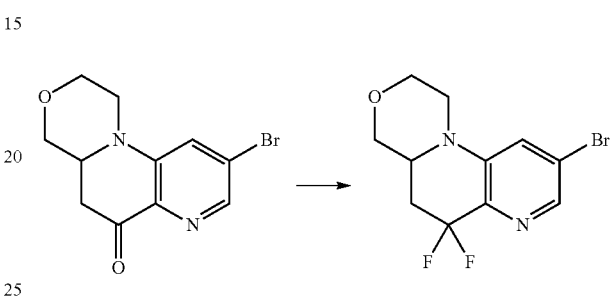

A round-bottom flask was charged with 9-bromo-1,2,4a,5-tetrahydro-[1,4]oxazino[4,3-a][1,5]naphthyridin-6(4H)-one (1 equiv), DCM (0.1 M), Deoxo-Fluor (3 equiv) and ethanol (0.1 equiv). The resulting mixture was stirred for 3 d, then diluted with saturated. aq. sodium bicarbonate solution and extracted with DCM (3×). The combined organic extracts were dried over sodium sulfate, filtered, and concentrated. The residue was purified by chromatography on silica gel (40-90% EtOAc/heptane) to give 9-bromo-6,6-difluoro-1,2,4,4a,5,6-hexahydro-[1,4]oxazino[4,3-a][1,5] naphthyridine (27.5% yield) as an off-white solid (top spot) as well as recovered starting material (35-40%). LCMS (m/z) (M+H)=304.9, Rt=1.24 min.

Synthesis of (9-chloro-1,2,4,4a,5,6-hexahydro-[1,4]oxazino[4,3-a][1,5]naphthyridine-5,5-diyl)dimethanol

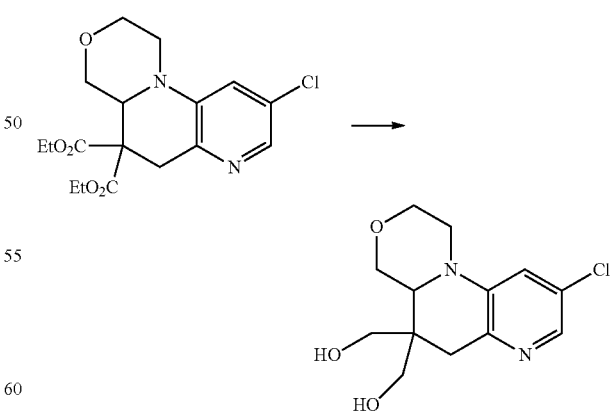

Diethyl 9-chloro-1,2,4,4a-tetrahydro-[1,4]oxazino[4,3-a][1,5]naphthyridine-5,5(6H)-dicarboxylate (1 equiv) was dissolved in DCM (0.2 M) and the reaction was cooled to −78° C. DIBAL-H (1 M in THF, 10 equiv) was added slowly and the reaction was stirred at −78° C. for 5 minutes. The reaction was taken out of the acetone/dry ice bath and then stirred at room temperature for 45 minutes before quenching with the addition of saturated Rochelle's salt solution. After gas evolution had stopped, DCM was added and the reaction was stirred at room temperature overnight. The layers were separated and the aqueous layer was washed three times with DCM, the combined organics were washed with brine, dried over MgSO₄, filtered and concentrated. The residue was purified by chromatography on silica gel (0-20% MeOH/DCM) and the resulting material was dried under high vacuum for 45 minutes to give (9-chloro-1,2,4,4a,5,6-hexahydro-[1,4]oxazino[4,3-a][1,5]naphthyridine-5,5-diyl) dimethanol (40% yield) as a white solid. $^1$H NMR (400 MHz, DMSO-d6) δ ppm 7.79 (d, J=2.0 Hz, 1H), 7.31 (d, J=2.0 Hz, 1H), 4.68 (br s, 1H), 4.57 (br s, 1H), 3.95 (dd, J=11.2, 2.8 Hz, 1H), 3.85 (d, J=12.3 Hz, 1H), 3.77 (dd, J=11.5, 3.1 Hz, 1H), 3.42 (t, J=11.0 Hz, 4H), 3.25 (dd, J=10.8, 2.9 Hz, 2H), 2.93 (td, J=12.6, 3.5 Hz, 1H), 2.61 (m, 3H). LCMS (m/z) (M+H)=285.2, Rt=0.55 min.

Synthesis of 9-chloro-2,4,4a,6-tetrahydro-1H-spiro[[1,4]oxazino[4,3-a][1,5]naphthyridine-5,3'-oxetane]

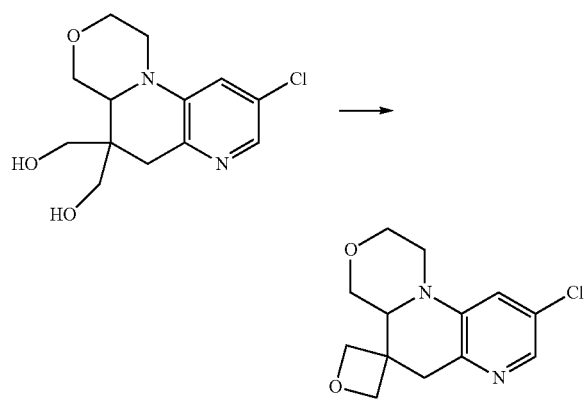

(9-chloro-1,2,4,4a,5,6-hexahydro-[1,4]oxazino[4,3-a][1,5]naphthyridine-5,5-diyl)dimethanol (1 equiv) was dissolved in THF (0.15 M) and the solution was cooled to 0° C. Then, butyllithium (2.5 M in hexanes, 1.1 equiv) was added dropwise and stirred for 20 minutes. A solution of p-toluenesulfonyl chloride (1 equiv) in THF was added and the mixture was stirred at 0° C. for 1 hour. Butyllithium (2.5 M in hexanes, 1.1 equiv) was added and the reaction was heated overnight at 60° C. The reaction was allowed to cool to room temperature, quenched with the addition of water and partitioned between EtOAc and water. The aqueous phase was washed with EtOAc, the combined organics were washed with brine, dried over magnesium sulfate, filtered and concentrated under reduced pressure. The residue was purified by chromatography on silica gel (0-10% MeOH/DCM) and the resulting material was dried under high vacuum overnight to give 9-chloro-2,4,4a,6-tetrahydro-1H-spiro[[1,4]oxazino[4,3-a][1,5]naphthyridine-5,3'-oxetane] (43.2% yield) as a brown solid. $^1$H NMR (400 MHz, DMSO-d6) δ ppm 7.83 (d, J=2.0 Hz, 1H), 7.33 (d, J=2.0 Hz, 1H), 4.54 (d, J=6.3 Hz, 1H), 4.49 (d, J=6.4 Hz, 1H), 4.26 (dd, J=12.8, 6.4 Hz, 2H), 4.17 (dd, J=11.2, 3.0 Hz, 1H), 3.84 (m, 2H), 3.61 (t, J=11.0 Hz, 1H), 3.52 (td, J=11.6, 2.5 Hz, 1H), 3.45 (dd, J=10.8, 3.1 Hz, 1H), 3.11 (s, 2H), 2.95 (td, J=12.4, 3.4 Hz, 1H). LCMS (m/z) (M+H)=267.3, Rt=0.77 min.

Synthesis of 9-chloro-1,2,4a,5-tetrahydro-[1,4]oxazino[4,3-a][1,5]naphthyridin-6(4H)-one

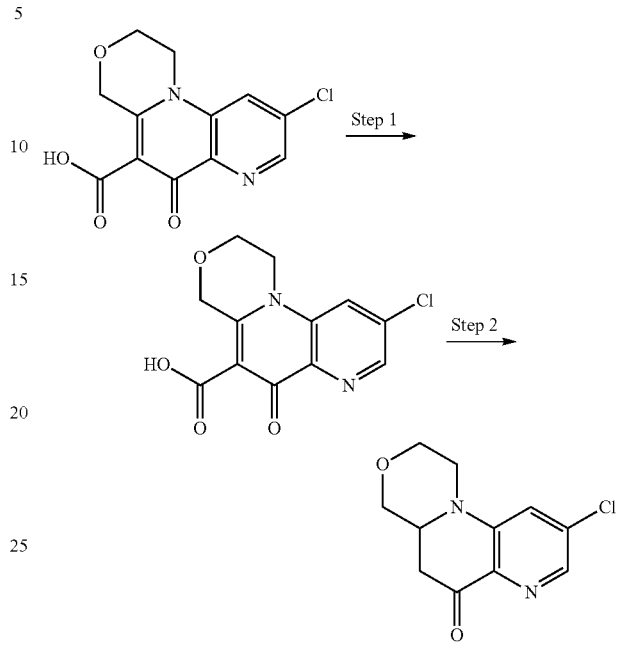

Step 1:

Ethyl 9-chloro-6-oxo-1,2,4,6-tetrahydro-[1,4]oxazino[4,3-a][1,5]naphthyridine-5-carboxylate (1 equiv) was suspended in water and acetic acid (0.2 M. Ratio 1:1.4). Sulfuric acid (6.5 equiv) was added to give a solution, which was heated at 110° C. for 3.5 hours. As the reaction progressed, a solid precipitated out of solution. The reaction was cooled down to room temperature, and then cooled further in an ice bath for 10 minutes. The precipitate was filtered off, the solid was washed with water and dried under a flow of N₂ over the weekend to give 9-chloro-6-oxo-1,2,4,6-tetrahydro-[1,4]oxazino[4,3-a][1,5]naphthyridine-5-carboxylic acid (80% yield) as a tan solid. $^1$H NMR (400 MHz, DMSO-d6) δ ppm 9.00 (d, J=1.9 Hz, 1H), 8.76 (d, J=2.0 Hz, 1H), 5.38 (s, 2H), 4.39 (t, J=5.4 Hz, 2H), 4.16 (t, J=5.4 Hz, 2H). Singal for carboxylic acid proton isn't observed. LCMS (m/z) (M+H)=281.2, Rt=0.72 min.

Step 2:

9-chloro-6-oxo-1,2,4,6-tetrahydro-[1,4]oxazino[4,3-a][1,5]naphthyridine-5-carboxylic acid (1 equiv) was suspended in MeOH (0.1 M) and then sodium borohydride (3.5 equiv) was added portion-wise. After complete addition, p-toluenesulfonic acid monohydrate (0.1 equiv) was added and the reaction was heated at 70° C. for 1 hour. The reaction was quenched by the addition of acetone and then concentrated. The residue was diluted with EtOAc and sonicated, water was added and the organic layer was separated and dried over magnesium sulfate, filtered and concentrated. The resulting solid was dried under high vacuum for 30 minutes to give 9-chloro-1,2,4a,5-tetrahydro-[1,4]oxazino[4,3-a][1,5]naphthyridin-6(4H)-one (80% yield) as a yellow solid. $^1$H NMR (400 MHz, DMSO-d6) δ ppm 8.11 (d, J=1.9 Hz, 1H), 7.76 (d, J=1.9 Hz, 1H), 4.02 (dd, J=11.7, 3.7 Hz, 1H), 3.93 (dd, J=11.7, 3.1 Hz, 1H), 3.82 (m, 1H), 3.63 (td, J=11.9, 2.8 Hz, 1H), 3.54 (m, 1H), 3.36 (t, J=11.2 Hz, 1H), 2.82 (td, J=12.2, 3.8 Hz, 1H), 2.59 (s, 1H), 2.56 (d, J=2.1 Hz, 1H). LCMS (m/z) (M+H)=239.2, Rt=0.85 min.

Synthesis of cis-9-chloro-5,5-dimethyl-1,2,4,4a,5,6-hexahydro-[1,4]oxazino[4,3-a][1,5]naphthyridin-6-ol Synthesis of cis-9-chloro-5,5-difluoro-1,2,4,4a,5,6-hexahydro-[1,4]oxazino[4,3-a][1,5]naphthyridin-6-ol

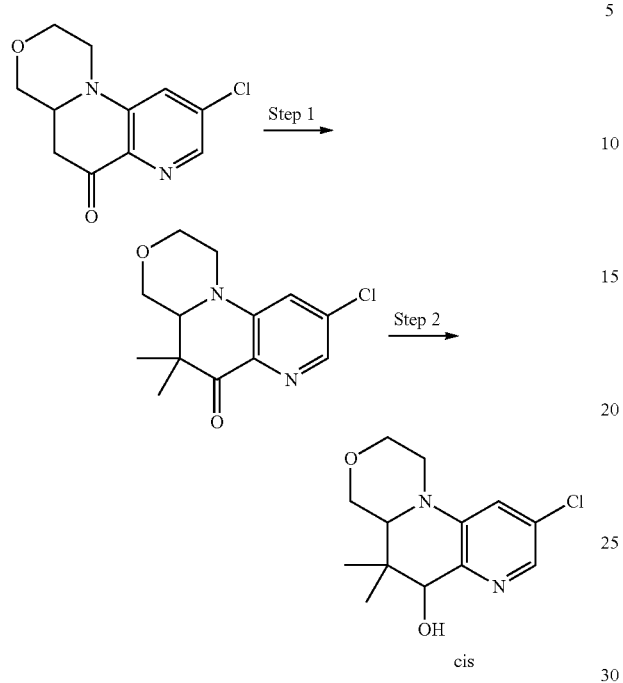

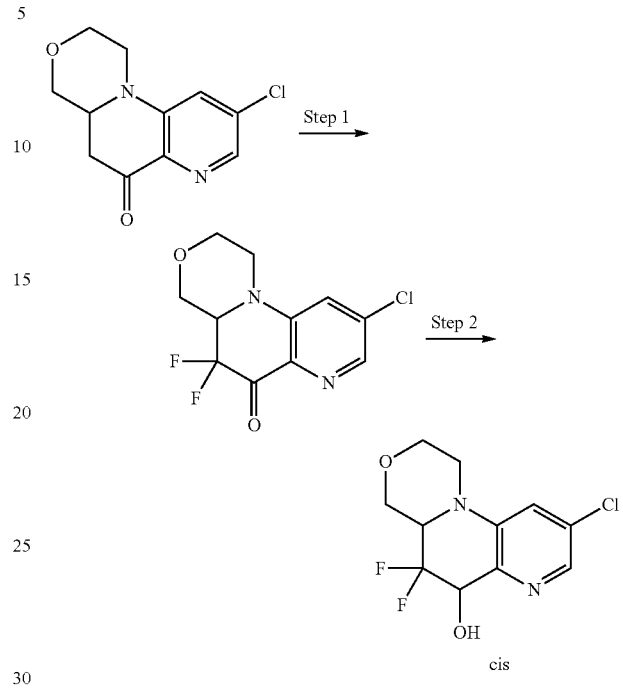

Step 1:
9-chloro-1,2,4a,5-tetrahydro-[1,4]oxazino[4,3-a][1,5]naphthyridin-6(4H)-one (1 equiv) was dissolved in THF (0.2 M) and the solution was cooled to 0° C. and sodium hydride (60% in mineral oil, 2.5 equiv) was added. The reaction was stirred at 0° C. for 30 minutes, iodomethane (2.5 equiv) was added and the reaction was stirred at room temperature for 45 minutes. The reaction was quenched by the addition of acetone and saturated ammonium chloride solution. The reaction was partitioned between EtOAc and water, the aqueous phase was separated and washed with EtOAc. The combined organics were washed with brine, dried over magnesium sulfate, concentrated and dried under high vacuum overnight to give 9-chloro-5,5-dimethyl-1,2,4a,5-tetrahydro-[1,4]oxazino[4,3-a][1,5]naphthyridin-6(4H)-one as a green film, which was used in the next step without further purification. LCMS (m/z) (M+H)=267.2, Rt=1.03 min.

Step 2:
9-chloro-5,5-dimethyl-1,2,4a,5-tetrahydro-[1,4]oxazino[4,3-a][1,5]naphthyridin-6(4H)-one (1 equiv) was dissolved in MeOH (0.2 M) and cooled in an ice bath, sodium borohydride (2 equiv) was added. After stirring at 0° C. for 5 minutes, the reaction was taken out of the ice bath and stirred at room temperature for 45 minutes. The reaction was quenched by the addition of acetone and saturated ammonium chloride solution. The reaction was partitioned between EtOAc and water, the aqueous phase was separated and washed with EtOAc. The combined organics were washed with brine, dried over magnesium sulfate and concentrated. The residue was purified by chromatography on silica gel (0-50% EtOAc/heptane) and the resulting material was dried under high vacuum for 1 hour to give cis-9-chloro-5,5-dimethyl-1,2,4,4a,5,6-hexahydro-[1,4]oxazino[4,3-a][1,5]naphthyridin-6-ol (61.4% yield) as a pale yellow film. LCMS (m/z) (M+H)=269.2, Rt=0.81 min.

Step 1:
9-chloro-1,2,4a,5-tetrahydro-[1,4]oxazino[4,3-a][1,5]naphthyridin-6(4H)-one (1 equiv) was dissolved in THF (0.15 M), sodium hydride (60% in mineral oil, 3 equiv) was added and the reaction was stirred at room temperature for 20 minutes. N-fluorobenzenesulfonimide (2 equiv) was added and the reaction was stirred at room temperature for 1 hour. The reaction was quenched by the addition of saturated ammonium chloride solution and was partitioned between EtOAc and water. The aqueous phase was washed with EtOAc, the combined organics were washed with saturated sodium bicarbonate solution, brine, dried over magnesium sulfate, filtered and concentrated. The resulting material was transferred to a pre-tared vial with DCM/MeOH and the solvent was concentrated and dried under high vacuum overnight to give 9-chloro-5,5-difluoro-1,2,4a,5-tetrahydro-[1,4]oxazino[4,3-a][1,5]naphthyridin-6(4H)-one as a brown oil, which was used in the next step without further purification. LCMS (m/z) (M+H)=275.2, Rt=1.07 min.

Step 2:
9-chloro-5,5-difluoro-1,2,4a,5-tetrahydro-[1,4]oxazino[4,3-a][1,5]naphthyridin-6(4H)-one (1 equiv) was dissolved in MeOH (0.2 M) and cooled in an ice bath, sodium borohydride (2 equiv) was added. After ten minutes stirring at 0° C., the reaction was taken out of the ice bath and stirred at room temperature for 1.5 hours. The reaction was quenched by the addition of acetone and saturated ammonium chloride solution. The reaction was partitioned between EtOAc and water, the aqueous phase was separated and washed with EtOAc. The combined organics were washed with brine, dried over magnesium sulfate and concentrated. The residue was purified by chromatography on silica gel (0-50% EtOAc/heptane) and the resulting material was dried under high vacuum for 30 minutes to give cis-9-chloro-5,5-difluoro-1,2,4,4a,5,6-hexahydro-[1,4]oxazino[4,3-a][1,5]naphthyridin-6-ol (57% yield) as a yellow solid. ¹H NMR (400 MHz, DMSO-d6) δ ppm 8.03 (d, J=1.7 Hz, 1H), 7.46 (d, J=1.6 Hz, 1H), 6.24 (br s, 1H), 4.89 (dd, J=19.6, 8.6 Hz, 1H), 4.06 (dd, J=11.0, 2.8 Hz, 1H), 3.94 (dd, J=11.6, 3.1 Hz, 1H), 3.80 (m, 2H), 3.65 (t, J=10.9 Hz, 1H), 3.54 (td, J=11.9, 2.6 Hz, 1H), 2.88 (td, J=12.1, 3.4 Hz, 1H). LCMS (m/z) (M+H)=277.0, Rt=0.96 min.

Synthesis of cis-9-chloro-6-(trifluoromethyl)-1,2,4,4a,5,6-hexahydro-[1,4]oxazino[4,3-a][1,5]naphthyridin-6-ol

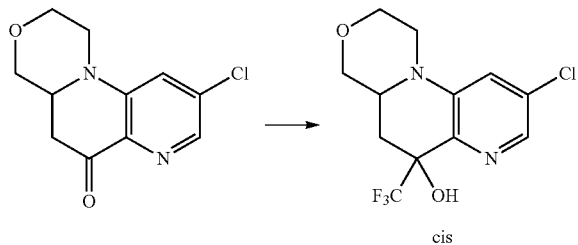 [SMILES: O=C1CC2COCCN2c2cc(Cl)cnc21 ; OC1(C(F)(F)F)CC2COCCN2c2cc(Cl)cnc21]

9-chloro-1,2,4a,5-tetrahydro-[1,4]oxazino[4,3-a][1,5] naphthyridin-6(4H)-one (1 equiv) was suspended in THF (0.2 M). Trimethyl(trifluoromethyl)silane (2M in THF) (2 equiv) was added, followed by cesium fluoride (0.1 equiv). The reaction was stirred at room temperature for 1.5 hours. 1M HCl (1 ml) was added and the reaction was stirred at room temperature overnight. The reaction was partitioned between EtOAc and water, the organic phase was washed with brine, dried over magnesium sulfate, filtered and concentrated. The residue was purified by chromatography on silica gel (0-30% EtOAc/heptane) and the resulting material was dried under high vacuum for 45 minutes to give cis-9-chloro-6-(trifluoromethyl)-1,2,4,4a,5,6-hexahydro-[1,4]oxazino[4,3-a][1,5]naphthyridin-6-ol acid (61% yield) as a pale pink solid. ¹H NMR (400 MHz, DMSO-d₆) δ ppm 7.97 (d, J=1.8 Hz, 1H), 7.49 (d, J=1.8 Hz, 1H), 6.48 (s, 1H), 3.94 (d, J=11.4 Hz, 2H), 3.85 (d, J=11.5 Hz, 1H), 3.52 (td, J=11.7, 2.6 Hz, 1H), 3.20 (m, 2H), 2.81 (td, J=12.3, 3.5 Hz, 1H), 2.36 (dd, J=14.2, 2.7 Hz, 1H), 1.74 (t, J=12.8 Hz, 1H). LCMS (m/z) (M+H)=309.0, Rt=1.33 min.

Synthesis of 9-bromo-1,2,4,4a,5,6-hexahydro-[1,4]oxazino[4,3-a][1,5]naphthyridin-6-amine

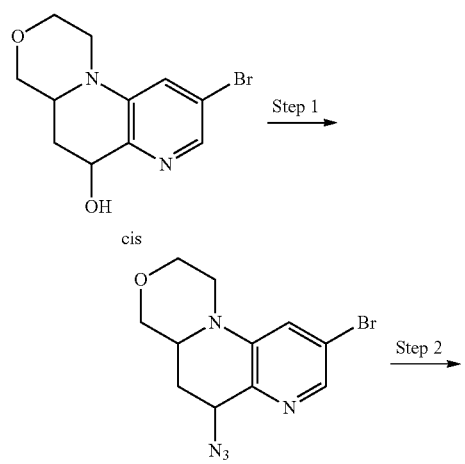

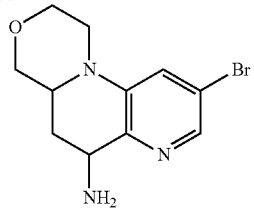

Step 1:

cis-9-bromo-1,2,4,4a,5,6-hexahydro-[1,4]oxazino[4,3-a][1,5]naphthyridin-6-ol was dissolved in toluene (0.2 M) and cooled to 0° C. Diphenylphosphoryl azide (1.5 equiv) and 1,8-Diazabicycloundec-7-ene (1.2 equiv) were added and the reaction was taken out of the ice bath and stirred overnight at room temperature. The reaction was concentrated under reduced pressure and partitioned between EtOAc and saturated sodium bicarbonate solution. The aqueous phase was washed with EtOAc, the combined organics were washed with brine, dried over magnesium sulfate, filtered and concentrated. The resulting material was dried under high vacuum for 30 minutes to give 6-azido-9-bromo-1,2,4,4a,5,6-hexahydro-[1,4]oxazino[4,3-a][1,5]naphthyridine as a brown oil, which was used in the next step without purification. LCMS (m/z) (M+H)=312.2, Rt=1.33 min.

Step 2:

6-azido-9-bromo-1,2,4,4a,5,6-hexahydro-[1,4]oxazino[4,3-a][1,5]naphthyridine (1 equiv) was dissolved in THF/H₂O (0.2 M. Ratio 10:1). Triphenylphosphine was added and the reaction was stirred at room temperature overnight. The reaction was concentrated under reduced pressure, toluene was added and then concentrated under reduced pressure. Et₂O was added and the precipitate was removed by filtration. The resulting material was purified by chromatography on silica gel (0-20% MeOH/DCM) and the resulting material was dried under high vacuum for 30 minutes to give 9-bromo-1,2,4,4a,5,6-hexahydro-[1,4]oxazino[4,3-a][1,5] naphthyridin-6-amine (32% yield) as a brown oil. LCMS (m/z) (M+H)=284.1, Rt=0.69 min.

Synthesis of 9-chloro-N-methyl-1,2,4,4a,5,6-hexahydro-[1,4]oxazino[4,3-a][1,5]naphthyridine-5-carboxamide

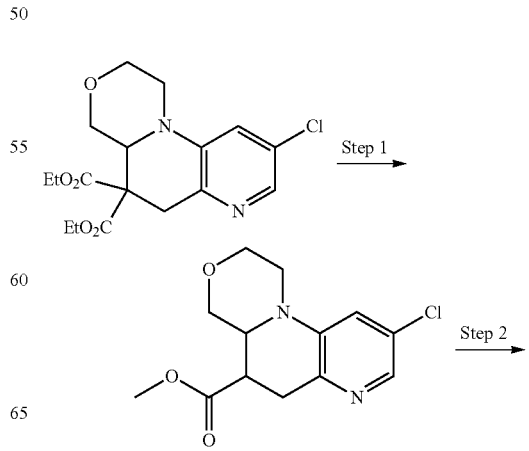

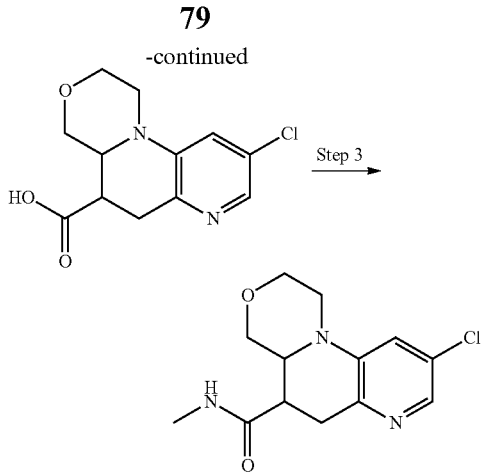

Step 1:

Diethyl 9-chloro-1,2,4,4a-tetrahydro-[1,4]oxazino[4,3-a][1,5]naphthyridine-5,5(6H)-dicarboxylate (1 equiv) was suspended in water and acetic acid (0.2 M. Ratio 1:1.4), sulfuric acid (10 equiv) was added resulting in a solution. The reaction was heated in a sealed vial for 6 hours and allowed to cool to room temperature overnight. The reaction was concentrated and the residue was taken up in MeOH, the solvent was concentrated under reduced pressure and the residue was partitioned between DCM and water, the aqueous layer was washed with DCM three times. The combined organics were washed with brine, dried over magnesium sulfate and concentrated. The resulting material was dried under high vacuum for 1 hour to give methyl 9-chloro-1,2,4,4a,5,6-hexahydro-[1,4]oxazino[4,3-a][1,5]naphthyridine-5-carboxylate as a brown oil, which was taken forward to the next step without further purification. LCMS (m/z) (M+H)=283.3, Rt=0.80 and 0.94 min. LCMS indicates approximately 1:1 mixture of diastereomers.

Step 2:

Methyl 9-chloro-1,2,4,4a,5,6-hexahydro-[1,4]oxazino[4,3-a][1,5]naphthyridine-5-carboxylate (1 equiv) was dissolved in THF/MeOH (0.2 M. Ratio 1:1). Lithium hydroxide (1 M aqueous solution, 2.5 equiv) was added and the reaction was stirred at room temperature for 1.5 hours. The reaction was concentrated and partitioned between EtOAc and water. The aqueous phase was acidified to pH 2-3 using 1M HCl, then partitioned between EtOAc and water. The organic phase was separated and the aqueous phase was washed with EtOAc, the combined organics were washed with brine and dried over magnesium sulfate. The solvent was concentrated and the resulting material was dried under high vacuum overnight to give 9-chloro-1,2,4,4a,5,6-hexahydro-[1,4]oxazino[4,3-a][1,5]naphthyridine-5-carboxylic acid as a cream solid, which was taken forward to the next step without further purification. $^1$H NMR (400 MHz, DMSO-$d_6$) δ ppm 12.77 (br s, 1H), 7.83 (d, J=1.9 Hz, 1H), 7.32 (d, J=1.8 Hz, 1H), 3.87 (q, J=11.0, 9.7 Hz, 2H), 3.76 (d, J=12.4 Hz, 1H), 3.49 (m, 2H), 3.24 (m, 1H), 2.94 (m, 3H), 2.63 (m, 1H). LCMS (m/z) (M+H)=269.1, Rt=0.76 min.

Step 3:

9-chloro-1,2,4,4a,5,6-hexahydro-[1,4]oxazino[4,3-a][1,5]naphthyridine-5-carboxylic acid (1 equiv) was suspended in DMF (0.2 M). EDC.HCl (1.2 equiv) and HOAt (1.2 equiv) was added, followed by methylamine (2.0 M in THF, 3 equiv) to give a solution. The reaction was stirred at room temperature for 2 hours, another portion of methylamine (2.0 M in THF, 3 equiv) was added and the reaction was stirred at room temperature for 1 hour. The reaction was partitioned between EtOAc and water, the organic phase was washed three times with water. The combined organics were then washed with brine, dried over magnesium sulfate, filtered and concentrated to give a solid. The solid was dried under high vacuum over the weekend to give trans-9-chloro-N-methyl-1,2,4,4a,5,6-hexahydro-[1,4]oxazino[4,3-a][1,5]naphthyridine-5-carboxamide (75% yield) as a cream solid. $^1$H NMR (400 MHz, DMSO-$d_6$) δ ppm 8.10 (d, J=4.0 Hz, 1H), 7.82 (d, J=2.0 Hz, 1H), 7.32 (d, J=2.0 Hz, 1H), 3.92 (d, J=8.1 Hz, 1H), 3.74 (m, 2H), 3.50 (td, J=12.0, 3.0 Hz, 1H), 3.15 (m, 2H), 2.94 (m, 1H), 2.83 (m, 3H), 2.62 (d, J=4.6 Hz, 3H). LCMS (m/z) (M+H)=282.2, Rt=0.52 and 0.65 min. LCMS indicates presence of two diastereomers, 85% major at 0.65 min and 15% minor at 0.52 mins.

9-chloro-1,2,4a,5-tetrahydro-[1,4]oxazino[4,3-a][1,5]naphthyridin-6(4H)-one

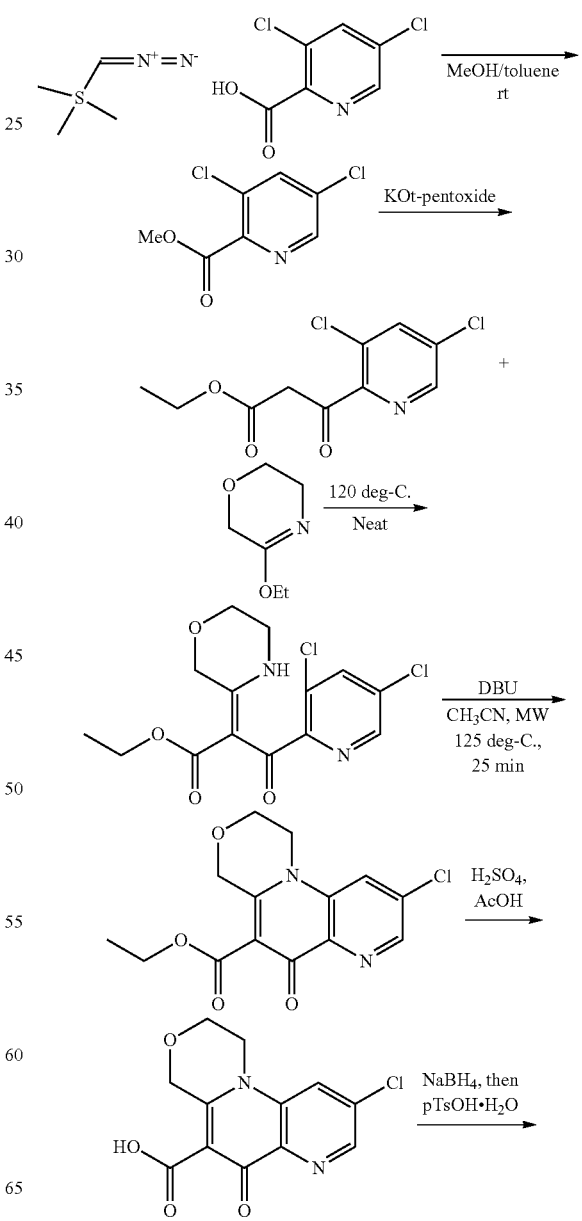

-continued

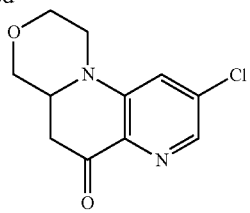

Step 1:

3,5-dichloropicolinic acid (1.0 equiv.) was dissolved in 5:1 toluene: methanol (0.5 M) and then TMS-diazomethane (1.2 equiv.) was added dropwise. The reaction mixture was agitated at room temperature for 1 h and quenched by addition of glacial acetic acid drop-wise until the effervescence had subsided and concentrated in vacuo and the residue was triturated with heptane and the dark brown precipitate methyl 3,5-dichloropicolinate was collected by filtration. LCMS (m/z) (M+H)=205.9, Rt=1.18 min.

Step 2:

Into a flask was charged methyl 3,5-dichloropicolinate (1.0 equiv.) and EtOAc (0.5M) and the mixture was cooled in an ice-bath. To the mixture was added potassium tert-pentoxide (2.0 M in THF) (1.2 equiv.) over 10 min during which the mixture turned turbid orange and the mixture lifted from the cooling bath. After 10 min, LCMS indicated formation of desired product as major species along with hydrolyzed SM (minor species). The reaction mixture was quenched by addition of sat'd NH4Cl and extracted with EtOAc. The organic layer was separated and dried (MgSO4), filtered and concentrated in vacuo and the residue purified by flash chromatography (0-30% EtOAc/heptane) to afford the desired product ethyl 3-(3,5-dichloropyridin-2-yl)-3-oxopropanoate as an orange oil. $^1$H NMR (400 MHz, CHLOROFORM-d) δ ppm 8.46-8.68 (m, 1H) 7.72-8.06 (m, 1H) 4.19 (q, J=7.13 Hz, 2H) 4.13 (s, 2H) 1.25 (t, J=7.09 Hz, 3H); LCMS (m/z) (M+H)=263.8, Rt=1.08 min.

Step 3:

ethyl 3-(3,5-dichloropyridin-2-yl)-3-oxopropanoate (1.0 equiv.) and 5-ethoxy-3,6-dihydro-2H-1,4-oxazine (2.0 equiv.) were combined in a 40 mL vial and heated at 120° C. for 96 h. The reaction mixture was cooled to room temperature and directly loaded onto 300 gram silica cartridge and purified by flash chromatography (0-100% EtOAc) affording product (E)-ethyl 3-(3,5-dichloropyridin-2-yl)-2-(morpholin-3-ylidene)-3-oxopropanoate in 71% isolated yield. LCMS (m/z) (M+H)=345.0, Rt=1.28 min.

Step 4:

Into a MW vial were charged product (E)-ethyl 3-(3,5-dichloropyridin-2-yl)-2-(morpholin-3-ylidene)-3-oxopropanoate (1.0 equiv.) and ACN (0.5 M). To the mixture was added DBU (2.0 equiv.) and the reaction was agitated at 120° C. in microwave for 25 min. LCMS of the crude mixture indicated formation of desired product as the major species. The reaction mixture was concentrated in vacuo and the residue directly purified by flash chromatography (0-10% MeOH/DCM) to afford the desired product ethyl 9-chloro-6-oxo-1,2,4,6-tetrahydro-[1,4]oxazino[4,3-a][1,5]naphthyridine-5-carboxylate in 49% isolated yield. LCMS (m/z) (M+H)=309.0, Rt=0.85 min.

Step 5:

Ethyl 9-chloro-6-oxo-1,2,4,6-tetrahydro-[1,4]oxazino[4,3-a][1,5]naphthyridine-5-carboxylate (1.0 equiv.) was suspended in Water and Acetic Acid (4:1, 0.2 M) and conc. sulfuric acid (6.5 equiv.) was added to give a solution. The reaction was heated at 110° C. for 3.5 hours. As the reaction progressed, a solid precipitated out reaction. The reaction mixture was cooled to room temperature and the solid was collected by suction filtration and air-dried under vacuum overnight to afford the desired product 9-chloro-6-oxo-1,2,4,6-tetrahydro-[1,4]oxazino[4,3-a][1,5]naphthyridine-5-carboxylic acid in 80% isolated yield. LCMS (m/z) (M+H)=280.9, Rt=0.74 min.

Step 6:

9-chloro-6-oxo-1,2,4,6-tetrahydro-[1,4]oxazino[4,3-a][1,5]naphthyridine-5-carboxylic acid (1.0 equiv.) was suspended in MeOH (0.08 M) and then NaBH4 (3.46 equiv.) was carefully added portion-wise. After complete NaBH4 addition and when the effervescence had subsided, pTSOH.H2O (0.1 equiv.) was added and the reaction was heated at 70° C. for 1 hour. The reaction was quenched by the addition of acetone and concentrated under reduced pressure. The residue was diluted with EtOAc and sonicated to dissolve the organics. Water was then added to dissolve the inorganic solids. The organic layer was separated and dried (MgSO4), filtered and concentrated to give a yellow solid. The solid was dried under high vacuum for 30 minutes to afford the desired product 9-chloro-1,2,4a,5-tetrahydro-[1,4]oxazino[4,3-a][1,5]naphthyridin-6(4H)-one in 80% isolated yield. LCMS (m/z) (M+H)=239.3, Rt=0.85 min.

2-chloro-5,6,6a,7,9,10-hexahydropyridazino[3',4':5,6]pyrido[2,1-c][1,4]oxazin-5-ol

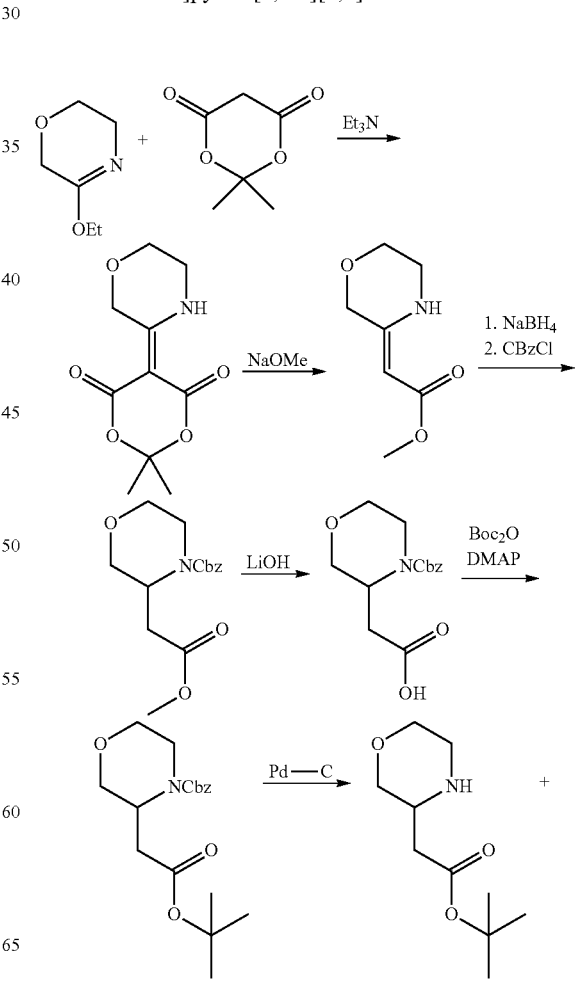

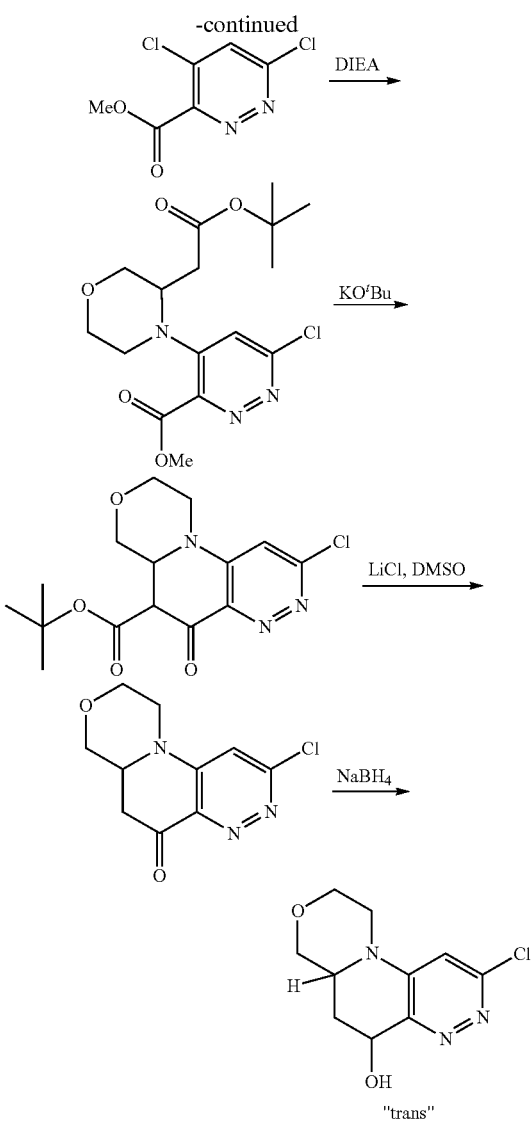

"trans"

Step 1:

5-ethoxy-3,6-dihydro-2H-1,4-oxazine (1.0 equiv.), 2,2-dimethyl-1,3-dioxane-4,6-dione (1.0 equiv.), triethylamine (0.2 equiv.) were combined in Benzene (1.0 M) into a 40 mL vial. The mixture was heated at 100° C. for 3 h and then LCMS indicated formation of desired product. M−H+=226.3, 0.71 min (basic method). The mixture was cooled to room temperature and the solvent evaporated in vacuo to afford quantitative yield of 2,2-dimethyl-5-(morpholin-3-ylidene)-1,3-dioxane-4,6-dione. LCMS (m/z) (M−H)=226.3, Rt=0.71 min.

Step 2:

2,2-dimethyl-5-(morpholin-3-ylidene)-1,3-dioxane-4,6-dione (1.0 equiv.) and NaOMe (1.2 equiv.) were suspended in MeOH (0.3 M) in a vial and the mixture heated to reflux. After 2 h, mostly desired product along with trace unreacted starting material is observed. MH+=159.0, 0.29 (visible by ELSD) is observed along with unreacted SM. The mixture was agitated at reflux overnight. The next morning, the mixture was cooled to room temperature and then concentrated in vacuo. The residue was dissolved in Sat'd NH$_4$Cl and extracted with EtOAc. The organic layer was dried (MgSO$_4$), filtered and concentrated in vacuo to afford (Z)-methyl 2-(morpholin-3-ylidene)acetate in 95% crude yield. LCMS (m/z) (M+H)=159.0, Rt=0.29 min.

Step 3:

(Z)-methyl 2-(morpholin-3-ylidene)acetate (1.0 equiv.) was dissolved in 4:1 dioxane/AcOH (0.5 M). The mixture was added NaBH$_4$ in portions and the mixture agitated at room temperature for 20 min upon which complete conversion to the desired product was observed by LCMS (m/z) (M+H)=160.1 0.10 min. The mixture was concentrated in vacuo until constant mass and then dissolved in THF (0.5 M) and then Sat'd NaHCO$_3$ (100 mL) was added. Then CBZCl (1.0 equiv.) was added and the mixture was agitated at room temperature. LCMS after 1 h indicated formation of desired product. The reaction mixture was diluted with EtOAc and the layers separated. The organic layer was washed with brine and dried (MgSO$_4$), filtered and concentrated in vacuo. The residue was purified by flash chromatography (0-100% EtOAc/heptane) to afford the desired product benzyl 3-(2-methoxy-2-oxoethyl)morpholine-4-carboxylate in 51% isolated yield as a colorless oil. LCMS (m/z) (M+H)=294.3, Rt=1.16 min.

Step 4:

Benzyl 3-(2-methoxy-2-oxoethyl)morpholine-4-carboxylate (1.0 equiv.) was dissolved in THF:MeOH:Water (3:2:1) (0.2 M) and then LiOH.H$_2$O (182 mg, 4.33 mmol was added. The mixture was agitated at 50° C. for 1 h and then at room temperature for 1 h. The reaction mixture was concentrated in vacuo and the residue acidified to pH=1 using 6 N HCl and the product was extracted with EtOAc. The organic layer was washed with brine and dried (MgSO$_4$), filtered and concentrated in vacuo to afford the crude acid 2-(4-((benzyloxy)carbonyl)morpholin-3-yl)acetic acid in quantitative yield. LCMS (m/z) (M−H)=277.9, Rt=1.07 min.

Step 5:

2-(4-((benzyloxy)carbonyl)morpholin-3-yl)acetic acid (1.0 equiv.) was charged into a flask and then Boc-anhydride (2.0 equiv.) and t-BuOH (1.0 M) were added. Then DMAP (0.2 equiv.) was added which led to instantaneous exotherm. The mixture was maintained at 50° C. in an oil bath for 1 h and concentrated in vacuo. The residue was purified by flash chromatography (0-40% EtOAc/heptane) to afford the desired product benzyl 3-(2-(tert-butoxy)-2-oxoethyl)morpholine-4-carboxylate as a viscous colorless oil. LCMS (m/z) (M+H-tBu)=280.2, Rt=1.42 min.

Step 6:

Benzyl 3-(2-(tert-butoxy)-2-oxoethyl)morpholine-4-carboxylate (1.0 equiv.) was dissolved in MeOH: EtOAc (1:1), 0.5 M and then Pd—C (0.14 equiv.) was added. The mixture was evacuated and purged with hydrogen (three times) and finally, the mixture was agitated under 1 atmosphere of hydrogen overnight. The next morning, LCMS indicated formation of desired product. The reaction mixture was filtered through celite and the filtrate concentrated in vacuo to constant mass, thus affording tert-butyl 2-(morpholin-3-yl)acetate in 91% isolated yield. LCMS (m/z) (M+H)=202.1, Rt=0.65 min.

Step 7:

Into a 3-dram vial were charged tert-butyl 2-(morpholin-3-yl)acetate (1.2 equiv.), methyl 4,6-dichloropyridazine-3-carboxylate (1.0 equiv.) and DMF (0.3 M). To the mixture at room temperature was added DIEA (3.0 equiv.). The mixture was agitated in heating block at 70° C. After 5 h, the mixture was concentrated in vacuo and the residue purified by flash chromatography (0-100% EtOAc/heptane) to afford the desired product methyl 4-(3-(2-(tert-butoxy)-2-oxoethyl)

morpholino)-6-chloropyridazine-3-carboxylate in 77% isolated yield. LCMS (m/z) (M+H)=372.1, Rt=1.25 min.

Step 8:

Methyl 4-(3-(2-(tert-butoxy)-2-oxoethyl)morpholino)-6-chloropyridazine-3-carboxylate (1.0 equiv.) was dissolved in toluene (0.1 M) and then treated drop-wise with 1.0 M KOtBu (1.1 equiv.) at room temperature. The mixture was agitated for 30 min and then quenched by addition of Sat'd NH$_4$Cl. The product was extracted with EtOAc. The organic layer was dried (MgSO$_4$), filtered and concentrated in vacuo to afford 90% yield of the crude product tert-butyl 2-chloro-5-oxo-5,6,6a,7,9,10-hexahydropyridazino[3',4':5,6]pyrido[2,1-c][1,4]oxazine-6-carboxylate; which was taken to the next step as such without any further purification. LCMS (m/z) (M+H)=340.0, Rt=1.25 min.

Step 9:

Tert-butyl 2-chloro-5-oxo-5,6,6a,7,9,10-hexahydropyridazino[3',4':5,6]pyrido[2,1-c][1,4]oxazine-6-carboxylate (1.0 equiv.) was dissolved in TFA (0.14) and the mixture placed under reflux (bath temperature=90° C.). After 90 min at reflux, the entire reaction mixture was poured onto solid Na$_2$CO$_3$ and after the effervescence had subsided, water (3 ml) was added and the product extracted twice with DCM. The organic layer was dried (MgSO$_4$), filtered and concentrated in vacuo to afford 2-chloro-6a,7,9,10-tetrahydropyridazino[3',4':5,6]pyrido[2,1-c][1,4]oxazin-5(6H)-one in 30.9% isolated yield as a pale yellow solid. LCMS (m/z) (M+H)=240.3, Rt=0.61 min.

Step 10:

2-chloro-6a,7,9,10-tetrahydropyridazino[3',4':5,6]pyrido[2,1-c][1,4]oxazin-5(6H)-one (1.0 equiv.) was suspended in MeOH (0.04 M) and then at room temperature was added NaBH$_4$ (2.0 equiv.). The mixture was agitated at room temperature for 10 min after which acetone was added to quench the reaction mixture. The volatiles were evaporated in vacuo and the residue taken up in EtOAc and washed with sat'd NH$_4$Cl. The organic layer was separated and dried (MgSO$_4$), filtered and concentrated in vacuo to afford (trans)-2-chloro-5,6,6a,7,9,10-hexahydropyridazino[3',4':5,6]pyrido[2,1-c][1,4]oxazin-5-ol in quantitative yield. LCMS (m/z) (M+H)=242.3, Rt=0.45 min.

diethyl 9-bromo-1,2,4,4a-tetrahydro-[1,4]oxazino[4,3-a]quinoline-5,5(6H)-dicarboxylate

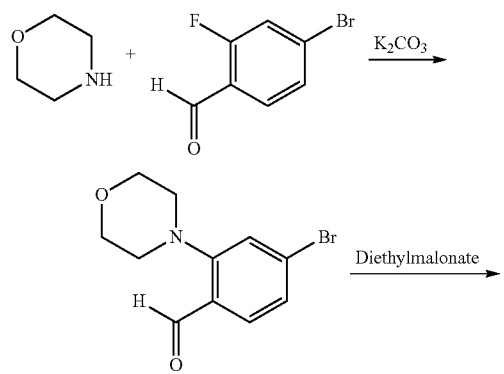

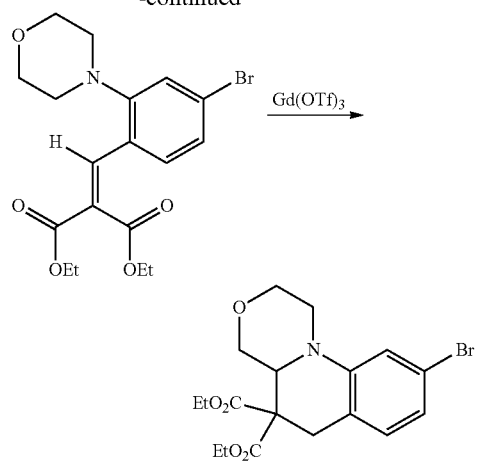

Step 1:

To a solution of 4-bromo-2-fluorobenzaldehyde (1.0 equiv.) and K$_2$CO$_3$ (1.15 equiv.) in DMF (1.0M) was added the morpholine (1.15 equiv.). The resulting reaction mixture was heated under reflux for 2 h upon which complete conversion to the desired product was observed. The reaction mixture was cooled to room temperature and let to stand overnight. The next morning, the reaction mixture was diluted with EtOAc and water and vigorously agitated. The organic layer was separated and washed with water and then brine and dried (MgSO$_4$), filtered and concentrated in vacuo and the residue was purified by flash chromatography (0-50% EtOAc/heptane) to afford the desired product 4-bromo-2-morpholinobenzaldehyde in 90% isolated yield as a light yellow solid. LCMS (m/z) (M+H)=271.8, Rt=1.33 min.

Step 2:

A mixture of 4-bromo-2-morpholinobenzaldehyde (1.0 equiv.), diethyl malonate (1.05 equiv.), piperidine (0.17 equiv.) and benzoic acid (0.11 equiv.) in Toluene (1.0 M) was refluxed using a Dean-Stark trap overnight. The next morning, LCMS indicated formation of desired product. The reaction mixture was concentrated in vacuo and the residue was purified by flash chromatography (0-100% EtOAc/heptane) to afford diethyl 2-(4-bromo-2-morpholinobenzylidene)malonate in 87% isolated yield the desired product as a yellow syrup. LCMS (m/z) (M+H)=414.3, Rt=1.65 min.

Step 3:

Into a 250 mL RB flask was added diethyl 2-(4-bromo-2-morpholinobenzylidene)malonate (1.0 equiv.) and then Acetonitrile (0.1 M). Then, gadolinium(III) trifluoromethanesulfonate (0.1 equiv.) was added in one portion. The entire mixture was agitated at 70° C. overnight. The crude reaction was cooled to room temperature and then filtered through celite and the filtrate concentrated in vacuo. The residue diethyl 9-bromo-1,2,4,4a-tetrahydro-[1,4]oxazino[4,3-a]quinoline-5,5(6H)-dicarboxylate was put under high vacuum until constant mass. LCMS (m/z) (M+H)=413.9, Rt=2.80 min (product analysis method in SQ4); $^1$H NMR (400 MHz, CDCl$_3$) δ ppm 6.83-6.92 (m, 3H) 4.10-4.29 (m, 4H) 3.84-4.04 (m, 3H) 3.60-3.74 (m, 3H) 3.06-3.28 (m, 3H) 1.26 (t, J=7.15 Hz, 3H) 1.19 (t, J=7.09 Hz, 3H).

(9-bromo-1,2,4,4a,5,6-hexahydro[1,4]oxazino[4,3-a]quinoline-5,5-diyl)dimethanol

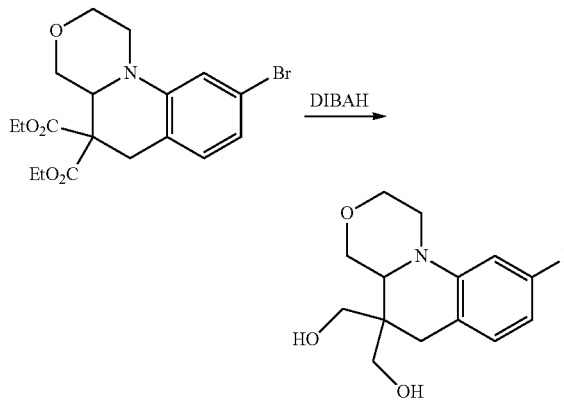

Step 1:

Diethyl 9-bromo-1,2,4,4a-tetrahydro-[1,4]oxazino[4,3-a]quinoline-5,5(6H)-dicarboxylate (1.0 equiv.) was dissolved in DCM (0.3 M) and cooled to −78° C. Then DIBAH (10.0 equiv.) (1.0 M in DCM) was added dropwise and the mixture let to warm to room temperature and agitate overnight. The next morning, the reaction mixture was poured onto ice-cold 1N HCl and the product extracted with EtOAc. The organic layer was dried (MgSO$_4$), filtered and concentrated in vacuo. The residue was purified by flash chromatography (0-100% EtOAc/heptane) to afford the desired product (9-bromo-1,2,4,4a,5,6-hexahydro-[1,4]oxazino[4,3-a]quinoline-5,5-diyl)dimethanol as a colorless solid in 77% isolated yield. LCMS (m/z) (M+H)=328.0, Rt=1.13 min.

(9-bromo-1,2,4,4a,5,6-hexahydro-[1,4]oxazino[4,3-a]quinolin-5-yl)methanol

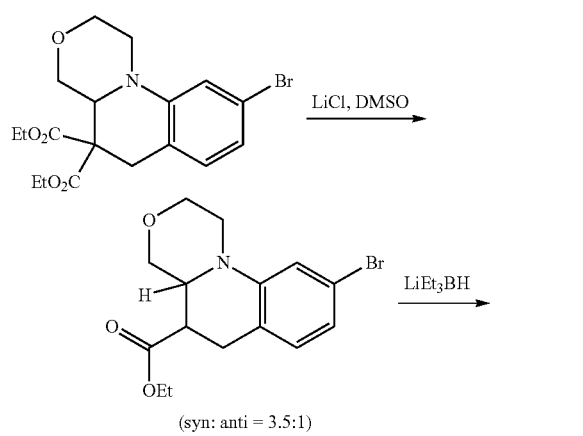

Step 1:

Into a 250 mL RB flask was charged crude diethyl 9-bromo-1,2,4,4a-tetrahydro-[1,4]oxazino[4,3-a]quinoline-5,5(6H)-dicarboxylate (1.0 equiv.) and the gummy residue was dissolved in DMSO (0.5 M). Then water (2.0 equiv.) followed by LiCl (2.0 equiv.) was added. The entire mixture was placed in an oil bath pre-heated to 180° C. After 1 h, complete decarboxylation was observed and the product mixture (3.5:1) was observed. RM cooled to room temperature and water (80 mL) was added. The mixture was extracted with EtOAc and the organic layer was dried (MgSO$_4$), filtered and concentrated in vacuo and the residue purified by flash chromatography (0-100% EtOAc/heptane) to afford the desired product ethyl 9-bromo-1,2,4,4a,5,6-hexahydro-[1,4]oxazino[4,3-a]quinoline-5-carboxylate as a 3.5:1 diastereomeric mixture in 89% isolated yield. LCMS: (m/z) (M+H)=341.9, Rt=1.23 (minor) and Rt=1.30 (major) min. $^1$H NMR (400 MHz, DMSO-d6) δ ppm 6.81-7.00 (m, 3H) 4.16-4.26 (m, 2H) 3.86-4.07 (m, 2H) 3.48-3.75 (m, 2H) 3.30-3.40 (m, 2H) 2.78-3.09 (m, 3H) 2.56-2.71 (m, 1H) 1.26-1.36 (m, 3H).

Step 2:

Into a 250 mL RB flask was added ethyl 9-bromo-1,2,4,4a,5,6-hexahydro-[1,4]oxazino[4,3-a]quinoline-5-carboxylate (1.0 equiv.) and THF (0.3) and the mixture cooled to 0° C. Then Super hydride (3.0 equiv.) was added. The mixture was let to warm to room temperature over 2 h upon which complete reduction of the ester material was observed. The reaction mixture was quenched by drop-wise addition of water and the product extracted with EtOAc and the organic layer was washed with Sat'd Na$_2$CO$_3$ and then dried (MgSO$_4$), filtered and concentrated in vacuo. The residue was azeotroped with MeOH to afford the desired product (9-bromo-1,2,4,4a,5,6-hexahydro-[1,4]oxazino[4,3-a]quinolin-5-yl)methanol as a white solid in quantitative yield. LCMS: LCMS: (m/z) (M+H)=299.9, Rt=1.26 min.

9-bromo-N-methyl-1,2,4,4a,5,6-hexahydro-[1,4]oxazino[4,3-a]quinoline-5-carboxamide

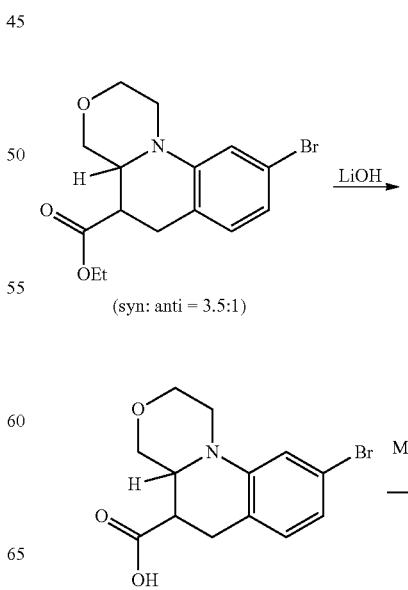

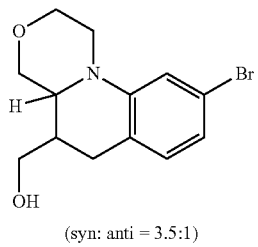

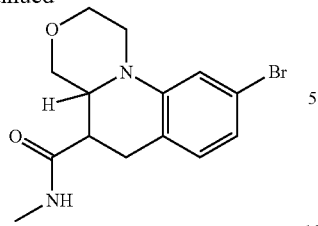

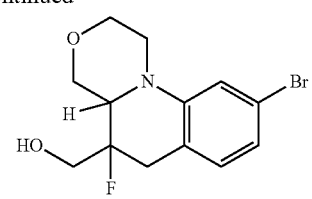

Step 1:

Ethyl 9-bromo-1,2,4,4a,5,6-hexahydro-[1,4]oxazino[4,3-a]quinoline-5-carboxylate (1.0 equiv.) was dissolved in THF:MeOH:Water (3:2:1) (0.25 M) and then LiOH.H$_2$O 5.0 equiv.) was added. The mixture was agitated at 50° C. for 1 h during which complete hydrolysis of the ester was observed. The reaction mixture was concentrated in vacuo. The residue was acidified to pH=1 using 4N aq. HCl and the product was back extracted with EtOAc. The organic layer was dried (MgSO$_4$), filtered and concentrated in vacuo to afford quantitative yield of desired product. The residue 9-bromo-1,2,4,4a,5,6-hexahydro-[1,4]oxazino[4,3-a]quinoline-5-carboxylic acid was taken to the next step without any further purification. LCMS: (m/z) (M+H)=313.9, Rt=1.24 min (minor) and Rt=1.29 (major).

Step 2:

Into a vial were charged 9-bromo-1,2,4,4a,5,6-hexahydro-[1,4]oxazino[4,3-a]quinoline-5-carboxylic acid (1.0 equiv.), EDC.HCl (1.2 equiv.), HOAT (1.2 equiv.), and DMF (0.3 M). To the mixture was added DIEA (2.5 equiv.) followed by Methylamine (2.0 M in THF) (1.2 equiv.) and the mixture agitated at room temperature overnight. The next morning, the reaction mixture was diluted with EtOAc and washed with water and then with sat'd Na$_2$CO$_3$ and dried (MgSO$_4$), filtered and concentrated in vacuo and the residue 9-bromo-N-methyl-1,2,4,4a,5,6-hexahydro-[1,4]oxazino[4,3-a]quinoline-5-carboxamide was obtained in quantitative yield and was taken to the next step as such. LCMS: (m/z) (M+H)=326.9, Rt=1.18 min.

(9-bromo-5-fluoro-1,2,4,4a,5,6-hexahydro-[1,4]oxazino[4,3-a]quinolin-5-yl)methanol Step 1:

Ethyl 9-bromo-1,2,4,4a,5,6-hexahydro-[1,4]oxazino[4,3-a]quinoline-5-carboxylate (1.0 equiv.) was dissolved in THF (0.2 M) and cooled to −78° C. Then LDA (1.3 equiv.) was added. Then the mixture was agitated for 30 min and then NFSI was added neat and the mixture let to warm to room temperature and agitate over 72 h. The reaction mixture was quenched by addition of water and Sat'd NH$_4$Cl and the product extracted with EtOAc. The combined organic layer was dried (MgSO$_4$), filtered and concentrated in vacuo. The residue was purified by flash chromatography (0-50% EtOAc/heptane) to afford the desired product ethyl 9-bromo-5-fluoro-1,2,4,4a,5,6-hexahydro-[1,4]oxazino[4,3-a]quinoline-5-carboxylate in 84% isolated yield. LCMS: (m/z) (M+H)=360.2, Rt=1.51 min.

Step 2:

ethyl 9-bromo-5-fluoro-1,2,4,4a,5,6-hexahydro-[1,4]oxazino[4,3-a]quinoline-5-carboxylate (1.0 equiv.) was dissolved in THF (0.1 M) and cooled in ice-bath. To the mixture was added Super-hydride (5.0 equiv.) and the mixture let to warm to room temperature overnight. The next morning, the reaction mixture was quenched by addition of water and then diluted with EtOAc and washed with Sat'd Na$_2$CO$_3$. The organic layer was dried (MgSO$_4$), filtered and concentrated in vacuo and the residue azeotroped twice with MeOH and dried under high vacuum to afford the desired product (9-bromo-5-fluoro-1,2,4,4a,5,6-hexahydro-[1,4]oxazino[4,3-a]quinolin-5-yl)methanol in a 5:1 diastereomeric ratio. LCMS: (m/z) (M+H)=318.2, Rt=1.83 (minor) and Rt=1.85 min (major).

9-bromo-5-methyl-1,2,4,4a,5,6-hexahydro-[1,4]oxazino[4,3-a]quinoline-5-carbonitrile

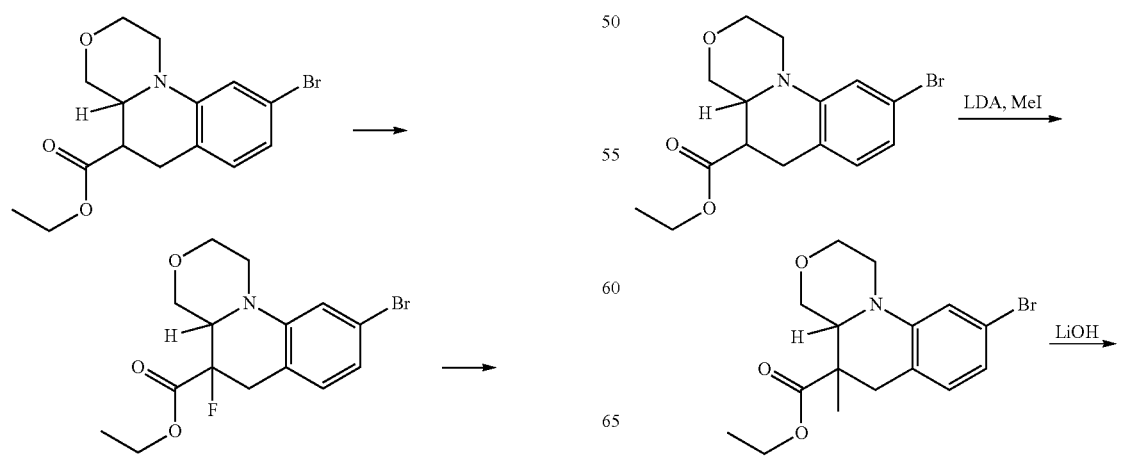

-continued

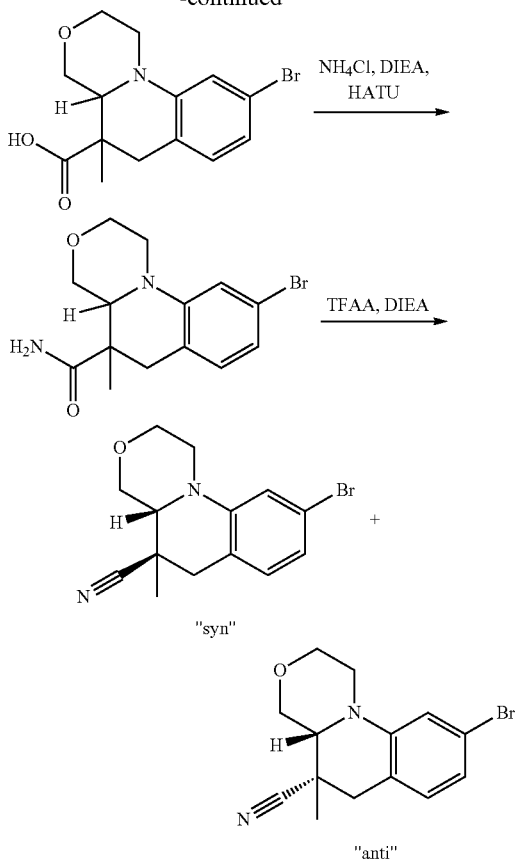

"syn"

"anti"

Step 1:

Ethyl 9-bromo-1,2,4,4a,5,6-hexahydro-[1,4]oxazino[4,3-a]quinoline-5-carboxylate (1.0 equiv.) was dissolved in THF (0.15 M) and cooled to −78° C. Then LDA (1.30 equiv.) was added. Then the mixture was agitated for 60 min and then 2.0 M MBTE solution of iodomethane (2.0 equiv.) was added. The mixture was warmed to room temperature and agitated for 1 h and then quenched by addition of water and then sat'd NH$_4$Cl. The product was extracted with EtOAc and the organic layer was dried (MgSO$_4$), filtered and concentrated in vacuo to afford the crude product ethyl 9-bromo-5-methyl-1,2,4,4a,5,6-hexahydro-[1,4]oxazino[4,3-a]quinoline-5-carboxylate in a 2.6:1 diastereomeric ratio, which was taken to the next step without any further purification. LCMS: (m/z) (M+H)=356.2, Rt=1.30 (major) and Rt=1.34 (minor) min.

Step 2:

9-bromo-5-methyl-1,2,4,4a,5,6-hexahydro-[1,4]oxazino[4,3-a]quinoline-5-carboxylate (1.0 equiv.) was dissolved in THF:MeOH:water (3:2:1 ratio) (0.1 M) and then LiOH.H$_2$O (5.0 equiv.) was added. The mixture was agitated at 70° C. in a heating block for 1 h. The mixture was then concentrated in vacuo. The residue was acidified with 6N HCl and the product extracted with EtOAc. The organic layer was dried (MgSO$_4$), filtered and concentrated in vacuo to afford the desired product 9-bromo-5-methyl-1,2,4,4a,5,6-hexahydro-[1,4]oxazino[4,3-a]quinoline-5-carboxylic acid, which was taken to the next step as such without any further purification. LCMS: (m/z) (M+H)=328.1, Rt=1.01 (major) and 1.04 (minor) min (SQ4).

Step 3:

9-bromo-5-methyl-1,2,4,4a,5,6-hexahydro-[1,4]oxazino[4,3-a]quinoline-5-carboxylic acid (1.0 equiv.), NH$_4$Cl (4.0 equiv.), HATU (1.3 equiv.) were combined in DMF (0.2 M). To the mixture was then DIEA (50 equiv.) was added. The mixture was agitated at room temperature for 1 h upon which complete conversion to the desired diastereomeric products was observed. The reaction mixture was dissolved in EtOAc and washed with Na$_2$CO$_3$ (sat'd) and then with water and then with brine. The organic layer was dried (MgSO$_4$), filtered and concentrated in vacuo. The residue 9-bromo-5-methyl-1,2,4,4a,5,6-hexahydro-[1,4]oxazino[4,3-a]quinoline-5-carboxamide was taken to the next step as such without any further purification. LCMS: (m/z) (M+H)=327.2, Rt=0.89 (major) and Rt=0.90 (minor) min (SQ4).

Step 4:

9-bromo-5-methyl-1,2,4,4a,5,6-hexahydro-[1,4]oxazino[4,3-a]quinoline-5-carboxamide (1.0 equiv.) was dissolved in DCM (0.2 M) and then Triethylamine (6.0 equiv.) was added. Then TFAA (4.5 equiv.) was added and the mixture agitated at room temperature for 2 h and the concentrated in vacuo. The residue was taken up in EtOAc and washed with Sat'd NH$_4$Cl and then with Na$_2$CO$_3$ and then brine and dried (MgSO$_4$), filtered and concentrated in vacuo. The residue was purified by flash chromatography (0-30% EtOAc/heptane) to afford the desired products. Diastereomer 1 (Syn) 9-bromo-5-methyl-1,2,4,4a,5,6-hexahydro-[1,4]oxazino[4,3-a]quinoline-5-carbonitrile: LCMS: (m/z) (M+H)=309.3, Rt=0.56 min, Diastereomer 2 (non-polar): LCMS: (m/z) (M+H)=309.3, 0.71 min.

tert-butyl (9-bromo-5-methyl-1,2,4,4a,5,6-hexahydro-[1,4]oxazino[4,3-a]quinolin-5-yl)carbamate

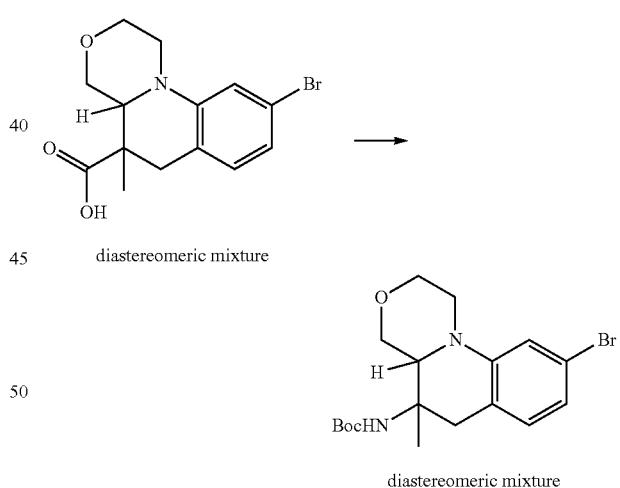

diastereomeric mixture diastereomeric mixture

Step 1:

Into a RB flask was charged 9-bromo-5-methyl-1,2,4,4a,5,6-hexahydro-[1,4]oxazino[4,3-a]quinoline-5-carboxylic acid (1.0 equiv.), tert-butanol 50 equiv.), DIEA (2.5 equiv.) and then DPPA (1.25 equiv.). The mixture was refluxed at 110° C. overnight. The next morning, the reaction mixture was concentrated in vacuo and the residue purified by flash chromatography (0-30% EtOAc/heptane) to afford the desired product tert-butyl (9-bromo-5-methyl-1,2,4,4a,5,6-hexahydro-[1,4]oxazino[4,3-a]quinolin-5-yl)carbamate in 13.9% isolated yield. LCMS: (m/z) (M+H)=399.3, Rt=1.18 min.

10-bromo-1,2,4,4a,5,6-hexahydro-8H-pyrido[2',1':2,3]pyrimido[6,1-c][1,4]oxazin-8-one

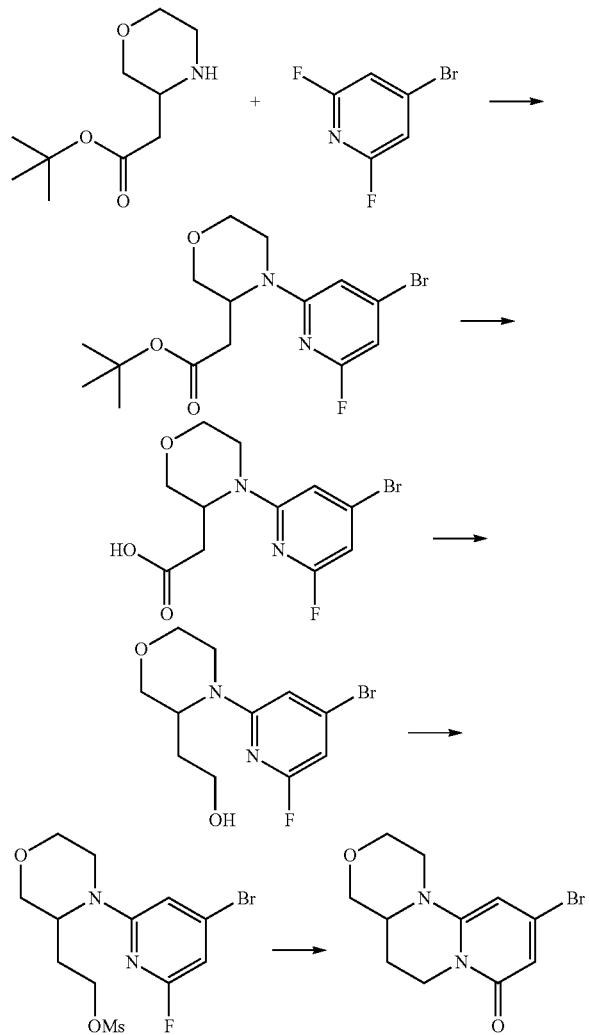

Step 1:
tert-butyl 2-(morpholin-3-yl)acetate (1.0 equiv.), 4-bromo-2,6-difluoropyridine (1.0 equiv.) and DIEA (3.0 equiv.) were combined in EtOH (0.5 M) were placed in a screw-capped vial and the mixture was heated at 100° C. for 48 h and cooled to room temperature and then concentrated in vacuo. The residue was purified by flash chromatography (0-50% EtOAc/heptane) to afford the desired product tert-butyl 2-(4-(4-bromo-6-fluoropyridin-2-yl)morpholin-3-yl) acetate as a colorless oil in 33% isolated yield. LCMS: (m/z) (M+H-56)=320.9, Rt=1.69 min.

Step 2:
Tert-butyl 2-(4-(4-bromo-6-fluoropyridin-2-yl)morpholin-3-yl)acetate (1.0 equiv.) was dissolved in DCM (0.2 M) and at room temperature was added TFA (58.4 equiv.). The mixture was agitated for 2 h and then concentrated in vacuo. The residue was dissolved in EtOAc and washed with water and dried (MgSO$_4$), filtered and concentrated in vacuo. The residue 2-(4-(4-bromo-6-fluoropyridin-2-yl)morpholin-3-yl)acetic acid was taken to the next step as such. LCMS: (m/z) (M+H-56)=319.1, Rt=1.23 min.

Step 3:
2-(4-(4-bromo-6-fluoropyridin-2-yl)morpholin-3-yl)acetic acid (1.0 equiv.) was dissolved in Tetrahydrofuran:Dioxane (1:1, 0.3 M) and then cooled to -15° C. Then 4-methylmorpholine (1.0 equiv.) followed by isobutyl chloroformate (1.0 equiv.) were added. The mixture was agitated for 10 min after which NaBH$_4$ (2.0 equiv.) dissolved in water (1 mL/20 mg of NaBH$_4$) was added. The mixture was let to warm to room temperature over 10 min and the mixture was quenched with acetone and the volatiles were evaporated in vacuo. The residue was taken up in EtOAc and washed twice with 1.0 N NaOH (to remove unreacted acid starting material). The organic layer was washed with brine and dried (MgSO$_4$), filtered and concentrated in vacuo. The residue 2-(4-(4-bromo-6-fluoropyridin-2-yl)morpholin-3-yl)ethanol obtained in 65.6% yield was taken to the next step without any further purification. LCMS: (m/z) (M+H)=306.9, Rt=1.24 min.

Step 4:
2-(4-(4-bromo-6-fluoropyridin-2-yl)morpholin-3-yl)ethanol (1.0 equiv.) was dissolved in DCM (0.1M) and Et$_3$N (5.0 equiv.) was added. The mixture was cooled to 0° C. and then MsCl (1.1 equiv.) was added dropwise. The mixture was agitated for 30 min in ice bath and then the solvent was removed in vacuo to afford 2-(4-(4-bromo-6-fluoropyridin-2-yl)morpholin-3-yl)ethyl methanesulfonate in quantitative crude yield. LCMS: (m/z) (M+H)=384.9, Rt=1.38 min.

Step 5:
2-(4-(4-bromo-6-fluoropyridin-2-yl)morpholin-3-yl)ethyl methanesulfonate (1.0 equiv.) was dissolved in dry-THF (0.05 M) and heated to reflux for 2 h. At this stage, Sat'd NaHCO$_3$ (5 mL) was added and the mixture heated at 60° C. for 2 h. The mixture was cooled to room temperature and extracted with EtOAc. The organic layer was dried (MgSO$_4$), filtered and concentrated in vacuo. The residue was purified by flash chromatography (0-10% MeOH/DCM) to afford the desired product 10-bromo-4,4a,5,6-tetrahydro-1H-pyrido[2',1':2,3]pyrimido[6,1-c][1,4]oxazin-8(2H)-one in 42% isolated yield. LCMS: (m/z) (M+H)=38286.9, Rt=0.95 min.

10-(5-amino-2-methylpyridin-3-yl)-1,2,5,5a,6,7-hexahydro-4H-[1,4]oxazepino[4,5-a]quinolin-7-ol

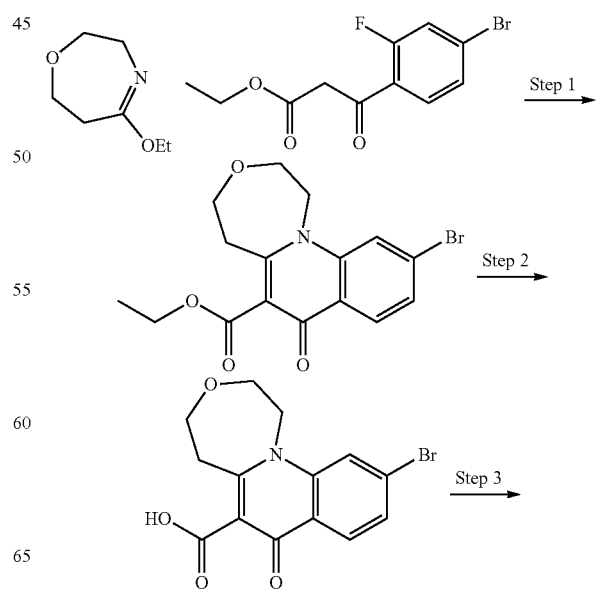

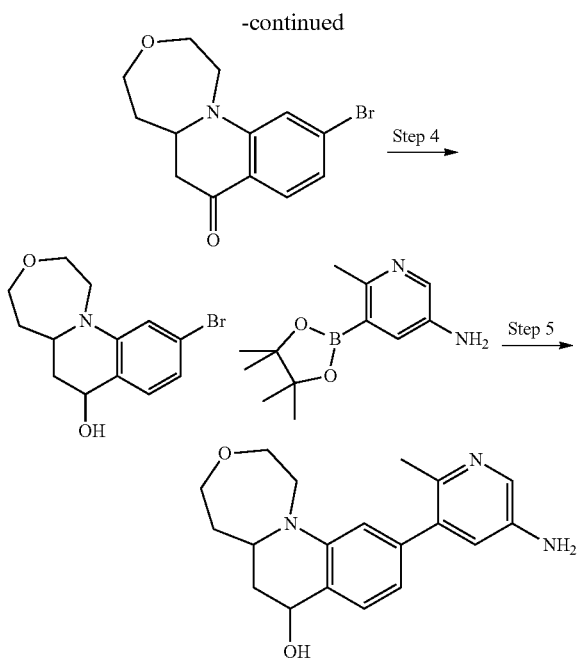

Step 1: A mixture of 5-ethoxy-2,3,6,7-tetrahydro-1,4-oxazepine (0.75 equiv.) and ethyl 3-(4-bromo-2-fluorophenyl)-3-oxopropanoate (1 equiv.) was heated in a sealed tube at 70° C. for 72 hr. The reaction mixture was allowed to come to r.t., diluted with minimum amount of DCM. It was purified by flash chromatography over silica gel (DCM with 10% MeOH) to give ethyl 10-bromo-7-oxo-1,2,5,7-tetrahydro-4H-[1,4]oxazepino[4,5-a]quinoline-6-carboxylate in 64.5% yield. LCMS (m/z) (M+H)=367.9, Rt=1.12 min.

Step 2:
To a solution of ethyl 10-bromo-7-oxo-1,2,5,7-tetrahydro-4H-[1,4]oxazepino[4,5-a]quinoline-6-carboxylate (1 equiv.) in THF:MeOH (3:2 ratio) was added solution of LiOH.H$_2$O (5 equiv.) in water (ratio 2, final concentration of reaction mixture; 0.19M). The reaction mixture was heated at 65° C. for 30 min. The reaction mixture was concentrated under reduced pressure and acidified to pH~1 by using 4N HCl in water. The solid obtained was filtered and the precipitate was air dried under vacuum to give 10-bromo-7-oxo-1,2,5,7-tetrahydro-4H-[1,4]oxazepino[4,5-a]quinoline-6-carboxylic acid in 87% yield. LCMS (m/z) (M+H)=339.8, Rt=1.13 min.

Step 3:
To a cooled mixture of 10-bromo-7-oxo-1,2,5,7-tetrahydro-4H-[1,4]oxazepino[4,5-a]quinoline-6-carboxylic acid (1 equiv.) at 0° C. in THF (0.15M), was dropwise added L-selectride (10 equiv.), and the reaction mixture was allowed to come to ambient temperature. It was further stirred at ambient temperature for another 2 hr. The reaction mixture was quenched with dropwise addition of MeOH until the effervescence has subsided. Then additional MeOH was added followed by p-toluenesulfonic acid monohydrate (0.1 eq.) and heated at 70° C. for 1.5 hr. The cooled reaction mixture was concentrated under reduced pressure, diluted with EtOAc, washed with water. The organic extracts were dried over sodium sulfate, filtered, and concentrated. The crude product was purified by flash chromatography over silica gel (heptanes with 60% ethyl acetate) to give 10-bromo-1,2,4,5,5a,6-hexahydro-7H-[1,4]oxazepino[4,5-a]quinolin-7-one in 39% yield. LCMS (m/z) (M+H)=297.9, Rt=1.26 min.

Step 4:
To a cooled mixture of 10-bromo-1,2,4,5,5a,6-hexahydro-7H-[1,4]oxazepino[4,5-a]quinolin-7-one (1 equiv.) at −20° C. in THF (0.1M), was d added L-selectride (4 equiv.), and the reaction mixture was allowed to come to ambient temperature over 1 hr. The reaction mixture was quenched with dropwise addition of H$_2$O. The reaction mixture was concentrated under reduced pressure, diluted with EtOAc, washed with sat. NH$_4$Cl solution. The organic extracts were dried over magnesium sulfate, filtered, and concentrated The crude product was purified by flash chromatography over silica gel (heptanes with 100% ethyl acetate) to give 10-bromo-1,2,5,5a,6,7-hexahydro-4H-[1,4]oxazepino[4,5-a]quinolin-7-ol in 100% yield. LCMS (m/z) (MH−H$_2$O)$^+$=281.9, Rt=1.20 min.

Step 5:
A mixture of 10-bromo-1,2,5,5a,6,7-hexahydro-4H-[1,4]oxazepino[4,5-a]quinolin-7-ol (1 equiv 6-methyl-5-(4,4,5,5-tetramethyl-1,3,2-dioxaborolan-2-yl)pyridin-3-amine (1.2 equiv.), Xphos G2-Pd-Cy (0.1 equiv.) and K$_3$PO$_4$ (2 equiv.) in dioxane:H$_2$O (0.08 M, 6:1 ratio) was irradiated in a microwave vial for 30 min at 130° C. The cooled crude product was purified by flash chromatography over silica gel (DCM with 15% MeOH) to give the desired product 10-(5-amino-2-methylpyridin-3-yl)-1,2,5,5a,6,7-hexahydro-4H-[1,4]oxazepino[4,5-a]quinolin-7-ol (56%). LCMS (m/z) (MH−H$_2$O)$^+$=326.1, Rt=0.72 min.

Synthesis of (rac)-(4a,10b-cis)-9-bromo-6-ethyl-4,4a,10b-tetrahydro-1H-pyrano[3,4-c][1,8]naphthyridin-5(2H)-one and (rac)-(4a,10b-trans)-9-bromo-6-ethyl-4,4a,6,10b-tetrahydro-1H-pyrano[3,4-c][1,8]naphthyridin-5(2H)-one

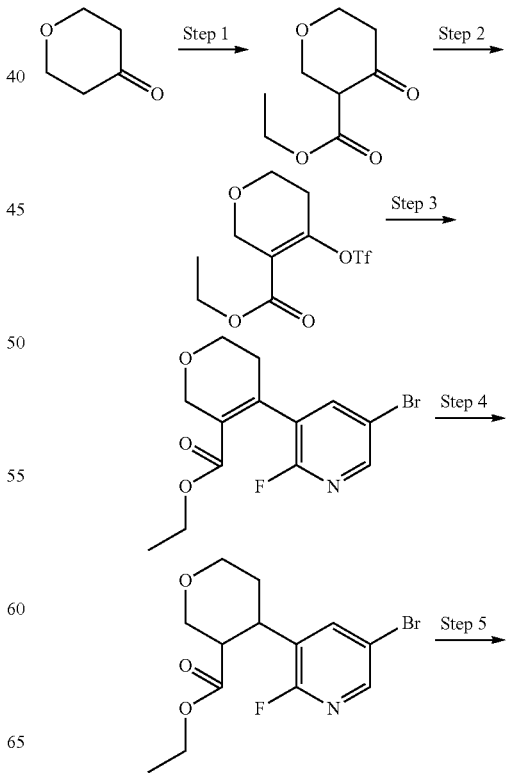

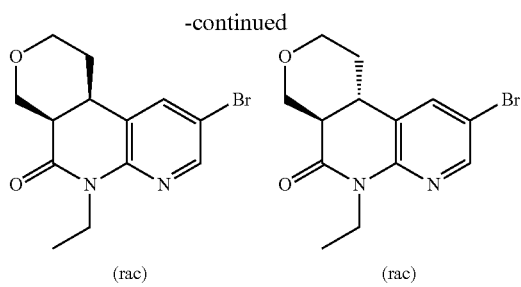

(rac)  (rac)

Step 1:

To a stirred solution of tetrahydropyran-4-one (1.0 equiv) in toluene (0.5 M) at −78° C. was slowly added LiHMDS (1 M in THF, 1.1 equiv) and the mixture was stirred for 30 min. Ethyl chloroformate (1.15 equiv) was then added and the reaction was allowed to warm to RT over 15 min. The reaction was quenched by the addition of saturated aqueous NH₄Cl. The layers were separated; the organics were washed with brine, dried over MgSO₄, filtered, and concentrated. The residue was adsorbed on Celite and purified by flash chromatography over silica gel (heptane with 0-40% ethyl acetate gradient) to give ethyl 4-oxotetrahydro-2H-pyran-3-carboxylate, as a colorless oil in 18% yield. LCMS (m/z) (M+H)=344.0, Rt=1.13 min. ¹H NMR (400 MHz, Chloroform-d) δ 11.71 (s, 1H), 4.11 (t, J=1.7 Hz, 2H), 4.06 (q, J=7.1 Hz, 2H), 3.69 (t, J=5.7 Hz, 2H), 2.23 (tt, J=5.7, 1.7 Hz, 2H), 1.13 (t, J=7.1 Hz, 3H).

Step 2:

To a stirred solution of ethyl 4-oxotetrahydro-2H-pyran-3-carboxylate (1.0 equiv) in THF (0.4 M) at 25° C. was slowly added 60% NaH (1.3 equiv) and the mixture was stirred for 2 h and then cooled to −78° C. N-phenyl-bis (trifluoromethanesulfonamide) (1.1 equiv) was then added and the reaction was allowed to warm to RT and stirred overnight. The reaction was quenched with saturated aqueous NaHCO₃ and extracted twice with EtOAc. The combined organics were dried over MgSO₄, filtered, and concentrated. The residue was purified by flash chromatography over silica gel (heptanes with 0-30% ethyl acetate gradient) to give ethyl 4-(((trifluoromethyl)sulfonyl)oxy)-5,6-dihydro-2H-pyran-3-carboxylate, as a light yellow oil in 122% yield. The excess yield is due to contamination from phenyltriflamide byproducts. 1H NMR (400 MHz, Chloroform-d) δ 4.45 (t, J=2.8 Hz, 2H), 4.29 (q, J=7.1 Hz, 2H), 3.89 (t, J=5.5 Hz, 2H), 2.53 (tt, J=5.5, 2.7 Hz, 2H), 1.33 (t, J=7.1 Hz, 3H).

Step 3:

A stirred solution of 4-(((trifluoromethyl)sulfonyl)oxy)-5,6-dihydro-2H-pyran-3-carboxylate (1.0 equiv), 5-bromo-2-fluoropyridine-3-boronic acid (1.05 equiv), and K2CO3 (2.5 equiv) in THF (0.2 M) was purged with N₂ for 5 min. Pd(Ph₃P)₄ (0.05 equiv) was added, and the mixture was purged again for 5 min and then heated at 65° C. for 4 h. The reaction was poured onto water and extracted twice with EtOAc The combined organics were washed with brine, dried over MgSO₄, filtered, and concentrated. The residue was adsorbed on Celite and purified by flash column chromatography over silica gel (heptane with 0-30% ethyl acetate gradient) to give ethyl 4-(5-bromo-2-fluoropyridin-3-yl)-5,6-dihydro-2H-pyran-3-carboxylate as a colorless oil in 66% yield. LCMS (m/z) (M+H)=330.0/332.0, Rt=1.04 min. ¹H NMR (400 MHz, Chloroform-d) δ 8.20 (dd, J=2.4, 1.4 Hz, 1H), 7.66 (dd, J=8.2, 2.5 Hz, 1H), 4.47 (t, J=2.8 Hz, 2H), 4.02 (q, J=7.1 Hz, 2H), 3.90 (t, J=5.5 Hz, 2H), 2.46 (tt, J=5.5, 2.8 Hz, 2H), 1.04 (t, J=7.1 Hz, 3H).

Step 4:

To a solution of ethyl 4-(5-bromo-2-fluoropyridin-3-yl)-5,6-dihydro-2H-pyran-3-carboxylate (1.0 equiv) in THF/MeOH (1:1; 0.05 M) at −78° C. under Ar was added SmI2 (0.1 M in THF, 5 equiv) dropwise. After addition, the solution was stirred under Ar at −78° C. for 2 hr. The reaction was quenched with half-saturated NaHCO₃, warmed to RT, and concentrated to remove excess THF/MeOH. The remaining mixture was extracted three times with EtOAc, and the combined organics were washed with brine, dried over MgSO₄, filtered, and concentrated. The crude material was adsorbed on Celite and purified by flash chromatography over silica gel (heptane with 0-30% ethyl acetate gradient) to give 4 ethyl 4-(5-bromo-2-fluoropyridin-3-yl)tetrahydro-2H-pyran-3-carboxylate as a diastereomeric mixture as a colorless oil in 58% yield. LCMS (m/z) (M+H)=332.1/334.1, Rt=0.99 and 1.03 min.

Step 5:

To a solution of 4 ethyl 4-(5-bromo-2-fluoropyridin-3-yl)tetrahydro-2H-pyran-3-carboxylate (1.0 equiv) in DMSO (0.2 M) were added i-Pr₂NEt (5 equiv) and EtNH₂ (2 M in THF, 3 equiv) and the mixture was heated at 120° C. for 72 h. The reaction was cooled to RT, poured onto half-saturated NH₄Cl, and extracted twice with EtOAc The combined organics were washed with water brine, dried over MgSO₄, filtered, and concentrated. The crude material was adsorbed on Celite and purified by flash chromatography over silica gel (heptane with 0-30% ethyl acetate gradient) to give (rac)-(4a,10b-trans)-9-bromo-6-ethyl-4,4a,6,10b-tetrahydro-1H-pyrano[3,4-c][1,8]naphthyridin-5(2H)-one as the earlier-eluting isomer as a white solid in 39% yield. LCMS (m/z) (M+H)=311.0/313.0, Rt=1.03 min. ¹H NMR (400 MHz, Chloroform-d) δ 8.32 (dd, J=2.3, 1.0 Hz, 1H), 7.53 (dd, J=2.2, 1.4 Hz, 1H), 4.51 (dd, J=11.9, 4.6 Hz, 1H), 4.20 (dt, J=13.8, 6.9 Hz, 2H), 4.12-4.00 (m, 1H), 3.57-3.48 (m, 2H), 2.86-2.75 (m, 1H), 2.38 (ddd, J=14.7, 10.5, 4.6 Hz, 1H), 2.17 (ddd, J=11.2, 4.0, 2.0 Hz, 1H), 1.74 (qd, J=12.5, 4.6 Hz, 1H), 1.20 (t, J=7.0 Hz, 4H). The later-eluting isomer was isolated to giv (rac)-(4a,10b-cis)-9-bromo-6-ethyl-4,4a,6,10b-tetrahydro-1H-pyrano[3,4-c][1,8]naphthyridin-5 (2H)-one as a white solid in 42% yield. LCMS (m/z) (M+H)=311.0/313.0, Rt=0.97 min. 1H NMR (400 MHz, Chloroform-d) δ 8.31 (d, J=2.3 Hz, 1H), 7.56 (d, J=2.4 Hz, 1H), 4.77-4.68 (m, 1H), 4.33-4.21 (m, 1H), 4.19-4.09 (m, 1H), 4.00 (ddd, J=11.5, 4.1, 2.3 Hz, 1H), 3.58-3.46 (m, 2H), 3.09 (dt, J=11.8, 5.1 Hz, 1H), 2.68-2.60 (m, 1H), 1.80-1.66 (m, 1H), 1.61 (d, J=2.8 Hz, 1H), 1.22 (t, J=7.0 Hz, 4H).

Synthesis of (rac)-(4a,10b-trans)-9-bromo-6-ethyl-4a-methyl-1,2,4,4a,6,10b-hexahydro-5H-pyrano[3,4-c][1,8]naphthyridin-5-one

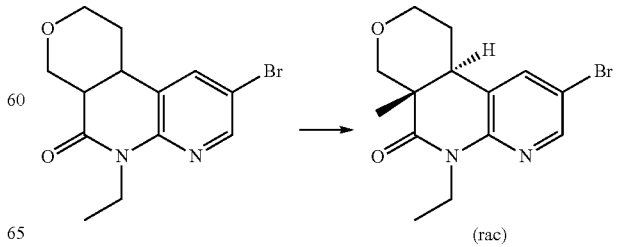

(rac)

To a stirred solution of 9-bromo-6-ethyl-4,4a,6,10b-tetrahydro-1H-pyrano[3,4-c][1,8]naphthyridin-5(2H)-one (mixture of diastereomers, 1 equiv) in THF (0.05 M) at −78° C. was added LDA (2 M in THF/heptane/ethyl benzene, 2 equiv) and the mixture was stirred for 30 min. MeI (equiv) was then added, and the mixture was stirred for 2 h. The reaction was quenched with saturated aqueous NH$_4$Cl and extracted twice with EtOAc The combined organics were washed with brine, dried over MgSO$_4$, filtered, and concentrated. The so-obtained residue was used as 9-bromo-6-ethyl-4a-methyl-4,4a,6,10b-tetrahydro-1H-pyrano[3,4-c][1,8]naphthyridin-5(2H)-one without further purification. LCMS (m/z) (M+H)=325.1/327.1, R$_t$=1.05 min.

Synthesis of 2-chloro-6-ethyl-6a,7,9,10-tetrahydro-6H-[1,4]oxazino[4,3-d]pyridazino[3,4-b][1,4]oxazine Step 1:

A vial was charged with 2,3,5-trichloropyridazine (1 equiv), morpholin-3-ylmethanol (1 equiv), DMF (1 M), and triethylamine (3 equiv). The resulting solution was heated to 90° C. for 6 h. The reaction mixture was cooled to room temperature, diluted with sat. aq. ammonium chloride solution and water, then extracted with EtOAc (4×). The combined organic extracts were washed with brine, dried over sodium sulfate, filtered, and concentrated. The residue was taken up in ether and stirred overnight. In the morning, the mixture was filtered, and the collected solid was washed with ether (2×), then dried under a flow of N$_2$ (g) to give (4-(3,6-dichloropyridazin-4-yl)morpholin-3-yl)methanol (52% yield) as a tan solid. 1H NMR (400 MHz, DMSO-d6) δ ppm 7.32 (s, 1H) 4.53-4.91 (m, 1H) 4.04-4.24 (m, 1H) 3.73-3.92 (m, 3H) 3.44-3.70 (m, 4H) 3.16 (br d, J=11.49 Hz, 1H). LCMS (m/z) (M+H)=264.2, Rt=0.79 min.

Step 2:

A round-bottom flask was charged with (4-(3,6-dichloropyridazin-4-yl)morpholin-3-yl)methanol (1 equiv) and DCM (0.2 M) to give a suspension. The flask was cooled in an ice-water bath for 5 min, then Dess-Martin periodinane (1.2 equiv) was added in one portion. After 1.5 h, the cooling bath was removed. The mixture was stirred for 2 h, then an additional portion of Dess-Martin (1.2 equiv) was added. After another 20 min of stirring, the mixture was diluted with sat. aq. sodium bicarbonate, then extracted with DCM (2×). The combined organic extracts were washed with aq. sodium thiosulfate solution (1×), which was back-extracted with DCM. The combined organic extracts were dried over sodium sulfate, filtered, and concentrated. The residue was concentrated from acetone (2×). The resulting solid was taken up in acetone then filtered and dried to give a tan solid. Filtration was repeated with the filtrate, and the two solids were combined. The solid was purified by chromatography on silica gel (24-g Redi-Sep column, 80-100% EtOAc/heptane) to give 4-(3,6-dichloropyridazin-4-yl)morpholine-3-carbaldehyde (50% yield) as a light-yellow solid. NMR was consistent with about 80% desired aldehyde. LCMS (m/z) (M+H$_2$O+H)=280.2, Rt=0.75 min.

Step 3:

An ice-cold solution of 4-(3,6-dichloropyridazin-4-yl)morpholine-3-carbaldehyde (1 equiv) in THF (0.1 M) was treated with a solution of ethylmagnesium bromide (1M in THF, 2 equiv). The cooling bath was removed, and the mixture was stirred for 1 h. The reaction mixture was diluted with sat. aq. ammonium chloride solution and extracted with EtOAc (3×). The combined organic extracts were dried over sodium sulfate, filtered, and concentrated to give a light-yellow foam. The residue was dissolved in DMF (0.1 M). Sodium hydride (60 wt % in mineral oil, 1.5 equiv) was added, and the resulting mixture was heated to 70° C. for 6 h. The mixture was then cooled to room temperature, diluted with water, and extracted with EtOAc (3×). The combined organic extracts were dried over sodium sulfate, filtered, and concentrated. The residue was purified by chromatography on silica gel (80-100% EtOAc/heptane) to give 2-chloro-6-ethyl-6a,7,9,10-tetrahydro-6H-[1,4]oxazino[4,3-d]pyridazino[3,4-b][1,4]oxazine (63% yield) as a mixture of stereoisomers. LCMS (m/z) (M+H)=256.1, Rt=0.89 min.

Synthesis of trans- and cis-ethyl 9-chloro-1,2,4,4a,5,6-hexahydro-[1,4]oxazino[4,3-a][1,5]naphthyridine-5-carboxylate

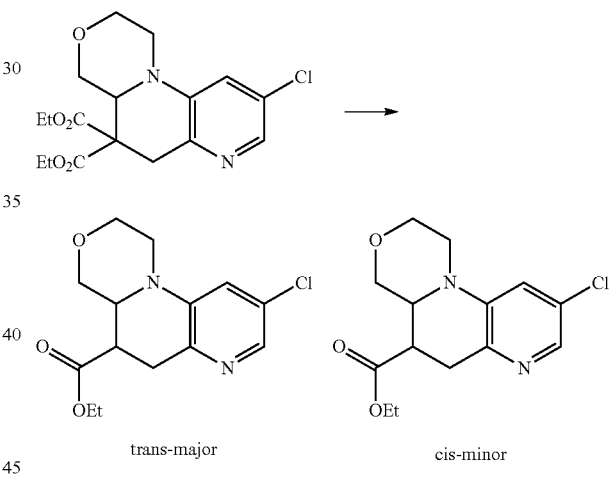

trans-major     cis-minor

A round-bottom flask was charged with diethyl 9-chloro-1,2,4,4a-tetrahydro-[1,4]oxazino[4,3-a][1,5]naphthyridine-5,5(6H)-dicarboxylate (1 equiv), LiCl (2 equiv), DMSO (0.5 M), and water (2 equiv). The flask was fitted with a reflux condenser and heated to 180° C. for 6 h, and the mixture was cooled to room temperature overnight. In the morning, the mixture was diluted with water and a small amount of brine, then extracted with EtOAc (3×). The combined organic extracts were dried over sodium sulfate, filtered, and concentrated. The residue was purified by chromatography on silica gel (0-50% EtOAc/heptane). The first eluting spot was collected to give trans-ethyl 9-chloro-1,2,4,4a,5,6-hexahydro-[1,4]oxazino[4,3-a][1,5]naphthyridine-5-carboxylate (69.0% yield); LCMS (m/z) (M+H) 297.0; Rt.=1.08 min. The second eluting spot was collected to give cis-ethyl 9-chloro-1,2,4,4a,5,6-hexahydro-[1,4]oxazino[4,3-a][1,5]naphthyridine-5-carboxylate (15.91% yield). LCMS (m/z) (M+H) 297.0; Rt.=0.93 min.

101

Intermediate 1. Synthesis of 2-(9-chloro-1,2,4,4a,5,6-hexahydro-[1,4]oxazino[4,3-a][1,5]naphthyridin-5-yl)propan-2-ol

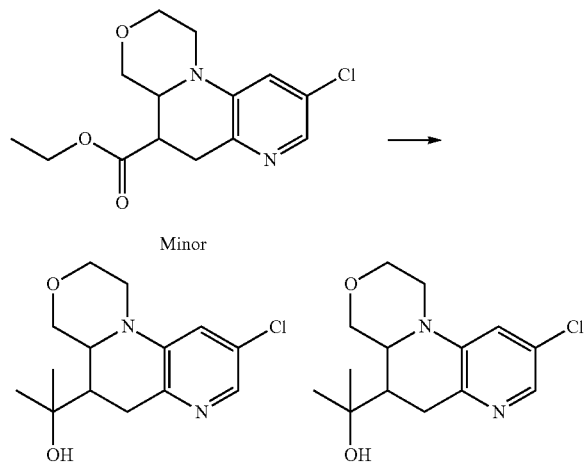

Minor

Step 1:
To an ice cold solution of ethyl 9-chloro-1,2,4,4a,5,6-hexahydro-[1,4]oxazino[4,3-a][1,5]naphthyridine-5-carboxylate (1.0 equiv.) in THF (0.07 M) was added MeMgI (7 equiv.) and allowed to come to ambient temperature. It was stirred for 2 hr and then placed back in the ice bath. The reaction mixture was quenched with NH₄Cl and extracted with DCM. The organic phase was washed with brine, dried over sodium sulfate, filtered, and concentrated. The crude product was purified by flash chromatography over silica gel (heptanes with 100% ethyl acetate) to give 2-(9-chloro-1,2,4,4a,5,6-hexahydro-[1,4]oxazino[4,3-a][1,5]naphthyridin-5-yl)propan-2-ol in 78% yield of two peaks after chiral separation. LCMS (m/z) (M+H)=283.1, Rt=0.80 min.

Intermediate 2. Synthesis of 2-(9-chloro-1,2,4,4a,5,6-hexahydro-[1,4]oxazino[4,3-a][1,5]naphthyridin-5-yl)propan-2-ol

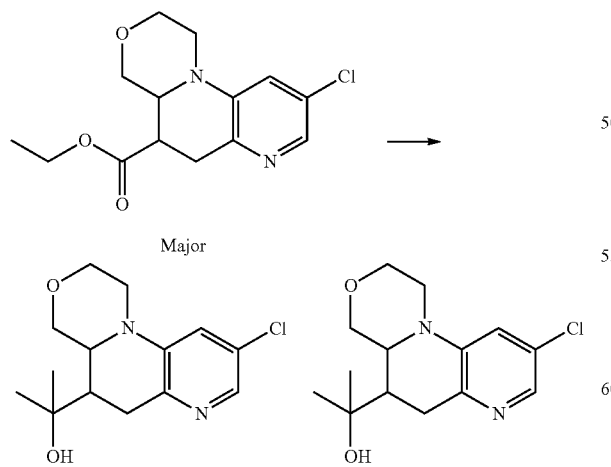

Major

Step 1:
To an ice cold solution of ethyl 9-chloro-1,2,4,4a,5,6-hexahydro-[1,4]oxazino[4,3-a][1,5]naphthyridine-5-car-

102 boxylate (1.0 equiv.) in THF (0.07 M) was added MeMgI (7 equiv.) and allowed to come to ambient temperature. It was stirred for 2 hr and then placed back in the ice bath. The reaction mixture was quenched with NH₄Cl and extracted with DCM. The organic phase was washed with brine, dried over sodium sulfate, filtered, and concentrated. The crude product was purified by flash chromatography over silica gel (heptanes with 100% ethyl acetate) to give 2-(9-chloro-1,2,4,4a,5,6-hexahydro-[1,4]oxazino[4,3-a][1,5]naphthyridin-5-yl)propan-2-ol in 100% yield of two peaks after chiral separation. LCMS (m/z) (M+H)=283.2, Rt=0.75 min.

Synthesis of 10-(5-amino-2-methylpyridin-3-yl)-1,2,5,5a,6,7-hexahydro-4H-[1,4]oxazepino[4,5-a]quinolin-7-ol

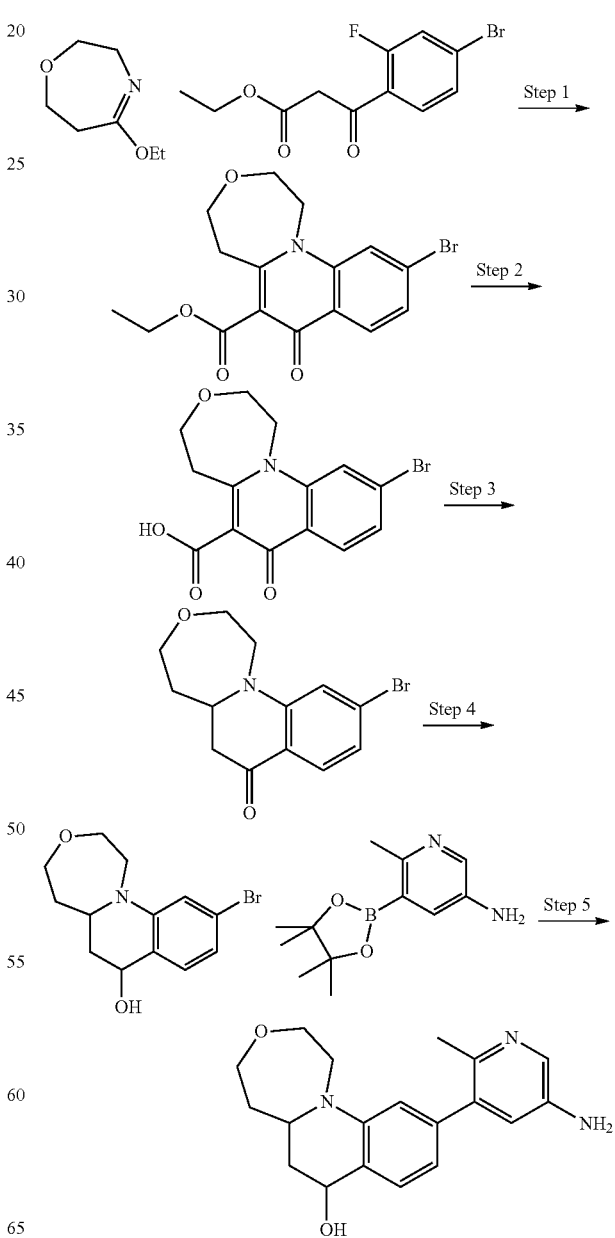

Step 1:

A mixture of 5-ethoxy-2,3,6,7-tetrahydro-1,4-oxazepine (0.75 equiv.) and ethyl 3-(4-bromo-2-fluorophenyl)-3-oxo-propanoate (1 equiv.) was heated in a sealed tube at 70° C. for 72 hr. The reaction mixture was allowed to come to r.t., diluted with minimum amount of DCM. It was purified by flash chromatography over silica gel (DCM with 10% MeOH) to give ethyl 10-bromo-7-oxo-1,2,5,7-tetrahydro-4H-[1,4]oxazepino[4,5-a]quinoline-6-carboxylate in 64.5% yield. LCMS (m/z) (M+H)=367.9, Rt=1.12 min.

Step 2:

To a solution of ethyl 10-bromo-7-oxo-1,2,5,7-tetrahydro-4H-[1,4]oxazepino[4,5-a]quinoline-6-carboxylate (1 equiv.) in THF:MeOH (3:2 ratio) was added solution of LiOH.H$_2$O (5 equiv.) in water (ratio 2, final concentration of reaction mixture; 0.19M). The reaction mixture was heated at 65° C. for 30 min. The reaction mixture was concentrated under reduced pressure and acidified to pH~1 by using 4N HCl in water. The solid obtained was filtered and the precipitate was air dried under vacuum to give 10-bromo-7-oxo-1,2,5,7-tetrahydro-4H-[1,4]oxazepino[4,5-a]quinoline-6-carboxylic acid in 87% yield. LCMS (m/z) (M+H)=339.8, Rt=1.13 min.

Step 3:

To a cooled mixture of 10-bromo-7-oxo-1,2,5,7-tetrahydro-4H-[1,4]oxazepino[4,5-a]quinoline-6-carboxylic acid (1 equiv.) at 0° C. in THF (0.15M), was dropwise added L-selectride (10 equiv.), and the reaction mixture was allowed to come to ambient temperature. It was further stirred at ambient temperature for another 2 hr. The reaction mixture was quenched with dropwise addition of MeOH until the effervescence has subsided. Then additional MeOH was added followed by p-toluenesulfonic acid monohydrate (0.1 eq.) and heated at 70° C. for 1.5 hr. The cooled reaction mixture was concentrated under reduced pressure, diluted with EtOAc, washed with water. The organic extracts were dried over sodium sulfate, filtered, and concentrated. The crude product was purified by flash chromatography over silica gel (heptanes with 60% ethyl acetate) to give 10-bromo-1,2,4,5,5a,6-hexahydro-7H-[1,4]oxazepino[4,5-a]quinolin-7-one in 39% yield. LCMS (m/z) (M+H)=297.9, Rt=1.26 min.

Step 4:

To a cooled mixture of 10-bromo-1,2,4,5,5a,6-hexahydro-7H-[1,4]oxazepino[4,5-a]quinolin-7-one (1 equiv.) at −20° C. in THF (0.1M), was d added L-selectride (4 equiv.), and the reaction mixture was allowed to come to ambient temperature over 1 hr. The reaction mixture was quenched with dropwise addition of H$_2$O. The reaction mixture was concentrated under reduced pressure, diluted with EtOAc, washed with sat. NH$_4$Cl solution. The organic extracts were dried over magnesium sulfate, filtered, and concentrated The crude product was purified by flash chromatography over silica gel (heptanes with 100% ethyl acetate) to give 10-bromo-1,2,5,5a,6,7-hexahydro-4H-[1,4]oxazepino[4,5-a]quinolin-7-ol in 100% yield. LCMS (m/z) (MH−H$_2$O)$^+$=281.9, Rt=1.20 min.

Step 5:

A mixture of 10-bromo-1,2,5,5a,6,7-hexahydro-4H-[1,4]oxazepino[4,5-a]quinolin-7-ol (1 equiv 6-methyl-5-(4,4,5,5-tetramethyl-1,3,2-dioxaborolan-2-yl)pyridin-3-amine (1.2 equiv.), Xphos G2-Pd-Cy (0.1 equiv.) and K$_3$PO$_4$ (2 equiv.) in dioxane:H$_2$O (0.08 M, 6:1 ratio) was irradiated in a microwave vial for 30 min at 130° C. The cooled crude product was purified by flash chromatography over silica gel (DCM with 15% MeOH) to give the desired product 10-(5-amino-2-methylpyridin-3-yl)-1,2,5,5a,6,7-hexahydro-4H-[1,4]oxazepino[4,5-a]quinolin-7-ol (56%). LCMS (m/z) (MH−H$_2$O)$^+$=326.1, Rt=0.72 min.

2-((9-bromo-1,2,4,4a,5,6-hexahydro-[1,4]oxazino[4,3-a][1,5]naphthyridin-6-yl)oxy)ethan-1-ol

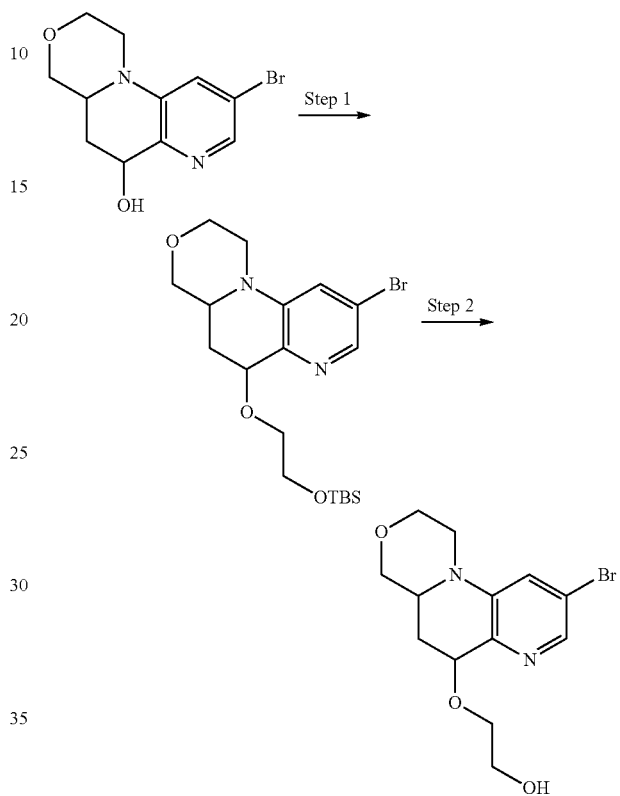

Step 1:

To an ice cold solution of 9-bromo-1,2,4,4a,5,6-hexahydro-[1,4]oxazino[4,3-a][1,5]naphthyridin-6-ol (1.0 equiv.) in DMF (0.13 M) was added NaH (2.5 equiv.) and stirred for 10 min. Then tert-butyl(2-iodoethoxy)dimethylsilane (2.5 equiv.) was then added and allowed the reaction mixture to come to ambient temperature. It was stirred for 3 hr, quenched with water and extracted with EtOAc. The organic phase was washed with sat. NaHCO$_3$. The combined aqueous layer was back extracted with EtOAc. The combined organic phase was washed with brine, dried over magnesium sulfate, filtered, and concentrated. The crude product was purified by flash chromatography over silica gel (hept with 0-100% ethyl acetate) to give 9-bromo-6-(2-((tert-butyldimethylsilyl)oxy)ethoxy)-1,2,4,4a,5,6-hexahydro-[1,4]oxazino[4,3-a][1,5]naphthyridine in 54.5% yield. LCMS (m/z) (M+H)=445.0, Rt=1.61 min.

Step 2:

To a solution of 9-bromo-6-(2-((tert-butyldimethylsilyl)oxy)ethoxy)-1,2,4,4a,5,6-hexahydro-[1,4]oxazino[4,3-a][1,5]naphthyridine (1 equiv.) in MeOH (0.2 M) was added 4M HCl in dioxane (20 equiv.) and stirred for 30 min. The reaction mixture was concentrated to dryness. The crude product was purified by flash chromatography over silica gel (DCM with 0-10% MeOH) to give 2-((9-bromo-1,2,4,4a,5,6-hexahydro-[1,4]oxazino[4,3-a][1,5]naphthyridin-6-yl)oxy)ethan-1-ol in 43% yield. LCMS (m/z) (M+H)=331.0, Rt=0.76 min.

105

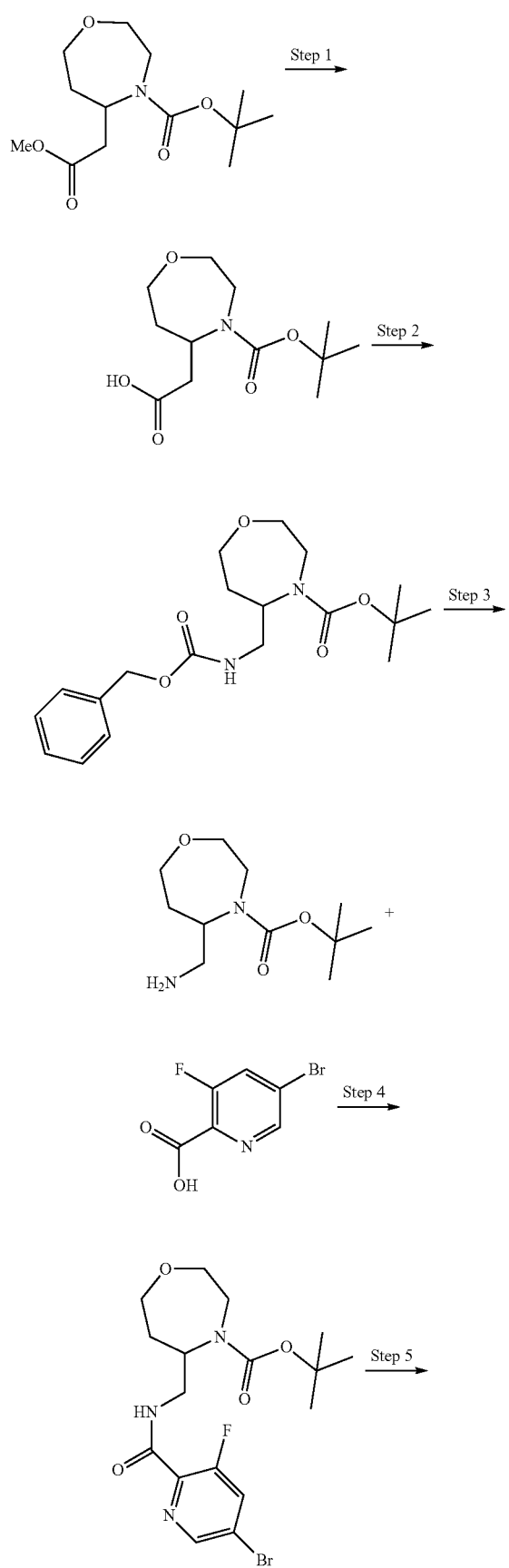

106

-continued

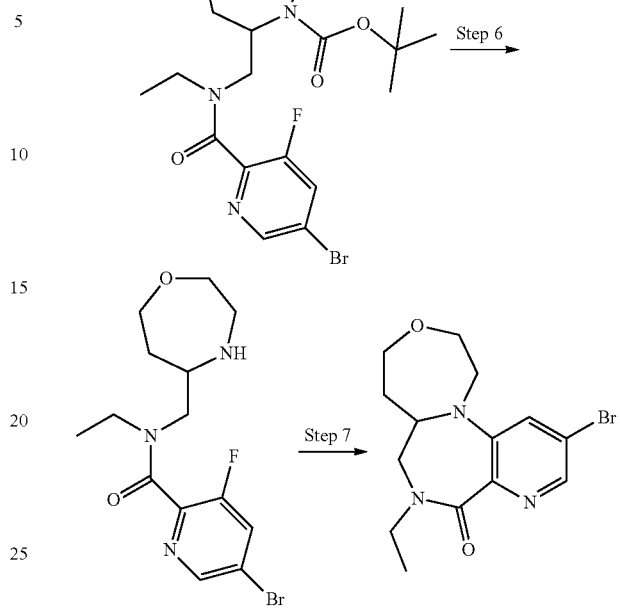

Step 1:

tert-butyl 5-(2-methoxy-2-oxoethyl)-1,4-oxazepane-4-carboxylate (2.096 g, 7.67 mmol) was dissolved in THF (30 mL) and then LiOH.H₂O (1.609 g, 38.3 mmol) dissolved in water (10 mL) was added. The mixture was agitated at room temperature for 1 h and then concentrated in vacuo. The residue was acidified to pH=5 using 4N HCl (aq.), The product was extracted with EtOAc and dried (MgSO₄), filtered and concentrated in vacuo. The residue 2-(4-(tert-butoxycarbonyl)-1,4-oxazepan-5-yl)acetic acid was taken to the next step without any further purification. LCMS (m/z) (M+H-100)=160.1, Rt=0.98 min.

Step 2:

2-(4-(tert-butoxycarbonyl)-1,4-oxazepan-5-yl)acetic acid (1.989 g, 7.67 mmol) was dissolved in Toluene (38.4 ml) and Et₃N (1.276 ml, 9.20 mmol) was added. To the mixture at room temperature was added DPPA (1.818 ml, 8.44 mmol) and the mixture agitated for 10 min. Then, benzyl alcohol (1.196 ml, 11.51 mmol) was added and the mixture heated to 110° C. overnight. The next morning, the mixture was concentrated in vacuo and the residue purified by flash chromatography (0-50% EtOAc/heptane, 80 gram column, 30 min) to afford tert-butyl 5-((((benzyloxy)carbonyl)amino)methyl)-1,4-oxazepane-4-carboxylate in 55% isolated yield. LCMS (m/z) (M+Na)=387.1, Rt=1.38 min.

Step 3:

Tert-butyl 5-((((benzyloxy)carbonyl)amino)methyl)-1,4-oxazepane-4-carboxylate carboxylate (1.0 equiv.) in MeOH (0.1 M) was added 10% Pd—C (0.15 equiv.). The reaction mixture was purged with hydrogen and hydrogenated with a balloon hydrogen overnight. The reaction mixture was filtered through a celite pad, and the pad was rinsed with MeOH. Filtrate was concentrated to dryness under reduced pressure to give product, tert-butyl 5-(aminomethyl)-1,4-oxazepane-4-carboxylate in 96% yield. LCMS (m/z) (M+H)=231.1, Rt=0.65 min.

Step 4:

Used the standard peptide coupling method used before. LCMS (m/z) (M+H)=334.1 (deboc fragment), Rt=1.26 min.

Step 5:

To an ice cold solution of tert-butyl 5-((5-bromo-3-fluoropicolinamido)methyl)-1,4-oxazepane-4-carboxylate (1.0 equiv.) in DMF (0.19 M) was added NaH (2.5 equiv.) and stirred for 1 hr. Bromoethane (2.5 equiv.) was then added and allowed the reaction mixture to come to ambient temperature. It was stirred for 1 hr, quenched with water and extracted with EtOAc. The organic phase was washed with sat. NaHCO$_3$. The combined aqueous layer was back extracted with EtOAc. The combined organic phase was washed with brine, dried over sodium sulfate, filtered, and concentrated. The crude product was purified by flash chromatography over silica gel (hept with 0-100% ethyl acetate) to give tert-butyl 5-((5-bromo-N-ethyl-3-fluoropicolinamido)methyl)-1,4-oxazepane-4-carboxylate in 74% yield. LCMS (m/z) (M+H)=362.1, Rt=1.36 min.

Step 6:

To a solution of tert-butyl 5-((5-bromo-N-ethyl-3-fluoropicolinamido)methyl)-1,4-oxazepane-4-carboxylate (1 equiv.) in DCM (0.21 M) was added 4M HCl in dioxane (5 equiv.) and stirred for 1 hr. The reaction mixture was concentrated to dryness to give the desired product, N-((1,4-oxazepan-5-yl)methyl)-5-bromo-N-ethyl-3-fluoropicolinamide in 100% yield. LCMS (m/z) (M+H)=36.0, Rt=0.75 min.

Step 7:

to a solution of N-((1,4-oxazepan-5-yl)methyl)-5-bromo-N-ethyl-3-fluoropicolinamide (1 equiv.) in NMP (0.21 M) was added DIPEA (6 equiv.) and the reaction mixture was stirred at 70° C. for 18 hrs. The reaction mixture was diluted with EtOAc, washed with water, brine, dried over sodium sulfate, filtered, and concentrated. The crude product was purified by C18 flash ISCO reverse phase column (no modifier) to give 11-bromo-7-ethyl-1,2,5,5a,6,7-hexahydropyrido[2',3':6,7][1,4]diazepino[1,2-d][1,4]oxazepin-8(4H)-one in 38.4% yield. Two peaks were isolated after chiral separation. LCMS (m/z) (M+H)=342.0, Rt=0.93 min.

Synthesis of 9-bromo-6-ethyl-4H-pyrido[2,3-b][1,2,4]triazolo[4,3-d][1,4]diazepin-5(6H)-one

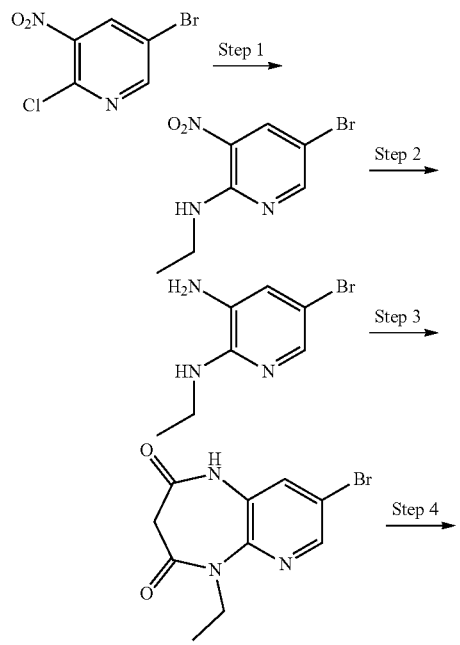

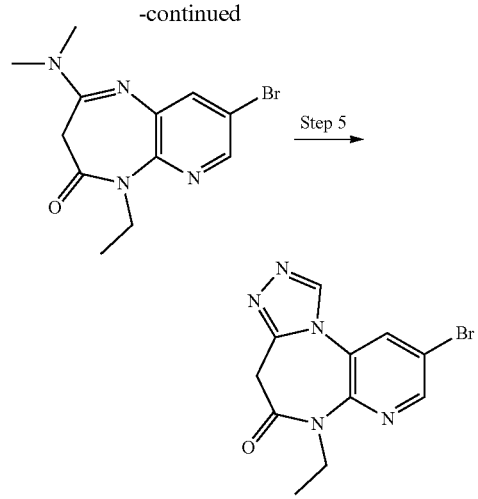

Step 1:

To a stirred solution of 2-chloro-5-bromo-3-nitropyridine (1.0 equiv) in DMSO (0.9 M) at 25° C. were added ethylamine (2 M in THF, 1.1 equiv) and Et$_3$N (1.8 equiv) and the reaction was stirred overnight. The reaction was poured onto water, stirred for 10 min, and then filtered. The so-obtained yellow solid was dried to provide 5-bromo-N-ethyl-3-nitropyridin-2-amine in 96% yield which was used without further purification. LCMS (m/z) (M+H)=246.0/248.0, Rt=1.13 min.

Step 2:

To a stirred solution of 5-bromo-N-ethyl-3-nitropyridin-2-amine (1.0 equiv) in 2.5:1 EtOH/water (0.36 M) at 25° C. were added NH$_4$Cl (5 equiv) followed by portionwise addition of Fe (5 equiv) and the reaction was heated to 105° C. and stirred for 4 h. The reaction was cooled to RT, diluted with EtOAc, and filtered through Celite. The filtrated was concentrated and purified by flash column chromatography over silica gel (heptane and 0-100% EtOAc gradient) to give 5-bromo-N2-ethylpyridine-2,3-diamine as a purple solid in 57% yield. LCMS (m/z) (M+H)=216.0/218.0, Rt=0.42 min.

Step 3:

Solutions of 5-bromo-N2-ethylpyridine-2,3-diamine (1.0 equiv) in THF (0.2 M) and malonyl chloride (1.2 equiv) in THF (0.25 M) were simultaneously added dropwise over 1 h (via syringe pumps) to a flask charged with THF (0.1 M relative to starting material) at 0° C. After addition was complete, the reaction was allowed to warm to 25° C. and stirred for 4.5 h. The reaction was concentrated. The residue was purified by flash column chromatography over silica gel (heptane and 0-100% EtOAc gradient) to provide 8-bromo-5-ethyl-1H-pyrido[2,3-b][1,4]diazepine-2,4(3H,5H)-dione as a white solid in 42% yield. LCMS (m/z) (M+H)=283.9/285.9, Rt=0.71 min.

Step 4:

To a solution of 8-bromo-5-ethyl-1H-pyrido[2,3-b][1,4]diazepine-2,4(3H,5H)-dione (1.0 equiv) in THF (0.14 M) at 0° C. were added dimethylamine (2 M in THF, 2.0 equiv) followed by TiCl$_4$ (1 M in DCM, 1.6 equiv) and the mixture was allowed to warm to RT and stirred for 3 h. The reaction mixture was diluted with EtOAc and brine and filtered through Celite. The filtrate was washed with brine, dried over MgSO$_4$, filtered and concentrated. The residue was purified by flash column chromatography over silica gel (heptane and 0-100% EtOAc gradient) to provide 8-bromo-2-(dimethylamino)-5-ethyl-3H-pyrido[2,3-b][1,4]diazepin- 4(5H)-one as a pale yellow oil in 78% yield. LCMS (m/z) (M+H)=311.0/313.0, Rt=1.00 min.

Step 5:

A mixture of 8-bromo-2-(dimethylamino)-5-ethyl-3H-pyrido[2,3-b][1,4]diazepin-4(5H)-one (1.0 equiv) and formic acid hydrazide (2.0 equiv) in 10:1 Dowtherm A/acetic acid (0.2 M) was heated to 150° C. and stirred for 2 h. The reaction mixture was diluted with DCM and purified by flash column chromatography over silica gel (DCM and 0-15% MeOH gradient) to give 9-bromo-6-ethyl-4H-pyrido[2,3-b][1,2,4]triazolo[4,3-d][1,4]diazepin-5(6H)-one as a white solid in 75% yield. LCMS (m/z) (M+H)=308.0/310.0, Rt=0.67 min.

Synthesis of 9-bromo-6-ethyl-4,4-dimethyl-4H-pyrido[2,3-b][1,2,4]triazolo[4,3-d][1,4]diazepin-5(6H)-one, Methyl 2-(4-(5-bromo-2-(ethyl(methyl)amino)pyridin-3-yl)-4H-1,2,4-triazol-3-yl)-2-methylpropanoate

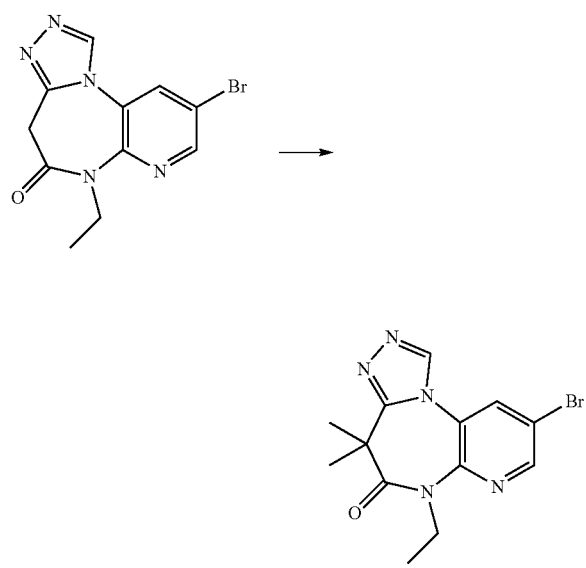

9-bromo-6-ethyl-4H-pyrido[2,3-b][1,2,4]triazolo[4,3-d][1,4]diazepin-5(6H)-one (1.0 equiv) was dissolved in DMF (0.1 M); the solution was cooled to 0° C. and sodium hydride (2.0 equiv) was slowly added. The reaction was stirred at 0° C. for 30 minutes, and then iodomethane (2.5 equiv) was added and the reaction was stirred at room temperature for 45 minutes. The reaction mixture was poured onto saturated aqueous NH$_4$Cl and extracted three times with EtOAc. The combined organics were washed with water and brine, dried over MgSO$_4$, filtered and concentrated. The so-obtained residue was used as 9-bromo-6-ethyl-4,4-dimethyl-4H-pyrido[2,3-b][1,2,4]triazolo[4,3-d][1,4]diazepin-5(6H)-one without further purification. LCMS (m/z) (M+H)=336.0/338.0, Rt=0.85 min.

Synthesis of 9-bromo-5-ethyl-4H-pyrido[2,3-f][1,2,4]triazolo[4,3-a][1,4]diazepin-6(5H)-one

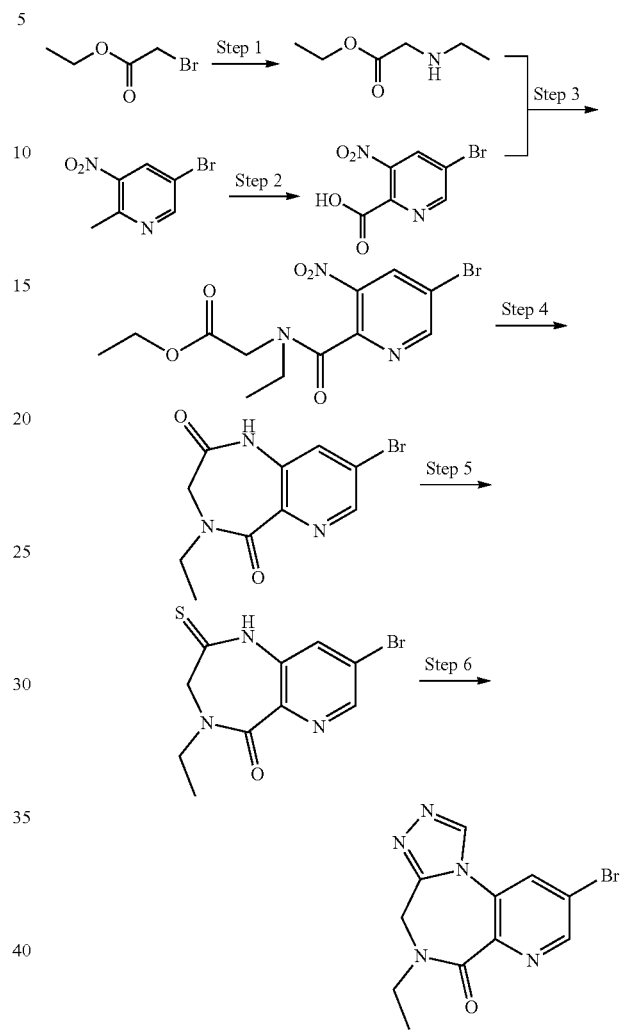

Step 1:

To a stirred solution of ethylamine (2 M in THF, 4.0 equiv) in MeCN (2.0 M) at 0° C. was added ethyl bromoacetate (1.0 equiv) and the mixture was allowed to warm to RT and stirred for 2 h. The reaction mixture was concentrated and then partitioned between EtOAc and 1 M NaOH. The aqueous layer was extracted with more EtOAc, and the combined organics were dried over MgSO$_4$, filtered, and concentrated. The so-obtained residue was used as ethyl 2-(ethylamino)acetate (59% yield) without further purification. $^1$H NMR (400 MHz, Chloroform-d) δ 4.19 (q, J=7.2 Hz, 2H), 3.40 (s, 2H), 2.65 (q, J=7.1 Hz, 2H), 1.27 (t, J=7.1 Hz, 3H), 1.12 (t, J=7.1 Hz, 3H).

Step 2:

A stirred mixture of 5-bromo-3-nitropicoline (1.0 equiv) and KMnO$_4$ (2.0 equiv) in water (0.2 M) was heated to 80° C. and stirred for 2 h. More KMnO$_4$ (4 equiv) was added, and the reaction was further heated to 100° C. and stirred overnight. The mixture was cooled and filtered through Celite while still slightly warm, washing with H$_2$O and EtOAc. The filtrate was extracted twice with EtOAc, and those organic extracts were discarded. The aqueous layer was acidified with HCl and extracted twice more with EtOAc. These combined organics were washed with brine, dried over MgSO$_4$, filtered and concentrated to 5-bromo-3-nitropicolinic acid as a yellow solid in 2.4% yield which was used without father purification. LCMS Rt=0.39 min.

Step 3:

5-bromo-3-nitropicolinic acid (1.0 equiv) and ethyl 2-(ethylamino)acetate (1.1 equiv) were taken up in DMA (0.15 M) at 25° C. HOAT (1.3 equiv), iPr$_2$EtN (3 equiv), and EDC (1.3 equiv) were added and the mixture was stirred overnight at 25° C. The mixture was poured onto water and extracted three times with ethyl acetate. The combined organics were washed with water and brine, dried over magnesium sulfate, filtered, and concentrated. The residue was purified by flash column chromatography over silica gel (heptane and 0-100% EtOAc gradient) to give ethyl 2-(5-bromo-N-ethyl-3-nitropicolinamido)acetate as a colorless oil in 69% yield. LCMS (m/z) (M+H)=360.1/362.1, Rt=0.92 min.

Step 4:

To a stirred solution of ethyl 2-(5-bromo-N-ethyl-3-nitropicolinamido)acetate (1.0 equiv) in acetic acid (0.1 M) was added Fe (10 equiv) the mixture was heated to 80° C. and stirred for 1 h. The reaction was cooled to room temperature and filtered through a short plug of Celite, washing with EtOAc and MeOH, and then concentrated. The resulting residue was suspended in DCM/MeOH and filtered, washing with both DCM and methanol. After concentrating again, the residue was taken up in DCM and poured onto 1:1 saturated aqueous NaHCO$_3$/brine. The mixture was extracted twice with DCM and then once with 30% i-PrOH/CHCl$_3$, and the combined organics were dried over MgSO$_4$, filtered, and concentrated. The residue was purified by flash column chromatography over silica gel (DCM and 0-15% MeOH gradient) to give 8-bromo-4-ethyl-3,4-dihydro-1H-pyrido[3,2-e][1,4]diazepine-2,5-dione as a white solid in 85% yield. LCMS (m/z) (M+H)=284.0/286.0, Rt=0.47 min.

Step 5:

To a stirred solution of 8-bromo-4-ethyl-3,4-dihydro-1H-pyrido[3,2-e][1,4]diazepine-2,5-dione (1.0 equiv) in dioxane (0.08 M) at RT was added Lawesson's reagent (0.5 equiv) and the mixture was heated to 65° C. and stirred for 1 h. The reaction was concentrated and purified by flash column chromatography over silica gel (heptane and 0-100% EtOAc gradient) to give 8-bromo-4-ethyl-2-thioxo-3,4-dihydro-1H-pyrido[3,2-e][1,4]diazepin-5(2H)-one as a white solid in 86% yield. LCMS (m/z) (M+H)=299.9/301.9, Rt=0.84 min.

Step 6:

To a stirred solution of 8-bromo-4-ethyl-2-thioxo-3,4-dihydro-1H-pyrido[3,2-e][1,4]diazepin-5(2H)-one (1.0 equiv) in n-butanol (0.1 M) at RT was added formic acid hydrazide (1.5 equiv) and the mixture was heated to 90° C. and stirred for 48 h. The reaction was diluted with DCM, concentrated, and purified by flash column chromatography over silica gel (DCM and 0-35% MeOH gradient) to provide 9-bromo-5-ethyl-4H-pyrido[2,3-f][1,2,4]triazolo[4,3-a][1,4]diazepin-6(5H)-one as a yellow oil in 72% yield. LCMS (m/z) (M+H)=308.1/310.1, Rt=0.44 min.

Syntheses of 10-bromo-7-ethyl-11b-methyl-1,4,7,11b-tetrahydro-[1,3]oxazino[3,4-c]quinazolin-6(2H)-one "Peak 1" and 10-bromo-7-ethyl-11b-methyl-1,4,7,11b-tetrahydro-[1,3]oxazino[3,4-c]quinazolin-6(2H)-one "Peak 2"

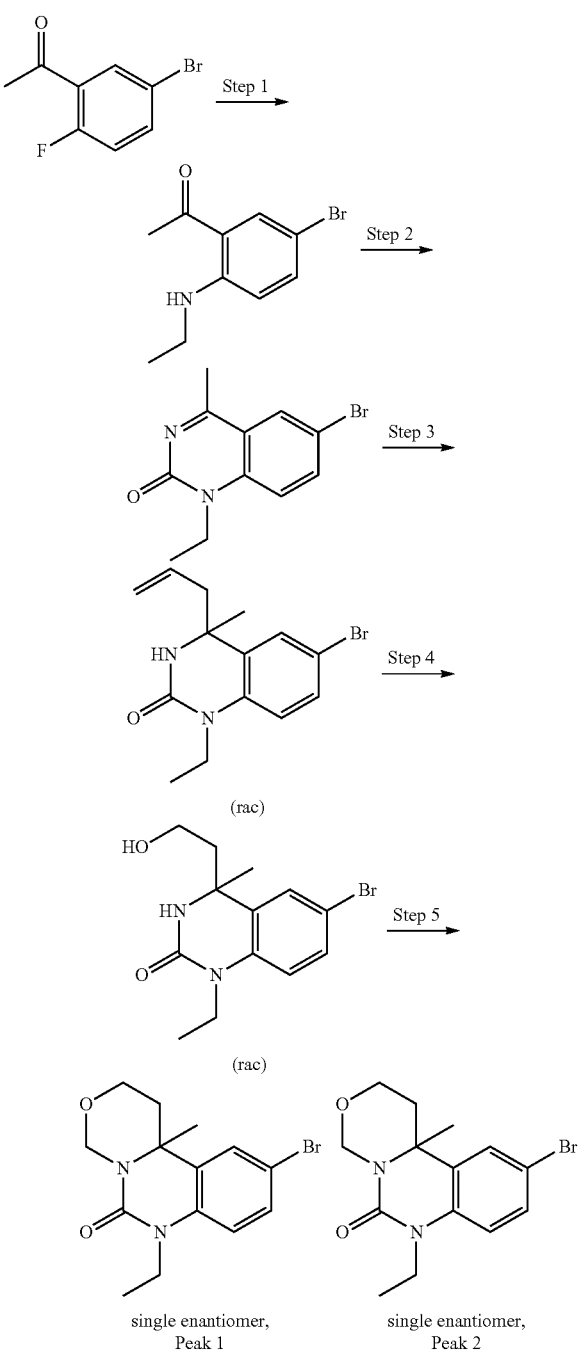

Step 1:

To a stirred solution of 5-bromo-2-fluoropyridine (1.0 equiv) in DMF (0.5 M) were added ethyl amine (2 M in THF, 1.2 equiv) and K$_2$CO$_3$ (1.5 equiv) and the mixture was heated at 115° C. overnight. The mixture was poured onto water and extracted three times with ethyl acetate. The combined organics were washed with water and brine, dried over magnesium sulfate, filtered, and concentrated. The residue was purified by flash column chromatography over silica gel (heptane and 0-30% EtOAc gradient) to provide 1-(5-bromo-2-(ethylamino)phenyl)ethanone as a yellow solid in 82% yield. LCMS (m/z) (M+H)=242.0/244.0, Rt=1.21.

Step 2:

To a stirred solution of 1-(5-bromo-2-(ethylamino)phenyl)ethanone (1.0 equiv) in acetic acid (0.18 M) at 25° C. was added sodium cyanate (1.5 equiv) and the reaction was stirred for 48 h. The mixture was poured onto water and extracted three times with ethyl acetate. The combined organics were washed with water and brine, dried over magnesium sulfate, filtered, and concentrated. The residue was purified by flash column chromatography over silica gel (heptane and 0-100% EtOAc gradient) to give 6-bromo-1-ethyl-4-methylquinazolin-2(1H)-one as a pale yellow solid in 17% yield. LCMS (m/z) (M+H)=266.9/268.9, Rt=0.76 min.

Step 3:

To a stirred solution of 6-bromo-1-ethyl-4-methylquinazolin-2(1H)-one (1.0 equiv) in THF (0.16 M) at 0° C. was slowly added allylmagnesium bromide (1 M in Et$_2$O, 1.7 equiv) and the reaction was allowed to warm to RT and stirred overnight. The mixture was poured onto 1 M citric acid and extracted three times with ethyl acetate. The combined organics were dried over magnesium sulfate, filtered, and concentrated. The residue was purified by flash column chromatography over silica gel (heptane and 0-100% EtOAc gradient) to provide 4-allyl-6-bromo-1-ethyl-4-methyl-3,4-dihydroquinazolin-2(1H)-one as a bright yellow solid in 53% yield. LCMS (m/z) (M+H)=309.0/311.0, Rt=1.10 min. $^1$H NMR (400 MHz, Chloroform-d) δ 7.35 (dd, J=8.7, 2.3 Hz, 1H), 7.24 (d, J=2.3 Hz, 1H), 6.79 (d, J=8.8 Hz, 1H), 5.67 (ddt, J=17.4, 10.2, 7.4 Hz, 1H), 5.20 (s, 1H), 5.16-5.04 (m, 2H), 3.92 (qd, J=7.2, 3.9 Hz, 2H), 2.42 (qd, J=13.7, 7.4 Hz, 2H), 1.49 (s, 3H), 1.23 (t, J=7.1 Hz, 3H).

Step 4:

O$_3$ was bubbled through a stirred solution of 4-allyl-6-bromo-1-ethyl-4-methyl-3,4-dihydroquinazolin-2(1H)-one (1.0 equiv) in 4:1 DCM/MeOH (0.03 M) at −78° C. until a persistent blue-grey color was observed (about 3 min). The reaction mixture was then purged with N$_2$; NaBH$_4$ (10 equiv) was added, and the mixture was allowed to warm to RT and stirred for 15 min. The mixture was concentrated and partitioned between EtOAc and 1 M citric acid. The aqueous layer was extracted twice more with ethyl acetate, and the combined organics were washed with water and brine, dried over magnesium sulfate, filtered, and concentrated. The so-obtained pale yellow foam was used as 6-bromo-1-ethyl-4-(2-hydroxyethyl)-4-methyl-3,4-dihydroquinazolin-2(1H)-one without further purification. LCMS (m/z) (M+H)=313.0/315.0, Rt=0.83 min.

Step 5:

A mixture of 6-bromo-1-ethyl-4-(2-hydroxyethyl)-4-methyl-3,4-dihydroquinazolin-2(1H)-one (1.0 equiv) in formic acid (70 equiv) and formaldehyde (37% in water, 35 equiv) was heated at 100° C. for 1 h. The mixture was cooled, basified with 10% Na$_2$CO$_3$, and concentrated to remove excess formic acid and formaldehyde. The remaining aqueous mixture was extracted three times with ethyl acetate, and the combined organics were washed with water and brine, dried over magnesium sulfate, filtered, and concentrated. The residue was purified by flash column chromatography over silica gel (heptane and 0-75% EtOAc gradient) to give the racemic product. This was further purified by chiral SFC (IA 4.6×100 mm column, 5-55% MeOH in CO$_2$ eluent). The first eluting peak afforded 10-bromo-7-ethyl-11b-methyl-1,4,7,11b-tetrahydro-[1,3]oxazino[3,4-c]quinazolin-6(2H)-one "Peak 1" as a colorless oil in 41% yield. The second peak afforded 10-bromo-7-ethyl-11b-methyl-1,4,7,11b-tetrahydro-[1,3]oxazino[3,4-c]quinazolin-6(2H)-one "Peak 2" as a colorless oil in 37% yield. NMR and LCMS data for each enantiomer were identical. LCMS (m/z) (M+H)=325.0/327.0, Rt=1.05 min. $^1$H NMR (400 MHz, Chloroform-d) δ 7.36 (dd, J=8.7, 2.3 Hz, 1H), 7.19 (d, J=2.3 Hz, 1H), 6.77 (d, J=8.8 Hz, 1H), 5.71-5.66 (m, 1H), 4.55 (d, J=10.1 Hz, 1H), 4.19-4.11 (m, 1H), 4.00 (dq, J=14.2, 7.1 Hz, 1H), 3.95-3.88 (m, 1H), 3.83 (dt, J=14.2, 7.1 Hz, 1H), 2.29 (td, J=13.1, 5.2 Hz, 1H), 1.95 (dt, J=13.2, 1.9 Hz, 1H), 1.53-1.47 (m, 3H), 1.25 (t, J=7.1 Hz, 3H).

Synthesis of (rac)-(5a,11b-cis)-10-bromo-7-ethyl-1,4,5,5a,7,11b-hexahydrooxepino[4,5-c][1,8]naphthyridin-6(2H)-one and (rac)-(5a,11b-trans)-10-bromo-7-ethyl-1,4,5,5a,7,11b-hexahydrooxepino[4,5-c][1,8]naphthyridin-6(2H)-one

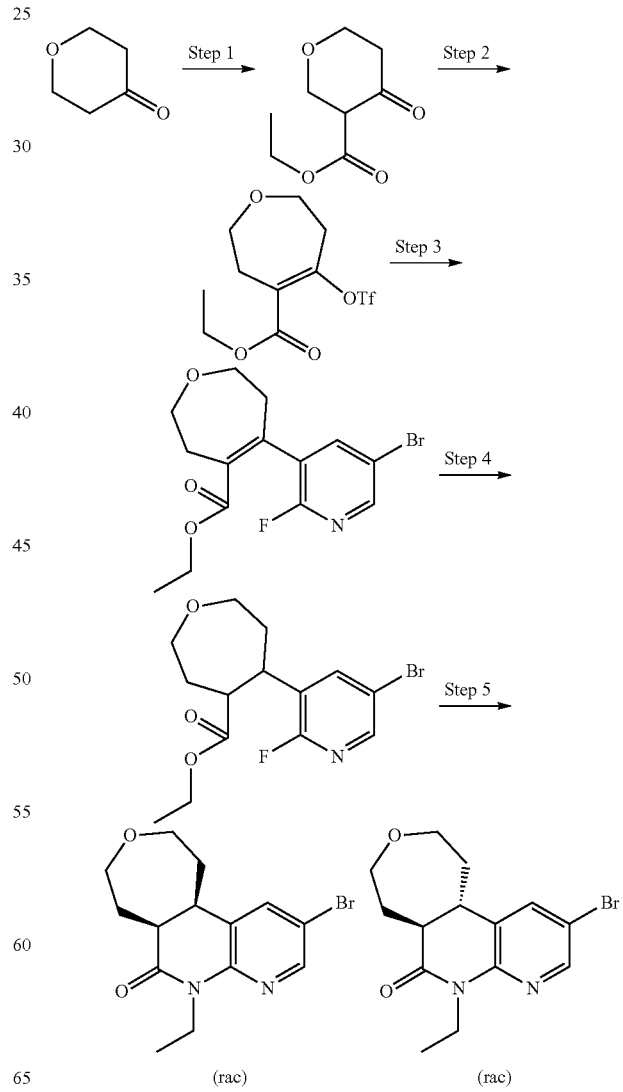

Step 1:

To a solution of 4-oxotetrahydropyran (1.0 equiv) in Et₂O (0.25 M) at −30° C. were added separately but simultaneously solutions of ethyl diazoacetate (1.3 equiv) and BF₃.OEt₂ (1.0 equiv), each in Et₂O (4 M) dropwise over 25 min. The mixture was allowed to stir at −30° C. for 1 h and then warmed to RT. The reaction was slowly quenched with 30% K₂CO₃ and the phases were separated. The aqueous layer was extracted twice with ethyl acetate, and the combined organics were dried over MgSO₄, filtered, and concentrated. The residue was purified by flash column chromatography over silica gel (heptane and 0-50% EtOAc gradient) to provide ethyl 5-oxooxepane-4-carboxylate as a colorless oil in 90% yield. LCMS (m/z) Rt=0.87 min.

Step 2:

To a stirred solution of ethyl 5-oxooxepane-4-carboxylate (1.0 equiv) in THF (0.4 M) at 25° C. was slowly added 60% NaH (1.3 equiv) and the mixture was stirred for 2 h and then cooled to −78° C. N-phenyl-bis(trifluoromethanesulfonamide) (1.1 equiv) was then added and the reaction was allowed to warm to RT and stirred overnight. The reaction was quenched with saturated aqueous NaHCO₃ and extracted twice with EtOAc. The combined organics were dried over MgSO₄, filtered, and concentrated. The residue was purified by flash chromatography over silica gel (heptanes with 0-30% ethyl acetate gradient) to give ethyl 5-(((trifluoromethyl)sulfonyl)oxy)-2,3,6,7-tetrahydrooxepine-4-carboxylate as a colorless oil in 73% yield. ¹H NMR (400 MHz, Chloroform-d) δ 4.30 (q, J=7.2 Hz, 2H), 3.85-3.76 (m, 4H), 2.86-2.74 (m, 4H), 1.36 (t, J=7.2 Hz, 3H).

Step 3:

A stirred mixture of ethyl 5-(((trifluoromethyl)sulfonyl)oxy)-2,3,6,7-tetrahydrooxepine-4-carboxylate (1.0 equiv), 5-bromo-2-fluoropyridine-3-boronic acid (1.05 equiv), and K₂CO₃ (2.5 equiv) in THF (0.2 M) was purged with N₂ for 5 min. Pd(Ph₃P)₄ (0.05 equiv) was added, and the mixture was purged again for 5 min and then heated at 65° C. for 2.5 h. The reaction was poured onto water and extracted twice with EtOAc The combined organics were washed with brine, dried over MgSO₄, filtered, and concentrated. The residue was purified by flash column chromatography over silica gel (heptane with 0-30% ethyl acetate gradient) to give ethyl 5-(5-bromo-2-fluoropyridin-3-yl)-2,3,6,7-tetrahydrooxepine-4-carboxylate as a pale yellow oil in 74% yield. LCMS (m/z) (M+H)=344.0/346.0, Rt=1.04 min. ¹H NMR (400 MHz, Chloroform-d) δ 8.17 (dd, J=2.4, 1.3 Hz, 1H), 7.60 (dd, J=8.2, 2.5 Hz, 1H), 3.96 (q, J=7.1 Hz, 2H), 3.84-3.75 (m, 4H), 2.96-2.86 (m, 2H), 2.78-2.70 (m, 2H), 0.96 (t, J=7.1 Hz, 3H).

Step 4:

N₂ was bubbled through a stirred solution of ethyl 5-(5-bromo-2-fluoropyridin-3-yl)-2,3,6,7-tetrahydrooxepine-4-carboxylate (1.0 equiv), phenylsilane (4 equiv), and TBHP (5.5 M in decane, 4 equiv) in iPrOH (0.05 M) at RT for 20 min. Mn(dpm)₃ (0.1 equiv) was then added and the mixture was further de-gassed for 30 sec more and then allowed to stir at RT for 22 h. The reaction mixture was concentrated and purified by flash column chromatography over silica gel (heptane and 0-50% EtOAc gradient) to give ethyl 5-(5-bromo-2-fluoropyridin-3-yl)oxepane-4-carboxylate as a diastereomeric mixture in 83% yield. LCMS (m/z) (M+H)=346.1/348.1, Rt=1.02 and 1.05 min.

Step 5:

To a solution of ethyl 5-(5-bromo-2-fluoropyridin-3-yl)oxepane-4-carboxylate (1.0 equiv) in DMSO (0.2 M) were added i-Pr₂NEt (4 equiv) and EtNH₂ (2 M in THF, 3.5 equiv) and the mixture was heated at 130° C. for 72 h. The reaction was cooled to RT, poured onto half-saturated NH₄Cl, and extracted twice with EtOAc The combined organics were washed with water and brine, dried over MgSO₄, filtered, and concentrated. The crude material was purified by flash chromatography over silica gel (heptane with 0-50% ethyl acetate gradient) to give (rac)-(5a,11b-trans)-10-bromo-7-ethyl-1,4,5,5a,7,11b-hexahydrooxepino[4,5-c][1,8]naphthyridin-6(2H)-one as the earlier-eluting isomer as a colorless oil in 16% yield. LCMS (m/z) (M+H)=325.0/327.0, Rt=1.05 min. ¹H NMR (400 MHz, Chloroform-d) δ 8.29 (dt, J=2.7, 1.4 Hz, 1H), 7.67-7.61 (m, 1H), 4.31-4.17 (m, 1H), 4.16-4.04 (m, 1H), 4.00 (dd, J=4.5, 3.4 Hz, 1H), 3.97 (ddd, J=4.4, 3.3, 1.4 Hz, 1H), 3.83-3.72 (m, 2H), 2.89-2.77 (m, 2H), 2.47 (ddd, J=13.9, 9.3, 2.5 Hz, 1H), 2.39 (dtd, J=14.5, 4.6, 1.4 Hz, 1H), 2.12-2.00 (m, 1H), 1.95 (dtd, J=14.2, 10.7, 3.1 Hz, 1H), 1.22 (t, J=7.0 Hz, 3H). The later-eluting isomer was isolated to give (rac)-(5a,11b-cis)-10-bromo-7-ethyl-1,4,5,5a,7,11b-hexahydrooxepino[4,5-c][1,8]naphthyridin-6(2H)-one as a white solid in 22% yield. LCMS (m/z) (M+H)=325.0/327.0, Rt=1.02 min. ¹H NMR (400 MHz, Chloroform-d) δ 8.29 (d, J=2.3 Hz, 1H), 7.58-7.52 (m, 1H), 4.26-4.16 (m, 1H), 4.16-4.05 (m, 1H), 3.90-3.66 (m, 4H), 3.16 (ddd, J=10.4, 4.6, 3.0 Hz, 1H), 2.93 (q, J=4.7 Hz, 1H), 2.45 (dtd, J=14.9, 4.7, 3.4 Hz, 1H), 2.05 (dtd, J=15.9, 10.4, 5.5 Hz, 1H), 1.93-1.80 (m, 1H), 1.69 (dq, J=15.1, 3.4 Hz, 1H), 1.20 (t, J=7.0 Hz, 3H).

Syntheses of (5a,11b-cis)-10-bromo-7-ethyl-1,4,5,5a,7,11b-hexahydrooxepino[4,5-c][1,8]naphthyridin-6(2H)-one "Peak 1" and (5a,11b-cis)-10-bromo-7-ethyl-1,4,5,5a,7,11b-hexahydrooxepino[4,5-c][1,8]naphthyridin-6(2H)-one "Peak 2"

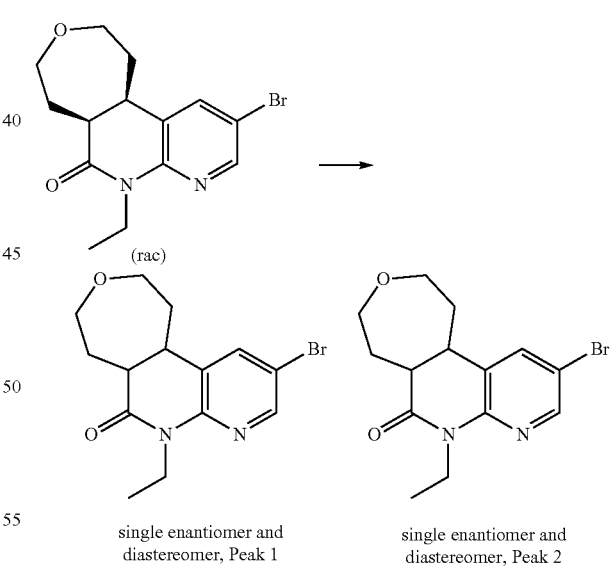

(rac)

single enantiomer and diastereomer, Peak 1 single enantiomer and diastereomer, Peak 2

(rac)-(5a,11b-cis)-10-bromo-7-ethyl-1,4,5,5a,7,11b-hexahydrooxepino[4,5-c][1,8]naphthyridin-6(2H)-one was subjected chiral SFC (IB 21×250 mm column, 10% i-PrOH in CO₂ eluent). The first eluting peak afforded (5a,11b-cis)-10-bromo-7-ethyl-1,4,5,5a,7,11b-hexahydrooxepino[4,5-c][1,8]naphthyridin-6(2H)-one "Peak 1" as a white solid in 38% yield. The second peak afforded (5a,11b-cis)-10-bromo-7-ethyl-1,4,5,5a,7,11b-hexahydrooxepino[4,5-c][1,8]naphthyridin-6(2H)-one "Peak 2" as a white solid in 40% yield.

LCMS data for each enantiomer were identical. LCMS (m/z) (M+H)=325.0/327.0, Rt=1.03 min.

Syntheses of (5a,11b-trans)-10-bromo-7-ethyl-1,4,5, 5a,7,11b-hexahydrooxepino[4,5-c][1,8]naphthyridin-6(2H)-one "Peak 1" and (5a,11b-trans)-10-bromo-7-ethyl-1,4,5,5a,7,11b-hexahydrooxepino[4,5-c][1,8]naphthyridin-6(2H)-one "Peak 2"

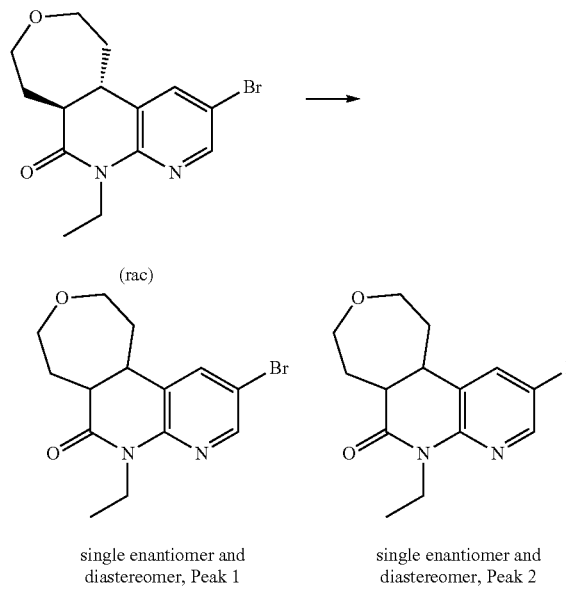

(rac)-(5a,11b-trans)-10-bromo-7-ethyl-1,4,5,5a,7,11b-hexahydrooxepino[4,5-c][1,8]naphthyridin-6(2H)-one was subjected chiral SFC (IC 21×250 mm column, 30% i-PrOH in CO₂ eluent). The first eluting peak afforded (5a,11b-trans)-10-bromo-7-ethyl-1,4,5,5a,7,11b-hexahydrooxepino[4,5-c][1,8]naphthyridin-6(2H)-one "Peak 1" as a white solid in 32% yield. The second peak afforded (5a,11b-trans)-10-bromo-7-ethyl-1,4,5,5a,7,11b-hexahydrooxepino[4,5-c][1,8]naphthyridin-6(2H)-one "Peak 2" as a white solid in 34% yield. LCMS data for each enantiomer were identical. LCMS (m/z) (M+H)=325.0/327.0, Rt=1.05 min.

Syntheses of (4aR,10bS)-9-bromo-6-ethyl-4,4a,6,10b-tetrahydro-1H-pyrano[3,4-c][1,8]naphthyridin-5(2H)-one and (4aS,10bR)-9-bromo-6-ethyl-4,4a,6,10b-tetrahydro-1H-pyrano[3,4-c][1,8]naphthyridin-5(2H)-one

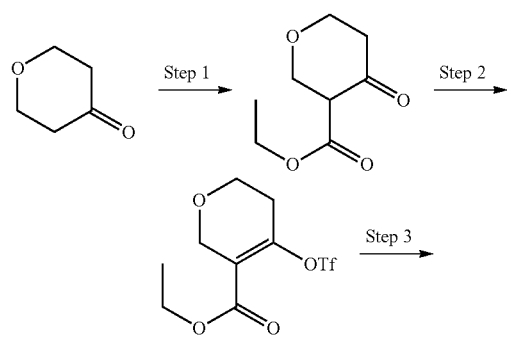

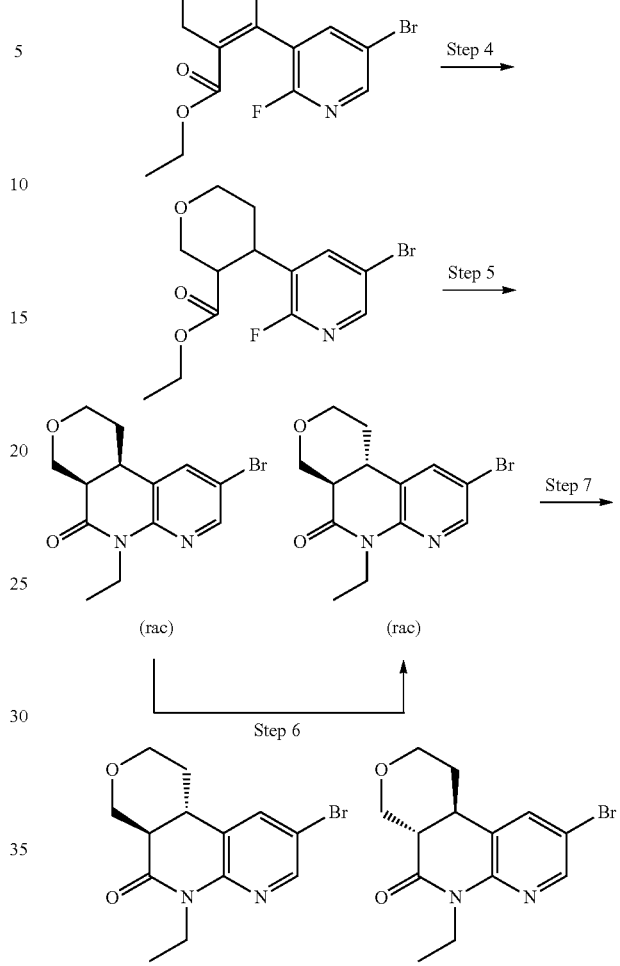

Step 1:

To a stirred solution of tetrahydropyran-4-one (1.0 equiv) in toluene (0.5 M) at −78° C. was slowly added LiHMDS (1 M in THF, 1.1 equiv) and the mixture was stirred for 30 min. Ethyl chloroformate (1.15 equiv) was then added and the reaction was allowed to warm to RT over 15 min. The reaction was quenched by the addition of saturated aqueous NH₄Cl. The layers were separated; the organics were washed with brine, dried over MgSO₄, filtered, and concentrated. The residue was purified by flash chromatography over silica gel (heptane with 0-40% ethyl acetate gradient) to give ethyl 4-oxotetrahydro-2H-pyran-3-carboxylate, as a colorless oil in 18% yield. LCMS (m/z) (M+H)=344.0, Rt=1.13 min. ¹H NMR (400 MHz, Chloroform-d) δ 11.71 (s, 1H), 4.11 (t, J=1.7 Hz, 2H), 4.06 (q, J=7.1 Hz, 2H), 3.69 (t, J=5.7 Hz, 2H), 2.23 (tt, J=5.7, 1.7 Hz, 2H), 1.13 (t, J=7.1 Hz, 3H).

Step 2:

To a stirred solution of ethyl 4-oxotetrahydro-2H-pyran-3-carboxylate (1.0 equiv) in THF (0.4 M) at 25° C. was slowly added 60% NaH (1.3 equiv) and the mixture was stirred for 2 h and then cooled to −78° C. N-phenyl-bis(trifluoromethanesulfonamide) (1.1 equiv) was then added and the reaction was allowed to warm to RT and stirred overnight. The reaction was quenched with saturated aqueous NaHCO₃ and extracted twice with EtOAc. The combined organics were dried over MgSO$_4$, filtered, and concentrated. The residue was purified by flash chromatography over silica gel (heptanes with 0-30% ethyl acetate gradient) to give ethyl 4-(((trifluoromethyl)sulfonyl)oxy)-5,6-dihydro-2H-pyran-3-carboxylate, as a light yellow oil in 122% yield. The excess yield is due to contamination from phenyltriflamide byproducts. $^1$H NMR (400 MHz, Chloroform-d) δ 4.45 (t, J=2.8 Hz, 2H), 4.29 (q, J=7.1 Hz, 2H), 3.89 (t, J=5.5 Hz, 2H), 2.53 (tt, J=5.5, 2.7 Hz, 2H), 1.33 (t, J=7.1 Hz, 3H).

Step 3:

A stirred solution of 4-(((trifluoromethyl)sulfonyl)oxy)-5,6-dihydro-2H-pyran-3-carboxylate (1.0 equiv), 5-bromo-2-fluoropyridine-3-boronic acid (1.05 equiv), and K$_2$CO$_3$ (2.5 equiv) in THF (0.2 M) was purged with N$_2$ for 5 min. Pd(Ph$_3$P)$_4$ (0.05 equiv) was added, and the mixture was purged again for 5 min and then heated at 65° C. for 4 h. The reaction was poured onto water and extracted twice with EtOAc The combined organics were washed with brine, dried over MgSO$_4$, filtered, and concentrated. The residue was adsorbed on Celite and purified by flash column chromatography over silica gel (heptane with 0-30% ethyl acetate gradient) to give ethyl 4-(5-bromo-2-fluoropyridin-3-yl)-5,6-dihydro-2H-pyran-3-carboxylate as a colorless oil in 66% yield. LCMS (m/z) (M+H)=330.0/332.0, Rt=1.04 min. $^1$H NMR (400 MHz, Chloroform-d) δ 8.20 (dd, J=2.4, 1.4 Hz, 1H), 7.66 (dd, J=8.2, 2.5 Hz, 1H), 4.47 (t, J=2.8 Hz, 2H), 4.02 (q, J=7.1 Hz, 2H), 3.90 (t, J=5.5 Hz, 2H), 2.46 (tt, J=5.5, 2.8 Hz, 2H), 1.04 (t, J=7.1 Hz, 3H).

Step 4:

N$_2$ was bubbled through a stirred solution of ethyl 4-(5-bromo-2-fluoropyridin-3-yl)-5,6-dihydro-2H-pyran-3-carboxylate (1.0 equiv), phenylsilane (4 equiv), and TBHP (5.5 M in decane, 4 equiv) in i-PrOH (0.07 M) at RT for 10 min. Mn(dpm)$_3$ (0.15 equiv) was then added and the mixture was further de-gassed for 30 sec more and then allowed to stir at RT overnight. The reaction mixture was concentrated and purified by flash column chromatography over silica gel (heptane and 0-100% EtOAc gradient) to provide ethyl 4-(5-bromo-2-fluoropyridin-3-yl)tetrahydro-2H-pyran-3-carboxylate as a diastereomeric mixture in 52% yield. LCMS (m/z) (M+H)=332.1/334.1, Rt=1.01 and 1.03 min.

Step 5:

To a solution of 4 ethyl 4-(5-bromo-2-fluoropyridin-3-yl)tetrahydro-2H-pyran-3-carboxylate (1.0 equiv) in DMSO (0.25 M) were added i-Pr$_2$NEt (4 equiv) and EtNH$_2$ (2 M in THF, 3.5 equiv) and the mixture was heated at 120° C. overnight. The reaction was cooled to RT, poured onto half-saturated NH$_4$Cl, and extracted twice with EtOAc The combined organics were washed with water brine, dried over MgSO$_4$, filtered, and concentrated. The crude material was purified by flash chromatography over silica gel (heptane with 0-30% ethyl acetate gradient) to give (rac)-(4a,10b-trans)-9-bromo-6-ethyl-4,4a,6,10b-tetrahydro-1H-pyrano[3,4-c][1,8]naphthyridin-5(2H)-one as the earlier-eluting isomer as a white solid in 36% yield. LCMS (m/z) (M+H)=311.0/313.0, Rt=1.04 min. $^1$H NMR (400 MHz, Chloroform-d) δ 8.32 (dd, J=2.3, 1.0 Hz, 1H), 7.53 (dd, J=2.2, 1.4 Hz, 1H), 4.51 (dd, J=11.9, 4.6 Hz, 1H), 4.20 (dt, J=13.8, 6.9 Hz, 2H), 4.12-4.00 (m, 1H), 3.57-3.48 (m, 2H), 2.86-2.75 (m, 1H), 2.38 (ddd, J=14.7, 10.5, 4.6 Hz, 1H), 2.17 (ddd, J=11.2, 4.0, 2.0 Hz, 1H), 1.74 (qd, J=12.5, 4.6 Hz, 1H), 1.20 (t, J=7.0 Hz, 4H). The later-eluting isomer was isolated to giv (rac)-(4a,10b-cis)-9-bromo-6-ethyl-4,4a,6,10b-tetrahydro-1H-pyrano[3,4-c][1,8]naphthyridin-5(2H)-one as a white solid in 44% yield. LCMS (m/z) (M+H)=311.0/313.0, Rt=0.98 min. 1H NMR (400 MHz, Chloroform-d) δ 8.31 (d, J=2.3 Hz, 1H), 7.56 (d, J=2.4 Hz, 1H), 4.77-4.68 (m, 1H), 4.33-4.21 (m, 1H), 4.19-4.09 (m, 1H), 4.00 (ddd, J=11.5, 4.1, 2.3 Hz, 1H), 3.58-3.46 (m, 2H), 3.09 (dt, J=11.8, 5.1 Hz, 1H), 2.68-2.60 (m, 1H), 1.80-1.66 (m, 1H), 1.61 (d, J=2.8 Hz, 1H), 1.22 (t, J=7.0 Hz, 4H).

Step 6:

A stirred mixture of (rac)-(4a,10b-cis)-9-bromo-6-ethyl-4,4a,6,10b-tetrahydro-1H-pyrano[3,4-c][1,8]naphthyridin-5(2H)-one (1.0 equiv) in EtOH (0.1 M) was gently heated with a heat gun until all solid was in solution. To this was added NaOEt (21% in EtOH, 1.0 equiv) and the mixture was stirred for 3 h at RT. The mixture was concentrated, and the residue was partitioned between EtOAc and half-saturated NH$_4$Cl. The aqueous layer was extracted twice with EtOAc, and the combined organics were washed with water and brine, dried over MgSO$_4$, filtered, and concentrated. The residue was purified by flash chromatography over silica gel (heptane and 0-50% EtOAc gradient) to provide (rac)-(4a,10b-trans)-9-bromo-6-ethyl-4,4a,6,10b-tetrahydro-1H-pyrano[3,4-c][1,8]naphthyridin-5(2H)-one in 38% yield along with recovered starting material in 58% yield. LCMS (m/z) (M+H)=310.9/312.9, Rt=1.04 min.

Step 7:

(rac)-(4a,10b-trans)-9-bromo-6-ethyl-4,4a,6,10b-tetrahydro-1H-pyrano[3,4-c][1,8]naphthyridin-5(2H)-one was subjected chiral SFC (ID 21×250 mm column, 15% MeOH in CO$_2$ eluent). The first eluting peak afforded (4aR,10bS)-9-bromo-6-ethyl-4,4a,6,10b-tetrahydro-1H-pyrano[3,4-c][1,8]naphthyridin-5(2H)-one as a white solid in 45% yield. The second peak afforded (4aS,10bR)-9-bromo-6-ethyl-4,4a,6,10b-tetrahydro-1H-pyrano[3,4-c][1,8]naphthyridin-5(2H)-one as a white solid in 46% yield. LCMS data for each enantiomer were identical. LCMS (m/z) (M+H)=311.0/313.0, Rt=1.04 min.

Syntheses of (4aR,10bS)-9-bromo-4,4a,6,10b-tetrahydro-1H-pyrano[3,4-c][1,8]naphthyridin-5(2H)-one and (4aS,10bR)-9-bromo-4,4a,6,10b-tetrahydro-1H-pyrano[3,4-c][1,8]naphthyridin-5(2H)-one

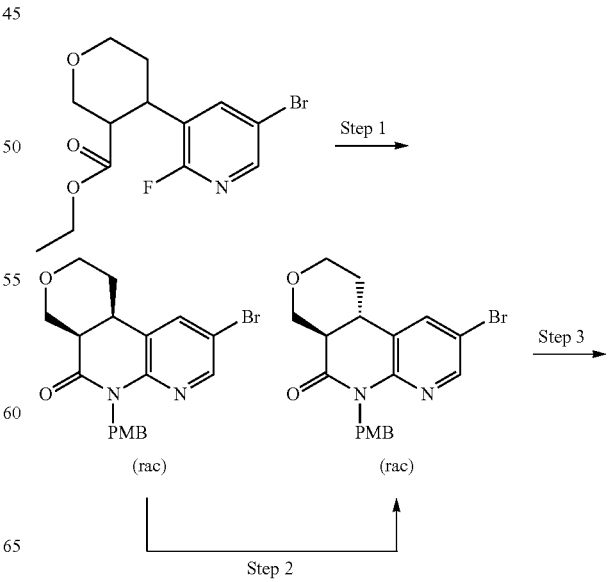

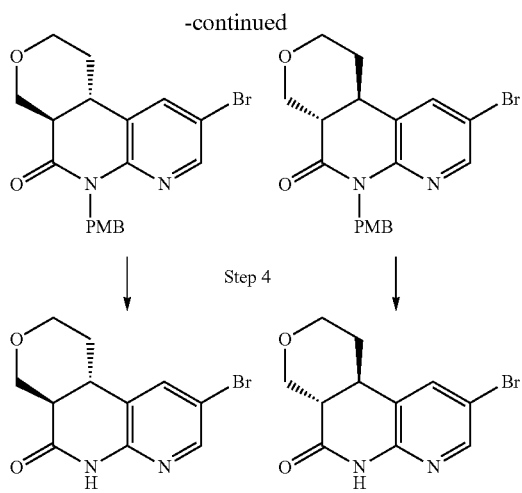

Step 1:

Ethyl 4-(5-bromo-2-fluoropyridin-3-yl)tetrahydro-2H-pyran-3-carboxylate (1.0 equiv) was dissolved in DMSO (0.2 m). i-Pr₂NEt (5 equiv) and 4-methoxybenzylamine (4.5 equiv) were added and the mixture was heated at 130° C. for 48 h. The reaction was poured onto half-saturated NH₄Cl and extracted twice with EtOAc The combined organics were washed with water and brine dried over MgSO₄, filtered, and concentrated. The residue was and purified by flash column chromatography over silica gel (heptane and 0-50% EtOAc gradient). The less polar product peak provided (rac)-(4a,10b-trans)-9-bromo-6-(4-methoxybenzyl)-4,4a,6,10b-tetrahydro-1H-pyrano[3,4-c][1,8]naphthyridin-5(2H)-one as a pale yellow solid in 38% yield. LCMS (m/z) (M+H)=403.1/405.1, Rt=1.20 min. ¹H NMR (400 MHz, Chloroform-d) δ 8.33 (dd, J=2.3, 1.0 Hz, 1H), 7.52 (dd, J=2.2, 1.4 Hz, 1H), 7.38-7.31 (m, 2H), 6.84-6.75 (m, 2H), 5.33-5.17 (m, 2H), 4.51 (dd, J=11.9, 4.6 Hz, 1H), 4.18 (dd, J=11.7, 3.9 Hz, 1H), 3.76 (s, 3H), 3.59-3.46 (m, 2H), 2.87-2.73 (m, 1H), 2.43 (ddd, J=14.7, 10.5, 4.6 Hz, 1H), 2.24-2.07 (m, 1H), 1.74 (qd, J=12.4, 4.6 Hz, 1H).

The more polar product peak gave (rac)-(4a,10b-cis)9-bromo-6-(4-methoxybenzyl)-4,4a,6,10b-tetrahydro-1H-pyrano[3,4-c][1,8]naphthyridin-5(2H)-one as a pale yellow foam in 41% yield. LCMS (m/z) (M+H)=403.1/405.1, Rt=1.16 min.

Step 2:

To a stirred mixture of (rac)-(4a,10b-cis)9-bromo-6-(4-methoxybenzyl)-4,4a,6,10b-tetrahydro-1H-pyrano[3,4-c][1,8]naphthyridin-5(2H)-one (1.0 equiv) in EtOH (0.2 M) was added NaOEt (21% in EtOH, 1.0 equiv) and the mixture was stirred overnight at RT. The mixture was concentrated, and the residue was partitioned between EtOAc and half-saturated NH₄Cl. The aqueous layer was extracted twice with EtOAc, and the combined organics were washed with water and brine, dried over MgSO₄, filtered, and concentrated. The residue was purified by flash column chromatography over silica gel (heptane and 0-50% EtOAc gradient) to provide (rac)-(4a,10b-trans)-9-bromo-6-(4-methoxybenzyl)-4,4a,6,10b-tetrahydro-1H-pyrano[3,4-c][1,8]naphthyridin-5(2H)-one in 66%. LCMS (m/z) (M+H)=403.1/405.1, Rt=1.20 min.

Step 3:

(rac)-(4a,10b-trans)-9-bromo-6-(4-methoxybenzyl)-4,4a,6,10b-tetrahydro-1H-pyrano[3,4-c][1,8]naphthyridin-5(2H)-one was subjected chiral SFC (ID 21×250 mm column, 30% MeOH in CO₂ containing 10 mM NH₄OH eluent). The first eluting peak afforded (4aR,10bS)-9-bromo-6-(4-methoxybenzyl)-4,4a,6,10b-tetrahydro-1H-pyrano[3,4-c][1,8]naphthyridin-5(2H)-one as a white foam in 40% yield. The second peak afforded (4aS,10bR)-9-bromo-6-(4-methoxy-benzyl)-4,4a,6,10b-tetrahydro-1H-pyrano[3,4-c][1,8]naphthyridin-5(2H)-one as a white foam in 42% yield. LCMS data for each enantiomer were identical. LCMS (m/z) (M+H)=403.1/405.1, Rt=1.20 min.

Step 4:

To a stirred solution of (4aS,10bR)-9-bromo-6-(4-methoxybenzyl)-4,4a,6,10b-tetrahydro-1H-pyrano[3,4-c][1,8]naphthyridin-5(2H)-one (1.0 equiv) in DCM (0.1 M) was slowly added triflic acid (6.5 equiv) and the mixture was stirred at 25° C. for 2 h. The reaction was concentrated to remove most of the DCM, diluted with water and saturated aqueous Na₂CO₃ was added to basify the mixture. The heterogeneous mixture was stirred for 5 min and then filtered, washing with water, Et₂O, and heptane. The so-obtained solid was dried under vacuum overnight to give an off-white solid The filtrate was poured into a separatory funnel and extracted three times with 30% i-PrOH/CHCl₃. The combined organics were dried over MgSO₄, filtered, and concentrated. The residue was purified by flash column chromatography over silica gel (DCM and 0-100% EtOAc gradient). Product isolated was combined with the previously isolated solid to provide (4aS,10bR)-9-bromo-4,4a,6,10b-tetrahydro-1H-pyrano[3,4-c][1,8]naphthyridin-5(2H)-one as a white solid in quantitative yield. In an analogous manner, (4aR,10bS)-9-bromo-6-(4-methoxybenzyl)-4,4a,6,10b-tetrahydro-1H-pyrano[3,4-c][1,8]naphthyridin-5(2H)-one provided (4aR,10bS)-9-bromo-4,4a,6,10b-tetrahydro-1H-pyrano[3,4-c][1,8]naphthyridin-5(2H)-one in quantitative yield. The LCMS and NMR spectra of the two enantiomers were identical. LCMS (m/z) (M+H)=283.0/285.0, Rt=0.70. ¹H NMR (400 MHz, DMSO-d6) δ 10.81 (s, 1H), 8.37-8.15 (m, 1H), 7.76 (s, 1H), 4.20 (dd, J=11.4, 4.4 Hz, 1H), 4.02 (dd, J=11.4, 3.5 Hz, 1H), 3.47-3.36 (m, 2H), 3.03-2.89 (m, 1H), 2.42 (ddd, J=14.6, 10.6, 4.4 Hz, 1H), 2.28 (d, J=11.4 Hz, 1H), 1.54 (qd, J=12.4, 4.5 Hz, 1H).

Synthesis of (4aS,10bR)-9-bromo-6-(2-hydroxyethyl)-4,4a,6,10b-tetrahydro-1H-pyrano[3,4-c][1,8]naphthyridin-5(2H)-one

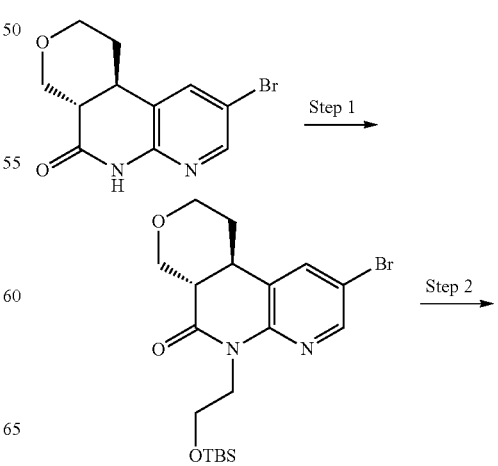

-continued

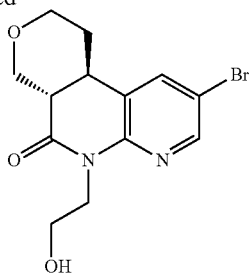

Step 1:
To a stirred solution of (4aS,10bR)-9-bromo-4,4a,6,10b-tetrahydro-1H-pyrano[3,4-c][1,8]naphthyridin-5(2H)-one (1.0 equiv) in DMF (0.1 M) at 25° C. were added $Cs_2CO_3$ (6 equiv) and (2-bromoethoxy)-tert-butyldimethylsilane (3 equiv) and the reaction was stirred for 4.5 h. The mixture was poured onto water and extracted three times with ethyl acetate. The combined organics were washed with water and brine, dried over magnesium sulfate, filtered, and concentrated. The residue purified by flash chromatography over silica gel (heptane and 0-40% EtOAc gradient) to give (4aS,10bR)-9-bromo-6-(2-((tert-butyldimethylsilyl)oxy)ethyl)-4,4a,6,10b-tetrahydro-1H-pyrano[3,4-c][1,8]naphthyridin-5(2H)-one as a white crystalline solid in 63% yield. LCMS (m/z) (M+H)=441.3/443.3, Rt=1.57 min Step 2:
To a stirred solution of (4aS,10bR)-9-bromo-6-(2-((tert-butyldimethylsilyl)oxy)ethyl)-4,4a,6,10b-tetrahydro-1H-pyrano[3,4-c][1,8]naphthyridin-5(2H)-one (1.0 equiv) in DCM (0.05 M) at 25° C. was added TfOH (1.5 equiv) and the reaction was stirred for 1 h. The mixture was partitioned between DCM and saturated aqueous $NaHCO_3$ and extracted three times with DCM. The combined organics were washed with brine, dried over magnesium sulfate, filtered, and concentrated. The residue was purified by flash column chromatography over silica gel (heptane and 0-100% EtOAc gradient) to provide (4aS,10bR)-9-bromo-6-(2-hydroxyethyl)-4,4a,6,10b-tetrahydro-1H-pyrano[3,4-c][1,8]naphthyridin-5(2H)-one as a colorless oil in 80% yield. LCMS (m/z) (M+H)=327.1/329.1, Rt=0.79 min Synthesis of (4aS,10bR)-9-bromo-6-isopropyl-4,4a,6,10b-tetrahydro-1H-pyrano[3,4-c][1,8]naphthyridin-5(2H)-one

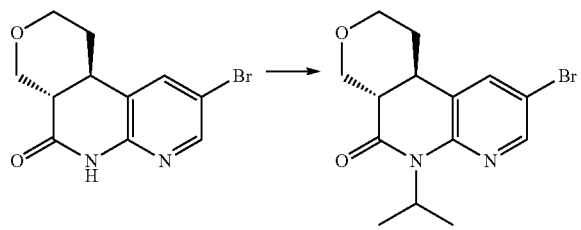 [SMILES: O=C1Nc2ncc(Br)cc2[C@@H]2CCOC[C@@H]12 ; CC(C)N1C(=O)[C@@H]2COCC[C@H]2c2cc(Br)cnc21]

To a stirred solution of (4aS,10bR)-9-bromo-4,4a,6,10b-tetrahydro-1H-pyrano[3,4-c][1,8]naphthyridin-5(2H)-one (1.0 equiv) in DMF (0.1 M) at 25° C. were added $Cs_2CO_3$ (3 equiv) and 2-iodopropane (2.0 equiv) and the reaction was stirred for 4.5 h. The mixture was poured onto water and extracted three times with ethyl acetate. The combined organics were washed with water and brine, dried over magnesium sulfate, filtered, and concentrated. The so-obtained residue was used as (4aS,10bR)-9-bromo-6-isopropyl-4,4a,6,10b-tetrahydro-1H-pyrano[3,4-c][1,8]naphthyridin-5(2H)-one without further purification. LCMS (m/z) (M+H)=325.0/327.0, Rt=1.17 min.

Synthesis of (4aS,10bR)-9-bromo-6-(2,2-difluoroethyl)-4,4a,6,10b-tetrahydro-1H-pyrano[3,4-c][1,8]naphthyridin-5(2H)-one

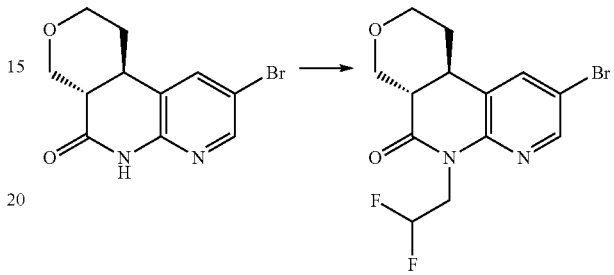

To a stirred solution of (4aS,10bR)-9-bromo-4,4a,6,10b-tetrahydro-1H-pyrano[3,4-c][1,8]naphthyridin-5(2H)-one (1.0 equiv) in DMF (0.1 M) at 25° C. were added $Cs_2CO_3$ (3 equiv) and 2-iodopropane (2.0 equiv) and the reaction was stirred for 4 h. The mixture was poured onto water and extracted three times with ethyl acetate. The combined organics were washed with water and brine, dried over magnesium sulfate, filtered, and concentrated. The so-obtained residue was used as (4aS,10bR)-9-bromo-6-(2,2-difluoroethyl)-4,4a,6,10b-tetrahydro-1H-pyrano[3,4-c][1,8]naphthyridin-5(2H)-one without further purification. LCMS (m/z) (M+H)=347.0/349.0, Rt=1.04 min.

Synthesis of (4aS,10bR)-9-bromo-6-(2-hydroxy-2-methylpropyl)-4,4a,6,10b-tetrahydro-1H-pyrano[3,4-c][1,8]naphthyridin-5(2H)-one

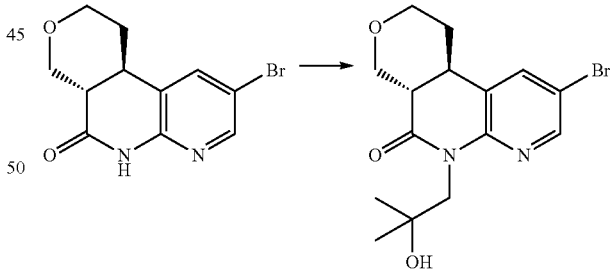

To a stirred solution of (4aS,10bR)-9-bromo-4,4a,6,10b-tetrahydro-1H-pyrano[3,4-c][1,8]naphthyridin-5(2H)-one (1.0 equiv) in DMF (0.15 M) at 25° C. were added $Cs_2CO_3$ (10 equiv), 1-chloro-2-methyl-2-propanol (7 equiv) and NaI (0.1 equiv) and the reaction was heated to 100° C. and stirred for 72 h. The mixture was poured onto water and extracted three times with ethyl acetate. The combined organics were washed with water and brine, dried over magnesium sulfate, filtered, and concentrated. The residue was purified by flash column chromatography over silica gel (heptane and 0-100% EtOAc gradient) to give (4aS,10bR)-9-bromo-6-(2-hydroxy-2-methylpropyl)-4,4a,6,10b-tetrahydro-1H-pyrano

[3,4-c][1,8]naphthyridin-5(2H)-one as a pale yellow solid in 22% yield LCMS (m/z) (M+H)=355.1/357.1, Rt=0.86 min.

Synthesis of (4aR,10bR)-9-bromo-6-ethyl-2,4,4a,5,6,10b-hexahydro-1H-pyrano[3,4-c][1,8]naphthyridine

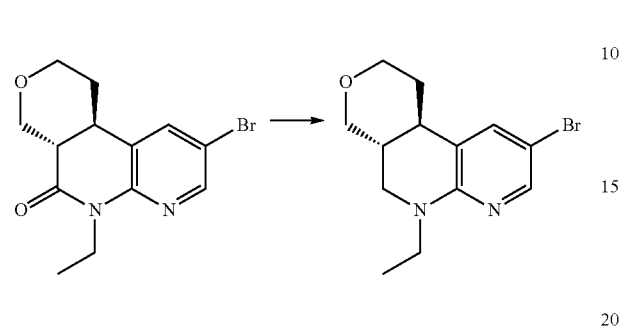

To a stirred solution of (4aS,10bR)-9-bromo-6-ethyl-4,4a,6,10b-tetrahydro-1H-pyrano[3,4-c][1,8]naphthyridin-5(2H)-one (1.0 equiv) in THF (0.2 M) at 25° C. was added BH₃.THF (1.0 M in THF, 3 equiv) and 2-iodopropane (2.0 equiv) and the reaction was heated to 60° C. stirred overnight. The reaction was quenched with MeOH, stirred for 5 min, and then and concentrated. The so-obtained residue was purified by flash column chromatography over silica gel (heptane and 0-100% EtOAc gradient) to give (4aR,10bR)-9-bromo-6-ethyl-2,4,4a,5,6,10b-hexahydro-1H-pyrano[3,4-c][1,8]naphthyridine as a white solid in 96% yield. LCMS (m/z) (M+H)=297.0/299.0, Rt=0.71 min.

Synthesis of (R)-10-chloro-7-(2-hydroxy-2-methylpropyl)-4,4a,5,7-tetrahydro-1H-[1,4]oxazino[4,3-d]pyrido[2,3-b][1,4]diazepin-6(2H)-one

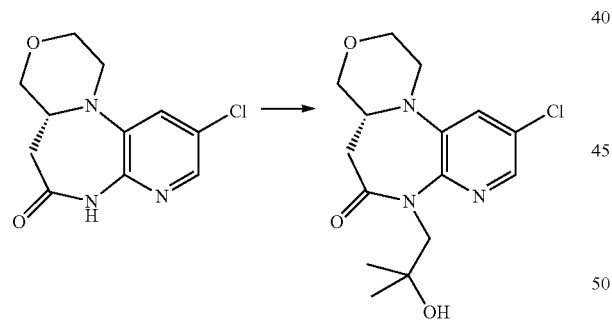

To a stirred solution (R)-10-chloro-4,4a,5,7-tetrahydro-1H-[1,4]oxazino[4,3-d]pyrido[2,3-b][1,4]diazepin-6(2H)-one in DMF (0.15 M) at 25° C. were added Cs₂CO₃ (5 equiv) and isobutylene oxide (3.5 equiv) and the reaction was heated to 100° C. and stirred for 48 h. The mixture was poured onto water and extracted three times with ethyl acetate. The combined organics were washed with water and brine, dried over magnesium sulfate, filtered, and concentrated. The residue was purified by flash column chromatography over silica gel (heptane and 0-100% EtOAc gradient) to give (R)-10-chloro-7-(2-hydroxy-2-methylpropyl)-4,4a,5,7-tetrahydro-1H-[1,4]oxazino[4,3-d]pyrido[2,3-b][1,4]diazepin-6(2H)-one as a yellow oil in 70% yield LCMS (m/z) (M+H)=326.8, Rt=0.75 min.

Syntheses of 11-chloro-1,2,4,5,5a,6-hexahydropyrido[3',2':2,3][1,4]diazepino[1,7-d][1,4]oxazepin-7(8H)-one "Peak 1" and 11-chloro-1,2,4,5,5a,6-hexahydropyrido[3',2':2,3][1,4]diazepino[1,7-d][1,4]oxazepin-7(8H)-one "Peak 2"

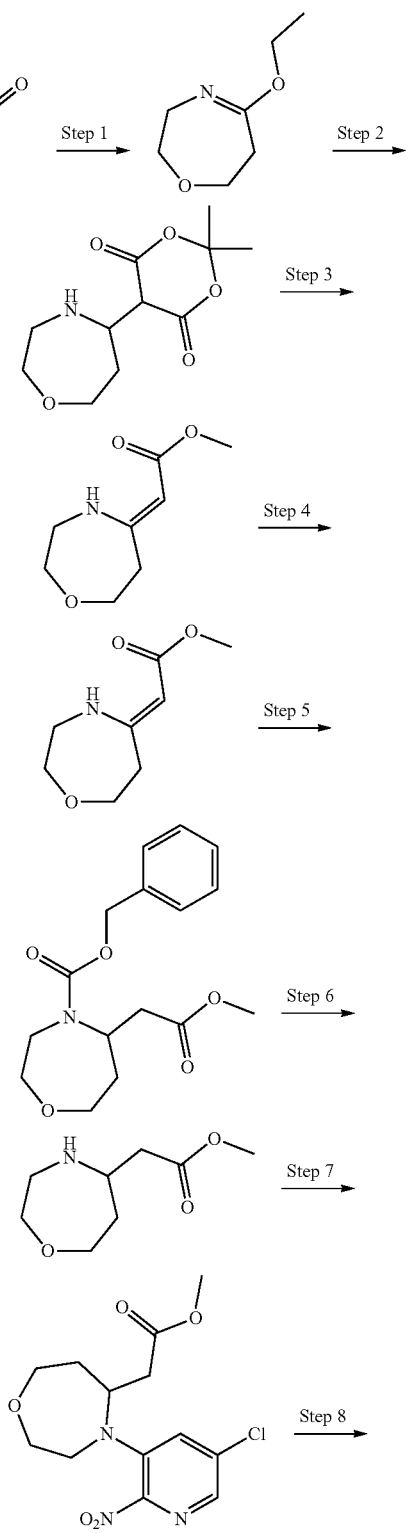

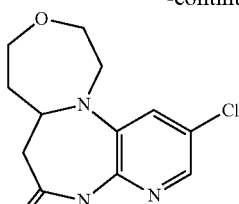
single enantiomer, Peak 1

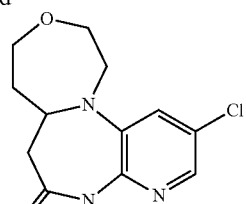
single enantiomer, Peak 2

Step 1:

1,4-Oxazepan-5-one (1 equiv) was dissolved into anhydrous DCM (0.98 M) with stirring. Triethyloxonium tetrafluoroborate (1 equiv) was added in several portions and the reaction was allowed to stir at 23° C. After 16 hr the reaction was shaken vigorously with saturated aqueous NaHCO$_3$ until the effervescence subsided. The organic layer was washed with brine and dried over anhydrous granular Na$_2$SO$_4$ then filtered and evaporated to yield a tan oily 5-ethoxy-2,3,6,7-tetrahydro-1,4-oxazepine in 89% yield. $^1$H NMR (400 MHz, Chloroform-d) δ 4.04 (q, J=7.1 Hz, 2H), 3.75-3.71 (m, 2H), 3.71-3.65 (m, 2H), 3.60-3.55 (m, 2H), 2.77-2.60 (m, 2H), 1.29 (t, J=7.1 Hz, 3H).

Step 2:

5-Ethoxy-2,3,6,7-tetrahydro-1,4-oxazepine (1 equiv) was dissolved into anhydrous benzene (1 M) with 2,2-dimethyl-1,3-dioxane-4,6-dione (1 equiv) and triethylamine (0.2 equiv) in a round bottom flask then heated to reflux with reflux condenser under an atmosphere of nitrogen. After 16 hr starting material had been consumed volatiles were removed and the crude oily 2,2-dimethyl-5-(1,4-oxazepan-5-ylidene)-1,3-dioxane-4,6-dione formed in 85% yield used as-is in the next step.

Step 3:

2,2-Dimethyl-5-(1,4-oxazepan-5-ylidene)-1,3-dioxane-4,6-dione (1 equiv) was dissolved into anhydrous MeoH (0.3 M) in a round bottom flask with reflux condenser and treated with sodium methoxide (3 equiv) added in one portion. The mixture was then heated to reflux with stirring under a nitrogen atmosphere. After three hours the volatiles were removed and the residue taken up into saturated ammonium chloride solution. The pH was further adjusted to ~7 with the addition of 6N HCl. The yellow solution was extracted with DCM three times. The organics were combined, washed with brine and dried over anhydrous Na$_2$SO$_4$ then filtered and evaporated to yield a crude yellow oily methyl 2-(1,4-oxazepan-5-ylidene)acetate which was used as-is in further chemistry. LCMS (m/z) (M+H)=172.0, Rt=0.74 min.

Step 4:

Methyl 2-(1,4-oxazepan-5-ylidene)acetate (1 equiv) was dissolved into a 25% mixture of acetic acid in dioxane (0.3 M). This solution was treated with sodium borohydride (1 equiv) portionwise. Initial yellow color fades slightly upon addition and as reaction progresses. After 30 min the reaction was filtered and evaporated to yield an oil which was taken up into a 50:50 mixture of THF and saturated NaHCO$_3$ (0.3 M) then treated with benzyl carbonochloridate (1 equiv) and allowed to stir vigorously overnight. After 16 hr the reaction was diluted with EtOAc and the layers separated. The organic layer was washed with brine and dried with Na$_2$SO$_4$. Volatiles were removed to yield a colorless crude oil which was purified by flash column chromatography over silica gel (heptane with 0-35% ethyl acetate gradient). Fractions containing desired product were combined and evaporated to yield a colorless oily benzyl 5-(2-methoxy-2-oxoethyl)-1,4-oxazepane-4-carboxylate in 39.4% yield. $^1$H NMR (400 MHz, Chloroform-d) δ 7.45-7.31 (m, 5H), 5.23-5.12 (m, 2H), 4.54 (ddq, J=19.7, 12.2, 6.5 Hz, 1H), 4.04-3.81 (m, 3H), 3.64 (d, J=18.8 Hz, 3H), 3.57-3.33 (m, 2H), 3.26-3.09 (m, 1H), 2.63 (ddd, J=14.7, 11.2, 5.9 Hz, 1H), 2.49 (td, J=14.7, 7.6 Hz, 1H), 2.26 (ddt, J=15.6, 12.4, 6.5 Hz, 1H), 1.92-1.76 (m, 1H). LCMS (m/z) (M+H)=308.3, Rt=0.98 min.

Step 5:

Benzyl 5-(2-methoxy-2-oxoethyl)-1,4-oxazepane-4-carboxylate (1 equiv) was dissolved into a 1:1 mixture of ethyl acetate and methanol (0.102 M) in a round bottom flask with stir bar. The reaction was purged of oxygen by evacuating and purging up with nitrogen. 10% Palladium on carbon (0.1 equiv) was added in one portion and the flask evacuated. The atmosphere was replaced with hydrogen from a balloon source (1 atm) and stirred vigorously. After 2 hours the was diluted with DCM and celite was added to aggregate the palladium on carbon. The reaction was carefully filtered through a pad of celite such that the filter cake never became dry. The filtrate was evaporated to yield a clear oily methyl 2-(1,4-oxazepan-5-yl)acetate in 93% yield which was pure enough to use as-is in further chemistry. $^1$H NMR (400 MHz, Chloroform-d) δ 3.89-3.74 (m, 3H), 3.72 (s, 3H), 3.33 (dtt, J=7.7, 5.6, 4.2 Hz, 1H), 3.06 (ddd, J=14.4, 4.3, 3.4 Hz, 1H), 2.94 (ddd, J=14.4, 8.7, 3.5 Hz, 1H), 2.49 (dd, J=6.7, 3.2 Hz, 2H), 2.09-2.02 (m, 2H), 2.02-1.93 (m, 1H), 1.72 (dddd, J=14.5, 9.5, 8.3, 4.4 Hz, 1H).

Step 6:

5-Chloro-3-fluoro-2-nitropyridine (1 equiv) was dissolved into of anhydrous DMF (0.182 M) along with methyl 2-(1,4-oxazepan-5-yl)acetate (1.1 equiv) and triethylamine (3 equiv). The mixture was heated to 80° C. under an atmosphere of nitrogen with reflux condenser and stirring overnight. After 16 hours the reaction was poured into H$_2$O and extracted three times with EtOAc. Organics were combined, washed with brine, and dried anhydrous Na$_2$SO$_4$. The volatiles were removed and the residue was purified by flash column chromatography over silica gel, eluting with heptane and 0-40% EtOAc gradient to give a yellow oil methyl 2-(4-(5-chloro-2-nitropyridin-3-yl)-1,4-oxazepan-5-yl)acetate in 54.4% yield. LCMS (m/z) (M+H)=330.1, Rt=0.91 min.

Step 7:

Methyl 2-(4-(5-chloro-2-nitropyridin-3-yl)-1,4-oxazepan-5-yl)acetate (1 equiv) was dissolved into 11 ml of glacial acetic acid along with iron dust (10 equiv) in a round bottom flask with magnetic stirring and reflux condenser. The reaction was heated to 80° C. whereupon it darkened and eventually an off-white suspension formed. The reaction was heated to 110° C. and left to for 16 hours, and then diluted into EtOAc and filtered through Celite. The filter cake was washed with EtOAc and DCM. The filtrate was evaporated and the residue partitioned between saturated aqueous NaHCO$_3$ and EtOAc to remove leftover acetic acid. The organic layer was washed with brine, dried over Na$_2$SO$_4$ then evaporated to yield a tan solid which was purified by flash column chromatography over silica gel (heptane with 40-80% ethyl acetate gradient) to give (rac)-11-chloro-1,2,4,5,5a,6-hexahydropyrido[3',2':2,3][1,4]diazepino[1,7-d][1,4]oxazepin-7(8H)-one as off white crystals in 63.3% yield. (rac)-11-Chloro-1,2,4,5,5a,6-hexahydropyrido[3',2':2,3][1,4]diazepino[1,7-d][1,4]oxazepin-7(8H)-one was subjected to chiral SFC (Whelk-O1 RR 21×250 mm column, 30% IPA in CO$_2$ eluent). The first eluting peak afforded 11-chloro-1,2,4,5,5a,6-hexahydropyrido[3',2':2,3]

[1,4]diazepino[1,7-d][1,4]oxazepin-7(8H)-one "Peak 1" as a white solid in 19.5% yield. The second eluting peak afforded 11-chloro-1,2,4,5,5a,6-hexahydropyrido[3',2':2,3][1,4]diazepino[1,7-d][1,4]oxazepin-7(8H)-one "Peak 2" as a white solid in 19.5% yield. NMR and LCMS data for each enantiomer matched that of the racemate.

Synthesis of 11-chloro-8-ethyl-1,2,4,5,5a,6-hexahydropyrido[3',2':2,3][1,4]diazepino[1,7-d][1,4]oxazepin-7(8H)-one

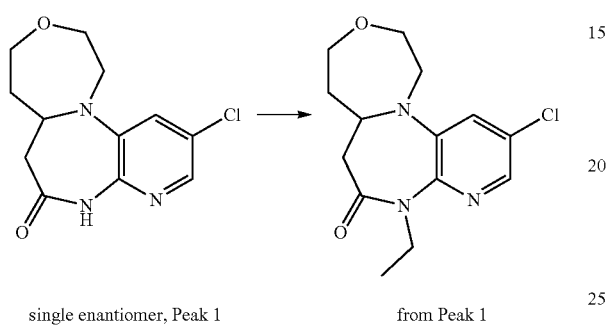

single enantiomer, Peak 1    from Peak 1

A vial was charged with 11-chloro-1,2,4,5,5a,6-hexahydropyrido[3',2':2,3][1,4]diazepino[1,7-d][1,4]oxazepin-7(8H)-one "Peak 1" (1 equivalent) dissolved into anhydrous DMF (0.1 M) and treated with Cs$_2$CO$_3$ (1.5 equivalent) and ethyl iodide (1.25 equivalent). The reaction was allowed to stir at room temperature for 16 hrs. The reaction was poured into water and extracted three times with EtOAc. The organics were combined and washed with brine and dried over Na$_2$SO$_4$. The volatiles were removed to yield a clear light tan oily 11-chloro-8-ethyl-1,2,4,5,5a,6-hexahydropyrido[3',2':2,3][1,4]diazepino[1,7-d][1,4]oxazepin-7(8H)-one (single enantiomer, from Peak 1) in 87% yield which was of sufficient purity to carry on as-is. LCMS (m/z) (M+H)=296.1, Rt=0.88 min.

In a similar fashion, 11-chloro-1,2,4,5,5a,6-hexahydropyrido[3',2':2,3][1,4]diazepino[1,7-d][1,4]oxazepin-7(8H)-one "Peak 2" was transformed to yield 11-chloro-8-ethyl-1,2,4,5,5a,6-hexahydropyrido[3',2':2,3][1,4]diazepino[1,7-d][1,4]oxazepin-7(8H)-one (single enantiomer, from Peak 2). The analytics of both enantiomers were identical.

Synthesis of 11-chloro-8-(2-hydroxyethyl)-1,2,4,5,5a,6-hexahydropyrido[3',2':2,3][1,4]diazepino[1,7-d][1,4]oxazepin-7(8H)-one

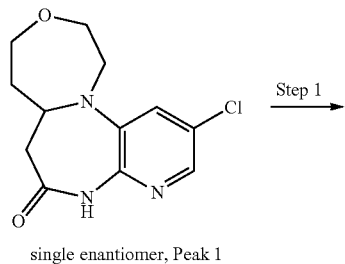

single enantiomer, Peak 1

Step 1:
11-Chloro-1,2,4,5,5a,6-hexahydropyrido[3',2':2,3][1,4]diazepino[1,7-d][1,4]oxazepin-7(8H)-one "single enantiomer, Peak 1" (1 equiv) was dissolved into anhydrous DMF (0.1 M) and treated with Cs$_2$CO$_3$ (1.5 equiv) and (2-bromoethoxy)(tert-butyl)dimethylsilane (1.25 equiv). The reaction was allowed to stir at room temperature for 1 hr whereupon sodium iodide (0.25 equiv) was added and the reaction was warmed to 55° C. using an oil bath overnight. After 16 hr the reaction was poured into H$_2$O and extracted three times with EtOAc. Organics were combined and dried with brine followed by Na$_2$SO$_4$. Volatiles were removed to yield a clear light tan oily 8-(2-((tert-butyldimethylsilyl)oxy)ethyl)-11-chloro-1,2,4,5,5a,6-hexahydropyrido[3',2':2,3][1,4]diazepino[1,7-d][1,4]oxazepin-7(8H)-one (single enantiomer, from Peak 1) in 83% yield which was of sufficient purity to carry on to further chemistry. LCMS (m/z) (M+H)=426.3, R$_f$=1.48 min.

Step 2:
8-(2-((Tert-butyldimethylsilyl)oxy)ethyl)-11-chloro-1,2,4,5,5a,6-hexahydropyrido[3',2':2,3][1,4]diazepino[1,7-d][1,4]oxazepin-7(8H)-one (1 equiv) was dissolved into anhydrous THF (0.111 M) and treated with TBAF in THF (1 M, 3 equiv). The reaction was allowed to stir at room temperature for 16 hr whereupon the volatiles were removed and the residue was purified by flash column chromatography over silica gel, eluting with heptane and 0-85% EtOAc gradient, to give 11-chloro-8-(2-hydroxyethyl)-1,2,4,5,5a,6-hexahydropyrido [3',2':2,3][1,4]diazepino[1,7-d][1,4]oxazepin-7(8H)-one (single enantiomer, from Peak 1) in 74% yield. LCMS (m/z) (M+H)=312.1, R$_f$=0.67 min.

In a similar fashion, 11-chloro-1,2,4,5,5a,6-hexahydropyrido[3',2':2,3][1,4]diazepino[1,7-d][1,4]oxazepin-7(8H)-one "Peak 2" was transformed to yield 11-chloro-8-(2-hydroxyethyl)-1,2,4,5,5a,6-hexahydropyrido[3',2':2,3][1,4]diazepino[1,7-d][1,4]oxazepin-7(8H)-one (single enantiomer, from Peak 2). The analytics for both enantiomers were identical.

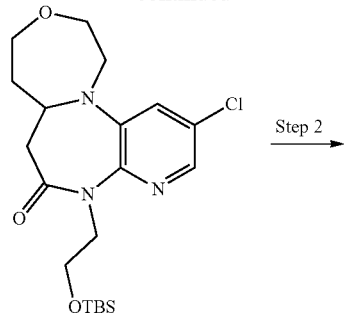

Step 2

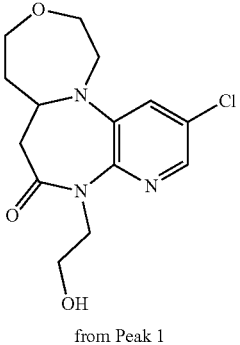

from Peak 1

131
Synthesis of (R)-10-chloro-7-ethyl-4,4a,5,7-tetrahydro-1H-[1,4]oxazino[4,3-d]pyrido[2,3-b][1,4]diazepin-6(2H)-one

132
Synthesis of (R)-10-Chloro-7-(2-hydroxyethyl)-4,4a,5,7-tetrahydro-1H-[1,4]oxazino[4,3-d]pyrido[2,3-b][1,4]diazepin-6(2H)-one

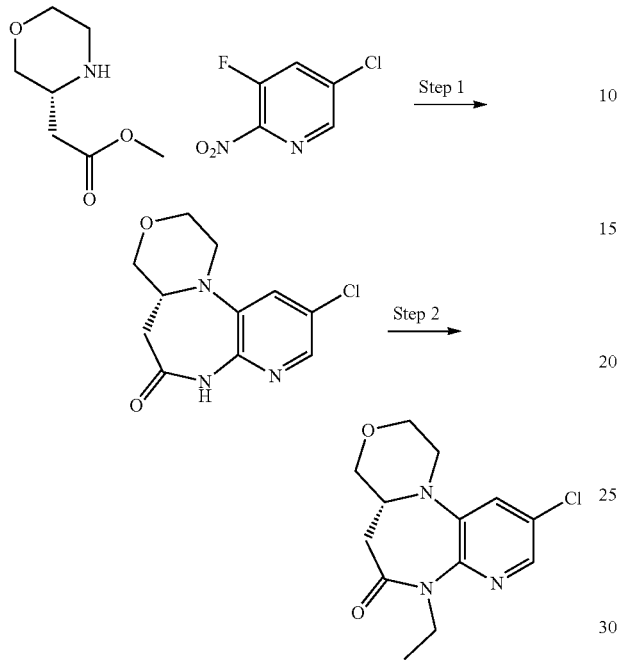

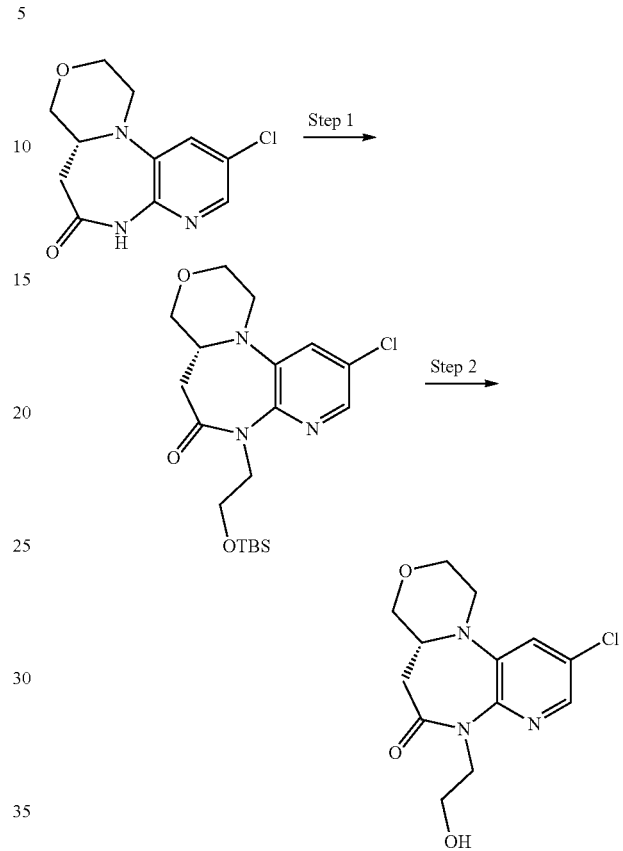

Step 1:

(R)-Methyl 2-(morpholin-3-yl)acetate (1.1 equiv) was dissolved into anhydrous DMF (0.206 M) along with 5-chloro-3-fluoro-2-nitropyridine (1 equiv) and TEA (3 equiv). This mixture was heated to 80° C. for 72 hours and then poured into water and extracted three times with EtOAc. The combined organics were washed with brine, dried over Na$_2$SO$_4$, and the volatiles were removed to yield a deep red oil which was taken up into a 1:1 mixture of AcOH:dioxane (0.139 M) and treated with iron dust (10 equiv). The reaction was then heated to 110° C. with reflux condenser and stirring. After 16 hr the reaction was filtered to remove excess iron and the volatiles removed. The residue was partitioned between EtOAc and sat aq NaHCO$_3$. The organic layer was washed with brine and dried over Na$_2$SO$_4$ then filtered. The volatiles were removed to yield (R)-10-chloro-4,4a,5,7-tetrahydro-1H-[1,4]oxazino[4,3-d]pyrido[2,3-b][1,4]diazepin-6(2H)-one in 31.9% yield which was used as-is in further chemistry. LCMS (m/z) (M+H)=254.0, R$_t$=0.61 min.

Step 2:

(R)-10-Chloro-4,4a,5,7-tetrahydro-1H-[1,4]oxazino[4,3-d]pyrido[2,3-b][1,4]diazepin-6(2H)-one (1 equiv) was dissolved into anhydrous DMF (0.197 M) and treated with cesium carbonate (2 equiv) and iodoethane (1.5 equiv). This mixture was stirred at room temperature for 72 hours. After this period of time the reaction was poured into H$_2$O and extracted three times with EtOAc. Organics were washed with brine, dried over Na$_2$SO$_4$ and evaporated to a crude oily (R)-10-chloro-7-ethyl-4,4a,5,7-tetrahydro-1H-[1,4]oxazino[4,3-d]pyrido[2,3-b][1,4]diazepin-6(2H)-one in 76% yield which was used as-is in further chemistry. LCMS (m/z) (M+H)=282.1, R$_t$=0.87 min.

Step 1:

(R)-10-Chloro-4,4a,5,7-tetrahydro-1H-[1,4]oxazino[4,3-d]pyrido[2,3-b][1,4]diazepin-6(2H)-one (1 equiv) was dissolved into anhydrous DMF (0.197 M) and treated with cesium carbonate (1.2 equiv) and tert-butyl(2-iodoethoxy)dimethylsilane (1.1 equiv). This mixture was stirred at room temperature for 16 hours and then was poured into H$_2$O and extracted three times with EtOAc. Organics were combined, washed with brine and dried with Na$_2$SO$_4$. After filtration the volatiles were removed to yield a crude oil which was purified by flash column chromatography over silica gel (heptane with 0-65% ethyl acetate gradient) to give (R)-7-(2-((tert-butyldimethylsilyl)oxy)ethyl)-10-chloro-4,4a,5,7-tetrahydro-1H-[1,4]oxazino[4,3-d]pyrido[2,3-b][1,4]diazepin-6(2H)-one in 81% yield. LCMS (m/z) (M+H)=412.3, R$_t$=1.42 min.

Step 2:

(R)-7-(2-((tert-butyldimethylsilyl)oxy)ethyl)-10-chloro-4,4a,5,7-tetrahydro-1H-[1,4]oxazino[4,3-d]pyrido[2,3-b][1,4]diazepin-6(2H)-one (1 equiv) was dissolved into MeOH (0.112 M) and treated with 1.25 M HCl in methanol (5 equiv). After 45 min the volatiles were removed and the residue was partitioned between EtOAc and sat aq NaHCO$_3$. Organics were washed with brine and dried with Na$_2$SO$_4$. The volatiles were removed and the so-obtained residue was purified by flash column chromatography over silica gel (heptane with 0-75% ethyl acetate gradient) to provide the desired (R)-10-chloro-7-(2-hydroxyethyl)-4,4a,5,7-tetrahydro-1H-[1,4]oxazino[4,3-d]pyrido[2,3-b][1,4]diazepin-6 (2H)-one in 73.3% yield. LCMS (m/z) (M+H)=298.0, $R_t$=0.64 min.

Synthesis of (S)-10-chloro-7-ethyl-4,4a,5,7-tetrahydro-1H-[1,4]oxazino[4,3-d]pyrido[2,3-b][1,4]diazepin-6(2H)-one

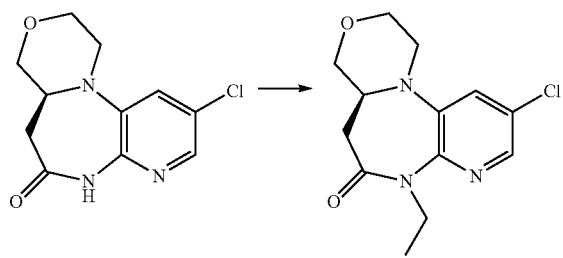 [SMILES: O=C1C[C@H]2COCCN2c2cc(Cl)cnc2N1 ; CCN1C(=O)C[C@H]2COCCN2c2cc(Cl)cnc21]

(S)-10-Chloro-4,4a,5,7-tetrahydro-1H-[1,4]oxazino[4,3-d]pyrido[2,3-b][1,4]diazepin-6(2H)-one (1 equiv) was dissolved into anhydrous DMF (0.066 M) and treated with cesium carbonate (2 equiv) and iodoethane (1.5 equiv). This mixture was stirred at room temperature for 72 hours. After this period of time the reaction was poured into $H_2O$ and extracted three times with EtOAc. Organics were combined, washed with brine, dried over $Na_2SO_4$ and evaporated to yield an oily (S)-10-chloro-7-ethyl-4,4a,5,7-tetrahydro-1H-[1,4]oxazino[4,3-d]pyrido[2,3-b][1,4]diazepin-6(2H)-one in 72.9% yield which was used as-is in further chemistry. LCMS (m/z) (M+H)=282.1, $R_t$=0.87 min.

Syntheses of (4a,11b-cis)-10-chloro-7-ethyl-4,4a,7,11b-tetrahydro-1H-pyrano[4,3-f]pyrido[2,3-d][1,3]oxazepin-6(2H)-one "Peak 1" and "Peak 2"

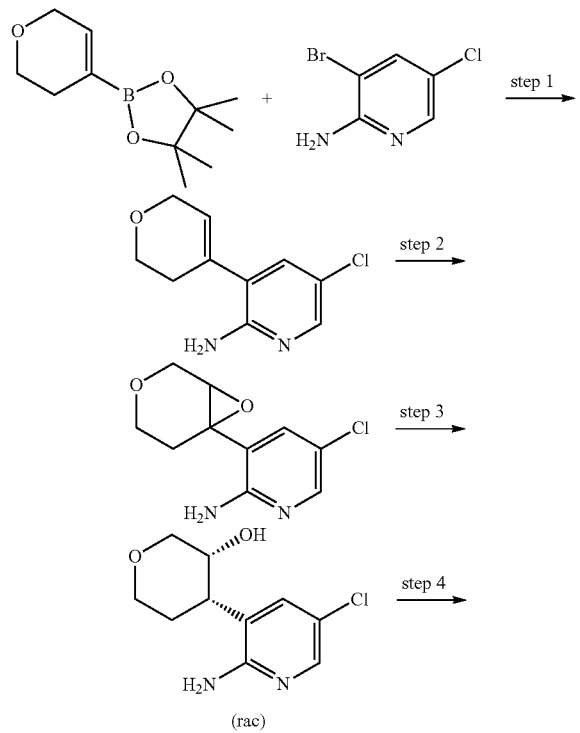

(rac)

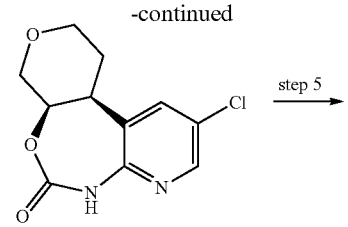

(rac)

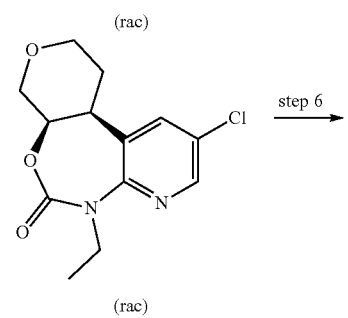

(rac)

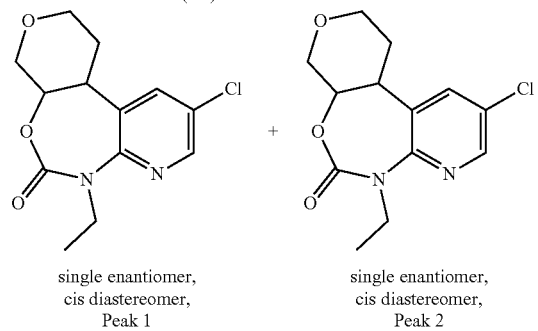

single enantiomer, cis diastereomer, Peak 1 single enantiomer, cis diastereomer, Peak 2

Step 1:
To a mixture of 3-bromo-5-chloropyridin-2-amine (1.0 equiv.), 2-(3,6-dihydro-2H-pyran-4-yl)-4,4,5,5-tetramethyl-1,3,2-dioxaborolane (1.15 equiv.), $K_3PO_4$ (2 equiv.), and X-Phos Pd G2 (5 mol %) under an atmosphere of nitrogen was added degassed 1,4-dioxane/water (4:1, 0.2 M), and the resulting suspension was heated to 60° C. and stirred for 5 hours. The reaction mixture was diluted with ethyl acetate, $MgSO_4$ was added, and the suspension was filtered through a pad of celite, washing with ethyl acetate. The residue was purified by flash column chromatography over silica gel (heptane with 0-70% ethyl acetate gradient) to afford 5-chloro-3-(3,6-dihydro-2H-pyran-4-yl)pyridin-2-amine as an off-white solid in 96% yield. LCMS (m/z) (M+H)=211.0, Rt=0.53 min. $^1$H NMR (400 MHz, CHLOROFORM-d) δ ppm 7.96 (d, J=2.53 Hz, 1H), 7.25 (d, J=2.53 Hz, 1H), 5.98 (tt, J=2.91, 1.52 Hz, 1H), 4.45-4.77 (m, 2H), 4.31 (q, J=2.78 Hz, 2H), 3.95 (t, J=5.43 Hz, 2H), 2.35-2.43 (m, 2H).

Step 2:
To a stirring solution of 5-chloro-3-(3,6-dihydro-2H-pyran-4-yl)pyridin-2-amine (1 equiv.) in t-butanol/water (2:1, 0.21 M) was added NBS (0.8 equiv.) in 4 portions over 10 minutes, and the resulting mixture was stirred at room temperature for 2 hours. Additional NBS (0.1 equiv.) was added in 1 portion, and the mixture was stirred at room temperature for 30 minutes. To this mixture was added aqueous 2 M NaOH (3.18 equiv.), and the mixture was stirred at room temperature for 1.5 hours. The reaction was transferred to a separatory funnel containing sat. aq. sodium thiosulfate and sat. aq. sodium bicarbonate (1:1) and extracted three times with ethyl acetate. The combined organic phases were dried over $MgSO_4$, filtered, and concentrated in vacuo. The residue was purified by flash chromatography over silica gel (heptane with 0-70% ethyl acetate gradient) to afford (rac)-3-(3,7-dioxabicyclo[4.1.0]heptan-6-yl)-5-chloropyridin-2-amine in 66% yield. LCMS (m/z) (M+H)=227.1, Rt=0.59 min. $^1$H NMR (400 MHz, CHLOROFORM-d) δ ppm 7.99 (d, J=2.45 Hz, 1H), 7.46 (d, J=2.45 Hz, 1H), 5.13 (br s, 2H), 4.23 (dd, J=13.69, 3.30 Hz, 1H), 4.04 (d, J=13.82 Hz, 1H), 3.55-3.71 (m, 2H), 3.37 (d, J=3.18 Hz, 1H), 2.23 (dd, J=6.54, 4.83 Hz, 2H).

Step 3:

To a mixture of 3-(3,7-dioxabicyclo[4.1.0]heptan-6-yl)-5-chloropyridin-2-amine (1 equiv.) and 10% Pd/C (10 mol %) under an atmosphere of nitrogen was added methanol (0.18 M) and triethylamine (2.5 equiv.). Hydrogen was introduced via a balloon, and the reaction was stirred at room temperature under an atmosphere of hydrogen for 3.5 hours. The reaction was put under an atmosphere of nitrogen, diluted with dichloromethane, and filtered through a pad of celite, washing extensively with dichloromethane. The crude product was purified by flash column chromatography over silica (dichloromethane with 0-10% methanol gradient) to afford (rac)-4-(2-amino-5-chloropyridin-3-yl)tetrahydro-2H-pyran-3-ol as a light tan solid in 41% yield. LCMS (m/z) (M+H)=229.0, Rt=0.37 min. $^1$H NMR (400 MHz, CHLOROFORM-d) δ ppm 7.94 (d, J=2.51 Hz, 1H), 7.52 (d, J=2.51 Hz, 1H), 4.39-5.30 (m, 2H), 4.17 (dd, J=11.54, 4.52 Hz, 1H), 4.06 (dd, J=12.05, 2.01 Hz, 1H), 3.99 (s, 1H), 3.71 (dd, J=12.05, 1.00 Hz, 1H), 3.61 (td, J=11.86, 2.13 Hz, 1H), 2.71-2.86 (m, 1H), 2.42 (qd, J=12.80, 4.52 Hz, 1H), 1.58 (br dd, J=13.55, 1.76 Hz, 1H).

Step 4:

To a mixture of (rac)-4-(2-amino-5-chloropyridin-3-yl)tetrahydro-2H-pyran-3-ol (1 equiv.) and CDI (1.7 equiv.) in a round-bottom flask with a condenser under an atmosphere of nitrogen was added acetonitrile (0.05 M), and the mixture was heated to 60° C. and stirred for 16 hours. Additional CDI (0.1 equiv.) was added, and the mixture was stirred at 60° C. for 1 hour. The reaction mixture was cooled to room temperature, and Sc(OTf)$_3$ (10 mol %) was added in a single portion. The reaction mixture was heated to reflux and stirred for 24 hours. The reaction mixture was concentrated to approximately one-sixth of the initial volume and filtered, washing with acetonitrile. The resulting white solid was recovered and dried in vacuo to afford (rac)-(4a,11b-cis)-10-chloro-4,4a,7,11b-tetrahydro-1H-pyrano[4,3-f]pyrido[2,3-d][1,3]oxazepin-6(2H)-one in 88% yield. LCMS (m/z) (M+H)=255.0, Rt=0.63 min. 1H NMR (400 MHz, DMSO-d6) δ ppm 9.92 (s, 1H), 8.23 (d, J=2.51 Hz, 1H), 7.91 (d, J=2.51 Hz, 1H), 4.78 (s, 1H), 3.87-4.03 (m, 2H), 3.46-3.64 (m, 2H), 3.29-3.35 (m, 1H), 1.92 (qd, J=12.55, 4.27 Hz, 1H), 1.73-1.85 (m, 1H).

Step 5:

To a stirring solution of (rac)-(4a,11b-cis)-10-chloro-4,4a,7,11b-tetrahydro-1H-pyrano[4,3-f]pyrido[2,3-d][1,3]oxazepin-6(2H)-one (1 equiv.) in DMF (0.3 M) was added cesium carbonate (1.5 equiv.) followed by ethyl iodide (1.2 equiv.), and the resulting mixture was stirred at room temperature for 3.5 hours. The reaction mixture was suspended in ethyl acetate (10 mL), and extracted with 0.1 M aq. HCl (10 mL) followed by brine (10 mL). The organic phase was dried over MgSO4, filtered, and concentrated in vacuo to afford (rac)-(4a,11b-cis)-10-chloro-7-ethyl-4,4a,7,11b-tetrahydro-1H-pyrano[4,3-f]pyrido[2,3-d][1,3]oxazepin-6(2H)-one as a white solid in 92% yield. LCMS (m/z) (M+H)=283.0, Rt=0.92 min. $^1$H NMR (400 MHz, CHLOROFORM-d) δ ppm 8.36 (d, J=2.01 Hz, 1H), 7.58-7.67 (m, 1H), 4.82 (ddd, J=8.28, 5.90, 4.14 Hz, 1H), 4.05-4.15 (m, 1H), 3.94-4.05 (m, 1H), 3.82-3.91 (m, 3H), 3.38-3.49 (m, 2H), 2.22-2.31 (m, 1H), 2.07-2.19 (m, 1H), 1.28 (t, J=7.03 Hz, 3H).

Step 6:

(rac)-(4a,11b-cis)-10-chloro-4,4a,7,11b-tetrahydro-1H-pyrano[4,3-f]pyrido[2,3-d][1,3]oxazepin-6(2H)-one was purified by chiral SFC (ID 21×250 mm 5 um, 20% isopropanol in CO$_2$ eluent). The first eluted peak afforded a single enantiomer of (4a,11b-cis)-10-chloro-4,4a,7,11b-tetrahydro-1H-pyrano[4,3-f]pyrido[2,3-d][1,3]oxazepin-6(2H)-one "Peak 1" as a white solid in 45% yield. The second eluted peak afforded the opposite enantiomer of (4a,11b-cis)-10-chloro-4,4a,7,11b-tetrahydro-1H-pyran[4,3-f]pyrido[2,3-d][1,3]oxazepin-6(2H)-one "Peak 2" as a white solid in 46% yield. The LCMS and $^1$H NMR data for the two enantiomers matched, and matched the characterization data reported for the racemate.

Syntheses of (4a,11b-cis)-10-chloro-7-(4-methoxybenzyl)-4,4a,7,11b-tetrahydro-1H-pyrano[4,3-f]pyrido[2,3-d][1,3]oxazepin-6(2H)-one "Peak 1" and "Peak 2"

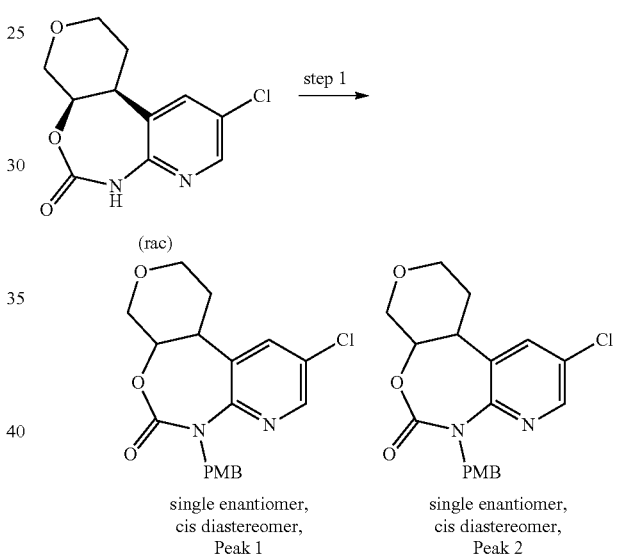

Step 1:

To a stirring suspension of (rac)-(4a5,11bR)-10-chloro-4,4a,7,11b-tetrahydro-1H-pyrano[4,3-f]pyrido[2,3-d][1,3]oxazepin-6(2H)-one (1 equiv.) and KI (5 mol %) in DMF (0.3 M) at room temperature was added 4-methoxybenzyl chloride (1.05 equiv.), and the resulting mixture was stirred for 18 hours. Additional 4-methoxybenzyl chloride (0.2 equiv.) was added, and the mixture was stirred for 3 hours. The reaction mixture was diluted with ethyl acetate and washed with 0.1 M aq. HCl and brine. The organic phase was dried over MgSO$_4$, filtered, and concentrated in vacuo to afford a yellow oil. The residue was purified by chiral SFC (OJ-H 21×250 mm, 20% MeOH in CO$_2$ eluent). The first eluted peak afforded one enantiomer of (4a,11b-cis)-10-chloro-7-(4-methoxybenzyl)-4,4a,7,11b-tetrahydro-1H-pyrano[4,3-f]pyrido[2,3-d][1,3]oxazepin-6(2H)-one "Peak 1" in 41% yield. The second eluted peak afforded the opposite enantiomer of (4a,11b-cis)-10-chloro-7-(4-methoxybenzyl)-4,4a,7,11b-tetrahydro-1H-pyrano[4,3-f]pyrido[2,3-d][1,3]oxazepin-6(2H)-one "Peak 2" in 42% yield. The LCMS and $^1$H NMR data for the two enantiomers matched. LCMS (m/z) (M+H)=375.0, Rt=1.11 min. 1H NMR (400 MHz, DMSO-d6) δ ppm 8.41 (d, J=2.53 Hz, 1H), 7.94 (d, J=2.27 Hz, 1H), 7.22 (d, J=8.84 Hz, 2H), 6.74-6.90 (m, 2H), 4.94-5.10 (m, 2H), 4.71-4.87 (m, 1H), 3.79 (ddd, J=11.37, 7.07, 3.79 Hz, 1H), 3.69 (s, 3H), 3.51-3.67 (m, 3H), 3.36-3.44 (m, 1H), 1.98 (dtd, J=14.49, 7.47, 7.47, 3.66 Hz, 1H), 1.75-1.86 (m, 1H).

Synthesis of (4a,11b-cis)-10-chloro-7-(2-hydroxyethyl)-4,4a,7,11b-tetrahydro-1H-pyrano[4,3-f]pyrido[2,3-d][1,3]oxazepin-6(2H)-one "from Peak 1"

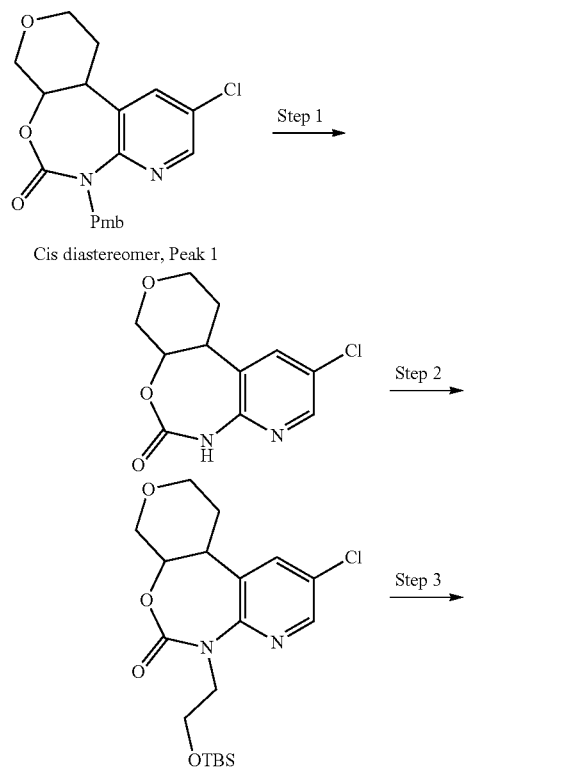

Step 1:
(4a,11b-cis)-10-Chloro-7-(4-methoxybenzyl)-4,4a,7,11b-tetrahydro-1H-pyrano[4,3-f]pyrido[2,3-d][1,3]oxazepin-6(2H)-one "Peak 1" (1 equiv) was dissolved into DCM (0.03 M) and treated with trifluoromethanesulfonic acid (5 equiv) at 23° C. in a pressure relieved screw cap vial. After stirring at RT for 15 min the reaction was quenched carefully with saturated aqueous NaHCO₃. Reaction was partitioned with 25% isopropanol in DCM. The organics were separated and washed with brine followed by drying over anhydrous granular Na₂SO₄. The volatiles were removed to yield of an off-white (4a,11b-cis)-10-chloro-4,4a,7,11b-tetrahydro-1H-pyrano[4,3-f]pyrido[2,3-d][1,3]oxazepin-6(2H)-one in 130% yield (p-methoxybenzyl alcohol is the likely impurity). LCMS (m/z) (M+H)=255.1, $R_t$=0.64 min.

Step 2:
(4a,11b-cis)-10-Chloro-4,4a,7,11b-tetrahydro-1H-pyrano[4,3-f]pyrido[2,3-d][1,3]oxazepin-6(2H)-one (1 equiv) was dissolved into anhydrous DMF (0.098 M) along with cesium carbonate (5 equiv), (2-bromoethoxy)(tert-butyl)dimethylsilane (3.5 equiv) and sodium iodide (1 equiv). The reaction was heated to 60° C. and left to stir for 3 hr. It was then poured into H₂O and extracted three times with EtOAc. Organics were combined, washed with brine, and dried over anhydrous granular Na₂SO₄. After decantation the volatiles were removed and the residue was purified by flash column chromatography over silica gel (heptane with 0-40% ethyl acetate gradient) to give (4a,11b-cis)-7-(2-((tert-butyldimethylsilyl)oxy)ethyl)-10-chloro-4,4a,7,11b-tetrahydro-1H-pyrano[4,3-f]pyrido[2,3-d][1,3]oxazepin-6(2H)-one in 81% yield. LCMS (m/z) (M+H)=413.2, $R_t$=1.81 min.

Step 3:
(4a,11b-cis)-7-(2-((Tert-butyldimethylsilyl)oxy)ethyl)-10-chloro-4,4a,7,11b-tetrahydro-1H-pyrano[4,3-f]pyrido[2,3-d][1,3]oxazepin-6(2H)-one (1 equiv) was dissolved into anhydrous MeOH (0.05 M) along with 1.25M HCl in methanol (5 equiv). Reaction was stirred for 2 hr and then the volatiles were removed. The residue was partitioned between EtOAc and saturated aqueous NaHCO₃. After the organic layer was washed with brine, dried over anhydrous granular Na₂SO₄ the volatiles were removed to yield a quite pure (4a,11b-cis)-10-chloro-7-(2-hydroxyethyl)-4,4a,7,11b-tetrahydro-1H-pyrano[4,3-f]pyrido[2,3-d][1,3]oxazepin-6(2H)-one "from Peak 1" in 71.8% yield which was used as-is in further chemistry. LCMS (m/z) (M+H)=299.1, $R_t$=0.68 min.

Synthesis of (4aR,11bR)-10-bromo-7-ethyl-4,4a,7,11b-tetrahydro-1H-pyrano[4,3-f]pyrido[2,3-d][1,3]oxazepin-6(2H)-one

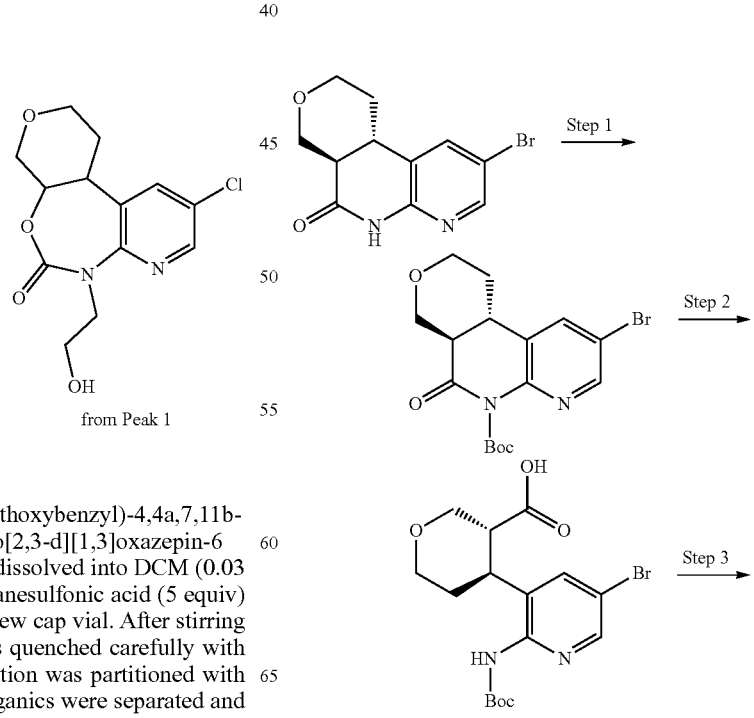

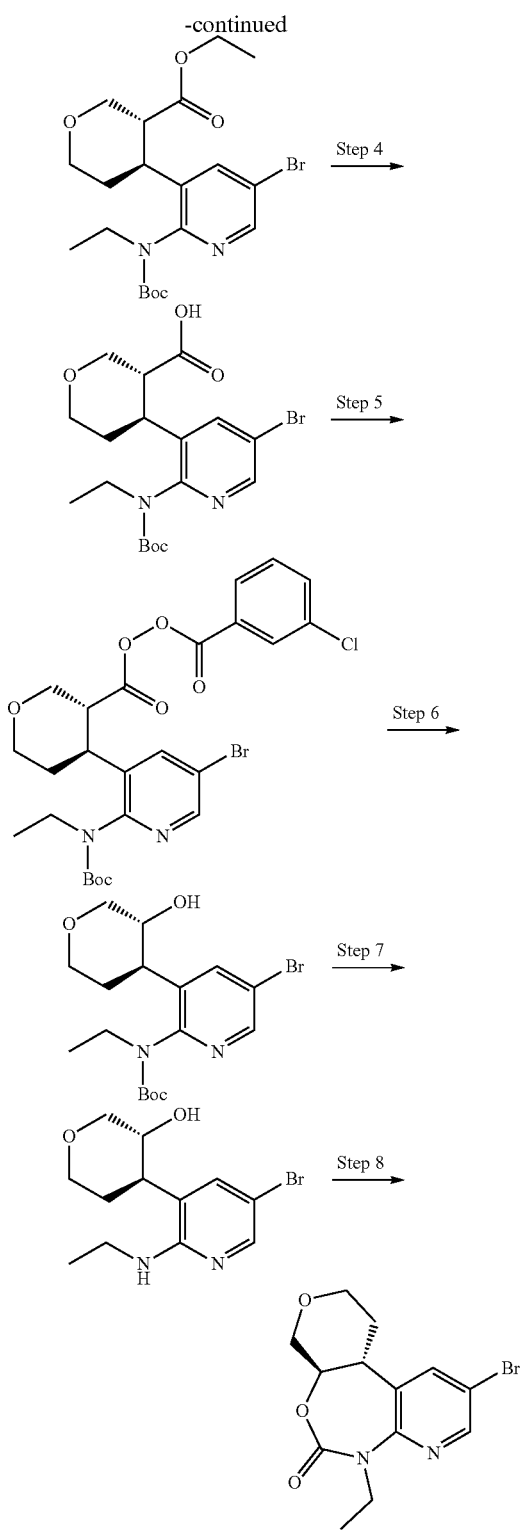

organics were washed with water and brine, dried over MgSO$_4$, filtered, and concentrated. The residue was purified by flash column chromatography over silica gel (heptane and 0-40% EtOAc gradient) to provide (4aR,10bS)-tert-butyl 9-bromo-5-oxo-4,4a,5,10b-tetrahydro-1H-pyrano[3,4-c][1,8]naphthyridine-6(2H)-carboxylate in 87% yield. $^1$H NMR (400 MHz, CHLOROFORM-d) δ ppm 8.33 (dd, J=2.15, 0.88 Hz, 1H), 7.61 (dd, J=2.15, 1.39 Hz, 1H), 4.51 (dd, J=12.00, 4.42 Hz, 1H), 4.21 (dd, J=11.75, 3.66 Hz, 1H), 3.45-3.62 (m, 2H), 2.87-3.05 (m, 1H), 2.50 (ddd, J=14.34, 10.29, 4.42 Hz, 1H), 2.41-2.59 (m, 1H), 2.16-2.28 (m, 1H), 1.77 (qd, J=12.29, 4.55 Hz, 1H), 1.52-1.63 (m, 9H).

Step 2:

To a stirred solution of (4aR,10bS)-tert-butyl 9-bromo-5-oxo-4,4a,5,10b-tetrahydro-1H-pyrano[3,4-c][1,8]naphthyridine-6(2H)-carboxylate (1.0 equiv) in THF (0.3 M) was added NaOH (2.5 equiv), and the mixture was heated to 50° C. and stirred for 2 h. The volatiles were removed under pressure, and the resulting residue was purified by HPLC (X-Bridge 50×50 uM column, 5-20% MeCN in 5 mM aq NH$_4$OH gradient) to provide (3R,4R)-4-(5-bromo-2-((tert-butoxycarbonyl)amino)pyridin-3-yl)tetrahydro-2H-pyran-3-carboxylic acid in 97% yield as a 2:1 diastereomeric mixture which was used without further purification. LCMS (m/z) (M+H)=400.9/402.9, Rt=0.83 and 0.87 min Step 3:

To a stirred solution of (3R,4R)-4-(5-bromo-2-((tert-butoxycarbonyl)amino)pyridin-3-yl)tetrahydro-2H-pyran-3-carboxylic acid (1.0 equiv) in DMF (0.12 M) at 25° C. were added Cs$_2$CO$_3$ (7.5 equiv) and iodoethane (15 equiv) and the reaction was heated to 50° C. and stirred for 5 h. The mixture was poured onto half-saturated aqueous NH$_4$Cl and extracted three times with ethyl acetate. The combined organics were dried over magnesium sulfate, filtered, and concentrated. The residue was purified by flash column chromatography over silica gel (heptane and 0-70% EtOAc) to give (3R,4S)-ethyl 4-(5-bromo-2-((tert-butoxycarbonyl)(ethypamino)pyridin-3-yl)tetrahydro-2H-pyran-3-carboxylate as a white solid in 73% yield. LCMS (m/z) (M+H)=457.0/459.0, Rt=1.30 min.

Step 4:

To a stirred solution of (3R,4S)-ethyl 4-(5-bromo-2-((tert-butoxycarbonyl)(ethyl)amino)pyridin-3-yl)tetrahydro-2H-pyran-3-carboxylate (1.0 equiv) in THF (0.16 M) was added NaOH (5 equiv) and the mixture was heated to 60° C. and stirred for 2 h. The volatiles were removed under reduced pressure and the resulting residue partitioned between saturated aqueous NH$_4$Cl and EtOAc. The aqueous layer was extracted twice more with EtOAc, and the combined organic phases were washed with brine, dried over MgSO$_4$, filtered, and concentrated. The so-obtained white foam was used as (3R,4S)-4-(5-bromo-2-((tert-butoxycarbonyl)(ethyl)amino)pyridin-3-yl)tetrahydro-2H-pyran-3-carboxylic acid, obtained in 80% yield without further purification. LCMS (m/z) (M+H)=429.0/431.0, Rt=0.96 min.

Step 5:

An approximately 0.03 M stock solution of "dry mCPBA" was prepared. 70% mCPBA was dissolved in DCM (0.03 M) and washed with saturated aqueous NaHCO$_3$. The organics were dried over MgSO$_4$ and filtered. The so-obtained solution was used in the subsequent reaction.

To a stirred solution of (3R,4S)-4-(5-bromo-2-((tert-butoxycarbonyl)(ethyl)amino)pyridin-3-yl)tetrahydro-2H-pyran-3-carboxylic acid (1.0 equiv) in DCM (0.2 M) at 0° C. were added DCC (1.3 equiv) and "dry mCPBA" (0.03 M in DCM, 1.3 equiv) and the reaction was stirred for 2 h at 0°

Step 1:

To a stirred solution of (4aR,10bS)-9-bromo-4,4a,6,10b-tetrahydro-1H-pyrano[3,4-c][1,8]naphthyridin-5(2H)-one (1.0 equiv) in DCM (0.1 M) were added i-Pr$_2$NEt (4 equiv), Boc$_2$O (1.5 equiv), and DMAP (0.2 equiv) and the mixture was heated to 50° C. and stirred overnight. The mixture was partitioned between EtOAc and saturated aqueous NH$_4$Cl and extracted three times with EtOAc, and the combined C. The reaction was filtered washing with DCM, and concentrated. The so-obtained residue was purified by flash column chromatography over silica gel (heptane and 0-60% EtOAc gradient) to give (3R,4S)-4-(5-bromo-2-((tert-butoxycarbonyl)(ethyl)amino)pyridin-3-yl)tetrahydro-2H-pyran-3-carboxylic 3-chlorobenzoic peroxyanhydride as a colorless oil in 69% yield. LCMS (m/z) (M+H-tBu)=527.1/529.1, Rt=1.42 mm.

Step 6:

A solution (3R,4S)-4-(5-bromo-2-((tert-butoxycarbonyl)(ethyl)amino)pyridin-3-yl)tetrahydro-2H-pyran-3-carboxylic 3-chlorobenzoic peroxyanhydride (1.0 equiv) in benzene (0.03 M) was heated to 80° C. and stirred overnight. The reaction mixture was concentrated and the residue was taken up in MeOH (0.05 M). $K_2CO_3$ (4 equiv) was added, and the mixture was stirred at RT for 5 h. The reaction was diluted with DCM, filtered, and concentrated. The residue was purified by flash column chromatography over silica gel (heptane and 0-60% EtOAc gradient) to give tert-butyl (5-bromo-3-((3R,4R)-3-hydroxytetrahydro-2H-pyran-4-yl)pyridin-2-yl)(ethyl)carbamate as a colorless oil in 49% yield. LCMS (m/z) (M+H-tBu)=345.1/347.1, Rt=1.00 min Step 7:

To a solution of tert-butyl (5-bromo-3-((3R,4R)-3-hydroxytetrahydro-2H-pyran-4-yl)pyridin-2-yl)(ethyl)carbamate (1.0 equiv) in dioxane (0.1 M) at 25° C. was added HCl (4 M aq, 15 equiv) and the mixture was stirred overnight. The reaction mixture was concentrated, and the residue was taken up in a mixture of EtOAc and saturated aqueous $Na_2CO_3$ and stirred vigorously for 10 min. After partitioning of the resulting mixture, the aqueous layer was extracted twice more with EtOAc. The combined organics were washed with brine, dried over $MgSO_4$, filtered, and concentrated to (3R,4R)-4-(5-bromo-2-(ethylamino)pyridin-3-yl)tetrahydro-2H-pyran-3-ol as a white solid in 93% yield which was used without further purification. LCMS (m/z) (M+H)=301.1/303.1, Rt=0.51 min. $^1$H NMR (400 MHz, Chloroform-d) δ 8.03 (d, J=2.3 Hz, 1H), 7.44 (d, J=2.2 Hz, 1H), 4.09 (dd, J=11.1, 4.9 Hz, 1H), 4.06-4.00 (m, 1H), 3.71 (td, J=10.0, 4.8 Hz, 1H), 3.50-3.43 (m, 1H), 3.40 (q, J=7.2, 5.9 Hz, 2H), 3.29 (dd, J=10.9, 10.1 Hz, 1H), 2.64 (ddd, J=13.4, 10.1, 3.7 Hz, 1H), 1.98-1.86 (m, 1H), 1.75 (ddd, J=11.8, 3.7, 1.9 Hz, 1H), 1.25 (t, J=7.2 Hz, 3H). $^1$H NMR (400 MHz, Methanol-d4) δ 7.90 (d, J=2.4 Hz, 1H), 7.50 (d, J=2.3 Hz, 1H), 3.99 (dd, J=10.9, 4.8 Hz, 1H), 3.94 (dd, J=11.4, 3.8 Hz, 1H), 3.72 (td, J=10.0, 4.8 Hz, 1H), 3.51 (td, J=11.7, 2.2 Hz, 1H), 3.36 (q, J=7.1 Hz, 2H), 3.25-3.18 (m, 1H), 2.70 (ddd, J=12.1, 10.1, 3.9 Hz, 1H), 1.79 (ddt, J=13.5, 3.6, 1.8 Hz, 1H), 1.72-1.61 (m, 1H), 1.21 (t, J=7.2 Hz, 3H).

Step 8:

A mixture of (3R,4R)-4-(5-bromo-2-(ethylamino)pyridin-3-yl)tetrahydro-2H-pyran-3-ol (1.0 equiv) and CDI (1.8 equiv) under $N_2$ was taken up in acetonitrile (0.075 M) and heated at 60° C. was overnight. Scandium trifluoromethanesulfonate (0.2 equiv) was then added, and the reaction was further heated to 105° C. stirred for 7 days. The reaction mixture was concentrated in vacuo, transferred to a separatory funnel containing half-saturated aqueous ammonium chloride and extracted twice with dichloromethane. The combined organic extracts were dried over $MgSO_4$, filtered, and concentrated. The residue was purified by flash column chromatography over silica gel (heptane and 0-50% EtOAc gradient) to provide ((4aR,11bR)-10-bromo-7-ethyl-4,4a,7,11b-tetrahydro-1H-pyrano[4,3-f]pyrido[2,3-d][1,3]oxazepin-6(2H)-one as a white solid in 61% yield. LCMS (m/z) (M+H)=327.1/329.1, Rt=0.92 min. $^1$H NMR (400 MHz, CHLOROFORM-d) δ ppm 8.47 (d, J=2.26 Hz, 1H), 7.64 (dd, J=2.26, 0.75 Hz, 1H), 4.25 (dd, J=10.79, 4.52 Hz, 1H), 4.04-4.19 (m, 3H), 3.96 (dq, J=13.80, 7.03 Hz, 1H), 3.48-3.62 (m, 2H), 2.85-3.01 (m, 1H), 2.00-2.10 (m, 2H), 1.28 (t, J=7.03 Hz, 3H).

Synthesis of 2-(1,1-difluoroethyl)-3-fluoro-N-(4-methyl-3-(4,4,5,5-tetramethyl-1,3,2-dioxaborolan-2-yl)phenyl)isonicotinamide

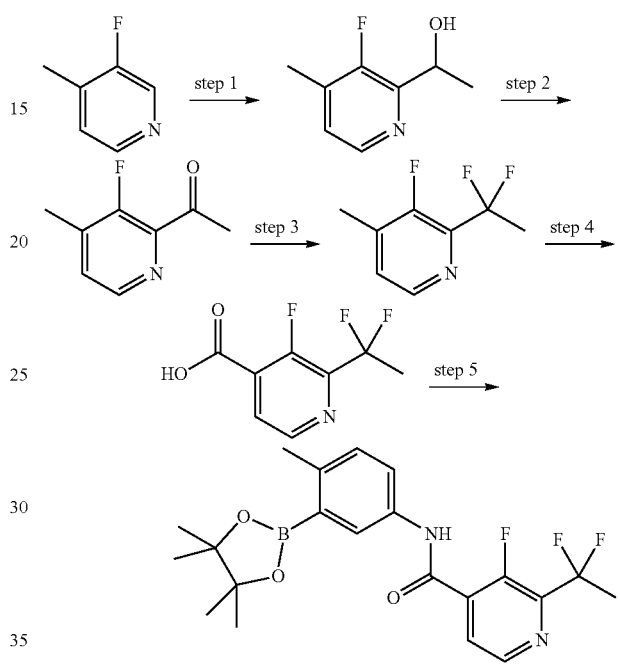

Step 1:

To a stirring solution of 3-fluoro-4-methylpyridine (1 equiv.) in THF (0.1 M) under an atmosphere of nitrogen in a heat gun-dried flask at -78° C. (dry ice/acetone bath) was added 1.6 M nBuLi in hexanes (1.05 equiv.), and the reaction mixture was stirred at -78° C. for 1.5 hours. To the reaction mixture at -78° C. was added acetaldehyde (1.05 equiv.) dropwise, and the reaction mixture was stirred at -78° C. for 1 hour. The reaction mixture was warmed to 0° C., stirred at this temperature for 5 minutes, then quenched via dropwise addition of water and allowed to gradually warm to room temperature. The reaction mixture was transferred to a separatory funnel containing water and extracted three times with ethyl acetate. The combined organic extracts were dried over $MgSO_4$, filtered, and concentrated in vacuo to afford a clear oil. The crude product was purified by flash column chromatography over silica (heptane with 0-50% ethyl acetate gradient) to afford (rac)-1-(3-fluoro-4-methylpyridin-2-yl)ethanol as a white solid in 43% yield. LCMS (m/z) (M+H)=156.0, Rt=0.43 min. $^1$H NMR (400 MHz, CHLOROFORM-d) δ ppm 8.23 (d, J=4.80 Hz, 1H), 7.13 (t, J=5.31 Hz, 1H), 5.11 (qd, J=6.53, 1.39 Hz, 1H), 4.12-4.77 (m, 1H), 2.36 (d, J=1.52 Hz, 3H), 1.50 (dd, J=6.57, 1.01 Hz, 3H).

Step 2:

To a stirring solution of (rac)-1-(3-fluoro-4-methylpyridin-2-yl)ethanol (1 equiv.) in toluene (0.26 M) was added $MnO_2$ (3 equiv.), and the reaction mixture was heated to 110° C. and stirred for 16 hours. The reaction mixture was diluted with dichloromethane, and filtered through a pad of celite, washing with dichloromethane. The filtrate was concentrated in vacuo. The residue was purified by flash column chromatography over silica (heptane with 0-30% ethyl acetate gradient) to afford 1-(3-fluoro-4-methylpyridin-2-yl)ethanone as a clear oil in 80% yield. LCMS (m/z) (M+H)=154.1, Rt=0.65 min. 1H NMR (400 MHz, CHLOROFORM-d) δ ppm 8.35 (d, J=4.55 Hz, 1H), 7.31-7.42 (m, 1H), 2.72 (d, J=1.26 Hz, 3H), 2.39 (d, J=1.26 Hz, 3H).

Step 3:

To a stirring solution of 1-(3-fluoro-4-methylpyridin-2-yl)ethanone (1 equiv.) in dichloromethane (0.5 M) and EtOH (1 mol %) under an atmosphere of nitrogen at 0° C. was added DAST (2.5 equiv.), and the reaction mixture was allowed to warm to room temperature and stirred for 6 days. The reaction mixture was cooled to 0° C. and quenched with sat. aq. NaHCO$_3$ (approximately 60 equiv.) slowly at 0° C., then allowed to warm to room temperature and transferred to a separatory funnel containing dichloromethane. At this time, rapid gas formation was still observed following addition of a few drops of sat. aq. NaHCO$_3$. The mixture was transferred to an Erlenmeyer flask, diluted with dichloromethane, stirred, and sat. aq. NaHCO$_3$ was added slowly over 30 minutes. The mixture was stirred for 1 hour at room temperature, after which pH paper showed that the aqueous phase was basic (pH 8-9) and no generation of gas was observed following addition of additional NaHCO$_3$. The mixture was transferred to a separatory funnel, the layers were separated, and the aqueous phase was reextracted once with dichloromethane. The combined organic extracts were dried over MgSO$_4$, filtered, and concentrated in vacuo. The residue was purified by flash column chromatography over silica (heptane with 0-30% ethyl acetate gradient) to afford 2-(1,1-difluoroethyl)-3-fluoro-4-methylpyridine as a yellow oil in 42% yield. LCMS (m/z) (M+H)=176.1, Rt=0.87 min. $^1$H NMR (400 MHz, CHLOROFORM-d) δ ppm 8.29 (d, J=4.80 Hz, 1H), 7.23-7.33 (m, 1H), 2.39 (d, J=2.02 Hz, 3H), 2.08 (t, J=18.82 Hz, 3H). $^{19}$F NMR (376 MHz, CHLOROFORM-d) δ ppm −89.59 (d, J=19.50 Hz, 2F), −127.75 (br t, J=19.50 Hz, 1F).

Step 4:

To a solution of 2-(1,1-difluoroethyl)-3-fluoro-4-methylpyridine (1 equiv.) in Water (0.38 M) was added KMnO$_4$ (3 equiv.) and the resulting mixture was heated to 80° C. and stirred for 6 hours. The reaction mixture was filtered through celite, washing with water and ethyl acetate. The biphasic mixture was transferred to a separatory funnel and the phases were separated. The aqueous phase was acidified with 1 M aq. HCl (approximately 0.5 equiv., difficult to determine exact pH due to the purple color of the aqueous phase) and extracted three times with ethyl acetate. The three post-acidification organic extracts were combined, dried over MgSO$_4$, filtered, and concentrated in vacuo to afford 2-(1,1-difluoroethyl)-3-fluoroisonicotinic acid as a brown solid in 18% yield. LCMS (m/z) (M+H)=206.1, Rt=0.58 min. $^1$H NMR (400 MHz, METHANOL-d4) δ ppm 8.51 (br d, J=3.79 Hz, 1H), 7.93 (br s, 1H), 2.06 (t, J=18.95 Hz, 3H). $^{19}$F NMR (376 MHz, METHANOL-d4) δ ppm −90.85 (d, J=19.50 Hz), −124.31 (br s).

Step 5:

A mixture of 4-methyl-3-(4,4,5,5-tetramethyl-1,3,2-dioxaborolan-2-yl)aniline (1.05 equiv.), 2-(1,1-difluoroethyl)-3-fluoroisonicotinic acid (1 equiv.), EDC.HCl (1.05 equiv.), and 1-hydroxy-7-azabenzotriazole (1.05 equiv.) under an atmosphere of nitrogen was dissolved in DMF (0.49 M), and the resulting mixture stirred for 2.5 hours at room temperature. The reaction was quenched with water, and the resulting precipitate was filtered, washing with water. The solid was dissolved in DCM and concentrated in vacuo to afford 2-(1,1-difluoroethyl)-3-fluoro-N-(4-methyl-3-(4,4,5,5-tetramethyl-1,3,2-dioxaborolan-2-yl)phenyl)isonicotinamide as a tan solid in 67% yield. LCMS (m/z) (M+H)=421.1, Rt=1.26 min. $^1$HNMR (400 MHz, CHLOROFORM-d) δ ppm 8.59 (d, J=4.80 Hz, 1H), 8.35 (br d, J=13.14 Hz, 1H), 8.14 (t, J=5.05 Hz, 1H), 7.93 (dd, J=8.08, 2.53 Hz, 1H), 7.71 (d, J=2.53 Hz, 1H), 7.19-7.25 (m, 1H), 2.45-2.60 (m, 3H), 2.15 (t, J=18.95 Hz, 3H), 1.37 (s, 12H). 19F NMR (376 MHz, CHLOROFORM-d) δ ppm −88.97 (d, J=20.65 Hz), −125.58−−125.35 (m).

Synthesis of N-(3-(8-ethyl-7-oxo-7,8-dihydro-1,8-naphthyridin-3-yl)-4-methylphenyl)-2-(trifluoromethyl)isonicotinamide

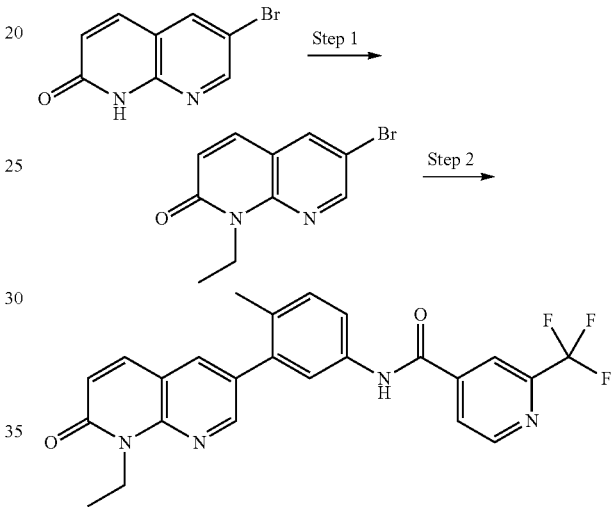

Step 1:

To a stirred solution of 6-bromo-1,8-naphthyridin-2(1H)-one (1 equiv) in DMF (0.2 M) at 25° C. were added cesium carbonate (1.3 equiv) and iodoethane (1.1 equiv) and the reaction was stirred for 30 min. The mixture was poured onto water and extracted three times with ethyl acetate. The combined organics were washed with water and brine, dried over MgSO$_4$, filtered, and concentrated to give 6-bromo-1-ethyl-1,8-naphthyridin-2(1H)-one as a yellow solid in 87% yield, which was used without further purification. LCMS (m/z) (M+H)=253.0/255.0, Rt=0.91 min Step 2:

To a stirred suspension of 6-bromo-1-ethyl-1,8-naphthyridin-2(1H)-one (1.0 equiv) and N-(4-methyl-3-(4,4,5,5-tetramethyl-1,3,2-dioxaborolan-2-yl)phenyl)-2-(trifluoromethyl)isonicotinamide (1.05 equiv) in THF (0.2 M) flushed with nitrogen gas, was added sequentially K$_3$PO$_4$ (0.5 M aq, 2 equiv) followed by XPhos Pd G2 catalyst (0.05 equiv) and XPhos (0.05 equiv). The resultant reaction mixture was heated at 45° C. for 45 min. The reaction was poured onto water and extracted twice with EtOAc, the combined organics were washed with brine, dried over MgSO$_4$, filtered, and concentrated. The residue was purified by flash column chromatography over silica gel, eluting with heptane and 0-100% EtOAc gradient to give N-(3-(8-ethyl-7-oxo-7,8-dihydro-1,8-naphthyridin-3-yl)-4-methylphenyl)-2-(trifluoromethyl)isonicotinamide as a pale yellow solid in 84% yield. $^1$H NMR (400 MHz, Methanol-d$_4$) δ 8.91 (d, J=5.0

Hz, 1H), 8.68 (d, J=2.3 Hz, 1H), 8.52 (s, 1H), 8.30 (s, 1H), 8.18-8.10 (m, 2H), 7.99 (d, J=9.5 Hz, 1H), 7.76-7.64 (m, 2H), 7.38 (d, J=8.2 Hz, 1H), 6.79 (d, J=9.5 Hz, 1H), 4.65 (q, J=7.0 Hz, 2H), 2.31 (s, 3H), 1.36 (t, J=7.0 Hz, 3H). LCMS (m/z) (M+H)=453.3, Rt=1.18 min.

Syntheses of (6aS, 6bS, 9aS, 9bS)-2-bromo-5-ethyl-6a,6b,7,9,9a,9b-hexahydrofuro[3',4':3,4]cyclobuta[1,2-c][1,8]naphthyridin-6(5H)-one and (6aR, 6bR, 9aR, 9bR)-2-bromo-5-ethyl-6a,6b,7,9,9a,9b-hexahydrofuro[3',4':3,4]cyclobuta[1,2-c][1,8]naphthyridin-6(5H)-one

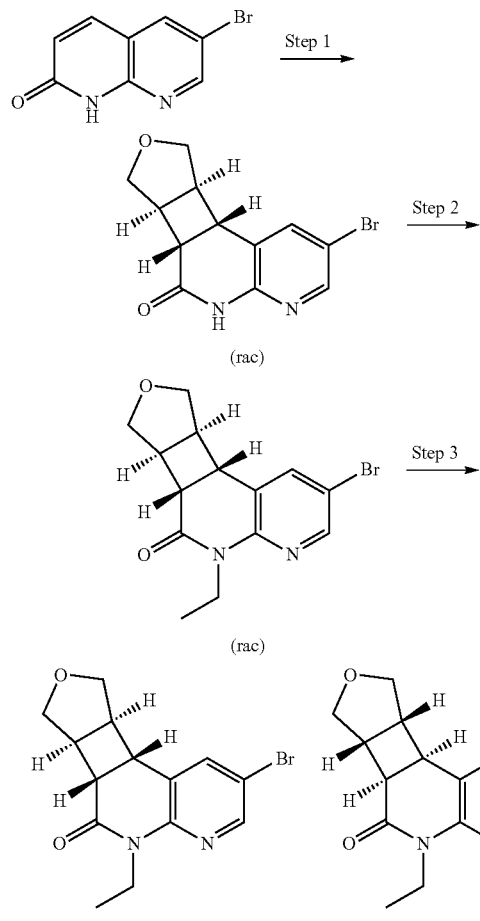

Step 1:

A mixture of 6-bromo-1,8-naphthyridin-2(1H)-one (1.0 equiv) and 2,5-dihydrofuran (10 equiv) in AcOH (0.05 M) was irradiated with UVA lamps (Rayonet reactor, RPR3500 A bulbs) at RT overnight. The mixture was filtered, washing with EtOAc, and the solids were dried in vacuo. The so-obtained residue was purified via flash chromatography over silica gel, eluting with DCM and 0-20% EtOAc gradient to provide the title (rac)-2-bromo-6a,6b,7,9,9a,9b-hexahydrofuro[3',4':3,4]cyclobuta[1,2-c][1,8]naphthyridin-6(5H)-one as a yellow solid in 9% yield. $^1$H NMR (400 MHz, DMSO-d6) δ 10.60 (s, 1H), 8.20 (m, 1H), 7.85 (m, 1H), 4.13 (d, J=9.4 Hz, 1H), 3.97 (d, J=9.6 Hz, 1H), 3.38 (m, 3H), 3.06 (d, J=8.9, 5.1 Hz, 1H), 2.90 (dd, J=9.7, 4.4 Hz, 1H), 2.84 (m, 1H). LCMS (m/z) (M+H)=295.1/297.1, Rt=0.69 min.

Step 2:

To a stirred solution of (rac)-2-bromo-6a,6b,7,9,9a,9b-hexahydrofuro[3',4':3,4]cyclobuta[1,2-c][1,8]naphthyridin-6(5H)-one (1.0 equiv) in DMF (0.1 M) at 25° C. were added Cs$_2$CO$_3$ (2.0 equiv) and iodoethane (1.75 equiv) and the reaction was stirred for 3.5 h. The mixture was poured onto water and extracted three times with ethyl acetate. The combined organics were washed with water and brine, dried over magnesium sulfate, filtered, and concentrated. The residue was purified by flash column chromatography over silica gel (heptane and 0-50% EtOAc) to give (rac)-2-bromo-5-ethyl-6a,6b,7,9,9a,9b-hexahydrofuro[3',4':3,4]cyclobuta[1,2-c][1,8]naphthyridin-6(5H)-one as a white solid in 68% yield. LCMS (m/z) (M+H)=323.0/325.0, Rt=0.99 min.

Step 3:

(rac)-2-bromo-5-ethyl-6a,6b,7,9,9a,9b-hexahydrofuro[3',4':3,4]cyclobuta[1,2-c][1,8]naphthyridin-6(5H)-one was subjected chiral SFC (IB 21×250 mm column, 15% i-PrOH in CO$_2$ eluent). The first eluting peak afforded (6aS, 6bS, 9aS, 9bS-2-bromo-5-ethyl-6a,6b,7,9,9a,9b-hexahydrofuro[3',4':3,4]cyclobuta[1,2-c][1,8]naphthyridin-6(5H)-one as a white solid in 43% yield. The second peak afforded (6aR, 6bR, 9aR, 9bR)-2-bromo-5-ethyl-6a,6b,7,9,9a,9b-hexahydrofuro[3',4':3,4]cyclobuta[1,2-c][1,8]naphthyridin-6(5H)-oneas a white solid in 39% yield. LCMS data for each enantiomer were identical. LCMS (m/z) (M+H)=323.0/325.0, Rt=0.99 min.

Syntheses of: 2-bromo-5-(2-hydroxyethyl)-6a,6b,7,9,9a,9b-hexahydrofuro[3',4':3,4]cyclobuta[1,2-c][1,8]naphthyridin-6(5H)-one "Peak 1" and 2-bromo-5-(2-hydroxyethyl)-6a,6b,7,9,9a,9b-hexahydrofuro[3',4':3,4]cyclobuta[1,2-c][1,8]naphthyridin-6(5H)-one "Peak 2"

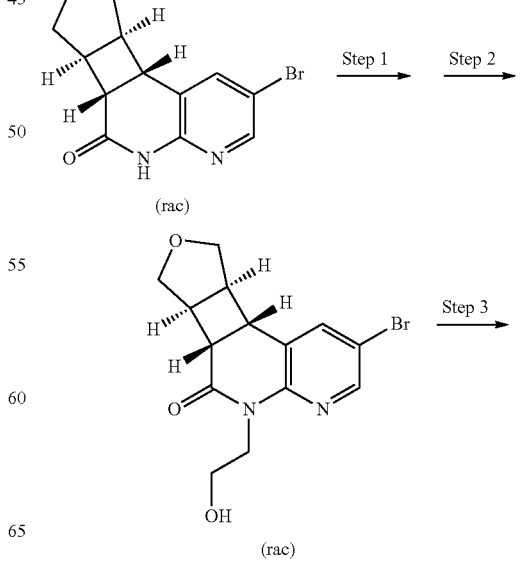

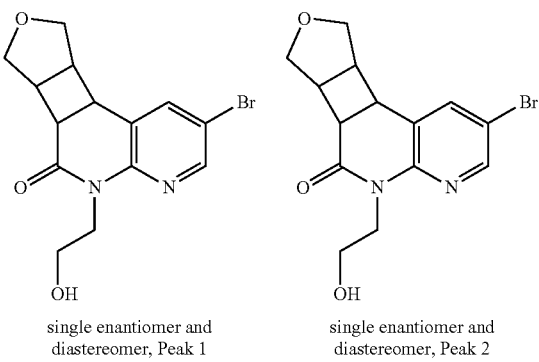

single enantiomer and diastereomer, Peak 1 | single enantiomer and diastereomer, Peak 2

Step 1:

To a stirred solution of (rac)-2-bromo-6a,6b,7,9,9a,9b-hexahydrofuro[3',4':3,4]cyclobuta[1,2-c][1,8]naphthyridin-6(5H)-one (1.0 equiv) in DMF (0.1 M) at 25° C. were added Cs$_2$CO$_3$ (12 equiv) and (2-bromoethoxy)-tert-butyldimethylsilane (8 equiv), and the reaction was stirred at RT for 24 h. The mixture was poured onto water and extracted three times with ethyl acetate. The combined organics were washed with water and brine, dried over magnesium sulfate, filtered, and concentrated. The residue was purified by flash column chromatography over silica gel (heptane and 0-60% EtOAc gradient) to give (rac)-2-bromo-5-(2-((tert-butyldimethylsilyl)oxy)ethyl)-6a,6b,7,9,9a,9b-hexahydrofuro[3',4':3,4]cyclobuta[1,2-c][1,8]naphthyridin-6(5H)-one as a colorless oil in 55% yield. LCMS (m/z) (M+H)=453.3/455.3, Rt=1.53 min.

Step 2:

To a stirred solution of (rac)-2-bromo-5-(2-((tert-butyldimethylsilyl)oxy)ethyl)-6a,6b,7,9,9a,9b-hexahydrofuro[3',4':3,4]cyclobuta[1,2-c][1,8]naphthyridin-6(5H)-one (1.0 equiv) in DCM (0.1 M) at 25° C. was added TfOH (1.5 equiv) and the reaction was stirred for 30 min. The mixture was partitioned between DCM and saturated aqueous NaHCO$_3$ and extracted three times with DCM. The combined organics were dried over magnesium sulfate, filtered, and concentrated. The residue was purified by flash column chromatography over silica gel (DCM and 0-20% MeOH gradient) to give (rac)-2-bromo-5-(2-hydroxyethyl)-6a,6b,7,9,9a,9b-hexahydrofuro[3',4':3,4]cyclobuta[1,2-c][1,8]naphthyridin-6(5H)-one as a white foam in 96% yield. LCMS (m/z) (M+H)=339.2/341.2, Rt=0.75 min.

Step 3:

(rac)-2-bromo-5-(2-hydroxyethyl)-6a,6b,7,9,9a,9b-hexahydrofuro[3',4':3,4]cyclobuta[1,2-c][1,8]naphthyridin-6(5H)-one was subjected chiral SFC (Lux Cellulose-4 21×250 mm column, 45% i-PrOH in CO$_2$ eluent). The first eluting peak afforded 2-bromo-5-(2-hydroxyethyl)-6a,6b,7,9,9a,9b-hexahydrofuro[3',4':3,4]cyclobuta[1,2-c][1,8]naphthyridin-6(5H)-one "Peak 1" as a white foam in 40% yield. The second peak afforded 2-bromo-5-(2-hydroxyethyl)-6a,6b,7,9,9a,9b-hexahydrofuro[3',4':3,4]cyclobuta[1,2-c][1,8]naphthyridin-6(5H)-one "Peak 2" as a white foam in 43% yield. LCMS data for each enantiomer were identical. LCMS (m/z) (M+H)=339.2/341.2, Rt=0.75 min.

Synthesis of 10-bromo-7-(2-hydroxyethyl)-1,4,5,5a,7,11b-hexahydrooxepino[4,5-c][1,8]naphthyridin-6(2H)-one "from Peak 4"

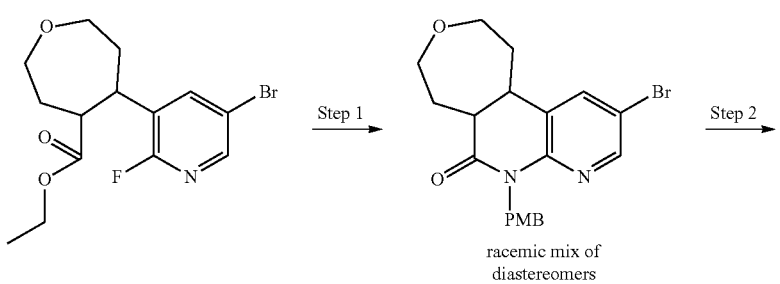

racemic mix of diastereomers

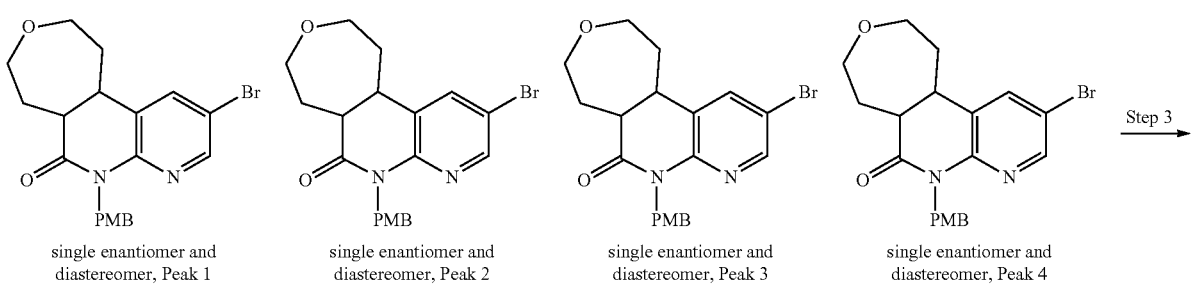

single enantiomer and diastereomer, Peak 1 | single enantiomer and diastereomer, Peak 2 | single enantiomer and diastereomer, Peak 3 | single enantiomer and diastereomer, Peak 4

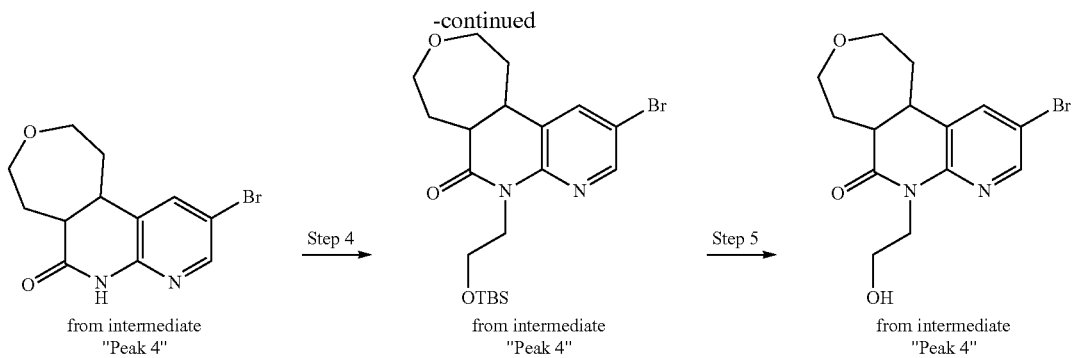

Step 1:

To a stirred solution of ethyl 5-(5-bromo-2-fluoropyridin-3-yl)oxepane-4-carboxylate (1.0 equiv) in NMP (0.2 M) were added i-Pr$_2$NEt (5 equiv) followed by 4-methoxybenzylamine (4.5 equiv) were added and the mixture was heated at 150° C. for 48 h. The reaction was poured onto half-saturated NH$_4$Cl, and extracted twice with EtOAc The combined organics were washed with water and with brine, dried over MgSO$_4$, filtered, and concentrated. The residue was purified by flash column chromatography over silica gel (heptane and 0-50% EtOAc gradient) to give 10-bromo-7-(4-methoxybenzyl)-1,4,5,5a,7,11b-hexahydrooxepino[4,5-c][1,8]naphthyridin-6(2H)-one as a diastereomeric mixture in 69% yield. LCMS (m/z) (M+H)=417.1/419.1, Rt=1.23 and 1.24 min.

Step 2:

10-bromo-7-(4-methoxybenzyl)-1,4,5,5a,7,11b-hexahydrooxepino[4,5-c][1,8]naphthyridin-6(2H)-one was subjected chiral SFC (IC 30×250 mm column, 45% i-PrOH in CO$_2$ eluent). The first eluting peak afforded 10-bromo-7-(4-methoxybenzyl)-1,4,5,5a,7,11b-hexahydrooxepino[4,5-c][1,8]naphthyridin-6(2H)-one "Peak 1" as a white foam in 29% yield. The second peak afforded 10-bromo-7-(4-methoxybenzyl)-1,4,5,5a,7,11b-hexahydrooxepino[4,5-c][1,8]naphthyridin-6(2H)-one "Peak 2" as a white foam in 29% yield. These two products were opposite enantiomers of the same diastereomer; LCMS data for each enantiomer were identical. LCMS (m/z) (M+H)=417.0/419.0, Rt=1.23 min. The third eluting peak afforded 10-bromo-7-(4-methoxybenzyl)-1,4,5,5a,7,11b-hexahydrooxepino[4,5-c][1,8]naphthyridin-6(2H)-one "Peak 3" as a white foam in 13% yield. The fourth peak afforded 10-bromo-7-(4-methoxybenzyl)-1,4,5,5a,7,11b-hexahydrooxepino[4,5-c][1,8]naphthyridin-6(2H)-one "Peak 4" as a white foam in 13% yield. These two products were opposite enantiomers of the same diastereomer; LCMS data for each enantiomer were identical. LCMS (m/z) (M+H)=417.0/419.0, Rt=1.24 min.

Step 3:

To a stirred solution of 10-bromo-7-(4-methoxybenzyl)-1,4,5,5a,7,11b-hexahydrooxepino[4,5-c][1,8]naphthyridin-6(2H)-one "Peak 4" (1.0 equiv) in DCM (0.15 M) was slowly added triflic acid (5 equiv) and the mixture was stirred at 25° C. for 1 h. The mixture was quenched slowly with saturated aqueous Na$_2$CO$_3$ and extracted three times with DCM. The combined organics were washed with brine, dried over magnesium sulfate, filtered, and concentrated. The residue was purified by flash column chromatography over silica gel (DCM and 0-100% EtOAc gradient) to give 10-bromo-1,4,5,5a,7,11b-hexahydrooxepino[4,5-c][1,8]naphthyridin-6(2H)-one "from Peak 4" as a crystalline white solid in 89% yield. LCMS (m/z) (M+H)=297.1/299.1, Rt=0.76.

Step 4:

To a stirred solution of 10-bromo-1,4,5,5a,7,11b-hexahydrooxepino[4,5-c][1,8]naphthyridin-6(2H)-one "from Peak 4" (1.0 equiv) in DMF (0.1 M) at 25° C. were added Cs$_2$CO$_3$ (6 equiv), (2-bromoethoxy)-tert-butyldimethylsilane (2.8 equiv), and the reaction was stirred for 3 h. The mixture was poured onto water and extracted three times with ethyl acetate. The combined organics were washed with water and brine, dried over magnesium sulfate, filtered, and concentrated. The residue was purified by flash column chromatography over silica gel (heptane and 0-50% EtOAc gradient) to provide 10-bromo-7-(2-((tert-butyldimethylsilyl)oxy)ethyl)-1,4,5,5a,7,11b-hexahydrooxepino[4,5-c][1,8]naphthyridin-6(2H)-one "from Peak 4" as a colorless oil in 88% yield. LCMS (m/z) (M+H)=455.2/457.2, Rt=1.61 min.

Step 5:

To a stirred solution of 10-bromo-7-(2-((tert-butyldimethylsilyl)oxy)ethyl)-1,4,5,5a,7,11b-hexahydrooxepino[4,5-c][1,8]naphthyridin-6(2H)-one "from Peak 4" (1.0 equiv) in DCM (0.1 M) at 25° C. was added TfOH (1.5 equiv) and the reaction was stirred for 1 h. The mixture was partitioned between DCM and saturated aqueous NaHCO$_3$ and extracted three times with DCM. The combined organics were dried over magnesium sulfate, filtered, and concentrated. The residue was purified by flash column chromatography over silica gel (heptane and 0-100% EtOAc gradient) to give 10-bromo-7-(2-hydroxyethyl)-1,4,5,5a,7,11b-hexahydrooxepino[4,5-c][1,8]naphthyridin-6(2H)-one "from Peak 4" as a colorless oil in 91% yield. LCMS (m/z) (M+H)=340.9/342.9, Rt=0.79 min.

Example 1

9-(2-methyl-5-(2-(trifluoromethyl)isonicotinamido)phenyl)-6-oxo-1,2,4,6-tetrahydro-[1,4]oxazino[4,3-a]quinoline-5-carboxylate

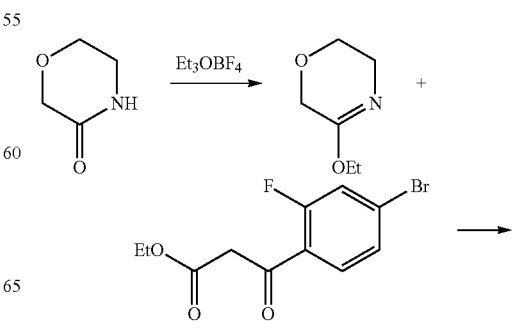

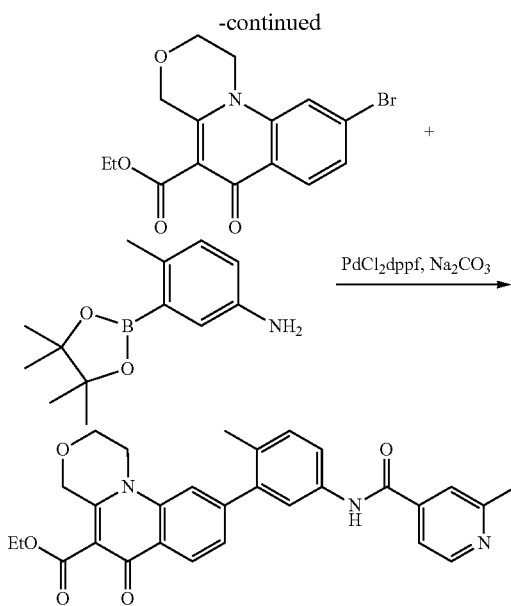

Step 1:

Into a 250 mL RB flask were charged morpholin-3-one (1.0 equiv.) and DCM (0.5 M). To the mixture at room temperature under nitrogen was added triethyloxonium tetrafluoroborate (1.0 M in DCM) (13.81 ml, 13.81 mmol) dropwise. The mixture was agitated at room temperature overnight and the next morning, the reaction mixture was quenched by addition of Sat'd NaHCO$_3$. The organic layer was separated and dried (MgSO$_4$), filtered and concentrated in vacuo (30° C., 250 mmHg) to afford the crude0020product 5-ethoxy-3,6-dihydro-2H-1,4-oxazine in quantitative. $^1$H NMR (400 MHz, CHLOROFORM-d) δ ppm 4.12 (q, J=7.13 Hz, 2H) 4.05 (t, J=1.41 Hz, 2H) 3.64-3.71 (m, 2H) 3.52-3.60 (m, 2H) 1.29 (t, J=7.09 Hz, 3H).

Step 2:

To the crude product 5-ethoxy-3,6-dihydro-2H-1,4-oxazine from above was added ethyl 3-(4-bromophenyl)-3-oxopropanoate (0.8 equiv.). The entire mixture was heated at 115° C. in a Teflon capped vessel for 8 hour upon which LCMS indicated formation of desired product. The reaction mixture was cooled to room temperature and let to stand over the weekend. The solid obtained was dissolved in DCM and purified by flash chromatography (0-10% MeOH/DCM) to afford the desired product ethyl 9-bromo-6-oxo-1,2,4,6-tetrahydro-[1,4]oxazino[4,3-a]quinoline-5-carboxylate. LCMS: (m/z) (M+H)=353.8, Rt=1.03 min.

Step 3:

Into a MW vial were charged ethyl 9-bromo-6-oxo-1,2,4,6-tetrahydro-[1,4]oxazino[4,3-a]quinoline-5-carboxylate, N-(4-methyl-3-(4,4,5,5-tetramethyl-1,3,2-dioxaborolan-2-yl)phenyl)-2-(trifluoromethyl)isonicotinamide (1.0 equiv.), PdCl$_2$(dppf).CH$_2$Cl$_2$ adduct (0.1 equiv.) and dioxane: DMF (5:1), 0.2 M and then 2M Na$_2$CO$_3$ (2.0 equiv). The entire mixture was heated in MW at 120° C. for 15 min, after which LCMS indicated formation of desired product. The reaction mixture was extracted with EtOAc and washed with water twice and dried (MgSO$_4$), filtered and concentrated in vacuo and the residue purified by reverse-phase HPLC to afford the desired product ethyl 9-(2-methyl-5-(2-(trifluoromethyl)isonicotinamido)phenyl)-6-oxo-1,2,4,6-tetrahydro-[1,4]oxazino[4,3-a]quinoline-5-carboxylate in 9% isolated yield. LCMS: (m/z) (M+H)=552.3, Rt=1.39 min. 1H NMR (400 MHz, DMSO-d6) d ppm 10.73 (s, 1H) 9.00 (d, J=5.01 Hz, 1H) 8.38 (s, 1H) 8.29 (d, J=8.19 Hz, 1H) 8.20 (d, J=5.14 Hz, 1H) 7.72-7.80 (m, 3H) 7.34-7.56 (m, 2H) 4.87 (s, 2H) 4.10-4.34 (m, 6H) 2.26 (s, 3H) 1.29 (t, J=7.15 Hz, 3H).

Example 2

9-(2-methyl-5-(2-(trifluoromethyl)isonicotinamido)phenyl)-6-oxo-1,2,4,6-tetrahydro-[1,4]oxazino[4,3-a]quinoline-5-carboxylic Acid

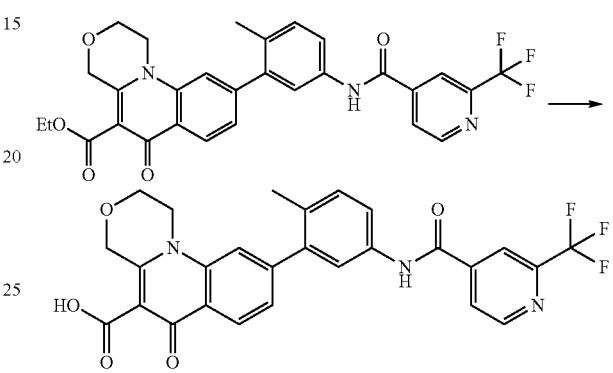

Step 1:

Into a vial was charged ethyl 9-(2-methyl-5-(2(trifluoromethyl)isonicotinamido)phenyl)-6-oxo-1,2,4,6-tetrahydro-[1,4]oxazino[4,3-a]quinoline-5-carboxylate (1.0 equiv.) and then THF:MeOH:Water (3:2:1) (0.2 M) was added and then LiOH.H2O (5.0 equiv was added. The mixture was agitated at 60° C. for 30 min, LCMS indicated formation of desired product as the major species. The reaction mixture was concentrated in vacuo and the residue dissolved in water (5 mL) and acidified to pH=1 using 4N HCl (in water). The product was extracted with EtOAc. The organic layer was dried (MgSO$_4$), filtered and concentrated in vacuo to give a pale orange solid, which was dissolved in DMSO and purified by reverse-phase HPLC (basic method) to provide the desired product in 6.8% isolated yield. LCMS: (m/z) (M+H)=524.3, Rt=0.81 min (basic method). 1H NMR (400 MHz, DMSO-d6) δ ppm 10.76 (s, 1H) 9.00 (d, J=5.01 Hz, 1H) 8.51 (d, J=8.31 Hz, 1H) 8.37 (s, 1H) 8.20 (d, J=4.89 Hz, 1H) 8.00 (s, 1H) 7.76-7.84 (m, 2H) 7.72 (dd, J=8.31, 1.10 Hz, 1H) 7.42 (d, J=8.31 Hz, 1H) 5.43 (s, 2H) 4.45 (t, J=5.20 Hz, 2H) 4.15 (t, J=5.26 Hz, 2H) 2.28 (s, 3H).

Example 3

(rac)-(trans)-N-(3-(6-hydroxy-1,2,4,4a,5,6-hexahydro-[1,4]oxazino[4,3-a]quinolin-9-yl)-4-methylphenyl)-2-(trifluoromethyl)isonicotinamide

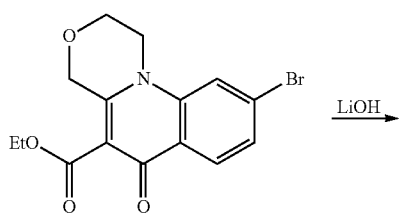

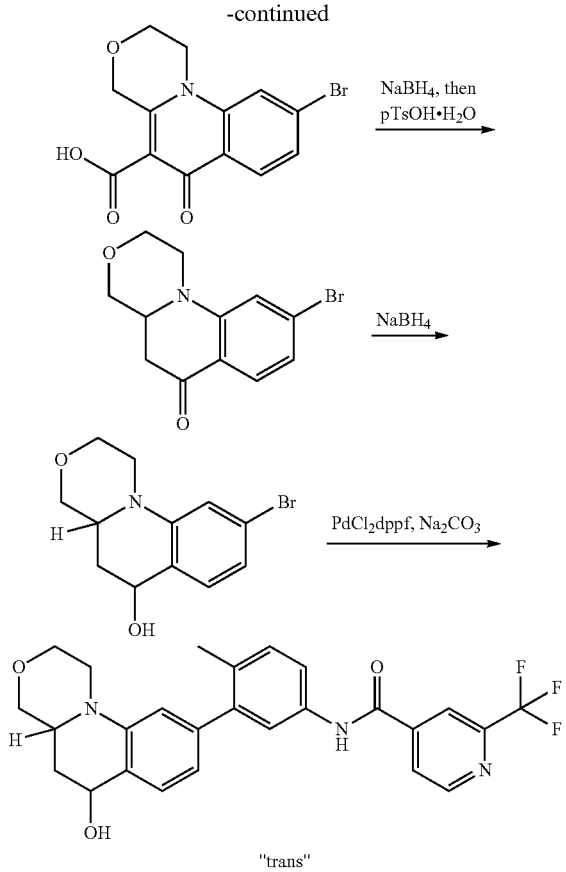

"trans"

Step 1:

Into a 30 mL vial was charged ethyl 9-bromo-6-oxo-1,2,4,6-tetrahydro-[1,4]oxazino[4,3-a]quinoline-5-carboxylate (1.0 equiv.) and then THF, MeOH and Water in (3:2:1 ratio, 0.2 M) followed by and LiOH.H$_2$O (5.0 equiv.) were added. The mixture was heated at 60° C. for 10 min upon which thick light yellow precipitate developed and it became difficult to stir. At this stage, water was added and then the slurry was heated for another 30 min to afford the complete hydrolysis of the ethyl ester. The reaction mixture was concentrated in vacuo and the residue acidified to pH=1 using 4.0 N HCl (aq). The precipitate was collected by filtrated and azeotroped twice with THF and once with toluene and dried under high vacuum until constant mass to afford the desired product 9-bromo-6-oxo-1,2,4,6-tetrahydro-[1,4]oxazino[4,3-a]quinoline-5-carboxylic acid in 77% isolated yield. LCMS: (m/z) (M+H)=325.8, Rt=1.12 min.

Step 2:

9-bromo-6-oxo-1,2,4,6-tetrahydro-[1,4]oxazino[4,3-a]quinoline-5-carboxylic acid (1.0 equiv.) was suspended in MeOH (0.15 M) and then NaBH$_4$ (4.0 equiv.) was added in small portions at room temperature in order to keep the effervescence in control. After completion of NaBH$_4$ addition, pTsOH.H$_2$O (0.1 equiv.) was added. The mixture was placed in an oil bath maintained at 70° C. and agitated for 1 h upon which LCMS indicated complete conversion to the desired product. The reaction mixture was cooled to room temperature and quenched by addition of acetone and then concentrated in vacuo. Sat'd NH$_4$Cl was added to the residue and the product was extracted with EtOAc and the organic layer was dried (MgSO$_4$), filtered and concentrated in vacuo. The residue was purified by flash chromatography (0-50% EtOAc/heptane) to afford the desired product 9-bromo-1,2,4a,5-tetrahydro-[1,4]oxazino[4,3-a]quinolin-6(4H)-one in 40.7% isolated yield as a faint yellow solid. LCMS: (m/z) (M+H)=283.8, Rt=1.29 min.

Step 3:

9-bromo-1,2,4a,5-tetrahydro-[1,4]oxazino[4,3-a]quinolin-6(4H)-one (1.0 equiv.) was suspended in MeOH (0.3 M) and cooled to The mixture was cooled to 0° C. and then sodium borohydride (2.0 equiv.) was added in portions and the mixture let to warm to room temperature and agitate for 2 h upon which LCMS indicated complete ketone reduction. The reaction mixture was quenched by addition of acetone and then the volatiles evaporated in vacuo. The residue was diluted with Sat'd NH$_4$Cl and extracted with EtOAc and the organic layer dried (MgSO$_4$), filtered and concentrated in vacuo to afford an off white solid, which was purified by flash chromatography (0-100% EtOAc/heptane) to afford the desired product (trans)-9-bromo-1,2,4,4a,5,6-hexahydro-[1,4]oxazino[4,3-a]quinolin-6-ol as an off white solid in 99% isolated yield. LCMS: (m/z) (M+H−H$_2$O)=267.9, Rt=1.16 min. The relative stereochemistry of the product was confirmed by 2D-NMR and the relative stereochemistry was established to be trans. $^1$H NMR (600 MHz, CHLOROFORM-d) δ ppm 7.22 (dd, J=8.19, 0.94 Hz, 1H) 6.86 (dd, J=8.14, 1.83 Hz, 1H) 6.80 (d, J=1.69 Hz, 1H) 4.78 (td, J=9.06, 6.45 Hz, 1H) 3.91-3.97 (m, 1H) 3.77 (ddd, J=11.20, 3.20, 0.85 Hz, 1H) 3.62 (td, J=11.72, 2.82 Hz, 1H) 3.44 (dd, J=12.33, 1.69 Hz, 1H) 3.28 (t, J=10.82 Hz, 1H) 3.17 (tt, J=10.76, 3.02 Hz, 1H) 2.79 (td, J=12.09, 3.58 Hz, 1H) 2.07 (ddd, J=12.42, 6.12, 2.92 Hz, 1H) 1.70 (d, J=8.47 Hz, 1H) 1.59 (dt, J=12.38, 10.75 Hz, 1H).

Step 4:

Into a MW vial were charged (trans)-9-bromo-1,2,4,4a,5,6-hexahydro-[1,4]oxazino[4,3-a]quinolin-6-ol (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.), PdCl$_2$(dppf).CH$_2$Cl$_2$ adduct (0.1 equiv.) and then Dioxane (0.13 M) and finally 2M Na$_2$CO$_3$ (2.5 equiv.). The mixture was agitated in MW at 120° C. for 15 min and cooled to room temperature. The product was extracted with EtOAc. The organic layer was dried (Na$_2$SO$_4$), filtered and concentrated in vacuo and the residue purified by reverse-phase HPLC to afford the desired product N-(3-(6-hydroxy-1,2,4,4a,5,6-hexahydro-[1,4]oxazino[4,3-a]quinolin-9-yl)-4-methylphenyl)-2-(trifluoromethyl)isonicotinamide as a free-base in 30.5% isolated yield. LCMS: (m/z) (M+H−H$_2$O)=466.2, Rt=1.30 min. 1H NMR (400 MHz, DMSO-d6) δ ppm 10.63 (s, 1H) 8.98 (d, J=4.89 Hz, 1H) 8.35 (s, 1H) 8.19 (d, J=5.01 Hz, 1H) 7.68 (dd, J=8.25, 2.26 Hz, 1H) 7.60 (d, J=2.32 Hz, 1H) 7.38-7.45 (m, 1H) 7.28 (d, J=8.44 Hz, 1H) 6.64-6.74 (m, 2H) 5.36 (d, J=6.85 Hz, 1H) 4.72-4.88 (m, 1H) 3.68-3.97 (m, 3H) 3.55 (td, J=11.62, 2.57 Hz, 1H) 3.08-3.27 (m, 2H) 2.62-2.79 (m, 1H) 2.22 (s, 3H) 1.90-2.04 (m, 1H) 1.43-1.61 (m, 1H).

Examples 4 and 5

(trans)-N-(3-(6-hydroxy-1,2,4,4a,5,6-hexahydro-[1,4]oxazino[4,3-a]quinolin-9-yl)-4-methylphenyl)-2-(trifluoromethyl)isonicotinamide

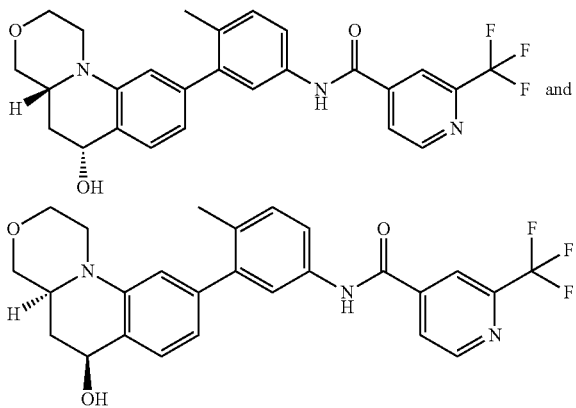

Racemic (trans)-N-(3-(6-hydroxy-1,2,4,4a,5,6-hexahydro-[1,4]oxazino[4,3-a]quinolin-9-yl)-4-methylphenyl)-2-(trifluoromethyl)isonicotinamide was resolved by chiral SFC. The first eluting peak afforded N-(3-((4aR,6R)-6-hydroxy-1,2,4,4a,5,6-hexahydro-[1,4]oxazino[4,3-a]quinolin-9-yl)-4-methylphenyl)-2-(trifluoromethyl)isonicotinamide. $^1$H NMR (400 MHz, DMSO-d6) δ ppm 10.63 (s, 1H) 8.98 (d, J=5.01 Hz, 1H) 8.36 (s, 1H) 8.19 (dd, J=5.01, 1.10 Hz, 1H) 7.68 (dd, J=8.25, 2.26 Hz, 1H) 7.60 (d, J=2.32 Hz, 1H) 7.39-7.45 (m, 1H) 7.28 (d, J=8.44 Hz, 1H) 6.64-6.73 (m, 2H) 5.36 (d, J=6.72 Hz, 1H) 4.68-4.83 (m, 1H) 3.67-3.97 (m, 3H) 3.55 (td, J=11.52, 2.38 Hz, 1H) 3.09-3.26 (m, 2H) 2.61-2.75 (m, 1H) 1.94-2.03 (m, 1H) 2.22 (s, 3H) 1.54 (q, J=11.37 Hz, 1H); (m/z) (M+H–H$_2$O)=466.2, Rt=1.30 min and the second eluting peak afforded N-(3-((4aS,6S)-6-hydroxy-1,2,4,4a,5,6-hexahydro-[1,4]oxazino[4,3-a]quinolin-9-yl)-4-methylphenyl)-2-(trifluoromethyl)isonicotinamide. $^1$H NMR (400 MHz, DMSO-d6) δ ppm 10.64 (s, 1H) 8.98 (d, J=5.01 Hz, 1H) 8.36 (s, 1H) 8.19 (d, J=4.89 Hz, 1H) 7.68 (dd, J=8.19, 2.20 Hz, 1H) 7.60 (d, J=2.20 Hz, 1H) 7.39-7.46 (m, 1H) 7.28 (d, J=8.44 Hz, 1H) 6.65-6.75 (m, 2H) 5.36 (d, J=6.72 Hz, 1H) 4.71-4.84 (m, 1H) 3.66-3.99 (m, 3H) 3.55 (td, J=11.52, 2.38 Hz, 1H) 3.08-3.26 (m, 2H) 2.63-2.76 (m, 1H) 2.22 (s, 3H) 1.90-2.05 (m, 1H) 1.54 (q, J=11.41 Hz, 1H); (m/z) (M+H–H$_2$O)=466.2, Rt=1.30.

The following compounds were made following step 4 of Example 3.

| Ex. No. | Structure | Name | Physical Data |
|---|---|---|---|
| 6 | "trans" | (rac)-2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.58 (s, 1 H) 8.75-9.14 (m, 1 H) 8.17 (s, 1 H) 8.02 (dd, J = 5.01, 1.35 Hz, 1 H) 7.68 (dd, J = 8.25, 2.26 Hz, 1H) 7.61 (d, J = 2.20 Hz, 1 H) 7.42 (dd, J = 7.76, 0.79 Hz, 1 H) 7.27 (d, J = 8.44 Hz, 1 H) 6.64-6.76 (m, 2 H) 5.36 (d, J = 6.85 Hz, 1 H) 4.73-4.87 (m, 1H) 3.68-3.99 (m, 3 H) 3.55 (td, J = 11.62, 2.57 Hz, 1 H) 3.08-3.25 (m, 2 H) 2.62-2.71 (m, 1 H) 2.22 (s, 3 H) 2.05 (t, J = 19.13 Hz, 4 H) 1.45-1.62 (m, 1 H); LCMS (m/z) (M + H – H$_2$O) = 552.1, Rt = 1.26 min. |
| 7 | "trans" | (rac)-2-(2-fluoropropan-2-yl)-N-(3-(6-hydroxy-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.50 (s, 1 H) 8.75 (d, J = 5.01 Hz, 1 H) 8.01 (s, 1 H) 7.81 (dd, J = 5.01, 1.59 Hz, 1 H) 7.68 (dd, J = 8.25, 2.26 Hz, 1 H) 7.60 (d, J = 2.20 Hz, 1 H) 7.36-7.45 (m, 1 H) 7.26 (d, J = 8.44 Hz, 1 H) 6.64-6.76 (m, 2 H) 5.36 (d, J = 6.72 Hz, 1 H) 4.70-4.89 (m, 1 H) 3.68-3.94 (m, 3 H) 3.55 (td, J = 11.58, 2.51 Hz, 1 H) 3.08-3.26 (m, 2 H) 2.67 (td, J = 12.01, 3.48 Hz, 1 H) 2.22 (s, 3 H) 1.92-2.05 (m, 1 H) 1.62-1.77 (m, 6 H) 1.43-1.59 (m, 1 H); LCMS (m/z) (M + H – H$_2$O) = 458.3, Rt = 1.28 min. |

-continued

| Ex. No. | Structure | Name | Physical Data |
|---|---|---|---|
| 8 | "trans" | (rac)-2-(2-cyanopropan-2-yl)-N-(3-(6-hydroxy-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.49 (s, 1 H) 8.80 (dd, J = 5.01, 0.73 Hz, 1 H) 7.99 (s, 1 H) 7.85 (dd, J = 5.01, 1.47 Hz, 1 H) 7.66 (dd, J = 8.25, 2.26 Hz, 1 H) 7.59 (d, J = 2.20 Hz, 1 H) 7.42 (dd, J = 7.76, 0.67 Hz, 1 H) 7.27 (d, J = 8.44 Hz, 1 H) 6.65-6.73 (m, 2 H) 5.36 (d, J = 6.72 Hz, 1 H) 4.69-4.87 (m, 1 H) 3.67-3.96 (m, 3 H) 3.55 (td, J = 11.62, 2.57 Hz, 1 H) 3.06-3.27 (m, 2 H) 2.67 (td, J = 11.98, 3.42 Hz, 1 H) 2.22 (s, 3 H) 1.94-2.04 (m, 1 H) 1.76 (s, 6 H) 1.42-1.61 (m, 1 H); LCMS (m/z) (M + H − H$_2$O) = 465.3, Rt = 1.22 min. |
| 9 | "trans" | (rac)-N-(5-(6-hydroxy-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, DMSO-d6) δ ppm 10.62 (s, 1 H) 8.82 (d, J = 2.45 Hz, 1 H) 8.21-8.38 (m, 2 H) 7.93-8.07 (m, 2 H) 7.81 (t, J = 7.83 Hz, 1 H) 7.45 (dd, J = 7.76, 0.79 Hz, 1 H) 6.71-6.81 (m, 2 H) 5.39 (d, J = 6.85 Hz, 1 H) 4.65-4.89 (m, 1 H) 3.70-3.99 (m, 3 H) 3.56 (td, J = 11.65, 2.51 Hz, 1 H) 3.09-3.27 (m, 2 H) 2.62-2.78 (m, 1 H) 2.42 (s, 3 H) 1.93-2.05 (m, 1 H) 1.46-1.60 (m, 1 H); LCMS (m/z) (M + H) = 484.2, Rt = 1.20 min. |
| 10 | "trans" | (rac)-N-(3-(6-hydroxy-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, DMSO-d6) δ ppm 10.80 (s, 1 H) 9.91 (d, J = 1.96 Hz, 1 H) 8.67 (d, J = 2.08 Hz, 1 H) 7.67 (dd, J = 8.19, 2.20 Hz, 1 H) 7.60 (d, J = 2.20 Hz, 1 H) 7.40-7.46 (m, 1 H) 7.31 (d, J = 8.44 Hz, 1 H) 6.65-6.74 (m, 2 H) 5.37 (d, J = 6.85 Hz, 1 H) 4.71-4.89 (m, 1 H) 3.67-4.00 (m, 3H) 3.55 (td, J = 11.58, 2.51 Hz, 1 H) 3.07-3.26 (m, 2 H) 2.62-2.77 (m, 1 H) 2.23 (s, 3 H) 1.92-2.04 (m, 1 H) 1.40-1.60 (m, 1 H); LCMS (m/z) (M + H − H$_2$O) = 467.3, Rt = 1.24 min. |
| 11 | "trans" | (rac)-2-(1,1-difluoroethyl)-N-(5-(6-hydroxy-1,2,4,4a,5,6-hexahydro-[1,4]oxazino[4,3-a]quinolin-9-yl)-6-methylpyridin-3-yl)isonicotinamide | $^1$H NMR (400 MHz, DMSO-d6) δ ppm 10.79 (s, 1 H) 8.90 (d, J = 5.01 Hz, 1 H) 8.82 (d, J = 2.45 Hz, 1 H) 8.26-8.27 (m, 1 H) 8.20 (s, 1 H) 7.92-8.10 (m, 1 H) 7.83-8.07 (m, 1 H) 7.41-7.52 (m, 1 H) 7.38-7.53 (m, 1 H) 6.80-6.81 (m, 1 H) 6.64-6.81 (m, 1 H) 5.30-5.48 (m, 1 H) 4.53-4.96 (m, 1 H) 3.71-4.17 (m, 4 H) 3.46-3.64 (m, 1 H) 3.04-3.26 (m, 3 H) 2.66-2.75 (m, 1 H) 2.43 (s, 3 H) 2.06 (t, J = 19.13 Hz, 4 H); LCMS (m/z) (M + H) = 481.2, Rt = 0.94 min. |
| 12 | "trans" | (rac)-2-(2-cyanopropan-2-yl)-N-(5-(6-hydroxy-1,2,4,4a,5,6-hexahydro-[1,4]oxazino[4,3-a]quinolin-9-yl)-6-methylpyridin-3-yl)isonicotinamide | $^1$H NMR (400 MHz, DMSO-d6) δ ppm 10.72 (s, 1 H) 8.63-9.04 (m, 2 H) 8.00 (dd, J = 17.61, 1.59 Hz, 2 H) 7.88 (dd, J = 5.07, 1.53 Hz, 1 H) 7.45 (dd, J = 7.83, 0.86 Hz, 1 H) 6.66-6.81 (m, 2 H) 5.40 (br s, 1 H) 4.78 (br dd, J = 10.33, 6.17 Hz, 1 H) 3.71-3.98 (m, 3 H) 3.56 (td, J = 11.65, 2.63 Hz, 1 H) 3.10-3.26 (m, 2 H) 2.68 (td, J = 12.07, 3.48 Hz, 1 H) 2.43 (s, 3 H) 1.95-2.06 (m, 1 H) 1.77 (s, 6 H) 1.44-1.64 (m, 1 H); LCMS (m/z) (M + H) = 484.2, Rt = 0.92 min. |

Examples 13 and 14

(trans)-2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide

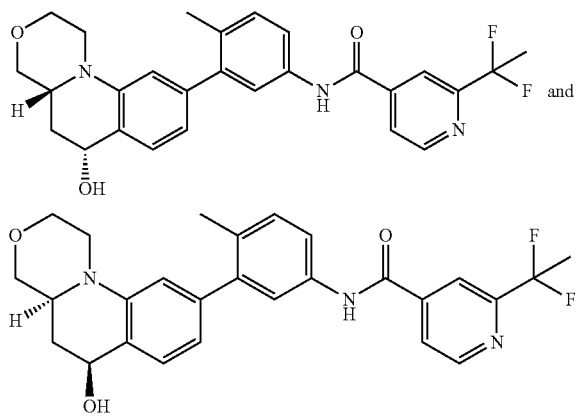

(trans)-2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide was resolved by chiral SFC. The first eluting peak afforded 2-(1,1-difluoroethyl)-N-(3-((4aR,6R)-6-hydroxy-1,2,4,4a,5,6-hexahydro-[1,4]oxazino[4,3-a]quinolin-9-yl)-4-methylphenyl)isonicotinamide. ¹H NMR (400 MHz, DMSO-d6) δ ppm 10.58 (s, 1H) 8.79-8.95 (m, 1H) 8.17 (s, 1H) 8.02 (dd, J=5.01, 1.34 Hz, 1H) 7.54-7.73 (m, 2H) 7.42 (dd, J=7.76, 0.67 Hz, 1H) 7.27 (d, J=8.44 Hz, 1H) 6.54-6.74 (m, 2H) 5.36 (br. s., 1H) 4.77 (dd, J=10.64, 6.24 Hz, 1H) 3.69-3.98 (m, 3H) 3.55 (td, J=11.62, 2.57 Hz, 1H) 3.05-3.25 (m, 2H) 2.67 (td, J=12.01, 3.48 Hz, 1H) 2.22 (s, 3H) 1.89-2.13 (m, 4H) 1.54 (q, J=11.37 Hz, 1H); LCMS (m/z) (M+H−H₂O)=462.1, Rt=1.38 min and the second eluting peak afforded 2-(1,1-difluoroethyl)-N-(3-((4aS,6S)-6-hydroxy-1,2,4,4a,5,6-hexahydro-[1,4]oxazino[4,3-a]quinolin-9-yl)-4-methylphenyl)isonicotinamide. ¹H NMR (400 MHz, DMSO-d6) δ ppm 10.58 (s, 1H) 8.79-8.95 (m, 1H) 8.17 (s, 1H) 8.02 (dd, J=5.01, 1.34 Hz, 1H) 7.54-7.73 (m, 2H) 7.42 (dd, J=7.76, 0.67 Hz, 1H) 7.27 (d, J=8.44 Hz, 1H) 6.54-6.74 (m, 2H) 5.36 (br. s., 1H) 4.77 (dd, J=10.64, 6.24 Hz, 1H) 3.69-3.98 (m, 3H) 3.55 (td, J=11.62, 2.57 Hz, 1H) 3.05-3.25 (m, 2H) 2.67 (td, J=12.01, 3.48 Hz, 1H) 2.22 (s, 3H) 1.89-2.13 (m, 4H) 1.54 (q, J=11.37 Hz, 1H); LCMS (m/z) (M+H−H₂O)=462.1, Rt=1.38 min.

(cis)-9-bromo-1,2,4,4a,5,6-hexahydro-[1,4]oxazino[4,3-a]quinolin-6-ol

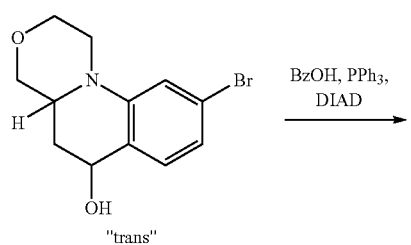

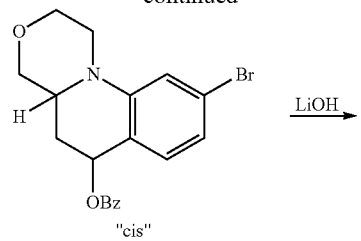

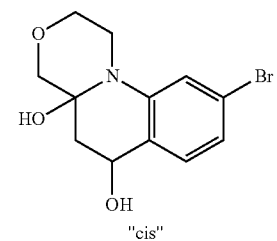

Step 1:

(trans)-9-bromo-1,2,4,4a,5,6-hexahydro-[1,4]oxazino[4,3-a]quinolin-6-ol (1.0 equiv.), Triphenylphosphine (1.2 equiv.), Benzoic acid (2.0 equiv.) were suspended in THF (0.25 M) and cooled to 0° C. Then DIAD (1.0 equiv.) was added dropwise. The mixture was let to warm to room temperature over 2 h upon which LCMS indicated formation of desired product. The reaction mixture was concentrated in vacuo and the residue purified by flash chromatography (0-30% EtOAc/heptane) to afford the desired product (cis)-9-bromo-1,2,4,4a,5,6-hexahydro-[1,4]oxazino[4,3-a]quinolin-6-yl benzoate in quantitative yield. LCMS: (m/z) (M+H)=390.1, Rt=1.71 min.

Step 2:

Into a 30 mL vial was charged (cis)-9-bromo-1,2,4,4a,5,6-hexahydro-[1,4]oxazino[4,3-a]quinolin-6-yl benzoate and THF, MeOH, Water (3:2:1 ratio, 0.2M) and then at room temperature LiOH.H₂O (258 mg, 6.16 mmol) was added. The mixture was agitated at 70° C. for 30 min and then product extracted with EtOAc. The organic layer was washed with Sat'd Na₂CO₃ and dried (MgSO₄), filtered and concentrated in vacuo to afford the desired product (cis)-9-bromo-1,2,4,4a,5,6-hexahydro-[1,4]oxazino[4,3-a]quinolin-6-ol as a colorless solid. LCMS: (m/z) (M+H−H₂O)=267.9, Rt=1.16 min.

Example 15

(rac)-(cis)-2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide

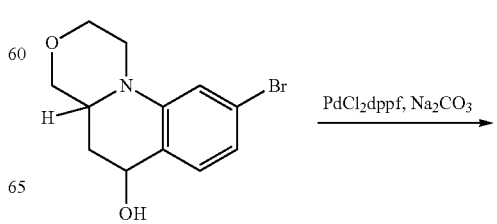

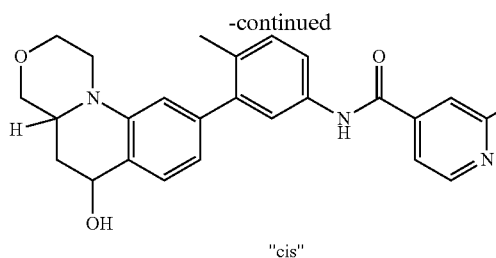

"cis"

Into a MW vial was added (cis)-9-bromo-1,2,4,4a,5,6-hexahydro-[1,4]oxazino[4,3-a]quinolin-6-ol (1.0 equiv.), 2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide (1.0 equiv), K₃PO₄ (2.0 equiv.), X-Phos G2 Pd-Cy (0.1 equiv.) and then dioxane: water (10:1) (0.2 M). The mixture was heated in MW at 120° C. for 30 min and then cooled to room temperature and the product extracted with EtOAc. The organic layer was dried (Na₂SO₄), filtered and concentrated in vacuo and the residue purified by flash chromatography (0-100% EtOAc/heptane) to afford the desired product as an off white solid which was dissolved in 50/50 ACN/water and lyophilized. LCMS (m/z) (M+H–H₂O)=466.3.1, Rt=1.31 min; ¹H NMR (400 MHz, DMSO-d6) δ ppm 10.63 (s, 1H) 8.98 (d, J=5.01 Hz, 1H) 8.35 (s, 1H) 8.19 (dd, J=4.95, 1.04 Hz, 1H) 7.58-7.72 (m, 2H) 7.15-7.49 (m, 2H) 6.79 (d, J=1.10 Hz, 1H) 6.63-6.73 (m, 1H) 5.10-5.44 (m, 1H) 4.43-4.88 (m, 1H) 3.48-4.06 (m, 4H) 3.01-3.29 (m, 2H) 2.73 (td, J=11.95, 3.48 Hz, 1H) 2.23 (s, 3H) 1.75 (dt, J=13.27, 2.48 Hz, 1H) 1.39-1.61 (m, 1H).

The following compounds were made following Example 15.

| Ex. No. | Structure | Name | Physical Data |
|---|---|---|---|
| 16 | 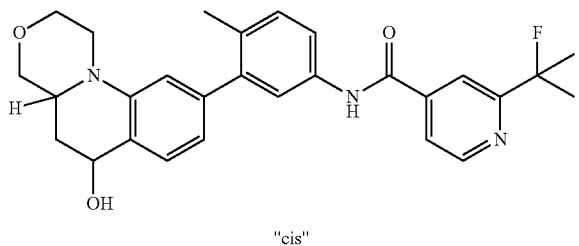 "cis" | (rac)-2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide | ¹H NMR (400 MHz, DMSO-d6) δ ppm 10.59 (s, 1 H) 8.87 (dd, J = 5.01, 0.61 Hz, 1 H) 8.17 (d, J = 0.61 Hz, 1 H) 8.02 (d, J = 5.01 Hz, 1 H) 7.58-7.73 (m, 2 H) 7.18-7.45 (m, 2 H) 6.79 (d, J = 1.10 Hz, 1 H) 6.63-6.74 (m, 1 H) 5.13-5.45 (m, 1 H) 4.52-4.89 (m, 1 H) 3.86-4.00 (m, 1 H) 3.69-3.84 (m, 2 H) 3.49-3.65 (m, 1 H) 3.10-3.29 (m, 2 H) 2.73 (td, J = 11.95, 3.48 Hz, 1 H) 2.22 (s, 3 H) 1.93-2.11 (m, 3 H) 1.75 (dt, J = 13.27, 2.48 Hz, 1H) 1.42-1.61 (m, 1 H); LCMS (m/z) (M + H − H₂O) = 462.4, Rt = 1.30 min. |
| 17 | 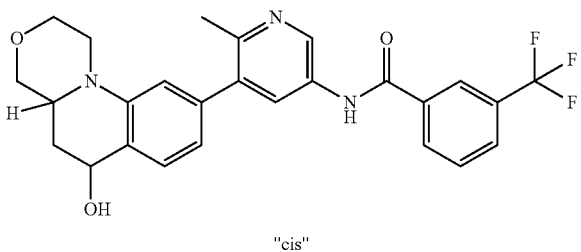 "cis" | (rac)-2-(2-fluoropropan-2-yl)-N-(3-(6-hydroxy-1,2,4,4a,5,6-hexahydro-[1,4]oxazino[4,3-a]quinolin-9-yl)-4-methylphenyl)isonicotinamide | ¹H NMR (400 MHz, DMSO-d6) δ ppm 10.51 (s, 1 H) 8.75 (d, J = 5.13 Hz, 1 H) 8.01 (s, 1 H) 7.81 (dd, J = 5.01, 1.59 Hz, 1 H) 7.67 (dd, J = 8.25, 2.26 Hz, 1 H) 7.55-7.64 (m, 1 H) 7.17-7.46 (m, 2 H) 6.79 (d, J = 1.10 Hz, 1 H) 6.63-6.73 (m, 1 H) 5.36 (d, J = 6.72 Hz, 1 H) 5.18 (d, J = 5.01 Hz, 8 H)4.72-4.83 (m, 1 H) 4.51-4.62 (m, 8 H) 3.87-4.03 (m, 1 H) 3.66-3.85 (m, 2 H) 3.59 (td, J = 11.68, 2.57 Hz, 1 H) 3.06-3.29 (m, 2 H) 2.64-2.82 (m, 1 H) 2.22 (s, 3 H) 1.64-1.78 (m, 7 H) 1.43-1.60 (m, 1 H); LCMS (m/z) (M + H − H₂O) = 458.4, Rt = 1.29 min. |
| 18 | "cis" | (rac)-N-(5-(6-hydroxy-1,2,4,4a,5,6-hexahydro-[1,4]oxazino[4,3-a]quinolin-9-yl)-6-methylpyridin-3-yl)-3-(trifluoromethyl)benzamide | ¹H NMR (400 MHz, DMSO-d6) δ ppm 10.50-10.87 (m, 1 H) 8.75-9.07 (m, 1 H) 8.24-8.47 (m, 2 H) 7.91-8.12 (m, 2 H) 7.81 (t, J = 7.83 Hz, 1 H)7.25 (d, J = 7.83 Hz, 1 H) 6.67-6.96 (m, 2 H) 5.13-5.49 (m, 1 H) 4.54-4.93 (m, 1 H) 3.71-4.05 (m, 3 H) 3.59 (td, J = 11.65, 2.63 Hz, 1 H) 3.11-3.27 (m, 2 H) 2.74 (td, J = 12.01, 3.48 Hz, 1 H) 2.42 (s, 3 H) 1.76 (dt, J = 13.30, 2.46 Hz, 1 H) 1.44-1.62 (m, 1 H); LCMS (m/z) (M + H) = 484.3, Rt = 1.22 min. |

Examples 19 and 20

(cis)-2-(1,1-difluoroethyl)-N-(3-(6-hydroxy-1,2,4,4a, 5,6-hexahydro-[1,4]oxazino[4,3-a]quinolin-9-yl)-4-methylphenyl)isonicotinamide

(cis2-(1,1-difluoroethyl)-N-(3-(6-hydroxy-1,2,4,4a,5,6-hexahydro-[1,4]oxazino[4,3-a]quinolin-9-yl)-4-methylphenyl)isonicotinamide was resolved by chiral SFC. The first eluting peak afforded 2-(1,1-difluoroethyl)-N-(3-((4aR,6S)-6-hydroxy-1,2,4,4a,5,6-hexahydro-[1,4]oxazino[4,3-a]quinolin-9-yl)-4-methylphenyl)isonicotinamide. $^1$H NMR (400 MHz, DMSO-d6) δ ppm 10.59 (s, 1H) 8.87 (d, J=5.01 Hz, 1H) 8.17 (s, 1H) 7.89-8.06 (m, 1H) 7.57-7.76 (m, 2H) 7.15-7.35 (m, 2H) 6.79 (d, J=1.10 Hz, 1H) 6.68 (dd, J=7.64, 1.41 Hz, 1H) 5.18 (d, J=4.52 Hz, 1H) 4.57 (d, J=2.32 Hz, 1H) 3.94 (dd, J=11.25, 2.93 Hz, 1H) 3.69-3.86 (m, 2H) 3.59 (td, J=11.58, 2.63 Hz, 1H) 3.12-3.28 (m, 2H) 2.73 (td, J=11.98, 3.55 Hz, 1H) 2.22 (s, 3H) 2.05 (t, J=19.13 Hz, 3H) 1.75 (dt, J=13.33, 2.38 Hz, 1H) 1.43-1.60 (m, 1H); LCMS (m/z) (M+H−H$_2$O)=462.4, Rt=1.30 min and the second eluting peak afforded 2-(1,1-difluoroethyl)-N-(3-((4aS,6R)-6-hydroxy-1,2,4,4a,5,6-hexahydro-[1,4]oxazino[4,3-a]quinolin-9-yl)-4-methylphenyl)isonicotinamide. $^1$H NMR (400 MHz, DMSO-d6) δ ppm 10.59 (s, 1H) 8.87 (d, J=5.01 Hz, 1H) 8.17 (s, 1H) 7.89-8.06 (m, 1H) 7.57-7.76 (m, 2H) 7.15-7.35 (m, 2H) 6.79 (d, J=1.10 Hz, 1H) 6.68 (dd, J=7.64, 1.41 Hz, 1H) 5.18 (d, J=4.52 Hz, 1H) 4.57 (d, J=2.32 Hz, 1H) 3.94 (dd, J=11.25, 2.93 Hz, 1H) 3.69-3.86 (m, 2H) 3.59 (td, J=11.58, 2.63 Hz, 1H) 3.12-3.28 (m, 2H) 2.73 (td, J=11.98, 3.55 Hz, 1H) 2.22 (s, 3H) 2.05 (t, J=19.13 Hz, 3H) 1.75 (dt, J=13.33, 2.38 Hz, 1H) 1.43-1.60 (m, 1H); LCMS (m/z) (M+H−H$_2$O)=462.4, Rt=1.30 min.

Example 21

(rac)-N-(3-(1,2,4,4a,5,6-hexahydro-[1,4]oxazino[4,3-a]quinolin-9-yl)-4-methylphenyl)-2-(trifluoromethyl)isonicotinamide

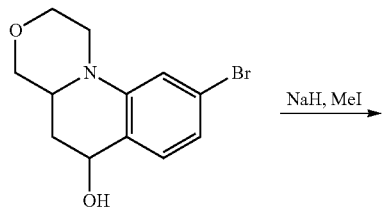

NaH, MeI →

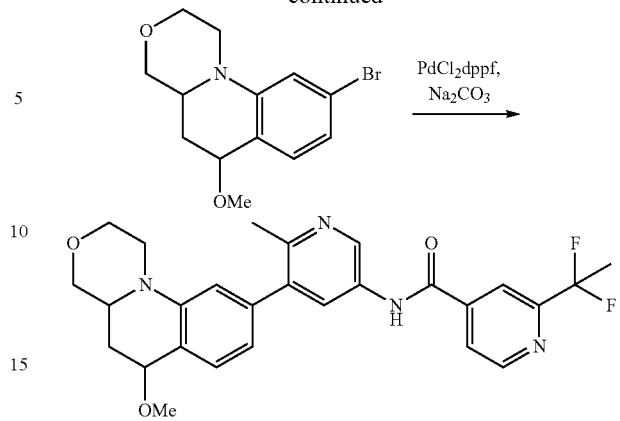

"trans"

Step 1:

Into a MW vial was charged (trans)-9-bromo-1,2,4,4a,5,6-hexahydro-[1,4]oxazino[4,3-a]quinolin-6-ol (1.0 equiv.) and then Triethylsilane (8.9 equiv.) followed by TFA (18.4 equiv). The mixture was agitated in MW at 140° C. for 15 min during which LCMS indicated formation of desired product. The reaction mixture was diluted with EtOAc and treated with Sat'd Na$_2$CO$_3$ and after the effervescence subsided, the product was extracted with EtOAc. The organic layer was dried (MgSO$_4$), filtered and concentrated in vacuo to afford the crude product 9-bromo-1,2,4,4a,5,6-hexahydro-[1,4]oxazino[4,3-a]quinoline which was taken to the next step as such. LCMS: (m/z) (M+H)=269.8, Rt=1.22 min.

Step 2:

9-bromo-1,2,4,4a,5,6-hexahydro-[1,4]oxazino[4,3-a]quinoline (1.0 equivN-(4-methyl-3-(4,4,5,5-tetramethyl-1,3,2-dioxaborolan-2-yl)phenyl)-2-(trifluoromethyl)isonicotinamide (1.0 equiv.), PdCl$_2$(dppf).CH$_2$Cl$_2$ adduct (0.1 equiv.) were combined in dioxane (1.5 mL) and then 2 M Na$_2$CO$_3$ (2.0 equiv.) was added. The mixture was heated in MW at 120° C. for 30 min and then cooled to room temperature. The mixture was extracted with EtOAc and dried (Na$_2$SO$_4$), filtered and concentrated in vacuo and purified by reverse-phase HPLC and the product fractions combined and lyophilized and the obtained solid was further purified by prep TLC (50% EtOAc/heptane), and the silica was scraped and suspended in DCM/MeOH (10:1) and filtered. The filtrate was concentrated in vacuo and dissolved in ACN/water (50:50) and frozen and lyophilized to afford N-(3-(1, 2,4,4a,5,6-hexahydro-[1,4]oxazino[4,3-a]quinolin-9-yl)-4-methylphenyl)-2-(trifluoromethyl)isonicotinamide in 4% isolated yield. LCMS (m/z) (M+H−H$_2$O)=468.1, Rt=1.58 min; $^1$H NMR (400 MHz, DMSO-d6) δ ppm 10.50-10.72 (m, 1H) 8.98 (d, J=5.01 Hz, 1H) 8.36 (s, 1H) 8.19 (dd, J=4.95, 1.16 Hz, 1H) 7.53-7.70 (m, 2H) 7.28 (d, J=8.31 Hz, 1H) 7.01 (d, J=7.46 Hz, 1H) 6.74 (d, J=1.22 Hz, 1H) 6.62 (dd, J=7.52, 1.41 Hz, 1H) 3.79-3.97 (m, 2H) 3.70 (d, J=11.62 Hz, 1H) 3.56 (td, J=11.62, 2.69 Hz, 1H) 3.21 (t, J=10.70 Hz, 1H) 3.00 (tt, J=10.38, 3.01 Hz, 1H) 2.80-2.93 (m, 1H) 2.64-2.78 (m, 2H) 2.22 (s, 3H) 1.77-1.98 (m, 1H) 1.49-1.67 (m, 1H).

Example 22

(rac)-N-(3-(6-hydroxy-6-methyl-1,2,4,4a,5,6-hexahydro-[1,4]oxazino[4,3-a]quinolin-9-yl)-4-methylphenyl)-2-(trifluoromethyl)isonicotinamide

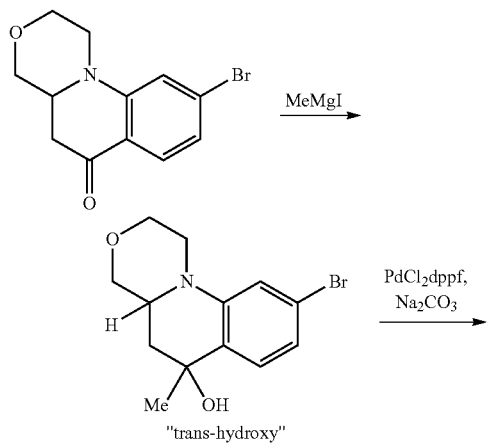

Step 1:

9-bromo-1,2,4a,5-tetrahydro-[1,4]oxazino[4,3-a]quinolin-6(4H)-one (1.0 equiv.) was dissolved in Tetrahydrofuran (0.1 M) and cooled to 0° C. Then methylmagnesium iodide (1.5 equiv.) was added dropwise upon which the mixture turns turbid yellow. After 2 h, reaction appears to be saturated. The reaction mixture was quenched with water and extracted with EtOAc. The organic layer was dried (MgSO$_4$), filtered and concentrated in vacuo. The residue was purified by flash chromatography (0-100% EtOAc/heptane) to afford the desired product (trans)-9-bromo-6-methyl-1,2,4,4a,5,6-hexahydro-[1,4]oxazino[4,3-a]quinolin-6-ol in 58% isolated yield. LCMS: (m/z) (M+H−H$_2$O)=281.9, Rt=1.22 min.

Step 2.

(trans)-9-bromo-6-methyl-1,2,4,4a,5,6-hexahydro-[1,4]oxazino[4,3-a]quinolin-6-ol (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.)), PdCl$_2$(dppf).CH$_2$Cl$_2$ adduct (0.1 equiv.) were combined in dioxane (0.1 M) and then 2 M Na$_2$CO$_3$ (2.0 equiv.) was added. The mixture was heated in MW at 120° C. for 25 min and then diluted with EtOAc. The organic layer was washed with brine and dried (MgSO$_4$), filtered and concentrated in vacuo. The residue was purified by flash chromatography (0-100% EtOAc/heptane) to afford the desired product N-(3-(6-hydroxy-6-methyl-1,2,4,4a,5,6-hexahydro-[1,4]oxazino[4,3-a]quinolin-9-yl)-4-methylphenyl)-2-(trifluoromethyl)isonicotinamide as an off-white solid. LCMS (m/z) (M+H−H$_2$O)=480.1, Rt=1.41 min; $^1$H NMR (400 MHz, DMSO-d6) δ ppm 10.53-10.66 (m, 1H) 8.99 (d, J=5.01 Hz, 1H) 8.35 (s, 1H) 8.18 (dd, J=5.01, 1.10 Hz, 1H) 7.60-7.73 (m, 2H) 7.49 (d, J=7.70 Hz, 1H) 7.28 (d, J=8.31 Hz, 1H) 6.58-6.75 (m, 2H) 4.97-5.14 (m, 1H) 3.51-4.01 (m, 4H) 2.99-3.26 (m, 2H) 2.64-2.80 (m, 1H) 2.23 (s, 3H) 1.69-1.86 (m, 2H) 1.34-1.54 (m, 3H).

The compound of Example 23 was prepared according to the above methods using appropriate starting materials:

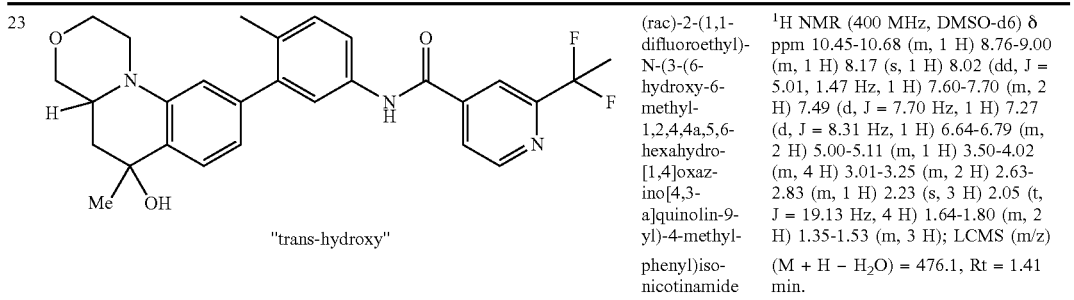

| | | |
|---|---|---|
| 23 | (rac)-2-(1,1-difluoroethyl)-N-(3-(6-hydroxy-6-methyl-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.45-10.68 (m, 1 H) 8.76-9.00 (m, 1 H) 8.17 (s, 1 H) 8.02 (dd, J = 5.01, 1.47 Hz, 1 H) 7.60-7.70 (m, 2 H) 7.49 (d, J = 7.70 Hz, 1 H) 7.27 (d, J = 8.31 Hz, 1 H) 6.64-6.79 (m, 2 H) 5.00-5.11 (m, 1 H) 3.50-4.02 (m, 4 H) 3.01-3.25 (m, 2 H) 2.63-2.83 (m, 1 H) 2.23 (s, 3 H) 2.05 (t, J = 19.13 Hz, 4 H) 1.64-1.80 (m, 2 H) 1.35-1.53 (m, 3 H); LCMS (m/z) (M + H − H$_2$O) = 476.1, Rt = 1.41 min. |

Examples 24 and 25

N-(3-(6-hydroxy-6-methyl-1,2,4,4a,5,6-hexahydro-[1,4]oxazino[4,3-a]quinolin-9-yl)-4-methylphenyl)-2-(trifluoromethyl)isonicotinamide

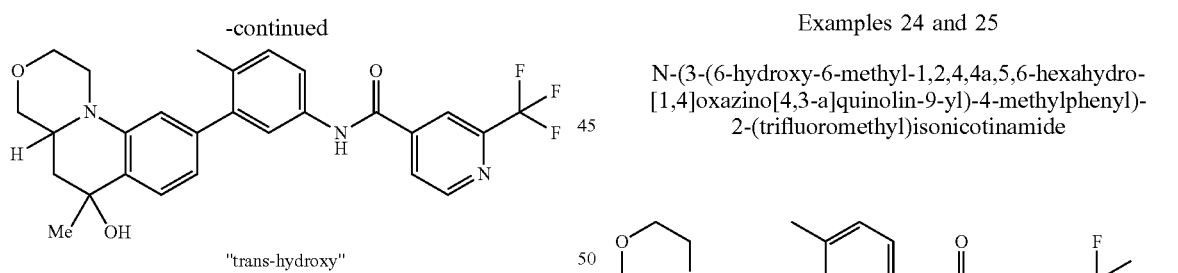

N-(3-(6-hydroxy-6-methyl-1,2,4,4a,5,6-hexahydro-[1,4]oxazino[4,3-a]quinolin-9-yl)-4-methylphenyl)-2-(trifluoromethyl)isonicotinamide was resolved by chiral SFC. The first eluting peak afforded 2-(1,1-difluoroethyl)-N-(3-((4aR,6R)-6-hydroxy-6-methyl-1,2,4,4a,5,6-hexahydro-[1,4]oxazino[4,3-a]quinolin-9-yl)-4-methylphenyl)isonicotinamide. ¹H NMR (400 MHz, DMSO-d6) δ ppm 10.57 (s, 1H) 8.87 (dd, J=5.01, 0.73 Hz, 1H) 8.17 (s, 1H) 8.02 (d, J=4.89 Hz, 1H) 7.60-7.71 (m, 2H) 7.49 (d, J=7.70 Hz, 1H) 7.27 (d, J=8.44 Hz, 1H) 6.65-6.76 (m, 2H) 5.04 (s, 1H) 3.70-3.98 (m, 3H) 3.56 (td, J=11.55, 2.57 Hz, 1H) 3.01-3.15 (m, 1H) 2.68-2.76 (m, 1H) 2.23 (s, 3H) 2.05 (t, J=19.13 Hz, 3H) 1.69-1.84 (m, 2H) 1.43 (s, 3H); LCMS (m/z) (M+H−H₂O)=476.1, Rt=1.41 min; and the second eluting peak afforded 2-(1,1-difluoroethyl)-N-(3-((4aS,6S)-6-hydroxy-6-methyl-1,2,4,4a,5,6-hexahydro-[1,4]oxazino[4,3-a]quinolin-9-yl)-4-methylphenyl)isonicotinamide. ¹H NMR (400 MHz, DMSO-d6) δ ppm 10.57 (s, 1H) 8.87 (dd, J=5.01, 0.61 Hz, 1H) 8.17 (s, 1H) 8.02 (dd, J=5.01, 1.59 Hz, 1H) 7.59-7.72 (m, 2H) 7.49 (d, J=7.70 Hz, 1H) 7.27 (d, J=8.44 Hz, 1H) 6.59-6.82 (m, 2H) 5.04 (br s, 1H) 3.70-4.02 (m, 3H) 3.56 (td, J=11.68, 2.57 Hz, 2H) 2.99-3.19 (m, 2H) 2.68-2.79 (m, 1H) 2.23 (s, 3H) 2.05 (t, J=19.13 Hz, 3H) 1.66-1.82 (m, 2H) 1.43 (s, 3H; LCMS (m/z) (M+H−H₂O)=476.1, Rt=1.41 min.

Examples 26 and 27

(rac)-N-(3-(6-hydroxy-4a-methyl-1,2,4,4a,5,6-hexahydro-[1,4]oxazino[4,3-a]quinolin-9-yl)-4-methylphenyl)-2-(trifluoromethyl)isonicotinamide

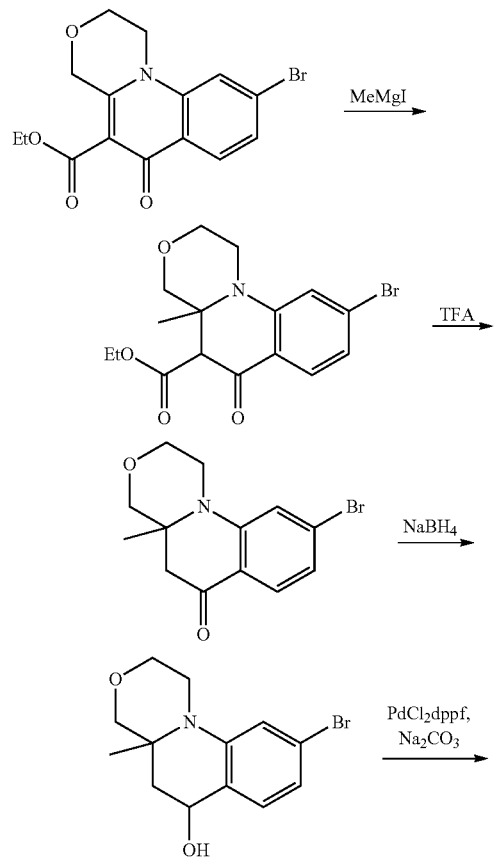

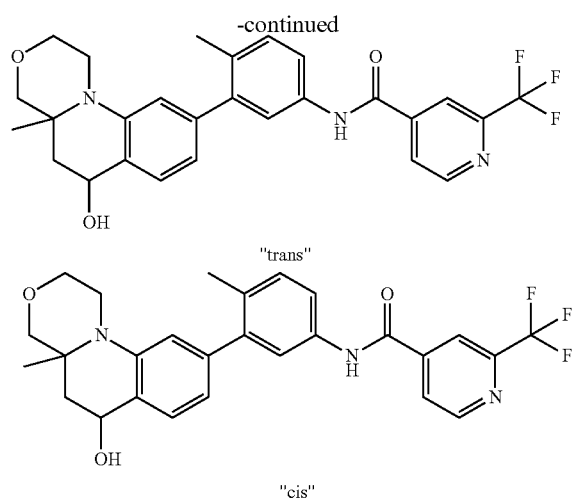

Step 1:
Ethyl 9-bromo-6-oxo-1,2,4,6-tetrahydro-[1,4]oxazino[4,3-a]quinoline-5-carboxylate (1.0 equiv.) was charged into a vial and CuI (2.0 equiv) followed by THF (0.1 M) were added. The mixture was cooled under nitrogen to −78° C. during which the reaction mass becomes very difficult to stir. Then methylmagnesium bromide (3.0 M in diethyl ether) (4.5 equiv.) was added dropwise and the mixture agitated vigorously at same temperature for 1 h during which LCMS indicated formation of desired product (LCMS: MH+=370.0, 1.45 min,) along with unreacted starting material. Accordingly, the reaction mixture was warmed to −40° C. and more MeMgBr (1.5 mL) was added and the mixture agitated for another hour. Finally, the reaction mixture was quenched by addition of citric acid and EtOAc. the biphasic mixture was filtered through celite and the aq. layer extracted with EtOAc. The combined organic layer was dried (MgSO₄), filtered and concentrated in vacuo and the residue purified by flash chromatography (0-30% EtOAc/heptane) to afford the desired product ethyl 9-bromo-4a-methyl-6-oxo-1,2,4,4a,5,6-hexahydro-[1,4]oxazino[4,3-a]quinoline-5-carboxylate as a yellow solid in 19% isolated yield. LCMS: (m/z) (M+H)=370.0, Rt=1.45 min).

Step 2:
9-bromo-4a-methyl-6-oxo-1,2,4,4a,5,6-hexahydro-[1,4]oxazino[4,3-a]quinoline-5-carboxylate (1.0 equiv.) was suspended in TFA (0.1 M) and heated at 120° C. for 3 h during which complete decarboxylation was observed. The reaction mixture was poured over Sat'd K₂CO₃ and the product extracted with EtOAc. The organic layer was dried (MgSO₄), filtered and concentrated in vacuo. The residue was purified by flash chromatography to afford the desired product 9-bromo-4a-methyl-1,2,4a,5-tetrahydro-[1,4]oxazino[4,3-a]quinolin-6(4H)-one as a faint yellow solid in 54% isolated. LCMS: (m/z) (M+H)=298.0, Rt=1.36 min).

Step 3:
9-bromo-4a-methyl-1,2,4a,5-tetrahydro-[1,4]oxazino[4,3-a]quinolin-6(4H)-one (1.0 equiv.) was suspended in MeOH (0.04 M) and then NaBH₄ (3.0 equiv) was added at room temperature. The mixture was agitated for 30 min and quenched by addition of acetone. The volatiles were evaporated in vacuo. The residue was diluted with EtOAc and washed with water and brine and dried (MgSO₄), filtered and concentrated in vacuo. The crude material 9-bromo-4a-methyl-1,2,4,4a,5,6-hexahydro-[1,4]oxazino[4,3-a]quinolin-6-ol was taken to the next step without any further purification. LCMS: (m/z) (M+H)=298.1, Rt=1.23 min).

Step 4:

Into a vial were charged 9-bromo-4a-methyl-1,2,4,4a,5,6-hexahydro-[1,4]oxazino[4,3-a]quinolin-6-ol (1.0 equiv.), PdCl$_2$(dppf).CH$_2$Cl$_2$ adduct (0.1 equiv.) were combined in dioxane (0.1 M) and then 2 M Na$_2$CO$_3$ (2.0 equiv.) was added. and the mixture agitated at 100° C. for 20 min in MW. The reaction mixture was cooled to room temperature and diluted with EtOAc and washed with brine. The organic layer was dried (MgSO$_4$), filtered and concentrated in vacuo. The residue was purified by basic HPLC to afford two separate diastereomers. The first eluting diastereomer was determined to be trans by 2D-NMR. (trans)-N-(3-(6-hydroxy-4a-methyl-1,2,4,4a,5,6-hexahydro-[1,4]oxazino[4,3-a]quinolin-9-yl)-4-methylphenyl)-2-(trifluoromethyl)isonicotinamide. LCMS: (m/z) (M+H)=494.4, Rt=1.33 min; $^1$H NMR (400 MHz, DMSO-d6) δ ppm 10.56 (s, 1H) 8.87 (dd, J=5.01, 0.61 Hz, 1H) 8.76-9.04 (m, 1H) 8.17 (d, J=0.61 Hz, 1H) 7.93-8.07 (m, 1H) 7.65-7.73 (m, 1H) 7.56-7.63 (m, 1H) 7.46 (dd, J=7.70, 0.86 Hz, 1H) 7.27 (d, J=8.56 Hz, 1H) 6.67 (dd, J=7.70, 1.47 Hz, 1H) 6.54-6.59 (m, 1H) 6.51 (s, 1H) 5.15-5.40 (m, 1H) 4.77 (dt, J=11.37, 6.72 Hz, 1H) 3.96 (dd, J=11.31, 3.61 Hz, 1H) 3.51-3.65 (m, 2H) 3.42 (dd, J=10.03, 2.45 Hz, 1H) 3.24 (d, J=11.25 Hz, 1H) 2.82 (td, J=12.35, 3.91 Hz, 1H) 2.22 (s, 3H) 2.05 (t, J=19.13 Hz, 3H) 1.87 (dd, J=12.17, 6.79 Hz, 1H) 1.50-1.64 (m, 1H) 1.04-1.21 (m, 3H). (cis)-N-(3-(6-hydroxy-4a-methyl-1,2,4,4a,5,6-hexahydro-[1,4]oxazino[4,3-a]quinolin-9-yl)-4-methylphenyl)-2-(trifluoromethyl)isonicotinamide. LCMS: (m/z) (M+H)=494.4, Rt=1.33 min; $^1$H NMR (400 MHz, DMSO-d6) δ ppm 10.57 (s, 1H) 8.87 (dd, J=5.01, 0.61 Hz, 1H) 8.18 (d, J=0.61 Hz, 1H) 8.03 (dd, J=5.01, 1.47 Hz, 1H) 7.70 (dd, J=8.25, 2.26 Hz, 1H) 7.62 (d, J=2.32 Hz, 1H) 7.18-7.39 (m, 2H) 6.72 (dd, J=7.70, 1.47 Hz, 1H) 6.58 (d, J=1.34 Hz, 1H) 5.23 (d, J=4.65 Hz, 1H) 4.63 (q, J=4.77 Hz, 1H) 3.96 (dd, J=11.13, 3.67 Hz, 1H) 3.48-3.62 (m, 2H) 3.26 (br d, J=2.81 Hz, 1H) 2.96 (td, J=12.26, 3.97 Hz, 1H) 2.22 (s, 3H) 2.05 (t, J=19.13 Hz, 3H) 1.84 (dd, J=13.63, 5.81 Hz, 1H) 1.69 (dd, J=13.57, 4.52 Hz, 1H) 1.19 (s, 3H).

Example 28

(rac)-N-(3-(6-amino-1,2,4,4a,5,6-hexahydro-[1,4]oxazino[4,3-a]quinolin-9-yl)-4-methylphenyl)-2-(trifluoromethyl)isonicotinamide

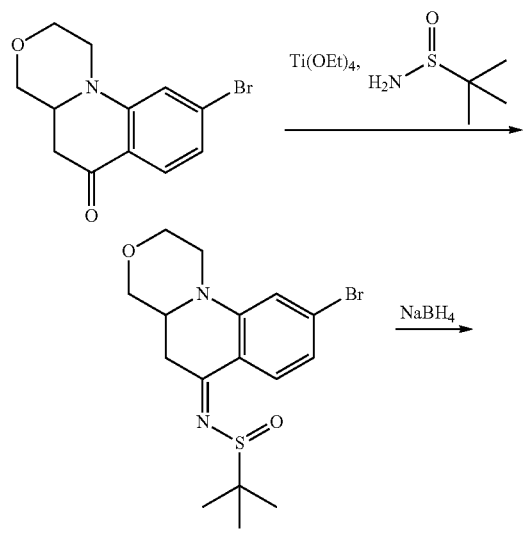

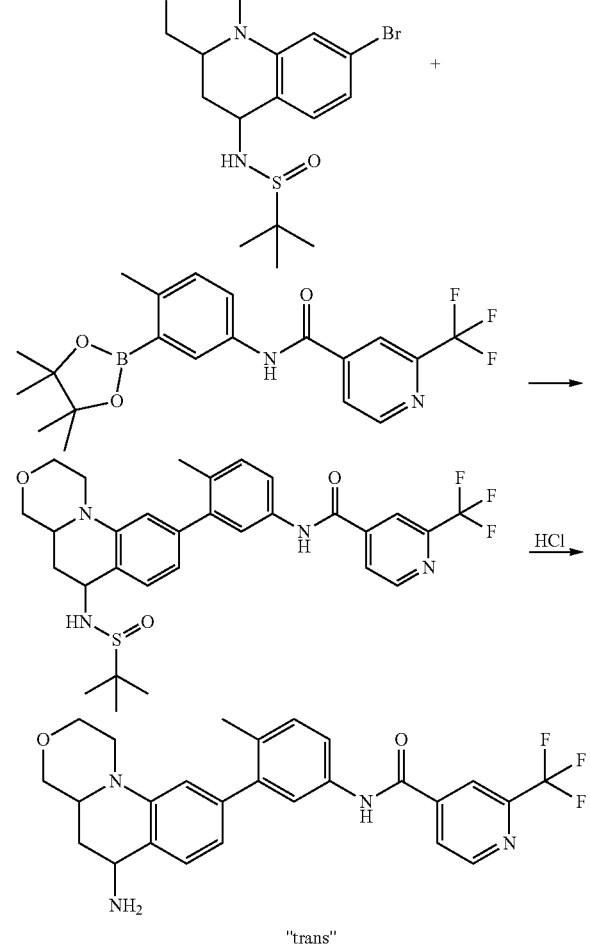

Step 1:

9-bromo-1,2,4a,5-tetrahydro-[1,4]oxazino[4,3-a]quinolin-6(4H)-one (1.0 equiv.) and Racemic-2-methylpropane-2-sulfinamide (1.0 equiv) were suspended in THF (0.5 M). To the mixture was added tetraethoxytitanium (2.0 equiv.) and the solution was agitated at 60° C. overnight. The next morning, LCMS indicated formation of the two requisite diastereomers along with unreacted starting material (major). Accordingly, added another 10 equiv of Titanium tetraethoxide and agitated at 70° C. for additional 24 h. After the elapsed time, the reaction mixture was diluted with EtOAc and brine and made slurry, which was then filtered through celite. The filtrate was concentrated in vacuo and the residue was purified by flash chromatography (0-50% EtOAc/heptane) to afford the desired product N-(9-bromo-1,2,4a,5-tetrahydro-[1,4]oxazino[4,3-a]quinolin-6(4H)-ylidene)-2-methylpropane-2-sulfinamide as a mixture of diastereomers. LCMS: (m/z) (M+H)=387.0, Rt=1.48 and Rt=1.52 min.

Step 2:

N-(9-bromo-1,2,4a,5-tetrahydro-[1,4]oxazino[4,3-a]quinolin-6(4H)-ylidene)-2-methylpropane-2-sulfinamide (1.0 equiv.) was dissolved in MeOH:THF (1:1) (0.06 M) and then NaBH$_4$ (2.0 equiv.) was added at room temperature and the reaction agitated for 1 h upon which LCMS indicated formation of desired product. The reaction mixture was quenched by addition of acetone and concentrated in vacuo.

The residue was dissolved in EtOAc and washed with Sat'd NH₄Cl and dried (MgSO₄), filtered and concentrated in vacuo to afford the crude product N-(9-bromo-1,2,4,4a,5,6-hexahydro-[1,4]oxazino[4,3-a]quinolin-6-yl)-2-methylpropane-2-sulfinamide in quantitative yield. LCMS: (m/z) (M+H)=388.9, Rt=1.35 and Rt=1.39 min.

Step 3:

N-(9-bromo-1,2,4a,5-tetrahydro-[1,4]oxazino[4,3-a]quinolin-6(4H)-ylidene)-2-methylpropane-2-sulfinamide (1.0 equiv.), PdCl₂(dppf).CH₂Cl₂ adduct (0.1 equiv.), N-(4-methyl-3-(4,4,5,5-tetramethyl-1,3,2-dioxaborolan-2-yl)phenyl)-2-(trifluoromethyl)isonicotinamide (1.0 equiv.) were charged into a microwave vial and then dioxane/DMF (6:1) (0.1 M) were added. Then 2M Na₂CO₃ (3.0 equiv) was added. The mixture was agitated in MW at 120° C. for 25 min upon which LCMS indicated formation of desired product as major species. The reaction mixture was diluted with EtOAc and washed with water and dried (MgSO₄), filtered and concentrated in vacuo to afford the crude product N-(3-(6-((tert-butylsulfinyl)amino)-1,2,4,4a,5,6-hexahydro-[1,4]oxazino[4,3-a]quinolin-9-yl)-4-methylphenyl)-2-(trifluoromethyl)isonicotinamide which was taken to the next step as such. LCMS: (m/z) (M+H)=587.2, Rt=1.55 min.

Step 4:

N-(3-(6-((tert-butylsulfinyl)amino)-1,2,4,4a,5,6-hexahydro-[1,4]oxazino[4,3-a]quinolin-9-yl)-4-methylphenyl)-2-(trifluoromethyl)isonicotinamide (1.0 equiv.) was dissolved in of MeOH (0.05 M) and treated with 4.0 N HCl in dioxane (40 equiv.). The mixture was agitated at room temperature for 30 min and concentrated in vacuo and the residue was dissolved in MeOH and purified by reverse-phase HPLC to afford the desired product N-(3-(6-amino-1,2,4,4a,5,6-hexahydro-[1,4]oxazino[4,3-a]quinolin-9-yl)-4-methylphenyl)-2-(trifluoromethyl)isonicotinamide in 10% yield as free base; ¹H NMR (400 MHz, DMSO-d6) δ ppm 10.70 (s, 1H) 8.99 (d, J=5.01 Hz, 1H) 8.50 (br. s., 2H) 8.36 (s, 1H) 8.20 (dd, J=4.95, 1.04 Hz, 1H) 7.63-7.71 (m, 2H) 7.48 (d, J=7.95 Hz, 1H) 7.31 (d, J=8.19 Hz, 1H) 6.87 (d, J=1.22 Hz, 1H) 6.81 (dd, J=7.89, 1.28 Hz, 1H) 4.58-4.75 (m, 1H) 3.85-4.06 (m, 3H) 3.76 (d, J=11.74 Hz, 1H) 3.59 (td, J=11.68, 2.45 Hz, 1H) 3.09-3.26 (m, 2H) 2.63-2.80 (m, 1H) 2.11-2.26 (m, 3H) 1.65 (q, J=11.53 Hz, 1H); LCMS: (m/z) (M–H)—=481.4, Rt=1.28 min (basic method).

Example 29

(rac)-N-(3-(6-acetamido-1,2,4,4a,5,6-hexahydro-[1,4]oxazino[4,3-a]quinolin-9-yl)-4-methylphenyl)-2-(trifluoromethyl)

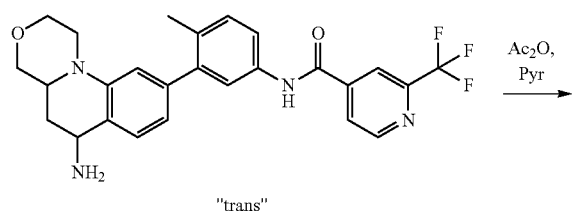

"trans"

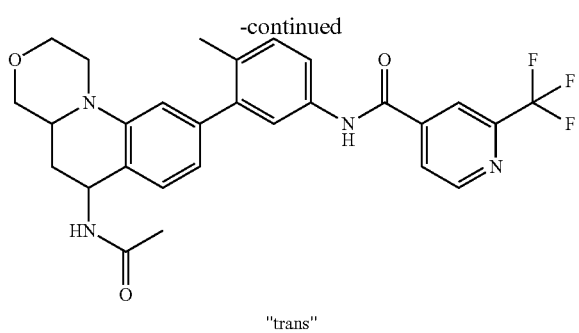

"trans"

Step 1:

N-(3-(6-amino-1,2,4,4a,5,6-hexahydro-[1,4]oxazino[4,3-a]quinolin-9-yl)-4-methylphenyl)-2-(trifluoromethyl)isonicotinamide was dissolved in Pyridine (0.05 M) and treated with Acetic anhydride (40 equiv). The mixture was agitated at room temperature for 30 min upon which LCMS indicated formation of desired product. RM was dissolved in EtOAc and washed with Sat'd NH₄Cl and then dried (MgSO₄), filtered and concentrated in vacuo. The residue was dissolved in DMSO and purified by reverse-phase HPLC to afford the desired product N-(3-(6-acetamido-1,2,4,4a,5,6-hexahydro-[1,4]oxazino[4,3-a]quinolin-9-yl)-4-methylphenyl)-2-(trifluoromethyl)isonicotinamide as free-base in 16% isolated yield. ¹H NMR (400 MHz, DMSO-d6) δ ppm 10.63 (s, 1H) 8.99 (d, J=5.01 Hz, 1H) 8.35 (s, 1H) 8.25 (d, J=8.93 Hz, 1H) 8.18 (dd, J=5.01, 1.10 Hz, 1H) 7.67 (dd, J=8.25, 2.26 Hz, 1H) 7.61 (d, J=2.20 Hz, 1H) 7.29 (d, J=8.44 Hz, 1H) 7.09 (dd, J=7.76, 0.92 Hz, 1H) 6.77 (d, J=1.22 Hz, 1H) 6.70 (dd, J=7.76, 1.41 Hz, 1H) 5.15 (ddd, J=11.62, 8.50, 6.54 Hz, 1H) 3.68-3.98 (m, 3H) 3.57 (td, J=11.62, 2.45 Hz, 1H) 3.08-3.24 (m, 2H) 2.62-2.74 (m, 1H) 2.15-2.25 (m, 3H) 1.86-1.99 (m, 4H) 1.47-1.60 (m, 1H); LCMS: (m/z) (M+H)=525.4, Rt=1.36 min.

Example 30

(rac)-(trans)-N-(3-(6-methoxy-1,2,4,4a,5,6-hexahydro-[1,4]oxazino[4,3-a]quinolin-9-yl)-4-methylphenyl)-2-(trifluoromethyl)isonicotinamide

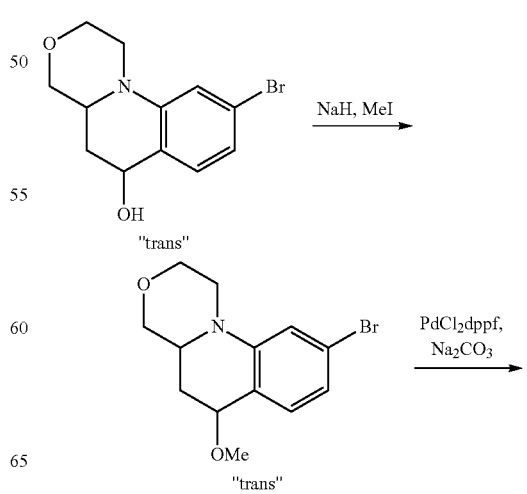

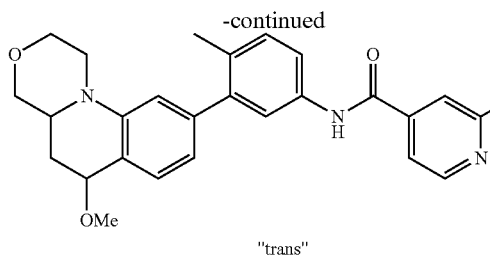

"trans"

Step 1:

trans-9-bromo-1,2,4,4a,5,6-hexahydro-[1,4]oxazino[4,3-a]quinolin-6-ol (1.0 equiv.) was dissolved in DMF (0.3M) and cooled to 0° C. Then NaH (1.2 equiv.) was added in one portion after which the reaction became pale yellow in color. The mixture was agitated for 10 min and then iodomethane (2.0 M in MTBE) (1.5 equiv.) was added dropwise and the mixture let to warm to room temperature. The mixture was agitated for 2 h and then quenched by addition of water. The product was extracted with EtOAc. The organic layer was dried (MgSO$_4$), filtered and concentrated in vacuo. The residue 9-bromo-6-methoxy-1,2,4,4a,5,6-hexahydro-[1,4]oxazino[4,3-a]quinoline was taken to the next step without any further purification. LCMS: (m/z) (M+H)=298.0, Rt=1.46 min.

Step 2:

Into a vial were charged 9-bromo-6-methoxy-1,2,4,4a,5,6-hexahydro-[1,4]oxazino[4,3-a]quinoline (1.0 equiv.), PdCl$_2$(dppf).CH$_2$Cl$_2$ adduct (0.1 equiv.), N-(4-methyl-3-(4,4,5,5-tetramethyl-1,3,2-dioxaborolan-2-yl)phenyl)-2-(trifluoromethyl)isonicotinamide (1.0 equiv.) were charged into a microwave vial and then dioxane (0.1 M) was added. Then 2 M Na$_2$CO$_3$ was added and the mixture agitated at 120° C. in MW for 30 min and then the mixture was cooled to room temperature and diluted with brine and EtOAc and filtered through celite. The organic layer was separated and passed through a plug of Na$_2$SO$_4$ and the filtrate concentrated in vacuo. The residue was dissolved in DMSO and purified by reverse-phase HPLC to afford the desired product N-(3-(6-methoxy-1,2,4,4a,5,6-hexahydro-[1,4]oxazino[4,3-a]quinolin-9-yl)-4-methylphenyl)-2-(trifluoromethyl)isonicotinamide as free base in 34% isolated yield. LCMS: (m/z) (M+H)=496.5, Rt=1.51 min. $^1$H NMR (400 MHz, DMSO-d6) δ ppm 1H NMR (400 MHz, DMSO-d6) ä ppm 10.63 (s, 1H) 8.99 (d, J=4.89 Hz, 1H) 8.36 (s, 1H) 8.19 (d, J=4.89 Hz, 1H) 8.03 (s, 1H) 7.54-7.74 (m, 2H) 7.23-7.37 (m, 1H) 6.61-6.79 (m, 1H) 4.59 (dd, J=10.15, 5.99 Hz, 1H) 3.79-3.98 (m, 2H) 3.72 (br d, J=11.74 Hz, 1H) 3.56 (td, J=11.62, 2.57 Hz, 1H) 3.39 (s, 3H) 3.07-3.30 (m, 2H) 2.68 (td, J=12.07, 3.48 Hz, 1H) 2.15-2.30 (m, 4H) 1.48 (q, J=11.09 Hz, 1H).

The following compounds were prepared using methods from the above examples, using appropriate starting materials:

| Ex. No. | Structure | Name | Physical Data |
|---|---|---|---|
| 31 | 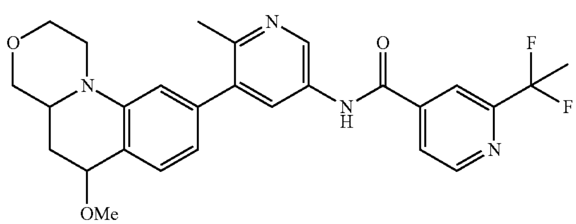 | (rac)-(trans)-2-(1,1-difluoroethyl)-N-(5-(6-methoxy-1,2,4,4a,5,6-hexahydro-[1,4]oxazino[4,3-a]quinolin-9-yl)-6-methylpyridin-3-yl)isonicotinamide | $^1$H NMR (400 MHz, DMSO-d6) δ ppm 10.84 (s, 1 H) 8.79-9.03 (m, 2 H) 8.21 (d, J = 0.61 Hz, 1 H) 7.98-8.09 (m, 2 H) 7.36 (dd, J = 7.76, 0.79 Hz, 1H) 6.63-6.88 (m, 2 H) 4.59 (dd, J = 9.96, 6.05 Hz, 1 H) 3.71-4.04 (m, 3 H) 3.52-3.63 (m, 2 H) 3.27 (d, J = 10.64 Hz, 2 H) 3.11-3.22 (m, 2 H) 2.67-2.78 (m, 1 H) 2.44 (s, 3 H) 2.27 (ddd, J = 12.23, 5.99, 2.32 Hz, 1 H) 2.06 (t, J = 19.13 Hz, 3 H) 1.40-1.60 (m, 1 H); LCMS (m/z) (M + H − H$_2$O) = 495.5, Rt = 1.27 min. |
| 32 | 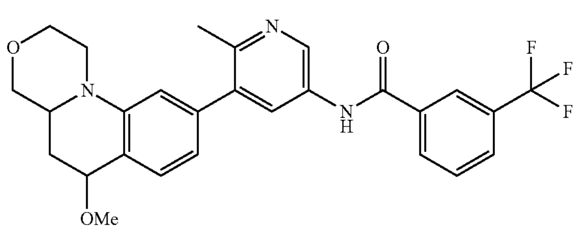 | (rac)-(trans)-N-(5-(6-methoxy-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, DMSO-d6) δ ppm 10.20-10.92 (m, 1 H) 8.78-8.98 (m, 1 H) 8.23-8.41 (m, 2 H) 7.94-8.10 (m, 2 H) 7.81 (t, J = 7.82 Hz, 1 H) 7.36 (dd, J = 7.76, 0.79 Hz, 1 H) 6.64-6.84 (m, 2 H) 4.59 (dd, J = 10.21, 6.05 Hz, 1 H) 3.72-4.00 (m, 3 H) 3.56 (td, J = 11.65, 2.63 Hz, 1 H) 3.40 (s, 3 H) 3.24-3.29 (m, 1 H) 3.11-3.21 (m, 1 H) 2.64-2.82 (m, 1 H) 2.42 (s, 3 H) 2.19-2.30 (m, 1 H) 1.36-1.59 (m, 1 H); LCMS (m/z) (M + H − H$_2$O) = 498.0, Rt = 1.40 min. |

Example 33

(trans)-N-(3-(6-methoxy-1,2,4,4a,5,6-hexahydro-[1,4]oxazino[4,3-a]quinolin-9-yl)-4-methylphenyl)-2-(trifluoromethyl)isonicotinamide

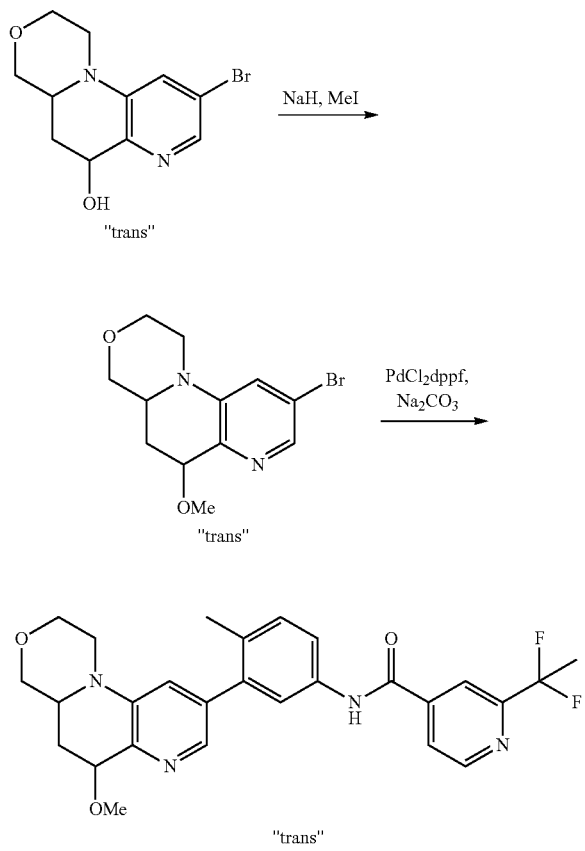

Step 1:
(trans)-9-bromo-1,2,4,4a,5,6-hexahydro-[1,4]oxazino[4,3-a][1,5]naphthyridin-6-ol (1.0 equiv.) was dissolved in DMF (0.1M) and cooled to 0° C. Then NaH (1.2 equiv.) was added in one portion after which the reaction became pale yellow in color. The mixture was agitated for 10 min and then iodomethane (2.0 M in MTBE) (1.5 equiv.) was added dropwise and the mixture let to warm to room temperature and agitate for 2 h upon which LCMS indicated formation of desired product. The reaction mixture was quenched by addition of water and the product extracted with EtOAc. The organic layer was washed with water and dried (MgSO₄), filtered and concentrated in vacuo and the residue 9-bromo-6-methoxy-1,2,4,4a,5,6-hexahydro-[1,4]oxazino[4,3-a][1,5]naphthyridine taken to the next step without any further purification. LCMS: (m/z) (M+H)=298.1, Rt=0.81 min.

Step 2:
Into a vial were charged 9-bromo-6-methoxy-1,2,4,4a,5,6-hexahydro-[1,4]oxazino[4,3-a][1,5]naphthyridine (crude) (1.0 equiv.), PdCl₂(dppf).CH₂Cl₂ adduct (0.1 equiv.), N-(4-methyl-3-(4,4,5,5-tetramethyl-1,3,2-dioxaborolan-2-yl)phenyl)-2-(trifluoromethyl)isonicotinamide (1.0 equiv.) were charged into a microwave vial and then dioxane (0.1 M) was added. Then 2 M Na₂CO₃ (2.5 equiv.) was added and the mixture agitated at 100° C. in a heating block for 1 h upon which complete conversion to desired product was observed. The reaction mixture was cooled to room temperature and diluted with brine and EtOAc and filtered through celite. The organic layer was separated and passed through a plug of Na₂SO₄ and the filtrate concentrated in vacuo. The residue was dissolved in DMSO and purified by reverse-phase HPLC to afford the desired product 2-(1,1-difluoroethyl)-N-(3-(6-methoxy-1,2,4,4a,5,6-hexahydro-[1,4]oxazino[4,3-a][1,5]naphthyridin-9-yl)-4-methylphenyl)isonicotinamide as free base in 49.6% isolated yield. LCMS: (m/z) (M+H)=495.2, Rt=1.25 min. ¹H NMR (400 MHz, DMSO-d6) δ ppm 10.64 (s, 1H) 8.88 (dd, J=5.01, 0.73 Hz, 1H) 8.18 (d, J=0.73 Hz, 1H) 8.03 (dd, J=5.07, 1.53 Hz, 1H) 7.91 (d, J=1.71 Hz, 1H) 7.74 (dd, J=8.31, 2.20 Hz, 1H) 7.65 (d, J=2.20 Hz, 1H) 7.33 (d, J=8.44 Hz, 1H) 7.18 (s, 1H) 4.53 (dd, J=9.41, 6.48 Hz, 1H) 3.70-3.98 (m, 3H) 3.55 (td, J=11.71, 2.75 Hz, 1H) 3.50 (s, 3H) 3.14-3.27 (m, 2H) 2.64-2.83 (m, 2H) 2.16-2.29 (m, 4H) 1.90-2.11 (m, 3H) 1.69 (dt, J=12.93, 9.86 Hz, 1H).

The compound of Example 34 was prepared using methods from the above examples and appropriate starting materials:

| | | |
|---|---|---|
| 34 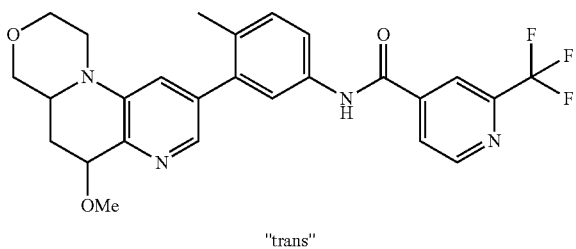 [SMILES: COC1CC2COCCN2c2cc(-c3cc(NC(=O)c4ccnc(C(F)(F)F)c4)ccc3C)cnc21] | (rac)-(trans)-N-(3-(6-methoxy-1,2,4,4a,5,6-hexahydro-[1,4]oxazino[4,3-a][1,5]naphthyridin-9-yl)-4-methylphenyl)-2-(trifluoromethyl)isonicotinamide | ¹H NMR (400 MHz, DMSO-d6) δ ppm 10.68 (s, 1 H) 8.99 (d, J = 5.01 Hz, 1 H) 8.36 (s, 1 H) 8.19 (dd, J = 5.01, 1.10 Hz, 1 H) 7.91 (d, J = 1.71 Hz, 1H) 7.73 (dd, J = 8.31, 2.20 Hz, 1 H) 7.65 (d, J = 2.20 Hz, 1 H) 7.34 (d, J = 8.44 Hz, 1 H) 7.17 (d, J = 1.71 Hz, 1 H) 4.53 (dd, J = 9.29, 6.48 Hz, 1 H) 3.69-3.97 (m, 3 H) 3.55 (td, J = 11.68, 2.69 Hz, 1 H) 3.49 (s, 3 H) 3.14-3.26 (m, 1 H) 2.64-2.84 (m, 1 H) 2.13-2.29 (m, 4 H) 1.69 (dt, J = 12.87, 9.83 Hz, 1 H); LCMS (m/z) (M + H) = 499.1, Rt = 1.28 min. |

Examples 35 and 36

2-(1,1-difluoroethyl)-N-(3-(6-methoxy-1,2,4,4a,5,6-hexahydro-[1,4]oxazino[4,3-a][1,5]naphthyridin-9-yl)-4-methylphenyl)isonicotinamide

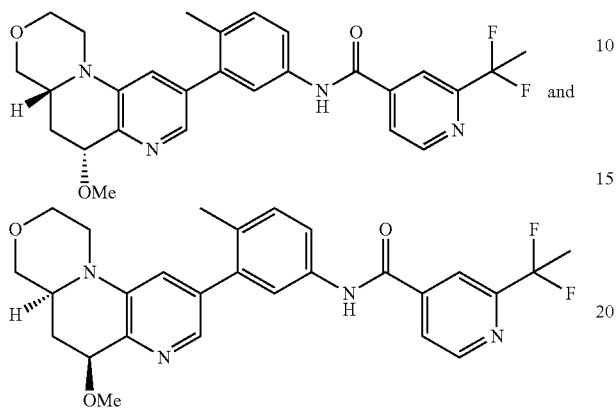

(trans)-N-(3-(6-methoxy-1,2,4,4a,5,6-hexahydro-[1,4]oxazino[4,3-a]quinolin-9-yl)-4-methylphenyl)-2-(trifluoromethyl)isonicotinamide was resolved by chiral SFC. The first eluting peak afforded 2-(1,1-difluoroethyl)-N-(3-((4aR,6R)-6-methoxy-1,2,4,4a,5,6-hexahydro-[1,4]oxazino[4,3-a]quinolin-9-yl)-4-methylphenyl)isonicotinamide; ¹H NMR (400 MHz, DMSO-d6) δ ppm 10.64 (s, 1H) 8.88 (dd, J=5.01, 0.73 Hz, 1H) 8.18 (d, J=0.73 Hz, 1H) 8.03 (dd, J=5.07, 1.53 Hz, 1H) 7.91 (d, J=1.71 Hz, 1H) 7.74 (dd, J=8.31, 2.20 Hz, 1H) 7.65 (d, J=2.20 Hz, 1H) 7.33 (d, J=8.44 Hz, 1H) 7.18 (s, 1H) 4.53 (dd, J=9.41, 6.48 Hz, 1H) 3.70-3.98 (m, 3H) 3.55 (td, J=11.71, 2.75 Hz, 1H) 3.50 (s, 3H) 3.14-3.27 (m, 2H) 2.64-2.83 (m, 2H) 2.16-2.29 (m, 4H) 1.90-2.11 (m, 3H) 1.69 (dt, J=12.93, 9.86 Hz, 1H); LCMS: (m/z) (M+H)=495.2, 1.25 min; and the second eluting peak 2-(1,1-difluoroethyl)-N-(3-((4aS,6S)-6-methoxy-1,2,4,4a,5,6-hexahydro-[1,4]oxazino[4,3-a]quinolin-9-yl)-4-methylphenyl)isonicotinamide; ¹H NMR (400 MHz, DMSO-d6) δ ppm 10.64 (s, 1H) 8.88 (dd, J=5.01, 0.73 Hz, 1H) 8.18 (d, J=0.73 Hz, 1H) 8.03 (dd, J=5.07, 1.53 Hz, 1H) 7.91 (d, J=1.71 Hz, 1H) 7.74 (dd, J=8.31, 2.20 Hz, 1H) 7.65 (d, J=2.20 Hz, 1H) 7.33 (d, J=8.44 Hz, 1H) 7.18 (s, 1H) 4.53 (dd, J=9.41, 6.48 Hz, 1H) 3.70-3.98 (m, 3H) 3.55 (td, J=11.71, 2.75 Hz, 1H) 3.50 (s, 3H) 3.14-3.27 (m, 2H) 2.64-2.83 (m, 2H) 2.16-2.29 (m, 4H) 1.90-2.11 (m, 3H) 1.69 (dt, J=12.93, 9.86 Hz, 1H); LCMS: (m/z) (M+H)=495.2, Rt=1.25 min.

(cis)-9-bromo-1,2,4,4a,5,6-hexahydro-[1,4]oxazino[4,3-a]quinolin-6-ol

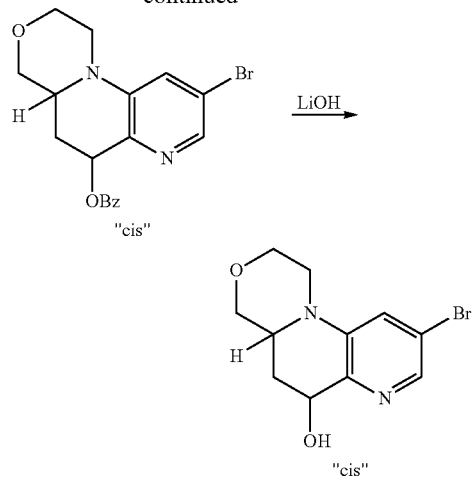

Step 1:

(trans)-9-bromo-1,2,4,4a,5,6-hexahydro-[1,4]oxazino[4,3-a][1,5]naphthyridin-6-ol (1.0 equiv.) Triphenylphosphine (1.2 equiv.), Benzoic acid (2.0 equiv.) were suspended in THF (0.25 M) and cooled to 0° C. Then DIAD (1.0 equiv.) was added dropwise and the mixture was let to warm to room temperature over 2 h upon which LCMS indicated formation of desired product. The reaction mixture was concentrated in vacuo and the residue purified by flash chromatography (0-30% EtOAc/heptane) to afford the desired product (cis)-9-bromo-1,2,4,4a,5,6-hexahydro-[1,4]oxazino[4,3-a][1,5]naphthyridin-6-yl benzoate in quantitative. LCMS: (m/z) (M+H)=390.1, Rt=1.71 min.

Step 2:

Into a 30 mL vial was charged (cis)-9-bromo-1,2,4,4a,5,6-hexahydro-[1,4]oxazino[4,3-a][1,5]naphthyridin-6-yl benzoate (1.0 equiv.) and THF (0.1) and then at room temperature, 1.0 M LiOH.H2O (5 equiv.) was added. The mixture was agitated at 70° C. for 1 h and then product extracted with EtOAc. The organic layer was washed with Sat'd Na₂CO₃ and dried (MgSO₄), filtered and concentrated in vacuo. The residue 9-bromo-1,2,4,4a,5,6-hexahydro-[1,4]oxazino[4,3-a][1,5]naphthyridin-6-ol was taken to the next step without any further purification assuming quantitative yield. LCMS: (m/z) (M+H)=285.8, Rt=1.16 min.

Example 37

(rac)-(cis)-N-(3-(6-hydroxy-1,2,4,4a,5,6-hexahydro-[1,4]oxazino[4,3-a][1,5]naphthyridin-9-yl)-4-methylphenyl)-2-(trifluoromethyl)isonicotinamide

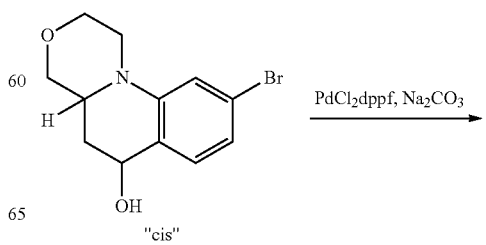

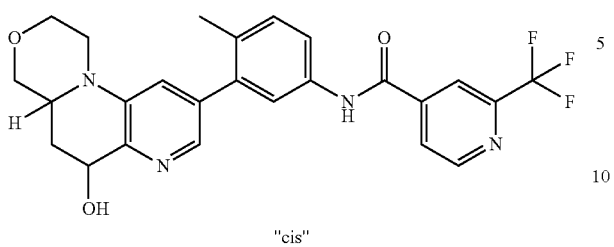

"cis"

Step 1:

Into a vial were charged 9-bromo-1,2,4,4a,5,6-hexahydro-[1,4]oxazino[4,3-a][1,5]naphthyridin-6-ol (1.0 equiv.), PdCl$_2$(dppf).CH$_2$Cl$_2$ adduct (0.1 equiv.), N-(4-methyl-3-(4,4,5,5-tetramethyl-1,3,2-dioxaborolan-2-yl)phenyl)-2-(trifluoromethyl)isonicotinamide (1.0 equiv.), 2M Na$_2$CO$_3$ (2.5 equiv.) and the mixture agitated at 100° C. in a heating block for 1 h upon which complete conversion to desired product was observed. The reaction mixture was cooled to room temperature and diluted with brine and EtOAc and filtered through celite. The organic layer was separated and passed through a plug of Na$_2$SO$_4$ and the filtrate concentrated in vacuo. The residue was dissolved in DMSO and purified by reverse-phase HPLC to afford the desired product N-(3-(6-hydroxy-1,2,4,4a,5,6-hexahydro-[1,4]oxazino[4,3-a][1,5]naphthyridin-9-yl)-4-methylphenyl)-2-(trifluoromethyl)isonicotinamide as free base in 54% isolated yield. LCMS: (m/z) (M+H)=485.1, Rt=1.21 min. $^1$H NMR (400 MHz, DMSO-d6) δ ppm 10.69 (s, 1H) 10.50-10.97 (m, 1H) 8.99 (d, J=5.01 Hz, 1H) 8.36 (s, 1H) 8.19 (dd, J=5.01, 1.10 Hz, 1H) 7.90 (d, J=1.59 Hz, 1H) 7.72 (dd, J=8.25, 2.26 Hz, 1H) 7.66 (d, J=2.32 Hz, 1H) 7.34 (d, J=8.44 Hz, 1H) 7.25 (d, J=1.47 Hz, 1H) 5.42 (br s, 1H) 4.60 (br s, 1H) 3.77-4.08 (m, 3H) 3.58 (td, J=11.65, 2.63 Hz, 1H) 3.10-3.27 (m, 2H) 2.75 (td, J=12.01, 3.48 Hz, 1H) 2.24 (s, 3H) 1.80-1.96 (m, 1H) 1.53-1.72 (m, 1H).

The compound of Example 38 was prepared using methods from the above examples, using appropriate starting materials:

Examples 39 and 40

(rac)-N-(3-(6-hydroxy-6-methyl-1,2,4,4a,5,6-hexahydro-[1,4]oxazino[4,3-a]quinolin-9-yl)-4-methylphenyl)-2-(trifluoromethyl)isonicotinamide

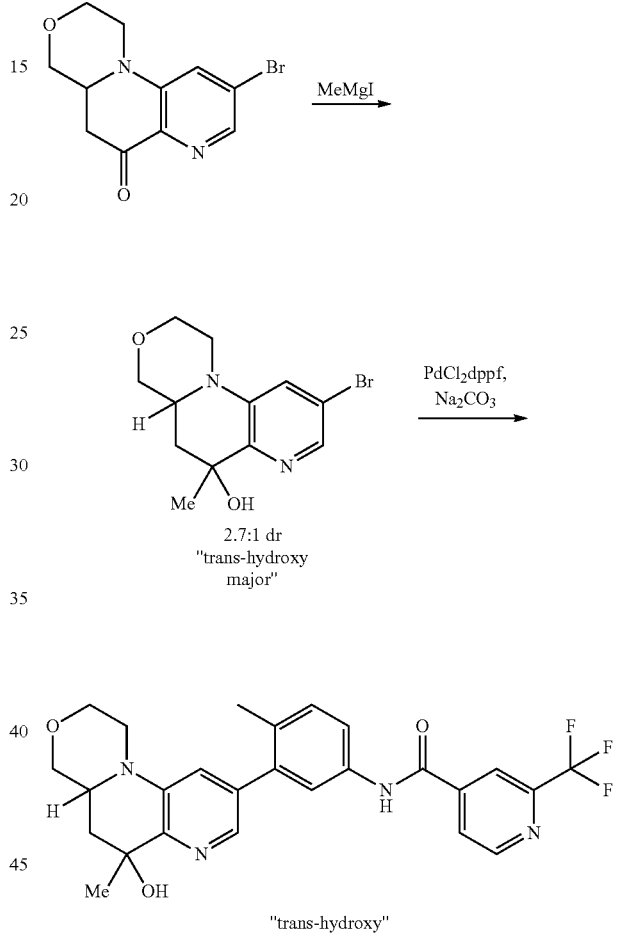

2.7:1 dr
"trans-hydroxy major"

"trans-hydroxy"

| 38 | 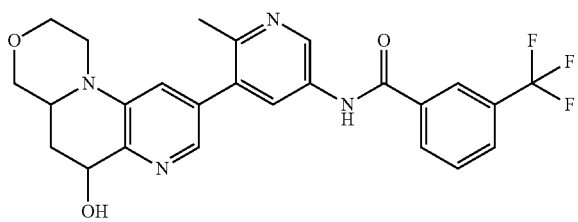 "cis" | (rac)-(cis)-N-(5-(6-hydroxy-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, DMSO-d6) δ ppm 10.68 (s, 1 H) 8.87 (d, J = 2.45 Hz, 1 H) 8.22-8.41 (m, 2 H) 8.05 (d, J = 2.45 Hz, 1 H) 8.00 (dd, J = 7.76, 0.67 Hz, 1 H) 7.94 (d, J = 1.71 Hz, 1 H) 7.81 (t, J = 7.82 Hz, 1 H) 7.33 (d, J = 1.59 Hz, 1 H) 5.54-5.54 (m, 1 H) 5.45 (d, J = 4.40 Hz, 1 H) 4.53-4.73 (m, 1H) 3.78-4.07 (m, 3 H) 3.58 (td, J = 11.68, 2.69 Hz, 1H) 3.13-3.27 (m, 2 H) 2.77 (td, J = 12.04, 3.55 Hz, 1 H) 2.44 (s, 3 H) 1.86 (br d, J = 13.69 Hz, 1H) 1.57-1.71 (m, 1 H); LCMS (m/z) (M + H) = 485.1, Rt = 1.14 min. |

-continued

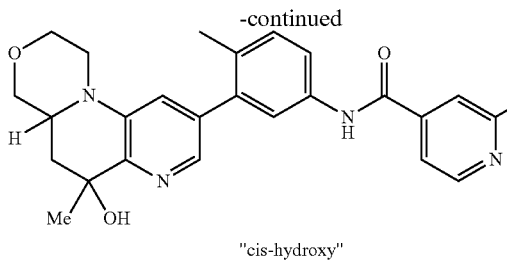

"cis-hydroxy"

Step 1:
9-bromo-1,2,4a,5-tetrahydro-[1,4]oxazino[4,3-a][1,5]naphthyridin-6(4H)-one (1.0 equiv.) was dissolved in Tetrahydrofuran (0.1 M) and cooled to 0° C. Then 3.0 M methylmagnesium iodide in ether (2.5 equiv.) was added dropwise upon which the mixture turns turbid yellow. After 2 h, reaction appears to be saturated. The reaction mixture was quenched with water and extracted with EtOAc. The organic layer was dried (MgSO$_4$), filtered and concentrated in vacuo. The residue was purified by flash chromatography (0-100% EtOAc/heptane) to afford the desired product 9-bromo-6-methyl-1,2,4,4a,5,6-hexahydro-[1,4]oxazino[4,3-a][1,5]naphthyridin-6-ol as a 2.7:1 diastereomeric mixture in which the trans-adduct was major; in 68.1% isolated yield. LCMS: (m/z) (M+H−H$_2$O)=301.0, Rt=0.78 min.

Step 2:
Into a vial were charged (trans)-9-bromo-6-methyl-1,2,4,4a,5,6-hexahydro-[1,4]oxazino[4,3-a][1,5]naphthyridin-6-ol (1.0 equiv.), PdCl$_2$(dppf).CH$_2$Cl$_2$ adduct (0.1 equiv.), N-(4-methyl-3-(4,4,5,5-tetramethyl-1,3,2-dioxaborolan-2-yl)phenyl)-2-(trifluoromethyl)isonicotinamide (1.0 equiv.) and 2M Na2CO3 (2.5 equiv.) and the mixture agitated at 120° C. in MW for 30 min and then the reaction mixture was cooled to room temperature and diluted with brine and EtOAc and filtered through celite. The organic layer was separated and passed through a plug of Na$_2$SO$_4$ and the filtrate concentrated in vacuo. The residue was dissolved in DMSO and purified by reverse-phase acidic HPLC to afford the desired diastereomers as TFA adducts.

(rac)-(trans)-N-(3-(6-hydroxy-6-methyl-1,2,4,4a,5,6-hexahydro-[1,4]oxazino[4,3-a][1,5]naphthyridin-9-yl)-4-methylphenyl)-2-(trifluoromethyl)isonicotinamide in 22% isolated yield. LCMS (m/z) (M+H)=499.1, Rt=1.02 min; $^1$H NMR (400 MHz, DMSO-d6) δ ppm 10.77 (s, 1H) 9.01 (d, J=4.89 Hz, 1H) 8.36 (s, 1H) 8.19 (dd, J=4.95, 1.16 Hz, 1H) 7.99 (d, J=1.34 Hz, 1H) 7.70-7.81 (m, 3H) 7.40 (d, J=8.44 Hz, 1H) 3.85-4.05 (m, 3H) 3.55 (td, J=11.83, 2.63 Hz, 1H) 3.35-3.47 (m, 1H) 3.24 (t, J=10.82 Hz, 1H) 2.96 (td, J=12.29, 3.42 Hz, 1H) 2.26 (s, 3H) 1.94-2.06 (m, 1H) 1.84 (t, J=12.59 Hz, 1H) 1.57 (s, 3H).

(rac)-(cis)-N-(3-(6-hydroxy-6-methyl-1,2,4,4a,5,6-hexahydro-[1,4]oxazino[4,3-a][1,5]naphthyridin-9-yl)-4-methylphenyl)-2-(trifluoromethyl)isonicotinamide in 16.4% isolated yield. LCMS (m/z) (M+H)=499.1, Rt=1.07 min; $^1$H NMR (400 MHz, DMSO-d6) δ ppm 10.59-10.95 (m, 1H) 8.88-9.11 (m, 1H) 8.36 (s, 1H) 8.19 (dd, J=5.01, 1.10 Hz, 1H) 7.99 (d, J=1.34 Hz, 1H) 7.64-7.85 (m, 3H) 7.31-7.51 (m, 2H) 3.92-4.06 (m, 2H) 3.76-3.90 (m, 1H) 3.42-3.66 (m, 1H) 3.15-3.38 (m, 2H) 2.71-3.05 (m, 1H) 2.26 (d, J=1.96 Hz, 3H) 1.79-2.09 (m, 1H) 1.50-1.69 (m, 4H).

The following compounds were prepared using methods from the above examples, using annronriate starting materials:

| Ex. No. | Structure | Name | Physical Data |
|---|---|---|---|
| 41 | 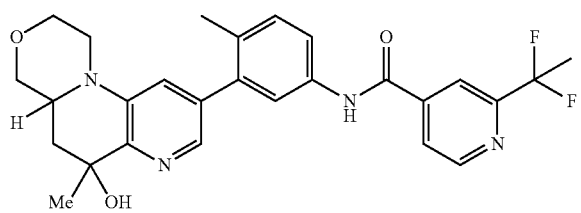<br>"trans-hydroxy" | (rac)-(trans)-2-(1,1-difluoroethyl)-N-(3-(6-hydroxy-6-methyl-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d6) δ ppm 1H NMR (400 MHz, DMSO-d6) ä ppm 10.60-10.80 (m, 1 H) 8.76-9.06 (m, 1 H) 8.12-8.28 (m, 1 H) 7.89-8.10 (m, 2 H) 7.63-7.87 (m, 3 H) 7.29-7.46 (m, 1 H) 3.90-4.00 (m, 3 H) 3.51-3.71 (m, 1 H) 3.38-3.51 (m, 1 H) 3.21-3.34 (m, 1 H) 2.96 (td, J = 12.20, 3.36 Hz, 1 H) 2.23-2.27(m, 3 H) 2.06 (t, J = 19.13 Hz, 4 H) 1.79-1.88 (m, 1 H) 1.53-1.62 (m, 3 H); LCMS (m/z) (M + H) = 4954., Rt = 0.98 min. |
| 42 | 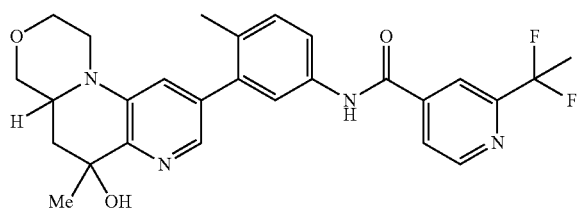<br>"cis-hydroxy" | (rac)-(cis)-2-(1,1-difluoroethyl)-N-(3-(6-hydroxy-6-methyl-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d6) δ ppm 10.67 (s, 1 H) 8.76-9.02 (m, 1 H) 8.17 (s, 1 H) 7.90-8.07 (m, 2 H) 7.64-7.79 (m, 2 H) 7.24-7.47 (m, 2 H) 3.97 (br dd, J = 11.25, 3.06 Hz, 2 H) 3.81-3.90 (m, 3 H) 3.58 (td, J = 11.74, 2.69 Hz, 1 H) 3.14-3.36 (m, 2 H) 2.78 (td, J = 12.13, 3.61 Hz, 1 H) 2.25 (s, 3 H) 2.05 (t, J = 19.13 Hz, 3 H) 1.51-1.90 (m, 4 H); LCMS (m/z) (M + H) = 4954., Rt = 1.03 min. |

| Ex. No. | Structure | Name | Physical Data |
|---|---|---|---|
| 43 | "trans-hydroxy" | (rac)-(trans)-N-(5-(6-hydroxy-6-methyl-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, DMSO-d6) δ ppm 10.80 (s, 1 H) 8.90 (d, J = 2.45 Hz, 1 H) 8.26-8.38 (m, 2 H) 8.21 (d, J = 2.45 Hz, 1 H) 8.08 (d, J = 1.34 Hz, 1H) 8.02 (dd, J = 7.82, 0.73 Hz, 1 H) 7.83 (t, J = 7.83 Hz, 2 H) 3.88-4.07 (m, 3 H) 3.56 (td, J = 11.71, 2.63 Hz, 1 H) 3.35-3.47 (m, 1 H) 3.16-3.30(m, 1 H) 2.95 (td, J = 12.26, 3.36 Hz, 1 H) 2.47 (s, 3 H) 2.03 (dd, J = 12.84, 2.57 Hz, 1 H) 1.83 (t, J = 12.65 Hz, 1 H) 1.56 (s, 3 H); LCMS (m/z) (M + H) = 495.4., Rt = 0.94 min. |
| 44 | "cis-hydroxy" | (rac)-(cis)-N-(5-(6-hydroxy-6-methyl-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, DMSO-d6) δ ppm 10.82 (s, 1 H) 8.95 (d, J = 2.32 Hz, 1 H) 8.27-8.40 (m, 2 H) 8.19 (d, J = 2.32 Hz, 1 H) 7.97-8.06 (m, 2 H)7.83 (t, J = 7.83 Hz, 1 H) 7.45 (s, 1 H) 3.98 (br dd, J = 11.55, 3.36 Hz, 5 H) 3.74-3.89 (m, 6 H) 3.59 (td, J = 11.71, 2.63 Hz, 2 H) 3.15-3.37 (m, 2 H)2.78 (td, J = 12.10, 3.55 Hz, 1 H) 1.86 (dd, J = 13.51, 2.26 Hz, 1 H) 1.48-1.73 (m, 4 H); LCMS (m/z) (M + H) = 495.4, Rt = 1.00 min. |

Example 45

(rac)-N-(4-methyl-3-(2-methyl-3b,4,6,7-tetrahydro-2H-[1,4]oxazino[4,3-a]pyrazolo[4,3-c]quinolin-10-yl)phenyl)-2-(trifluoromethyl)isonicotinamide

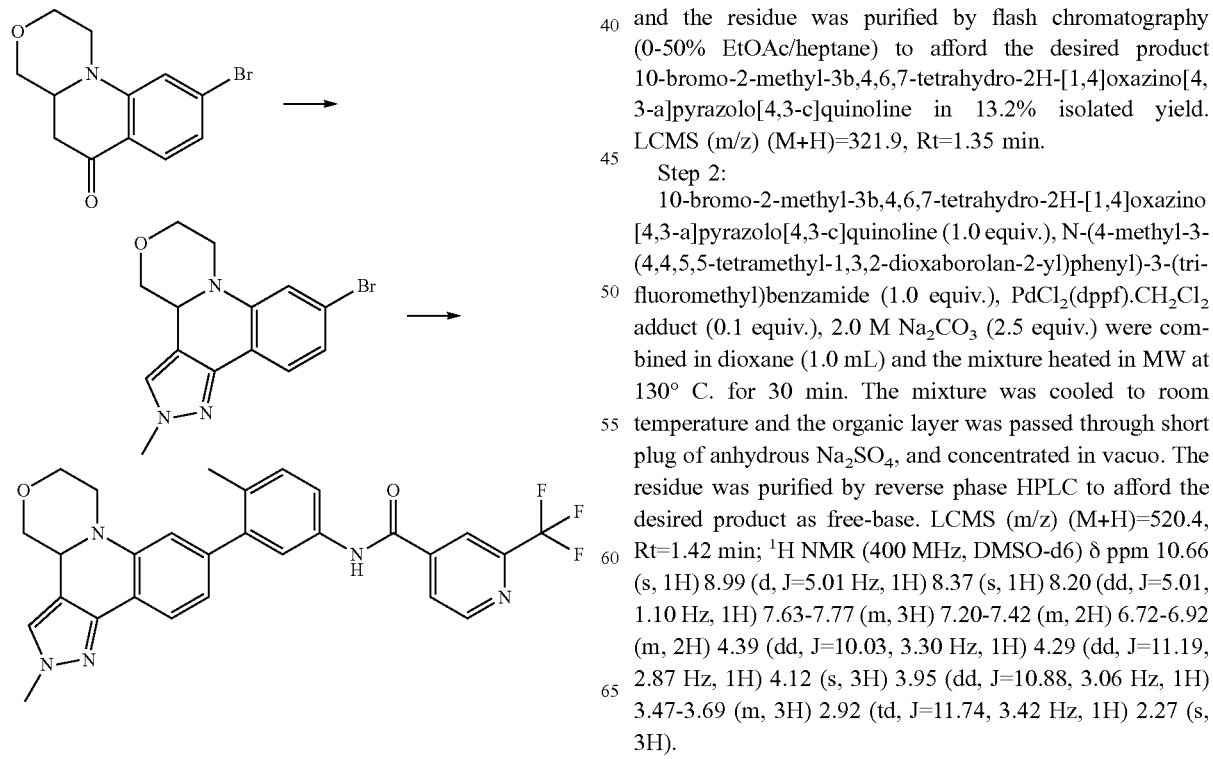

Step 1:
9-bromo-1,2,4a,5-tetrahydro-[1,4]oxazino[4,3-a]quinolin-6(4H)-one (1.0 equiv.) was treated with DMF-DMA (15 equiv.) and the mixture heated at 100° C. for 3 h and concentrated in vacuo. The residue was dissolved in EtOH (0.2M) and treated with methylhydrazine (5 equiv.). This mixture was agitated at room temperature over 72 h to afford a yellow suspension. The solvent was evaporated in vacuo and the residue was purified by flash chromatography (0-50% EtOAc/heptane) to afford the desired product 10-bromo-2-methyl-3b,4,6,7-tetrahydro-2H-[1,4]oxazino[4,3-a]pyrazolo[4,3-c]quinoline in 13.2% isolated yield. LCMS (m/z) (M+H)=321.9, Rt=1.35 min.

Step 2:
10-bromo-2-methyl-3b,4,6,7-tetrahydro-2H-[1,4]oxazino[4,3-a]pyrazolo[4,3-c]quinoline (1.0 equiv.), N-(4-methyl-3-(4,4,5,5-tetramethyl-1,3,2-dioxaborolan-2-yl)phenyl)-3-(trifluoromethyl)benzamide (1.0 equiv.), PdCl$_2$(dppf).CH$_2$Cl$_2$ adduct (0.1 equiv.), 2.0 M Na$_2$CO$_3$ (2.5 equiv.) were combined in dioxane (1.0 mL) and the mixture heated in MW at 130° C. for 30 min. The mixture was cooled to room temperature and the organic layer was passed through short plug of anhydrous Na$_2$SO$_4$, and concentrated in vacuo. The residue was purified by reverse phase HPLC to afford the desired product as free-base. LCMS (m/z) (M+H)=520.4, Rt=1.42 min; $^1$H NMR (400 MHz, DMSO-d6) δ ppm 10.66 (s, 1H) 8.99 (d, J=5.01 Hz, 1H) 8.37 (s, 1H) 8.20 (dd, J=5.01, 1.10 Hz, 1H) 7.63-7.77 (m, 3H) 7.20-7.42 (m, 2H) 6.72-6.92 (m, 2H) 4.39 (dd, J=10.03, 3.30 Hz, 1H) 4.29 (dd, J=11.19, 2.87 Hz, 1H) 4.12 (s, 3H) 3.95 (dd, J=10.88, 3.06 Hz, 1H) 3.47-3.69 (m, 3H) 2.92 (td, J=11.74, 3.42 Hz, 1H) 2.27 (s, 3H).

Example 46

(rac)(trans)-2-(1,1-difluoroethyl)-N-(3-(5-hydroxy-5,6,6a,7,9,10-hexahydropyridazino[3',4':5,6]pyrido[2,1-c][1,4]oxazin-2-yl)-4-methylphenyl)isonicotinamide

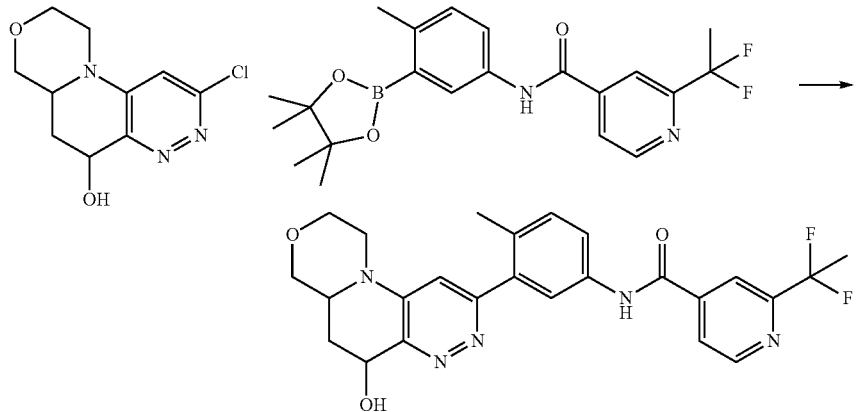

Into a MW vial were charged 2-(1,1-difluoroethyl)-N-(4-methyl-3-(4,4,5,5-tetramethyl-1,3,2-dioxaborolan-2-yl)phenyl)isonicotinamide (1.0 equiv.), 2-chloro-5,6,6a,7,9,10-hexahydropyridazino[3',4':5,6]pyrido[2,1-c][1,4]oxazin-5-ol (1.0 equiv.), K₃PO₄ (3.0 equiv.), X-Phos G2 Pd-cycle (0.1 equiv.) and dioxane:DMF:Water(5:1:1) (0.1 M). The vial was capped and agitated in MW at 130° C. for 30 min and the mixture was cooled to room temperature and then diluted with EtOAc. The organic layer was passed through a plug of MgSO₄ and the filtrate concentrated in vacuo. The residue was purified by reverse-phase basic HPLC to afford the desired product (trans)-2-(1,1-difluoroethyl)-N-(3-(5-hydroxy-5,6,6a,7,9,10-hexahydropyridazino[3',4':5,6]pyrido[2,1-c][1,4]oxazin-2-yl)-4-methylphenyl)isonicotinamide as free-base. LCMS (m/z) (M+H)=482.4, Rt=0.72 min. ¹H NMR (400 MHz, DMSO-d6) δ ppm 10.69 (s, 1H) 8.88 (dd, J=5.01, 0.61 Hz, 1H) 8.19 (d, J=0.61 Hz, 1H) 8.04 (dd, J=5.01, 1.59 Hz, 1H) 7.71-7.83 (m, 2H) 7.35 (d, J=8.07 Hz, 1H) 6.96 (br s, 1H) 5.73 (br s, 1H) 4.79-5.00 (m, 1H) 3.78-4.01 (m, 3H) 3.51 (td, J=11.71, 2.51 Hz, 2H) 3.29 (br s, 1H) 2.94 (br s, 1H) 2.28 (s, 3H) 2.23 (ddd, J=12.81, 5.72, 3.48 Hz, 1H) 2.05 (t, J=19.13 Hz, 3H) 1.55-1.73 (m, 1H).

The following compounds were prepared using methods from the above examples, using appropriate starting materials:

| Ex. No. | Structure | Name | Physical Data |
|---|---|---|---|
| 47 | "trans" | (rac)-(trans)-N-(5-(5-hydroxy-5,6,6a,7,9,10-hexahydropyridazino[3',4':5,6]pyrido[2,1-c][1,4]oxazin-2-yl)-6-methylpyridin-3-yl)-3-(trifluoromethyl)benzamide | ¹H NMR (400 MHz, DMSO-d6) δ ppm 10.51-10.84 (m, 1 H) 8.92 (d, J = 2.45 Hz, 1 H) 8.34 (s, 1 H) 8.30 (d, J = 7.83 Hz, 1 H) 8.21 (d, J = 2.32 Hz, 1H) 8.00 (d, J = 7.83 Hz, 1 H) 1.11-7.85 (m, 1 H) 7.07 (br s, 1 H) 5.76 (br s, 1 H) 4.83-5.05 (m, 1 H) 3.83-4.09 (m, 3 H) 3.44-3.68 (m, 2 H) 3.35(s, 1 H) 2.85-3.09 (m, 1 H) 2.48-2.49 (m, 3 H) 2.23 (ddd, J = 12.93, 5.65, 3.30 Hz, 1 H) 1.67 (dt, J = 12.72, 10.64 Hz, 1 H); LCMS (m/z) (M + H) = 486.1, Rt = 0.92 min. |
| 48 | "trans" | (rac)-(trans)-N-(3-(5-hydroxy-5,6,6a,7,9,10-hexahydro-pyridazino[3',4':5,6]pyrido[2,1-c][1,4]oxazin-2-yl)-4-methylphenyl)-2-(trifluoromethyl)isonicotinamide | ¹H NMR (400 MHz, DMSO-d6) δ ppm 15.05 (br s, 1 H) 10.91 (s, 1 H) 9.02 (d, J = 5.01 Hz, 1 H) 8.32-8.41 (m, 1 H) 8.20 (dd, J = 4.95, 1.16 Hz, 1 H) 7.99 (d, J = 2.20 Hz, 1 H) 7.83 (dd, J = 8.31, 2.20 Hz, 1 H) 7.38-7.53 (m, 2 H) 6.17 (br s, 1 H) 4.84 (dd, J = 10.76, 5.14 Hz, 1 H) 4.26 (br d, J = 13.33 Hz, 1 H) 3.83-4.09 (m, 3 H) 3.12-3.32 (m, 2 H) 2.15-2.39 (m, 4 H) 1.78 (dt, J = 12.84, 10.45 Hz, 1 H); LCMS (m/z) (M + H) = 486.5, Rt = 1.10 min. |

Example 49

(rac)-N-(3-(5,5-bis(hydroxymethyl)-1,2,4,4a,5,6-hexahydro-[1,4]oxazino[4,3-a]quinolin-9-yl)-4-methylphenyl)-2-(trifluoromethyl)isonicotinamide

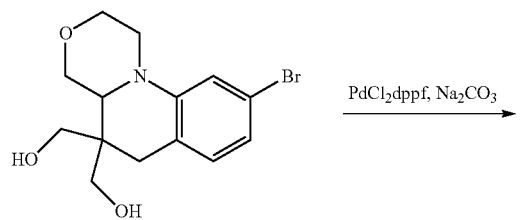

(0.1 M). The mixture was heated in MW at 120° C. for 20 min and then cooled to room temperature and the product extracted with EtOAc. The organic layer was dried (Na$_2$SO$_4$), filtered and concentrated in vacuo and the residue purified by reverse-phase HPLC to afford the desired product N-(3-(5,5-bis(hydroxymethyl)-1,2,4,4a,5,6-hexahydro-[1,4]oxazino[4,3-a]quinolin-9-yl)-4-methylphenyl)-2-(trifluoromethyl)isonicotinamide as free-base. LCMS (m/z) (M+H)=528.2, Rt=1.29 min. $^1$H NMR (400 MHz, DMSO-d6) δ ppm 10.61 (s, 1H) 8.99 (d, J=5.01 Hz, 1H) 8.36 (s, 1H) 8.19 (dd, J=5.01, 1.10 Hz, 1H) 7.67 (dd, J=8.25, 2.26 Hz, 1H) 7.61 (d, J=2.20 Hz, 1H) 7.28 (d, J=8.31 Hz, 1H) 7.01 (d, J=7.58 Hz, 1H) 6.77 (d, J=0.98 Hz, 1H) 6.60 (dd, J=7.52, 1.28 Hz, 1H) 4.44-4.68 (m, 2H) 3.70-4.05 (m, 3H) 3.35-3.56 (m, 6H) 3.11-3.29 (m, 1H) 2.87 (td, J=12.38, 3.36 Hz, 1H) 2.52-2.71 (m, 2H) 2.23 (s, 3H).

The following compounds were prepared using methods from the above examples, using appropriate starting materials:

| | | | |
|---|---|---|---|
| 50 | 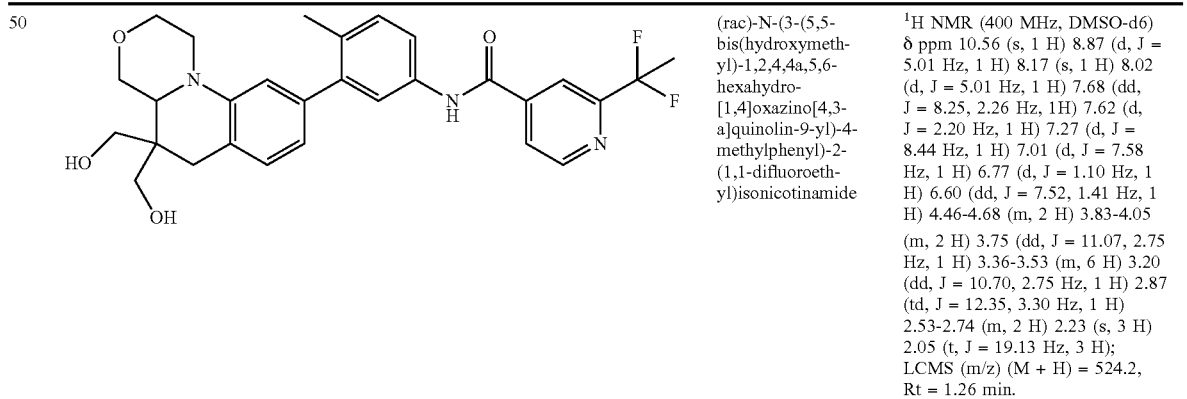 | (rac)-N-(3-(5,5-bis(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | $^1$H NMR (400 MHz, DMSO-d6) δ ppm 10.56 (s, 1 H) 8.87 (d, J = 5.01 Hz, 1 H) 8.17 (s, 1 H) 8.02 (d, J = 5.01 Hz, 1 H) 7.68 (dd, J = 8.25, 2.26 Hz, 1H) 7.62 (d, J = 2.20 Hz, 1 H) 7.27 (d, J = 8.44 Hz, 1 H) 7.01 (d, J = 7.58 Hz, 1 H) 6.77 (d, J = 1.10 Hz, 1 H) 6.60 (dd, J = 7.52, 1.41 Hz, 1 H) 4.46-4.68 (m, 2 H) 3.83-4.05 (m, 2 H) 3.75 (dd, J = 11.07, 2.75 Hz, 1 H) 3.36-3.53 (m, 6 H) 3.20 (dd, J = 10.70, 2.75 Hz, 1 H) 2.87 (td, J = 12.35, 3.30 Hz, 1 H) 2.53-2.74 (m, 2 H) 2.23 (s, 3 H) 2.05 (t, J = 19.13 Hz, 3 H); LCMS (m/z) (M + H) = 524.2, Rt = 1.26 min. |
| 51 | 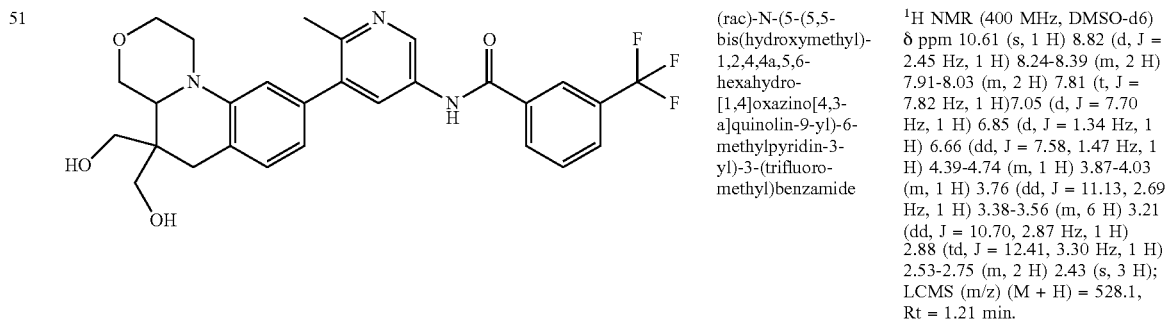 | (rac)-N-(5-(5,5-bis(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, DMSO-d6) δ ppm 10.61 (s, 1 H) 8.82 (d, J = 2.45 Hz, 1 H) 8.24-8.39 (m, 2 H) 7.91-8.03 (m, 2 H) 7.81 (t, J = 7.82 Hz, 1 H) 7.05 (d, J = 7.70 Hz, 1 H) 6.85 (d, J = 1.34 Hz, 1 H) 6.66 (dd, J = 7.58, 1.47 Hz, 1 H) 4.39-4.74 (m, 1 H) 3.87-4.03 (m, 1 H) 3.76 (dd, J = 11.13, 2.69 Hz, 1 H) 3.38-3.56 (m, 6 H) 3.21 (dd, J = 10.70, 2.87 Hz, 1 H) 2.88 (td, J = 12.41, 3.30 Hz, 1 H) 2.53-2.75 (m, 2 H) 2.43 (s, 3 H); LCMS (m/z) (M + H) = 528.1, Rt = 1.21 min. |

-continued

| | | | |
|---|---|---|---|
| 50 | 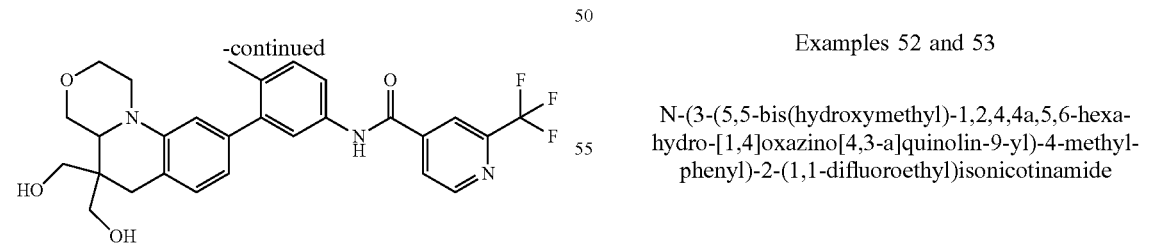 | | |

Step 1:

Into a MW vial was added (9-bromo-1,2,4,4a,5,6-hexahydro-[1,4]oxazino[4,3-a]quinoline-5,5-diyl)dimethanol (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.), K$_3$PO$_4$ (51.7 mg, 0.244 mmol), X-Phos G2 Pd-Cycle (0.1 equiv.) and dioxane:DMF:water (5:1:1)

Examples 52 and 53

N-(3-(5,5-bis(hydroxymethyl)-1,2,4,4a,5,6-hexahydro-[1,4]oxazino[4,3-a]quinolin-9-yl)-4-methylphenyl)-2-(1,1-difluoroethyl)isonicotinamide

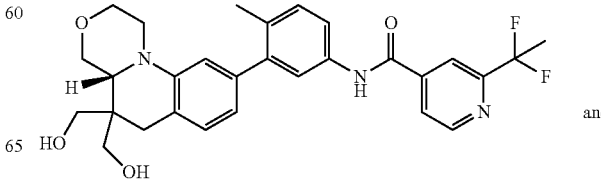

and

189

-continued

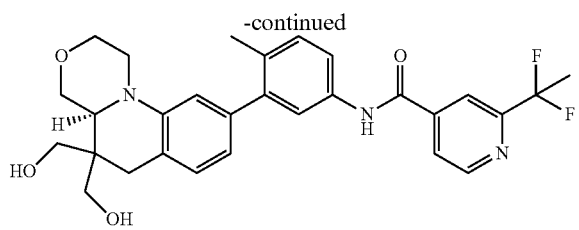

190

-continued

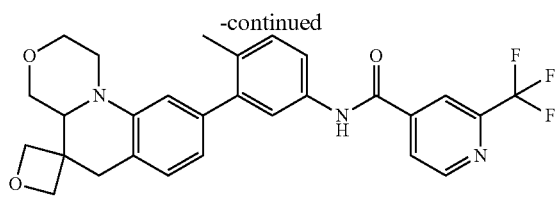

N-(3-(5,5-bis(hydroxymethyl)-1,2,4,4a,5,6-hexahydro-[1,4]oxazino[4,3-a]quinolin-9-yl)-4-methylphenyl)-2-(1,1-difluoroethyl)isonicotinamide was resolved by chiral SFC. The first eluting peak afforded (R)—N-(3-(5,5-bis(hydroxymethyl)-1,2,4,4a,5,6-hexahydro-[1,4]oxazino[4,3-a]quinolin-9-yl)-4-methylphenyl)-2-(1,1-difluoroethyl)isonicotinamide; $^1$H NMR (400 MHz, DMSO-d6) δ ppm 10.56 (s, 1H) 8.87 (d, J=5.13 Hz, 1H) 8.17 (s, 1H) 8.03 (d, J=4.89 Hz, 1H) 7.68 (dd, J=8.25, 2.26 Hz, 1H) 7.62 (d, J=2.20 Hz, 1H) 7.27 (d, J=8.31 Hz, 1H) 7.01 (d, J=7.58 Hz, 1H) 6.78 (d, J=0.86 Hz, 1H) 6.60 (dd, J=7.52, 1.28 Hz, 1H) 4.44-4.69 (m, 2H) 3.71-4.05 (m, 3H) 3.36-3.56 (m, 6H) 3.20 (dd, J=10.64, 2.69 Hz, 1H) 2.82-2.99 (m, 1H) 2.52-2.71 (m, 2H) 2.23 (s, 3H) 2.05 (t, J=19.07 Hz, 3H); LCMS: (m/z) (M+H)=524.2, Rt=1.26 min; and the second eluting peak afforded (S)—N-(3-(5,5-bis(hydroxymethyl)-1,2,4,4a,5,6-hexahydro-[1,4]oxazino[4,3-a]quinolin-9-yl)-4-methylphenyl)-2-(1,1-difluoroethyl)isonicotinamide; $^1$H NMR (400 MHz, DMSO-d6) δ ppm 10.56 (s, 1H) 8.87 (d, J=5.13 Hz, 1H) 8.17 (s, 1H) 8.03 (d, J=4.89 Hz, 1H) 7.68 (dd, J=8.25, 2.26 Hz, 1H) 7.62 (d, J=2.20 Hz, 1H) 7.27 (d, J=8.31 Hz, 1H) 7.01 (d, J=7.58 Hz, 1H) 6.78 (d, J=0.86 Hz, 1H) 6.60 (dd, J=7.52, 1.28 Hz, 1H) 4.44-4.69 (m, 2H) 3.71-4.05 (m, 3H) 3.36-3.56 (m, 6H) 3.20 (dd, J=10.64, 2.69 Hz, 1H) 2.82-2.99 (m, 1H) 2.52-2.71 (m, 2H) 2.23 (s, 3H) 2.05 (t, J=19.07 Hz, 3H); LCMS: (m/z) (M+H)=524.2, Rt=1.26 min.

Example 54

(rac)-N-(4-methyl-3-(2,4,4a,6-tetrahydro-1H-spiro[[1,4]oxazino[4,3-a]quinoline-5,3'-oxetan]-9-yl)phenyl)-2-(trifluoromethyl)isonicotinamide

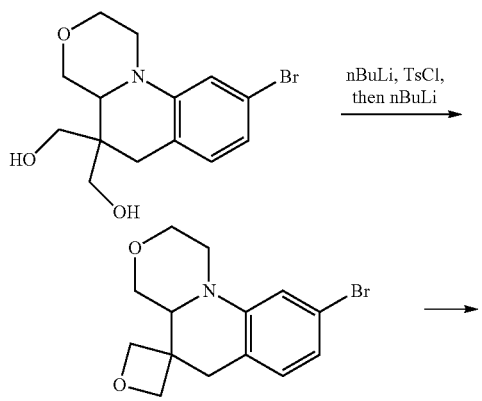

Step 1:

(9-bromo-1,2,4,4a,5,6-hexahydro-[1,4]oxazino[4,3-a]quinoline-5,5-diyl)dimethanol (1.0 equiv.) was dissolved in THF (0.15 M) and cooled to 0° C. Then, butyllithium (0.95 equiv.) was added dropwise and the mixture agitated for 10 min. Then TsCl (1.0 equiv.) in THF was added and the mixture agitated for 1 h during which the desired tosylate intermediate was seen as the major product by LCMS: (m/z) (M+H)=524.2, 1.26 min. Then butyllithium (0.95 equiv.) was added and the mixture heated at 60° C. for 3 h during which desired product appears to be the major adduct. The reaction mixture was quenched by addition of water and the product extracted with EtOAc. The organic layer was dried (MgSO$_4$), and the product purified by flash chromatography (0-50% EtOAc/heptane) to afford the desired product 9-bromo-2,4,4a,6-tetrahydro-1H-spiro[[1,4]oxazino[4,3-a]quinoline-5,3'-oxetane] in 79% isolated yield. LCMS: (m/z) (M+H)=311.9, Rt=1.36 min.

Step 2:

Into a MW vial was added 9-bromo-2,4,4a,6-tetrahydro-1H-spiro[[1,4]oxazino[4,3-a]quinoline-5,3'-oxetane] (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.), K$_3$PO$_4$ (0.1 equiv.), X-Phos G2 Pd-Cycle (0.1 equiv.) and then dioxane:water (10:1) (0.1 M) was added. The vial was capped and the mixture was heated in MW at 120° C. for 20 min and then cooled to room temperature and the product extracted with EtOAc. The organic layer was dried (Na$_2$SO$_4$), filtered and concentrated in vacuo and the residue purified by reverse-phase HPLC to afford the desired product N-(4-methyl-3-(2,4,4a,6-tetrahydro-1H-spiro[[1,4]oxazino[4,3-a]quinoline-5,3'-oxetan]-9-yl)phenyl)-2-(trifluoromethyl)isonicotinamideas free base; LCMS: (m/z) (M+H)=510.1, Rt=1.40 min. $^1$H NMR (400 MHz, DMSO-d6) δ ppm 10.61 (s, 1H) 8.98 (d, J=5.01 Hz, 1H) 8.36 (s, 1H) 8.18 (dd, J=4.89, 1.10 Hz, 1H) 7.67 (dd, J=8.19, 2.32 Hz, 1H) 7.61 (d, J=2.32 Hz, 1H) 7.28 (d, J=8.44 Hz, 1H) 7.08 (d, J=7.70 Hz, 1H) 6.77 (d, J=1.22 Hz, 1H) 6.64 (dd, J=7.58, 1.47 Hz, 1H) 4.48-4.67 (m, 2H) 4.26 (t, J=5.99 Hz, 2H) 4.17 (dd, J=11.13, 2.93 Hz, 1H) 3.78-3.93 (m, 2H) 3.63 (t, J=10.94 Hz, 1H) 3.55 (td, J=11.68, 2.45 Hz, 1H) 3.36 (dd, J=10.70, 3.00 Hz, 1H) 3.01-3.14 (m, 2H) 2.90 (td, J=12.38, 3.48 Hz, 1H) 2.22 (s, 3H).

The following compounds were prepared using methods from the above examples, using appropriate starting materials:

| | | | |
|---|---|---|---|
| 55 | 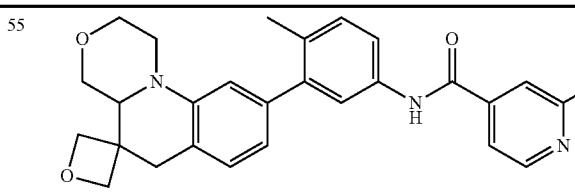 | (rac)-2-(1,1-difluoroethyl)-N-(4-methyl-3-(2,4,4a,6-tetrahydro-1H-spiro[[1,4]oxazino[4,3-a]quinoline-5,3'-oxetan]-9-yl)phenyl)isonicotinamide | $^1$H NMR (400 MHz, DMSO-d6) δ ppm 10.56 (s, 1 H) 8.87 (d, J = 5.01 Hz, 1 H) 8.17 (s, 1 H) 8.02 (dd, J = 5.01, 1.34 Hz, 1 H) 7.67 (dd, J = 8.25, 2.26 Hz, 1 H) 7.61 (d, J = 2.20 Hz, 1 H) 7.26 (d, J = 8.44 Hz, 1 H) 7.08 (d, J = 7.58 Hz, 1 H) 6.77 (d, J = 1.22 Hz, 1 H) 6.64 (dd, J = 7.58, 1.34 Hz, 1 H) 4.47-4.66 (m, 2 H) 4.26 (t, J = 6.11 Hz, 2 H) 4.17 (dd, J = 11.13, 2.93 Hz, 1 H) 3.84 (dd, J = 11.68, 2.26 Hz, 2 H) 3.63 (t, J = 10.94 Hz, 1 H) 3.55 (td, J = 11.49, 2.08 Hz, 1 H) 3.38 (dd, J = 10.70, 3.00 Hz, 1 H) 2.98-3.14 (m, 2 H) 2.90 (td, J = 12.44, 3.61 Hz, 1 H) 2.21 (s, 3 H) 2.05 (t, J = 19.13 Hz, 3 H)LCMS (m/z) (M + H) = 506.1, Rt = 1.39 min. |
| 56 | 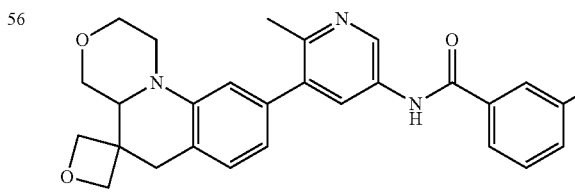 | (rac)-N-(6-methyl-5-(2,4,4a,6-tetrahydro-1H-spiro[[1,4]oxazino[4,3-a]quinoline-5,3'-oxetan]-9-yl)pyridin-3-yl)-3-(trifluoromethyl)benzamide | $^1$H NMR (400 MHz, DMSO-d6) δ ppm 10.60 (s, 1 H) 8.81 (d, J = 2.57 Hz, 1 H) 8.32 (s, 1 H) 8.28 (d, J = 7.95 Hz, 1 H) 7.92-8.03 (m, 2 H) 7.81 (t, J = 7.83 Hz, 1 H) 7.12 (d, J = 7.58 Hz, 1 H) 6.84 (d, J = 1.22 Hz, 1 H) 6.69 (dd, J = 7.58, 1.34 Hz, 1 H) 4.48-4.65 (m, 2 H) 4.26 (t, J = 5.93 Hz, 2 H) 4.17 (dd, J = 11.19, 2.87 Hz, 1 H) 3.80-3.92 (m, 2 H) 3.63 (t, J = 11.00 Hz, 1 H) 3.55 (td, J = 11.71, 2.63 Hz, 1 H) 3.38 (dd, J = 10.76, 3.06 Hz, 1 H) 3.01-3.16 (m, 2 H) 2.92 (td, J = 12.38, 3.48 Hz, 1 H) 2.42 (s, 3 H)LCMS (/m/z) (M + H) = 528.1, Rt = 1.21 min. |

Examples 57 and 58

2-(1,1-difluoroethyl)-N-(4-methyl-3-(2,4,4a,6-tetrahydro-1H-spiro[[1,4]oxazino[4,3-a]quinoline-5,3'-oxetan]-9-yl)phenyl)isonicotinamide

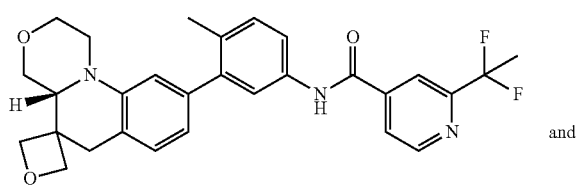

and

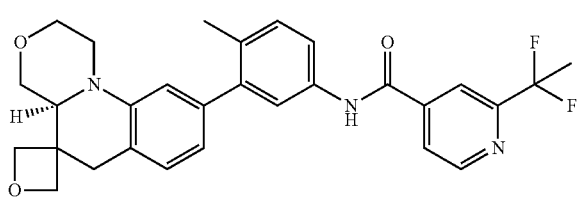

2-(1,1-difluoroethyl)-N-(4-methyl-3-(2,4,4a,6-tetrahydro-1H-spiro[[1,4]oxazino[4,3-a]quinoline-5,3'-oxetan]-9-yl)phenyl)isonicotinamide was resolved by chiral SFC. The first eluting peak afforded (R)-2-(1,1-difluoroethyl)-N-(4-methyl-3-(1',2',4',4a'-tetrahydro-6'H-spiro[oxetane-3,5'-[1,4]oxazino[4,3-a]quinolin]-9'-yl)phenyl)isonicotinamide; $^1$H NMR (400 MHz, DMSO-d6) δ ppm 10.56 (s, 1H) 8.87 (d, J=5.01 Hz, 1H) 8.17 (s, 1H) 8.02 (dd, J=5.07, 1.41 Hz, 1H) 7.56-7.75 (m, 2H) 7.26 (d, J=8.44 Hz, 1H) 7.08 (d, J=7.58 Hz, 1H) 6.77 (d, J=1.22 Hz, 1H) 6.64 (dd, J=7.58, 1.47 Hz, 1H) 4.46-4.68 (m, 2H) 4.13-4.31 (m, 3H) 3.84 (dd, J=11.68, 2.26 Hz, 2H) 3.49-3.68 (m, 2H) 3.38 (d, J=3.06 Hz, 1H) 2.99-3.14 (m, 2H) 2.90 (td, J=12.47, 3.55 Hz, 1H) 2.21 (s, 3H) 1.95-2.12 (m, 3H).; LCMS: (m/z) (M+H)=506.1, Rt=1.39 min; and the second eluting peak afforded (S)-2-(1,1-difluoroethyl)-N-(4-methyl-3-(1',2',4',4a'-tetrahydro-6'H-spiro[oxetane-3,5'-[1,4]oxazino[4,3-a]quinolin]-9'-yl)phenyl)isonicotinamide; $^1$H NMR (400 MHz, DMSO-d6) δ ppm 10.56 (s, 1H) 8.87 (d, J=5.01 Hz, 1H) 8.17 (s, 1H) 8.02 (dd, J=5.07, 1.41 Hz, 1H) 7.56-7.75 (m, 2H) 7.26 (d, J=8.44 Hz, 1H) 7.08 (d, J=7.58 Hz, 1H) 6.77 (d, J=1.22 Hz, 1H) 6.64 (dd, J=7.58, 1.47 Hz, 1H) 4.46-4.68 (m, 2H) 4.13-4.31 (m, 3H) 3.84 (dd, J=11.68, 2.26 Hz, 2H) 3.49-3.68 (m, 2H) 3.38 (d, J=3.06 Hz, 1H) 2.99-3.14 (m, 2H) 2.90 (td, J=12.47, 3.55 Hz, 1H) 2.21 (s, 3H) 1.95-2.12 (m, 3H).; LCMS: (m/z) (M+H)=506.1, Rt=1.39 min.

Example 59

(rac)-N-(3-(5-(hydroxymethyl)-1,2,4,4a,5,6-hexahydro-[1,4]oxazino[4,3-a]quinolin-9-yl)-4-methylphenyl)-2-(trifluoromethyl)isonicotinamide

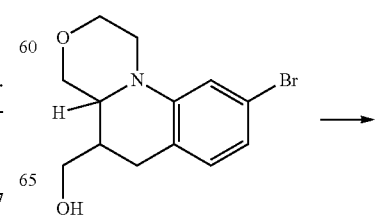

193
-continued

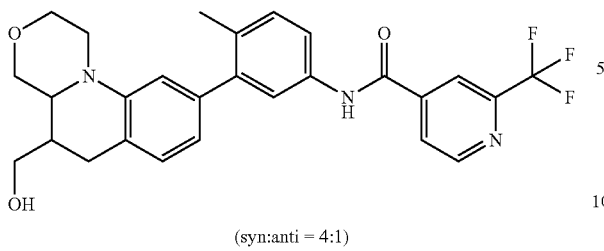

(syn:anti = 4:1)

Step 1:

Into a MW vial was added (9-bromo-1,2,4,4a,5,6-hexahydro-[1,4]oxazino[4,3-a]quinolin-5-yl)methanol (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.), K₃PO₄ (2.0 equiv.), X-Phos G2 Pd-Cycle (0.1 equiv.) and then dioxane:DMF:Water (5:1:0.2) (0.1 M) was added. The mixture was heated in MW at 120° C. for 20 min and then cooled to room temperature and the product extracted with EtOAc. The organic layer was dried (Na₂SO₄), filtered and concentrated in vacuo and the residue purified by reverse-phase HPLC and then column chromatography (0-100% EtOAc/heptane) to afford the desired product N-(3-(5-(hydroxymethyl)-1,2,4,4a,5,6-hexahydro-[1,4]oxazino[4,3-a]quinolin-9-yl)-4-methylphenyl)-2-(trifluoromethyl)isonicotinamideas 4:1 diastereomeric mixture. LCMS: (m/z) (M+H)=498.4, Rt=1.34 min. ¹H NMR (400 MHz, DMSO-d6) δ ppm 10.61 (s, 1H) 8.98 (d, J=5.01 Hz, 1H) 8.36 (s, 1H) 8.19 (dd, J=4.95, 1.04 Hz, 1H) 7.67 (dd, J=8.19, 2.20 Hz, 1H) 7.58-7.64 (m, 1H) 7.28 (d, J=8.44 Hz, 1H) 6.98-7.09 (m, 1H) 6.58-6.83 (m, 2H) 3.94 (dd, J=11.19, 3.00 Hz, 1H) 3.74-3.90 (m, 2H) 3.46-3.71 (m, 3H) 2.59-2.94 (m, 5H) 2.22 (s, 4H) 1.63-1.83 (m, 1H).

The following compounds were prepared using methods from the above examples, using appropriate starting materials:

194

Examples 62 and 63

2-(1,1-difluoroethyl)-N-(3-(5-(hydroxymethyl)-1,2,4,4a,5,6-hexahydro-[1,4]oxazino[4,3-a]quinolin-9-yl)-4-methylphenyl)isonicotinamide

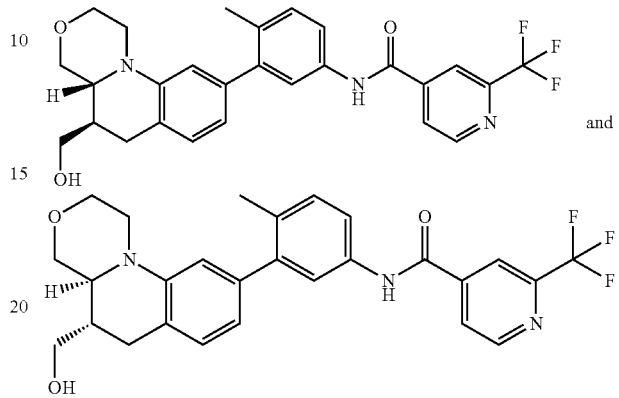

and 2-(1,1-difluoroethyl)-N-(3-(5-(hydroxymethyl)-1,2,4,4a,5,6-hexahydro-[1,4]oxazino[4,3-a]quinolin-9-yl)-4-methylphenyl)isonicotinamide was resolved by chiral SFC to afford single enantiomers of each diastereomer. The first eluting peak afforded N-(3-((4aR,5R)-5-(hydroxymethyl)-1,2,4,4a,5,6-hexahydro-[1,4]oxazino[4,3-a]quinolin-9-yl)-4-methylphenyl)-2-(trifluoromethyl)isonicotinamide; ¹H NMR (400 MHz, DMSO-d6) δ 10.57 (s, 1H) 8.87 (d, J=5.01 Hz, 1H) 8.17 (s, 1H) 8.03 (d, J=4.65 Hz, 1H) 7.68 (dd, J=8.19, 2.20 Hz, 1H) 7.62 (d, J=2.08 Hz, 1H) 7.27 (d, J=8.44 Hz, 1H) 7.05 (d, J=7.58 Hz, 1H) 6.62-6.75 (m, 2H) 4.69 (t, J=5.14 Hz, 1H) 3.81-4.04 (m, 2H) 3.52-3.75 (m, 2H) 3.34-3.39 (m, 2H) 3.22-3.28 (m, 1H) 2.76-2.93 (m, 2H) 2.57-2.69 (m, 2H) 2.22 (s, 3H) 2.05 (t, J=19.13 Hz, 3H) 1.70-1.84 (m, 1H);

| 60 | 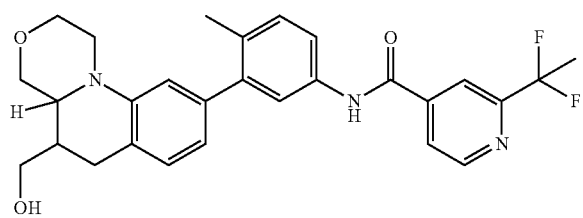 (syn: anti = 4:1) | (rac)-2-(1,1-difluoroethyl)-N-(3-(5-(hydroxymethyl)-1,2,4,4a,5,6-hexahydro-[1,4]oxazino[4,3-a]quinolin-9-yl)-4-methylphenyl)isonicotinamide | ¹H NMR (400 MHz, DMSO-d6) δ ppm 10.57 (s, 1 H) 8.87 (dd, J = 5.01, 0.61 Hz, 1 H) 8.17 (s, 1 H) 8.02 (dd, J = 5.01, 1.35 Hz, 1 H) 7.52-7.78 (m, 2H) 7.27 (d, J = 8.44 Hz, 1 H) 6.99-7.10 (m, 1 H) 6.58-6.83 (m, 2 H) 4.55-4.78 (m, 1 H) 3.73-4.00 (m, 2 H) 3.44-3.72 (m, 2 H) 3.35 (t, J = 5.50 Hz, 2 H) 3.22-3.29 (m, 1 H) 2.57-2.90 (m, 4 H) 2.22 (s, 3 H) 2.05 (t, J = 19.13 Hz, 3 H) 1.67-1.84 (m, 1 H)); LCMS (m/z) (M + H) = 494.1, Rt = 1.34 min. |
| --- | --- | --- | --- |
| 61 | 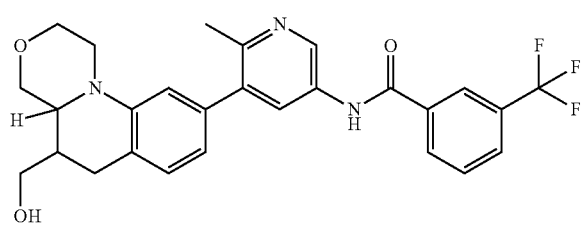 (syn: anti = 4:1) | (rac)-N-(5-(5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | ¹H NMR (400 MHz, DMSO-d6) δ ppm 10.61 (s, 1 H) 8.82 (d, J = 2.44 Hz, 1 H) 8.17-8.47 (m, 2 H) 7.95-8.07 (m, 2 H) 7.81 (t, J = 7.83 Hz, 1H) 6.99-7.15 (m, 1 H) 6.62-6.90 (m, 2 H) 4.55-4.81 (m, 1 H) 3.66-4.06 (m, 3 H) 3.46-3.64 (m, 1 H) 3.36 (t, J = 5.50 Hz, 2 H) 3.22-3.29 (m, 1 H), 2.56-3.00 (m, 4 H) 2.42 (s, 3 H) 1.68-2.16 (m, 1 H); LCMS (m/z) (M + H) = 528.1, Rt = 1.21 min. |

LCMS: (m/z) (M+H)=494.1, Rt=2.36 min (SQ4); and the fourth eluting peak afforded N-(3-((4aS,5S)-5-(hydroxymethyl)-1,2,4,4a,5,6-hexahydro-[1,4]oxazino[4,3-a]quinolin-9-yl)-4-methylphenyl)-2-(trifluoromethyl)isonicotinamide; $^1$H NMR (400 MHz, DMSO-d6) δ 10.57 (s, 1H) 8.87 (d, J=5.01 Hz, 1H) 8.17 (s, 1H) 8.03 (d, J=4.65 Hz, 1H) 7.68 (dd, J=8.19, 2.20 Hz, 1H) 7.62 (d, J=2.08 Hz, 1H) 7.27 (d, J=8.44 Hz, 1H) 7.05 (d, J=7.58 Hz, 1H) 6.62-6.75 (m, 2H) 4.69 (t, J=5.14 Hz, 1H) 3.81-4.04 (m, 2H) 3.52-3.75 (m, 2H) 3.34-3.39 (m, 2H) 3.22-3.28 (m, 1H) 2.76-2.93 (m, 2H) 2.57-2.69 (m, 2H) 2.22 (s, 3H) 2.05 (t, J=19.13 Hz, 3H) 1.70-1.84 (m, 1H); LCMS: (m/z) (M+H)=494.1, Rt=2.36 min (SQ4).

Examples 64 and 65

2-(1,1-difluoroethyl)-N-(3-(5-(hydroxymethyl)-1,2,4a,5,6-hexahydro-[1,4]oxazino[4,3-a]quinolin-9-yl)-4-methylphenyl)isonicotinamide

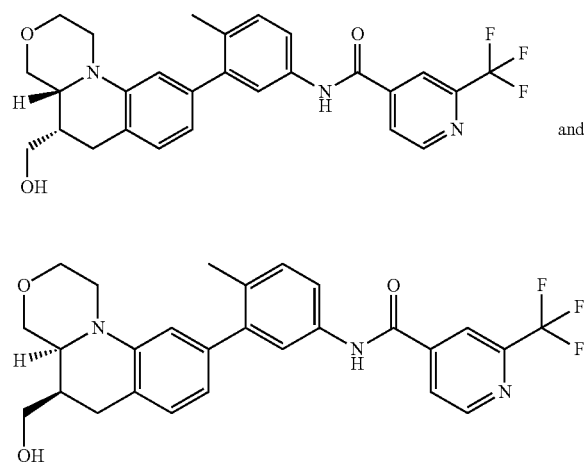

and

Chiral SFC of 2-(1,1-difluoroethyl)-N-(3-(5-(hydroxymethyl)-1,2,4,4a,5,6-hexahydro-[1,4]oxazino[4,3-a]quinolin-9-yl)-4-methylphenyl)isonicotinamide afforded second eluting peak as N-(3-((4aR,5S)-5-(hydroxymethyl)-1,2,4,4a,5,6-hexahydro-[1,4]oxazino[4,3-a]quinolin-9-yl)-4-methylphenyl)-2-(trifluoromethyl)isonicotinamide isonicotinamide; $^1$H NMR (400 MHz, DMSO-d6) δ 10.56 (s, 1H) 8.87 (d, J=5.01 Hz, 1H) 8.17 (s, 1H) 8.02 (d, J=5.01 Hz, 1H) 7.68 (dd, J=8.25, 2.26 Hz, 1H) 7.61 (d, J=2.20 Hz, 1H) 7.27 (d, J=8.44 Hz, 1H) 7.01 (d, J=7.58 Hz, 1H) 6.77 (d, J=1.10 Hz, 1H) 6.58-6.63 (m, 1H) 4.59 (t, J=4.89 Hz, 1H) 3.71-3.90 (m, 3H) 3.43-3.64 (m, 3H) 2.63-2.95 (m, 3H) 2.22 (s, 3H) 1.87-2.13 (m, 5H); LCMS: (m/z) (M+H)=494.1, Rt=2.34 min (SQ4); and the third eluting peak afforded N-(3-((4aS,5R)-5-(hydroxymethyl)-1,2,4,4a,5,6-hexahydro-[1,4]oxazino[4,3-a]quinolin-9-yl)-4-methylphenyl)-2-(trifluoromethyl)isonicotinamide; $^1$H NMR (400 MHz, DMSO-d6) δ 10.56 (s, 1H) 8.87 (d, J=5.01 Hz, 1H) 8.17 (s, 1H) 8.02 (d, J=5.01 Hz, 1H) 7.68 (dd, J=8.25, 2.26 Hz, 1H) 7.61 (d, J=2.20 Hz, 1H) 7.27 (d, J=8.44 Hz, 1H) 7.01 (d, J=7.58 Hz, 1H) 6.77 (d, J=1.10 Hz, 1H) 6.58-6.63 (m, 1H) 4.59 (t, J=4.89 Hz, 1H) 3.71-3.90 (m, 3H) 3.43-3.64 (m, 3H) 2.63-2.95 (m, 3H) 2.22 (s, 3H) 1.87-2.13 (m, 5H); LCMS: (m/z) (M+H)=494.1, Rt=2.34 min (SQ4).

Example 66

(rac)-N-methyl-9-(2-methyl-5-(2-(trifluoromethyl)isonicotinamido)phenyl)-1,2,4,4a,5,6-hexahydro-[1,4]oxazino[4,3-a]quinoline-5-carboxamide

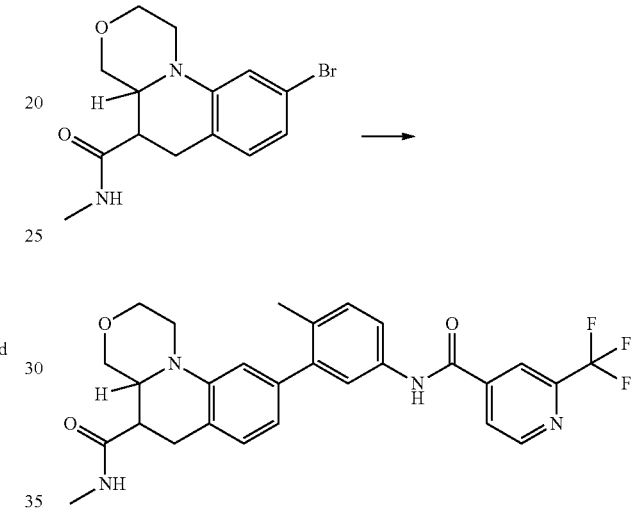

Step 1:

Into a MW vial was added 9-bromo-N-methyl-1,2,4,4a,5,6-hexahydro-[1,4]oxazino[4,3-a]quinoline-5-carboxamide (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.), K$_3$PO$_4$ (2.0 equiv.), X-Phos G2 Pd-Cycle (0.1 equiv.) and then dioxane:DMF:Water (5:1:0.2) (0.1 M). The mixture was heated in MW at 120° C. for 20 min and then cooled to room temperature and the product extracted with EtOAc. The organic layer was dried (Na$_2$SO$_4$), filtered and concentrated in vacuo and the residue purified by reverse-phase HPLC to afford the desired product N-methyl-9-(2-methyl-5-(2-(trifluoromethyl)isonicotinamido)phenyl)-1,2,4,4a,5,6-hexahydro-[1,4]oxazino[4,3-a]quinoline-5-carboxamide as free-base in 33.3% isolated yield in 4:1 diastereomeric ratio. $^1$H NMR (400 MHz, DMSO-d6) δ 10.63 (s, 1H) 8.99 (d, J=4.89 Hz, 1H) 8.36 (s, 1H) 8.19 (dd, J=5.01, 0.98 Hz, 1H) 8.08 (q, J=4.40 Hz, 1H) 7.57-7.74 (m, 2H) 7.28 (d, J=8.31 Hz, 1H) 7.04 (d, J=7.58 Hz, 1H) 6.78 (d, J=1.10 Hz, 1H) 6.61-6.69 (m, 1H) 3.39-3.97 (m, 4H) 2.73-3.25 (m, 5H) 2.55-2.68 (m, 3H) 2.39-2.47 (m, 1H) 2.16-2.26 (m, 3H) LCMS: (m/z) (M+H)=525.1, Rt=1.33 min.

The following compounds were prepared using methods from the above examples, using appropriate starting materials:

| | | | |
|---|---|---|---|
| 67 | 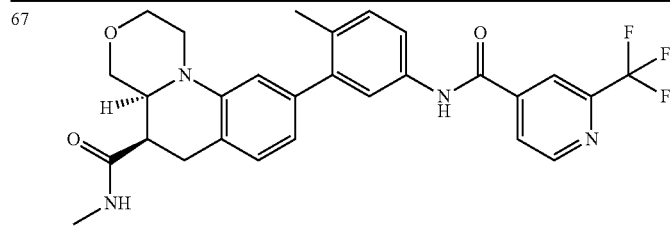 | (rac)-9-(5-(2-(1,1-difluoroethyl)iso-nicotinamido)-2-methylphenyl)-N-methyl-1,2,4,4a,5,6-hexahydro-[1,4]oxazino[4,3-a]quinoline-5-carboxamide | $^1$H NMR (400 MHz, DMSO-d6) δ ppm 10.58 (s, 1 H) 8.87 (d, J = 5.14 Hz, 1 H) 8.17 (s, 1 H) 8.08 (q, J = 4.48 Hz, 1 H) 8.02 (d, J = 3.67 Hz, 1 H) 7.68 (dd, J = 8.19, 2.20 Hz, 1 H) 7.61 (d, J = 2.20 Hz, 1 H) 7.27 (d, J = 8.44 Hz, 1 H) 7.04 (d, J = 7.58 Hz, 1 H) 6.78 (d, J = 1.22 Hz, 1 H) 6.61-6.68 (m, 1 H) 3.40-4.00 (m, 4 H) 2.73-3.24 (m, 4 H) 2.57-2.65 (m, 3 H) 2.37-2.47 (m, 1 H) 2.22 (s, 3 H) 2.05 (t, J = 19.13 Hz, 3 H); LCMS (m/z) (M + H) = 521.2, Rt = 1.30 min. |
| 68 | 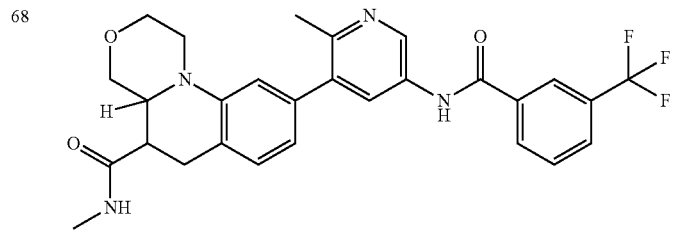<br>(syn: anti = 4:1) | (rac)-N-methyl-9-(2-methyl-5-(3-(trifluoromethyl)benzamido)pyridin-3-yl)-1,2,4,4a,5,6-hexahydro-[1,4]oxazino[4,3-a]quinoline-5-carboxamide | $^1$H NMR (400 MHz, DMSO-d6) δ ppm 10.84 (br. s., 1 H) 8.98 (s, 1 H) 8.26-8.40 (m, 3 H) 8.20 (br. s., 1 H) 8.09 (q, J = 4.40 Hz, 1 H) 8.02 (d, J = 7.82 Hz, 1 H) 7.83 (t, J = 7.82 Hz, 1 H) 7.08-7.14 (m, 1 H) 6.90 (s, 1 H) 6.74 (dd, J = 7.64, 1.53 Hz, 1 H) 3.63-4.00 (m, 20 H) 3.35-3.58 (m, 5H) 2.74-3.24 (m, 8 H) 2.57-2.70 (m, 5 H) 2.38-2.46 (m, 2 H); LCMS (m/z) (M + H) = 528.1, Rt = 1.21 min. |

Examples 69 and 70

9-(5-(2-(1,1-difluoroethyl)isonicotinamido)-2-methylphenyl)-N-methyl-1,2,4,4a,5,6-hexahydro-[1,4]oxazino[4,3-a]quinoline-5-carboxamide

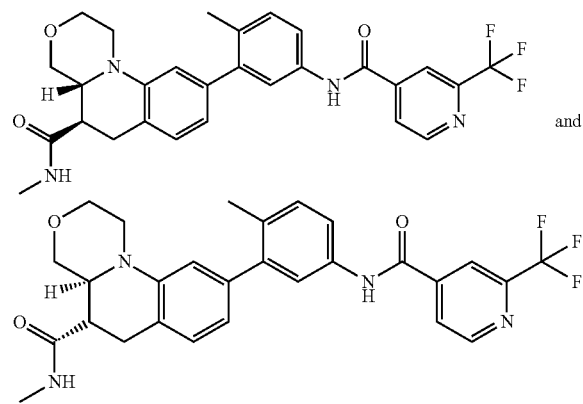

Chiral SFC of 9-(5-(2-(1,1-difluoroethyl)isonicotinamido)-2-methylphenyl)-N-methyl-1,2,4,4a,5,6-hexahydro-[1,4]oxazino[4,3-a]quinoline-5-carboxamide afforded separation of all four possible compounds. The first eluting peak methyl (4aR,5R)-9-(2-methyl-5-(2-(trifluoromethyl)isonicotinamido)phenyl)-1,2,4,4a,5,6-hexahydro-[1,4]oxazino[4,3-a]quinoline-5-carboxylate; $^1$H NMR (400 MHz, DMSO-d6) δ 10.58 (s, 1H) 8.87 (d, J=5.01 Hz, 1H) 8.17 (s, 1H) 8.03 (d, J=5.01 Hz, 1H) 7.89 (q, J=4.40 Hz, 1H) 7.57-7.75 (m, 2H) 7.27 (d, J=8.44 Hz, 1H) 7.05 (d, J=7.58 Hz, 1H) 6.77 (d, J=1.10 Hz, 1H) 6.62 (dd, J=7.52, 1.41 Hz, 1H) 3.88 (d, J=13.08 Hz, 1H) 3.61-3.78 (m, 2H) 3.41-3.55 (m, 3H) 2.97-3.10 (m, 1H) 2.73-2.92 (m, 3H) 2.62 (d, J=4.52 Hz, 3H) 2.23 (s, 3H) 2.05 (t, J=19.13 Hz, 3H); LCMS: (m/z) (M+H)=521.1, Rt=2.25 min (SQ4); and the second eluting peak methyl (4aS,5S)-9-(2-methyl-5-(2-(trifluoromethyl)isonicotinamido)phenyl)-1,2,4,4a,5,6-hexahydro-[1,4]oxazino[4,3-a]quinoline-5-carboxylate; $^1$H NMR (400 MHz, DMSO-d6) δ 10.58 (s, 1H) 8.87 (d, J=5.01 Hz, 1H) 8.17 (s, 1H) 8.03 (d, J=5.01 Hz, 1H) 7.89 (q, J=4.40 Hz, 1H) 7.57-7.75 (m, 2H) 7.27 (d, J=8.44 Hz, 1H) 7.05 (d, J=7.58 Hz, 1H) 6.77 (d, J=1.10 Hz, 1H) 6.62 (dd, J=7.52, 1.41 Hz, 1H) 3.88 (d, J=13.08 Hz, 1H) 3.61-3.78 (m, 2H) 3.41-3.55 (m, 3H) 2.97-3.10 (m, 1H) 2.73-2.92 (m, 3H) 2.62 (d, J=4.52 Hz, 3H) 2.23 (s, 3H) 2.05 (t, J=19.13 Hz, 3H); LCMS: (m/z) (M+H)=521.1, Rt=2.25 min (SQ4).

Examples 71 and 72

9-(5-(2-(1,1-difluoroethyl)isonicotinamido)-2-methylphenyl)-N-methyl-1,2,4,4a,5,6-hexahydro-[1,4]oxazino[4,3-a]quinoline-5-carboxamide

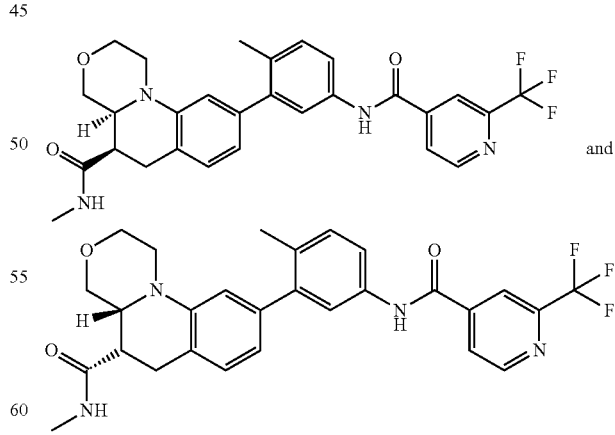

Chiral SFC of 9-(5-(2-(1,1-difluoroethyl)isonicotinamido)-2-methylphenyl)-N-methyl-1,2,4,4a,5,6-hexahydro-[1,4]oxazino[4,3-a]quinoline-5-carboxamide afforded the third peak as methyl (4aS,5R)-9-(2-methyl-5-(2-(trifluoromethyl)isonicotinamido)phenyl)-1,2,4,4a,5,6-hexahydro-[1,4]

oxazino[4,3-a]quinoline-5-carboxylate; $^1$H NMR (400 MHz, DMSO-d6) δ 10.58 (s, 1H) 8.78-8.95 (m, 1H) 8.17 (s, 1H) 8.08 (q, J=4.36 Hz, 1H) 8.02 (dd, J=5.07, 1.41 Hz, 1H) 7.68 (dd, J=8.19, 2.20 Hz, 1H) 7.62 (d, J=2.20 Hz, 1H) 7.27 (d, J=8.44 Hz, 1H) 7.04 (d, J=7.58 Hz, 1H) 6.78 (d, J=1.10 Hz, 1H) 6.64 (dd, J=7.58, 1.34 Hz, 1H) 3.89 (dd, J=11.25, 2.81 Hz, 1H) 3.67-3.82 (m, 2H) 3.53 (td, J=11.58, 2.63 Hz, 1H) 3.04-3.22 (m, 2H) 2.90-3.01 (m, 1H) 2.72-2.84 (m, 2H) 2.63 (d, J=4.65 Hz, 3H) 2.22 (s, 3H) 2.05 (t, J=19.13 Hz, 3H); LCMS: (m/z) (M+H)=521.1, Rt=2.26 min (SQ4). The fourth eluting peak afforded methyl (4aR,5S)-9-(2-methyl-5-(2-(trifluoromethyl)isonicotinamido)phenyl)-1,2,4,4a,5,6-hexahydro-[1,4]oxazino[4,3-a]quinoline-5-carboxylate; $^1$H NMR (400 MHz, DMSO-d6) δ 10.58 (s, 1H) 8.78-8.95 (m, 1H) 8.17 (s, 1H) 8.08 (q, J=4.36 Hz, 1H) 8.02 (dd, J=5.07, 1.41 Hz, 1H) 7.68 (dd, J=8.19, 2.20 Hz, 1H) 7.62 (d, J=2.20 Hz, 1H) 7.27 (d, J=8.44 Hz, 1H) 7.04 (d, J=7.58 Hz, 1H) 6.78 (d, J=1.10 Hz, 1H) 6.64 (dd, J=7.58, 1.34 Hz, 1H) 3.89 (dd, J=11.25, 2.81 Hz, 1H) 3.67-3.82 (m, 2H) 3.53 (td, J=11.58, 2.63 Hz, 1H) 3.04-3.22 (m, 2H) 2.90-3.01 (m, 1H) 2.72-2.84 (m, 2H) 2.63 (d, J=4.65 Hz, 3H) 2.22 (s, 3H) 2.05 (t, J=19.13 Hz, 3H); LCMS: (m/z) (M+H)=521.1, Rt=2.26 min (SQ4).

Example 73

(rac)-N-ethyl-9-(2-methyl-5-(2-(trifluoromethyl)isonicotinamido)phenyl)-1,2,4,4a,5,6-hexahydro-[1,4]oxazino[4,3-a]quinoline-5-carboxamide

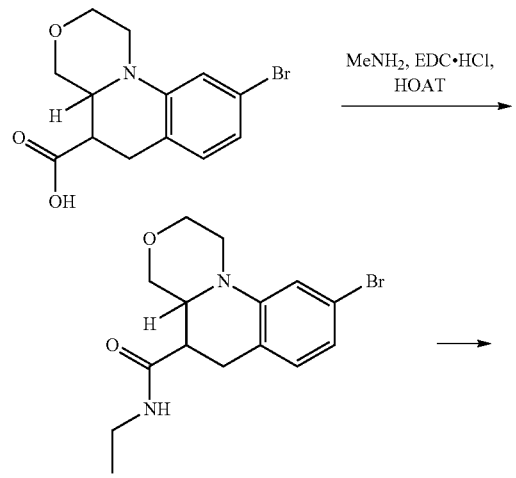

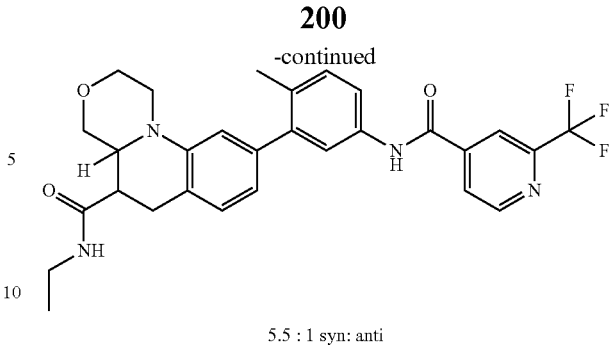

5.5 : 1 syn: anti

Step 1:

Into a Vial were charged 9-bromo-1,2,4,4a,5,6-hexahydro-[1,4]oxazino[4,3-a]quinoline-5-carboxylic acid (1.0 equiv.), EDC.HCl (1.2 equiv.), HOAT (1.2 equiv.), and DMF (0.3 M). To the mixture was added DIEA (2.5 equiv.) followed by ethylamine (in THF) (1.2 equiv.) and the mixture agitated at room temperature overnight. The next morning, the reaction mixture was diluted with EtOAc and washed with water and then with sat'd Na₂CO₃ and dried (MgSO₄), filtered and concentrated in vacuo and the residue 9-bromo-N-ethyl-1,2,4,4a,5,6-hexahydro-[1,4]oxazino[4,3-a]quinoline-5-carboxamide was obtained in quantitative yield and was taken to the next step as such. LCMS: (m/z) (M+H)=340.9, Rt=1.27 min.

Step 2:

Into a MW vial was added 9-bromo-N-ethyl-1,2,4,4a,5,6-hexahydro-[1,4]oxazino[4,3-a]quinoline-5-carboxamide (1.0 equiv.), N-(4-methyl-3-(4,4,5,5-tetramethyl-1,3,2-dioxaborolan-2-yl)phenyl)-2-(trifluoromethyl)isonicotinamide (1.0 equiv.), K₃PO₄ (2.0 equiv.), X-Phos G2 Pd-Cycle (0.1 equiv.) and then dioxane:DMF:Water (5:1:0.2) (0.1 M). The mixture was heated in MW at 120° C. for 20 min and then cooled to room temperature and the product extracted with EtOAc. The organic layer was dried (Na₂SO₄), filtered and concentrated in vacuo and the residue purified by reverse-phase HPLC to afford the desired product N-ethyl-9-(2-methyl-5-(2-(trifluoromethyl)isonicotinamido)phenyl)-1,2,4,4a,5,6-hexahydro-[1,4]oxazino[4,3-a]quinoline-5-carboxamide as free-base in 33.3% isolated yield in 5.5:1 diastereomeric ratio. $^1$H NMR (400 MHz, DMSO-d6) δ 10.62 (s, 1H) 8.99 (d, J=5.01 Hz, 1H) 8.36 (s, 1H) 8.09-8.24 (m, 2H) 7.68 (dd, J=8.19, 2.32 Hz, 1H) 7.61 (d, J=2.32 Hz, 1H) 7.28 (d, J=8.44 Hz, 1H) 7.05 (d, J=7.58 Hz, 1H) 6.78 (d, J=1.10 Hz, 1H) 6.64 (dd, J=7.58, 1.34 Hz, 1H) 3.89 (dd, J=11.19, 2.75 Hz, 1H) 3.64-3.82 (m, 2H) 3.03-3.23 (m, 4H) 2.87-3.00 (m, 1H) 2.71-2.83 (m, 2H) 2.38-2.47 (m, 1H) 2.22 (s, 3H) 1.05 (t, J=7.21 Hz, 3H) LCMS: (m/z) (M+H)=539.2, Rt=1.38 min.

The following compounds were prepared using methods from the above examples, using appropriate starting materials:

| Ex. No. | Structure | Name | Physical Data |
|---|---|---|---|
| 74 | (structure shown; syn:anti = 5.5:1) | (rac)-9-(5-(2-(1,1-difluoroethyl)isonicotinamido)-2-methylphenyl)-N-ethyl-1,2,4,4a,5,6-hexahydro-[1,4]oxazino[4,3-a]quinoline-5-carboxamide | $^1$H NMR (400 MHz, DMSO-d6) δ ppm 10.58 (s, 1 H) 8.87 (d, J = 5.01 Hz, 1 H) 8.08-8.22 (m, 2 H) 8.02 (d, J = 5.01 Hz, 1 H) 7.58-7.73 (m, 2 H) 7.27 (d, J = 8.44 Hz, 1 H) 6.96-7.08 (m, 1 H) 6.78 (d, J = 0.98 Hz, 1 H) 6.57-6.66 (m, 1 H) 3.68-4.00 (m, 3 H) 3.43-3.60 (m, 1 H) 3.03-3.26 (m, 4 H) 2.86-3.00 (m, 1 H) 2.69-2.84 (m, 3 H) 2.38-2.46 (m, 1 H) 2.22 (s, 3 H) 2.05 (t, J = 19.13 Hz, 3 H) 1.05 (t, J = 7.27 Hz, 3 H); LCMS (m/z) (M + H) = 535.2, Rt = 1.35 min |

| Ex. No. | Structure | Name | Physical Data |
|---|---|---|---|
| 75 | syn:anti = 5.5:1 | (rac)-N-ethyl-9-(2-methyl-5-(3-(trifluoromethyl)benzamido)pyridin-3-yl)-1,2,4,4a,5,6-hexahydro-[1,4]oxazino[4,3-a]quinoline-5-carboxamide | $^1$H NMR (400 MHz, DMSO-d6) δ ppm 10.62 (s, 1 H) 8.82 (d, J = 2.45 Hz, 1 H) 8.26 -8.37 (m, 2 H) 8.15 (t, J = 5.50 Hz, 1 H) 7.96-8.06 (m, 2 H) 7.81 (t, J = 7.82 Hz, 1 H) 7.04-7.12 (m, 1 H) 6.81-6.88 (m, 1 H) 6.64-6.75 (m, 1 H) 3.64-3.98 (m, 3 H) 3.40-3.61 (m, 2 H) 2.90-3.24 (m, 4 H) 2.71-2.88 (m, 2 H) 2.36-2.46 (m, 4 H) 0.95-1.16 (m, 3 H) LCMS (m/z) (M + H) = 539.2, Rt = 1.29 min. |

Examples 76 and 77

9-(5-(2-(1,1-difluoroethyl)isonicotinamido)-2-methylphenyl)-N-ethyl-1,2,4,4a,5,6-hexahydro-[1,4]oxazino[4,3-a]quinoline-5-carboxamide

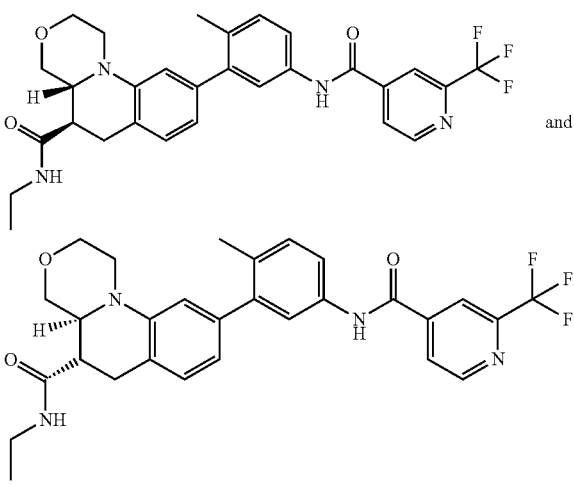

Chiral SFC 9-(5-(2-(1,1-difluoroethyl)isonicotinamido)-2-methylphenyl)-N-ethyl-1,2,4,4a,5,6-hexahydro-[1,4]oxazino[4,3-a]quinoline-5-carboxamide afforded separation of all 4 compounds but only the two major enantiomers were taken towards characterization and analysis. The first eluting peak methyl (4aR,5R)—N-ethyl-9-(2-methyl-5-(2-(trifluoromethyl)isonicotinamido)phenyl)-1,2,4,4a,5,6-hexahydro-[1,4]oxazino[4,3-a]quinoline-5-carboxamide; $^1$H NMR (400 MHz, DMSO-d6) δ 10.58 (s, 1H) 8.87 (d, J=5.01 Hz, 1H) 8.10-8.21 (m, 2H) 8.02 (d, J=4.89 Hz, 1H) 7.59-7.74 (m, 2H) 7.27 (d, J=8.31 Hz, 1H) 7.05 (d, J=7.58 Hz, 1H) 6.78 (d, J=0.73 Hz, 1H) 6.64 (dd, J=7.58, 1.22 Hz, 1H) 3.89 (dd, J=11.13, 2.57 Hz, 1H) 3.69-3.82 (m, 2H) 3.53 (td, J=11.58, 2.38 Hz, 1H) 3.03-3.24 (m, 4H) 2.87-3.01 (m, 1H) 2.70-2.82 (m, 2H) 2.44 (ddd, J=12.01, 9.81, 5.07 Hz, 1H) 2.22 (s, 3H) 2.05 (t, J=19.13 Hz, 3H) 1.05 (t, J=7.21 Hz, 3H); LCMS: (m/z) (M+H)=535.1, Rt=2.39 min (SQ4); and the second eluting peak afforded (4aS,5S)—N-ethyl-9-(2-methyl-5-(2-(trifluoromethyl)isonicotinamido)phenyl)-1,2,4,4a,5,6-hexahydro-[1,4]oxazino[4,3-a]quinoline-5-carboxamide; $^1$H NMR (400 MHz, DMSO-d6) δ ppm 10.58 (s, 1H) 8.87 (d, J=5.01 Hz, 1H) 8.10-8.21 (m, 2H) 8.02 (d, J=4.89 Hz, 1H) 7.59-7.74 (m, 2H) 7.27 (d, J=8.31 Hz, 1H) 7.05 (d, J=7.58 Hz, 1H) 6.78 (d, J=0.73 Hz, 1H) 6.64 (dd, J=7.58, 1.22 Hz, 1H) 3.89 (dd, J=11.13, 2.57 Hz, 1H) 3.69-3.82 (m, 2H) 3.53 (td, J=11.58, 2.38 Hz, 1H) 3.03-3.24 (m, 4H) 2.87-3.01 (m, 1H) 2.70-2.82 (m, 2H) 2.44 (ddd, J=12.01, 9.81, 5.07 Hz, 1H) 2.22 (s, 3H) 2.05 (t, J=19.13 Hz, 3H) 1.05 (t, J=7.21 Hz, 3H); LCMS: (m/z) (M+H)=535.1, Rt=2.39 min (SQ4).

Example 78

(rac)-2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide

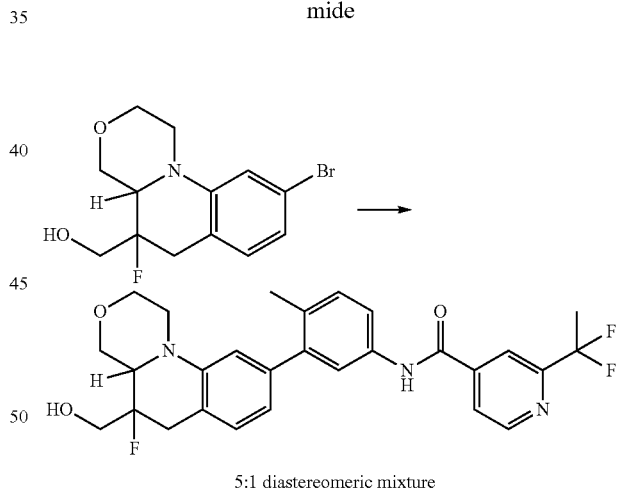

5:1 diastereomeric mixture

Step 1:

(9-bromo-5-fluoro-1,2,4,4a,5,6-hexahydro-[1,4]oxazino[4,3-a]quinolin-5-yl)methanol (111 mg, 0.35 mmol), PdCl$_2$(dppf).CH$_2$Cl$_2$ adduct (28.6 mg, 0.035 mmol), 2-(1,1-difluoroethyl)-N-(4-methyl-3-(4,4,5,5-tetramethyl-1,3,2-dioxaborolan-2-yl)phenyl)isonicotinamide (1.0 equiv.) were combined in Dioxane (0.1 M) and then 2.0 M Na$_2$CO$_3$ (2.0 equiv.) was added. The mixture was heated in heated in a heating block at 105° C. for 2 h. After the elapsed time, LCMS indicated formation of desired product. The reaction mixture was cooled to rt and then extracted with EtOAc. The combined organic layer was dried (MgSO$_4$), filtered and concentrated in vacuo. The residue was purified by flash chromatography (0-100% EtOAc/heptane) to afford the desired product. LCMS: (m/z) (M+H)=512.3, Rt=2.35 min (SQ4). ¹H NMR (400 MHz, DMSO-d6) δ ppm 10.58 (s, 1H) 8.87 (dd, J=5.07, 0.67 Hz, 1H) 8.17 (s, 1H) 8.02 (dd, J=4.95, 1.41 Hz, 1H) 7.68 (dd, J=8.25, 2.26 Hz, 1H) 7.57-7.65 (m, 1H) 7.28 (d, J=8.44 Hz, 1H) 7.03-7.14 (m, 1H) 6.76-6.84 (m, 1H) 6.59-6.71 (m, 1H) 5.28 (br s, 1H) 3.75-4.13 (m, 3H) 3.43-3.69 (m, 4H) 2.77-3.39 (m, 8H) 2.23 (s, 3H) 1.94-2.13 (m, 3H).

The following compound of Example 79 was prepared using methods from the above examples, using appropriate starting materials:

Rt=2.33 min (SQ8); the third eluting peak afforded 2-(1,1-difluoroethyl)-N-(3-((4aR,5R)-5-fluoro-5-(hydroxymethyl)-1,2,4,4a,5,6-hexahydro-[1,4]oxazino[4,3-a]quinolin-9-yl)-4-methylphenyl)isonicotinamide; ¹H NMR (400 MHz, DMSO-d6) δ (pm) 10.58 (s, 1H) 8.87 (d, J=4.89 Hz, 1H) 8.18 (s, 1H) 8.03 (br d, J=4.77 Hz, 1H) 7.49-7.80 (m, 2H) 7.28 (d, J=8.31 Hz, 1H) 7.09 (d, J=7.58 Hz, 1H) 6.57-6.88 (m, 2H) 5.29 (br t, J=5.56 Hz, 1H) 4.03 (br dd, J=10.94, 2.38 Hz, 1H) 3.73-3.91 (m, 2H) 3.41-3.65 (m, 4H) 2.99-3.29 (m, 2H) 2.73-2.94 (m, 2H) 2.23 (s, 3H) 2.05 (t, J=19.07 Hz, 3H); LCMS: (m/z) (M+H)=512.3, Rt=2.33 min (SQ8).

| | | |
|---|---|---|
| 79 | 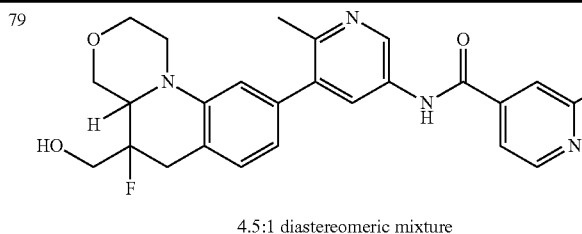<br>4.5:1 diastereomeric mixture | (rac)-2-(1,1-difluoroethyl)-N-(5-(5-fluoro-5-(hydroxymethyl)-1,2,4,4a,5,6-hexahydro-[1,4]oxazino[4,3-a]quinolin-9-yl)-6-methylpyridin-3-yl)isonicotinamide | ¹H NMR (400 MHz, DMSO-d6) δ ppm 10.80 (s, 1 H) 8.90 (dd, J = 5.01, 0.61 Hz, 1 H) 8.83 (d, J = 2.45 Hz, 1H) 8.20 (s, 1 H) 7.99-8.06 (m, 2 H) 7.04-7.21 (m, 1 H) 6.83-6.90 (m, 1 H) 6.64-6.78 (m, 1 H) 5.08-5.43 (m, 1 H) 4.03 (dd, J = 11.19, 3.00 Hz, 1 H) 3.75-3.97 (m, 2 H) 3.40-3.69 (m, 5 H) 2.76-3.39 (m, 10 H) 2.44 (s, 3 H) 1.88-2.13 (m, 3 H); LCMS (m/z) (M + H) = 513.2, Rt = 1.16 min. |

Examples 80 and 81

2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide

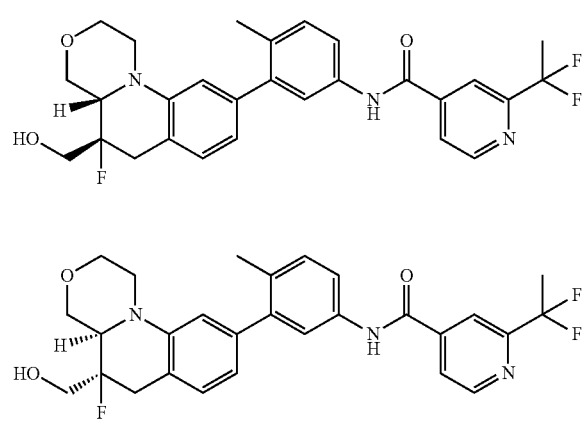

Chiral SFC of 2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide afforded separation of all 4 compounds. The first eluting peak methyl 2-(1,1-difluoroethyl)-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)isonicotinamide; ¹H NMR (400 MHz, DMSO-d6) δ (ppm) 10.58 (s, 1H) 8.87 (d, J=5.01 Hz, 1H) 8.18 (s, 1H) 8.03 (br d, J=4.65 Hz, 1H) 7.56-7.73 (m, 2H) 7.28 (d, J=8.31 Hz, 1H) 7.09 (d, J=7.58 Hz, 1H) 6.78 (s, 1H) 6.70 (d, J=7.58 Hz, 1H) 5.29 (t, J=5.75 Hz, 1H) 4.03 (dd, J=11.19, 2.75 Hz, 1H) 3.73-3.92 (m, 2H) 3.43-3.64 (m, 4H) 3.01-3.29 (m, 2H) 2.73-2.92 (m, 2H) 2.23 (s, 3H) 2.05 (t, J=19.07 Hz, 3H); LCMS: (m/z) (M+H)=512.3, Examples 82 and 83

2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide

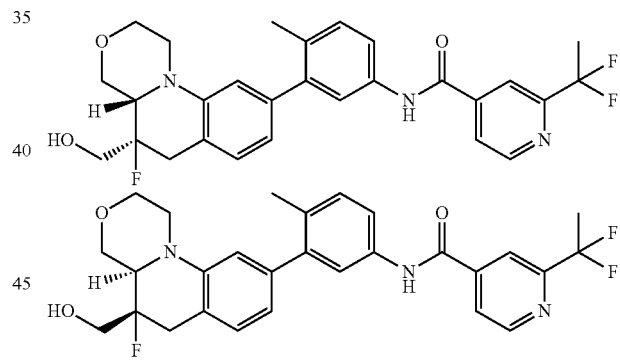

Chiral SFC of 2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide afforded the second peak as 2-(1,1-difluoroethyl)-N-(3-((4aS,5R)-5-fluoro-5-(hydroxymethyl)-1,2,4,4a,5,6-hexahydro-[1,4]oxazino[4,3-a]quinolin-9-yl)-4-methylphenyl)isonicotinamide. ¹H NMR (400 MHz, DMSO-d6) δ (ppm) 10.58 (s, 1H) 8.87 (d, J=5.50 Hz, 1H) 8.17 (s, 1H) 8.02 (d, J=4.89 Hz, 1H) 7.59-7.77 (m, 2H) 7.28 (d, J=8.44 Hz, 1H) 7.07 (d, J=7.70 Hz, 1H) 6.80 (d, J=1.10 Hz, 1H) 6.66 (dd, J=7.52, 1.41 Hz, 1H) 5.19 (t, J=5.75 Hz, 1H) 3.74-3.95 (m, 3H) 3.37-3.71 (m, 5H) 2.78-3.11 (m, 3H) 2.23 (s, 3H) 2.05 (t, J=19.13 Hz, 3H); LCMS: (m/z) (M+H)=512.3, Rt=2.34 min (SQ8) and the fourth eluting fraction afforded 2-(1,1-difluoroethyl)-N-(3-((4aR,5S)-5-fluoro-5-(hydroxymethyl)-1,2,4,4a,5,6-hexahydro-[1,4]oxazino[4,3-a]quinolin-9-yl)-4- methylphenyl)isonicotinamide. ¹H NMR (400 MHz, DMSO-d6) δ (ppm) 10.58 (s, 1H) 8.87 (br d, J=4.89 Hz, 1H) 8.17 (s, 1H) 8.02 (br d, J=4.52 Hz, 1H) 7.49-7.73 (m, 2H) 7.28 (br d, J=8.19 Hz, 1H) 7.07 (br d, J=7.58 Hz, 1H) 6.80 (s, 1H) 6.66 (br d, J=7.46 Hz, 1H) 5.19 (br t, J=5.44 Hz, 1H) 3.78-4.04 (m, 3H) 3.39-3.76 (m, 6H) 2.77-3.15 (m, 3H) 2.23 (s, 3H) 2.05 (br t, J=19.13 Hz, 3H);); LCMS: (m/z) (M+H)=512.3, Rt=2.34 min (SQ8).

Examples 84 and 85

2-(1,1-difluoroethyl)-N-(5-(5-fluoro-5-(hydroxymethyl)-1,2,4,4a,5,6-hexahydro-[1,4]oxazino[4,3-a]quinolin-9-yl)-6-methylpyridin-3-yl)isonicotinamide

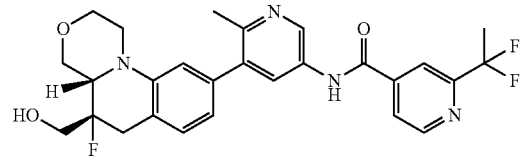

and

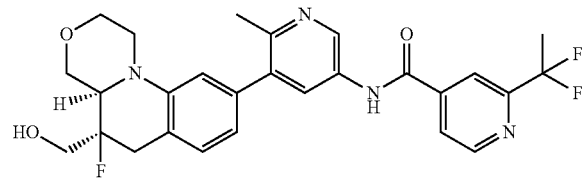

Chiral SFC 2-(1,1-difluoroethyl)-N-(5-(5-fluoro-5-(hydroxymethyl)-1,2,4,4a,5,6-hexahydro-[1,4]oxazino[4,3-a]quinolin-9-yl)-6-methylpyridin-3-yl)isonicotinamide afforded separation of all 4 compounds but only the major enantiomeric pair was taken towards characterization. The first eluting peak 2-(1,1-difluoroethyl)-N-(5-((4aS,5S)-5-fluoro-5-(hydroxymethyl)-1,2,4,4a,5,6-hexahydro-[1,4]oxazino[4,3-a]quinolin-9-yl)-6-methylpyridin-3-yl)isonicotinamide. ¹H NMR (400 MHz, DMSO-d6) δ (ppm) 10.80 (s, 1H) 8.90 (d, J=5.01 Hz, 1H) 8.83 (d, J=2.32 Hz, 1H) 8.20 (s, 1H) 7.86-8.10 (m, 2H) 7.13 (d, J=7.58 Hz, 1H) 6.86 (s, 1H) 6.75 (d, J=7.58 Hz, 1H) 5.75 (s, 1H) 5.30 (t, J=5.75 Hz, 1H) 4.03 (dd, J=11.13, 2.69 Hz, 1H) 3.78-3.93 (m, 2H) 3.41-3.63 (m, 4H) 2.99-3.30 (m, 2H) 2.78-2.95 (m, 2H) 2.44 (s, 3H) 2.06 (t, J=19.13 Hz, 3H); LCMS: (m/z) (M+H)=513.2, Rt=1.45 min (SQ8); the second eluting peak afforded 2-(1,1-difluoroethyl)-N-(5-((4aR,5R)-5-fluoro-5-(hydroxymethyl)-1,2,4,4a,5,6-hexahydro-[1,4]oxazino[4,3-a]quinolin-9-yl)-6-methylpyridin-3-yl)isonicotinamide; ¹H NMR (400 MHz, DMSO-d6) δ (pm) 10.58 (s, 1H) 8.87 (d, J=4.89 Hz, 1H) 8.18 (s, 1H) 8.03 (br d, J=4.77 Hz, 1H) 7.49-7.80 (m, 2H) 7.28 (d, J=8.31 Hz, 1H) 7.09 (d, J=7.58 Hz, 1H) 6.57-6.88 (m, 2H) 5.29 (br t, J=5.56 Hz, 1H) 4.03 (br dd, J=10.94, 2.38 Hz, 1H) 3.73-3.91 (m, 2H) 3.41-3.65 (m, 4H) 2.99-3.29 (m, 2H) 2.73-2.94 (m, 2H) 2.23 (s, 3H) 2.05 (t, J=19.07 Hz, 3H); LCMS: (m/z) (M+H)=512.3, Rt=2.33 min (SQ8).

Example 86

(rac)-N-(5-(5-cyano-5-methyl-1,2,4,4a,5,6-hexahydro-[1,4]oxazino[4,3-a]quinolin-9-yl)-6-methylpyridin-3-yl)-2-(1,1-difluoroethyl)isonicotinamide

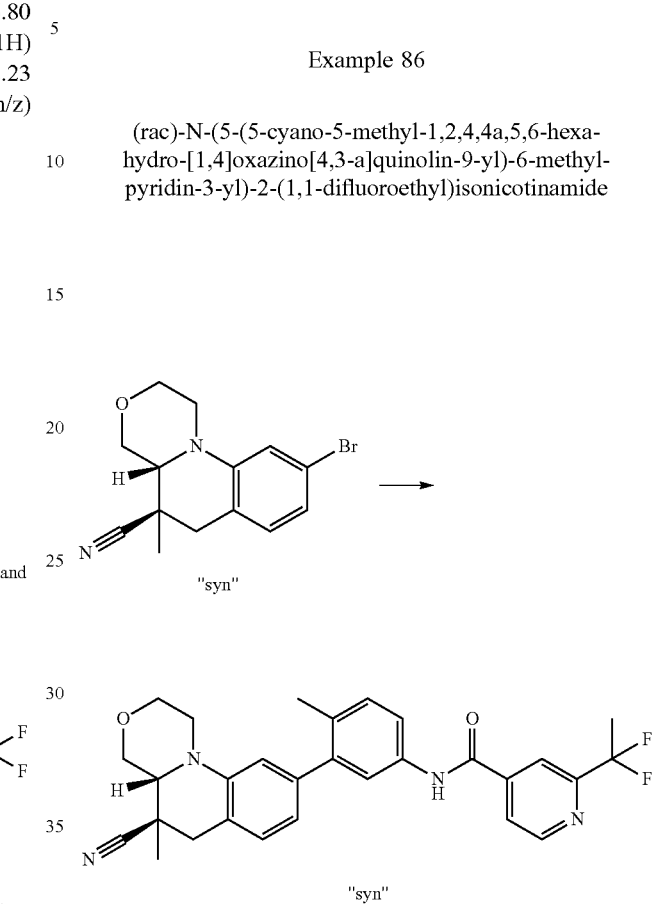

Into a vial were charged 9-bromo-5-methyl-1,2,4,4a,5,6-hexahydro-[1,4]oxazino[4,3-a]quinoline-5-carbonitrile (1.0 equiv.), 2-(1,1-difluoroethyl)-N-(4-methyl-3-(4,4,5,5-tetramethyl-1,3,2-dioxaborolan-2-yl)phenyl)isonicotinamide (1.0 equiv.), PdCl₂(dppf).CH₂Cl₂ adduct (0.1 equiv.), Dioxane (0.1 M) and then 2M Na₂CO₃ (3.0 equiv.). The mixture was agitated at 100° C. in a heating block for 1 h and then the product was extracted with EtOAc. The organic layer was dried (Na₂SO₄), filtered and concentrated in vacuo. The residue was purified by flash chromatography (0-100% EtOAc/heptane) to afford the desired product as free base. LCMS: (m/z) (M+H)=503.2, Rt=1.47 min. ¹H NMR (400 MHz, DMSO-d6) δ (ppm) 10.57 (s, 1H) 8.87 (dd, J=5.01, 0.73 Hz, 1H) 8.18 (d, J=0.73 Hz, 1H) 8.03 (dd, J=5.01, 1.47 Hz, 1H) 7.71 (dd, J=8.25, 2.26 Hz, 1H) 7.64 (d, J=2.20 Hz, 1H) 7.29 (d, J=8.44 Hz, 1H) 7.08 (d, J=7.70 Hz, 1H) 6.89 (d, J=1.10 Hz, 1H) 6.74 (dd, J=7.64, 1.41 Hz, 1H) 4.19 (dd, J=11.31, 3.12 Hz, 1H) 3.81-4.03 (m, 2H) 3.58 (td, J=11.77, 2.63 Hz, 1H) 3.36-3.44 (m, 1H) 2.97-3.14 (m, 3H) 2.77 (td, J=12.10, 3.67 Hz, 1H) 2.24 (s, 3H) 2.05 (t, J=19.13 Hz, 3H) 1.43 (s, 3H).

The following compounds were prepared using methods from the above examples, using appropriate starting materials:

| Ex. No. | Structure | Name | Physical Data |
|---|---|---|---|
| 87 | "syn" | (rac)-N-(5-(5-cyano-5-methyl-1,2,4,4a,5,6-hexahydro-[1,4]oxazino[4,3-a]quinolin-9-yl)-6-methylpyridin-3-yl)-2-(1,1-difluoroethyl)isonicotinamide | $^1$H NMR (400 MHz, DMSO-d6) δ ppm 10.79 (s, 1 H) 8.90 (dd, J = 5.07, 0.67 Hz, 1 H) 8.84 (d, J = 2.45 Hz, 1 H) 8.21 (dd, J = 1.47, 0.86 Hz, 1 H) 7.91-8.09 (m, 2 H) 7.12 (d, J = 7.58 Hz, 1 H) 6.97 (d, J = 1.34 Hz, 1 H) 6.79 (dd, J = 7.70, 1.47 Hz, 1 H) 4.20 (dd, J = 11.25, 3.18 Hz, 1 H) 3.84-4.03 (m, 2H) 3.58 (td, J = 11.77, 2.63 Hz, 1 H) 3.39 (t, J = 10.94 Hz, 1 H) 2.95-3.17 (m, 3 H) 2.79 (td, J = 12.07, 3.61 Hz, 1 H) 2.44 (s, 3 H) 1.96-2.12 (m, 3 H) 1.44 (s, 3 H) LCMS (m/z) (M + H) = 504.1, Rt = 1.29 min |
| 88 | "anti" | (rac)-N-(3-(5-cyano-5-methyl-1,2,4,4a,5,6-hexahydro-[1,4]oxazino[4,3-a]quinolin-9-yl)-4-methylphenyl)-2-(1,1-difluoroethyl)isonictinamide | $^1$H NMR (400 MHz, DMSO-d6) δ ppm 10.51-10.65 (m, 1 H) 8.87 (dd, J = 5.07, 0.67 Hz, 1 H) 8.18 (d, J = 0.61 Hz, 1 H) 8.02 (dd, J = 5.07, 1.53 Hz, 1H) 7.69 (dd, J = 8.25, 2.26 Hz, 1 H) 7.63 (d, J = 2.32 Hz, 1 H) 7.28 (d, J = 8.44 Hz, 1 H) 7.08 (d, J = 7.70 Hz, 1 H) 6.89 (d, J = 1.34 Hz, 1 H) 6.72 (dd, J = 7.58, 1.47 Hz, 1 H) 3.84-4.08 (m, 3 H) 3.34-3.64 (m, H) 2.81-3.00 (m, 2 H) 2.22 (s, 3 H) 2.05 (t, J = 19.13 Hz, 3 H) 1.35 (s, 3 H); LCMS (m/z) (M + H) = 503.1, Rt = 1.52 min. |
| 89 | "anti" | (rac)-N-(5-(5-cyano-5-methyl-1,2,4,4a,5,6-hexahydro-[1,4]oxazino[4,3-a]quinolin-9-yl)-6-methylpyridin-3-yl)-2-(1,1-difluoroethyl)isonicotinamide | $^1$H NMR (400 MHz, DMSO-d6) δ ppm 10.99 (s, 1 H) 8.85-9.01 (m, 2 H) 8.16-8.26 (m, 2 H) 8.05 (dd, J = 5.07, 1.53 Hz, 1 H) 7.15 (d, J = 7.70 Hz, 1H) 7.02 (d, J = 1.34 Hz, 1 H) 6.82 (dd, J = 7.64, 1.41 Hz, 1 H) 3.84-4.03 (m, 9 H) 3.31-3.58 (m, 5 H) 2.82-3.04 (m, 2 H) 2.06 (t, J = 19.20 Hz, 3 H)1.36 (s, 3 H); LCMS (m/z) (M + H) = 504.1, Rt = 1.33 min. |
| 90 | "syn" | (rac)-N-(3-(5-cyano-1,2,4,4a,5,6-hexahydro-[1,4]oxazino[4,3-a]quinolin-9-yl)-4-methylphenyl)-2-(1,1-difluoroethyl)isonicotinamid | LCMS: (m/z) (M + H) = 489.1, Rt = 1.47 min. $^1$H NMR (400 MHz, DMSO-d6) δ (ppm) 10.58 (s, 1 H) 8.87 (dd, J = 5.01, 0.61 Hz, 1 H) 8.17 (d, J = 0.73 Hz, 1 H) 8.02 (dd, J = 5.01, 1.47 Hz, 1 H) 7.69 (dd, J = 8.19, 2.20 Hz, 1 H) 7.62 (d, J = 2.32 Hz, 1 H) 7.28 (d, J = 8.44 Hz, 1 H) 7.11 (d, J = 7.70 Hz, 1 H) 6.83 (d, J = 1.22 Hz, 1 H) 6.72 (dd, J = 7.58, 1.47 Hz, 1 H) 3.98-4.10 (m, 1 H) 3.92 (dd, J = 11.25, 2.81 Hz, 1 H) 3.76 (br d, J = 11.98 Hz, 1 H) 3.57 (td, J = 11.55, 2.69 Hz, 1 H) 3.36-3.50 (m, 1H) 3.23-3.31 (m, 2 H) 3.05-3.20 (m, 2 H) 2.82 (td, J = 11.98, 3.55 Hz, 1 H) 2.21 (s, 3 H) 2.05 (t, J = 19.13 Hz, 3 H). |
| 91 | "syn" | (rac)-N-(5-(5-cyano-1,2,4,4a,5,6-hexahydro-[1,4]oxazino[4,3-a]quinolin-9-yl)-6-methylpyridin-3-yl)-2-(1,1-difluoroethyl)isonicotinamide | 1H NMR (400 MHz, DMSO-d6) δ ppm 11.02 (s, 1 H) 8.88-9.03 (m, 2 H) 8.15-8.31 (m, 2 H) 8.05 (dd, J = 5.07, 1.53 Hz, 1 H) 7.18 (d, J = 7.70 Hz, 1H) 6.96 (d, J = 1.34 Hz, 1 H) 6.82 (dd, J = 7.58, 1.47 Hz, 1 H) 4.02 (dd, J = 10.94, 2.02 Hz, 1 H) 3.94 (br dd, J = 11.31, 2.87 Hz, 1 H) 3.78 (br d, J = 12.10 Hz, 1 H) 3.57 (td, J = 11.55, 2.69 Hz, 1 H) 3.39-3.46 (m, 1 H) 3.24-3.37 (m, 2 H) 3.09-3.21 (m, 2 H) 2.85 (td, J = 12.04, 3.55 Hz, 1 H) 2.06 (t, J = 19.20 Hz, 3 H); LCMS (m/z) (M + H) = 490.5, Rt = 1.31 min. |

Examples 92 and 93

N-(3-(5-amino-5-methyl-1,2,4,4a,5,6-hexahydro-[1,4]oxazino[4,3-a]quinolin-9-yl)-4-methylphenyl)-2-(1,1-difluoroethyl)isonicotinamide

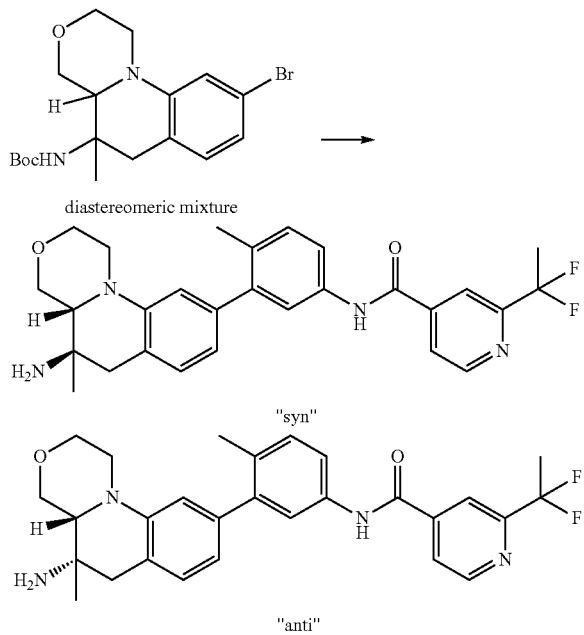

Into a MW vial was charged PdCl₂(dppf).CH₂Cl₂ adduct (0.1 equiv.), 2-(1,1-difluoroethyl)-N-(4-methyl-3-(4,4,5,5-tetramethyl-1,3,2-dioxaborolan-2-yl)phenyl)isonicotinamide (1.0 equiv.), tert-butyl (9-bromo-5-methyl-1,2,4,4a,5,6-hexahydro-[1,4]oxazino[4,3-a]quinolin-5-yl)carbamate (1.0 equiv.) and then dioxane (0.2 M) and then 2.0 M Na₂CO₃ (2.5 equiv.) was added. The mixture was agitated in MW at 120° C. for 30 min and then diluted with EtOAc. The organic layer was separated and dried and treated with MeOH (0.1 M) and 4 N HCl in dioxane (40.0 equiv.) and agitated at room temperature for 4 h and concentrated in vacuo. The residue was dissolved in DMSO and purified by reverse phase HPLC (during which separation of the two diastereomers was observed) and then by acidic method to afford the desired product as TFA adduct.

(rac)-(syn)-N-(3-(5-amino-5-methyl-1,2,4,4a,5,6-hexahydro-[1,4]oxazino[4,3-a]quinolin-9-yl)-4-methylphenyl)-2-(1,1-difluoroethyl)isonicotinamide ((3.1% Isolated Yield)

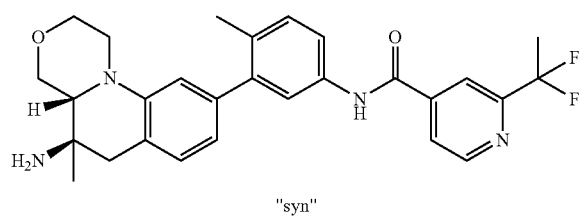 [SMILES: Cc1ccc(NC(=O)c2ccnc(C(C)(F)F)c2)cc1-c1ccc2c(c1)N1CCOC[C@H]1[C@](C)(N)C2]

LCMS: (m/z) (M+H)=493.1, Rt=1.65 min (SQ4). ¹H NMR (400 MHz, DMSO-d6) δ (ppm) 10.60 (s, 1H) 8.74-8.97 (m, 1H) 8.14 (br d, J=16.26 Hz, 4H) 8.02 (dd, J=5.01, 1.47 Hz, 1H) 7.57-7.82 (m, 2H) 7.29 (d, J=8.44 Hz, 1H) 7.12 (d, J=7.70 Hz, 1H) 6.94 (d, J=1.10 Hz, 1H) 6.74 (dd, J=7.58, 1.34 Hz, 1H) 3.75-4.11 (m, 3H) 3.49-3.60 (m, 2H) 2.79-3.06 (m, 3H) 2.23 (s, 3H) 2.05 (t, J=19.13 Hz, 3H) 1.29 (s, 3H).

(rac)-(anti)-N-(3-(5-amino-5-methyl-1,2,4,4a,5,6-hexahydro-[1,4]oxazino[4,3-a]quinolin-9-yl)-4-methylphenyl)-2-(1,1-difluoroethyl)isonicotinamide ((3.0% Isolated Yield)

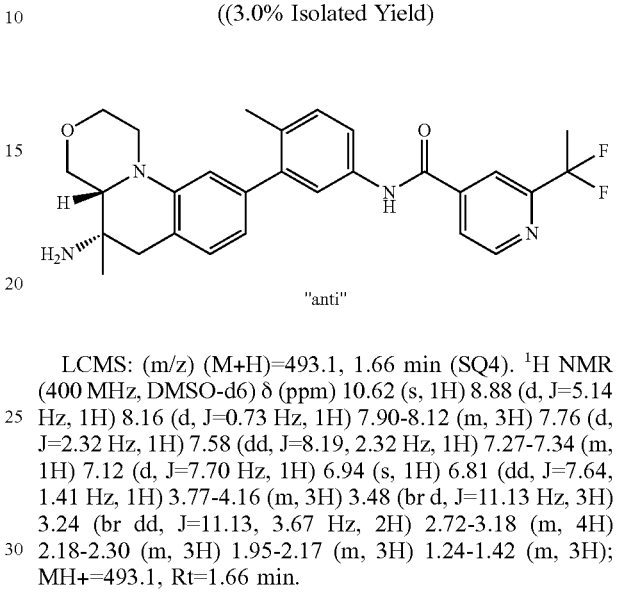

LCMS: (m/z) (M+H)=493.1, 1.66 min (SQ4). ¹H NMR (400 MHz, DMSO-d6) δ (ppm) 10.62 (s, 1H) 8.88 (d, J=5.14 Hz, 1H) 8.16 (d, J=0.73 Hz, 1H) 7.90-8.12 (m, 3H) 7.76 (d, J=2.32 Hz, 1H) 7.58 (dd, J=8.19, 2.32 Hz, 1H) 7.27-7.34 (m, 1H) 7.12 (d, J=7.70 Hz, 1H) 6.94 (s, 1H) 6.81 (dd, J=7.64, 1.41 Hz, 1H) 3.77-4.16 (m, 3H) 3.48 (br d, J=11.13 Hz, 3H) 3.24 (br dd, J=11.13, 3.67 Hz, 2H) 2.72-3.18 (m, 4H) 2.18-2.30 (m, 3H) 1.95-2.17 (m, 3H) 1.24-1.42 (m, 3H); MH+=493.1, Rt=1.66 min.

Example 94

(rac)-N-(4-methyl-3-(8-oxo-2,4,4a,5,6,8-hexahydro-1H-pyrido[2',1':2,3]pyrimido[6,1-c][1,4]oxazin-10-yl)phenyl)-2-(trifluoromethyl)isonicotinamide

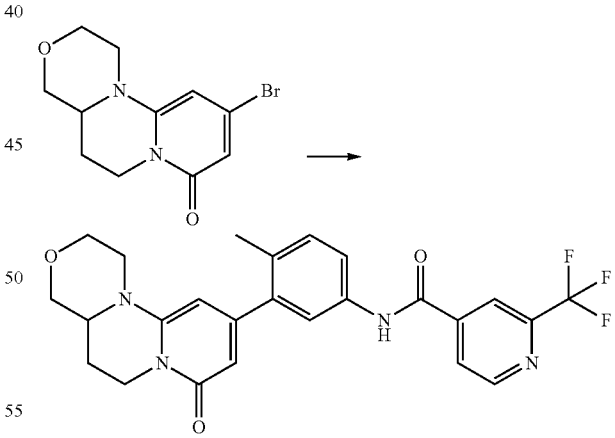

10-bromo-4,4a,5,6-tetrahydro-1H-pyrido[2',1':2,3]pyrimido[6,1-c][1,4]oxazin-8(2H)-one (1.0 equiv.), PdCl₂(dppf).CH₂Cl₂ adduct (0.1 equiv.), N-(4-methyl-3-(4,4,5,5-tetramethyl-1,3,2-dioxaborolan-2-yl)phenyl)-2-(trifluoromethyl)isonicotinamide (1.0 equiv.) were combined in Dioxane (0.1 M) and then 2.0 M Na₂CO₃ (2.5 equiv.) was added. The mixture was agitated in MW at 130° C. for 40 min and then the product extracted with EtOAc. The organic layer was passed through a plug of anhydrous Na₂SO₄, and the filtrate concentrated in vacuo and the residue was purified by reverse-phase HPLC to afford the desired product N-(4-methyl-3-(8-oxo-2,4,4a,5,6,8-hexahydro-1H-pyrido[2',1':2,3]pyrimido[6,1-c][1,4]oxazin-10-yl)phenyl)-2-(trifluoromethyl)isonicotinamide as a free-base. LCMS: (m/z) (M+H)=485.1, Rt=1.28 min. ¹H NMR (400 MHz, DMSO-d6) δ (ppm) 10.66 (s, 1H) 8.99 (d, J=5.01 Hz, 1H) 8.36 (s, 1H) 8.19 (dd, J=4.95, 1.16 Hz, 1H) 7.58-7.74 (m, 2H) 7.29 (d, J=8.19 Hz, 1H) 5.63 (d, J=1.59 Hz, 1H) 5.54 (d, J=1.47 Hz, 1H) 3.91-4.03 (m, 2H) 3.74-3.89 (m, 2H) 3.63 (br d, J=13.08 Hz, 1H) 3.53 (td, J=11.68, 2.69 Hz, 1H) 3.33-3.40 (m, 1H) 3.27 (d, J=10.76 Hz, 2H) 3.07 (td, J=12.35, 3.55 Hz, 1H) 2.27 (s, 3H) 1.96-2.12 (m, 1H) 1.55-1.70 (m, 1H).

The following compound was prepared using methods from the above examples, using appropriate starting materials

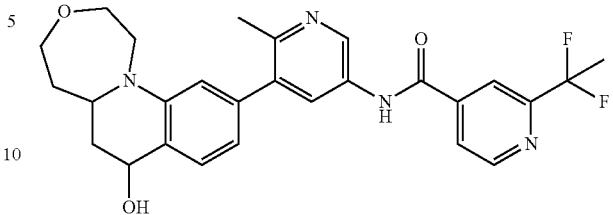

2-(1,1-difluoroethyl)isonicotinic acid (1 equiv.), 10-(5-amino-2-methylpyridin-3-yl)-1,2,5,5a,6,7-hexahydro-4H-

| 95 | 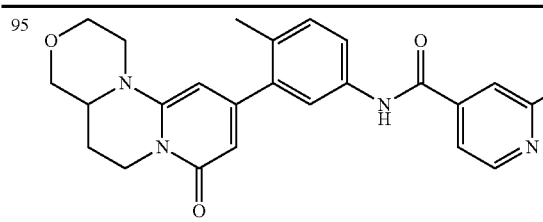 | (rac)-2-(1,1-difluoroethyl)-N-(4-methyl-3-(8-oxo-2,4,4a,5,6,8-hexahydro-1H-pyrido[2',1':2,3]pyrimido [6,1-c][1,4]oxazin-10-yl)phenyl) isonicotinamide | ¹H NMR (400 MHz, DMSO-d6) δ ppm 10.61 (s, 1 H) 8.88 (dd, J = 5.07, 0.67 Hz, 1 H) 8.17 (d, J = 0.61 Hz, 1 H) 8.02 (dd, J = 5.07, 1.53 Hz, 1 H) 7.63-7.73 (m, 2 H) 7.28 (d, J = 8.31 Hz, 1 H) 5.63 (d, J = 1.59 Hz, 1 H) 5.54 (d, J = 1.47 Hz, 1 H) 3.90-3.99 (m, 2 H) 3.76-3.88 (m, 2 H) 3.63 (br d, J = 12.96 Hz, 1 H) 3.53 (td, J = 11.68, 2.69 Hz, 1 H) 3.33-3.41 (m, 1 H) 3.22-3.31 (m, 2 H) 3.07 (td, J = 12.32, 3.48 Hz, 1 H) 2.26 (s, 3 H) 2.05 (t, J = 19.13 Hz, 3 H) 1.56-1.69 (m, 1 H).; LCMS (m/z) (M + H) = 485.1, Rt = 1.25 min. |

Example 96

(rac)-2-(1,1-difluoroethyl)-N-(5-(7-hydroxy-1,2,5,5a,6,7-hexahydro-4H-[1,4]oxazepino[4,5-a]quinolin-10-yl)-6-methylpyridin-3-yl)isonicotinamide

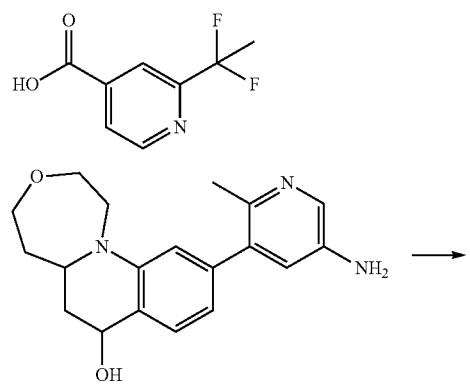

[1,4]oxazepino[4,5-a]quinolin-7-ol (1.0 equiv.), EDC.HCl (1.2 equiv.), HOAT (1.2 equiv.) in DMF (0.1 M) were stirred at inert atmosphere for 1 h. The reaction mixture was first purified by flash chromatography over silica gel (DCM with 10% MeOH) to give the >90% pure desired racemate and diastereomeric product 2-(1,1-difluoroethyl)-N-(5-(7-hydroxy-1,2,5,5a,6,7-hexahydro-4H-[1,4]oxazepino[4,5-a]quinolin-10-yl)-6-methylpyridin-3-yl)isonicotinamide (49%). ¹H NMR (400 MHz, Methanol-d4) δ 8.87-8.78 (m, 2H), 8.21 (s, 1H), 8.06 (d, J=2.5 Hz, 1H), 7.98 (dd, J=5.1, 1.5 Hz, 1H), 7.38 (dd, J=7.7, 0.7 Hz, 1H), 6.63 (dd, J=7.6, 1.5 Hz, 1H), 6.56 (d, J=1.3 Hz, 1H), 4.81-4.75 (m, 1H), 3.93-3.71 (m, 6H), 3.51-3.44 (m, 1H), 2.48 (s, 3H), 2.33-2.16 (m, 2H), 2.09-1.95 (m, 5H). LCMS (m/z) (M+H)=495.2, Rt=0.95 min.

The following compounds were prepared using methods from the above examples, using appropriate starting materials:

| 97 | 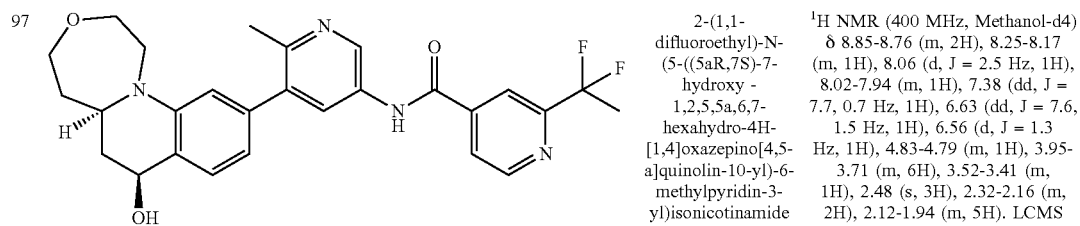 | 2-(1,1-difluoroethyl)-N-(5-((5aR,7S)-7-hydroxy-1,2,5,5a,6,7-hexahydro-4H-[1,4]oxazepino[4,5-a]quinolin-10-yl)-6-methylpyridin-3-yl)isonicotinamide | ¹H NMR (400 MHz, Methanol-d4) δ 8.85-8.76 (m, 2H), 8.25-8.17 (m, 1H), 8.06 (d, J = 2.5 Hz, 1H), 8.02-7.94 (m, 1H), 7.38 (dd, J = 7.7, 0.7 Hz, 1H), 6.63 (dd, J = 7.6, 1.5 Hz, 1H), 6.56 (d, J = 1.3 Hz, 1H), 4.83-4.79 (m, 1H), 3.95-3.71 (m, 6H), 3.52-3.41 (m, 1H), 2.48 (s, 3H), 2.32-2.16 (m, 2H), 2.12-1.94 (m, 5H). LCMS (m/z) (M + H) = 495.2, Rt = 0.95 |

| | | |
|---|---|---|
| 98 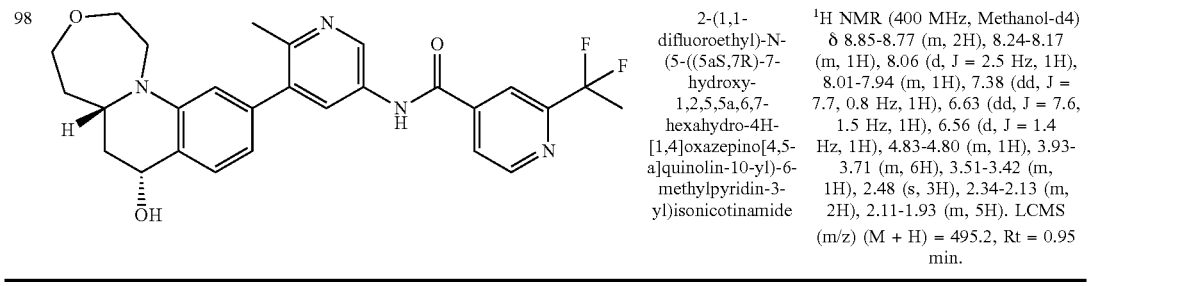 | 2-(1,1-difluoroethyl)-N-(5-((5aS,7R)-7-hydroxy-1,2,5,5a,6,7-hexahydro-4H-[1,4]oxazepino[4,5-a]quinolin-10-yl)-6-methylpyridin-3-yl)isonicotinamide | ¹H NMR (400 MHz, Methanol-d4) δ 8.85-8.77 (m, 2H), 8.24-8.17 (m, 1H), 8.06 (d, J = 2.5 Hz, 1H), 8.01-7.94 (m, 1H), 7.38 (dd, J = 7.7, 0.8 Hz, 1H), 6.63 (dd, J = 7.6, 1.5 Hz, 1H), 6.56 (d, J = 1.4 Hz, 1H), 4.83-4.80 (m, 1H), 3.93-3.71 (m, 6H), 3.51-3.42 (m, 1H), 2.48 (s, 3H), 2.34-2.13 (m, 2H), 2.11-1.93 (m, 5H). LCMS (m/z) (M + H) = 495.2, Rt = 0.95 min. |

Example 99

(rac)-(cis)2-(1,1-difluoroethyl)-N-(5-(7-hydroxy-1,2,5,5a,6,7-hexahydro-4H-[1,4]oxazepino[4,5-a]quinolin-10-yl)-6-methylpyridin-3-yl)isonicotinamide

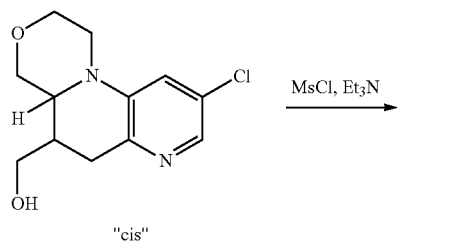

"cis"

MsCl, Et₃N →

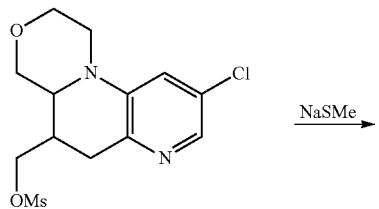

NaSMe →

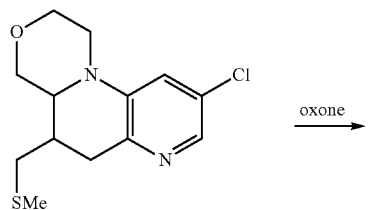

oxone →

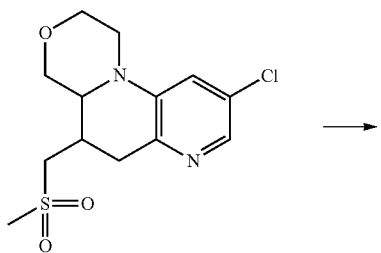

→

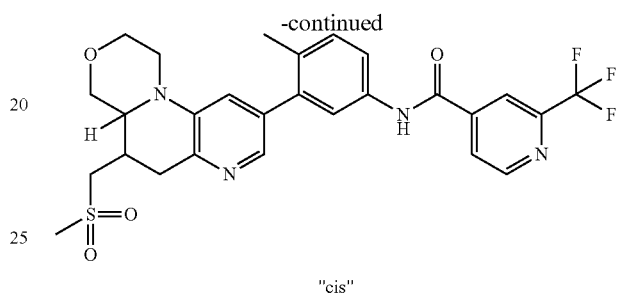

"cis"

Step 1:

Into a vial were charged (9-bromo-1,2,4,4a,5,6-hexahydro-[1,4]oxazino[4,3-a]quinolin-5-yl)methanol (1.0 equiv.) and DCM. The mixture was cooled to 0° C. and Et₃N (3.0 equiv.) was added. To the mixture was then added MsCl (1.1 equiv.) and the mixture agitated for 30 min and then quenched by addition of water and Sat'd NH₄Cl. The product was extracted with DCM. The organic layer was separated and dried (MgSO₄), filtered and concentrated in vacuo to afford the crude product (9-chloro-1,2,4,4a,5,6-hexahydro-[1,4]oxazino[4,3-a][1,5]naphthyridin-5-yl)methyl methanesulfonate in quantitative yield. LCMS (m/z) (M+H)=333.2, Rt=0.86 min.

Step 2:

(9-chloro-1,2,4,4a,5,6-hexahydro-[1,4]oxazino[4,3-a][1,5]naphthyridin-5-yl)methyl methanesulfonate (1.0 equiv.) was dissolved in DMF (0.1 M) and treated with NaSMe (1.5 equiv.). The mixture was agitated at room temperature for 30 min after which the mixture was quenched with sat'd NaHCO₃ and water and the product extracted with EtOAc. The organic layer was dried (MgSO₄), filtered and concentrated in vacuo to afford the crude product 9-chloro-5-((methylthio)methyl)-1,2,4,4a,5,6-hexahydro-[1,4]oxazino[4,3-a][1,5]naphthyridine, which was taken to the next step as such. LCMS (m/z) (M+H)=285.2, Rt=0.95 min.

Step 3:

9-chloro-5-((methylthio)methyl)-1,2,4,4a,5,6-hexahydro-[1,4]oxazino[4,3-a][1,5]naphthyridine (1.0 equiv.) was dissolved in DMF (0.2 M) and treated with oxone (2.5 equiv.). The mixture was agitated at room temperature for 45 min upon which LCMS indicated complete formation of desired product. The mixture was diluted with EtOAc and filtered through celite. The filtrate was washed with water twice and then dried (MgSO₄), filtered and concentrated in vacuo. The residue 9-chloro-5-((methylsulfonyl)methyl)-1,2,4,4a,5,6-hexahydro-[1,4]oxazino[4,3-a][1,5]naphthyridine was obtained in 33% isolated yield was taken to the next step as such without any further purification. LCMS (m/z) (M+H)=317.3, Rt=0.74 min.

Step 4:

9-chloro-5-((methylsulfonyl)methyl)-1,2,4,4a,5,6-hexahydro-[1,4]oxazino[4,3-a][1,5]naphthyridine (1.0 equiv.), X-Phos-Pd-Cycle-G2 (0.1 equiv.), 2-(1,1-difluoroethyl)-N-(4-methyl-3-(4,4,5,5-tetramethyl-1,3,2-dioxaborolan-2-yl)phenyl)isonicotinamide (1.0 equiv.) and $K_3PO_4$ (3.0 equiv.) were combined in dioxane: water (10:1) (0.1 M). The mixture was agitated in MW at 130° C. for 40 min and then the product extracted with EtOAc. The organic layer was passed through a plug of anhydrous $Na_2SO_4$, and the filtrate concentrated in vacuo. The residue was purified by reverse-phase HPLC to afford the desired product 2-(1,1-difluoroethyl)-N-(4-methyl-3-(5-((methylsulfonyl)methyl)-1,2,4,4a,5,6-hexahydro-[1,4]oxazino[4,3-a][1,5]naphthyridin-9-yl)phenyl)isonicotinamide as a free-base. LCMS (m/z) (M+H)=557.3, Rt=0.79 min. 1H NMR (400 MHz, DMSO-d6) δ (ppm) 10.63 (s, 1H) 8.88 (dd, J=5.01, 0.61 Hz, 1H) 8.18 (d, J=0.61 Hz, 1H) 8.03 (dd, J=5.01, 1.59 Hz, 1H) 7.83 (d, J=1.34 Hz, 1H) 7.73 (dd, J=8.31, 2.32 Hz, 1H) 7.66 (d, J=2.20 Hz, 1H) 7.32 (d, J=8.44 Hz, 1H) 7.21 (br s, 1H) 4.05 (dd, J=11.19, 2.75 Hz, 1H) 3.79-3.91 (m, 2H) 3.52 (td, J=11.62, 2.45 Hz, 1H) 3.40-3.47 (m, 1H) 3.10-3.27 (m, 4H) 3.06 (s, 3H) 2.79-2.97 (m, 2H) 2.23 (s, 3H) 2.05 (t, J=19.13 Hz, 3H).

Example 100

(rac)-(cis)-9-(5-(2-(1,1-difluoroethyl)isonicotinamido)-2-methylphenyl)-1,2,4,4a,5,6-hexahydro-[1,4]oxazino[4,3-a]quinoline-5-carboxylic Acid

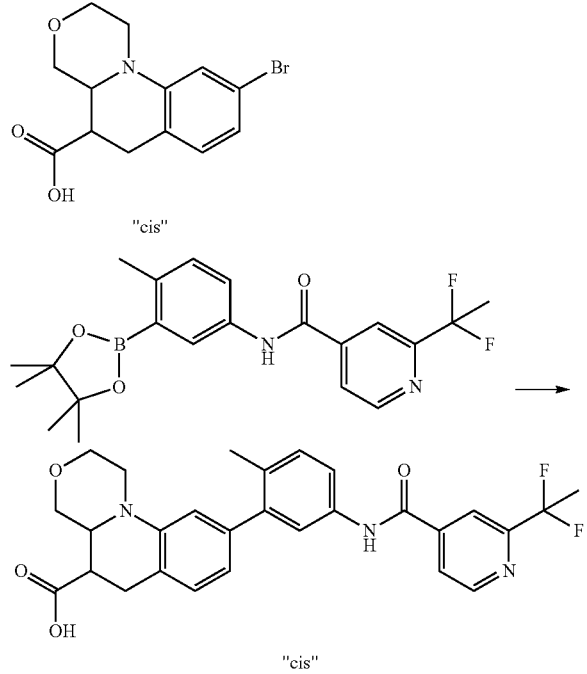

A mixture of 9-bromo-1,2,4,4a,5,6-hexahydro-[1,4]oxazino[4,3-a]quinoline-5-carboxylic acid (1.0 equiv.), 2-(1,1-difluoroethyl)-N-(4-methyl-3-(4,4,5,5-tetramethyl-1,3,2-dioxaborolan-2-yl)phenyl)isonicotinamide (1.1 equiv.), $PdCl_2$(dppf).$CH_2Cl_2$ adduct (0.1 equiv.) and 2 M $Na_2CO_3$ (3 equiv.) in Dioxane (0.16 M, degassed) was irradiated in a microwave for 1 h at 110° C. The cooled reaction mixture was quickly run through flash chromatography over silica gel (EtOAc with 50% MeOH). It was then purified via reverse phase BASIC prep-HPLC. The pure fractions were lyophilized to give the desired final racemate and diastereomeric product, (rac)-9-(5-(2-(1,1-difluoroethyl)isonicotinamido)-2-methylphenyl)-1,2,4,4a,5,6-hexahydro-[1,4]oxazino[4,3-a]quinoline-5-carboxylic acid (34%). $^1$H NMR (400 MHz, Methanol-d4) δ 8.83-8.75 (m, 1H), 8.17 (s, 1H), 7.99-7.91 (m, 1H), 7.62 (ddd, J=7.9, 5.6, 2.3 Hz, 1H), 7.52 (dd, J=4.8, 2.4 Hz, 1H), 7.26 (d, J=8.3 Hz, 1H), 7.05 (d, J=7.6 Hz, 1H), 6.81-6.74 (m, 1H), 6.67 (dd, J=7.6, 1.4 Hz, 1H), 4.03 (dd, J=11.1, 2.7 Hz, 1H), 3.99-3.92 (m, 1H), 3.87-3.78 (m, OH), 3.76-3.64 (m, 2H), 3.62-3.56 (m, OH), 3.42-3.34 (m, 1H), 3.22 (td, J=9.8, 3.0 Hz, 1H), 2.55 (ddd, J=11.0, 9.4, 5.4 Hz, 1H), 2.24 (s, 3H), 2.03 (t, J=18.7 Hz, 3H). LCMS (m/z) (M+H)=508.1, Rt=0.87 min.

Example 101 rac-cis-N-(3-(6-hydroxy-1,2,4,4a,5,6-hexahydro-[1,4]oxazino[4,3-a][1,5]naphthyridin-9-yl)-4-methylphenyl)-2-(trifluoromethyl)isonicotinamide

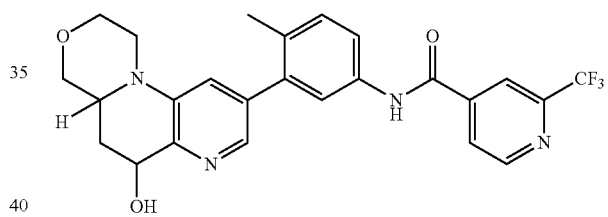

A vial was charged with 9-bromo-1,2,4,4a,5,6-hexahydro-[1,4]oxazino[4,3-a][1,5]naphthyridin-6-ol (1 equiv), N-(4-methyl-3-(4,4,5,5-tetramethyl-1,3,2-dioxaborolan-2-yl)phenyl)-2-(trifluoromethyl)isonicotinamide (1.2 equiv), and $PdCl_2$(dppf)-$CH_2Cl_2$ (0.1 equiv), potassium carbonate (3 equiv), and 3:1 1,4-dioxane/water (0.2 M). The was sealed and heated to 80° C. overnight. In the morning, the mixture was cooled and extracted with EtOAc (3×). The combined organic extracts were concentrated in vacuo. The residue was purified by chromatography on silica gel (50-100% EtOAc/heptane) to give N-(3-(6-hydroxy-1,2,4,4a,5,6-hexahydro-[1,4]oxazino[4,3-a][1,5]naphthyridin-9-yl)-4-methylphenyl)-2-(trifluoromethyl)isonicotinamide (65.5% yield) as a white foam. $^1$H NMR (400 MHz, DMSO-d6) δ ppm 10.68 (s, 1H) 8.99 (d, J=5.01 Hz, 1H) 8.36 (s, 1H) 8.19 (dd, J=4.95, 1.04 Hz, 1H) 7.91 (d, J=1.71 Hz, 1H) 7.73 (dd, J=8.25, 2.26 Hz, 1H) 7.65 (d, J=2.20 Hz, 1H) 7.34 (d, J=8.44 Hz, 1H) 7.17 (d, J=1.71 Hz, 1H) 5.22 (d, J=3.55 Hz, 1H) 4.77 (ddd, J=10.73, 6.76, 3.55 Hz, 1H) 3.82-3.95 (m, 2H) 3.75 (d, J=11.37 Hz, 1H) 3.50-3.64 (m, 1H) 3.21-3.29 (m, 2H) 2.66-2.76 (m, 1H) 2.24 (s, 3H) 2.06-2.19 (m, 1H) 1.54-1.65 (m, 1H). LCMS (m/z) (M+H)=485.3, Rt=0.99 min.

Examples 102 and 103

N-(3-((4aR,6R)-6-Hydroxy-1,2,4,4a,5,6-hexahydro-[1,4]oxazino[4,3-a][1,5]naphthyridin-9-yl)-4-methylphenyl)-2-(trifluoromethyl)isonicotinamide and N-(3-((4aS,6S)-6-hydroxy-1,2,4,4a,5,6-hexahydro-[1,4]oxazino[4,3-a][1,5]naphthyridin-9-yl)-4-methylphenyl)-2-(trifluoromethyl)isonicotinamide

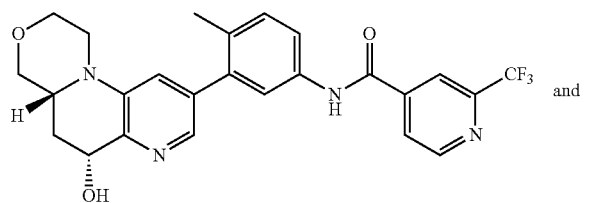

and

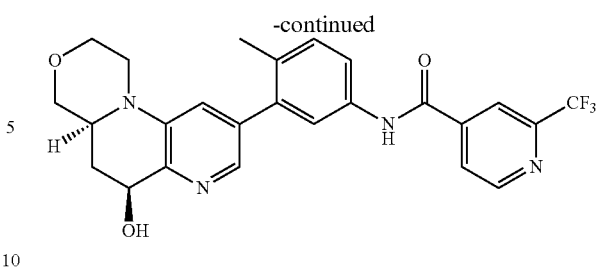

rac-N-(3-(6-Hydroxy-1,2,4,4a,5,6-hexahydro-[1,4]oxazino[4,3-a][1,5]naphthyridin-9-yl)-4-methylphenyl)-2-(trifluoromethyl)isonicotinamide was subjected to chiral SFC. The first eluting peak afforded N-(3-((4aR,6R)-6-hydroxy-1,2,4,4a,5,6-hexahydro-[1,4]oxazino[4,3-a][1,5]naphthyridin-9-yl)-4-methylphenyl)-2-(trifluoromethyl)isonicotinamide as a white solid. The second eluting peak afforded N-(3-((4aS,6S)-6-hydroxy-1,2,4,4a,5,6-hexahydro-[1,4]oxazino[4,3-a][1,5]naphthyridin-9-yl)-4-methylphenyl)-2-(trifluoromethyl)isonicotinamide as a white solid. NMR and LCMS data for each enantiomer matched that of the racemate.

The following compounds were prepared using methods from the above examples, using appropriate starting materials:

| # | Structure | Name | Data |
|---|---|---|---|
| 104 | 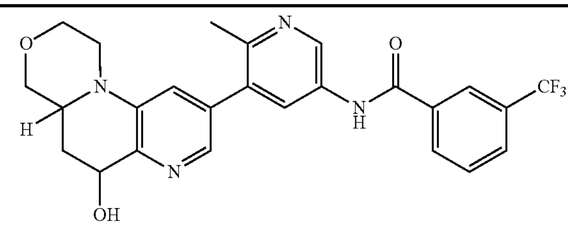 | rac-cis-N-(5-(6-Hydroxy-1,2,4,4a,5,6-hexahydro-[1,4]oxazino[4,3-a][1,5]naphthyridin-9-yl)-6-methylpyridin-3-yl)-3-(trifluoromethyl)benzamide | ¹H NMR (400 MHz, DMSO-d6) δ ppm 10.67 (s, 1 H) 8.83-8.91 (m, 1 H) 8.25-8.36 (m, 2 H) 7.94-8.11 (m, 3 H) 7.73-7.86 (m, 1 H) 7.25 (d, J = 1.59 Hz, 1 H) 5.26 (d, J = 3.67 Hz, 1 H) 4.72-4.84 (m, 1 H) 3.72-3.95 (m, 3 H) 3.47-3.63 (m, 1 H) 3.22-3.29 (m, 2 H) 2.65-2.83 (m, 1 H) 2.44 (s, 3 H) 2.09-2.19 (m, 1 H) 1.53-1.66 (m, 1 H). LCMS (m/z) (M + H) = 485.3, Rt = 0.89 min |
| 105 | 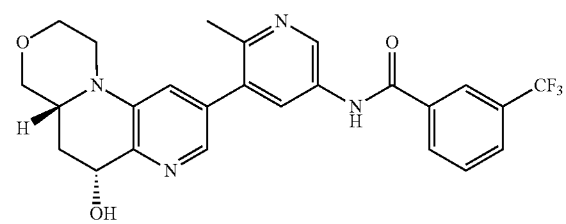 [SMILES: Cc1ncc(NC(=O)c2cccc(C(F)(F)F)c2)cc1-c1cnc2c(c1)N1CCOC[C@H]1C[C@H]2O] | N-(5-((4aR,6R)-6-Hydroxy-1,2,4,4a,5,6-hexahydro-[1,4]oxazino[4,3-a][1,5]naphthyridin-9-yl)-6-methylpyridin-3-yl)-3-(trifluoromethyl)benzamide | 66 (m, 1 H). LCMS (m/z) (M + H) = 485.3, Rt = 0.89 min |
| 106 | 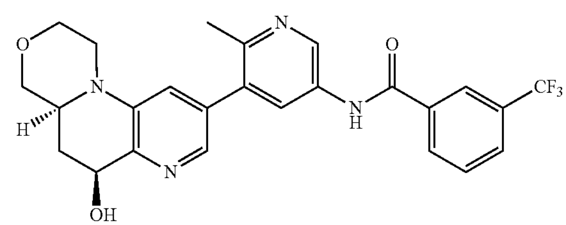 [SMILES: Cc1ncc(NC(=O)c2cccc(C(F)(F)F)c2)cc1-c1cnc2c(c1)N1CCOC[C@@H]1C[C@@H]2O] | N-(5-((4aS,6S)-6-Hydroxy-1,2,4,4a,5,6-hexahydro-[1,4]oxazino[4,3-a][1,5]naphthyridin-9-yl)-6-methylpyridin-3-yl)-3-(trifluoromethyl)benzamide | 66 (m, 1 H). LCMS (m/z) (M + H) = 485.3, Rt = 0.89 min |
| 107 | 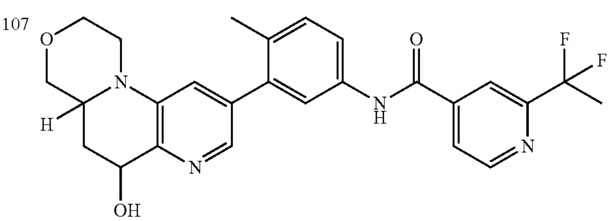 | rac-cis-2-(1,1-Difluoroethyl)-N-(3-(6-hydroxy-1,2,4,4a,5,6-hexahydro-[1,4]oxazino[4,3-a][1,5]naphthyridin-9-yl)-4-methylphenyl)isonicotinamide | ¹H NMR (400 MHz, DMSO-d6) δ ppm 10.64 (s, 1 H) 8.88 (d, J = 4.52 Hz, 1 H) 8.18 (s, 1 H) 8.03 (d, J = 4.89 Hz, 1 H) 7.91 (d, J = 1.59 Hz, 1 H) 7.73 (dd, J = 8.31, 2.20 Hz, 1 H) 7.65 (d, J = 2.20 Hz, 1 H) 7.33 (d, J = 8.44 Hz, 1 H) 7.17 (d, J = 1.59 Hz, 1 H) 5.22 (d, J = 3.30 Hz, 1 H) 4.63-4.86 (m, 1 H) 3.81-3.97 (m, 2 H) 3.75 (d, J = 11.98 Hz, 1 H) 3.56 (td, J = 11.71, 2.75 Hz, 1 H) 3.19-3.29 (m, 2 H) 2.63-2.80 (m, 1 H) 2.24 (s, 3 H) 2.14 (dd, J = 11.07, 6.66 Hz, 1 H) 1.99-2.11 (m, 3 H) 1.59 (d, |

| # | Structure | Name | Data |
|---|---|---|---|
| 108 | (structure) | 2-(1,1-Difluoroethyl)-N-(3-((4aR,6R)-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d6) δ ppm 10.64 (s, 1 H) 8.88 (d, J = 4.52 Hz, 1 H) 8.18 (s, 1 H) 8.03 (d, J = 4.89 Hz, 1 H) 7.91 (d, J = 1.59 Hz, 1 H) 7.73 (dd, J = 8.31, 2.20 Hz, 1 H) 7.65 (d, J = 2.20 Hz, 1 H) 7.33 (d, J = 8.44 Hz, 1 H) 7.17 (d, J = 1.59 Hz, 1 H) 5.22 (d, J = 3.30 Hz, 1 H) 4.63-4.86 (m, 1 H) 3.81-3.97 (m, 2 H) 3.75 (d, J = 11.98 Hz, 1 H) 3.56 (td, J = 11.71, 2.75 Hz, 1 H) 3.19-3.29 (m, 2 H) 2.63-2.80 (m, 1 H) 2.24 (s, 3 H) 2.14 (dd, J = 11.07, 6.66 Hz, 1 H) 1.99-2.11 (m, 3 H) 1.59 (d, J = 11.86 Hz, 1 H). LCMS (m/z) (M + H) = 481.3, Rt = 0.96 min. |
| 109 | (structure) | 2-(1,1-difluoroethyl)-N-(3-((4aS,6S)-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d6) δ ppm 10.64 (s, 1 H) 8.88 (d, J = 4.52 Hz, 1 H) 8.18 (s, 1 H) 8.03 (d, J = 4.89 Hz, 1 H) 7.91 (d, J = 1.59 Hz, 1 H) 7.73 (dd, J = 8.31, 2.20 Hz, 1 H) 7.65 (d, J = 2.20 Hz, 1 H) 7.33 (d, J = 8.44 Hz, 1 H) 7.17 (d, J = 1.59 Hz, 1 H) 5.22 (d, J = 3.30 Hz, 1 H) 4.63-4.86 (m, 1 H) 3.81-3.97 (m, 2 H) 3.75 (d, J = 11.98 Hz, 1 H) 3.56 (td, J = 11.71, 2.75 Hz, 1 H) 3.19-3.29 (m, 2 H) 2.63-2.80 (m, 1 H) 2.24 (s, 3 H) 2.14 (dd, J = 11.07, 6.66 Hz, 1 H) 1.99-2.11 (m, 3 H) 1.59 (d, J = 11.86 Hz, 1 H). LCMS (m/z) (M + H) = 481.3, Rt = 0.96 min. |
| 110 | (structure) | rac-N-(4-methyl-3-(6-oxo-1,2,4,4a,5,6-hexahydro-[1,4]oxazino[4,3-a][1,5]naphthyridin-9-yl)phenyl)-2-(trifluoromethyl)isonicotinamide | $^1$H NMR (400 MHz, DMSO-d6) δ ppm 10.74 (s, 1 H) 9.00 (d, J = 5.01 Hz, 1 H) 8.37 (s, 1 H) 8.20 (dd, J = 4.95, 1.04 Hz, 1 H) 8.13 (d, J = 1.59 Hz, 1 H) 7.78 (dd, J = 8.25, 2.26 Hz, 1 H) 7.70 (d, J = 2.20 Hz, 1 H) 7.57 (d, J = 1.59 Hz, 1 H) 7.39 (d, J = 8.44 Hz, 1 H) 3.85-4.07 (m, 3 H) 3.66 (td, J = 11.83, 2.63 Hz, 1 H) 3.48-3.61 (m, 1 H) 3.36-3.45 (m, 1 H) 2.81 (td, J = 12.13, 3.73 Hz, 1 H) 2.56-2.65 (m, 2 H) 2.26 (s, 3 H). LCMS (m/z) (M + H) = 483.1, Rt = 1.21 min. |
| 111 | (structure) | rac-N-(3-(6,6-Difluoro-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, DMSO-d6) δ ppm 10.72 (s, 1 H) 8.99 (d, J = 5.01 Hz, 1 H) 8.36 (s, 1 H) 8.15-8.22 (m, 1 H) 8.06 (d, J = 1.59 Hz, 1 H) 7.75 (dd, J = 8.25, 2.26 Hz, 1 H) 7.68 (d, J = 2.20 Hz, 1 H) 7.45 (s, 1 H) 7.37 (d, J = 8.44 Hz, 1 H) 3.93-4.03 (m, 2 H) 3.85 (d, J = 11.25 Hz, 1 H) 3.60 (td, J = 11.80, 2.69 Hz, 1 H) 3.25-3.42 (m, 2 H) 2.79 (td, J = 12.10, 3.42 Hz, 1 H) 2.24 (s, 3 H) 2.11-2.22 (m, 1 H). LCMS (m/z) (M + H) = 505.1, Rt = 1.48 min. |
| 112 | (structure) | rac-N-(4-Methyl-3-(5-oxo-1,2,4,4a,5,6-hexahydropyrido[2',3':5,6]pyrazino[2,1-c][1,4]oxazin-9-yl)phenyl)-2-(trifluoromethyl)isonicotinamide | $^1$H NMR (400 MHz, DMSO-d$_6$) δ ppm 11.13 (s, 1 H) 10.68 (s, 1 H) 8.99 (d, J = 5.01 Hz, 1 H) 8.37 (s, 1 H) 8.20 (d, J = 5.22 Hz, 1 H) 7.65-7.76 (m, 3 H) 7.34 (d, J = 8.44 Hz, 1 H) 7.15 (s, 1 H) 4.21 (dd, J = 11.55, 3.73 Hz, 1 H) 3.96 (dd, J = 11.13, 3.55 Hz, 1 H) 3.77 (dd, J = 10.27, 3.67 Hz, 1 H) 3.36-3.62 (m, 7 H) 3.25-3.29 (m, 2 H) 2.81 (td, J = 12.35, 3.67 Hz, 1 H) 2.38-2.46 (m, 2 H) 2.25 (s, 3 H). LCMS (m/z) (M + H) 484.1, Rt = 1.34 min. |

| | | | |
|---|---|---|---|
| 113 | | rac-N-(3-(6-Ethyl-5-oxo-1,2,4,4a,5,6-hexahydropyrido[2',3':5,6]pyrazino[2,1-c][1,4]oxazin-9-yl)-4-methylphenyl)-2-(trifluoromethyl)isonicotinamide | $^1$H NMR (400 MHz, DMSO-d6) δ ppm 10.69 (s, 1 H) 8.99 (d, J = 5.01 Hz, 1 H) 8.37 (s, 1 H) 8.19 (dd, J = 4.89, 1.10 Hz, 1 H) 7.87 (d, J = 1.83 Hz, 1 H) 7.67-7.75 (m, 2 H) 7.35 (d, J = 8.07 Hz, 1 H) 7.20 (d, J = 1.71 Hz, 1 H) 4.11-4.29 (m, 2 H) 3.93-4.11 (m, 2 H) 3.82 (dd, J = 10.33, 3.85 Hz, 1 H) 3.35-3.63 (m, 3 H) 2.73-2.96 (m, 1 H) 2.27 (s, 3 H) 1.18 (t, J = 6.97 Hz, 3 H). LCMS (m/z) (M + H) 512.2; Rt = 1.59 min. |
| 114 | | (S)-N-(3-(6-Ethyl-5-oxo-1,2,4,4a,5,6-hexahydropyrido[2',3':5,6]pyrazino[2,1-c][1,4]oxazin-9-yl)-4-methylphenyl)-2-(trifluoromethyl)isonicotinamide | $^1$H NMR (400 MHz, DMSO-d6) δ ppm 10.69 (s, 1 H) 8.99 (d, J = 5.01 Hz, 1 H) 8.37 (s, 1 H) 8.19 (dd, J = 4.89, 1.10 Hz, 1 H) 7.87 (d, J = 1.83 Hz, 1 H) 7.67-7.75 (m, 2 H) 7.35 (d, J = 8.07 Hz, 1 H) 7.20 (d, J = 1.71 Hz, 1 H) 4.11-4.29 (m, 2 H) 3.93-4.11 (m, 2 H) 3.82 (dd, J = 10.33, 3.85 Hz, 1 H) 3.35-3.63 (m, 3 H) 2.73-2.96 (m, 1 H) 2.27 (s, 3 H) 1.18 (t, J = 6.97 Hz, 3 H). LCMS (m/z) (M + H) 512.2; Rt = 1.59 min. |
| 115 | | (R)-N-(3-(6-ethyl-5-oxo-1,2,4,4a,5,6-hexahydropyrido 2',3':5,6]pyrazino[2,1-c][1,4]oxazin-9-yl)-4-methylphenyl)-2-(trifluoromethyl)isonicotinamide | $^1$H NMR (400 MHz, DMSO-d6) δ ppm 10.69 (s, 1 H) 8.99 (d, J = 5.01 Hz, 1 H) 8.37 (s, 1 H) 8.19 (dd, J = 4.89, 1.10 Hz, 1 H) 7.87 (d, J = 1.83 Hz, 1 H) 7.67-7.75 (m, 2 H) 7.35 (d, J = 8.07 Hz, 1 H) 7.20 (d, J = 1.71 Hz, 1 H) 4.11-4.29 (m, 2 H) 3.93-4.11 (m, 2 H) 3.82 (dd, J = 10.33, 3.85 Hz, 1 H) 3.35-3.63 (m, 3 H) 2.73-2.96 (m, 1 H) 2.27 (s, 3 H) 1.18 (t, J = 6.97 Hz, 3 H). LCMS (m/z) (M + H) 512.2; Rt = 1.59 min. |

Example 116 rac-trans-2-(1,1-Difluoroethyl)-N-(3-(5-(hydroxymethyl)-1,2,4,4a,5,6-hexahydro-[1,4]oxazino[4,3-a][1,5]naphthyridin-9-yl)-4-methylphenyl)isonicotinamide

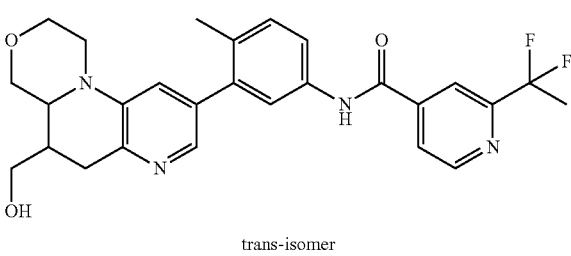 [SMILES: Cc1ccc(NC(=O)c2ccnc(C(C)(F)F)c2)cc1-c1cnc2c(c1)N1CCOCC1C(CO)C2]

trans-isomer

The title compound was prepared via Suzuki coupling: A vial was charged with trans-2-(1,1-difluoroethyl)-N-(4-methyl-3-(4,4,5,5-tetramethyl-1,3,2-dioxaborolan-2-yl)phenyl)isonicotinamide (1 equiv), 2-(1,1-difluoroethyl)-N-(4-methyl-3-(4,4,5,5-tetramethyl-1,3,2-dioxaborolan-2-yl)phenyl)isonicotinamide (1.2 equiv), XPhos 2nd Generation Precatalyst (0.05 equiv), potassium phosphate (3 equiv), and 5:1 1,4-dioxane-water (0.2 M). The vial was sealed and heated to 120° C. for 1 h in the microwave. The mixture was cooled and extracted with EtOAc (3×). The combined organic extracts were concentrated. The residue was purified by reverse-phase HPLC (basic) to afford of rac-trans-2-(1,1-difluoroethyl)-N-(3-(5-(hydroxymethyl)-1,2,4,4a,5,6-hexahydro-[1,4]oxazino[4,3-a][1,5]naphthyridin-9-yl)-4-methylphenyl)isonicotinamide (50% yield) as a white solid after lyophilization. 1H NMR (400 MHz, DMSO-d6) δ ppm 10.62 (s, 1H) 8.87 (d, J=5.11 Hz, 1H) 8.18 (s, 1H) 8.03 (d, J=5.11 Hz, 1H) 7.81 (d, J=1.71 Hz, 1H) 7.72 (dd, J=8.25, 2.14 Hz, 1H) 7.64 (d, J=2.20 Hz, 1H) 7.32 (d, J=8.44 Hz, 1H) 7.12 (d, J=1.47 Hz, 1H) 4.75 (t, J=5.14 Hz, 1H) 4.05 (dd, J=11.25, 2.93 Hz, 1H) 3.88 (dd, J=11.31, 3.12 Hz, 1H) 3.74 (br d, J=11.98 Hz, 1H) 3.34-3.58 (m, 3H) 3.24-3.29 (m, 1H) 2.94-3.01 (m, 1H) 2.74-2.87 (m, 3H) 2.23 (s, 3H) 2.05 (t, J=19.13 Hz, 3H) 1.86 (td, J=9.14, 5.81 Hz, 1H). LCMS (m/z) (M+H) 495.1; Rt=0.98 min.

Examples 117 and 118

2-(1,1-Difluoroethyl)-N-(3-((4aR,5R)-5-(hydroxymethyl)-1,2,4,4a,5,6-hexahydro-[1,4]oxazino[4,3-a][1,5]naphthyridin-9-yl)-4-methylphenyl)isonicotinamide and 2-(1,1-difluoroethyl)-N-(3-((4aS,5S)-5-(hydroxymethyl)-1,2,4,4a,5,6-hexahydro-[1,4]oxazino[4,3-a][1,5]naphthyridin-9-yl)-4-methylphenyl)isonicotinamide

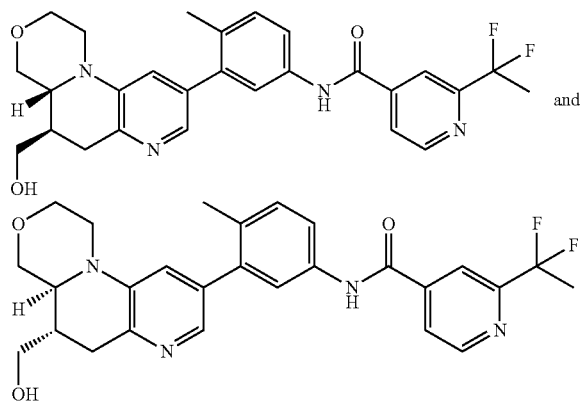

rac-trans-2-(1,1-Difluoroethyl)-N-(3-(5-(hydroxymethyl)-1,2,4,4a,5,6-hexahydro-[1,4]oxazino[4,3-a][1,5]naphthyridin-9-yl)-4-methylphenyl)isonicotinamide was subject to chiral SFC. The first eluting enantiomer afforded 2-(1,1-difluoroethyl)-N-(3-((4aR,5R)-5-(hydroxymethyl)-1,2,4,4a,5,6-hexahydro-[1,4]oxazino[4,3-a][1,5]naphthyridin-9-yl)-4-methylphenyl)isonicotinamide as a white solid. The second eluting enantiomer afforded 2-(1,1-difluoroethyl)-N-(3-((4aS,5S)-5-(hydroxymethyl)-1,2,4,4a,5,6-hexahydro-[1,4]oxazino[4,3-a][1,5]naphthyridin-9-yl)-4-methylphenyl)isonicotinamide as a white solid. NMR and LCMS data for each enantiomer matched that of the racemate.

Example 119 rac-trans-N-(5-(5-(Hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide

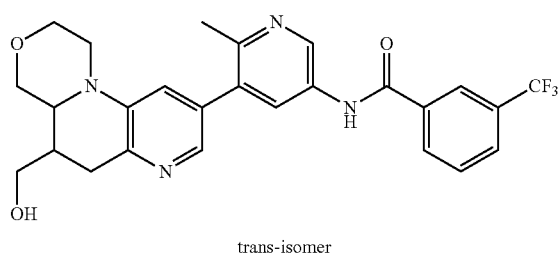 [SMILES: Cc1ncc(NC(=O)c2cccc(C(F)(F)F)c2)cc1-c1cnc2c(c1)N1CCOCC1C(CO)C2]

trans-isomer

The title compound was prepared via Suzuki coupling: $^1$H NMR (400 MHz, DMSO-d6) δ ppm 10.66 (s, 1H) 8.86 (d, J=2.45 Hz, 1H) 8.26-8.35 (m, 2H) 8.04 (s, 1H) 7.99 (d, J=7.42 Hz, 1H) 7.79-7.87 (m, 2H) 7.20 (d, J=1.71 Hz, 1H) 4.76 (t, J=5.20 Hz, 1H) 3.99-4.14 (m, 1H) 3.88 (dd, J=11.25, 3.06 Hz, 1H) 3.77 (br d, J=11.98 Hz, 1H) 3.33-3.58 (m, 3H) 3.25-3.30 (m, 1H) 3.17 (d, J=5.26 Hz, 1H) 3.00 (ddd, J=10.33, 8.62, 3.18 Hz, 1H) 2.75-2.89 (m, 3H) 2.43 (s, 3H) 1.87 (td, J=9.14, 5.69 Hz, 1H). LCMS (m/z) (M+H) 499.1, Rt=0.90 min.

Examples 120 and 121

N-(5-((4aR,5R)-5-(Hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide and N-(5-((4aS,5S)-5-(hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide

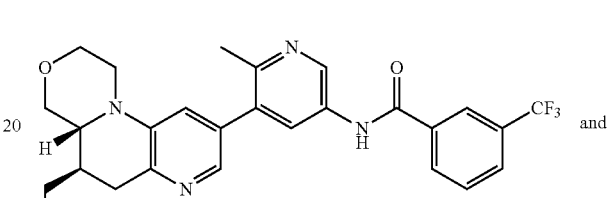

rac-trans-N-(5-(5-(Hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide was subjected to chiral SFC. The first eluting peak afforded N-(5-((4aR,5R)-5-(hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide as a white solid. The second eluting peak afforded N-(5-((4aS,5S)-5-(hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide as a white solid. NMR and LCMS data for each enantiomer matched that of the racemate.

Examples 122 and 123 rac-trans-N-(3-(5-(Hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide and rac-cis-N-(3-(5-(hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide trans

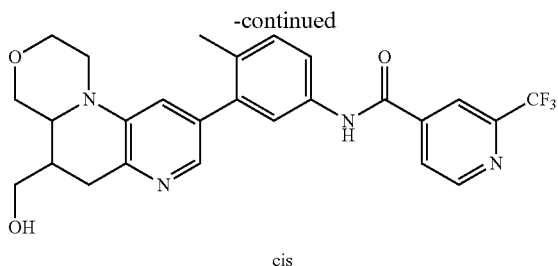

cis

A vial was charged with (9-chloro-1,2,4,4a,5,6-hexahydro-[1,4]oxazino[4,3-a][1,5]naphthyridin-5-yl)methanol (1:1 cis/trans, 1 equiv), N-(4-methyl-3-(4,4,5,5-tetramethyl-1,3,2-dioxaborolan-2-yl)phenyl)-2-(trifluoromethyl)isonicotinamide (1.2 equiv), XPhos 2nd Gen Precatalyst (0.1 equiv), potassium phosphate (3 equiv), and 5:1 1,4-dioxane-water (0.1 M). The vial was sealed and heated to 120° C. for 1 h in the microwave. The mixture was cooled, then extracted with EtOAc (3×). The combined organic extracts were concentrated. The residue was purified by reverse-phase HPLC (basic). Fractions containing product were combined and partially concentrated in vacuo, then extracted with DCM (3×). The combined organic extracts were dried over sodium sulfate, filtered, and concentrated to give N-(3-(5-(hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide (1:1 cis/trans, 65.5% yield) as a white solid. This material was subjected to SFC on a chiral column. The first eluting peak afforded rac-trans-N-(3-(5-(hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide as a white solid: $^1$H NMR (400 MHz, DMSO-$d_6$) δ ppm 10.67 (s, 1H) 8.99 (d, J=5.01 Hz, 1H) 8.36 (s, 1H) 8.19 (dd, J=4.95, 1.04 Hz, 1H) 7.78-7.84 (m, 1H) 7.72 (dd, J=8.31, 2.20 Hz, 1H) 7.64 (d, J=2.08 Hz, 1H) 7.33 (d, J=8.44 Hz, 1H) 7.09-7.21 (m, 1H) 4.63-4.81 (m, 1H) 4.06 (dd, J=11.31, 3.00 Hz, 1H) 3.88 (br dd, J=11.43, 3.12 Hz, 1H) 3.81 (br s, 1H) 3.74 (br d, J=12.10 Hz, 1H) 3.49-3.62 (m, 1H) 3.40-3.49 (m, 2H) 3.24-3.29 (m, 1H) 2.92-3.03 (m, 1H) 2.74-2.91 (m, 3H) 2.23 (s, 3H) 1.80-1.93 (m, 1H). LCMS (m/z) (M+H)=499.1, Rt=1.00 min. The second eluting peak afforded rac-cis-N-(3-(5-(hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide as a white solid: $^1$H NMR (400 MHz, DMSO-$d_6$) δ ppm 10.66 (s, 1H) 8.99 (d, J=5.01 Hz, 1H) 8.36 (s, 1H) 8.19 (dd, J=5.01, 1.10 Hz, 1H) 7.82 (d, J=1.59 Hz, 1H) 7.72 (dd, J=8.25, 2.26 Hz, 1H) 7.64 (d, J=2.20 Hz, 1H) 7.33 (d, J=8.44 Hz, 1H) 7.18 (d, J=1.71 Hz, 1H) 4.67 (t, J=5.01 Hz, 1H) 3.73-3.90 (m, 3H) 3.45-3.64 (m, 3H) 3.33-3.42 (m, 2H) 2.81-2.98 (m, 3H) 2.23 (s, 3H) 2.10-2.20 (m, 1H). LCMS (m/z) (M+H)=499.1, Rt=1.00 min.

The following compounds were prepared using methods from the above examples, using appropriate starting materials:

| 124 | 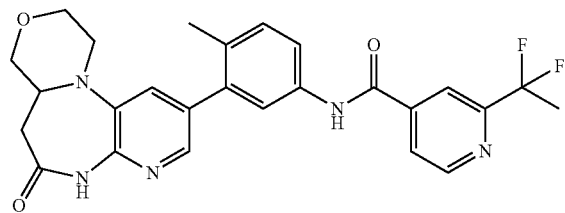 [SMILES: Cc1ccc(NC(=O)c2ccnc(C(C)(F)F)c2)cc1-c1cnc2c(c1)N1CCOCC1CC(=O)N2] | rac-2-(1,1-Difluoroethyl)-N-(4-methyl-3-(6-oxo-1,2,4a,5,6,7-hexahydro-4H-[1,4]oxazino[4,3-d]pyrido[2,3-b][1,4]diazepin-10-yl)phenyl)isonicotinamide | $^1$H NMR (400 MHz, DMSO-$d_6$) δ ppm 10.65 (s, 1 H) 10.09 (s, 1 H) 8.88 (d, J = 5.10 Hz, 1 H) 8.19 (s, 1 H) 8.01-8.05 (m, 2 H) 7.74 (d, J = 7.83 Hz, 1 H) 7.70 (s, 1 H) 7.47 (d, J = 1.96 Hz, 1 H) 7.35 (d, J = 8.31 Hz, 1 H) 3.76-3.91 (m, 2 H) 3.37-3.57 (m, 4 H) 2.97 (br d, J = 11.49 Hz, 1 H) 2.66-2.75 (m, 1 H) 2.27 (s, 3 H) 1.98-2.12 (m, 4 H). LCMS (m/z) (M + H) = 494.1, Rt = 1.23 min. |
| --- | --- | --- | --- |
| 125 | 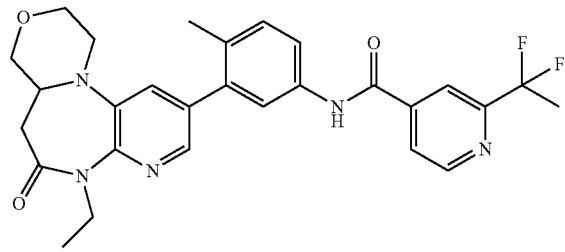 [SMILES: CCN1C(=O)CC2COCCN2c2cc(-c3cc(NC(=O)c4ccnc(C(C)(F)F)c4)ccc3C)cnc21] | rac-2-(1,1-Difluoroethyl)-N-(3-(7-ethyl-6-oxo-1,2,4a,5,6,7-hexahydro-4H-[1,4]oxazino[4,3-d]pyrido[2,3-b][1,4]diazepin-10-yl)-4-methylphenyl)isonicotinamide | $^1$H NMR (400 MHz, DMSO-$d_6$) δ ppm 10.66 (s, 1 H) 8.88 (d, J = 5.07 Hz, 1 H) 8.18 (dd, J = 5.93, 1.28 Hz, 2 H) 8.03 (d, J = 5.06 Hz, 1 H) 7.74 (s, 1 H) 7.75 (d, J = 7.58 Hz, 2 H) 7.52 (d, J = 2.08 Hz, 1 H) 7.36 (d, J = 9.29 Hz, 1 H) 3.96-4.06 (m, 1 H) 3.77-3.89 (m, 3 H) 3.48 (q, J = 10.51 Hz, 2H) 3.23-.29 (m, 1 H) 2.94 (br d, J = 10.51 Hz, 1 H) 2.64-2.71 (m, 1 H) 2.25-2.35 (m, 3 H) 1.98-2.15 (m, 4 H) 1.11-1.19 (m, 3 H). LCMS (m/z) (M + H) = 522.2, Rt = 1.41 min. |
| 126 | 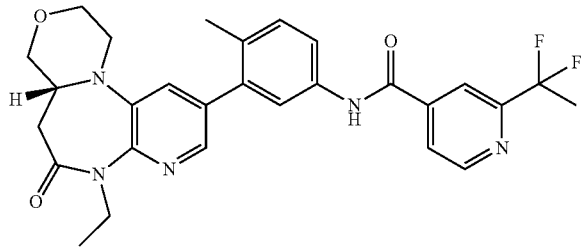 [SMILES: CCN1C(=O)C[C@@H]2COCCN2c2cc(-c3cc(NC(=O)c4ccnc(C(C)(F)F)c4)ccc3C)cnc21] | (R)-2-(1,1-Difluoroethyl)-N-(3-(7-ethyl-6-oxo-1,2,4a,5,6,7-hexahydro-4H-[1,4]oxazino[4,3-d]pyrido[2,3-b][1,4]diazepin-10-yl)-4-methylphenyl)isonicotinamide | $^1$H NMR (400 MHz, DMSO-$d_6$) δ ppm 10.66 (s, 1 H) 8.88 (d, J = 5.07 Hz, 1 H) 8.18 (dd, J = 5.93, 1.28 Hz, 2 H) 8.03 (d, J = 5.06 Hz, 1 H) 7.74 (s, 1 H) 7.75 (d, J = 7.58 Hz, 2 H) 7.52 (d, J = 2.08 Hz, 1 H) 7.36 (d, J = 9.29 Hz, 1 H) 3.96-4.06 (m, 1 H) 3.77-3.89 (m, 3 H) 3.48 (q, J = 10.51 Hz, 2H) 3.23-3.29 (m, 1 H) 2.94 (br d, J = 10.51 Hz, 1 H) 2.64-2.71 (m, 1 H) 2.25-2.35 (m, 3 H) 1.98-2.15 (m, 4 H) 1.11-1.19 (m, 3 H). LCMS (m/z) (M + H) = 522.2, Rt = 1.41 min. |

| | | | |
|---|---|---|---|
| 127 | 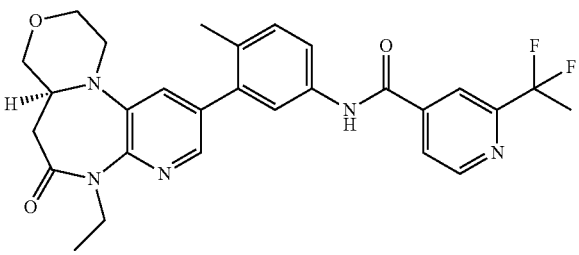 [SMILES: CCN1C(=O)C[C@H]2COCCN2c2cc(-c3cc(NC(=O)c4ccnc(C(C)(F)F)c4)ccc3C)cnc21] | (S)-2-(1,1-difluoroethyl)-N-(3-(7-ethyl-6-oxo-1,2,4a,5,6,7-hexahydro-4H-[1,4]oxazino[4,3-d]pyrido[2,3-b][1,4]diazepin-10-yl)-4-methylphenyl)isonicotinamide | $^1$H NMR (400 MHz, DMSO-d$_6$) δ ppm 10.66 (s, 1 H) 8.88 (d, J = 5.07 Hz, 1 H) 8.18 (dd, J = 5.93, 1.28 Hz, 2 H) 8.03 (d, J = 5.06 Hz, 1 H) 7.74 (s, 1 H) 7.75 (d, J = 7.58 Hz, 2 H) 7.52 (d, J = 2.08 Hz, 1 H) 7.36 (d, J = 9.29 Hz, 1 H) 3.96-4.06 (m, 1 H) 3.77-3.89 (m, 3 H) 3.48 (q, J = 10.51 Hz, 2H) 3.23-3.29 (m, 1 H) 2.94 (br d, J = 10.51 Hz, 1 H) 2.64-2.71 (m, 1 H) 2.25-2.35 (m, 3 H) 1.98-2.15 (m, 4 H) 1.11-1.19 (m, 3 H). LCMS (m/z) (M + H) = 522.2, Rt = 1.41 min. |
| 128 | 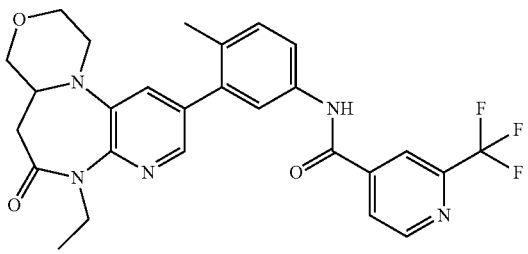 [SMILES: CCN1C(=O)CC2COCCN2c2cc(-c3cc(NC(=O)c4ccnc(C(F)(F)F)c4)ccc3C)cnc21] | rac-N-(3-(7-Ethyl-6-oxo-1,2,4a,5,6,7-hexahydro-4H-[1,4]oxazino[4,3-d]pyrido[2,3-b][1,4]diazepin-10-yl)-4-methylphenyl)-2-(trifluoromethyl)isonicotinamide | $^1$H NMR (400 MHz, DMSO-d$_6$) δ ppm 10.70 (s, 1 H) 9.00 (d, J = 5.01 Hz, 1 H) 8.37 (s, 1 H) 8.18-8.21 (m, 1 H) 8.18 (s, 1 H) 7.73 (s, 1 H) 7.74 (d, J = 7.26 Hz, 2 H) 7.52 (d, J = 2.08 Hz, 1 H) 7.37 (d, J = 9.05 Hz, 1 H) 3.96-4.06 (m, 1 H) 3.77-3.90 (m, 3 H) 3.39-3.57 (m, 3 H) 2.94 (br d, J = 11.37 Hz, 1 H) 2.54-2.71 (m, 1 H) 2.28 (s, 3 H) 2.12 (d, J = 13.45 Hz, 1 H) 1.08-1.25 (m, 3 H). LCMS (m/z) (M + H) = 526.2, Rt = 1.45 min. |
| 129 | 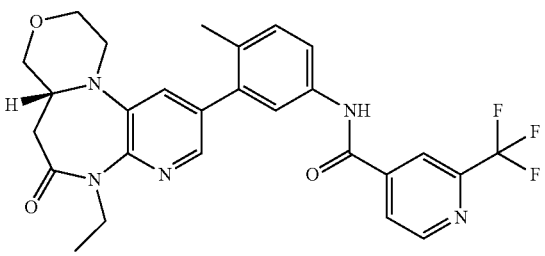 [SMILES: CCN1C(=O)C[C@@H]2COCCN2c2cc(-c3cc(NC(=O)c4ccnc(C(F)(F)F)c4)ccc3C)cnc21] | (R)-N-(3-(7-Ethyl-6-oxo-1,2,4a,5,6,7-hexahydro-4H-[1,4]oxazino[4,3-d]pyrido[2,3-b][1,4]diazepin-10-yl)-4-methylphenyl)-2-(trifluoromethyl)isonicotinamide | $^1$H NMR (400 MHz, DMSO-d$_6$) δ ppm 10.70 (s, 1 H) 9.00 (d, J = 5.01 Hz, 1 H) 8.37 (s, 1 H) 8.18-8.21 (m, 1 H) 8.18 (s, 1 H) 7.73 (s, 1 H) 7.74 (d, J = 7.26 Hz, 2 H) 7.52 (d, J = 2.08 Hz, 1 H) 7.37 (d, J = 9.05 Hz, 1 H) 3.96-4.06 (m, 1 H) 3.77-3.90 (m, 3 H) 3.39-3.57 (m, 3 H) 2.94 (br d, J = 11.37 Hz, 1 H) 2.54-2.71 (m, 1 H) 2.28 (s, 3 H) 2.12 (d, J = 13.45 Hz, 1 H) 1.08-1.25 (m, 3 H). LCMS (m/z) (M + H) = 526.2, Rt = 1.45 min. |
| 130 | 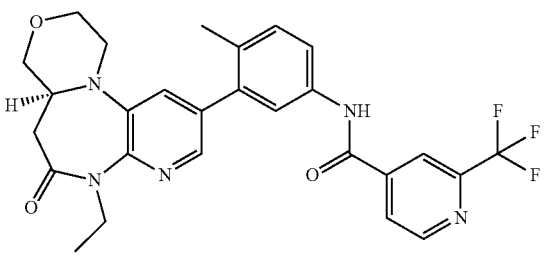 | (S)-N-(3-(7-ethyl-6-oxo-1,2,4a,5,6,7-hexahydro-4H-[1,4]oxazino[4,3-d]pyrido[2,3-b][1,4]diazepin-10-yl)-4-methylphenyl)-2-(trifluoromethyl)isonicotinamide | $^1$H NMR (400 MHz, DMSO-d$_6$) δ ppm 10.70 (s, 1 H) 9.00 (d, J = 5.01 Hz, 1 H) 8.37 (s, 1 H) 8.18-8.21 (m, 1 H) 8.18 (s, 1 H) 7.73 (s, 1 H) 7.74 (d, J = 7.26 Hz, 2 H) 7.52 (d, J = 2.08 Hz, 1 H) 7.37 (d, J = 9.05 Hz, 1 H) 3.96-4.06 (m, 1 H) 3.77-3.90 (m, 3 H) 3.39-3.57 (m, 3 H) 2.94 (br d, J = 11.37 Hz, 1 H) 2.54-2.71 (m, 1 H) 2.28 (s, 3 H) 2.12 (d, J = 13.45 Hz, 1 H) 1.08-1.25 (m, 3 H). LCMS (m/z) (M + H) = 526.2, Rt = 1.45 min. |
| 131 | 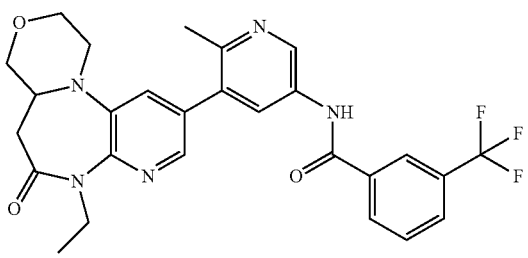 [SMILES: CCN1C(=O)CC2COCCN2c2cc(-c3cc(NC(=O)c4cccc(C(F)(F)F)c4)cnc3C)cnc21] | rac-N-(5-(7-Ethyl-6-oxo-1,2,4a,5,6,7-hexahydro-4H-[1,4]oxazino[4,3-d]pyrido[2,3-b][1,4]diazepin-10-yl)-6-methylpyridin-3-yl)-3-(trifluoromethyl)benzamide | $^1$H NMR (400 MHz, DMSO-d$_6$) δ ppm 10.70 (s, 1 H) 8.87 (d, J = 2.45 Hz, 1 H) 8.22-8.36 (m, 2 H) 8.14 (d, J = 2.45 Hz, 1 H) 8.00 (d, J = 7.82 Hz, 1 H) 7.79-7.85 (m, 1 H) 7.61 (d, J = 2.08 Hz, 1 H) 4.02 (br dd, J = 13.33, 6.85 Hz, 1 H) 3.66-3.91 (m, 3 H) 3.35-3.62 (m, 3 H) 2.90-3.02 (m, 1 H) 2.63-2.82 (m, 2 H) 2.13 (d, J = 13.57 Hz, 1 H) 1.16 (t, J = 7.03 Hz, 3 H). LCMS (m/z) (M + H) = 526.5, Rt = 1.10 min. |
| 132 | 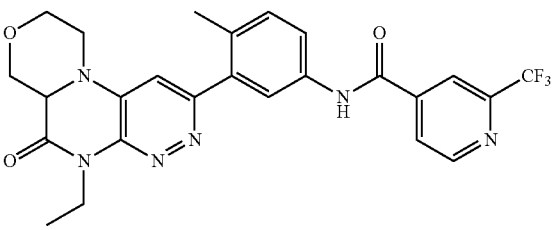 | rac-N-(3-(5-Ethyl-6-oxo-5,6,6a,7,9,10-hexahydropyridazino[3',4':5,6]pyrazino[2,1-c][1,4]oxazin-2-yl)-4-methylphenyl)-2-(trifluoromethyl)isonicotinamide | $^1$H NMR (400 MHz, DMSO-d$_6$) δ ppm 10.73 (s, 1 H) 9.00 (d, J = 4.89 Hz, 1 H) 8.38 (s, 1 H) 8.20 (dd, J = 5.01, 1.10 Hz, 1 H) 7.85 (d, J = 2.20 Hz, 1 H) 7.78 (dd, J = 8.25, 2.26 Hz, 1 H) 7.37 (d, J = 8.44 Hz, 1 H) 7.04 (s, 1 H) 4.12-4.30 (m, 4 H) 3.93-4.06 (m, 1 H) 3.77 (br d, J = 11.00 Hz, 1 H) 3.52-3.61 (m, 2 H) 2.89-2.99 (m, 1 H) 2.32 (s, 3 H) 1.15-1.32 (m, 6 H). LCMS (m/z) (M + H) = 512.2, Rt = 1.02 min. |

| | | | |
|---|---|---|---|
| 133 | 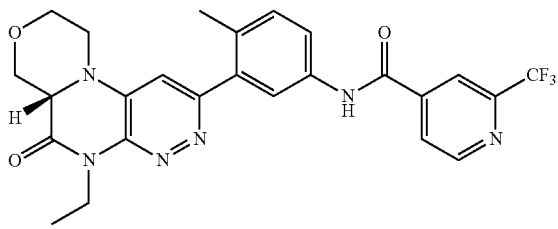 [SMILES: CCN1C(=O)[C@@H]2COCCN2c2cc(-c3cc(NC(=O)c4ccnc(C(F)(F)F)c4)ccc3C)nnc21] | (S)-N-(3-(5-Ethyl-6-oxo-5,6,6a,7,9,10-hexahydropyridazino[3',4':5,6]pyrazino[2,1-c][1,4]oxazin-2-yl)-4-methylphenyl)-2-(trifluoromethyl)isonicotinamide | ¹H NMR (400 MHz, DMSO-d₆) δ ppm 10.73 (s, 1 H) 9.00 (d, J = 4.89 Hz, 1 H) 8.38 (s, 1 H) 8.20 (dd, J = 5.01, 1.10 Hz, 1 H) 7.85 (d, J = 2.20 Hz, 1 H) 7.78 (dd, J = 8.25, 2.26 Hz, 1 H) 7.37 (d, J = 8.44 Hz, 1 H) 7.04 (s, 1 H) 4.12-4.30 (m, 4 H) 3.93-4.06 (m, 1 H) 3.77 (br d, J = 11.00 Hz, 1 H) 3.52-3.61 (m, 2 H) 2.89-2.99 (m, 1 H) 2.32 (s, 3 H) 1.15-1.32 (m, 6 H). LCMS (m/z) (M + H) = 512.2, Rt = 1.02 min. |
| 134 | 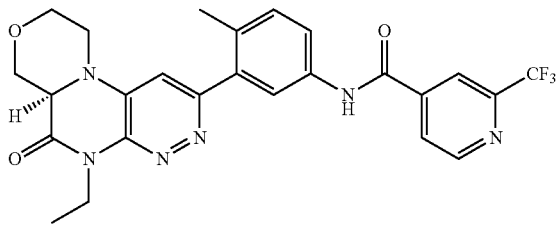 [SMILES: CCN1C(=O)[C@H]2COCCN2c2cc(-c3cc(NC(=O)c4ccnc(C(F)(F)F)c4)ccc3C)nnc21] | (R)-N-(3-(5-ethyl-6-oxo-5,6,6a,7,9,10-hexahydropyridazino[3',4':5,6]pyrazino[2,1-c][1,4]oxazin-2-yl)-4-methylphenyl)-2-(trifluoromethyl)isonicotinamide | ¹H NMR (400 MHz, DMSO-d₆) δ ppm 10.73 (s, 1 H) 9.00 (d, J = 4.89 Hz, 1 H) 8.38 (s, 1 H) 8.20 (dd, J = 5.01, 1.10 Hz, 1 H) 7.85 (d, J = 2.20 Hz, 1 H) 7.78 (dd, J = 8.25, 2.26 Hz, 1 H) 7.37 (d, J = 8.44 Hz, 1 H) 7.04 (s, 1 H) 4.12-4.30 (m, 4 H) 3.93-4.06 (m, 1 H) 3.77 (br d, J = 11.00 Hz, 1 H) 3.52-3.61 (m, 2 H) 2.89-2.99 (m, 1 H) 2.32 (s, 3 H) 1.15-1.32 (m, 6 H). LCMS (m/z) (M + H) = 512.2, Rt = 1.02 min. |
| 135 | 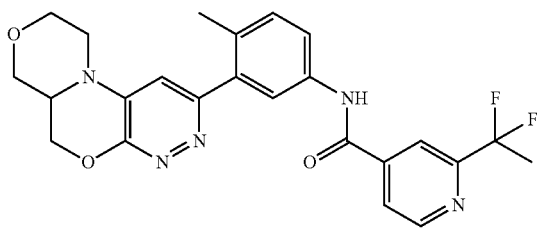 [SMILES: Cc1ccc(NC(=O)c2ccnc(C(C)(F)F)c2)cc1-c1cc2c(nn1)OCC1COCCN21] | rac-2-(1,1-Difluoroethyl)-N-(4-methyl-3-(6a,7,9,10-tetrahydro-6H-[1,4]oxazino[4,3-d]pyridazino[3,4-b][1,4]oxazin-2-yl)phenyl)isonicotinamide | ¹H NMR (400 MHz, DMSO-d₆) δ ppm 10.67 (s, 1 H) 8.88 (d, J = 5.01 Hz, 1 H) 8.19 (s, 1 H) 8.04 (d, J = 5.19 Hz, 1 H) 7.78 (s, 1 H) 7.77 (d, J = 7.29 Hz, 2 H) 7.33 (d, J = 9.17 Hz, 1H) 7.04 (s, 1 H) 4.51 (dd, J = 11.13, 3.18 Hz, 1 H) 4.10 (dd, J = 11.13, 9.17 Hz, 1 H) 3.96 (ddd, J = 14.82, 11.46, 3.42 Hz, 2 H) 3.82 (br d, J = 11.13 Hz, 1 H) 3.36-3.59 (m, 2 H) 3.12-3.27 (m, 1 H) 2.89-3.02 (m, 1 H) 2.28 (s, 3 H) 2.05 (t, J = 19.13 Hz, 3 H). LCMS (m/z) (M + H) = 468.5, Rt = 0.91 min. |
| 136 | 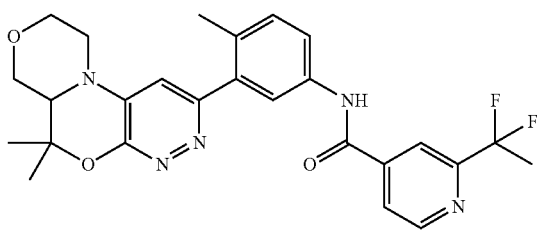 [SMILES: Cc1ccc(NC(=O)c2ccnc(C(C)(F)F)c2)cc1-c1cc2c(nn1)OC(C)(C)C1COCCN21] | rac-2-(1,1-Difluoroethyl)-N-(3-(6,6-dimethyl-6a,7,9,10-tetrahydro-6H-[1,4]oxazino[4,3-d]pyridazino[3,4-b][1,4]oxazin-2-yl)-4-methylphenyl)isonicotinamide | ¹H NMR (400 MHz, DMSO-d₆) δ ppm 10.65 (s, 1 H) 8.88 (d, J = 5.12 Hz, 1 H) 8.18-8.21 (m, 1 H) 8.04 (d, J = 5.16 Hz, 1 H) 7.79 (s, 1 H) 7.78 (d, J = 9.58 Hz, 1 H) 7.33 (d, J = 7.95 Hz, 1 H) 7.07 (s, 1 H) 3.93-4.08 (m, 2 H) 3.87 (dd, J = 12.59, 1.83 Hz, 1 H) 3.57 (td, J = 11.92, 2.81 Hz, 1 H) 3.33-3.41 (m, 1 H) 3.24-3.30 (m, 1 H) 2.95 (td, J = 12.38, 3.97 Hz, 1 H) 2.29 (s, 3 H) 1.98-2.12 (m, 3 H) 1.43 (s, 3 H) 1.28 (s, 3 H). LCMS (m/z) (M + H) = 496.1, Rt = 1.01 min. |
| 137 | 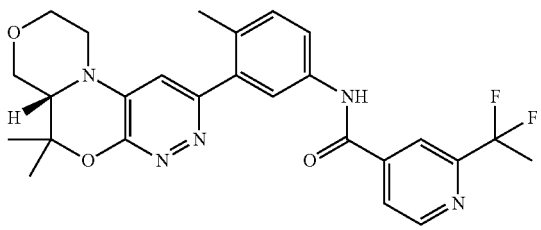 [SMILES: Cc1ccc(NC(=O)c2ccnc(C(C)(F)F)c2)cc1-c1cc2c(nn1)OC(C)(C)[C@@H]1COCCN21] | (S)-2-(1,1-Difluoroethyl)-N-(3-(6,6-dimethyl-6a,7,9,10-tetrahydro-6H-[1,4]oxazino[4,3-d]pyridazino[3,4-b][1,4]oxazin-2-yl)-4-methylphenyl)isonicotinamide | ¹H NMR (400 MHz, DMSO-d6) δ ppm 10.65 (s, 1 H) 8.88 (d, J = 5.12 Hz, 1 H) 8.18-8.21 (m, 1 H) 8.04 (d, J = 5.16 Hz, 1 H) 7.79 (s, 1 H) 7.78 (d, J = 9.58 Hz, 1 H) 7.33 (d, J = 7.95 Hz, 1 H) 7.07 (s, 1 H) 3.93-4.08 (m, 2 H) 3.87 (dd, J = 12.59, 1.83 Hz, 1 H) 3.57 (td, J = 11.92, 2.81 Hz, 1 H) 3.33-3.41 (m, 1 H) 3.24-3.30 (m, 1 H) 2.95 (td, J = 12.38, 3.97 Hz, 1 H) 2.29 (s, 3 H) 1.98-2.12 (m, 3 H) 1.43 (s, 3 H) 1.28 (s, 3 H). LCMS (m/z) (M + H) = 496.1, Rt = 1.01 min. |

| | | | |
|---|---|---|---|
| 138 | 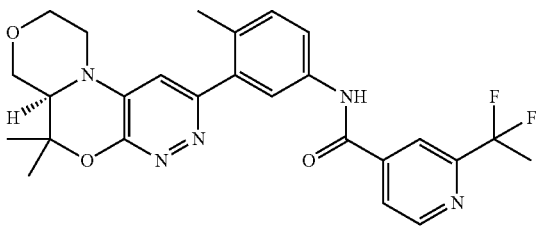 [SMILES: Cc1ccc(NC(=O)c2ccnc(C(C)(F)F)c2)cc1-c1cc2c(nn1)OC(C)(C)[C@H]1COCCN21] | (R)-2-(1,1-Difluoroethyl)-N-(3-(6,6-dimethyl-6a,7,9,10-tetrahydro-6H-[1,4]oxazino[4,3-d]pyridazino[3,4-b][1,4]oxazin-2-yl)-4-methylphenyl)isonicotinamide | $^1$H NMR (400 MHz, DMSO-d$_6$) δ ppm 10.65 (s, 1 H) 8.88 (d, J = 5.12 Hz, 1 H) 8.18-8.21 (m, 1 H) 8.04 (d, J = 5.16 Hz, 1 H) 7.79 (s, 1 H) 7.78 (d, J = 9.58 Hz, 1 H) 7.33 (d, J = 7.95 Hz, 1 H) 7.07 (s, 1 H) 3.93-4.08 (m, 2 H) 3.87 (dd, J = 12.59, 1.83 Hz, 1 H) 3.57 (td, J = 11.92, 2.81 Hz, 1 H) 3.33-3.41 (m, 1 H) 3.24-3.30 (m, 1 H) 2.95 (td, J = 12.38, 3.97 Hz, 1 H) 2.29 (s, 3 H) 1.98-2.12 (m, 3 H) 1.43 (s, 3 H) 1.28 (s, 3 H). LCMS (m/z) (M + H) = 496.1, Rt = 1.01 min. |
| 139 | 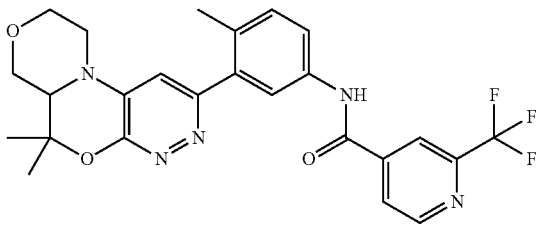 | rac-N-(3-(6,6-dimethyl-6a,7,9,10-tetrahydro-6H-[1,4]oxazino[4,3-d]pyridazino[3,4-b][1,4]oxazin-2-yl)-4-methylphenyl)-2-(trifluoromethyl)isonicotinamide | $^1$H NMR (400 MHz, DMSO-d$_6$) δ ppm 10.70 (s, 1 H) 8.99 (d, J = 5.01 Hz, 1 H) 8.38 (s, 1 H) 8.20 (d, J = 5.12 Hz, 1 H) 7.78 (d, J = 9.24 Hz, 2 H) 7.34 (d, J = 7.95 Hz, 1 H) 7.07 (s, 1 H) 3.92-4.08 (m, 2 H) 3.85-3.92 (m, 1 H) 3.57 (td, J = 11.89, 2.75 Hz, 2 H) 3.24-3.30 (m, 1 H) 2.95 (td, J = 12.32, 3.85 Hz, 1 H) 2.29 (s, 3 H) 1.43 (s, 3 H) 1.28 (s, 3 H). LCMS (m/z) (M + H) = 500.1, Rt = 1.03 min. |
| 140 | 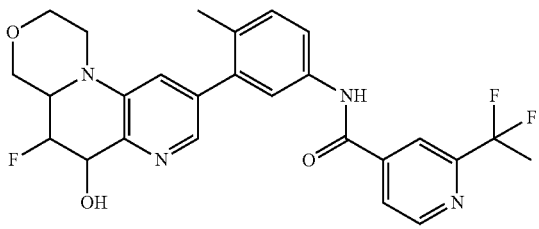 [SMILES: Cc1ccc(NC(=O)c2ccnc(C(C)(F)F)c2)cc1-c1cnc2c(c1)N1CCOCC1C(F)C2O] | rac-2-(1,1-difluoroethyl)-N-(3-((4aS*,5S*,6S*)-5-fluoro-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.65 (s, 1 H) 8.77-8.99 (m, 1 H) 8.13-8.23 (m, 1 H) 8.02 (s, 2 H) 7.61-7.80 (m, 2 H) 7.30-7.41 (m, 1 H) 7.13-7.26 (m, 1 H) 5.79-5.94 (m, 1 H) 4.77-4.92 (m, 1 H) 4.53-4.73 (m, 1 H) 3.91-4.16 (m, 3 H) 3.71-3.84 (m, 1 H) 3.48-3.63 (m, 3 H) 2.65-2.88 (m, 1 H) 2.23 (s, 3 H) 1.92-2.16 (m, 4 H). LCMS (m/z) (M + H) = 499.5, Rt = 1.03 min. |
| 141 | 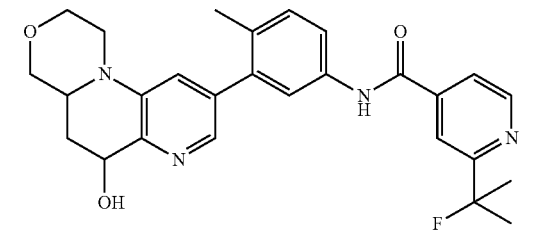 [SMILES: Cc1ccc(NC(=O)c2ccnc(C(C)(C)F)c2)cc1-c1cnc2c(c1)N1CCOCC1CC2O] | rac-cis-2-(2-fluoropropan-2-yl)-N-(3-(6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.57 (s, 1H), 8.75 (d, J = 5.0 Hz, 1H), 8.02 (s, 1H), 7.91 (s, 1H), 7.82 (dd, J = 4.8, 0.8 Hz, 1H), 7.73 (dd, J = 8.0, 1.6 Hz, 1H), 7.66 (s, 1H), 7.32 (d, J = 8.3 Hz, 1H), 7.17 (s, 1H), 5.23 (d, J = 2.3 Hz, 1H), 4.77 (m, 1H), 3.91 (m, 1H), 3.85 (d, J = 8.0 Hz, 1H), 3.75 (d, J = 11.7 Hz, 1H), 3.57 (m, 1H), 3.26 (m, 2H), 2.72 (td, J = 12.0, 3.3 Hz, 1H), 2.24 (s, 3H), 2.15 (dd, J = 11.6, 6.5 Hz, 1H), 1.71 (d, J = 22.1 Hz, 6H), 1.59 (m, 1H). LCMS (m/z) (M + H) = 477.5, Rt = 0.97 min. |
| 142 | 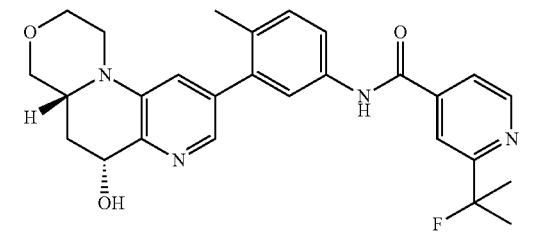 [SMILES: Cc1ccc(NC(=O)c2ccnc(C(C)(C)F)c2)cc1-c1cnc2c(c1)N1CCOC[C@H]1C[C@H]2O] | 2-(2-fluoropropan-2-yl)-N-(3-((4aR,6R)-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.57 (s, 1H), 8.75 (d, J = 5.0 Hz, 1H), 8.02 (s, 1H), 7.91 (s, 1H), 7.82 (dd, J = 4.8, 0.8 Hz, 1H), 7.73 (dd, J = 8.0, 1.6 Hz, 1H), 7.66 (s, 1H), 7.32 (d, J = 8.3 Hz, 1H), 7.17 (s, 1H), 5.23 (d, J = 2.3 Hz, 1H), 4.77 (m, 1H), 3.91 (m, 1H), 3.85 (d, J = 8.0 Hz, 1H), 3.75 (d, J = 11.7 Hz, 1H), 3.57 (m, 1H), 3.26 (m, 2H), 2.72 (td, J = 12.0, 3.3 Hz, 1H), 2.24 (s, 3H), 2.15 (dd, J = 11.6, 6.5 Hz, 1H), 1.71 (d, J = 22.1 Hz, 6H), 1.59 (m, 1H). LCMS (m/z) (M + H) = 477.5, Rt = 0.97 min. |

| 143 | 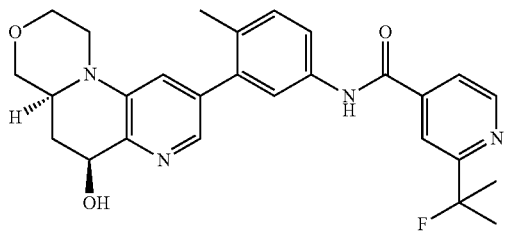 [SMILES: Cc1ccc(NC(=O)c2ccnc(C(C)(C)F)c2)cc1-c1cnc2c(c1)N1CCOC[C@@H]1C[C@@H]2O] | 2-(2-fluoropropan-2-yl)-N-(3-((4aS,6S)-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.57 (s, 1H), 8.75 (d, J = 5.0 Hz, 1H), 8.02 (s, 1H), 7.91 (s, 1H), 7.82 (dd, J = 4.8, 0.8 Hz, 1H), 7.73 (dd, J = 8.0, 1.6 Hz, 1H), 7.66 (s, 1H), 7.32 (d, J = 8.3 Hz, 1H), 7.17 (s, 1H), 5.23 (d, J = 2.3 Hz, 1H), 4.77 (m, 1H), 3.91 (m, 1H), 3.85 (d, J = 8.0 Hz, 1H), 3.75 (d, J = 11.7 Hz, 1H), 3.57 (m, 1H), 3.26 (m, 2H), 2.72 (td, J = 12.0, 3.3 Hz, 1H), 2.24 (s, 3H), 2.15 (dd, J = 11.6, 6.5 Hz, 1H), 1.71 (d, J = 22.1 Hz, 6H), 1.59 (m, 1H). LCMS (m/z) (M + H) = 477.5, Rt = 0.97 min. |
|---|---|---|---|
| 144 | 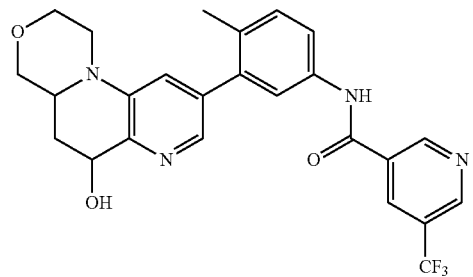 | rac-cis-N-(3-(6-hydroxy-1,2,4,4a,5,6-hexahydro-[1,4]oxazino[4,3-a][1,5]naphthyridin-9-yl)-4-methylphenyl)-5-(trifluoromethyl)nicotinamide | $^1$H NMR (400 MHz, DMSO-d$_6$) δ ppm 10.56 (s, 1H), 9.30 (s, 1H), 9.11 (s, 1H), 8.61 (s, 1H), 7.84 (s, 1H), 7.66 (d, J = 7.3 Hz, 1H), 7.58 (s, 1H), 7.27 (d, J = 8.2 Hz, 1H), 7.10 (s, 1H), 5.16 (s, 1H), 4.70 (br s, 1H), 3.81 (dd, J = 26.2, 8.8 Hz, 2H), 3.68 (d, J = 11 Hz, 1H), 3.49 (m, 2H), 2.65 (m, 1H), 2.17 (s, 3H), 2.08 (d, J = 6.9 Hz, 1H), 1.52 (d, J = 11.4 Hz, 1H). Signal for one aliphatic proton is hidden by solvent peak. LCMS (m/z) (M + H) = 485.1, Rt = 1.00 min. |
| 145 | 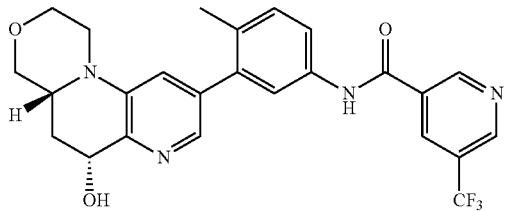 [SMILES: Cc1ccc(NC(=O)c2cncc(C(F)(F)F)c2)cc1-c1cnc2c(c1)N1CCOC[C@H]1C[C@H]2O] | N-(3-((4aR,6R)-6-hydroxy-1,2,4,4a,5,6-hexahydro-[1,4]oxazino[4,3-a][1,5]naphthyridin-9-yl)-4-methylphenyl)-5-(trifluoromethyl)nicotinamide | $^1$H NMR (400 MHz, DMSO-d$_6$) δ ppm 10.56 (s, 1H), 9.30 (s, 1H), 9.11 (s, 1H), 8.61 (s, 1H), 7.84 (s, 1H), 7.66 (d, J = 7.3 Hz, 1H), 7.58 (s, 1H), 7.27 (d, J = 8.2 Hz, 1H), 7.10 (s, 1H), 5.16 (s, 1H), 4.70 (br s, 1H), 3.81 (dd, J = 26.2, 8.8 Hz, 2H), 3.68 (d, J = 11 Hz, 1H), 3.49 (m, 2H), 2.65 (m, 1H), 2.17 (s, 3H), 2.08 (d, J = 6.9 Hz, 1H), 1.52 (d, J = 11.4 Hz, 1H). Signal for one aliphatic proton is hidden by solvent peak. LCMS (m/z) (M + H) = 485.1, Rt = 1.00 min. |
| 146 | 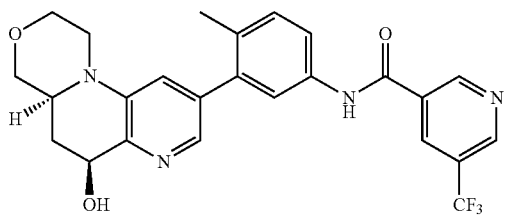 [SMILES: Cc1ccc(NC(=O)c2cncc(C(F)(F)F)c2)cc1-c1cnc2c(c1)N1CCOC[C@@H]1C[C@@H]2O] | N-(3-((4aS,6S)-6-hydroxy-1,2,4,4a,5,6-hexahydro-[1,4]oxazino[4,3-a][1,5]naphthyridin-9-yl)-4-methylphenyl)-5-(trifluoromethyl)nicotinamide | $^1$H NMR (400 MHz, DMSO-d$_6$) δ ppm 10.56 (s, 1H), 9.30 (s, 1H), 9.11 (s, 1H), 8.61 (s, 1H), 7.84 (s, 1H), 7.66 (d, J = 7.3 Hz, 1H), 7.58 (s, 1H), 7.27 (d, J = 8.2 Hz, 1H), 7.10 (s, 1H), 5.16 (s, 1H), 4.70 (br s, 1H), 3.81 (dd, J = 26.2, 8.8 Hz, 2H), 3.68 (d, J = 11 Hz, 1H), 3.49 (m, 2H), 2.65 (m, 1H), 2.17 (s, 3H), 2.08 (d, J = 6.9 Hz, 1H), 1.52 (d, J = 11.4 Hz, 1H). Signal for one aliphatic proton is hidden by solvent peak. LCMS (m/z) (M + H) = 485.1, Rt = 1.00 min. |
| 147 | 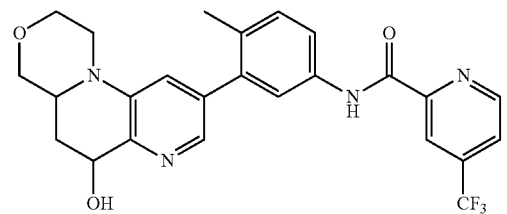 [SMILES: Cc1ccc(NC(=O)c2cc(C(F)(F)F)ccn2)cc1-c1cnc2c(c1)N1CCOCC1CC2O] | rac-cis-N-(3-(6-hydroxy-1,2,4,4a,5,6-hexahydro-[1,4]oxazino[4,3-a][1,5]naphthyridin-9-yl)-4-methylphenyl)-4-(trifluoromethyl)picolinamide | $^1$H NMR (400 MHz, DMSO-d$_6$) δ ppm 10.79 (br s, 1H), 9.03 (d, J = 5.0 Hz, 1H), 8.34 (s, 1H), 8.10 (d, J = 4.6 Hz, 1H), 7.93 (s, 1H), 7.87 (dd, J = 8.2, 2.0 Hz, 1H), 7.81 (d, J = 1.8 Hz, 1H), 7.32 (d, J = 8.3 Hz, 1H), 7.18 (s, 1H), 5.23 (s, 1H), 4.77 (m, 1H), 3.92 (d, J = 9.0 Hz, 1H), 3.85 (d, J = 8.0 Hz, 1H), 3.75 (d, J = 11.7 Hz, 1H), 3.57 (t, J = 10.5 Hz, 1H), 2.72 (td, J = 12.0, 3.3 Hz, 1H), 2.25 (s, 3H), 2.15 (dd, J = 11.6, 6.5 Hz, 1H), 1.60 (m, 1H). LCMS (m/z) (M + H) = 485.4, Rt = 1.06 min. |

| | | | |
|---|---|---|---|
| 148 | 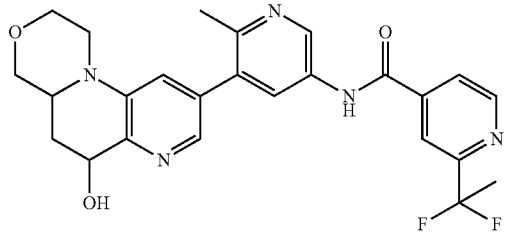 [SMILES: Cc1ncc(NC(=O)c2ccnc(C(C)(F)F)c2)cc1-c1cnc2c(c1)N1CCOCC1CC2O] | rac-cis-2-(1,1-difluoroethyl)-N-(5-(6-hydroxy-1,2,4,4a,5,6-hexahydro-[1,4]oxazino[4,3-a][1,5]naphthyridin-9-yl)-6-methylpyridin-3-yl)isonicotinamide | $^1$H NMR (400 MHz, DMSO-d$_6$) δ ppm 10.78 (s, 1H), 8.84 (d, J = 4.6 Hz, 1H), 8.80 (s, 1H), 8.14 (s, 1H), 7.98 (s, 2H), 7.89 (s, 1H), 7.18 (s, 1H), 5.20 (d, J = 2.9 Hz, 1H), 4.70 (br s, 1H), 3.85 (d, J = 10.4 Hz, 1H), 3.79 (d, J = 7.3 Hz, 1H), 3.70 (d, J = 12.0 Hz, 1H), 3.49 (t, J = 10.8 Hz, 1H), 3.21 (m, 1H), 2.66 (t, J = 10.6 Hz, 1H), 2.37 (s, 3H), 2.08 (m, 2H), 1.99 (t, J = 19.1 Hz, 3H), 1.53 (q, J = 10.4, 9.7 Hz, 1H). LCMS (m/z) (M + H) = 482.3, Rt = 0.80 min. |
| 149 | 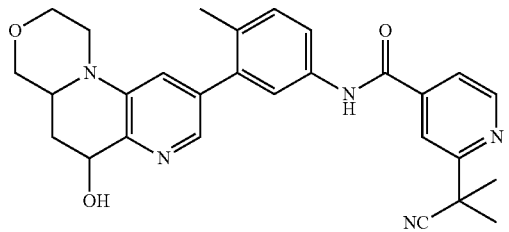 [SMILES: Cc1ccc(NC(=O)c2ccnc(C(C)(C)C#N)c2)cc1-c1cnc2c(c1)N1CCOCC1CC2O] | rac-cis-2-(2-cyanopropan-2-yl)-N-(3-(6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.56 (s, 1H), 8.81 (d, J = 5.0 Hz, 1H), 8.00 (s, 1H), 7.91 (d, J = 1.3 Hz, 1H), 7.86 (dd, J = 5.0, 1.2 Hz, 1H), 7.71 (dd, J = 8.2, 2.0 Hz, 1H), 7.64 (d, J = 1.9 Hz, 1H), 7.33 (d, J = 8.4 Hz, 1H), 7.17 (d, J = 1.2 Hz, 1H), 5.23 (d, J = 3.5 Hz, 1H), 4.77 (m, 1H), 3.92 (dd, J = 11.3, 2.6 Hz, 1H), 3.85 (d, J = 8.0 Hz, 1H), 3.75 (d, J = 11.7 Hz, 1H), 3.56 (td, J = 11.6, 2.4 Hz, 1H), 3.25 (m, 2H), 2.71 (td, J = 12.0, 3.4 Hz, 1H), 2.24 (s, 3H), 1.77 (s, 6H), 1.59 (m, 1H). LCMS (m/z) (M + H) = 484.5, Rt = 0.95 min. |
| 150 | 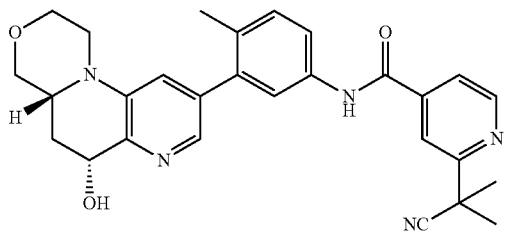 [SMILES: Cc1ccc(NC(=O)c2ccnc(C(C)(C)C#N)c2)cc1-c1cnc2c(c1)N1CCOC[C@H]1C[C@H]2O] | 2-(2-cyanopropan-2-yl)-N-(3-((4aR,6R)-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.56 (s, 1H), 8.81 (d, J = 5.0 Hz, 1H), 8.00 (s, 1H), 7.91 (d, J = 1.3 Hz, 1H), 7.86 (dd, J = 5.0, 1.2 Hz, 1H), 7.71 (dd, J = 8.2, 2.0 Hz, 1H), 7.64 (d, J = 1.9 Hz, 1H), 7.33 (d, J = 8.4 Hz, 1H), 7.17 (d, J = 1.2 Hz, 1H), 5.23 (d, J = 3.5 Hz, 1H), 4.77 (m, 1H), 3.92 (dd, J = 11.3, 2.6 Hz, 1H), 3.85 (d, J = 8.0 Hz, 1H), 3.75 (d, J = 11.7 Hz, 1H), 3.56 (td, J = 11.6, 2.4 Hz, 1H), 3.25 (m, 2H), 2.71 (td, J = 12.0, 3.4 Hz, 1H), 2.24 (s, 3H), 1.77 (s, 6H), 1.59 (m, 1H). LCMS (m/z) (M + H) = 484.5, Rt = 0.95 min. |
| 151 | 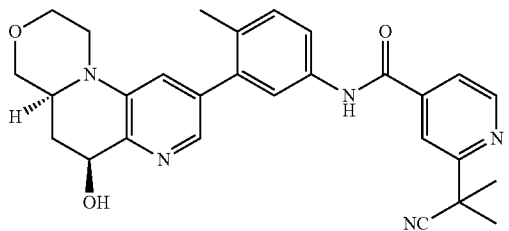 [SMILES: Cc1ccc(NC(=O)c2ccnc(C(C)(C)C#N)c2)cc1-c1cnc2c(c1)N1CCOC[C@@H]1C[C@@H]2O] | 2-(2-cyanopropan-2-yl)-N-(3-((4aS,6S)-6-hydroxy-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.56 (s, 1H), 8.81 (d, J = 5.0 Hz, 1H), 8.00 (s, 1H), 7.91 (d, J = 1.3 Hz, 1H), 7.86 (dd, J = 5.0, 1.2 Hz, 1H), 7.71 (dd, J = 8.2, 2.0 Hz, 1H), 7.64 (d, J = 1.9 Hz, 1H), 7.33 (d, J = 8.4 Hz, 1H), 7.17 (d, J = 1.2 Hz, 1H), 5.23 (d, J = 3.5 Hz, 1H), 4.77 (m, 1H), 3.92 (dd, J = 11.3, 2.6 Hz, 1H), 3.85 (d, J = 8.0 Hz, 1H), 3.75 (d, J = 11.7 Hz, 1H), 3.56 (td, J = 11.6, 2.4 Hz, 1H), 3.25 (m, 2H), 2.71 (td, J = 12.0, 3.4 Hz, 1H), 2.24 (s, 3H), 1.77 (s, 6H), 1.59 (m, 1H). LCMS (m/z) (M + H) = 484.5, Rt = 0.95 min. |
| 152 | 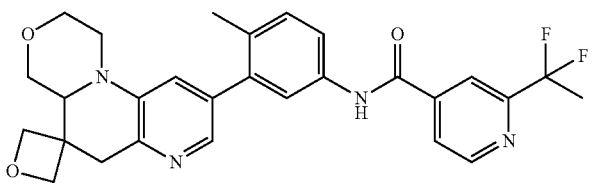 [SMILES: Cc1ccc(NC(=O)c2ccnc(C(C)(F)F)c2)cc1-c1cnc2c(c1)N1CCOCC1C1(COC1)C2] | rac-2-(1,1-difluoroethyl)-N-(4-methyl-3-(2,4,4a,6-tetrahydro-1H-spiro[[1,4]oxazino[4,3-a][1,5]naphthyridine-5,3'-oxetan]-9-yl)phenyl)isonicotinamide | $^1$H NMR (400 MHz DMSO-d$_6$) δ ppm 10.61 (s, 1H), 8.88 (d, J = 5.0 Hz, 1H), 8.18 (s, 1H), 8.02 (d, J = 4.7 Hz, 1H), 7.85 (d, J = 1.0 Hz, 1H), 7.72 (dd, J = 8.2, 2.0 Hz, 1H), 7.65 (d, J = 1.9 Hz, 1H), 7.32 (d, J = 8.4 Hz, 1H), 7.20 (d, J = 1.2 Hz, 1H), 4.57 (dd, J = 20.1, 6.3 Hz, 2H), 4.33 (dd, J = 13.9, 6.3 Hz, 2H), 4.22 (dd, J = 11.2, 2.7 Hz, 1H), 3.86 (d, J = 11.1 Hz, 2H), 3.69 (t, J = 11.0 Hz, 1H), 3.57 (t, J = 10.6 Hz, 1H), 3.43 (dd, J = 10.7, 2.9 Hz, 1H), 3.21 (s, 2H), 2.93 (td, J = 12.6, 3.4 Hz, 1H), 2.22 (s, 3H), 2.05 (t, J = 19.1 Hz, 3H). LCMS (m/z) (M + H) = 507.5, Rt = 0.98 min. |

| # | Structure | Name | Data |
|---|---|---|---|
| 153 | 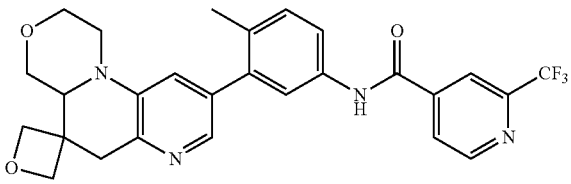 [SMILES: Cc1ccc(NC(=O)c2ccnc(C(F)(F)F)c2)cc1-c1cnc2c(c1)N1CCOCC1C1(COC1)C2] | rac-2-(1,1-difluoroethyl)-N-(4-methyl-3-(2,4,4a,6-tetrahydro-1H-spiro[[1,4]oxazino[4,3-a][1,5]naphthyridine-5,3'-oxetan]-9-yl)phenyl)isonicotinamide | 1H NMR (400 MHz, DMSO-d$_6$) δ ppm 10.78 (s, 1H), 9.00 (d, J = 4.9 Hz, 1H), 8.36 (s, 1H), 8.19 (d, J = 4.8 Hz, 1H), 8.13 (s, 1H), 7.76 (d, J = 1.7 Hz, 1H), 7.72 (m, 2H), 7.39 (d, J = 8.3 Hz, 1H), 4.61 (d, J = 6.5 Hz, 2H), 4.55 (d, J = 6.5 Hz, 2H), 4.39 (dd, J = 6.4, 2.3 Hz, 2H), 4.20 (d, J = 9.1 Hz, 1H), 4.04 (d, J = 12.6 Hz, 1H) 3.88 (d, J = 11.1 Hz, 1H), 3.67 (m, 2H), 3.57 (m, 1H), 3.08 (td, J = 12.6, 3.1 Hz, 1H), 2.25 (s, 3H). LCMS (m/z) (M + H) = 511.3, Rt = 1.00 min. |
| 154 | 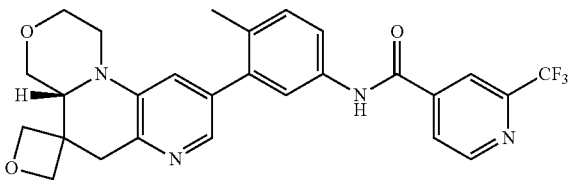 [SMILES: Cc1ccc(NC(=O)c2ccnc(C(F)(F)F)c2)cc1-c1cnc2c(c1)N1CCOC[C@H]1C1(COC1)C2] | (R)-N-(4-methyl-3-(1',2',4',4a'-tetrahydro-6'H-spiro[oxetane-3,5'-[1,4]oxazino[4,3-a][1,5]naphthyridin]-9'-yl)phenyl)-2-(trifluoromethyl)isonicotinamide | $^1$H NMR (400 MHz, DMSO-d$_6$) δ ppm 10.78 (s, 1H), 9.00 (d, J = 4.9 Hz, 1H), 8.36 (s, 1H), 8.19 (d, J = 4.8 Hz, 1H), 8.13 (s, 1H), 7.76 (d, J = 1.7 Hz, 1H), 7.72 (m, 2H), 7.39 (d, J = 8.3 Hz, 1H), 4.61 (d, J = 6.5 Hz, 2H), 4.55 (d, J = 6.5 Hz, 2H), 4.39 (dd, J = 6.4, 2.3 Hz, 2H), 4.20 (d, J = 9.1 Hz, 1H), 4.04 (d, J = 12.6 Hz, 1H) 3.88 (d, J = 11.1 Hz, 1H), 3.67 (m, 2H), 3.57 (m, 1H), 3.08 (td, J = 12.6, 3.1 Hz, 1H), 2.25 (s, 3H). LCMS (m/z) (M + H) = 511.3, Rt = 1.00 min. |
| 155 | 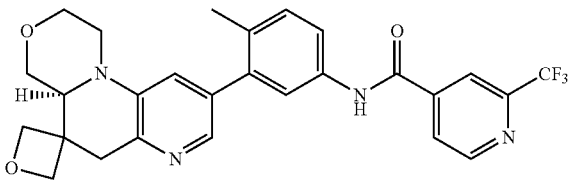 [SMILES: Cc1ccc(NC(=O)c2ccnc(C(F)(F)F)c2)cc1-c1cnc2c(c1)N1CCOC[C@@H]1C1(COC1)C2] | (S)-N-(4-methyl-3-(1',2',4',4a'-tetrahydro-6'H-spiro[oxetane-3,5'-[1,4]oxazino[4,3-a][1,5]naphthyridin]-9'-yl)phenyl)-2-(trifluoromethyl)isonicotinamide | $^1$H NMR (400 MHz, DMSO-d$_6$) δ ppm 10.78 (s, 1H), 9.00 (d, J = 4.9 Hz, 1H), 8.36 (s, 1H), 8.19 (d, J = 4.8 Hz, 1H), 8.13 (s, 1H), 7.76 (d, J = 1.7 Hz, 1H), 7.72 (m, 2H), 7.39 (d, J = 8.3 Hz, 1H), 4.61 (d, J = 6.5 Hz, 2H), 4.55 (d, J = 6.5 Hz, 2H), 4.39 (dd, J = 6.4, 2.3 Hz, 2H), 4.20 (d, J = 9.1 Hz, 1H), 4.04 (d, J = 12.6 Hz, 1H) 3.88 (d, J = 11.1 Hz, 1H), 3.67 (m, 2H), 3.57 (m, 1H), 3.08 (td, J = 12.6, 3.1 Hz, 1H), 2.25 (s, 3H). LCMS (m/z) (M + H) = 511.3, Rt = 1.00 min. |
| 156 | 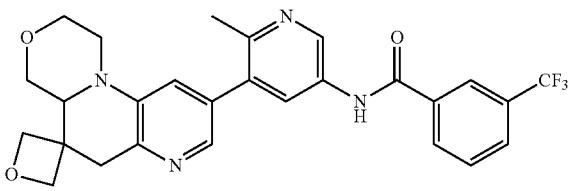 [SMILES: Cc1ncc(NC(=O)c2cccc(C(F)(F)F)c2)cc1-c1cnc2c(c1)N1CCOCC1C1(COC1)C2] | rac-N-(6-methyl-5-(2,4,4a,6-tetrahydro-1H-spiro[[1,4]oxazino[4,3-a][1,5]naphthyridine-5,3'-oxetan]-9-yl)pyridin-3-yl)-3-(trifluoromethyl)benzamide | $^1$H NMR (400 MHz, DMSO-d$_6$) δ ppm 10.65 (s, 1H), 8.85 (d, J = 2.4 Hz, 1H), 8.32 (s, 1H), 8.28 (d, J = 8.0 Hz, 1H) 8.03 (d, J = 2.4 Hz, 1H), 8.00 (d, J = 7.8 Hz, 1H), 7.89 (d, J = 1.7 Hz, 1H), 7.81 (t, J = 7.8 Hz, 1H), 7.28 (d, J = 1.7 Hz, 1H), 4.59 (d, J = 6.3 Hz, 1H), 4.54 (d, J = 6.3 Hz, 1H), 4.34 (d, J = 6.4 Hz, 1H), 4.31 (d, J = 6.3 Hz, 1H), 4.22 (dd, J = 11.3, 3.0 Hz, 1H), 3.89 (d, J = 4.4 Hz, 1H), 3.86 (d, J = 3.8 Hz, 1H), 3.68 (t, J = 11.0 Hz, 1H), 3.57 (td, J = 11.8, 2.5 Hz, 1H), 3.45 (dd, J = 10.7, 3.1 Hz, 1H), 3.21 (s, 2H), 2.94 (m, 1H), 2.42 (s, 3H). LCMS (m/z) (M + H) = 511.4, Rt = 0.91 min. |
| 157 | 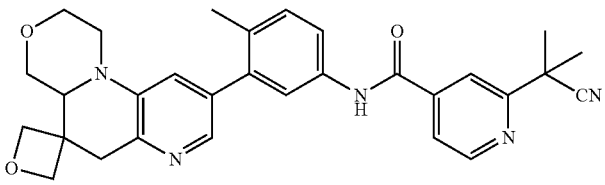 [SMILES: Cc1ccc(NC(=O)c2ccnc(C(C)(C)C#N)c2)cc1-c1cnc2c(c1)N1CCOCC1C1(COC1)C2] | rac-2-(2-cyanopropan-2-yl)-N-(4-methyl-3-(2,4,4a,6-tetrahydro-1H-spiro[[1,4]oxazino[4,3-a][1,5]naphthyridine-5,3'-oxetan]-9-yl)phenyl)isonicotinamide | $^1$H NMR (400 MHz, DMSO-d$_6$) δ ppm 10.52 (s, 1H), 8.80 (d, J = 5.1 Hz, 1H), 7.99 (s, 1H), 7.85 (m, 2H), 7.70 (dd, J = 8.2, 2.2 Hz, 1H), 7.62 (d, J = 2.1 Hz, 1H), 7.32 (d, J = 8.5 Hz, 1H), 7.19 (d, J = 1.6 Hz, 1H), 4.59 (d, J = 6.2 Hz, 1H), 4.54 (d, J = 6.3 Hz, 1H), 4.34 (d, J = 6.4 Hz, 1H), 4.30 (d, J = 6.3 Hz, 1H), 4.21 (m, 1H), 3.87 (s, 1H), 3.85 (s, 1H), 3.68 (t, J = 11.0 Hz, 1H), 3.57 (td, J = 11.8, 2.5 Hz, 1H), 3.43 (dd, J = 10.5, 2.9 Hz, 1H), 3.20 (s, 2H), 2.92 (m, 1H), 2.22 (s, 3H), 1.76 (s, 6H). LCMS (m/z) (M + H) = 510.5, Rt = 0.96 min. |

| | | | |
|---|---|---|---|
| 158 | (structure) | rac-N-(3-(5,5-bis(hydroxymethyl)-yl)-1,2,4,4a,5,6-hexahydro-[1,4]oxazino[4,3-a][1,5]naphthyridin-9-yl)-4-methylphenyl)-2-(1,1-difluoroethyl)isonicotinamide | ¹H NMR (400 MHz, DMSO-d₆) δ ppm 10.55 (s, 1H), 8.81 (d, J = 4.8 Hz, 1H), 8.11 (s, 1H), 7.96 (d, J = 4.5 Hz, 1H), 7.74 (s, 1H), 7.65 (d, J = 6.5 Hz, 1H), 7.58 (s, 1H), 7.25 (d, J = 8.3 Hz, 1H), 7.12 (s, 1H), 4.63 (s, 1H), 4.51 (s, 1H), 3.91 (d, J = 8.8 Hz, 1H), 3.83 (d, J = 12.4 Hz, 1H), 3.71 (d, J = 9.3 Hz, 1H), 2.83 (t, J = 10.9 Hz, 1H), 2.67 (m, 2H), 3.36 (m, 6H), 2.17 (s, 3H), 1.98 (t, J = 19.1 Hz, 3H). Signal for one aliphatic proton is hidden under solvent peak. LCMS (m/z) (M + H) = 525.4, Rt = 0.93 min. |
| 159 | (structure) | rac-N-(3-(5,5-bis(hydroxymethyl)-1,2,4,4a,5,6-hexahydro-[1,4]oxazino[4,3-a][1,5]naphthyridin-9-yl)-4-methylphenyl)-4-(trifluoromethyl)picolinamide | ¹H NMR (400 MHz, DMSO-d₆) δ ppm 10.86 (s, 1H), 9.04 (d, J = 5.0 Hz, 1H), 8.34 (s, 1H), 8.11 (d, J = 3.6 Hz, 2H), 7.91 (m, 2H), 7.78 (s, 1H), 7.38 (d, J = 8.3 Hz, 1H), 4.11 (d, J = 12.8 Hz, 1H), 4.02 (d, J = 8.9 Hz, 1H), 3.82 (m, 1H), 3.47 (m, 8H), 3.09 (m, 2H), 2.92 (m, 2H), 2.27 (s, 3H). Eight aliphatic proton signals appear to overlap with water peak. LCMS (m/z) (M + H) = 529.4, Rt = 1.02 min. |
| 160 | (structure) | rac-cis-2-(1,1-difluoroethyl)-N-(3-(6-hydroxy-5,5-dimethyl-1,2,4,4a,5,6-hexahydro-[1,4]oxazino[4,3-a][1,5]naphthyridin-9-yl)-4-methylphenyl)isonicotinamide | ¹H NMR (400 MHz, DMSO-d₆) δ ppm 10.62 (s, 1H), 8.88 (d, J = 5.0 Hz, 1H), 8.18 (s, 1H), 8.03 (d, J = 5.0 Hz, 1H), 7.90 (d, J = 1.5 Hz, 1H), 7.74 (dd, J =+) 8.3, 2.2 Hz, 1H), 7.67 (d, J = 2.2 Hz, 1H), 7.33 (d, J = 8.4 Hz, 1H), 7.24 (d, J = 1.4 Hz, 1H), 5.04 (s, 1H), 4.33 (s, 1H), 3.97 (dd, J = 11.2, 2.9 Hz, 1H), 3.88 (dd, J = 11.5, 2.4 Hz, 2H), 3.50 (q, J = 10.8, 9.9 Hz, 2H), 3.08 (dd, J = 10.6, 3.1 Hz, 1H), 2.85 (td, J = 12.3, 3.6 Hz, 1H), 2.24 (s, 3H), 2.05 (t, J = 19.1 Hz, 3H), 1.08 (s, 3H), 0.81 (s, 3H). LCMS (m/z) (M + H) = 509.5, Rt = 1.03 min. |
| 161 | (structure) | 2-(1,1-difluoroethyl)-N-(3-((4aR,6R)-6-hydroxy-5,5-dimethyl-1,2,4,4a,5,6-hexahydro-[1,4]oxazino[4,3-a][1,5]naphthyridin-9-yl)-4-methylphenyl)isonicotinamide | ¹H NMR (400 MHz, DMSO-d₆) δ ppm 10.62 (s, 1H), 8.88 (d, J = 5.0 Hz, 1H), 8.18 (s, 1H), 8.03 (d, J = 5.0 Hz, 1H), 7.90 (d, J = 1.5 Hz, 1H), 7.74 (dd, J = 8.3, 2.2 Hz, 1H), 7.67 (d, J = 2.2 Hz, 1H), 7.33 (d, J = 8.4 Hz, 1H), 7.24 (d, J = 1.4 Hz, 1H), 5.04 (s, 1H), 4.33 (s, 1H), 3.97 (dd, J = 11.2, 2.9 Hz, 1H), 3.88 (dd, J = 11.5, 2.4 Hz, 2H), 3.50 (q, J = 10.8, 9.9 Hz, 2H), 3.08 (dd, J = 10.6, 3.1 Hz, 1H), 2.85 (td, J = 12.3, 3.6 Hz, 1H), 2.24 (s, 3H), 2.05 (t, J = 19.1 Hz, 3H), 1.08 (s, 3H), 0.81 (s, 3H). LCMS (m/z) (M + H) = 509.5, Rt = 1.03 min. |
| 162 | (structure) | N-(3-((4aR,6R)-5,5-difluoro-6-hydroxy-1,2,4,4a,5,6-hexahydro-[1,4]oxazino[4,3-a][1,5]naphthyridin-9-yl)-4-methylphenyl)-2-(1,1-difluoroethyl)isonicotinamide | ¹H NMR (400 MHz, DMSO-d₆) δ ppm 10.62 (s, 1H), 8.88 (d, J = 5.0 Hz, 1H), 8.18 (s, 1H), 8.03 (d, J = 5.0 Hz, 1H), 7.90 (d, J = 1.5 Hz, 1H), 7.74 (dd, J = 8.3, 2.2 Hz, 1H), 7.67 (d, J = 2.2 Hz, 1H), 7.33 (d, J = 8.4 Hz, 1H), 7.24 (d, J = 1.4 Hz, 1H), 5.04 (s, 1H), 4.33 (s, 1H), 3.97 (dd, J = 11.2, 2.9 Hz, 1H), 3.88 (dd, J = 11.5, 2.4 Hz, 2H), 3.50 (q, J = 10.8,. 9.9 Hz, 2H), 3.08 (dd, J = 10.6, 3.1 Hz, 1H), 2.85 (td, J = 12.3, 3.6 Hz, 1H), 2.24 (s, 3H), 2.05 (t, J = 19.1 Hz, 3H), 1.08 (s, 3H), 0.81 (s, 3H). LCMS (m/z) (M + H) = 509.5, Rt = 1.03 min. |

-continued

| | | | |
|---|---|---|---|
| 163 | 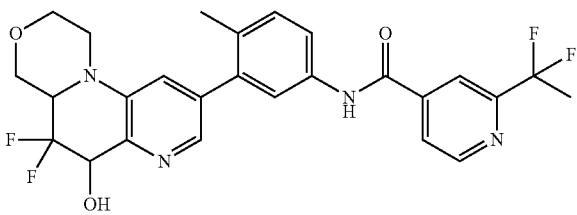 | rac-cis-N-(3-(5,5-difluoro-6-hydroxy-1,2,4,4a,5,6-hexahydro-[1,4]oxazino[4,3-a][1,5]naphthyridin-9-yl)-4-methylphenyl)-2-(1,1-difluoroethyl)isonicotinamide | $^1$H NMR (400 MHz, DMSO-d$_6$) δ ppm 10.65 (s, 1H), 8.88 (d, J = 5.1 Hz, 1H), 8.17 (s, 1H), 8.03 (m, 2H), 7.74 (dd, J = 8.3, 2.1 Hz, 1H), 7.68 (d, J = 2.0 Hz, 1H), 7.35 (d, J = 8.4 Hz, 1H), 7.31 (d, J = 1.4 Hz, 1H), 6.17 (br s, 1H), 4.99 (m, 1H), 4.09 (d, J = 8.0 Hz, 1H), 3.94 (d, J = 8.7 Hz, 1H), 3.88 (d, J = 11.8 Hz, 1H), 3.79 (m, 1H), 3.68 (t, J = 10.7 Hz, 1H), 3.58 (m, 1H), 2.86 (m, 1H), 2.24 (s, 3H), 2.05 (t, J = 19.1 Hz, 3H). LCMS (m/z) (M + H) = 517.4, Rt = 1.10 min. |
| 164 | 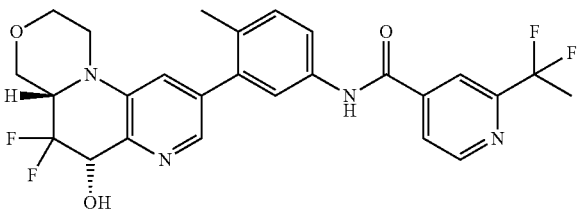 | N-(3-((4aS,6S)-5,5-difluoro-6-hydroxy-1,2,4,4a,5,6-hexahydro-[1,4]oxazino[4,3-a][1,5]naphthyridin-9-yl)-4-methylphenyl)-2-(1,1-difluoroethyl)isonicotinamide | $^1$H NMR (400 MHz, DMSO-d$_6$) δ ppm 10.65 (s, 1H), 8.88 (d, J = 5.1 Hz, 1H), 8.17 (s, 1H), 8.03 (m, 2H), 7.74 (dd, J = 8.3, 2.1 Hz, 1H), 7.68 (d, J = 2.0 Hz, 1H), 7.35 (d, J = 8.4 Hz, 1H), 7.31 (d, J = 1.4 Hz, 1H), 6.17 (br s, 1H), 4.99 (m, 1H), 4.09 (d, J = 8.0 Hz, 1H), 3.94 (d, J = 8.7 Hz, 1H), 3.88 (d, J = 11.8 Hz, 1H), 3.79 (m, 1H), 3.68 (t, J = 10.7 Hz, 1H), 3.58 (m, 1H), 2.86 (m, 1H), 2.24 (s, 3H), 2.05 (t, J = 19.1 Hz, 3H). LCMS (m/z) (M + H) = 517.4, Rt = 1.10 min. |
| 165 | 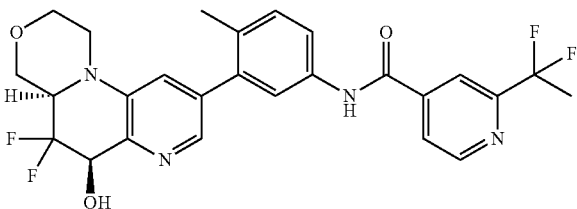 [SMILES: Cc1ccc(NC(=O)c2ccnc(C(C)(F)F)c2)cc1-c1cnc2c(c1)N1CCOC[C@@H]1C(F)(F)[C@@H]2O] | N-(3-((4aR,6R)-5,5-difluoro-6-hydroxy-1,2,4,4a,5,6-hexahydro-[1,4]oxazino[4,3-a][1,5]naphthyridin-9-yl)-4-methylphenyl)-2-(1,1-difluoroethyl)isonicotinamide | $^1$H NMR (400 MHz, DMSO-d$_6$) δ ppm 10.65 (s, 1H), 8.88 (d, J = 5.1 Hz, 1H), 8.17 (s, 1H), 8.03 (m, 2H), 7.74 (dd, J = 8.3, 2.1 Hz, 1H), 7.68 (d, J = 2.0 Hz, 1H), 7.35 (d, J = 8.4 Hz, 1H), 7.31 (d, J = 1.4 Hz, 1H), 6.17 (br s, 1H), 4.99 (m, 1H), 4.09 (d, J = 8.0 Hz, 1H), 3.94 (d, J = 8.7 Hz, 1H), 3.88 (d, J = 11.8 Hz, 1H), 3.79 (m, 1H), 3.68 (t, J = 10.7 Hz, 1H), 3.58 (m, 1H), 2.86 (m, 1H), 2.24 (s, 3H), 2.05 (t, J = 19.1 Hz, 3H). LCMS (m/z) (M + H) = 517.4, Rt = 1.10 min. |
| 166 | 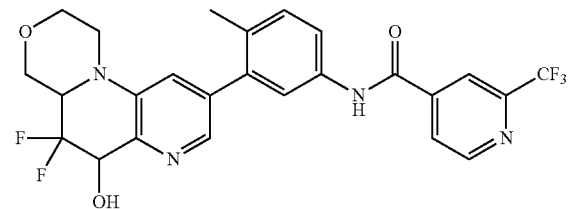 [SMILES: Cc1ccc(NC(=O)c2ccnc(C(F)(F)F)c2)cc1-c1cnc2c(c1)N1CCOCC1C(F)(F)C2O] | rac-cis-N-(3-(5,5-difluoro-6-hydroxy-1'2'4'4a'5'6-hexahydro-[1,4]oxazino[4,3-a][1,5]naphthyridin-9-yl)-4-methylphenyl)-2-(trifluoromethyl)isonicotinamide | $^1$H NMR (400 MHz, DMSO-d$_6$) δ ppm 10.70 (s, 1H), 8.99 (d, J = 4.9 Hz, 1H), 8.36 (s, 1H), 8.19 (d, J = 4.8 Hz, 1H), 8.04 (d, J = 1.4 Hz, 1H), 7.73 (dd, J = 8.3, 2.1 Hz, 1H), 7.68 (d, J = 2.1 Hz, 1H), 7.36 (d, J = 8.4 Hz, 1H), 7.31 (s, 1H), 6.16 (s, 1H), 4.99 (m, 1H), 4.09 (d, J = 8.5 Hz, 1H), 3.94 (m, 1H), 3.88 (d, J = 12.0 Hz, 1H), 3.78 (m, 1H), 3.68 (t, J = 10.8 Hz, 1H), 3.58 (t, J = 10.6 Hz, 1H), 2.86 (m, 1H), 2.24 (s, 3H). LCMS (m/z) (M + H) = 521.4, Rt = 1.13 min. |
| 167 | 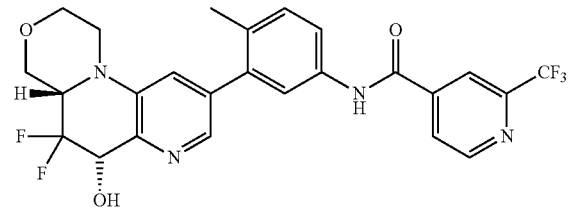 | N-(3-((4aS,6S)-5,5-difluoro-6-hydroxy-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, DMSO-d$_6$) δ ppm 10.70 (s, 1H), 8.99 (d, J = 4.9 Hz, 1H), 8.36 (s, 1H), 8.19 (d, J = 4.8 Hz, 1H), 8.04 (d, J = 1.4 Hz, 1H), 7.73 (dd, J = 8.3, 2.1 Hz, 1H), 7.68 (d, J = 2.1 Hz, 1H), 7.36 (d, J = 8.4 Hz, 1H), 7.31 (s, 1H), 6.16 (s, 1H), 4.99 (m, 1H), 4.09 (d, J = 8.5 Hz, 1H), 3.94 (m, 1H), 3.88 (d, J = 12.0 Hz, 1H), 3.78 (m, 1H), 3.68 (t, J = 10.8 Hz, 1H), 3.58 (t, J = 10.6 Hz, 1H), 2.86 (m, 1H), 2.24 (s, 3H). LCMS (m/z) (M + H) = 521.4, Rt = 1.13 min. |

| | | | |
|---|---|---|---|
| 168 | 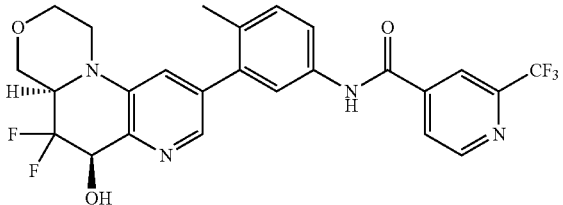 [SMILES: Cc1ccc(NC(=O)c2ccnc(C(F)(F)F)c2)cc1-c1cnc2c(c1)N1CCOC[C@@H]1C(F)(F)[C@@H]2O] | N-(3-((4aR,6R)-5,5-difluoro-6-hydroxy-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, DMSO-d$_6$) δ ppm 10.70 (s, 1H), 8.99 (d, J = 4.9 Hz, 1H), 8.36 (s, 1H), 8.19 (d, J = 4.8 Hz, 1H), 8.04 (d, J = 1.4 Hz, 1H), 7.73 (dd, J = 8.3, 2.1 Hz, 1H), 7.68 (d, J = 2.1 Hz, 1H), 7.36 (d, J = 8.4 Hz, 1H), 7.31 (s, 1H), 6.16 (s, 1H), 4.99 (m, 1H), 4.09 (d, J = 8.5 Hz, 1H), 3.94 (m, 1H), 3.88 (d, J = 12.0 Hz, 1H), 3.78 (m, 1H), 3.68 (t, J = 10.8 Hz, 1H), 3.58 (t, J =10.6 Hz, 1H), 2.86 (m, 1H), 2.24 (s, 3H). LCMS (m/z) (M + H) = 521.4, Rt = 1.13 min. |
| 169 | 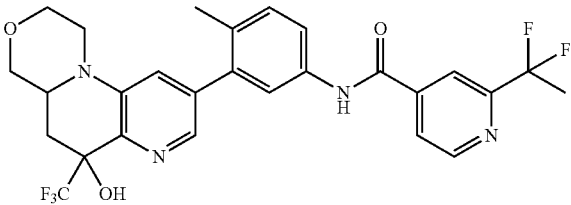 [SMILES: Cc1ccc(NC(=O)c2ccnc(C(C)(F)F)c2)cc1-c1cnc2c(c1)N1CCOCC1CC2(O)C(F)(F)F] | rac-cis-2-(1,1-difluoroethyl)-N-(3-(6-hydroxy-6-(trifluoromethyl)-1,2,4,4a,5,6-hexahydro-[1,4]oxazino[4,3-a][1,5]naphthyridin-9-yl)-4-methylphenyl)isonicotinamide | $^1$H NMR (400 MHz, DMSO-d$_6$) δ ppm 10.63 (s, 1H), 8.88 (d, J = 5.0 Hz, 1H), 8.18 (s, 1H), 8.03 (d, J = 4.9 Hz, 1H), 7.98 (d, J = 1.5 Hz, 1H), 7.76 (dd, J = 8.3, 2.1 Hz, 1H), 7.68 (d, J = 2.1 Hz, 1H), 7.35 (d, J = 9.2 Hz, 2H), 6.42 (br s, 1H), 3.93 (m, 3H), 3.55 (m, 1H), 3.21 (m, 2H), 2.79 (m, 1H), 2.38 (m, 1H), 2.25 (s, 3H), 2.05 (t, J = 19.1 Hz, 3H), 1.80 (m, 1H). LCMS (m/z) (M + H) = 549.1, Rt = 1.42 min. |
| 170 | 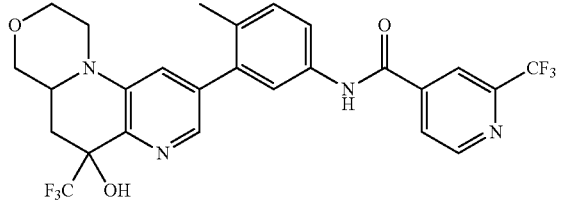 [SMILES: Cc1ccc(NC(=O)c2ccnc(C(F)(F)F)c2)cc1-c1cnc2c(c1)N1CCOCC1CC2(O)C(F)(F)F] | rac-cis-N-(3-(6-hydroxy-6-(trifluoromethyl)-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, DMSO-d$_6$) δ ppm 10.67 (s, 1H), 9.00 (d, J = 5.0 Hz, 1H), 8.36 (s, 1H), 8.19 (d, J = 5.0 Hz, 1H), 7.98 (d, J = 1.6 Hz, 1H), 7.75 (dd, J = 8.3, 2.3 Hz, 1H), 7.68 (d, J = 2.2 Hz, 1H), 7.36 (d, J = 8.4 Hz, 1H), 7.34 (d, J = 1.6 Hz, 1H), 6.42 (s, 1H), 3.93 (m, 3H), 3.55 (m, 1H), 3.22 (m, 2H), 2.80 (m, 1H), 2.38 (m, 1H), 2.25 (s, 3H), 1.81 (m, 1H). LCMS (m/z) (M + H) = 553.1, Rt = 1.46 min. |
| 171 | 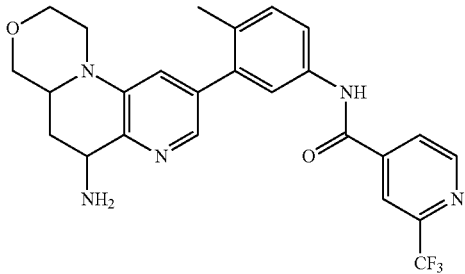 [SMILES: Cc1ccc(NC(=O)c2ccnc(C(F)(F)F)c2)cc1-c1cnc2c(c1)N1CCOCC1CC2N] | rac-N-(3-(6-amino-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, DMSO-d$_6$) δ ppm 10.68 (s, 1H), 8.99 (d, J = 5.0 Hz, 1H), 8.36 (s, 1H), 8.19 (d, J = 4.9 Hz, 1H), 7.95-7.83 (m, 1H), 7.71 (dd, J = 8.2, 2.1 Hz, 1H), 7.66 (d, J = 2.0 Hz, 1H), 7.34 (d, J = 8.3 Hz, 1H), 7.19 (d, J = 16.7 Hz, 1H),4.01-3.90 (m, 2H), 3.86 (dd, J = 16.6, 7.5 Hz, 1H), 3.77 (s, 1H), 3.62-3.51 (m, 1H), 3.24 (dd, J = 13.5, 7.2 Hz, 2H), 2.75 (td, J = 12.1, 3.5 Hz, 1H), 2.24 (s, 3H), 1.81-1.61 (m, 1H). Signal for two exchangeable protons of amine are not observed, signal for one aliphatic proton is hidden under solvent peak. LCMS (m/z) (M + H) = 484.1, Rt = 1.02 min. |
| 172 | 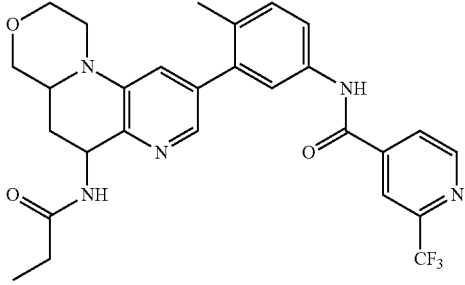 [SMILES: CCC(=O)NC1CC2COCCN2c2cc(-c3cc(NC(=O)c4ccnc(C(F)(F)F)c4)ccc3C)cnc21] | rac-N-(4-methyl-3-(6-propionamido-1,2,4,4a,5,6-hexahydro-[1,4]oxazino[4,3-a][1,5]naphthyridin-9-yl)phenyl)-2-(trifluoromethyl)isonicotinamide | $^1$H NMR (400 MHz, DMSO-d$_6$) δ ppm 10.69 (s, 1H), 8.99 (d, J = 4.9 Hz, 1H), 8.35 (s, 1H), 8.27 (d, J = 7.5 Hz, 1H), 8.19 (d, J = 4.6 Hz, 1H), 7.91 (d, J = 5.2 Hz, 1H), 7.70 (s, 1H), 7.68 (d, J = 8.5 Hz, 1H), 7.35 (d, J = 8.2 Hz, 1H), 7.29 (s, 1H), 5.00 (m, 1H), 3.89 (m, 3H), 3.57 (q, J = 12.0 11.0 Hz, 1H), 3.22 (dd, ,J = 10.8, 6.3 Hz, 1H), 3.11 (t, J = 10.8 Hz, 1H), 2.77 (m, 1H), 2.25 (s, 3H), 2.13 (dq, J = 22.6, 7.5 Hz, 2H), 1.80 (d, J = 13.4 Hz, 1H), 1.64 (m, 1H), 1.03 (dt, J = 11.0, 7.6 Hz, 3H). LCMS (m/z) (M + H) = 540.4, Rt = 1.04 min. |

| | | |
|---|---|---|
| 173 | 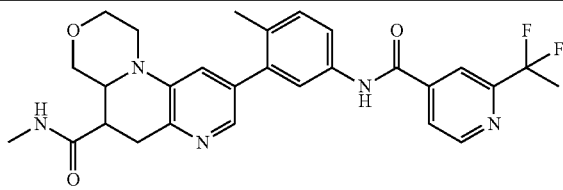 | rac-9-(5-(2-(1,1-difluoroethyl)isonicotinamido)-2-methylphenyl)-N-methyl-1,2,4,4a,5,6-hexahydro-[1,4]oxazino[4,3-a][1,5]naphthyridine-5-carboxamide | $^1$H NMR (400 MHz, DMSO-d$_6$) δ ppm 10.56 (s, 1H), 8.81 (d, J = 4.8 Hz, 1H), 8.11 (s, 1H), 8.05 (m, 1H), 7.96 (d, J = 4.3 Hz, 1H), 7.74 (d, J = 15.7 Hz, 1H), 7.66 (d, J = 8.1 Hz, 1H), 7.58 (s, 1H), 7.25 (d, J = 8.2 Hz, 1H), 7.12 (d, J = 6.8 Hz, 1H), 3.85 (d, J = 9.0 Hz, 1H), 3.67 (m, 2H), 3.46 (t, J = 11.0 Hz, 1H), 3.09 (dq, J = 29.2, 9.9, 9.5 Hz, 2H), 2.89 (m, 2H), 2.73 (t, J = 10.5 Hz, 1H), 2.58 (d, J = 4.4 Hz, 3H), 2.54 (m, 1H), 2.16 (s, 3H), 1.98 (t, J = 19.1 Hz, 3H). LCMS (m/z) (M + H) = 522.4, Rt = 0.95 min. |

Example 225

(rac)-2-(1,1-difluoroethyl)-N-(3-((4a,10b-trans)-6-ethyl-5-oxo-1,4,4a,5,6,10b-hexahydro-2H-pyrano[3,4-c][1,8]naphthyridin-9-yl)-4-methylphenyl)isonicotinamide

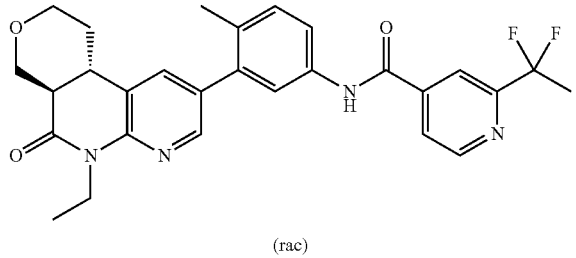 [SMILES: CCN1C(=O)[C@H]2COCC[C@@H]2c2cc(-c3cc(NC(=O)c4ccnc(C(C)(F)F)c4)ccc3C)cnc21]

(rac)

A vial was charged with (rac)-(4a,10b-trans)-9-bromo-6-ethyl-4,4a,6,10b-tetrahydro-1H-pyrano[3,4-c][1,8]naphthyridin-5(2H)-one (1.0 equiv) and 2-(1,1-difluoroethyl)-N-(4-methyl-3-(4,4,5,5-tetramethyl-1,3,2-dioxaborolan-2-yl)phenyl)isonicotinamide (1.05 equiv). THF (0.1 M) and K3PO4 (0.5 M aq, 2 equiv) were added, and the flask was purged with N$_2$. XPhos Pd G2 (0.05 equiv) and XPhos (0.05 equiv) were added, and the reaction was heated at 45° C. for 1 h. The reaction was poured onto water and extracted twice with EtOAc. The combined organics were washed with brine, dried over MgSO$_4$, filtered, and concentrated. The residue was adsorbed on Celite and purified by flash column chromatography over silica gel (heptane with 0-100% ethyl acetate gradient) to give (rac)-2-(1,1-difluoroethyl)-N-(3-((4a,10b-trans)-6-ethyl-5-oxo-1,4,4a,5,6,10b-hexahydro-2H-pyrano[3,4-c][1,8]naphthyridin-9-yl)-4-methylphenyl)isonicotinamide as a white solid in 90% yield LCMS (m/z) (M+H)=507.1, Rt=1.19 min. $^1$H NMR (400 MHz, DMSO-d6) δ 10.68 (s, 1H), 8.89 (d, J=5.0 Hz, 1H), 8.35-8.25 (m, 1H), 8.19 (s, 1H), 8.04 (d, J=4.8 Hz, 1H), 7.73 (d, J=8.8 Hz, 2H), 7.62 (s, 1H), 7.36 (d, J=8.1 Hz, 1H), 4.32-4.14 (m, 2H), 4.02 (dt, J=13.0, 5.6 Hz, 2H), 3.44 (q, J=10.6 Hz, 2H), 3.05-2.89 (m, 1H), 2.58-2.53 (m, 1H), 2.33 (d, J=9.9 Hz, 1H), 2.27 (s, 3H), 2.06 (t, J=19.1 Hz, 3H), 1.59 (qd, J=12.4, 4.3 Hz, 1H), 1.17 (t, J=6.9 Hz, 3H).

The following examples were prepared using methods from example 225, using appropriate starting materials.

Example 226

(rac)-2-(1,1-difluoroethyl)-N-(3-((4a,10b-cis)-6-ethyl-5-oxo-1,4,4a,5,6,10b-hexahydro-2H-pyrano[3,4-c][1,8]naphthyridin-9-yl)-4-methylphenyl)isonicotinamide

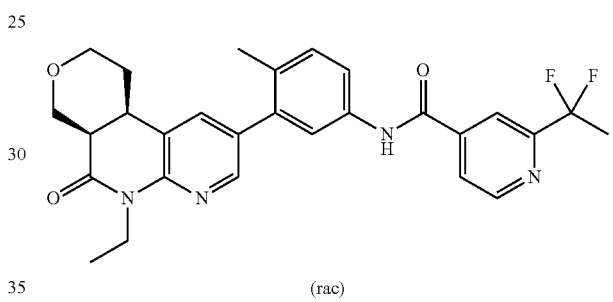

(rac)

LCMS (m/z) (M+H)=507.1, Rt=1.14 min. $^1$H NMR (400 MHz, DMSO-d6) δ 10.67 (s, 1H), 8.89 (d, J=5.0 Hz, 1H), 8.28 (d, J=2.2 Hz, 1H), 8.19 (s, 1H), 8.03 (d, J=4.9 Hz, 1H), 7.78-7.67 (m, 3H), 7.35 (d, J=9.0 Hz, 1H), 4.50 (d, J=11.0 Hz, 1H), 4.21 (dq, J=13.6, 6.8 Hz, 1H), 4.09 (dq, J=13.7, 6.8 Hz, 1H), 3.84 (d, J=11.1 Hz, 1H), 3.52-3.39 (m, 2H), 3.30 (dd, J=11.7, 5.7 Hz, 1H), 2.87 (d, J=5.4 Hz, 1H), 2.27 (s, 3H), 2.06 (t, J=19.2 Hz, 3H), 1.60 (d, J=10.1 Hz, 1H), 1.50 (qd, J=12.8, 12.4, 4.2 Hz, 1H), 1.18 (t, J=6.9 Hz, 3H).

Example 227

(rac)-2-(1,1-difluoroethyl)-N-(3-((4a,10b-trans)-6-ethyl-4a-methyl-5-oxo-1,4,4a,5,6,10b-hexahydro-2H-pyrano[3,4-c][1,8]naphthyridin-9-yl)-4-methylphenyl)isonicotinamide

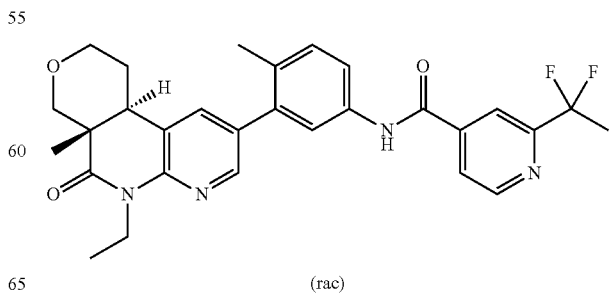

(rac)

LCMS (m/z) (M+H)=521.1, Rt=1.20 min. ¹H NMR (400 MHz, DMSO-d6) δ 10.67 (s, 1H), 8.89 (d, J=5.0 Hz, 1H), 8.30 (d, J=2.2 Hz, 1H), 8.20 (s, 1H), 8.04 (d, J=4.8 Hz, 1H), 7.81-7.65 (m, 3H), 7.35 (d, J=8.3 Hz, 1H), 4.41 (d, J=11.2 Hz, 1H), 4.20 (dq, J=13.6, 6.8 Hz, 1H), 4.09 (dq, J=13.6, 6.8 Hz, 1H), 3.86 (dd, J=11.1, 3.9 Hz, 1H), 3.42 (t, J=11.1 Hz, 1H), 3.10 (d, J=11.3 Hz, 1H), 2.96 (dd, J=12.4, 4.4 Hz, 1H), 2.27 (s, 3H), 2.06 (t, J=19.2 Hz, 3H), 1.64 (dd, J=13.3, 4.0 Hz, 1H), 1.44 (qd, J=12.8, 4.6 Hz, 1H), 1.16 (t, J=6.9 Hz, 3H), 0.85 (s, 3H).

Examples 228 & 229

2-(1,1-difluoroethyl)-N-(3-((4aR,10bS)-6-ethyl-5-oxo-1,4,4a,5,6,10b-hexahydro-2H-pyrano[3,4-c][1,8]naphthyridin-9-yl)-4-methylphenyl)isonicotinamide and 2-(1,1-difluoroethyl)-N-(3-((4aS,10bR)-6-ethyl-5-oxo-1,4,4a,5,6,10b-hexahydro-2H-pyrano[3,4-c][1,8]naphthyridin-9-yl)-4-methylphenyl) isonicotinamide

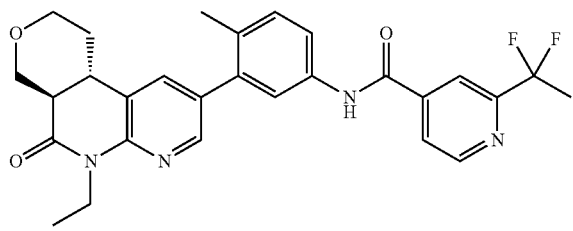

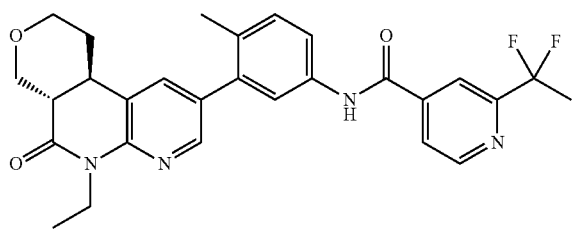

(rac)-2-(1,1-difluoroethyl)-N-(3-((4a,10b-trans)-6-ethyl-5-oxo-1,4,4a,5,6,10b-hexahydro-2H-pyrano[3,4-c][1,8]naphthyridin-9-yl)-4-methylphenyl)isonicotinamide was subjected to chiral SFC (Whelk-O1 RR 21×250 mm column, 5-55% MeOH in CO₂ eluent). The first eluting peak afforded 2-(1,1-difluoroethyl)-N-(3-((4aR,10bS)-6-ethyl-5-oxo-1,4,4a,5,6,10b-hexahydro-2H-pyrano[3,4-c][1,8]naphthyridin-9-yl)-4-methylphenyl)isonicotinamide as a white solid. The second eluting peak afforded 2-(1,1-difluoroethyl)-N-(3-((4aS,10bR)-6-ethyl-5-oxo-1,4,4a,5,6,10b-hexahydro-2H-pyrano[3,4-c][1,8]naphthyridin-9-yl)-4-methylphenyl) isonicotinamide as a white solid. NMR and LCMS data for each enantiomer matched that of the racemate.

Examples 230 & 231

2-(1,1-difluoroethyl)-N-(3-((4aR,10bR)-6-ethyl-5-oxo-1,4,4a,5,6,10b-hexahydro-2H-pyrano[3,4-c][1,8]naphthyridin-9-yl)-4-methylphenyl)isonicotinamide and 2-(1,1-difluoroethyl)-N-(3-((4aS,10bS)-6-ethyl-5-oxo-1,4,4a,5,6,10b-hexahydro-2H-pyrano[3,4-c][1,8]naphthyridin-9-yl)-4-methylphenyl) isonicotinamide

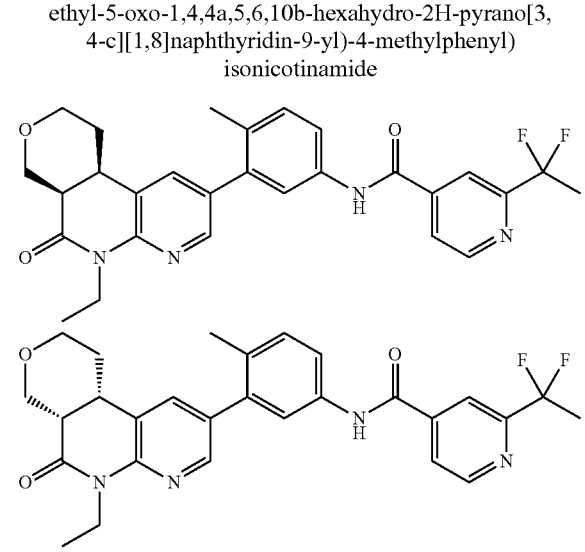

(rac)-2-(1,1-difluoroethyl)-N-(3-((4a,10b-cis)-6-ethyl-5-oxo-1,4,4a,5,6,10b-hexahydro-2H-pyrano[3,4-c][1,8]naphthyridin-9-yl)-4-methylphenyl)isonicotinamide was subjected to chiral SFC (ID 30×250 mm 5 um column, 5-55% IPA in CO₂ eluent). The first eluting peak afforded 2-(1,1-difluoroethyl)-N-(3-((4aR,10bR)-6-ethyl-5-oxo-1,4,4a,5,6,10b-hexahydro-2H-pyrano[3,4-c][1,8]naphthyridin-9-yl)-4-methylphenyl)isonicotinamide as a white solid. The second eluting peak afforded 2-(1,1-difluoroethyl)-N-(3-((4aS,10bS)-6-ethyl-5-oxo-1,4,4a,5,6,10b-hexahydro-2H-pyrano[3,4-c][1,8]naphthyridin-9-yl)-4-methylphenyl)isonicotinamide as a white solid. NMR and LCMS data for each enantiomer matched that of the racemate.

Examples 232 & 233

2-(1,1-difluoroethyl)-N-(3-((4aS,10bS)-6-ethyl-4a-methyl-5-oxo-1,4,4a,5,6,10b-hexahydro-2H-pyrano[3,4-c][1,8]naphthyridin-9-yl)-4-methylphenyl)isonicotinamide and 2-(1,1-difluoroethyl)-N-(3-((4aR,10bR)-6-ethyl-4a-methyl-5-oxo-1,4,4a,5,6,10b-hexahydro-2H-pyrano[3,4-c][1,8]naphthyridin-9-yl)-4-methylphenyl)isonicotinamide

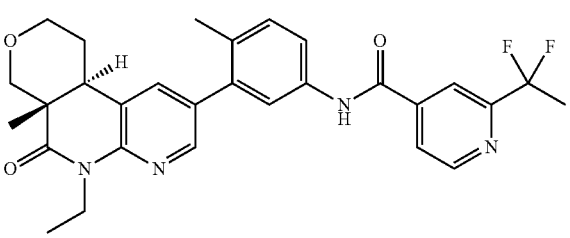

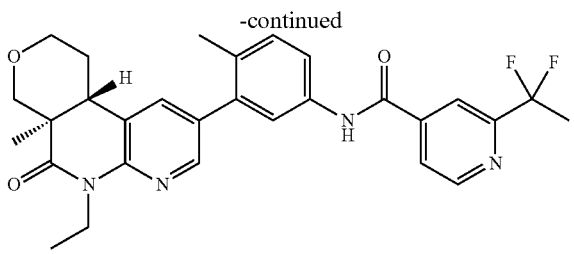

(rac)-2-(1,1-difluoroethyl)-N-(3-((4a,10b-trans)-6-ethyl-4a-methyl-5-oxo-1,4,4a,5,6,10b-hexahydro-2H-pyrano[3,4-c][1,8]naphthyridin-9-yl)-4-methylphenyl)isonicotinamide was subjected to chiral SFC (ID 30×250 mm 5 um column, 5-55% IPA in CO₂ eluent). The first eluting peak afforded 2-(1,1-difluoroethyl)-N-(3-((4aS,10bS)-6-ethyl-4a-methyl-5-oxo-1,4,4a,5,6,10b-hexahydro-2H-pyrano[3,4-c][1,8]naphthyridin-9-yl)-4-methylphenyl)isonicotinamide as a white solid. The second eluting peak afforded 2-(1,1-difluoroethyl)-N-(3-((4aR,10bR)-6-ethyl-4a-methyl-5-oxo-1,4,4a,5,6,10b-hexahydro-2H-pyrano[3,4-c][1,8]naphthyridin-9-yl)-4-methylphenyl)isonicotinamide as a white solid. NMR and LCMS data for each enantiomer matched that of the racemate.

Example 234: (rac)-2-(1,1-difluoroethyl)-N-(3-((4a,10b-trans)-6-ethyl-5-oxo-1,4,4a,5,6,10b-hexahydro-2H-pyrano[3,4-c][1,8]naphthyridin-9-yl)-4-methylphenyl)isonicotinamide

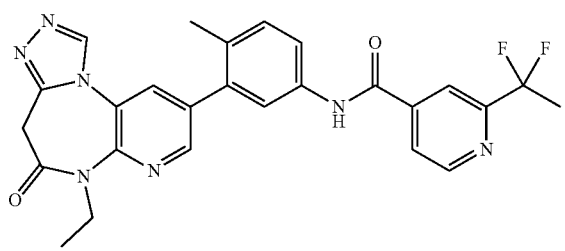 [SMILES: CCN1C(=O)Cc2nncn2-c2cc(-c3cc(NC(=O)c4ccnc(C(C)(F)F)c4)ccc3C)cnc21]

A vial was charged with 9-bromo-6-ethyl-4H-pyrido[2,3-b][1,2,4]triazolo[4,3-d][1,4]diazepin-5(6H)-one (1.0 equiv) and 2-(1,1-difluoroethyl)-N-(4-methyl-3-(4,4,5,5-tetramethyl-1,3,2-dioxaborolan-2-yl)phenyl)isonicotinamide (1.05 equiv). Dioxane (0.07 M) and K₃PO₄ (0.5 M aq, 2.0 equiv) were added, and the flask was purged with N₂. XPhos Pd G2 (0.05 equiv) and XPhos (0.05 equiv) were added, and the reaction was heated at 90° C. for 1 h. The reaction was diluted with DCM, dried over MgSO₄, filtered, and concentrated. The residue was purified by flash column chromatography over silica gel (DCM and 0-20% MeOH gradient) to provide 2-(1,1-difluoroethyl)-N-(3-(6-ethyl-5-oxo-5,6-dihydro-4H-pyrido[2,3-b][1,2,4]triazolo[4,3-d][1,4]diazepin-9-yl)-4-methylphenyl)isonicotinamide as a white solid in 75% yield. LCMS (m/z) (M+H)=504.2, Rt=0.98 min. ¹H NMR (400 MHz, Methanol-d4) δ 9.11 (s, 1H), 8.83-8.76 (m, 1H), 8.70 (d, J=2.1 Hz, 1H), 8.24 (d, J=2.1 Hz, 1H), 8.21-8.16 (m, 1H), 7.96 (dd, J=5.1, 1.5 Hz, 1H), 7.84 (d, J=2.2 Hz, 1H), 7.64 (dd, J=8.3, 2.3 Hz, 1H), 7.40 (d, J=8.4 Hz, 1H), 4.14 (bs, 2H), 4.03 (bs, 2H), 2.37 (s, 3H), 2.03 (t, J=18.7 Hz, 3H), 1.28 (t, J=7.0 Hz, 3H).

Example 235: "Peak 1" enantiomer of N-(3-((4a,11b-cis)-7-ethyl-6-oxo-1,4,4a,6,7,11b-hexahydro-2H-pyrano[4,3-f]pyrido[2,3-d][1,3]oxazepin-10-yl)-4-methylphenyl)-2-(trifluoromethyl)isonicotinamide

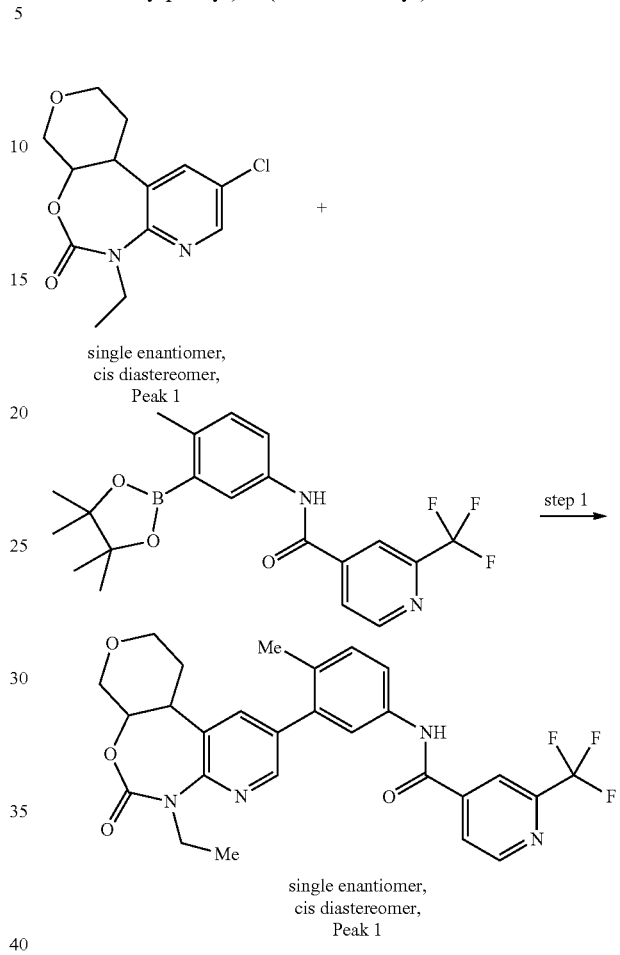

To a mixture of (4a,11b-cis)-10-chloro-4,4a,7,11b-tetrahydro-1H-pyrano[4,3-f]pyrido[2,3-d][1,3]oxazepin-6(2H)-one "Peak 1" (1 equiv.), N-(4-methyl-3-(4,4,5,5-tetramethyl-1,3,2-dioxaborolan-2-yl)phenyl)-2-(trifluoromethyl)isonicotinamide (1.1 equiv.), XPhos Pd G2 (5 mol %), and XPhos (5 mol %) under an atmosphere of nitrogen at room temperature was added degassed 1,4-dioxane (0.14 M) and degassed aqueous 0.5 M aq. K₃PO₄ (2 equiv.) and the reaction was heated to 80° C. and stirred for 1 hour. The reaction was poured into water and extracted three times with ethyl acetate and three times with dichloromethane. The combined organic phases were dried over MgSO₄, filtered, and concentrated in vacuo. The residue was purified by flash column chromatography (heptane with 0-80% ethyl acetate gradient) then HPLC (X-bridge 30×50 mm 5 μm column, water with 35-60% acetonitrile gradient, 5 mM NH₄OH) to afford the "Peak 1" enantiomer of N-(3-((4aS, 11bR)-7-ethyl-6-oxo-1,4,4a,6,7,11b-hexahydro-2H-pyrano[4,3-f]pyrido[2,3-d][1,3]oxazepin-10-yl)-4-methylphenyl)-2-(trifluoromethyl)isonicotinamide as a white solid in 71% yield. LCMS (m/z) (M+H)=527.0, Rt=1.18 min. ¹H NMR (400 MHz, CHLOROFORM-d) δ ppm 8.97 (d, J=5.02 Hz, 1H), 8.41 (d, J=1.25 Hz, 1H), 8.16 (s, 1H), 8.12 (br s, 1H), 7.99 (br d, J=4.52 Hz, 1H), 7.67 (br s, 2H), 7.62 (br d, J=8.28 Hz, 1H), 7.39 (d, J=8.28 Hz, 1H), 4.83 (br t, J=8.28 Hz, 1H), 4.04-4.26 (m, 2H), 3.78-3.96 (m, 3H), 3.41-3.52 (m, 2H), 2.26-2.40 (m, 4H), 2.05-2.21 (m, 1H), 1.34 (t, J=7.03 Hz, 3H).

Example 236: N-(3-((4aR,10bS)-6-ethyl-5-oxo-1,4,4a,5,6,10b-hexahydro-2H-pyrano[3,4-c][1,8]naphthyridin-9-yl)-4-methylphenyl)-2-(trifluoromethyl)isonicotinamide

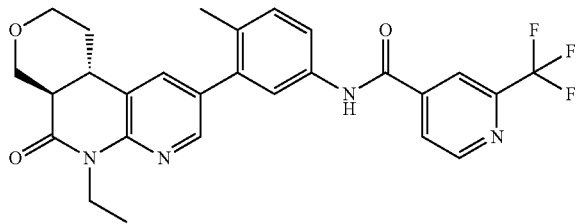 [SMILES: CCN1C(=O)[C@H]2COCC[C@@H]2c2cc(-c3cc(NC(=O)c4ccnc(C(F)(F)F)c4)ccc3C)cnc21]

(4aR,10bS)-9-Bromo-6-ethyl-1,2,4,4a,6,10b-hexahydro-5H-pyrano[3,4-c][1,8]naphthyridin-5-one (1 equiv) was combined with N-(4-methyl-3-(4,4,5,5-tetramethyl-1,3,2-dioxaborolan-2-yl)phenyl)-2-(trifluoromethyl)isonicotinamide (1.05 equiv) and dissolved into dioxane (0.085 M) along with $K_3PO_4$ solution (0.5M aqueous, 2 equiv) in a round bottom flask with a water condenser and nitrogen atmosphere. Suspension was degassed by sparging with nitrogen gas for 15 minutes. X-Phos Pd G2 (0.05 equiv) and X-Phos (0.05 equiv) were added and then the reaction mixture was heated with a pre-heated oil bath to 80° C. for 16 hr. After this time the reaction was diluted with EtOAc and treated with anhydrous granular $Na_2SO_4$. Reaction was filtered and volatiles removed to yield a crude brown oil which was purified by flash column chromatography over silica gel (heptane and 0-60% EtOAc gradient) to give N-(3-((4aR,10bS)-6-ethyl-5-oxo-2,4,4a,5,6,10b-hexahydro-1H-pyrano[3,4-c][1,8]naphthyridin-9-yl)-4-methylphenyl)-2-(trifluoromethyl)isonicotinamide as a white solid in 78% yield. LCMS (m/z) (M+H)=511.1985, Rt=3.89 min. $^1$H NMR (400 MHz, Methanol-d4) δ 8.91 (d, J=5.0 Hz, 1H), 8.30 (s, 1H), 8.28-8.24 (m, 1H), 8.16-8.08 (m, 1H), 7.69-7.60 (m, 3H), 7.35 (d, J=9.1 Hz, 1H), 4.41 (dd, J=11.6, 4.5 Hz, 1H), 4.29 (dt, J=13.9, 6.9 Hz, 1H), 4.12 (dq, J=13.9, 7.0 Hz, 2H), 3.63-3.45 (m, 2H), 2.97 (s, 1H), 2.49 (ddd, J=14.8, 10.5, 4.5 Hz, 1H), 1.73 (qd, J=12.4, 4.6 Hz, 1H), 1.48-1.42 (m, 2H), 1.30-1.13 (m, 5H).

The following were prepared using the same methods as described for Example 234-236 above using the appropriate starting materials. Products were purified by flash column chromatography over silica gel, HPLC, and/or SFC methods as appropriate:

| Ex. No. | Structure | Name | Physical Data |
|---|---|---|---|
| 237 | 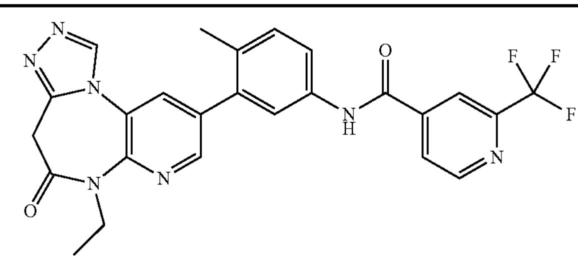 | N-(3-(6-ethyl-5-oxo-5,6-dihydro-4H-pyrido[2,3-b][1,2,4]triazolo[4,3-d][1,4]diazepin-9-yl)-4-methylphenyl)-2-(trifluoromethyl)isonicotinamide | $^1$H NMR (400 MHz, Methanol-d4) δ 9.11 (s, 1H), 8.91 (d, J = 5.0 Hz, 1H), 8.69 (d, J = 2.1 Hz, 1H), 8.30 (s, 1H), 8.24 (d, J = 2.1 Hz, 1H), 8.12 (dd, J = 5.0, 1.2 Hz, 1H), 7.85 (d, J = 2.2 Hz, 1H), 7.64 (dd, J = 8.3, 2.3 Hz, 1H), 7.40 (d, J = 8.4 Hz, 1H), 4.14 (bs, 2H), 4.03 (s, 2H), 2.37 (s, 3H), 1.29 (t, J = 7.0 Hz, 3H). LCMS (m/z) (M+ H) = 508.2, Rt = 1.00 min |
| 238 | 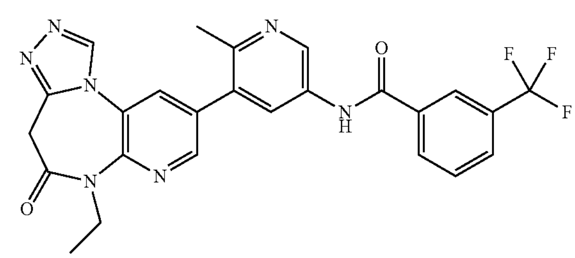 [SMILES: CCN1C(=O)Cc2nncn2-c2cc(-c3cc(NC(=O)c4cccc(C(F)(F)F)c4)cnc3C)cnc21] | N-(5-(6-ethyl-5-oxo-5,6-dihydro-4H-pyrido[2,3-b][1,2,4]triazolo[4,3-d][1,4]diazepin-9-yl)-6-methylpyridin-3-yl)-3-(trifluoromethyl)benzamide | $^1$H NMR (400 MHz, Methanol-d4) δ 9.11 (s, 1H), 8.83 (d, J = 2.4 Hz, 1H), 8.76 (d, J = 2.1 Hz, 1H), 8.34 (dd, J = 10.4, 2.3 Hz, 2H), 8.31 (s, 1H), 8.25 (d, J = 7.9 Hz, 1H), 7.93 (d, J = 7.8 Hz, 1H), 7.76 (t, J = 7.8 Hz, 1H), 4.15 (s, 2H), 4.05 (s, 2H), 2.58 (s, 3H), 1.30 (t, J = 7.0 Hz, 3H). LCMS (m/z) (M + H) = 508.2, Rt = 0.93 min |
| 239 | 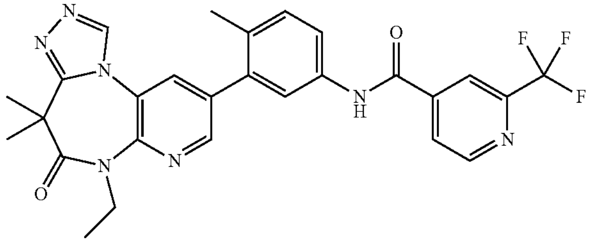 [SMILES: CCN1C(=O)C(C)(C)c2nncn2-c2cc(-c3cc(NC(=O)c4ccnc(C(F)(F)F)c4)ccc3C)cnc21] | N-(3-(6-ethyl-4,4-dimethyl-5-oxo-5,6-dihydro-4H-pyrido[2,3-b][1,2,4]-triazolo[4,3-d][1,4]diazepin-9-yl)-4-methylphenyl)-2-(trifluoromethyl)isonicotinamide | $^1$H NMR (400 MHz, Methanol-d4) δ 9.09 (s, 1H), 8.91 (d, J = 5.0 Hz, 1H), 8.68 (d, J = 1.9 Hz, 1H), 8.31 (s, 1H), 8.24 (d, J = 1.9 Hz, 1H), 8.13 (d, J = 4.6 Hz, 1H), 7.85 (d, J = 2.0 Hz, 1H), 7.66 (dd, J = 8.3, 2.0 Hz, 1H), 7.41 (d, J = 8.3 Hz, 1H), 4.09-4.20 (m, 2 h), 2.36 (s, 3H), 1.88 (s, 3H), 1.33 (t, J = 6.9 Hz, 3H), 1.25 (s, 3H). LCMS (m/z) (M + H) = 536.2, Rt = 1.13 min |

| Ex. No. | Structure | Name | Physical Data |
|---|---|---|---|
| 240 | 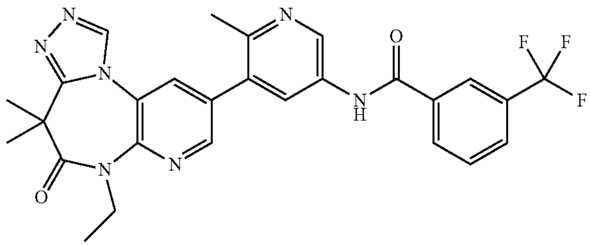 [SMILES: CCN1C(=O)C(C)(C)c2nncn2-c2cc(-c3cc(NC(=O)c4cccc(C(F)(F)F)c4)cnc3C)cnc21] | N-(5-(6-ethyl-4,4-dimethyl-5-oxo-5,6-dihydro-4H-pyrido[2,3-b][1,2,4]triazolo[4,3-d][1,4]diazepin-9-yl)-6-methylpyridin-3-yl)-3-(trifluoromethyl)benzamide | ¹H NMR (400 MHz, Methanol-d4) δ 9.11 (s, 1H), 8.83 (d, J = 2.4 Hz, 1H), 8.74 (d, J = 2.1 Hz, 1H), 8.34 (dd, J = 10.9, 2.3 Hz, 2H), 8.31 (s, 1H), 8.25 (d, J = 7.9 Hz, 1H), 7.93 (d, J = 7.8 Hz, 1H), 7.76 (t, J = 7.8 Hz, 1H), 4.10-4.30 (m, 2 H), 2.58 (s, 3H), 1.91 (s, 3H), 1.35 (t, J = 6.9 Hz, 4H), 1.25 (s, 3H). LCMS (m/z) (M + H) = 536.2, Rt = 1.02 min |
| 241 | 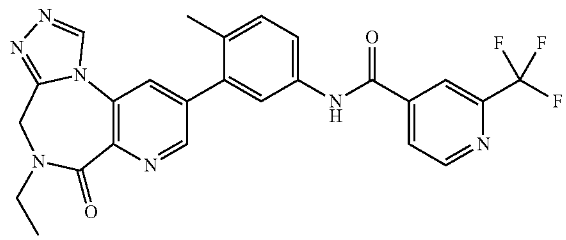 [SMILES: CCN1Cc2nncn2-c2cc(-c3cc(NC(=O)c4ccnc(C(F)(F)F)c4)ccc3C)cnc2C1=O] | N-(3-(5-ethyl-6-oxo-5,6-dihydro-4H-pyrido[2,3-f][1,2,4]-triazolo[4,3-a][1,4]diazepin-9-yl)-4-methylphenyl)-2-(trifluoromethyl)isonicotinamide | ¹H NMR (400 MHz, Methanol-d4) δ 9.21 (s, 1H), 8.91 (d, J = 5.0 Hz, 1H), 8.85 (d, J = 1.8 Hz, 1H), 8.30 (d, J = 1.7 Hz, 2H), 8.13 (dd, J = 5.0, 1.2 Hz, 1H), 7.85 (d, J = 2.3 Hz, 1H), 7.70 (dd, J = 8.3, 2.3 Hz, 1H), 7.43 (d, J = 8.4 Hz, 1H), 4.84 (s, 2H), 3.80 (q, J = 7.0 Hz, 2H), 2.37 (s, 3H), 1.27 (t, J = 7.2 Hz, 4H). LCMS (m/z) (M + H) = 508.1, Rt = 0.83 min |
| 242 | single enantiomer from Peak 1 intermediate | N-(3-(7-ethyl-11b-methyl-6-oxo-1,2,4,6,7,11b-hexahydro-[1,3]oxazino[3,4-c]quinazolin-10-yl)-4-methylphenyl)-2-(trifluoromethyl)isonicotinamide | ¹H NMR (400 MHz, Methanol-d4) δ 8.90 (d, J = 5.0 Hz, 1H), 8.30 (s, 1H), 8.15-8.08 (m, 1H), 7.62 (d, J = 7.3 Hz, 2H), 7.35-7.27 (m, 2H), 7.23 (d, J = 1.8 Hz, 1H), 7.12 (d, J = 8.4 Hz, 1H), 5.59 (d, J = 10.0 Hz, 1H), 4.63 (d, J = 10.0 Hz, 1H), 4.16-3.86 (m, 4H), 2.28 (s, 3H), 2.25-2.11 (m, 2H), 1.58 (s, 3H), 1.28 (t, J = 7.0 Hz, 3H). LCMS (m/z) (M + H) = 525.2, Rt = 1.24 min |
| 243 | single enantiomer from Peak 1 intermediate | N-(5-(7-ethyl-11b-methyl-6-(mo-1,2,4,6,7,11b-hexahydro-[1,3]oxazino[3,4-c]quinazolin-10-yl)-6-methylpyridin-3-yl)-3-(trifluoromethyl)benzamide | ¹H NMR (400 MHz, Methanol-d4) δ 8.80 (d, J = 2.4 Hz, 1H), 8.30 (s, 1H), 8.24 (d, J = 7.9 Hz, 1H), 8.12 (d, J = 2.4 Hz, 1H), 7.92 (d, J = 7.8 Hz, 1H), 7.75 (t, J = 7.8 Hz, 1H), 7.37 (dd, J = 8.4, 2.0 Hz, 1H), 7.31 (d, J = 2.0 Hz, 1H), 7.17 (d, J = 8.5 Hz, 1H), 5.59 (d, J = 10.1 Hz, 1H), 4.64 (d, J = 10.0 Hz, 1H), 4.17-3.88 (m, 4H), 2.50 (s, 3H), 2.31-2.15 (m, 2H), 1.59 (s, 3H), 1.28 (t, J = 7.0 Hz, 3H). LCMS (m/z) (M + H) = 525.3, Rt = 1.04 min |
| 244 | single enantiomer from Peak 2 intermediate | N-(3-(7-ethyl-11b-methyl-6-oxo-1,2,4,6,7,11b-hexahydro-[1,3]oxazino[3,4-c]quinazolin-10-yl)-4-methylphenyl)-2-(trifluoromethyl)isonicotinamide | ¹H NMR (400 MHz, Methanol-d4) δ 8.90 (d, J = 5.0 Hz, 1H), 8.30 (s, 1H), 8.15-8.07 (m, 1H), 7.61 (s, 2H), 7.30 (dt, J = 8.9, 2.0 Hz, 2H), 7.23 (d, J = 1.9 Hz, 1H), 7.12 (d, J = 8.5 Hz, 1H), 5.59 (d, J = 10.0 Hz, 1H), 4.63 (d, J = 10.0 Hz, 1H), 4.16-3.87 (m, 4H), 2.27 (s, 3H), 2.25-2.13 (m, 2H), 1.58 (s, 3H), 1.27 (q, J = 6.6, 6.1 Hz, 4H). LCMS (m/z) (M + H) = 525.3, Rt = 1.23 min |

| Ex. No. | Structure | Name | Physical Data |
|---|---|---|---|
| 245 | 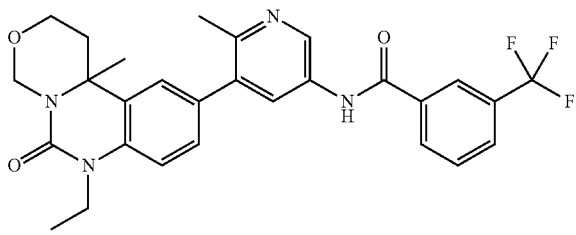<br>single enantiomer<br>from Peak 2 intermediate | N-(5-(7-ethyl-11b-methyl-6-oxo-1,2,4,6,7,11b-hexahydro-[1,3]oxazino[3,4-c]quinazolin-10-yl)-6-methylpyridin-3-yl)-3-(trifluoromethyl) benzamide | $^1$H NMR (400 MHz, Methanol-d4) δ 8.80 (d, J = 2.4 Hz, 1H), 8.30 (s, 1H), 8.24 (d, J = 7.9 Hz, 1H), 8.12 (d, J = 2.4 Hz, 1H), 7.91 (d, J = 7.8 Hz, 1H), 7.75 (t, J = 7.8 Hz, 1H), 7.37 (dd, J = 8.4, 1.9 Hz, 1H), 7.31 (d, J = 1.9 Hz, 1H), 7.17 (d, J = 8.5 Hz, 1H), 5.59 (d, J = 10.0 Hz, 1H), 4.64 (d, J = 10.0 Hz, 1H), 4.17-3.83 (m, 4H), 2.50 (s, 3H), 2.28-2.13 (m, 2H), 1.59 (s, 3H), 1.28 (t, J = 7.0 Hz, 3H). LCMS (m/z) (M + H) = 525.3, Rt = 1.04 min |
| 246 | 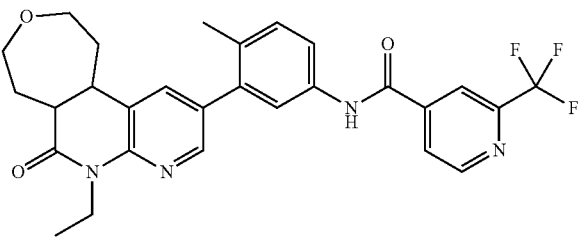<br>cis-diastereomer<br>single enantomer from Peak 1 intermediate | N-(3-((5a, 11b-cis)-7-ethyl-6-oxo-1,2,4,5,5a,6,7,11b-octahydrooxepino[4,5-c][1,8]naphthyridin-10-yl)-4-methylphenyl)-2-(trifluoromethyl) isonicotinamide | $^1$H NMR (400 MHz, Methanol-d4) δ 8.91 (d, J = 5.0 Hz, 1H), 8.30 (s, 1H), 8.24 (d, J = 2.2 Hz, 1H), 8.16-8.08 (m, 1H), 7.70-7.61 (m, 3H), 7.34 (d, J = 8.1 Hz, 1H), 4.30 (dq, J = 13.9, 7.0 Hz, 1H), 4.18 (dq, J = 13.9, 7.0 Hz, 1H), 3.97 (ddd, J = 12.8, 9.4, 3.7 Hz, 1H), 3.84-3.65 (m, 3H), 3.33 (m, 1H), 3.09 (q, J = 4.8 Hz, 1H), 2.45 (dq, J = 13.5, 4.4 Hz, 1H), 2.30 (s, 3H), 1.99 (dtq, J = 14.6, 9.5, 4.9 Hz, 2H), 1.83-1.69 (m, 1H), 1.24 (t, J = 7.0 Hz, 3H). LCMS (m/z) (M ++) H) = 525.3, Rt = 1.21 min |
| 247 | 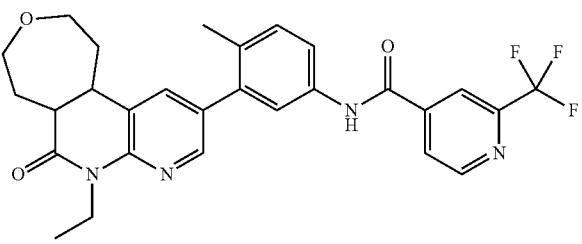<br>cis-diastereomer<br>single enantomer from Peak 2 intermediate | N-(3-((5a, 11b-cis)-7-ethyl-6-oxo-1,2,4,5,5a,6,7,11b-octahydrooxepino 4,5-c][1,8]naphthyridin-10-yl)-4-methylphenyl)-2-(trifluoromethyl) isonicotinamide | $^1$H NMR (400 MHz, Methanol-d4) δ 8.91 (d, J = 5.0 Hz, 1H), 8.30 (s, 1H), 8.24 (d, J = 2.2 Hz, 1H), 8.15-8.07 (m, 1H), 7.71-7.60 (m, 3H), 7.34 (d, J = 8.1 Hz, 1H), 4.30 (dq, J = 13.9, 7.0 Hz, 1H), 4.18 (dq, J = 13.9, 7.0 Hz, 1H), 3.97 (ddd, J = 12.8, 9.4, 3.7 Hz, 1H), 3.87-3.64 (m, 3H), 3.33 (m, 1H), 3.09 (q, J = 4.8 Hz, 1H), 2.45 (dq, J = 13.5, 4.4 Hz, 1H), 2.30 (s, 3H), 1.99 (dtq, J = 20.0, 9.5, 4.9 Hz, 2H), 1.77 (dq, J = 14.8, 3.1 Hz, 1H), 1.24 (t, J = 7.0 Hz, 3H). LCMS (m/z) (M + H) = 525.3, Rt = 1.21 min |
| 248 | 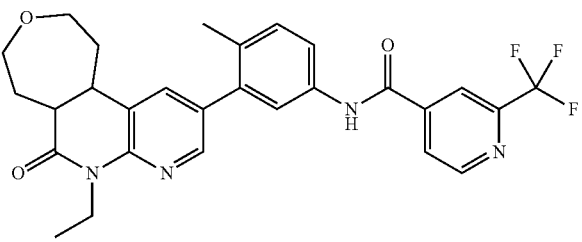<br>trans-diastereomer<br>single enantomer from Peak 1 intermediate | N-(3-((5a, 11b-trans)-7-ethyl-6-oxo-1,2,4,5,5a,6,7,11b-octahydrooxepino 4,5-c][1,8]naphthyridin-10-yl)-4-methylphenyl)-2-(trifluoromethyl) nicotinamide | $^1$H NMR (400 MHz, Methanol-d4) δ 8.91 (d, J = 5.0 Hz, 1H), 8.30 (s, 1H), 8.27-8.22 (m, 1H), 8.12 (dd, J = 5.0, 1.2 Hz, 1H), 7.75 -7.70 (m, 1H), 7.66 (dq, J = 4.5, 2.3 Hz, 2H), 7.39-7.33 (m, 1H), 4.32 (dq, J = 13.9, 6.9 Hz, 1H), 4.17 (dq, J = 13.9, 7.0 Hz, 1H), 3.97 (dt, J = 12.1, 4.1 Hz, 2H), 3.89 - 3.75 (m, 2H), 2.98 (td, J = 12.3, 10.3, 4.3 Hz, 1H), 2.73 (dq, J = 15.5, 3.3 Hz, 1H), 2.65-2.51(m, 2H), 2.30 (s, 3H), 2.10 (dddd, J = 15.7, 11.4, 9.2, 4.4 Hz, 1H), 2.02-1.89 (m, 1H), 1.26 (t, J = 7.0 Hz, 3H). LCMS (m/z) (M + H) = 525.3, Rt = 1.24 min |

-continued

| Ex. No. | Structure | Name | Physical Data |
|---|---|---|---|
| 249 | trans-diastereomer single enantiomer from Peak 2 intermediate | N-(3-((5a, 11b-trans)-7-ethyl-6-oxo-1,2,4,5,5a,6,7,11b octahydrooxepino[4,5-c][1,8]naphthyridin-4,5-10-yl)-4-methylphenyl)-2-(trifluoromethyl)isonicotinamide | ¹H NMR (400 MHz, Methanol-d4) δ 8.91 (d, J = 5.0 Hz, 1H), 8.30 (s, 1H), 8.26-8.21 (m, 1H), 8.15-8.07 (m, 1H), 7.72 (s, 1H), 7.66 (dq, J = 4.5, 2.2 Hz, 2H), 7.39-7.29 (m, 1H), 4.32 (dq, J = 13.9, 6.9 Hz, 1H), 4.17 (dq, J = 13.9, 7.0 Hz, 1H), 3.97 (dt, J = 12.1, 4.0 Hz, 2H), 3.90-3.71 (m, 2H), 3.04-2.92 (m, 1H), 2.73 (dq, J = 15.5, 3.3 Hz, 1H), 2.64-2.50 (m, 2H), 2.30 (s, 3H), 2.16-2.04 (m, 1H), 2.02-1.93 (m, 1H), 1.26 (t, J = 7.0 Hz, 3H). LCMS (m/z) (M + H) = 525.3, Rt = 1.24 min |
| 250 | trans-diastereomer single enantiomer from Peak 2 intermediate | N-(5-((5a, 11b-trans)-7-ethyl-6-oxo-1,2,4,5,5a,6,7,11b-octahydrooxepino[4,5-c][1,8]naphthyridin-10-yl)-6-methylpyridin-3-yl)-3-(trifluoromethyl)benzamide | ¹H NMR (400 MHz, Methanol-d4) δ 8.84 (d,J = 2.4 Hz,1H),8.34-8.29 (m, 2H), 8.24 (d, J = 7.9 Hz, 1H), 8.17 (d, J = 2.4 Hz, 1H), 7.92 (d, J = 7.8 Hz, 1H), 7.81-7.78 (m, 1H), 7.75 (t, J = 7.8 Hz, 1H), 4.33 (dq, J = 13.9, 7.0 Hz, 1H), 4.18 (dq, J = 13.9, 7.0 Hz, 1H), 3.97 (dt, J = 6.8, 3.5 Hz, 2H), 3.91-3.82 (m, 1H), 3.82-3.75 (m, 1H), 3.00 (td, J = 12.2, 10.3, 4.3 Hz, 1H), 2.73 (dq, J = 15.5, 3.3 Hz, 1H), 2.65-2.54 (m, 2H), 2.51 (s, 3H), 2.11 (dddd, J = 15.7, 11.4, 9.3, 4.5 Hz, 1H), 2.05-1.92 (m, 1H), 1.26 (t, J = 7.0 Hz, 3H). LCMS (m/z) (M + H) = 525.1, Rt = 1.12 min |
| 251 | trans-diastereomer single enantiomer from Peak 2 intermediate | N-(5-((5a, 11b-trans)-7-ethyl-6-oxo-1,2,4,5,5a, 6,7,11b-octahydrooxepino[4,5-c][1,8]naphthyridin-10-yl)-6-methylpyridin-3-yl)-2-(2-fluoropropan-2-yl)isonicotinamide | ¹H NMR (400 MHz, Methanol-d4) δ 8.84 (d, J = 2.4 Hz, 1H), 8.72 (d, J = 5.1 Hz, 1H), 8.34-8.28 (m, 1H), 8.17 (d, J = 2.4 Hz, 1H), 8.10 (s, 1H), 7.80 (dd, J = 5.3, 1.6 Hz, 2H), 4.33 (dq, J = 13.9, 6.9 Hz, 1H), 4.17 (dq, J = 13.9, 7.0 Hz, 1H), 3.96 (dt, J = 7.2, 3.8 Hz, 2H), 3.91-3.82 (m, 1H), 3.77 (dd, J = 11.7, 3.4 Hz, 1H), 2.99 (td, J = 12.2, 10.4, 4.2 Hz, 1H), 2.73 (dq, J = 15.5, 3.3 Hz, 1H), 2.66-2.53 (m, 2H), 2.10 (dddd, J = 15.7, 11.4, 9.4, 4.5 Hz, 1H), 1.98 (dtd, J = 14.1, 10.7, 3.2 Hz, 1H), 1.76 (s, 3H), 1.70 (s, 3H), 1.26 (t, J = 7.0 Hz, 3H). LCMS (m/z) (M + H) = 518.2. Rt = 1.00 min |
| 252 | 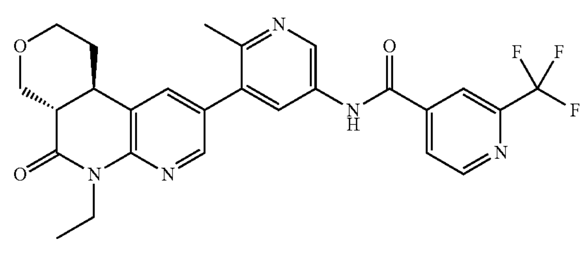 [SMILES: CCN1C(=O)[C@@H]2COCC[C@H]2c2cc(-c3cc(NC(=O)c4ccnc(C(F)(F)F)c4)cnc3C)cnc21] | N-(5-((4aS, 10bR)-6-ethyl-5-oxo-2,4,4a,5,6,10b-hexahydro-1H-pyrano[3,4-c][1,8]naphthyridin-9-yl)-6-methylpyridin-3-yl)-2-(trifluoromethyl)isonicotinamide | ¹H NMR (400 MHz, Methanol-d4) δ 8.93 (d, J = 5.0 Hz, 1H), 8.86 (d, J = 2.4 Hz, 1H), 8.37-8.29 (m, 2H), 8.19 (d, J = 2.4 Hz, 1H), 8.17-8.11 (m, 1H), 7.70 (s, 1H), 4.41 (dd, J = 11.6, 4.5 Hz, 1H), 4.30 (dq, J = 13.8, 6.9 Hz, 1H), 4.13 (dq, J = 13.8, 6.9 Hz, 2H), 3.63-3.46 (m, 2H), 2.99 (s, 1H), 2.59-2.45 (m, 4H), 2.38-2.26 (m, 1H), 1.74 (qd, J = 12.5, 4.6 Hz, 1H), 1.25 (t, J = 7.0 Hz, 3H). LCMS (m/z) (M + H) = 512.1, Rt = 0.97 min |
| 253 | 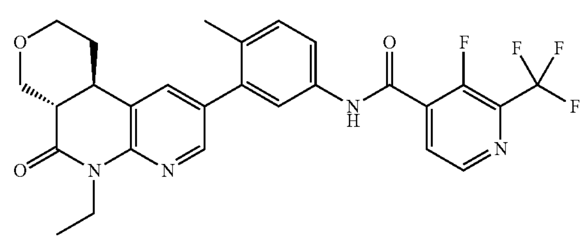 [SMILES: CCN1C(=O)[C@@H]2COCC[C@H]2c2cc(-c3cc(NC(=O)c4ccnc(C(F)(F)F)c4F)ccc3C)cnc21] | N-(3-((4aS, 10bR)-6-ethyl-5-oxo-2,4,4a,5,6,10b-hexahydro-1H-pyrano[3,4-c][1,8]naphthyridin 9-yl)-4-methylphenyl)-3-fluoro-2-(trifluoromethyl)isonicotinamide | ¹H NMR (400 MHz, Methanol-d4) δ 8.65 (d, J = 4.7 Hz, 1H), 8.28-8.19 (m, 1H), 7.96 (t, J = 4.8 Hz, 1H), 7.61 (d, J = 8.3 Hz, 3H), 7.35 (d, J = 8.0 Hz, 1H), 4.41 (dd, J = 11.6, 4.5 Hz, 1H), 4.29 (dq, J = 13.9, 7.0 Hz, 1H), 4.12 (dq, J = 13.9, 7.0 Hz, 2H), 3.63-3.49 (m, 2H), 2.96 (s, 1H), 2.49 (ddd, J = 14.7, 10.5, 4.5 Hz, 1H), 2.37-2.25 (m, 4H), 1.73 (qd, J = 12.4, 4.6 Hz, 1H), 1.24 (t, J = 7.0 Hz, 3H). LCMS |

| Ex. No. | Structure | Name | Physical Data |
|---|---|---|---|
| | | | (m/z) (M + H) = 529.1, Rt = 1.26 min |
| 254 | 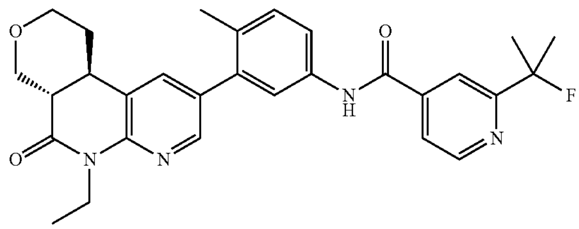 [SMILES: CCN1C(=O)[C@@H]2COCC[C@H]2c2cc(-c3cc(NC(=O)c4ccnc(C(C)(C)F)c4)ccc3C)cnc21] | N-(3-((4aS, 10bR)-6-ethyl-5-oxo-2,4,4a,5,6,10b-hexahydro-1H-pyrano[3,4-c][1,8]naphthyridin-9-yl)-4-methylphenyl)-2-(2-fluoropropan-2-yl)isonicotinamide | ¹H NMR (400 MHz, Methanol-d4) δ 8.69 (d, J = 5.1 Hz, 1H), 8.31-8.23 (m, 1H), 8.06 (s, 1H), 7.77 (dd, J = 5.1, 1.7 Hz, 1H), 7.67-7.59 (m, 3H), 7.34 (d, J = 9.1 Hz, 1H), 4.41 (dd, J = 11.6, 4.5 Hz, 1H), 4.30 (dq, J = 13.9, 7.0 Hz, 1H), 4.13 (dq, J = 13.9, 6.9 Hz, 2H), 3.67-3.49 (m, 2H), 2.97 (s, 1H), 2.49 (ddd, J = 14.7, 10.5, 4.5 Hz, 1H), 2.37-2.28 (m, 4H), 1.73 (m, 7H), 1.25 (t, J = 7.0 Hz, 3H). LCMS (m/z) (M + H) = 503.1, Rt = 1.22 min |
| 255 | 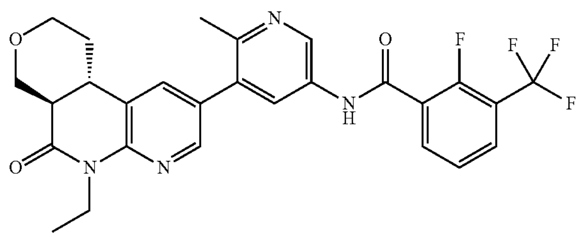 [SMILES: CCN1C(=O)[C@H]2COCC[C@@H]2c2cc(-c3cc(NC(=O)c4cccc(C(F)(F)F)c4F)cnc3C)cnc21] | N-(5-((4aR, 10bS)-6-ethyl-5-oxo-2,4,4a,5,6,10b-hexahydro-1H-pyrano[3,4-c][1,8]naphthyridin-9-yl)-6-methylpyridin-3-yl)-2-fluoro-3-(trifluoromethyl)benzamide | ¹H NMR (400 MHz, Methanol-d4) δ 8.78 (d, J = 2.5 Hz, 1H), 8.32 (dd, J = 2.1, 0.7 Hz, 1H), 8.14 (d, J = 2.5 Hz, 1H), 8.01 (dd, J = 14.2, 1.3 Hz, 1H), 7.91 (t, J = 7.3 Hz, 1H), 7.71-7.64 (m, 1H), 7.51 (t, J = 7.8 Hz, 1H), 4.41 (dd, J = 11.6, 4.5 Hz, 1H), 4.30 (dq, J = 13.9, 6.9 Hz, 1H), 4.13 (dq, J = 14.2, 7.1 Hz, 2H), 3.63-3.48 (m, 2H), 3.04-2.92 (m, 1H), 2.56-2.44 (m, 4H), 2.37-2.30 (m, 1H), 1.74 (qd, J = 12.5, 4.6 Hz, 1H), 1.24 (td, J = 7.1, 4.1 Hz, 3H). LCMS (m/z) (M + H) = 529.2, Rt = 1.05 min |
| 256 | 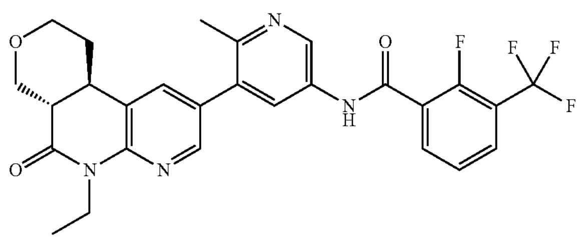 [SMILES: CCN1C(=O)[C@@H]2COCC[C@H]2c2cc(-c3cc(NC(=O)c4cccc(C(F)(F)F)c4F)cnc3C)cnc21] | N-(5-((4aS, 10bR)-6-ethyl-5-oxo-2,4,4a,5,6,10b-hexahydro-1H-pyrano[3,4-c][1,8]naphthyridin-9-yl)-6-methylpyridin-3-yl)-2-fluoro-3-(trifluoromethyl)benzamide | ¹H NMR (400 MHz, Methanol-d4) δ 8.78 (d, J = 2.5 Hz, 1H), 8.32 (dd, J = 2.1, 0.8 Hz, 1H), 8.14 (d, J = 2.5 Hz, 1H), 8.06-7.98 (m, 1H), 7.93-7.86 (m, 1H), 7.73-7.65 (m, 1H), 7.51 (t, J = 7.8 Hz, 1H), 4.41 (dd, J = 11.6, 4.5 Hz, 1H), 4.30 (dq, J = 13.9, 7.0 Hz, 1H), 4.13 (dq, J = 14.1, 7.1 Hz, 2H), 3.62-3.48 (m, 2H), 3.03-2.93 (m, 1H), 2.58-2.43 (m, 4H), 2.37-2.29 (m, 1H), 1.74 (qd, J = 12.5, 4.6 Hz, 1H), 1.24 (td, J = 7.1, 4.0 Hz, 3H). LCMS (m/z) (M + H) = 529.3, Rt = 1.05 min |
| 257 | 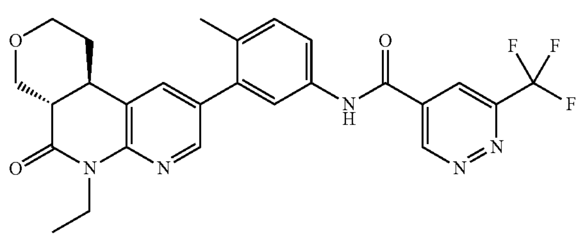 [SMILES: CCN1C(=O)[C@@H]2COCC[C@H]2c2cc(-c3cc(NC(=O)c4cnnc(C(F)(F)F)c4)ccc3C)cnc21] | N-(3-((4aS, 10bR)-6-ethyl-5-oxo-2,4,4a,5,6,10b-hexahydro-1H-pyrano[3,4-c][1,8]naphthyridin-9-yl)-4-methylphenyl)-6-(trifluoromethyl)pyridazine-4-carboxamide | ¹H NMR (400 MHz, DMSO-d6) δ 10.90 (s, 1H), 9.92 (d, J = 1.7 Hz, 1H), 8.69 (d, J = 1.8 Hz, 1H), 8.36-8.22 (m, 1H), 7.72 (d, J = 7.2 Hz, 2H), 7.62 (s, 1H), 7.39 (d, J = 8.7 Hz, 1H), 4.26 (dd, J = 11.4, 4.4 Hz, 1H), 4.17 (dt, J = 13.5, 6.8 Hz, 1H), 4.01 (dq, J = 13.9, 6.5 Hz, 2H), 3.44 (q, J = 10.5 Hz, 2H), 3.05-2.94 (m, 1H), 2.28 (s, 4H), 1.59 (qd, J = 12.4, 4.3 Hz, 1H), 1.18 (t, J = 7.0 Hz, 4H). LCMS (m/z) (M + H) = 512.0, Rt = 1.17 min |
| 258 | 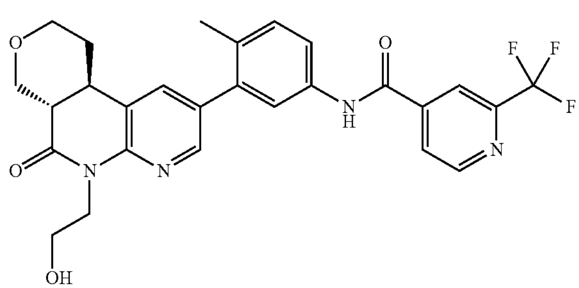 [SMILES: Cc1ccc(NC(=O)c2ccnc(C(F)(F)F)c2)cc1-c1cnc2c(c1)[C@@H]1CCOC[C@H]1C(=O)N2CCO] | N-(3-((4aS, 10bR)-6-(2-hydroxyethyl)-5-oxo-2,4,4a,5,6,10b-hexahydro-1H-pyrano[3,4-c][1,8]naphthyridin-9-yl)-4-methylphenyl)-2-(trifluoromethyl)isonicotinamide | ¹H NMR (400 MHz, Methanol-d4) δ 8.90 (d, J = 5.0 Hz, 1H), 8.30 (s, 1H), 8.25 (d, J = 1.3 Hz, 1H), 8.12 (d, J = 4.9 Hz, 1H), 7.68-.61 (m, 3H), 7.35 (d, J = 9.0 Hz, 1H), 4.53-4.46 (m, 1H), 4.41 (dd, J = 11.7, 4.5 Hz, 1H), 4.24-4.17 (m, 1H), 4.17-4.10 (m, 1H), 3.82-3.76 (m, 2H), 3.63-3.49 (m, 2H), 3.08-2.96 (m, 1H), 2.53 (ddd, J = 14.7, 10.5, 4.5 Hz, 1H), 2.33 (d, J = 12.8 Hz, 1H), 2.29 (s, 3H), 1.80-1.67 (m, 1H). LCMS (m/z) (M + H) = 527.0, Rt = 1.05 min |

| Ex. No. | Structure | Name | Physical Data |
|---|---|---|---|
| 259 | 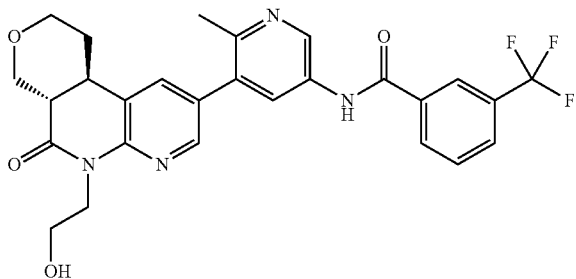 | N-(5-((4aS, 10bR)-6-(2-hydroxyethyl)-5-oxo-2,4,4a,5,6,10b-hexahydro-1H-pyrano[3,4-c][1,8]naphthyridin-9-yl)-6-methylpyridin-3-yl)-3-(trifluoromethyl)benzamide | 1H NMR (400 MHz, Methanol-d4) δ 8.83 (d, J = 2.4 Hz, 1H), 8.35-8.27 (m, 2H), 8.24 (d, J = 8.0 Hz, 1H), 8.17 (d, J = 2.4 Hz, 1H), 7.92 (d, J = 7.8 Hz, 1H), 7.75 (t, J = 7.8 Hz, 1H), 7.71 (s, 1H), 4.50 (dt, J = 12.1, 6.0 Hz, 1H), 4.42 (dd, J = 11.7, 4.5 Hz, 1H), 4.25-4.18 (m, 1H), 4.18-4.10 (m, 1H), 3.79 (td, J = 6.1, 2.0 Hz, 2H), 3.63-3.49 (m, 2H), 3.04 (s, 1H), 2.61-2.53 (m, 1H), 2.51 (s, 3H), 1.75 (qd, J = 12.4, 4.6 Hz, 1H). LCMS (m/z) (M + H) = 527.3, Rt = 0.86 min |
| 260 | 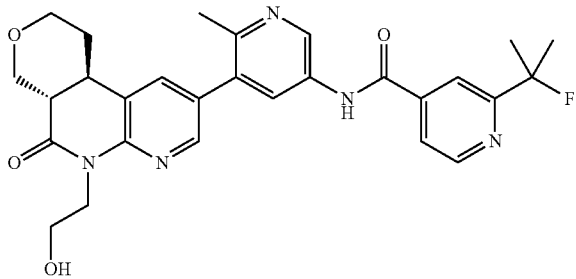 | 2-(2-fluoropropan-2-yl)-N-(5-((4aS, 10bR)-66-(2-hydroxyethyl)-5-oxo-2,4,4a,5,6,10b-hexahydro-1H-pyrano[3,4-c][1,8]naphthyridin-9-yl)-6-methylpyridin-3-yl)isonicotinamide | ¹H NMR (400 MHz, Methanol-d4) δ 8.84 (d, J = 2.5 Hz, 1H), 8.74-8.69 (m, 1H), 8.31 (dd, J = 2.1, 0.8 Hz, 1H), 8.17 (d, J = 2.5 Hz, 1H), 8.09 (s, 1H), 7.80 (dd, J = 5.1, 1.7 Hz, 1H), 7.70 (dd, J = 2.1, 1.4 Hz, 1H), 4.55-4.45 (m, 1H), 4.42 (dd, J = 11.6, 4.5 Hz, 1H), 4.26-4.19 (m, 1H), 4.19-4.11 (m, 1H), 3.79 (td, J = 6.2, 2.2 Hz, 2H), 3.63-3.50 (m, 2H), 3.09-2.99 (m, 1H), 2.60-2.53 (m, 1H), 2.51 (s, 3H), 2.35 (d, J = 13.1 Hz, 1H), 1.80 (d, J = 4.5 Hz, 1H), 1.76 (s, 3H), 1.70 (d, J = 1.3 Hz, 3H). LCMS (m/z) (M + H) = 520.2, Rt = 0.76 min |
| 261 | 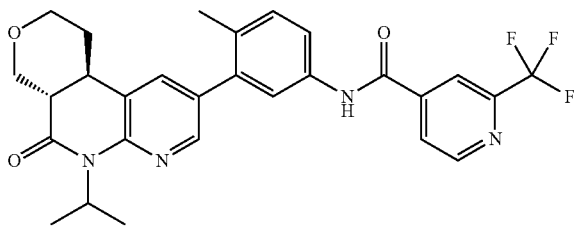 [SMILES: Cc1ccc(NC(=O)c2ccnc(C(F)(F)F)c2)cc1-c1cnc2c(c1)[C@@H]1CCOC[C@H]1C(=O)N2C(C)C] | N-(3-((4aS, 10bR)-6-isopropyl-5-oxo-2,4,4a,5,6,10b-hexahydro-1H-pyrano[3,4-c][1,8]naphthyridin-9-yl)-4-methylphenyl)-2-(trifluoromethyl)isonicotinamide | ¹H NMR (400 MHz, DMSO-d6) δ 10.73 (s, 1H), 9.00 (d, J = 4.9 Hz, 1H), 8.37 (s, 1H), 8.31-8.25 (m, 1H), 8.20 (d, J = 4.6 Hz, 1H), 7.72 (d, J = 6.7 Hz, 2H), 7.60 (s, 1H), 7.37 (d, J = 8.9 Hz, 1H), 5.23 (p, J = 6.8 Hz, 1H), 4.22 (dd, J = 11.4, 4.4 Hz, 1H), 4.02 (dd, J = 11.0, 3.3 Hz, 1H), 3.52-3.30 (m, 3H), 3.03-2.86 (m, 1H), 2.44 (ddd, J = 14.6, 10.6, 4.6 Hz, 1H), 2.28 (s, 3H), 1.63-1.53 (m, 1H), 1.51 (d, J = 6.9 Hz, 3H), 1.44 (d, J = 6.8 Hz, 3H). LCMS (m/z) (M + H) = 525.2, Rt = 1.33 min |
| 262 | 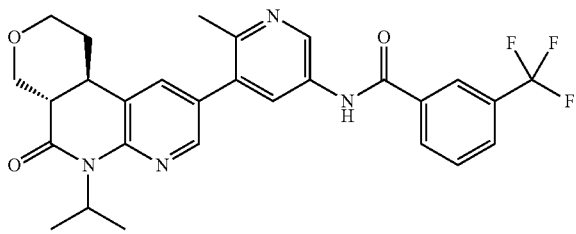 [SMILES: Cc1ncc(NC(=O)c2cccc(C(F)(F)F)c2)cc1-c1cnc2c(c1)[C@@H]1CCOC[C@H]1C(=O)N2C(C)C] | N-(5-((4aS, 10bR)-6-isopropyl-5-oxo-2,4,4a,5,6,10b-hexahydro-1H-pyrano[3,4-c][1,8]naphthyridin-9-yl)-6-methylpyridin-3-yl)-3-(trifluoromethyl)benzamide | ¹H NMR (400 MHz, Methanol-d4) δ 8.84 (d, J = 2.5 Hz, 1H), 8.35-8.28 (m, 2H), 8.23 (t, J = 8.2 Hz, 1H), 8.17 (d, J =+) 2.4 Hz, 1H), 7.92 (d, J = 7.8 Hz, 1H), 7.75 (td, J = 7.8, 3.7 Hz, 1H), 7.67 (dd, J = 2.1, 1.3 Hz, 1H), 5.31 (hept, J = 6.9 Hz, 1H), 4.37 (dd, J = 11.7, 4.6 Hz, 1H), 4.13 (dd, J = 11.5, 3.7 Hz, 1H), 3.53 (ddd, J = 24.6, 11.7, 10.5 Hz, 2H), 2.95 (s, 1H), 2.52 (d, J = 4.0 Hz, 4H), 2.42 (ddd, J = 14.7, 10.5, 4.6 Hz, 1H), 2.34-2.27 (m, 1H), 1.72 (qd, J = 12.5, 4.6 Hz, 1H), 1.57 (d, J = 6.9 Hz, 4H), 1.50 (d, J = 6.9 Hz, 3H). LCMS (m/z) (M + H) = 524.9, Rt = 1.13 min |

| Ex. No. | Structure | Name | Physical Data |
|---|---|---|---|
| 263 | 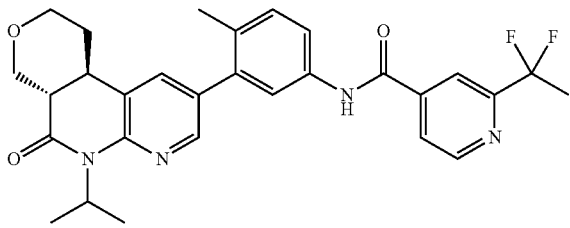 [SMILES: Cc1ccc(NC(=O)c2ccnc(C(C)(F)F)c2)cc1-c1cnc2c(c1)[C@@H]1CCOC[C@H]1C(=O)N2C(C)C] | 2-(1,1-difluoroethyl)-N-(3-((4aS, 10bR)-6-isopropyl-5-oxo-2,4,4a,5,6,10b-hexahydro-1H-pyrano[3,4-c][1,8]naphthyridin-9-yl)-4-methylphenyl) isonicotinamide | ¹H NMR (400 MHz, DMSO-d6) δ 10.69 (bs, 1 H), 8.89 (d, J = 4.8 Hz, 1H), 8.29 (s, 1H), 8.19 (s, 1H), 8.04 (d, J = 4.4 Hz, 1H), 7.73 (d, J = 7.4 Hz, 2H), 7.60 (s, 1H), 7.36 (d, J = 8.1 Hz, 1H), 5.23 (p, J = 6.7 Hz, 1H), 4.22 (dd, J = 11.3, 4.2 Hz, 1H), 4.02 (d, J = 8.0 Hz, 1H), 3.52-3.27 (m, 2H), 2.95 (t, J = 11.2 Hz, 1H), 2.47-2.38 (m, 1H), 2.28 (s, 4H), 2.06 (t, J = 19.1 Hz, 4H), 1.62-1.55 (m, 1H), 1.52 (d, J = 6.8 Hz, 3H), 1.44 (d, J = 6.8 Hz, 3H). LCMS (m/z) (M + H) = 521.1, Rt = 1.30 min |
| 264 | 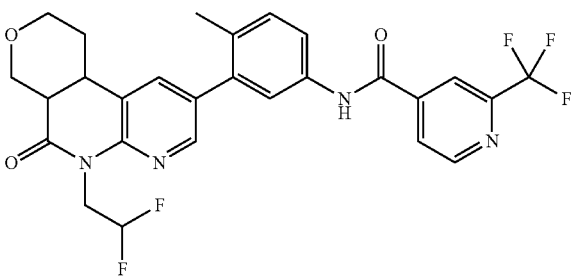 [SMILES: Cc1ccc(NC(=O)c2ccnc(C(F)(F)F)c2)cc1-c1cnc2c(c1)C1CCOCC1C(=O)N2CC(F)F] | N-(3-((4aS, 10bR)-6-(2,2-difluoroethyl)-5-oxo-2,4,4a,5,6,10b-hexahydro-1H-pyrano[3,4-c][1,8]naphthyridin-9-yl)-4-methylphenyl)-2-(trifluoromethyl) isonicotinamide | ¹H NMR (400 MHz, Methanol-d4) δ 8.90 (d, J = 5.0 Hz, 1H), 8.32-8.21 (m, 2H), 8.12 (d, J = 4.9 Hz, 1H), 7.66 (d, J = 8.0 Hz, 3H), 7.35 (d, J = 8.0 Hz, 1H), 6.23 (t, J =+) 4.4 Hz, 1H), 4.81 (tdd, J = 15.1, 10.1, 5.4 Hz, 1H), 4.41 (dd, J = 11.5, 4.4 Hz, 1H), 4.34 (dtd, J = 14.1, 7.9, 7.1, 3.2 Hz, 1H), 4.14 (dd, J = 11.5, 3.8 Hz, 1H), 3.68-3.47 (m, 2H), 3.02 (s, 1H), 2.57 (ddd, J = 14.6, 10.5, 4.5 Hz, 1H), 2.40-2.32 (m, 1H), 2.29 (s, 3H), 1.75 (qd, J = 12.4, 4.5 Hz, 1H). LCMS (m/z) (M + H) = 547.2, Rt = 1.24 min |
| 265 | 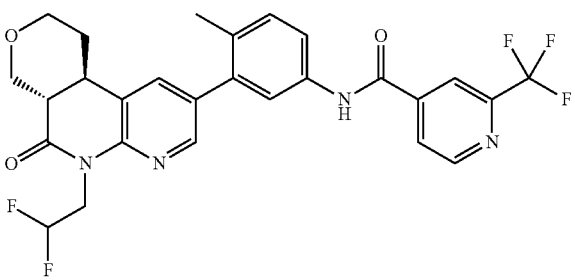 | 2-(1,1-difluoroethyl)-N-(3-((4aS, 10bR)-6-(2,2-difluoroethyl)-5-oxo-2,4,4a,5,6,10b-hexahydro-1H-pyrano[3,4-c][1,8]naphthyridin-9-yl)4-methylphenyl) isonicotinamide | ¹H NMR (400 MHz, Methanol-d4) δ 8.81 (d, J = 5.0 Hz, 1H), 8.33-8.25 (m, 1H), 8.18 (s, 1H), 7.97 (d, J = 4.5 Hz, 1H), 7.66 (d, J = 8.4 Hz, 3H), 7.35 (d, J = 8.0 Hz, 1H), 6.24 (t, J = 4.4 Hz, 1H), 4.81 (tdd, J = 15.1, 10.1, 5.4 Hz, 1H), 4.42 (dd, J = 11.5, 4.4 Hz, 1H), 4.34 (dddd, J = 13.9, 11.6, 7.0, 3.0 Hz, 1H), 4.14 (dd, J = 11.5, 3.8 Hz, 1H), 3.59 (d, J = 13.0 Hz, 1H), 3.53 (d, J = 11.4 Hz, 1H), 3.03 (s, 1H), 2.57 (ddd, J = 14.6, 10.5, 4.5 Hz, 1H), 2.40-2.32 (m, 1H), 2.30 (s, 3H), 2.04 (t, J = 18.7 Hz, 3H), 1.75 (qd, J = 12.4, 4.5 Hz, 1H). LCMS (m/z) (M + H) = 543.2, Rt = 1.22 min |
| 266 | 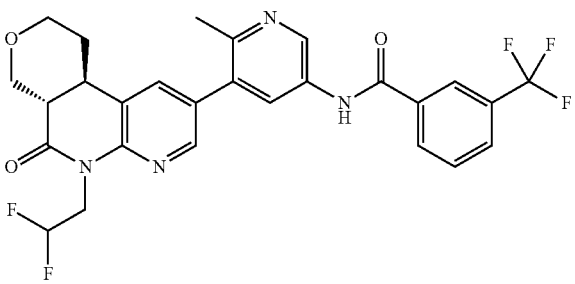 [SMILES: Cc1ncc(NC(=O)c2cccc(C(F)(F)F)c2)cc1-c1cnc2c(c1)[C@@H]1CCOC[C@H]1C(=O)N2CC(F)F] | N-(5-((4aS, 10bR)-6-(2,2-difluoroethyl)-5-oxo-2,4,4a,5,6,10b-hexahydro-1H-pyrano[3,4-c][1,8]naphthyridin-9-yl)-6-methylpyridin-3-yl)-3-(trifluoromethyl) benzamide | ¹H NMR (400 MHz, Methanol-d4) δ 8.84 (d, J = 2.4 Hz, 1H), 8.36-8.32 (m, 1H), 8.30 (s, 1H), 8.24 (d, J = 7.9 Hz 1H), 8.18 (d, J = 2.3 Hz 1H), 7.92 (d, J = 7.8 Hz, 1H), 7.79-7.67 (m, 2H), 6.24 (t, J = 4.4 Hz, 1H), 4.81 (ddt, J = 15.0, 10.2, 5.1 Hz, 1H), 4.42 (dd, J = 11.8, 4.4 Hz, 1H), 4.40-4.27 (m, 1H), 4.15 (dd, J = 11.5, 3.8 Hz, 1H), 3.56 (q, J = 12.1, 11.4 Hz, 2H), 3.04 (s, 1H), 2.59 (ddd, J = 14.6, 10.5, 4.5 Hz, 1H), 2.51 (s, 3H), 2.37 (d, J = 13.4 Hz, 1H), 1.77 (qd, J = 12.4, 4.5 Hz, 1H). LCMS (m/z) (M + H) = 547.2, Rt = 1.10 min |

-continued

| Ex. No. | Structure | Name | Physical Data |
|---|---|---|---|
| 267 | 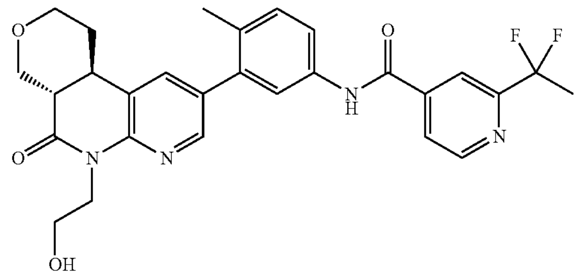 [SMILES: Cc1ccc(NC(=O)c2ccnc(C(C)(F)F)c2)cc1-c1cnc2c(c1)[C@@H]1CCOC[C@H]1C(=O)N2CCO] | 2-(1,1-difluoroethyl)-N-(3-((4aS, 10bR)-6-(2-hydroxyethyl)-5-oxo-2,4,4a,5,6,10b-hexahydro-1H-pyrano[3,4-c][1,8]naphthyridin-9-yl)-4-methylphenyl)isonicotinamide | 1H NMR (400 MHz, Methanol-d4) δ 8.80 (d, J = 5.1 Hz, 1H), 8.25 (d, J = 1.3 Hz, 1H), 8.17 (s, 1H), 7.96 (d, J = 5.0 Hz, 1H), 7.70-7.56 (m, 3H), 7.34 (d, J = 9.2 Hz, 1H), 4.49 (dt, J = 13.2, 5.9 Hz, 1H), 4.41 (dd, J = 11.7, 4.5 Hz, 1H), 4.20 (dt, J = 13.3, 6.6 Hz, 1H), 4.16-4.09 (m, 1H), 3.79 (td, J = 6.2, 1.6 Hz, 2H), 3.64-3.49 (m, 2H), 3.08-2.97 (m, 1H), 2.53 (ddd, J = 14.6, 10.5, 4.5 Hz, 1H), 2.37-2.31 (m, 1H), 2.29 (s, 3H), 2.03 (t, J = 18.7 Hz, 3H), 1.74 (qd, J = 12.4, 4.6 Hz, 1H). LCMS (m/z) (M + H) = 523.1, Rt = 1.02 min |
| 268 | 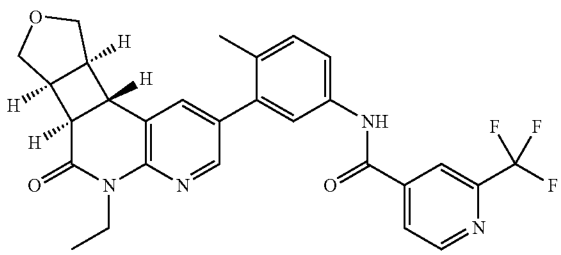 [SMILES: CCN1C(=O)[C@H]2[C@H]3COC[C@H]3[C@@H]2c2cc(-c3cc(NC(=O)c4ccnc(C(F)(F)F)c4)ccc3C)cnc21] | N-(3-((6aS, 6bS, 9aS, 9bS)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)-2-(trifluoromethyl)isonicotinamide | 1H NMR (400 MHz, Methanol-d4) δ 8.90 (d, J = 5.0 Hz, 1H), 8.30 (s, 1H), 8.25 (d, J = 2.1 Hz, 1H), 8.16-8.08 (m, 1H), 7.65 (d, J = 7.4 Hz, 2H), 7.58 (d, J = 1.6 Hz, 1H), 7.33 (d, J = 8.2 Hz, 1H), 4.30 (q, J = 6.9 Hz, 2H), 4.16 (dd, J = 15.0, 9.7 Hz, 2H), 3.53 (ddd, J = 14.8, 9.7, 5.1 Hz, 2H), 3.49-3.43 (m, 1H), 3.17 (td, J = 10.8, 9.3, 6.0 Hz, 2H), 2.95-2.86 (m, 1H), 2.29 (s, 3H), 1.25 (t, J = 7.0 Hz, 3H). LCMS (m/z) (M + H) = 523.2, Rt = 1.18 min |
| 269 | 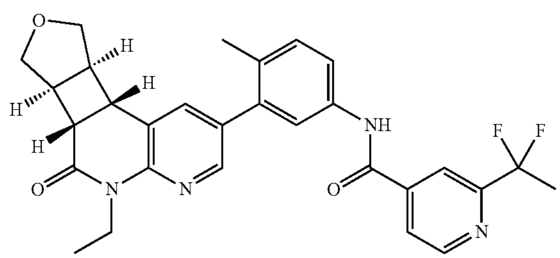 [SMILES: CCN1C(=O)[C@@H]2[C@H]3COC[C@H]3[C@@H]2c2cc(-c3cc(NC(=O)c4ccnc(C(C)(F)F)c4)ccc3C)cnc21] | 2-(1,1-difluoroethyl)-N-(3-((6aS, 6bS, 9aS, 9bS)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)isonicotinamide | 1H NMR (400 MHz, Methanol-d4) δ 8.80 (d, J = 5.0 Hz, 1H), 8.25 (d, J = 2.1 Hz, 1H), 7.96 (d, J = 4.3 Hz, 1H), 7.64 (d, J = 7.6 Hz, 2H), 7.58 (d, J = 1.6 Hz, 1H), 7.33 (d, J = 7.9 Hz, 1H), 4.30 (q, J = 6.9 Hz, 2H), 4.16 (dd, J = 15.7, 9.7 Hz, 2H), 3.54 (td, J = 9.6, 4.8 Hz, 2H), 3.50-3.43 (m, 1H), 3.17 (td, J = 10.9, 9.3, 6.0 Hz, 2H), 2.97-2.84 (m, 1H), 2.28 (s, 3H), 2.03 (t, J = 18.7 Hz, 3H), 1.25 (t, J = 6.9 Hz, 3H). LCMS (m/z) (M + H) = 519.2, Rt = 1.15 min |
| 270 | 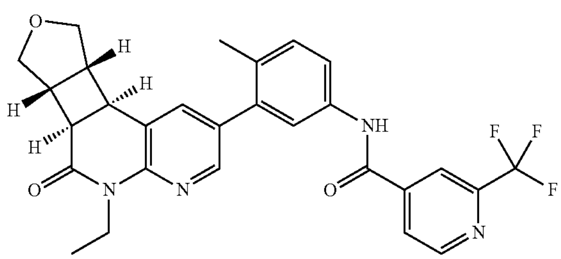 [SMILES: CCN1C(=O)[C@H]2[C@@H]3COC[C@@H]3[C@H]2c2cc(-c3cc(NC(=O)c4ccnc(C(F)(F)F)c4)ccc3C)cnc21] | N-(3-((6aR, 6bR, 9aR, 9bR)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)-2-(trifluoromethyl)isonicotinamide | 1H NMR (400 MHz, Methanol-d4) δ 8.93 (d, J = 5.0 Hz, 1H), 8.32 (s, 1H), 8.27 (d, J = 2.1 Hz, 1H), 8.17-8.12 (m, 1H), 7.67 (d, J = 7.3 Hz, 2H), 7.62-7.57 (m, 1H), 7.36 (d, J = 8.8 Hz, 1H), 4.32 (q, J = 7.0 Hz, 2H), 4.19 (dd, J = 15.0, 9.7 Hz, 2H), 3.56 (td, J = 9.6, 4.8 Hz, 2H), 3.50 (dd, J = 9.3, 4.5 Hz, 1H), 3.25-3.13 (m, 2H), 2.98-2.90 (m, 1H), 2.31 (s, 3H), 1.28 (t, J = 7.0 Hz, 3H). LCMS (m/z) (M + H) = 523.2, Rt = 1.18 min |
| 271 | 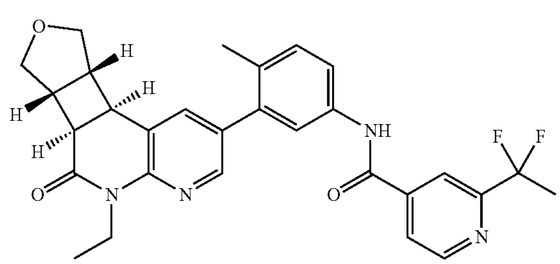 [SMILES: CCN1C(=O)[C@H]2[C@@H]3COC[C@@H]3[C@H]2c2cc(-c3cc(NC(=O)c4ccnc(C(C)(F)F)c4)ccc3C)cnc21] | 2-(1,1-difluoroethyl)-N-(3-((6aR, 6bR, 9aR, 9bR)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)isonicotinamide | 1H NMR (400 MHz, Methanol-d4) δ 8.85-8.80 (m, 1H), 8.27 (d, J = 2.2 Hz, 1H), 8.22-8.15 (m, 1H), 7.98 (dd, J = 5.0, 1.5 Hz, 1H), 7.66 (d, J = 7.5 Hz, 2H), 7.63-7.56 (m, 1H), 7.35 (d, J = 8.0 Hz, 1H), 4.32 (q, J = 7.0 Hz, 2H), 4.19 (dd, J = 15.7, 9.7 Hz, 2H), 3s.56 (td, J = 9.6, 4.8 Hz, 2H), 3.52-3.45 (m, 1H), 3.24-3.13 (m, 2H), 3.01-2.89 (m, 1H), 2.31 (s, 3H), 2.05 (t, J = 18.7 Hz, 3H), 1.28 (t, J = 7.0 Hz, 3H). LCMS (m/z) (M + H) = 519.2, Rt = 1.16 min |

| Ex. No. | Structure | Name | Physical Data |
|---|---|---|---|
| 272 | 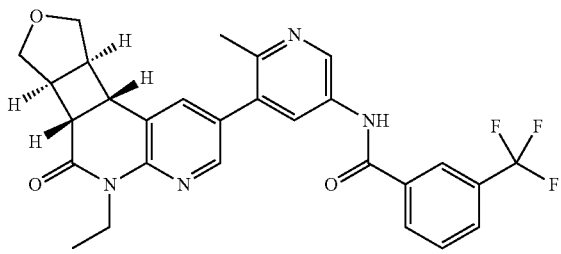 [SMILES: CCN1C(=O)[C@@H]2[C@H]3COC[C@H]3[C@@H]2c2cc(-c3cc(NC(=O)c4cccc(C(F)(F)F)c4)cnc3C)cnc21] | N-(5-((6aS, 6bS, 9aS, 9bS)-5-ethyl-6-oxo-5,6,6a,6b,7,9,9a,9b-octahydrofuro[3',4':3,4]cyclobuta[1,2-c][1,8]naphthyridin-2-yl)-6-methylpyridin-3-yl)-3-(trifluoromethyl)benzamide | ¹H NMR (400 MHz, Methanol-d4) δ 8.73 (d, J = 2.4 Hz, 1H), 8.22 (q, J = 3.6, 2.5 Hz, 2H), 8.15 (d, J = 7.9 Hz, 1H), 8.08 (d, J = 2.4 Hz, 1H), 7.83 (d, J = 7.8 Hz, 1H), 7.66 (t, J = 7.8 Hz, 1H), 7.57 (dd, J = 2.2, 0.7 Hz, 1H), 4.22 (q, J = 7.0 Hz, 2H), 4.11 (d, J = 9.6 Hz, 1H), 4.06 (d, J = 9.7 Hz, 1H), 3.44 (ddt, J = 19.5, 9.6, 4.4 Hz, 3H), 3.16-3.06 (m, 2H), 2.88-2.81 (m, 1H), 2.42 (s, 3H), 1.17 (t, J = 7.0 Hz, 3H). LCMS (m/z) (M + H) = 523.9, Rt = 0.93 min |
| 273 | 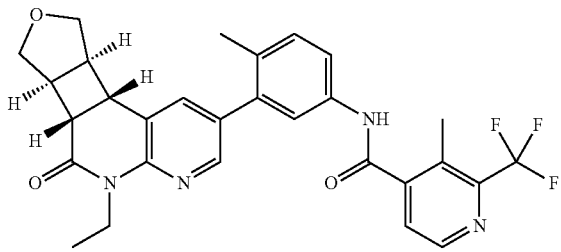 | N-(3-((6aS, 6bS, 9aS, 9bS)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)-3-fluoro-2-(trifluoromethyl)isonicotinamide | ¹H NMR (400 MHz, Methanol-d4) δ 8.65 (d, J = 4.7 Hz, 1H), 8.24 (d, J = 2.2 Hz, 1H), 7.95 (t, J = 4.8 Hz, 1H), 7.63-7.55 (m, 3H), 7.33 (d, J = 8.2 Hz 1H), 4.30 (q, J = 7.0 Hz, 2H), 4.16 (dd, J = 15.9, 9.7 Hz, 2H), 3.53 (ddd, J = 14.9, 9.7, 5.2 Hz, 2H), 3.47 (dd, J = 9.5, 4.3 Hz, 1H), 3.23-3.11 (m, 2H), 2.94-2.89 (m, 1H), 2.28 (d, J = 3.5 Hz, 3H), 1.25 (t, J = 7.0 Hz, 3H). LCMS (m/z) (M + H) = 541.1, Rt = 1.13 min |
| 274 | 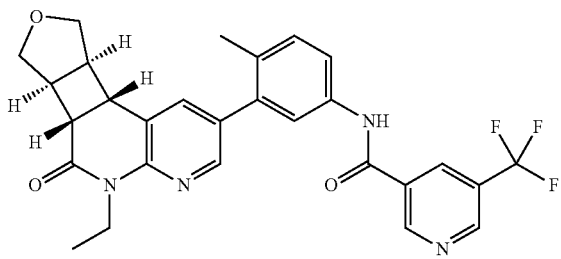 [SMILES: CCN1C(=O)[C@@H]2[C@H]3COC[C@H]3[C@@H]2c2cc(-c3cc(NC(=O)c4cncc(C(F)(F)F)c4)ccc3C)cnc21] | N-(3-((6aS, 6bS, 9aS, 9bS)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)-5-(trifluoromethyl)nicotinamide | ¹H NMR (400 MHz, Methanol-d4) δ 9.38-9.30 (m, 1H), 9.11-9.02 (m, 1H), 8.66 (s, 1H), 8.24 (d, J = 2.1 Hz, 1H), 7.64 (d, J = 8.8 Hz, 2H), 7.58 (d, J = 1.6 Hz, 1H), 7.32 (d , J = 8.0 Hz, 1H), 4.30 (q, J = 6.9 Hz, 2H), 4.16 (dd, J = 15.5, 9.7 Hz, 2H), 3.53 (ddd, J = 14.7, 9.7, 5.1 Hz, 2H), 3.47 (dd, J = 9.5, 4.3 Hz, 1H), 3.18 (ddd, J = 14.3, 10.7, 4.8 Hz, 2H), 2.98-2.85 (m, 1H), 2.28 (s, 3H), 1.25 (t, J = 6.9 Hz, 3H). LCMS (m/z) (M + H) = 523.1, Rt = 1.09 min |
| 275 | 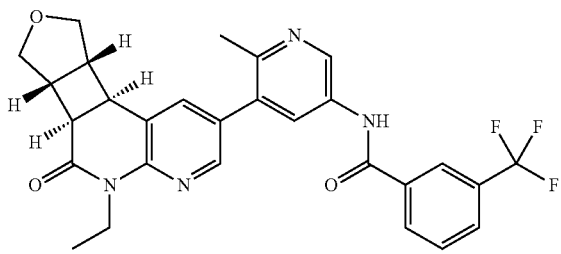 [SMILES: CCN1C(=O)[C@H]2[C@@H]3COC[C@@H]3[C@H]2c2cc(-c3cc(NC(=O)c4cccc(C(F)(F)F)c4)cnc3C)cnc21] | N-(5-((6aR, 6bR, 9aR, 9bR)-5-ethyl-6-oxo-5,6,6a,6b,7,9,9a,9b-octahydrofuro[3',4':3,4]cyclobuta[1,2-c][1,8]naphthyridin-2-yl)-6-methylpyridin-3-yl)-3-(trifluoromethyl)benzamide | ¹H NMR (400 MHz, Methanol-d4) δ 8.82 (d, J = 2.4 Hz, 1H), 8.33-8.28 (m, 2H), 8.24 (d, J = 8.0 Hz, 1H), 8.17 (d, J = 2.4 Hz, 1H), 7.92 J = 78 Hz, 1H), 7.75 (t, J = 7.8 Hz, 1H), 7.66 (dd, J = 2.2, 0.7 Hz, 1H), 4.31 (q, J = 7.0 Hz, 2H), 4.17 (dd, J = 19.1, 9.7 Hz, 2H), 3.53 (ddt, J = 15.7, 11.0, 5.5 Hz, 4H), 3.19 (ddd, J = 13.4, 8.4, 3.7 Hz, 2H), 2.97-2.87 (m, 1H), 2.51 (s, 3H), 1.26 (t, J = 7.0 Hz, 3H). LCMS (m/z) (M + H) = 523.3, Rt = 1.03 min |
| 276 | 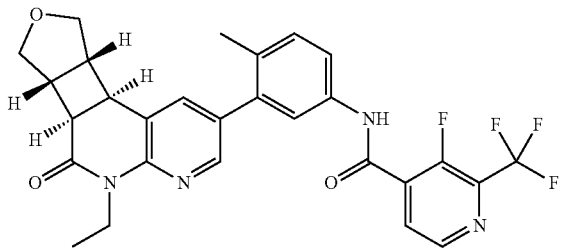 [SMILES: CCN1C(=O)[C@H]2[C@@H]3COC[C@@H]3[C@H]2c2cc(-c3cc(NC(=O)c4ccnc(C(F)(F)F)c4F)ccc3C)cnc21] | N-(3-((6aR, 6bR, 9aR, 9bR)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)-3-fluoro-2-(trifluoromethyl)isonicotinamide | 1H NMR (400 MHz, Methanol-d4) δ 8.65 (d, J = 4.7 Hz, 1H), 8.24 (d, J = 2.2 Hz, 1H), 7.95 (t, J = 4.8 Hz, 1H), 7.64-7.55 (m, 3H), 7.33 (d, J = 8.2 Hz, 1H), 4.30 (q, J = 7.0 Hz, 2H), 4.16 (dd, J = 16.0, 9.7 Hz, 2H), 3.53 (ddd, J = 14.9, 9.7, 5.2 Hz, 2H), 3.49-3.44 (m, 1H), 3.18 (ddt, J = 14.2, 9.4, 4.9 Hz, 2H), 2.94-2.87 (m, 1H), 2.28 (s, 3H), 1.25 (t, J = 7.0 Hz, 3H). LCMS (m/z) (M + H) = 541.2, Rt = 1.13 min |

| Ex. No. | Structure | Name | Physical Data |
|---|---|---|---|
| 277 | 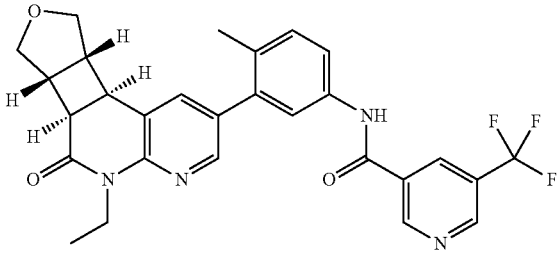 [SMILES: CCN1C(=O)[C@H]2[C@@H]3COC[C@@H]3[C@H]2c2cc(-c3cc(NC(=O)c4cncc(C(F)(F)F)c4)ccc3C)cnc21] | N-(3-((6aR, 6bR, 9aR, 9bR)-5-ethyl-6-oxo-5,6,6a,6b,7,9,9a,9b-octahydrofuro[3',4':3,4]cyclobuta[1,2-c][1,8]naphthyridin-2-yl)-4-methylphenyl)-5-(trifluoromethyl) nicotinamide | $^1$H NMR (400 MHz, Methanol-d4) δ 9.34 (d, J = 1.8 Hz, 1H), 9.10-9.03 (m, 1H), 8.66 (s, 1H), 8.25 (d, J = 2.2 Hz, 1H), 7.68-7.60 (m, 2H), 7.60-7.56 (m, 1H), 7.33 (d, J = 7.9 Hz, 1H), 4.30 (q, J = 7.0 Hz, 2H), 4.16 (dd, J = 15.4, 9.7 Hz, 2H), 3.53 (ddd, J = 14.7, 9.7, 5.2 Hz, 2H), 3.47 (dd, J = 9.4, 4.3 Hz, 1H), 3.23-3.14 (m, 2H), 2.94-2.86 (m, 1H), 2.28 (s, 3H), 1.25 (t, J = 7.0 Hz, 3H). LCMS (m/z) (M + H) = 523.2, Rt = 1.09 min |
| 278 | 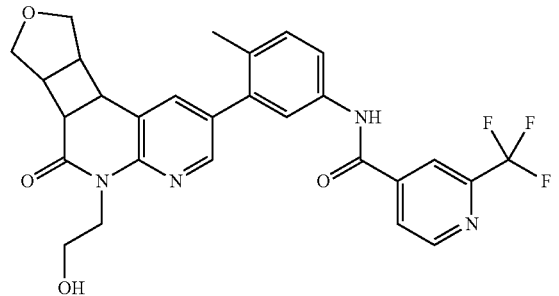<br>single enantomer and diastereomer from Peak 1 intermediate | N-(3-(5-(2-hydroxyethyl)-6-oxo-5,6,6a,6b,7,9,9a,9b-octahydrofuro[3',4':3,4]cyclobuta[1,2-c][1,8]naphthyridin-2-yl)-4-methylphenyl)-2-(trifluoromethyl) isonicotinamide | $^1$H NMR (400 MHz, Methanol-d4) δ 8.90 (d, J = 5.0 Hz, 1H), 8.30 (s, 1H), 8.23 (d, J = 2.2 Hz, 1H), 8.15-8.09 (m, 1H), 7.64 (d, J = 7.6 Hz, 2H), 7.61-7.56 (m, 1H), 7.33 (d, J = 7.9 Hz, 1H), 4.44 (t, J = 6.4 Hz, 2H), 4.16 (dd, J = 17.5, 9.7 Hz, 2H), 3.81 (t, J = 6.4 Hz, 2H), 3.60-3.44 (m, 3H), 3.21 (ddt, J = 14.6, 9.7, 5.1 Hz, 2H), 2.97-2.88 (m, 1H), 2.28 (s, 3H). LCMS (m/z) (M + H) = 539.3, Rt = 1.02 min |
| 279 | 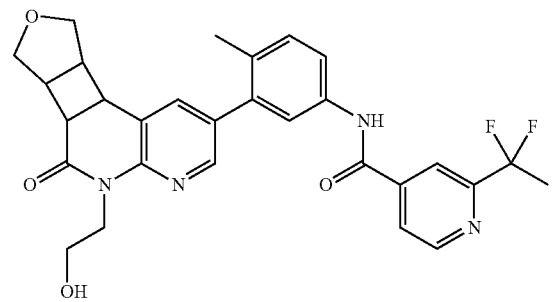<br>single enantomer and diastereomer from Peak 1 intermediate | 2-(1,1-difluoroethyl)-N-(3-(5-(2-hydroxyethyl)-6-oxo-5,6,6a,6b,7,9,9a,9b-octahydrofuro[3',4':3,4]cyclobuta[1,2-c][1,8]naphthyridin-2-yl)-4-methylphenyl) isonicotinamide | $^1$H NMR (400 MHz, Methanol-d4) δ 8.80 (d, J = 5.2 Hz, 1H), 8.23 (d, J = 2.2 Hz, 1H), 8.17 (s, 1H), 7.96 (dd, J = 5.0, 1.4 Hz, 1H), 7.67-7.61 (m, 2H), 7.59 (d, J = 1.6 Hz, 1H), 7.33 (d, J = 7.8 Hz, 1H), 4.44 (t, J = 6.4 Hz, 2H), 4.16 (dd, J = 18.2, 9.7 Hz, 2H), 3.81 (t, J = 6.4 Hz, 2H), 3.58-3.44 (m, 3H), 3.21 (ddt, J = 18.4, 9.6, 4.9 Hz, 2H), 2.94 (dt, J = 8.7, 4.9 Hz, 1H), 2.28 (s, 3H), 2.03 (t, J = 18.7 Hz, 3H). LCMS (m/z) (M + H) = 535.4, Rt = 1.00 min |
| 280 | 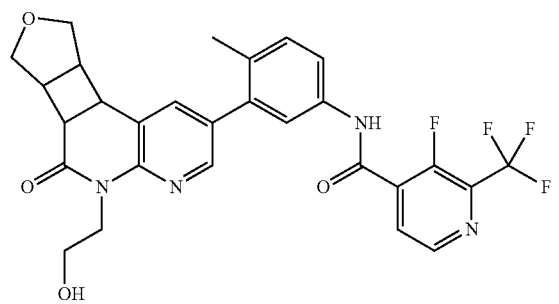<br>single enantomer and diastereomer from Peak 1 intermediate | 3-fluoro-N-(3-(5-(2-hydroxyethyl)-6-oxo-5,6,6a,6b,7,9,9a,9b-octahydrofuro[3',4':3,4]cyclobuta[1,2-c][1,8]naphthyridin-2-yl)-4-methylphenyl)-2-(trifluoromethyl) isonicotinamide | $^1$H NMR (400 MHz, Methanol-d4) δ 8.65 (d, J = 4.7 Hz, 1H), 8.22 (d, J = 2.1 Hz, 1H), 7.95 (t, J = 4.8 Hz, 1H), 7.64-7.54 (m, 3H), 7.33 (d, J = 8.2 Hz, 1H), 4.44 (t, J = 6.4 Hz, 2H), 4.16 (dd, J = 18.5, 9.7 Hz, 2H), 3.81 (t, J = 6.4 Hz, 2H), 3.59-3.43 (m, 3H), 3.21 (ddd, J = 18.0, 8.5, 5.1 Hz, 2H), 2.98-2.90 (m, 1H), 2.27 (s, 3H). LCMS (m/z) (M + H) = 557.4, Rt = 1.05 min |

| Ex. No. | Structure | Name | Physical Data |
|---|---|---|---|
| 281 | 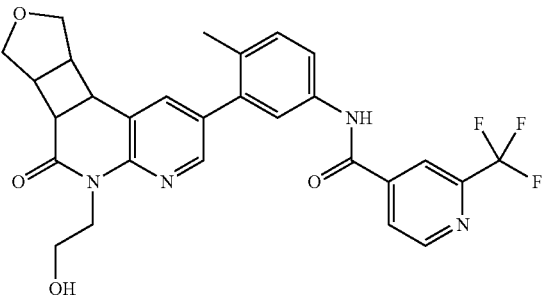<br>single enantomer and diastereomer from Peak 2 intermediate | N-(3-(5-(2-hydroxyethyl)-6-oxo-5,6,6a,6b,7,9,9a,9b-octahydrofuro[3',4':3,4]cyclobuta[1,2-c][1,8]naphthyridin-2-yl)--4-methylphenyl)-2-(trifluoromethyl)isonicotinamide | $^1$H NMR (400 MHz, Methanol-d4) δ 8.90 (d, J = 5.0 Hz, 1H), 8.30 (s, 1H), 8.23 (d, J = 2.0 Hz, 1H), 8.12 (d, J = 4.4 Hz, 1H), 7.64 (d, J = 7.7 Hz, 2H), 7.59 (d, J = 1.6 Hz, 1H), 7.33 (d, J = 7.9 Hz, 1H), 4.44 (t, J = 6.4 Hz, 2H), 4.16 (dd, J = 17.6, 9.7 Hz, 2H), 3.81 (t, J = 6.4 Hz, 2H), 3.52 (ddt, J = 20.0, 9.5, 4.6 Hz, 3H), 3.21 (ddt, J = 14.3, 9.5, 4.8 Hz, 2H), 2.98-2.86 (m, 1H), 2.28 (s, 3H). LCMS (m/z) (M + H) = 539.3, Rt = 1.02 min |
| 283 | 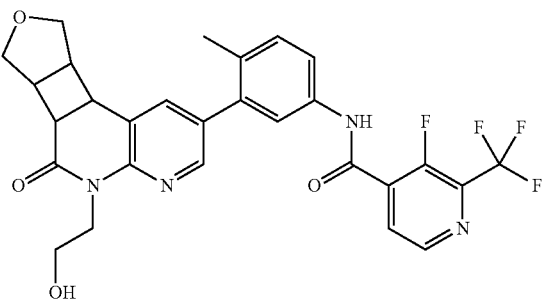<br>single enantomer and diastereomer from Peak 2 intermediate | 3-fluoro-N-(3-(5-(2-hydroxyethyl)-6-oxo-5,6,6a,6b,7,9,9a,9b-octahydrofuro[3',4':3,4]cyclobuta[1,2-c][1,8]naphthyridin-2-yl)-4-methylphenyl)-2-(trifluoromethyl)-2-isonicotinamide | $^1$H NMR (400 MHz, Methanol-d4) δ 8.65 (d, J = 4.7 Hz, 1H), 8.22 (d, J = 2.1 Hz, 1H), 7.95 (t, J = 4.8 Hz, 1H), 7.63-7.53 (m, 3H), 7.33 (d, J = 8.2 Hz, 1H), 4.44 (t, J = 6.4 Hz, 2H), 4.16 (dd, J = 18.5, 9.7 Hz, 2H), 3.81 (t, J = 6.4 Hz, 2H), 3.60-3.44 (m, 3H), 3.20 (ddd, J = 18.4, 8.6, 5.1 Hz, 2H), 2.97-2.87 (m, 1H), 2.27 (s, 3H). LCMS (m/z) (M + H) = 557.4, Rt = 1.05 min |
| 284 | 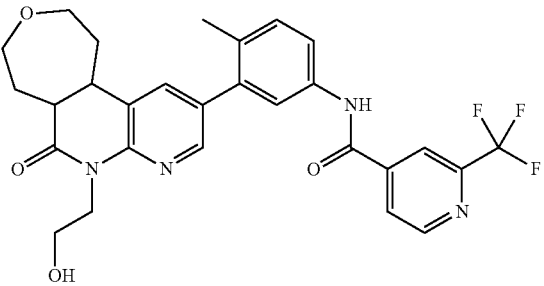<br>single enantomer and diastereomer from Peak 4 intermediate | N-(3-(7-(2-hydroxyethyl)-6-oxo-1,2,4,5,5a,6,7,11b-octahydrooxepino[4,5-c][1,8]naphthyridin-10-yl)-4-methylphenyl)-2-(trifluoromethyl)isonicotinamide | $^1$H NMR (400 MHz, Methanol-d4) δ 8.91 (d, J = 5.0 Hz, 1H), 8.30 (s, 1H), 8.26-8.22 (m, 1H), 8.12 (dd, J = 5.0, 1.3 Hz, 1H), 7.77-7.72 (m, 1H), 7.65 (dd, J = 5.6, 2.3 Hz, 2H), 7.38-7.32 (m, 1H), 4.53 (dt, J = 13.0, 5.9 Hz, 1H), 4.25 (dt, J = 13.1, 6.5 Hz, 1H), 3.97 (ddd, J = 11.6, 6.4, 3.5 Hz, 2H), 3.89-3.73 (m, 4H), 3.04 (ddd, J = 14.2, 10.4, 4.3 Hz, 1H), 2.72 (dq, J = 15.5, 3.3 Hz, 1H), 2.67-2.50 (m, 2H), 2.29 (s, 3H), 2.12 (dddd, J = 15.7, 11.4, 9.2, 4.4 Hz, 1H), 2.03-1.92 (m, 1H). LCMS (m/z) (M + H) = 541.4, Rt = 1.06 min |
| 285 | 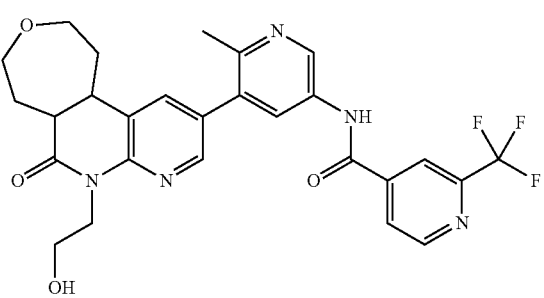<br>single enantomer and diastereomer from Peak 4 intermediate | N-(5-(7-(2-hydroxyethyl)-6-oxo-1,2,4,5,5a,6,7,11b-octahydrooxepino[4,5-c][1,8]naphthyridin-10-yl)-6-methylpyridin-3-yl)-3-(trifluoromethyl)benzamide | $^1$H NMR (400 MHz, Methanol-d4) δ 8.83 (d, J = 2.4 Hz, 1H), 8.33-8.28 (m, 2H), 8.24 (d, J = 7.9 Hz, 1H), 8.17 (d, J = 2.4 Hz, 1H), 7.92 (d, J = 7.8 Hz, 1H), 7.82-7.78 (m, 1H), 7.75 (t, J = 7.8 Hz, 1H), 4.53 (dt, J = 12.3, 6.0 Hz, 1H), 4.25 (dt, J = 13.1, 6.5 Hz, 1H), 3.97 (dq, J = 11.7, 4.2 Hz, 2H), 3.89-3.74 (m, 4H), 3.05 (ddd, J = 14.2, 10.4, 4.2 Hz, 1H), 2.72 (dq, J = 15.5, 3.3 Hz, 1H), 2.68-2.53 (m, 2H), 2.51 (s, 3H), 2.12 (dddd, J = 15.6, 11.3, 9.2, 4.4 Hz, 1H), 1.99 (dtd, J = 14.0, 10.7, 3.2 Hz, 1H). LCMS (m/z) (M + H) = 541.4, Rt = 0.91 min |

| Ex. No. | Structure | Name | Physical Data |
|---|---|---|---|
| 286 | 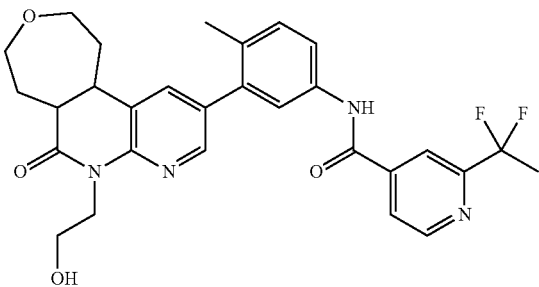<br>single enantomer and diastereomer from Peak 4 intermediate | 2-(1,1-difluoroethyl)-N-(3-(7-(2-hydroxyethyl)-6-oxo-1,2,4,5,5a,6,7,11b-octahydrooxepino[4,5-c][1,8]naphthyridin-10-yl)-4-methylphenyl) isonicotinamide | $^1$H NMR (400 MHz, Methanol-d4) δ 8.80 (d, J = 4.9 Hz, 1H), 8.28-8.21 (m, 1H), 8.18 (s, 1H), 8.00-7.93 (m, 1H), 7.73 (s, 1H), 7.65 (dd, J = 5.6, 2.3 Hz, 2H), 7.37-7.28 (m, 1H), 4.59-4.47 (m, 1H), 4.24 (dt, J = 13.1, 6.5 Hz, 1H), 3.97 (dq, J = 10.8, 3.6 Hz, 2H), 3.90-3.70 (m, 4H), 3.09-2.99 (m, 1H), 2.72 (dq, J = 15.5, 3.3 Hz, 1H), 2.66-2.51 (m, 2H), 2.29 (s, 3H), 2.16-2.09 (m, 1H), 2.08-1.93 (m, 4H). LCMS (m/z) (M + H) = 537.4, Rt = 1.03 min |
| 287 | 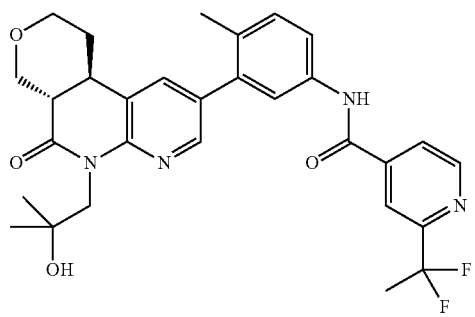 [SMILES: Cc1ccc(NC(=O)c2ccnc(C(C)(F)F)c2)cc1-c1cnc2c(c1)[C@@H]1CCOC[C@H]1C(=O)N2CC(C)(C)O] | 2-(1,1-difluoroethyl)-N-(3-((4aS,10bR)-6-(2-hydroxy-2-methylpropyl)-5-oxo-2,4,4a,5,6,10b-hexahydro-1H-pyrano[3,4-c][1,8]naphthyridin-9-yl)-4-methylphenyl) isonicotinamide | 1H NMR (400 MHz, Methanol-d4) δ 8.83-8.78 (m, 1H), 8.24 (d, J = 1.3 Hz, 1H), 8.20-8.16 (m, 1H), 7.96 (dd, J = 5.0, 1.4 Hz, 1H), 7.70-7.63 (m, 3H), 7.34 (d, J = 8.1 Hz, 1H), 4.67 (d, J = 14.2 Hz, 1H), 4.40 (dd, J = 11.7, 4.5 Hz, 1H), 4.14 (dd, J = 11.6, 3.8 Hz, 1H), 3.91 (d, J = 14.2 Hz, 1H), 3.64-3.49 (m, 2H), 3.05 (s, 1H), 2.57 (ddd, J = 14.6, 10.5, 4.5 Hz, 1H), 2.39-2.31 (m, 1H), 2.29 (s, 3H), 2.03 (t, J = 18.7 Hz, 3H), 1.75 (qd, J = 12.4, 4.6 Hz, 1H), 1.26 (s, 3H), 1.14 (s, 3H). LCMS (m/z) (M + H) = 551.2, Rt = 1.04 min |
| 288 | 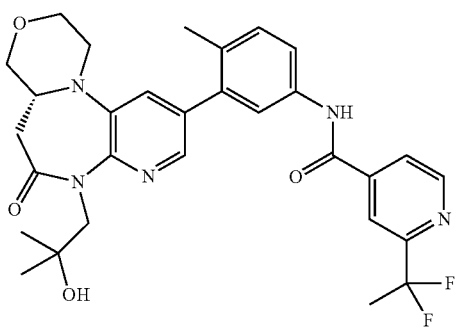 | (R)-N-(3-(7-(2-hydroxy-2-methylpropyl)-6-oxo-2,4,4a,5,6,7-hexahydro-1H-[1,4]oxazino[4,3-d]pyrido[2,3-b][1,4]diazepin-10-yl)-4-methylphenyl)-2-(trifluoromethyl) isonicotinamide | $^1$H NMR (400 MHz, Methanol-d4) δ 8.90 (d, J = 5.0 Hz, 1H), 8.30 (s, 1H), 8.17 (d, J = 1.9 Hz, 1H), 8.14-8.09 (m, 1H), 7.73 (d, J = 2.2 Hz, 1H), 7.65 (dd, J = 8.3, 2.3 Hz, 1H), 7.61 (d, J = 1.9 Hz, 1H), 7.36 (d, J = 8.4 Hz, 1H), 4.36 (d, J = 14.0 Hz, 1H), 3.94 (t, J = 11.7 Hz, 2H), 3.87 (d, J = 9.3 Hz, 1H), 3.67 (q, J = 10.9 Hz, 2H), 3.41 (s, 1H), 3.01 (d, J = 10.9 Hz, 1H), 2.83 (dd, J = 13.3, 7.5 Hz, 1H), 2.30 (s, 3H), 2.22 (d, J = 13.7 Hz, 1H), 1.20 (d, J = 3.8 Hz, 3H), 1.14 (s, 3H). LCMS (m/z) (M + H) = 570.2, Rt = 0.99 min. |
| 289 | 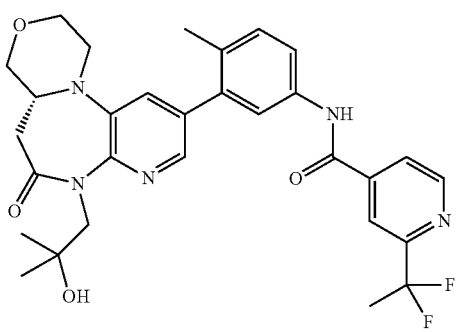 [SMILES: Cc1ccc(NC(=O)c2ccnc(C(C)(F)F)c2)cc1-c1cnc2c(c1)N1CCOC[C@H]1CC(=O)N2CC(C)(C)O] | (R)-2-(1,1-difluoroethyl)-N-(3-(7-(2-hydroxy-2-methylpropyl)-6-oxo-2,4,4a,5,6,7-hexahydro-1H-[1,4]oxazino[4,3-d]pyrido[2,3-b][1,4]diazepin-10-yl)-4-methylphenyl) isonicotinamide | $^1$H NMR (400 MHz, Methanol-d4) δ 8.83-8.77 (m, 1H), 8.17 (d, J = 2.0 Hz, 2H), 7.96 (dd, J = 5.0, 1.4 Hz, 1H), 7.73 (d, J = 2.2 Hz, 1H), 7.65 (dd, J = 8.3, 2.3 Hz, 1H), 7.61 (d, J = 2.0 Hz, 1H), 7.36 (d, J = 8.4 Hz, 1H), 4.36 (d, J = 14.0 Hz, 1H), 3.94 (t, J = 12.1 Hz, 2H), 3.87 (d, J = 9.2 Hz, 1H), 3.67 (q, J = 11.0 Hz, 2H), 3.42 (s, 1H), 3.01 (d, J = 10.9 Hz, 1H), 2.83 (dd, J = 13.4, 7.5 Hz, 1H), 2.30 (s, 3H), 2.22 (d, J = 13.7 Hz, 1H), 2.03 (t, J = 18.7 Hz, 3H), 1.20 (s, 3H), 1.14 (s, 3H). LCMS (m/z) (M + H) = 566.2, Rt = 0.96 min |

| Ex. No. | Structure | Name | Physical Data |
|---|---|---|---|
| 290 | 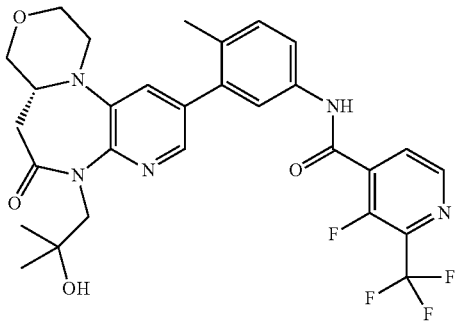 [SMILES: Cc1ccc(NC(=O)c2ccnc(C(F)(F)F)c2F)cc1-c1cnc2c(c1)N1CCOC[C@H]1CC(=O)N2CC(C)(C)O] | (R)-3-fluoro-N-(3-(7-(2-hydroxy-2-methylpropyl)-6-oxo-2,4,4a,5,6,7-hexahydro-1H-[1,4]oxazino[4,3-d]pyrido[2,3-b][1,4]diazepin-10-yl)-4-methylphenyl)-2-(trifluoromethyl)isonicotinamide | $^1$H NMR (400 MHz, Methanol-d4) δ 8.65 (d, J = 4.7 Hz, 1H), 8.16 (d, J = 1.9 Hz, 1H), 7.96 (t, J = 4.8 Hz, 1H), 7.69 (d, J = 2.2 Hz, 1H), 7.59 (dd, J = 9.2, 2.0 Hz, 2H), 7.36 (d, J = 8.3 Hz, 1H), 4.64 (s, 1H), 4.35 (d, J = 14.0 Hz, 1H), 3.94 (t, J = 11.0 Hz, 2H), 3.87 (d, J = 9.4 Hz, 1H), 3.67 (q, J = 11.0 Hz, 2H), 3.42 (s, 1H), 3.36 (s, 1H), 3.01 (d, J = 10.9 Hz, 1H), 2.83 (dd, J = 13.3, 7.5 Hz, 1H), 2.30 (s, 3H), 2.22 (d, J = 13.8 Hz, 1H), 1.20 (s, 3H), 1.14 (s, 3H). LCMS (m/z) (M + H) = 588.3, Rt = 1.01 min. |
| 291 | 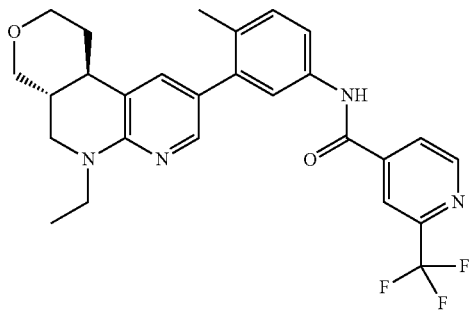 | N-(3-((4aR, 10bR)-6-ethyl-2,4,4a,5,6,10b-hexahydro-1H-pyrano[3,4-c][1,8]naphthyridin-9-yl)-4-methylpheny)-2-(trifluoromethyl)isonicotinamide | $^1$H NMR (400 MHz, Methanol-d4) δ 8.89 (d, J = 5.05 Hz, 1 H), 8.29 (s, 1 H), 8.11 (dd, J = 5.05, 1.26 Hz, 1 H), 7.83 (d, J = 1.52 Hz, 1 H), 7.60 (dd, J = 8.08, 2.27 Hz, 1 H), 7.55 (d, J = 2.27 Hz, 1 H), 7.27 (dt, J = 3.79, 2.15 Hz, 2 H), 4.11 (td, J = 11.87, 3.79 Hz, 2 H), 3.73 (dq, J = 13.96, 7.05 Hz, 1 H), 3.51-3.64 (m, 2 H), 3.30 (m, 1 H), 3.19 (dt, J = 19.01, 11.21 Hz, 2 H), 2.59 (td, J = 11.56, 4.17 Hz, 1 H), 2.27 (s, 3 H), 2.16-2.25 (m, 1 H), 1.78 (qt, J = 11.22, 4.26 Hz, 1 H), 1.55 (qd, J = 12.29, 4.55 Hz, 1 H), 1.19 (t, J = 7.07 Hz, 3 H). LCMS (m/z) (M + H) = 498.2, Rt = 0.99 min. |
| 292 | 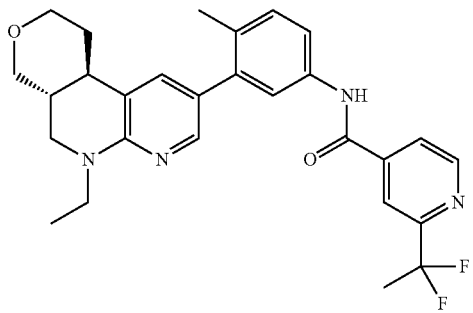 | 2-(1,1-difluoroethyl)-N-(3-((4aR, 10bR)-6-ethyl-2,4,4a,5,6,10b-hexahydro-1H-pyrano[3,4-c][1,8]naphthyridin-9-yl)-4-methylphenyl)isonicotinamide | $^1$H NMR (400 MHz, Methanol-d4) δ 8.78 (d, J = 5.05 Hz, 1 H), 8.17 (d, J = 0.76 Hz, 1 H), 7.90-7.99 (m, 1 H), 7.83 (d, J = 1.52 Hz, 1 H), 7.59 (dd, J = 8.08, 2.27 Hz, 1 H), 7.55 (d, J = 2.27 Hz, 1 H), 7.21-7.32 (m, 2 H), 4.04-4.19 (m, 2 H), 3.72 (sxt, J = 7.02 Hz, 1 H), 3.53-3.64 (m, 2 H), 3.32-3.34 (m, 1 H), 3.19 (dt, J = 19.14, 11.15 Hz, 2 H), 2.59 (td, J = 11.37, 3.79 Hz, 1 H), 2.27 (s, 3 H), 2.19-2.25 (m, 1 H), 1.93-2.11 (m, 3 H), 1.78 (qt, J = 11.18, 4.33 Hz, 1 H), 1.55 (qd, J = 12.34, 4.67 Hz, 1 H), 1.19 (t, J = 6.95 Hz, 3 H). LCMS (m/z) (M + H) = 494.3, Rt = 1.03 min. |
| 293 | 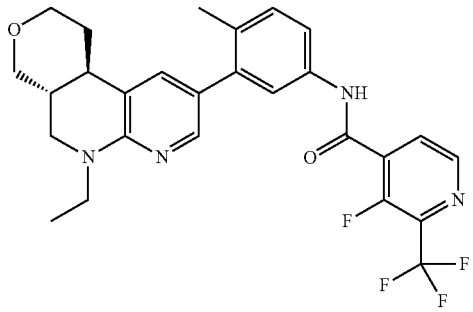 [SMILES: CCN1C[C@@H]2COCC[C@H]2c2cc(-c3cc(NC(=O)c4ccnc(C(F)(F)F)c4F)ccc3C)cnc21] | N-(3-((4aR, 10bR)-6-ethyl-2,4,4a,5,6,10b-hexahydro-1H-pyrano[3,4-c][1,8]naphthyridin-9-yl)-4-methylphenyl)-3-fluoro-2-(trifluoromethyl)isonicotinamide | $^1$H NMR (400 MHz, Methanol-d4) δ 8.63 (d, J = 4.55 Hz, 1 H), 7.94 (t, J = 4.80 Hz, 1 H), 7.82 (dd, J = 2.40, 0.88 Hz, 1 H), 7.55 (dd, J = 8.08, 2.27 Hz, 1 H), 7.51 (d, J = 2.27 Hz, 1 H), 7.24-7.29 (m, 2 H), 4.10 (td, J = 11.94, 3.92 Hz, 2 H), 3.72 (dq, J = 14.12, 7.00 Hz, 1 H), 3.52-3.64 (m, 2 H), 3.28 (d, J = 4.29 Hz, 1 H), 3.18 (dt, J = 18.57, 11.31 Hz, 2 H), 2.58 (td, J = 11.37, 3.79 Hz, 1 H), 2.27 (s, 3 H), 2.21-2.25 (m, 1 H), 1.70-1.85 (m, 1 H), 1.55 (qd, J = 12.29, 4.55 Hz, 1 H), 1.13-1.24 (m, 3 H). LCMS (m/z) (M + H) = 516.4, Rt = 0.96 min. |

| Ex. No. | Name | Physical Data |
|---|---|---|
| 294 | N-(5-((4aR, 10bR)-6-ethyl-2,4,4a,5,6,10b-hexahydro-1H-pyrano[3,4-c][1,8]naphthyridin-9-yl)-6-methylpyridin-3-yl)-2-fluoro-3-(trifluoromethyl)benzamide | ¹H NMR (400 MHz, Methanol-d4) δ 8.72 (d, J = 2.53 Hz, 1 H), 7.94-8.05 (m, 2 H), 7.82-7.93 (m, 2 H), 7.49 (t, J = 7.71 Hz, 1 H), 7.24-7.35 (m, 1 H), 4.03-4.17 (m, 2 H), 3.73 (dq, J = 14.02, 7.03 Hz, 1 H), 3.51-3.65 (m, 2 H), 3.31-3.34 (m, 1 H), 3.19 (dt, J = 14.97, 11.34 Hz, 2 H), 2.59 (td, J = 11.37, 3.54 Hz, 1 H), 2.43-2.53 (m, 3 H), 2.21-2.37 (m, 1 H), 1.68-1.86 (m, 1 H), 1.56 (qd, J = 12.29, 4.55 Hz, 1 H), 1.15-1.23 (m, 3 H). LCMS (m/z) (M + H) = 515.2, Rt = 0.86 min. |
| 295 | N-(5-((4aR, 10bR)-6-ethyl-2,4,4a,5,6,10b-hexahydro-1H-pyrano[3,4-c][1,8]naphthyridin-9-yl)-6-methylpyridin-3-yl)-3-(trifluoromethyl)benzamide | ¹H NMR (400 MHz, Methanol-d4) δ 8.72-8.80 (m, 1 H), 8.29 (s, 1 H), 8.23 (br d, J = 7.83 Hz, 1 H), 8.05 (d, J = 2.27 Hz, 1 H), 7.86-7.95 (m, 2 H), 7.66-7.78 (m, 1 H), 7.31 (d, J = 1.52 Hz, 1 H), 4.04-4.18 (m, 2 H), 3.66-3.80 (m, 1 H), 3.52-3.65 (m, 2 H), 3.32-3.36 (m, 1 H), 3.08-3.26 (m, 2 H), 2.53-2.65 (m, 1 H), 2.43-2.53 (m, 3 H), 2.21-2.36 (m, 1 H), 1.70-1.87 (m, 1 H), 1.56 (qd, J = 12.21, 4.29 Hz, 1H), 1.13-1.24 (m, 3 H). LCMS (m/z) (M + H) = 497.1, Rt = 0.90 min. |
| 296 | N-(5-((4aS,11bR-cis)-7-ethyl-6-oxo-2,4,4a,6,7,11b-hexahydro-1H-pyrano[4,3-f]pyrido[2,3-d][1,3]oxazepin-10-yl)-6-methylpyridin-3-yl)-3-(trifluoromethyl)benzamide<br>single enantiomer from Peak 1 intermediate | ¹H NMR (400 MHz, CHLOROFORM-d) δ ppm 8.77 (br s, 1 H), 8.25-8.60 (m, 3 H), 8.22 (s, 1 H), 8.18 (br d, J = 7.78 Hz, 1 H), 7.89 (d, J = 7.78 Hz, 1 H), 7.71 (t, J = 7.78 Hz, 1 H), 7.67 (d, J = 2.01 Hz, 1 H), 4.86 (ddd, J = 7.53, 5.52, 4.02 Hz, 1 H), 4.04-4.24 (m, 2 H), 3.82-3.98 (m, 3 H), 3.46-3.60 (m, 2 H), 2.62 (s, 3 H), 2.26-2.39 (m, 1 H), 2.04-2.22 (m, 1 H), 1.36 (t, J = 7.03 Hz, 3 H). LCMS (m/z) (M + H) = 527.1, Rt = 1.07 min. |
| 297 | N-(3-((4aS,11bR-cis)7-ethyl-6-oxo-2,4,4a,6,7,11b-hexahydro-1H-pyrano[4,3-f]pyrido[2,3-d][1,3]oxazepin-10-yl)-4-methylphenyl)-2-(trifluoromethyl)isonicotinamide<br>single enantiomer from Peak 2 intermediate | ¹H NMR (400 MHz, CHLOROFORM-d) δ ppm 8.96 (d, J = 5.05 Hz, 1 H), 8.42 (d, J = 2.02 Hz, 1 H), 8.31 (s, 1 H), 8.19 (s, 1 H), 8.02 (d, J = 4.29 Hz, 1 H), 7.69-7.78 (m, 2 H), 7.66 (br d, J = 8.34 Hz, 1 H), 7.39 (d, J = 8.34 Hz, 1 H), 4.80-4.92 (m, 1 H), 4.09-4.30 (m, 2 H), 3.81-3.94 (m, 3 H), 3.43-3.54 (m, 2 H), 2.26-2.38 (m, 4 H), 2.09-2.22 (m, 1 H), 1.34 (t, J = 7.07 Hz, 3 H). LCMS (m/z) (M + H) = 527.2, Rt = 1.17 min. |
| 298 | N-(5-((4aS,11bR-cis)-7-ethyl-6-oxo-2,4,4a,6,7,11b-hexahydro-1H-pyrano[4,3-f]pyrido[2,3-d][1,3]oxazepin-10-yl)-6-methylpyridin-3-yl)-3-(trifluoromethyl)benzamide<br>single enantiomer from Peak 2 intermediate | 1H NMR (400 MHz, CHLOROFORM-d) δ ppm 8.84 (br s, 1 H), 8.32-8.68 (m, 3 H), 8.17-8.31 (m, 2 H), 7.89 (d, J = 7.83 Hz, 1 H), 7.63-7.77 (m, 2 H), 4.86 (ddd, J = 7.52, 5.49, 3.92 Hz, 1 H), 4.03-4.25 (m, 2 H), 3.80-3.96 (m, 3 H), 3.49-3.59 (m, 2 H), 2.64 (s, 3 H), 2.26-2.41 (m, 1 H), 2.05-2.20 (m, 1 H), 1.36 (t, J = 7.07 Hz, 3 H). LCMS (m/z) (M + H) = 527.1, Rt = 1.07 min. |

| Ex. No. | Structure | Name | Physical Data |
|---|---|---|---|
| 299 | single enantiomer from Peak 2 intermediate | N-(3-((4aS,11bR-cis)-7-ethyl-6-oxo-2,4,4a,6,7,11b-hexahydro-1H-pyrano[4,3-f]pyrido[2,3-d][1,3]oxazepin-10-yl)-4-methylphenyl)-3-fluoro-2-(trifluoromethyl)isonicotinamide | $^1$H NMR (400 MHz, CHLOROFORM-d) δ ppm 8.73 (d, J = 4.80 Hz, 1 H), 8.41 (d, J = 2.27 Hz, 1 H), 8.36 (br d, J = 12.38 Hz, 1 H), 8.27 (t, J = 5.18 Hz, 1 H), 7.68 (d, J = 2.27 Hz, 1 H), 7.66 (d, J = 1.77 Hz, 1 H), 7.57 (dd, J = 8.34, 2.27 Hz, 1 H), 7.39 (d, J = 8.34 Hz, 1 H), 4.87 (ddd, J = 8.02, 5.75, 4.17 Hz, 1 H), 4.02-4.26 (m, 2 H), 3.82-3.95 (m, 3 H), 3.45-3.55 (m, 2 H), 2.27-2.39 (m, 4 H), 2.08-2.21 (m, 1 H), 1.35 (t, J = 7.07 Hz, 3 H). LCMS (m/z) (M + H) = 545.2, Rt = 1.21 min. |
| 300 | single enantiomer from Peak 2 intermediate | N-(5-((4aS,11bR-cis)-7-ethyl-6-oxo-2,4,4a,6,7,11b-hexahydro-1H-pyrano[4,3-f]pyrido[2,3-d][1,3]oxazepin-10-yl)-6-methylpyridin-3-yl)-2-fluoro-3-(trifluoromethyl)benzamide | $^1$H NMR (400 MHz, CHLOROFORM-d) δ ppm 8.72 (br s, 1 H), 8.59 (br s, 1 H), 8.44 (d, J = 2.02 Hz, 1 H), 8.24-8.42 (m, 2 H), 7.88 (t, J = 6.82 Hz, 1 H), 7.66 (d, J = 1.52 Hz, 1 H), 7.49 (t, J = 7.71 Hz, 1 H), 4.78-4.92 (m, 1 H), 4.03-4.25 (m, 2 H), 3.80-3.98 (m, 3 H), 3.46-3.61 (m, 2 H), 2.60 (s, 3 H), 2.27-2.39 (m, 1 H), 2.07-2.23 (m, 1 H), 1.36 (t, J = 7.07 Hz, 3 H). LCMS (m/z) (M + H) = 545.2, Rt = 1.04 min. |
| 301 | single enantiomer from Peak 2 intermediate | N-(3-((4aS,11bR-cis)-7-ethyl-6-oxo-2,4,4a,6,7,11b-hexahydro-1H-pyrano[4,3-f]pyrido[2,3-d][1,3]oxazepin-10-yl)-4-methylphenyl)-6-(trifluoromethyl)pyridazine-4-carboxamide | $^1$H NMR (400 MHz, DMSO-d6) δ ppm 10.89 (s, 1 H), 9.92 (d, J = 2.02 Hz, 1 H), 8.68 (d, J = 2.02 Hz, 1 H), 8.40 (d, J = 2.02 Hz, 1 H), 7.86 (d, J = 2.02 Hz, 1 H), 7.66-7.79 (m, 2 H), 7.40 (d, J = 8.08 Hz, 1 H), 4.73-4.84 (m, 1 H), 3.90-4.03 (m, 2 H), 3.80-3.90 (m, 1 H), 3.60-3.72 (m, 2 H), 3.48-3.60 (m, 2 H), 2.29 (s, 3 H), 2.15 (ddt, J = 10.67, 7.07, 3.63, 3.63 Hz, 1 H), 1.88-2.00 (m, 1 H), 1.26 (t, J = 6.95 Hz, 3 H). LCMS (m/z) (M + H) = 528.1, Rt = 1.10 min. |
| 302 | single enantiomer from Peak 2 intermediate | 2-(1,1-difluoroethyl)-N-(3-((4aS,11bR-cis)-7-ethyl-6-oxo-2,4,4a,6,7,11b-hexahydro-1H-pyrano[4,3-f]pyrido[2,3-d][1,3]oxazepin-10-yl)-methylphenyl)isonicotinamide | $^1$H NMR (400 MHz, DMSO-d6) δ ppm 10.66 (s, 1 H), 8.89 (d, J = 5.05 Hz, 1 H), 8.40 (d, J = 2.27 Hz, 1 H), 8.19 (s, 1 H), 8.03 (d, J = 5.05 Hz, 1 H), 7.86 (d, J = 2.02 Hz, 1 H), 7.71-7.79 (m, 2 H), 7.37 (d, J = 8.34 Hz, 1 H), 4.73-4.82 (m, 1 H), 3.96 (tt, J = 13.58, 6.76 Hz, 2 H), 3.80-3.89 (m, 1 H), 3.60-3.72 (m, 2 H), 3.49-3.59 (m, 2 H), 2.28 (s, 3 H), 2.11-2.22 (m, 1 H), 2.05 (t, J = 19.07 Hz, 3 H), 1.97 (br s, 1 H), 1.25 (t, J = 6.95 Hz, 3 H). LCMS (m/z) (M + H) = 523.1, Rt = 1.15 min. |
| 303 | 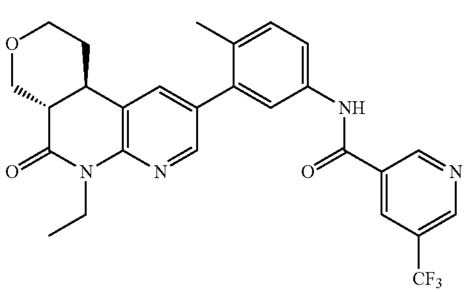 [SMILES: CCN1C(=O)[C@@H]2COCC[C@H]2c2cc(-c3cc(NC(=O)c4cncc(C(F)(F)F)c4)ccc3C)cnc21] | N-(3-((4aS,10bR)-6-ethyl-5-oxo-2,4,4a,5,6,10b-hexahydro-1H-pyrano[3,4-c][1,8]naphthyridin-9-yl)-4-methylphenyl)-5-(trifluoromethyl)nicotinamide | $^1$H NMR (400 MHz, DMSO-d6) δ ppm 10.65 (s, 1 H), 9.38 (d, J = 1.77 Hz, 1 H), 9.19 (d, J = 1.26 Hz, 1 H), 8.69 (s, 1 H), 8.29 (d, J = 1.52 Hz, 1 H), 7.68-7.75 (m, 2 H), 7.61 (s, 1 H), 7.36 (d, J = 8.08 Hz, 1 H), 4.22-4.30 (m, 1 H), 4.12-4.21 (m, 1 H), 3.95-4.08 (m, 2 H), 3.44 (q, J = 10.86 Hz, 2 H), 2.92-3.04 (m, 1 H), 2.52-2.57 (m, 1 H), 2.25-2.36 (m, 4 H), 1.59 (qd, J = 12.29, 4.29 Hz, 1 H), 1.18 (t, J = 6.95 Hz, 3 H). LCMS (m/z) (M + H) = 511.1, Rt = |

-continued

| Ex. No. | Structure | Name | Physical Data |
|---|---|---|---|
| | | | 1.21 min. |
| 304 | 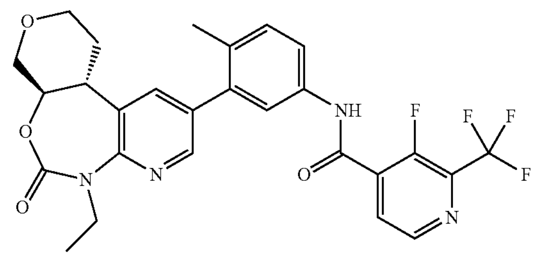 [SMILES: CCN1C(=O)O[C@H]2COCC[C@@H]2c2cc(-c3cc(NC(=O)c4ccnc(C(F)(F)F)c4F)ccc3C)cnc21] | N-(3-((4aR, 11bR)-7-ethyl-6-oxo-2,4,4a,6,7,11b-hexahydro-1H-pyrano[4,3-f]pyrido[2,3-d][1,3]oxazepin-10-yl)-4-methylphenyl)-3-fluoro-2-(trifluoromethyl)isonicotinamide | ¹H NMR (400 MHz, CHLOROFORM-d) δ ppm 8.73 (d, J = 4.80 Hz, 1 H), 8.43 (d, J = 2.27 Hz, 1 H), 8.37 (br d, J = 12.38 Hz, 1 H), 8.27 (t, J = 5.18 Hz, 1 H), 7.66 (d, J = 2.27 Hz, 1 H), 7.58 (dd, J = 8.21, 2.40 Hz, 1 H), 7.53 (d, J = 1.77 Hz, 1 H), 7.39 (d, J = 8.34 Hz, 1 H), 3.99-4.33 (m, 5 H), 3.50-3.66 (m, 2 H), 2.91-3.09 (m, 1 H), 2.33 (s, 3 H), 2.03-2.19 (m, 2 H), 1.35 (t, J = 6.95 Hz, 3 H). LCMS (m/z) (M + H) = 545.2, Rt = 1.11 min. |
| 305 | 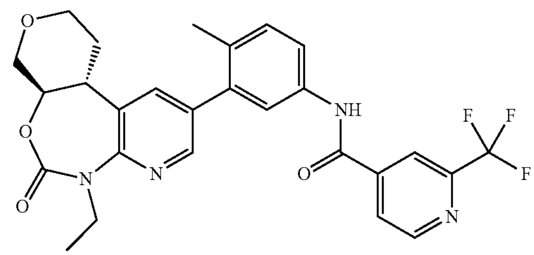 [SMILES: CCN1C(=O)O[C@H]2COCC[C@@H]2c2cc(-c3cc(NC(=O)c4ccnc(C(F)(F)F)c4)ccc3C)cnc21] | N-(3-((4aR,11bR)-7-ethyl-6-oxo-2,4,4a,6,7,11b-hexahydro-1H-pyrano[4,3-f]pyrido[2,3-d][1,3]oxazepin-10-yl)-4-methylphenyl)-2-(trifluoromethyl)isonicotinamide | ¹H NMR (400 MHz, CHLOROFORM-d) δ ppm 8.96 (d, J = 4.80 Hz, 1 H), 8.42 (d, J = 2.27 Hz, 1 H), 8.14 (s, 1 H), 7.96 (br d, J = 3.28 Hz, 2 H), 7.65 (s, 1 H), 7.59 (br d, J = 8.08 Hz, 1 H), 7.51 (d, J = 1.77 Hz, 1 H), 7.39 (d, J = 8.08 Hz, 1 H), 3.98-4.30 (m, 5 H), 3.51-3.66 (m, 2 H), 2.94-3.08 (m, 1 H), 2.33 (s, 3 H), 2.04-2.13 (m, 2 H), 1.34 (t, J = 6.95 Hz, 3 H). LCMS (m/z) (M + H) = 527.2, Rt = 1.10 min. |
| 306 | 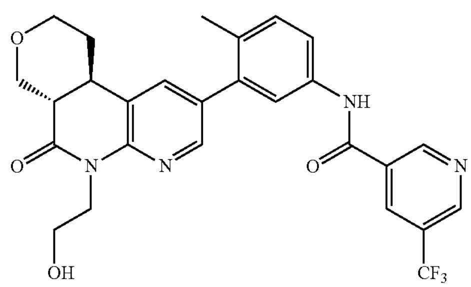 [SMILES: Cc1ccc(NC(=O)c2cncc(C(F)(F)F)c2)cc1-c1cnc2c(c1)[C@@H]1CCOC[C@H]1C(=O)N2CCO] | N-(3-((4aS,10bR)-6-(2-hydroxyethyl)-5-oxo-2,4,4a,5,6,10b-hexahydro-1H-pyrano[3,4-c][1,8]naphthyridin-9-yl)-4-methylphenyl)-5-(trifluoromethyl)nicotinamide | ¹H NMR (400 MHz, DMSO-d6) ppm 10.65 (s, 1 H), 9.38 (d, J = 1.77 Hz, 1 H), 9.19 (d, J = 1.01 Hz, 1 H), 8.69 (s, 1 H), 8.28 (d, J = 1.52 Hz, 1 H), 7.69-7.75 (m, 2 H), 7.61 (s, 1 H), 7.36 (d, J = 8.08 Hz, 1 H), 4.78 (t, J = 5.81 Hz, 1 H), 4.21-4.36 (m, 2 H), 3.97-4.12 (m, 2 H), 3.36-3.68 (m, 4 H), 2.90-3.07 (m, 1 H), 2.52-2.58 (m, 1 H), 2.30-2.37 (m, 1 H), 2.27 (s, 3 H), 1.59 (qd, J = 12.25, 4.42 Hz, 1 H). LCMS (m/z) (M + H) = 527.1, Rt = 1.03 min. |
| 307 | 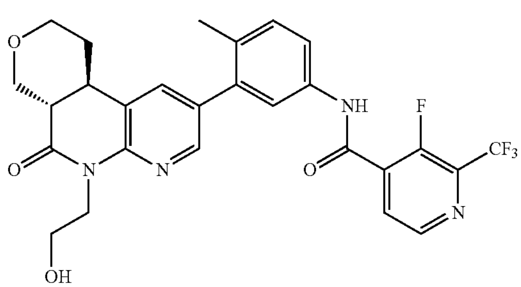 [SMILES: Cc1ccc(NC(=O)c2ccnc(C(F)(F)F)c2F)cc1-c1cnc2c(c1)[C@@H]1CCOC[C@H]1C(=O)N2CCO] | 3-fluoro-N-(3-((4aS, 10bR)-6-(2-hydroxyethyl)-5-oxo-2,4,4a,5,6,10b-hexahydro-1H-pyrano[3,4-c][1,8]naphthyridin-9-yl)-4-methylphenyl)-2-(trifluoromethyl)isonicotinamide | ¹H NMR (400 MHz, DMSO-d6) δ ppm 10.75-11.01 (m, 1 H), 8.76 (d, J = 4.77 Hz, 1 H), 8.27 (d, J = 1.51 Hz, 1 H), 8.10 (t, J = 4.77 Hz, 1 H), 7.57-7.66 (m, 3 H), 7.36 (d, J = 8.03 Hz, 1 H), 4.45-5.10 (m, 1 H), 4.19-4.36 (m, 2 H), 3.94-4.12 (m, 2 H), 3.41-3.64 (m, 4 H), 2.92-3.06 (m, 1 H), 2.52-2.58 (m, 1 H), 2.29-2.38 (m, 1 H), 2.26 (s, 3 H), 1.58 (qd, J = 12.21, 4.52 Hz, 1 H). LCMS (m/z) (M + H) = 545.2, Rt = 1.01 min. |
| 308 | 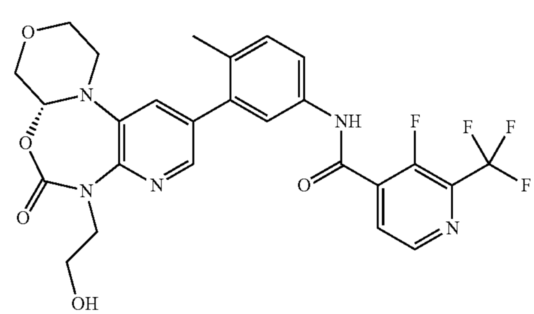 | (R)-2-(1,1-difluoroethyl)-3-fluoro-N-(3-(7-(2-hydroxyethyl)-6-oxo-2,4,4a,5,6,7-hexahydro-1H-[1,4]oxazino[4,3-d]pyrido[2,3-b][1,4]diazepin-10-yl)-4-methylphenyl)isonicotinamide | ¹H NMR (400 MHz, METHANOL-d4) δ ppm 8.55 (d, J = 4.80 Hz, 1 H), 8.18 (d, J = 1.77 Hz, 1 H), 7.80 (t, J = 4.80 Hz, 1 H), 7.68 (d, J = 2.27 Hz, 1 H), 7.54-7.65 (m, 2 H), 7.36 (d, J = 8.08 Hz, 1 H), 4.25-4.41 (m, 1 H), 3.79-3.98 (m, 4 H), 3.61-3.76 (m, 3 H), 3.44 (br d, J = 8.59 Hz, 1 H), 3.32-3.37 (m, 1 H), 3.01 (br d, J = 11.37 Hz, 1 H), 2.79 (dd, J = 13.77, 7.45 Hz, 1 H), 2.31 (s, 3 H), 2.22 (d, J = 13.64 Hz, 1 H), 2.08 (t, J = 18.95 Hz, 3 H). LCMS (m/z) (M + H) = 556.1, Rt = 0.94 min. |

| Ex. No. | Structure | Name | Physical Data |
|---|---|---|---|
| 309 | 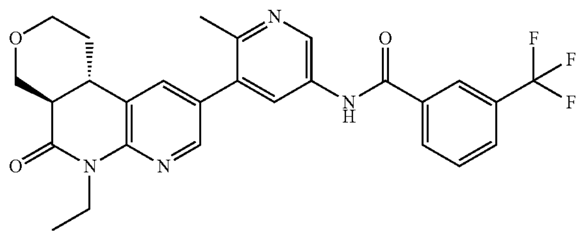 [SMILES: CCN1C(=O)[C@H]2COCC[C@@H]2c2cc(-c3cc(NC(=O)c4cccc(C(F)(F)F)c4)cnc3C)cnc21] | N-(5-((4aR, 10bS)-6-ethyl-5-oxo-1,4,4a,5,6,10b-hexahydro-2H-pyrano[3,4-c][1,8]naphthyridin-9-yl)-6-methylpyridin-3-yl)-3-(trifluoromethyl)benzamide | 1H NMR (400 MHz, Methanol-d4) δ 8.84 (d, J = 2.5 Hz, 1H), 8.33 (dd, J = 2.2, 0.8 Hz, 1H), 8.31 (s, 1H), 8.25 (d, J = 7.9 Hz, 1H), 8.18 (d, J = 2.5 Hz, 1H), 7.92 (d, J = 7.9 Hz, 1H), 7.76 (t, J =+) 7.9 Hz, 1H), 7.72-7.67 (m, 1H), 4.42 (dd, J = 11.7, 4.5 Hz, 1H), 4.31 (dq, J = 13.9, 6.9 Hz, 1H), 4.13 (dd, J = 13.1, 7.0 Hz, 2H), 3.64-3.43 (m, 3H), 3.05-2.91 (m, 1H), 2.52 (s, 3H), 2.34 (d, J = 9.6 Hz, 1H), 1.75 (qd, J = 12.4, 4.6 Hz, 1H), 1.24 (d, J = 7.0 Hz, 3H). LCMS (m/z) (M + H) = 511.1989, Rt = 3.07 min |
| 310 | 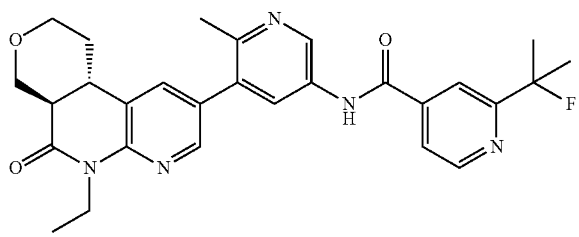 [SMILES: CCN1C(=O)[C@H]2COCC[C@@H]2c2cc(-c3cc(NC(=O)c4ccnc(C(C)(C)F)c4)cnc3C)cnc21] | N-(5-((4aR, 10bS)-6-ethyl-5-oxo-1,4,4a,5,6,10b-hexahydro-2H-pyrano[3,4-c][1,8]naphthyridin-9-yl)-6-methylpyridin-3-yl)-2-(2-fluoropropan-2-yl)isonicotinamide | 1H NMR (400 MHz, Methanol-d4) δ 8.85 (d, J = 2.5 Hz, 1H), 8.72 (d, J = 5.1 Hz, 1H), 8.33 (d, J = 1.4 Hz, 1H), 8.18 (d, J = 2.5 Hz, 1H), 8.10 (s, 1H), 7.80 (dd, J = 5.1, 1.7 Hz, 1H), 7.71-7.64 (m, 1H), 4.41 (dd, J = 11.7, 4.5 Hz, 1H), 4.31 (dq, J = 13.8, 7.0 Hz, 1H), 4.13 (dq, J = 13.8, 6.9 Hz, 2H), 3.65-3.44 (m, 2H), 2.99 (s, 1H), 2.52 (s, 5H), 2.39-2.26 (m, 1H), 1.73 (d, J = 21.9 Hz, 6H), 1.26 (q, J = 7.2 Hz, 3H). LCMS (m/z) (M + H) = 504.2410, Rt = 2.70 min |
| 311 | 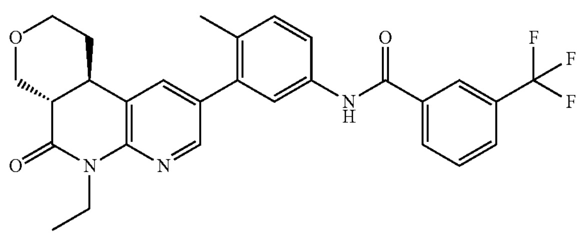 [SMILES: CCN1C(=O)[C@@H]2COCC[C@H]2c2cc(-c3cc(NC(=O)c4cccc(C(F)(F)F)c4)ccc3C)cnc21] | N-(3-((4aS, 10bR)-6-ethyl-5-oxo-1,4,4a,5,6,10b-hexahydro-2H-pyrano[3,4-c][1,8]naphthyridin-9-yl)-4-methylphenyl)-2-(trifluoromethyl)isonicotinamide | 1H NMR (400 MHz, Methanol-d4) δ 8.90 (t, J = 4.9 Hz, 1H), 8.30 (s, 1H), 8.26 (dd, J = 2.1, 0.8 Hz, 1H), 8.12 (dd, J = 5.0, 1.2 Hz, 1H), 7.69-7.60 (m, 3H), 7.38-7.31 (m, 1H), 4.41 (dd, J =+) 11.6, 4.5 Hz, 1H), 4.30 (dq, J = 13.9, 7.0 Hz, 1H), 4.12 (dd, J = 13.1, 7.0 Hz, 2H), 3.64-3.46 (m, 2H), 3.02-2.91 (m, 1H), 2.48 (dtd, J = 16.1, 11.5, 11.0, 5.4 Hz, 1H), 1.73 (qd, J = 12.5, 4.6 Hz, 2H), 1.49-1.41 (m, 3H), 1.25 (d, J = 7.0 Hz, 3H). LCMS (m/z) (M + H) = 511.1971, Rt = 3.88 min |
| 312 | 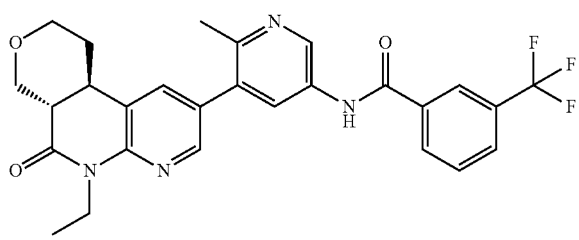 [SMILES: CCN1C(=O)[C@@H]2COCC[C@H]2c2cc(-c3cc(NC(=O)c4cccc(C(F)(F)F)c4)cnc3C)cnc21] | N-(5-((4aS, 10bR)-6-ethyl-5-oxo-1,4,4a,5,6,10b-hexahydro-2H-pyrano[3,4-c][1,8]naphthyridin-9-yl)-6-methylpyridin-3-yl)-3-(trifluoromethyl)benzamide | 1H NMR (400 MH, Methanol-d4) δ 8.84 (d, J = 2.5 Hz, 1H), 8.35-8.29 (m, 2H), 8.25 (d, J = 7.8 Hz, 1H), 8.18 (d, J = 2.5 Hz, 1H), 7.92 (d, J = 7.8 Hz, 1H), 7.75 (t, J = 7.8 Hz, 1H), 7.70 (dd, J = 2.1, 1.4 Hz, 1H), 4.42 (dd, J = 11.6, 4.5 Hz, 1H), 4.31 (dq, J = 13.9, 7.0 Hz, 1H), 4.13 (dq, J = 13.9, 7.0 Hz, 2H), 3.63-3.46 (m, 2H), 3.04-2.94 (m, 1H), 2.56-2.44 (m, 4H), 2.34 (d, J = 9.4 Hz, 1H), 1.80-1.69 (m, 1H), 1.25 (t, J = 7.0 Hz, 3H). LCMS (m/z) (M + H) = 511.1969, Rt = 3.07 min |
| 313 | 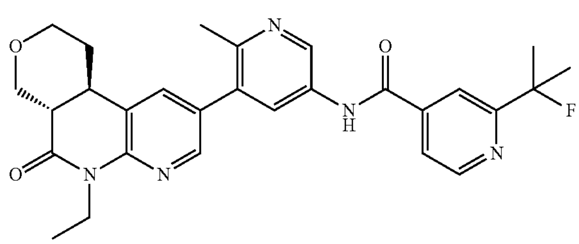 [SMILES: CCN1C(=O)[C@@H]2COCC[C@H]2c2cc(-c3cc(NC(=O)c4ccnc(C(C)(C)F)c4)cnc3C)cnc21] | N-(5-((4aS, 10bR)-6-ethyl-5-oxo-1,4,4a,5,6,10b-hexahydro-2H-pyrano[3,4-c][1,8]naphthyridin-9-yl)-6-methylpyridin-3-yl)-2-(2-fluoropropan-2-yl)isonicotinamide | 1H NMR (400 MHz, Methanol-d4) δ 8.85 (d, J = 2.4 Hz, 1H), 8.72 (d, J = 5.1 Hz, 1H), 8.34-8.29 (m, 1H), 8.18 (d, J = 2.4 Hz, 1H), 8.10 (s, 1H), 7.80 (dd, J = 5.1, 1.6 Hz, 1H), 7.70 (s, 1H), 4.41 (dd, J = 11.6, 4.4 Hz, 1H), 4.30 (dt, J = 13.8, 6.9 Hz, 1H), 4.12 (dt, J = 13.8, 7.1 Hz, 2H), 3.55 (dt, J = 18.8, 11.3 Hz, 3H), 2.98 (s, 1H), 2.59-2.43 (m, 5H), 1.73 (d, J = 21.9 Hz, 6H), 1.26 (q, J = 7.1 Hz, 3H) LCMS (m/z) (M + H) = 504.2417, Rt = 2.70 min |

| Ex. No. | Structure | Name | Physical Data |
|---|---|---|---|
| 314 | 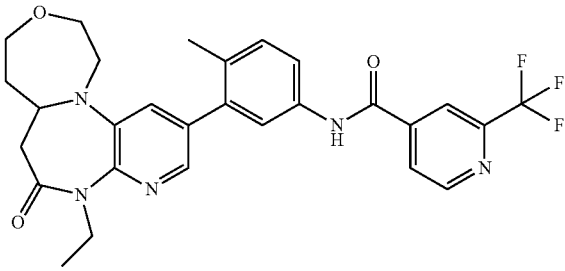<br>single enantiomer<br>from Peak 2 intermediate | N-(3-(8-ethyl-7-oxo-1,2,4,5,5a,6,7,8-octahydropyrido[3',2':2,3][1,4]diazepino[1,7-d][1,4]oxazepin-11-yl)-4-methylphenyl)-2-(trifluoromethyl)isonicotinamide | 1H NMR (400 MHz, Methanol-d4) δ 8.91 (d, J = 5.0 Hz, 1H), 8.30 (s, 1H), 8.21-8.07 (m, 2H), 7.75-7.61 (m, 3H), 7.36 (d, J = 8.3 Hz, 1H), 4.06 (qd, J = 6.9, 2.7 Hz, 2H), 3.94 (dddd, J = 13.8, 12.5, 7.6, 3.1 Hz, 3H), 3.87-3.74 (m, 2H), 3.56-3.35 (m, 2H), 2.64 (dd, J = 13.2, 5.4 Hz, 1H), 2.40-2.24 (m, 4H), 2.23-2.05 (m, 1H), 1.93-1.83 (m, 1H), 1.18 (t, J = 7.1 Hz, 3H). LCMS (m/z) (M + H) = 540.3, Rt = 1.16 min |
| 315 | 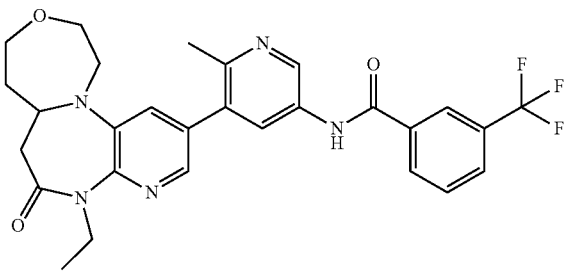<br>single enantiomer<br>from Peak 2 intermediate | N-(5-(8-ethyl-7-oxo-1,2,4,5,5a,6,7,8-octahydropyrido[3',2':2,3][1,4]diazepino[1,7-d][1,4]oxazepin-11-yl)-6-methylpyridin-3-yl)-3-(trifluoromethyl)benzamide | $^1$H NMR (400 MHz, Methanol-d4) δ 8.84 (d, J = 2.4 Hz, 1H), 8.31 (s, 1H), 8.29-8.17 (m, 3H), 7.92 (d, J = 7.8 Hz, 1H), 7.81-7.62 (m, 2H), 4.07 (qd, J = 6.8, 2.0 Hz, 2H), 4.01-3.90 (m, 3H), 3.90-3.73 (m, 2H), 3.47 (dt, J = 8.4, 4.0 Hz, 2H), 2.66 (dd, J = 13.3, 5.3 Hz, 1H), 2.54 (s, 3H), 2.35 (dd, J = 13.3, 6.5 Hz, 1H), 2.14 (ddd, J = 15.1, 8.2, 3.2 Hz, 1H), 2.00-1.85 (m, 1H), 1.19 (d, J = 7.1 Hz, 3H). LCMS (m/z) (M + H) = 540.3, Rt = 0.98 min |
| 316 | 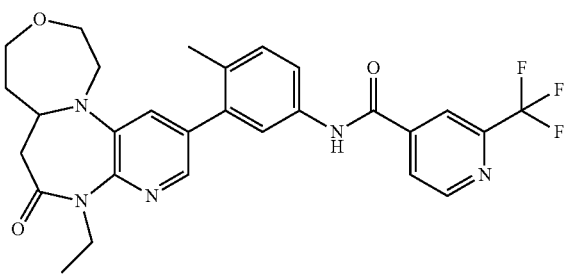<br>single enantiomer<br>from Peak 1 intermediate | N-(3-(8-ethyl-7-oxo-1,2,4,5,5a,6,7,8-octahydropyrido[3',2':2,3][1,4]diazepino[1,7-d][1,4]oxazepin-11-yl)-4-methylphenyl)-2-(trifluoromethyl)isonicotinamide | 1H NMR (400 MHz, Methanol-d4) δ 8.90 (d, J = 5.0 Hz, 1H), 8.30 (s, 1H), 8.12 (dd, J = 7.1, 1.6 Hz, 2H), 7.76-7.58 (m, 3H), 7.35 (d, J = 8.3 Hz, 1H), 4.06 (qd, J = 6.9, 2.6 Hz, 2H), 4.00-3.72 (m, 5H), 3.51-3.36 (m, 2H), 2.63 (dd, J = 13.2, 5.4 Hz, 1H), 2.45-2.25 (m, 4H), 2.24-2.04 (m, 1H), 1.90 (dd, J = 15.1, 2.4 Hz, 1H), 1.18 (t, J = 7.1 Hz, 3H). LCMS (m/z) (M + H) = 540.3, Rt = 1.16 min |
| 317 | 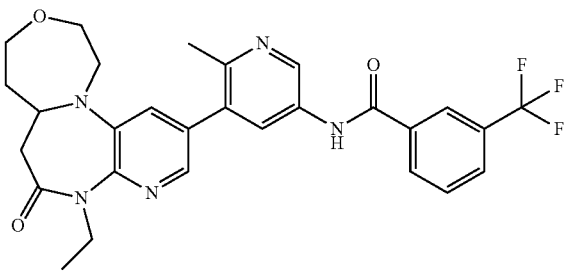<br>single enantiomer<br>from Peak 1 intermediate | N-(5-(8-ethyl-7-oxo-1,2,4,5,5a,6,7,8-octahydropyrido[3',2':2,3][1,4]diazepino[1,7-d][1,4]oxazepin-11-yl)-6-methylpyridin-3-yl)-3-(trifluoromethyl)benzamide | $^1$H NMR (400 MHz, Methanol-d4) δ 8.84 (d, J = 2.5 Hz, 1H), 8.31 (s, 1H), 8.25 (d, J = 7.9 Hz, 1H), 8.21 (d, J = 2.5 Hz, 1H), 8.19 (d, J= 2.0 Hz, 1H), 7.92 (d, J = 7.8 Hz, 1H), 7.75 (t, J = 7.8 Hz, 1H), 7.70 (d, J = 2.1 Hz, 1H), 4.07 (qd, J = 6.9, 2.3 Hz, 2H), 4.02-3.89 (m, 3H), 3.89-3.72 (m, 2H), 3.47 (dt, J = 8.2, 3.9 Hz, 2H), 2.66 (dd, J = 13.3, 5.4 Hz, 1H), 2.54 (s, 3H), 2.35 (dd, J = 13.3, 6.5 Hz, 1H), 2.16 (ddd, J = 14.2, 10.0, 4.8 Hz, 1H), 1.97-1.87 (m, 1H), 1.22-1.17 (m, 3H). LCMS (m/z) (M + H) = 540.2, Rt = 0.98 min |

| Ex. No. | Structure | Name | Physical Data |
|---|---|---|---|
| 318 | 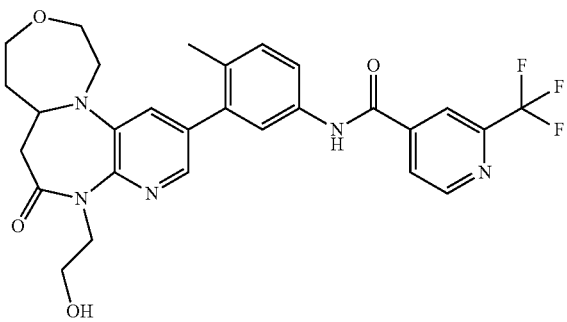<br>single enantiomer<br>from Peak 2 intermediate | N-(3-(8-(2-hydroxyethyl)-7-oxo-1,2,4,5,5a,6,7,8-octahydropyrido[3',2':2,3][1,4]diazepino[1,7-d][1,4]oxazepin-11-yl)-4-methylphenyl)-2-(trifluoromethyl)isonicotinamide | 1H NMR (400 MHz, Methanol-d4) δ 8.90 (d, J = 5.0 Hz, 1H), 8.30 (s, 1H), 8.12 (dd, J = 4.2, 1.6 Hz, 2H), 7.71 (d, J = 2.3 Hz, 1H), 7.69-7.62 (m, 2H), 7.35 (d, J = 8.3 Hz, 1H), 4.12 (t, J = 5.9 Hz, 2H), 4.02-3.89 (m, 3H), 3.79 (dddd, J = 17.0, 13.2, 9.4, 5.0 Hz, 4H), 3.50-3.40 (m, 2H), 2.69 (dd, J = 13.3, 5.3 Hz, 1H), 2.38 (dd, J = 13.3, 6.6 Hz, 1H), 2.31 (s, 3H), 2.23-2.04 (m, 1H), 1.91 (dq, J = 15.0, 3.5 Hz, 1H). LCMS (m/z) (M + H) = 556.3, Rt = 1.02 min |
| 319 | 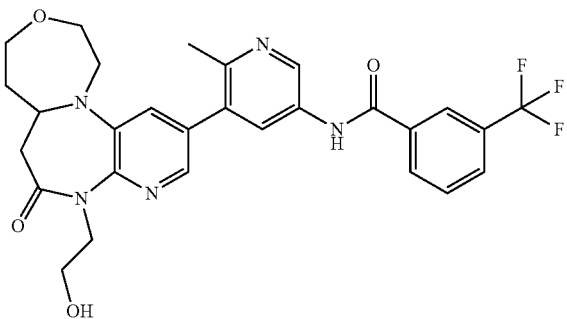<br>single enantiomer<br>from Peak 2 intermediate | N-(5-(8-(2-hydroxyethyl)-7-oxo-1,2,4,5,5a,6,7,8-octahydropyrido[3',2':2,3][1,4]diazepino[1,7-d][1,4]oxazepin-11-yl)-6-methylpyridin-3-yl)-3-(trifluoromethyl)benzamide | 1H NMR (400 MHz, Methanol-d4) δ 8.84 (d, J = 2.5 Hz, 1H), 8.30 (s, 1H), 8.26-8.20 (m, 2H), 8.17 (d, J = 2.0 Hz, 1H), 7.92 (d, J = 7.9 Hz, 1H), 7.78-7.69 (m, 2H), 4.14 (td, J = 5.9, 1.5 Hz, 2H), 4.02-3.89 (m, 3H), 3.89-3.74 (m, 4H), 3.54-3.40 (m, 2H), 2.71 (dd, J = 13.3, 5.2 Hz, 1H), 2.53 (s, 3H), 2.40 (dd, J = 13.4, 6.5 Hz, 1H), 2.16 (dd, J = 9.8, 4.5 Hz, 1H), 1.93 (dd, J = 15.1, 2.4 Hz, 1H). LCMS (m/z) (M + H) = 556.3, Rt = 0.85 min |
| 320 | 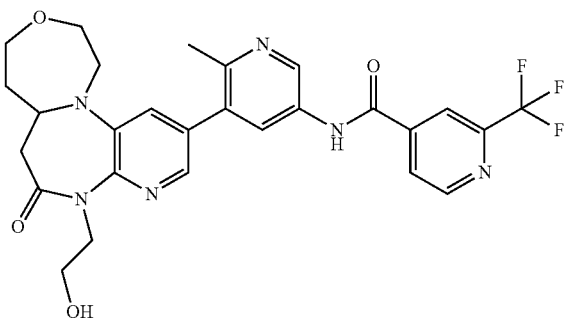<br>single enantiomer<br>from Peak 1 intermediate | N-(3-(8-(2-hydroxyethyl)-7-oxo-1,2,4,5,5a,6,7,8-octahydropyrido[3',2':2,3][1,4]diazepino[1,7-d][1,4]oxazepin-11-yl)-4-methylphenyl)-2-(trifluoromethyl)isonicotinamide | 1H NMR (400 MHz, Methanol-d4) δ 8.91 (d, J = 5.0 Hz, 1H), 8.30 (s, 1H), 8.14-8.09 (m, 2H), 7.72 (d, J = 2.2 Hz, 1H), 7.67 (dd, J = 7.4, 1.8 Hz, 2H), 7.36 (d, J = 8.3 Hz, 1H), 4.12 (t, J = 5.9 Hz, 2H), 3.95 (dp, J = 12.8, 4.4, 3.9 Hz, 3H), 3.89-3.69 (m, 4H), 3.47 (dt, J = 7.9, 3.8 Hz, 2H), 2.69 (dd, J = 13.3, 5.3 Hz, 1H), 2.38 (dd, J = 13.3, 6.6 Hz, 1H), 2.32 (s, 3H), 2.14 (dq, J = 9.6, 5.6, 5.1 Hz, 2H), 1.96-1.87 (m, 1H). LCMS (m/z) (M + H) = 556.2, Rt = 1.02 min |
| 322 | 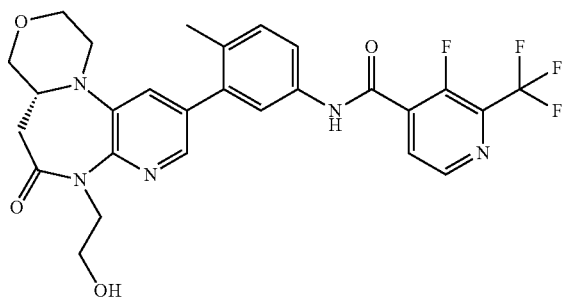 [SMILES: Cc1ccc(NC(=O)c2ccnc(C(F)(F)F)c2F)cc1-c1cnc2c(c1)N1CCOC[C@H]1CC(=O)N2CCO] | (R)-3-fluoro-N-(3-(7-(2-hydroxyethyl)-6-oxo-2,4,4a,5,6,7-hexahydro-1H-[1,4]oxazino[4,3-d]pyrido[2,3-b][1,4]diazepin-10-yl)-4-methylphenyl)-2-(trifluoromethyl)isonicotinamide | 1H NMR (400 MHz, DMSO-d6) δ 10.90 (s, 1H), 8.76 (d, J = 4.7 Hz, 1H), 8.17 (d, J = 2.0 Hz, 1H), 8.11 (t, J = 4.8 Hz, 1H), 7.67 (d, J = 2.2 Hz, 1H), 7.62 (dd, J = 8.2, 2.2 Hz, 1H), 7.53 (d, J = 2.0 Hz, 1H), 7.37 (d, J = 8.4 Hz, 1H), 4.87 (t, J = 5.5 Hz, 1H), 4.12 (s, 1H), 3.85 (t, J = 11.8 Hz, 2H), 3.78-3.60 (m, 2H), 3.48 (dt, J = 19.1, 11.0 Hz, 3H), 3.34-3.21 (m, 2H), 2.94 (d, J = 10.8 Hz, 1H), 2.70 (dd, J = 13.4, 7.3 Hz, 1H), 2.27 (s, 3H), 2.18-2.04 (m, 1H). LCMS (m/z) (M + H) = 560.1838, Rt = 3.09 min |

| Ex. No. | Name | Physical Data |
|---|---|---|
| 323 | (R)-N-(3-(7-(2-hydroxyethyl)-6-oxo-2,4,4a,5,6,7-hexahydro-1H-[1,4]oxazino[4,3-d]pyrido[2,3-b][1,4]diazepin-10-yl)-4-methylphenyl)-6-(trifluoromethyl)pyridazine-4-carboxamide | 1H NMR (400 MHz, Methanol-d4) δ 9.87 (d, J = 2.0 Hz, 1H), 8.59 (d, J = 2.0 Hz, 1H), 8.18 (d, J = 2.0 Hz, 1H), 7.75 (d, J = 2.3 Hz, 1H), 7.68 (dd, J = 8.3, 2.3 Hz, 1H), 7.60 (d, J = 2.0 Hz, 1H), 7.38 (d, J = 8.4 Hz, 1H), 4.35 (d, J = 8.0 Hz, 1H), 3.98-3.78 (m, 5H), 3.75-3.60 (m, 3H), 3.00 (d, J = 11.1 Hz, 1H), 2.79 (dd, J = 13.7, 7.5 Hz, 1H), 2.32 (s, 3H), 2.22 (d, J = 13.7 Hz, 1H), 1.45 (s, 1H). LCMS (m/z) (M + H) = 543.19, Rt = 0.93 min |
| 324 | (S)-N-(3-(7-(2-hydroxyethyl)-6-oxo-2,4,4a,5,6,7-hexahydro-1H-[1,4]oxazino[4,3-d]pyrido[2,3-b][1,4]diazepin-10-yl)-4-methylphenyl)-6-(trifluoromethyl)pyridazine-4-carboxamide | 1H NMR (400 MHz, Methanol-d4) δ 9.87 (d, J = 2.0 Hz, 1H), 8.59 (d, J = 2.0 Hz, 1H), 8.18 (d, J = 2.0 Hz' 1H), 7.75 (d, J = 2.3 Hz, 1H), 7.68 (dd, J = 8.3, 2.3 Hz, 1H), 7.60 (d, J = 2.0 Hz, 1H), 7.38 (d, J = 8.4 Hz, 1H), 4.35 (d, J = 8.0 Hz, 1H), 3.98-3.78 (m, 5H), 3.75-3.60 (m, 3H), 3.00 (d, J = 11.1 Hz, 1H), 2.79 (dd, J = 13.7, 7.5 Hz, 1H), 2.32 (s, 3H), 2.22 (d, J = 13.7 Hz, 1H), 1.45 (s, 1H). LCMS (m/z) (M + H) = 543.19, Rt = 0.93 min |
| 325 | (R)-N-(3-(7-ethyl-6-oxo-2,4,4a,5,6,7-hexahydro-1H-[1,4]oxazino[4,3-d]pyrido[2,3-b][1,4]diazepin-10-yl)-4-methylphenyl)-6-(trifluoromethyl)pyridazine-4-carboxamide | $^1$H NMR (400 MHz, Methanol-d$_4$) δ 9.90 (d, J = 1.9 Hz, 1H), 8.62 (d, J = 2.0 Hz, 1H), 8.21 (d, J = 2.0 Hz, 1H), 7.77 (d, J = 2.2 Hz, 1H), 7.71 (dd, J = 8.3, 2.3 Hz, 1H), 7.60 (d, J = 2.0 Hz, 1H), 7.40 (d, J = 8.3 Hz, 1H), 4.14-4.00 (m, J = 6.9 Hz, 2H), 3.97 (dd, J = 11.1, 2.1 Hz, 1H), 3.88 (dd, J = 10.9, 2.5 Hz, 1H), 3.72-3.62 (m, 2H), 3.45-3.34 (m, 2H), 3.00 (d, J = 11.3 Hz, 1H), 2.77 (dd, J = 13.7, 7.5 Hz, 1H), 2.35 (s, 3H), 2.20 (d, J = 13.7 Hz, 1H), 1.20 (d, J = 7.1 Hz, 3H). LCMS (m/z) (M + H) = 527.1, Rt = 1.07 min |
| 326 | (S)-N-(3-(7-ethyl-6-oxo-2,4,4a,5,6,7-hexahydro-1H-[1,4]oxazino[4,3-d]pyrido[2,3-b][1,4]diazepin-10-yl)-4-methylphenyl)-6-(trifluoromethyl)pyridazine-4-carboxamide | $^1$H NMR (400 MHz, Methanol-d$_4$) δ 9.90 (d, J = 2.0 Hz, 1H), 8.62 (d, J = 2.0 Hz, 1H), 8.21 (d, J = 2.0 Hz, 1H), 7.77 (d, J = 2.3 Hz, 1H), 7.71 (dd, J = 8.3, 2.3 Hz, 1H), 7.60 (d, J = 2.0 Hz, 1H), 7.40 (d, J = 8.3 Hz, 1H), 4.08 (p, J = 6.5 Hz, 2H), 3.97 (dd, J = 11.2, 2.3 Hz, 1H), 3.88 (dd, J = 11.0, 2.6 Hz, 1H), 3.73-3.61 (m, 2H), 3.47-3.34 (m, 2H), 3.00 (d, J = 11.2 Hz, 1H), 2.77 (dd, J = 13.7, 7.5 Hz, 1H), 2.35 (s, 3H), 2.20 (d, J = 13.7 Hz, 1H), 1.20 (d, J = 7.1 Hz, 3H). LCMS (m/z) (M + H) = 527.1, Rt = 1.07 min |
| 327 | (R)-N-(3-(7-ethyl-6-oxo-2,4,4a,5,6,7-hexahydro-1H-[1,4]oxazino[4,3-d]pyrido[2,3-b][1,4]diazepin-10-yl)-4-methylphenyl)-3-fluoro-2-(trifluoromethyl)isonicotinamide | 1H NMR (400 MHz, Methanol-d4) δ 8.56 (d, J = 4.7 Hz, 1H), 8.08 (d, J = 2.0 Hz, 1H), 7.86 (t, J = 4.8 Hz, 1H), 7.58 (d, J = 2.3 Hz, 1H), 7.50 (dd, J = 8.3, 2.3 Hz, 1H), 7.47 (d, J = 2.0 Hz, 1H), 7.26 (d, J = 8.3 Hz, 1H), 3.95 (hept, J = 6.8 Hz, 2H), 3.84 (dd, J = 11.1, 2.2 Hz, 1H), 3.76 (dd, J = 11.0, 2.5 Hz, 1H), 3.54 (q, J = 10.0, 9.3 Hz, 2H), 3.30 (t, J = 7.9 Hz, 1H), 2.88 (d, J = 11.3 Hz, 1H), 2.65 (dd, J = 13.7, 7.5 Hz, 1H), 2.21 (s, 3H), 2.07 (d, J = 13.6 Hz, 1H), 1.08 (t, J = 7.1 Hz, 3H). LCMS (m/z) (M + H) = 544.4, Rt = 1.16 min |

| Ex. No. | Structure | Name | Physical Data |
|---|---|---|---|
| 328 | 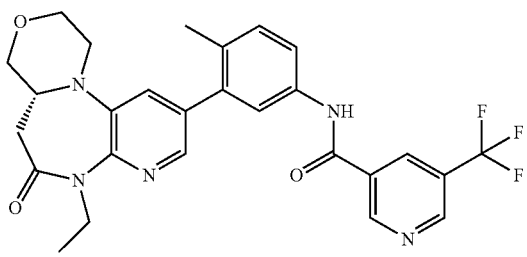 [SMILES: CCN1C(=O)C[C@@H]2COCCN2c2cc(-c3cc(NC(=O)c4cncc(C(F)(F)F)c4)ccc3C)cnc21] | (R)-N-(3-(7-ethyl-6-oxo-2,4,4a,5,6,7-hexahydro-1H-[1,4]oxazino[4,3-d]pyrido[2,3-b][1,4]diazepin-10-yl)-4-methylphenyl)-5-(trifluoromethyl)nicotinamide | $^1$H NMR (400 MHz, Methanol-d$_4$) δ 9.25 (d, J = 1.6 Hz, 1H), 8.98 (s, 1H), 8.57 (s, 1H), 8.10 (d, J = 2.0 Hz, 1H), 7.63 (d, J = 2.2 Hz, 1H), 7.56 (dd, J = 8.3, 2.2 Hz, 1H), 7.48 (d, J = 2.0 Hz, 1H), 7.27 (d, J = 8.3 Hz, 1H), 3.96 (hept, J = 6.8 Hz, 2H), 3.85 (d, J = 9.4 Hz, 1H), 3.76 (dd, J = 11.0, 2.4 Hz, 1H), 3.61-3.50 (m, 2H), 3.31 (s, 2H), 2.89 (d, J = 11.4 Hz, 1H), 2.65 (dd, J = 13.6, 7.5 Hz, 1H), 2.23 (s, 3H), 2.08 (d, J = 13.7 Hz, 1H), 1.09 (t, J = 7.1 Hz, 3H). LCMS (m/z) (M + H) = 526.2, Rt = 1.04 min |
| 329 | 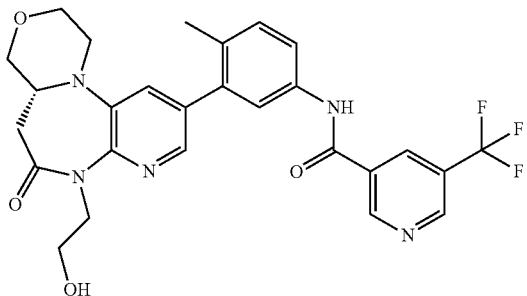 [SMILES: Cc1ccc(NC(=O)c2cncc(C(F)(F)F)c2)cc1-c1cnc2c(c1)N1CCOC[C@H]1CC(=O)N2CCO] | (R)-N-(3-(7-(2-hydroxyethyl)-6-oxo-2,4,4a,5,6,7-hexahydro-1H-[1,4]oxazino[4,3-d]pyrido[2,3-b][1,4]diazepin-10-yl)-4-methylphenyl)-5-(trifluoromethyl)nicotinamide | $^1$H NMR (400 MHz, Methanol-d$_4$) δ 9.37 (d, J = 1.9 Hz, 1H), 9.12-9.08 (m, 1H), 8.69 (s, 1H), 8.21 (d, J = 2.0 Hz, 1H), 7.75 (d, J = 2.2 Hz, 1H), 7.68 (dd, J = 8.3, 2.3 Hz, 1H), 7.63 (d, J = 2.0 Hz, 1H), 7.39 (d, J = 8.3 Hz, 1H), 4.42-4.32 (m, 1H), 4.00-3.94 (m, 1H), 3.93-3.81 (m, 3H), 3.77-3.63 (m, 3H), 3.41 (dd, J = 23.6, 5.1 Hz, 2H), 3.03 (d, J = 11.9 Hz, 1H), 2.82 (dd, J = 13.7, 7.5 Hz, 1H), 2.34 (s, 3H), 2.24 (d, J = 13.7 Hz, 1H). LCMS (m/z) (M + H) = 542.3, Rt = 0.90 min |
| 330 | 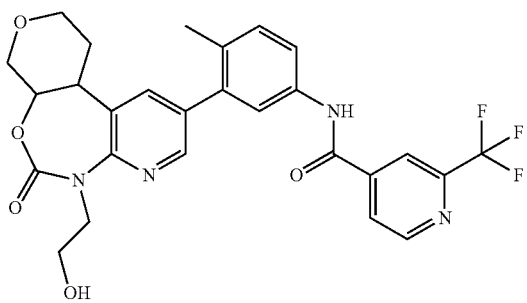<br>cis diastereomer<br>single enantiomer<br>from Peak 1 intermediate | N-(3-((4,11b-cis)-7-(2-hydroxyethyl)-6-oxo-2,4,4a,6,7,11b-hexahydro-1H-pyrano[4,3-f]pyrido[2,3-d][1,3]oxazepin-10-yl)-4-methylphenyl)-2-(trifluoromethyl)isonicotinamide | $^1$H NMR (400 MHz, Methanol-d$_4$) δ 8.92 (d, J = 5.0 Hz, 1H), 8.39 (d, J = 2.3 Hz, 1H), 8.32 (s, 1H), 8.14 (dd, J = 5.0, 1.3 Hz, 1H), 8.11 (d, J = 2.3 Hz, 1H), 7.73 (dd, J = 8.2, 2.3 Hz, 1H), 7.69 (d, J = 2.2 Hz, 1H), 7.38 (d, J = 8.3 Hz, 1H), 4.70-4.61 (m, 2H), 4.30 (q, J = 8.6 Hz, 1H), 4.20 (q, J = 8.3 Hz, 1H), 4.07 (dd, J = 11.3, 3.9 Hz, 1H), 3.97-3.88 (m, 2H), 3.76-3.68 (m, 1H), 3.62 (td, J = 11.9, 2.0 Hz, 1H), 3.32-3.27 (m, 1H), 2.42 (qd, J = 12.8, 4.6 Hz, 1H), 2.33 (s, 3H), 1.61-1.51 (m, 1H). LCMS (m/z) (M + H) = 543.1857, Rt = 2.77 min |
| 331 | 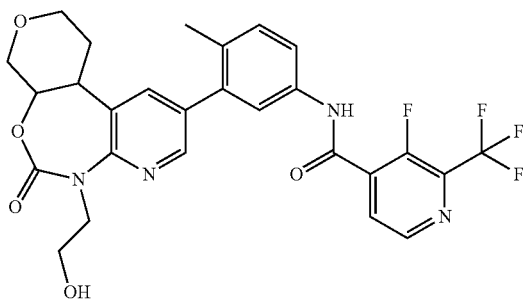<br>cis diastereomer<br>single enantiomer<br>from Peak 1 intermediate | 3-fluoro-N-(3-((4,11b-cis)-7-(2-hydroxyethyl)-6-oxo-2,4,4a,6,7,11b-hexahydro-1H-pyrano[4,3-f]pyrido[2,3-d][1,3]oxazepin-10-yl)-4-methylphenyl)-2-(trifluoromethyl)isonicotinamide | $^1$H NMR (400 MHz, Methanol-d$_4$) δ 8.55 (d, J = 4.7 Hz, 1H), 8.27 (d, J = 2.3 Hz, 1H), 7.99 (d, J = 2.3 Hz, 1H), 7.86 (t, J = 4.8 Hz, 1H), 7.57 (dd, J = 8.2, 2.2 Hz, 1H), 7.53 (d, J = 2.2 Hz, 1H), 7.27 (d, J = 8.3 Hz, 1H), 4.53 (t, J = 8.1 Hz, 2H), 4.18 (q, J = 8.5 Hz, 1H), 4.08 (q, J = 8.2 Hz, 1H), 3.95 (dd, J = 11.3, 3.8 Hz, 1H), 3.86-3.75 (m, 2H), 3.59 (d, J = 11.8 Hz, 1H), 3.50 (td, J = 11.9, 1.8 Hz, 1H), 3.22-3.15 (m, 1H), 2.30 (qt, J = 12.8, 6.3 Hz, 1H), 2.21 (s, 3H), 1.46 (d, J = 12.7 Hz, 1H). LCMS (m/z) (M + H) = 561.1757, Rt = 2.88 min |

| Ex. No. | Structure | Name | Physical Data |
|---|---|---|---|
| 332 | (structure shown) cis diastereomer single enantiomer from Peak 1 intermediate | 2-(1,1-difluoroethyl)-N-(3-((4,11b-cis)-7-(2-hydroxyethyl)-6-oxo-2,4,4a,6,7,11b-hexahydro-1H-pyrano[4,3-f]pyrido[2,3-d][1,3]oxazepin-10-yl)-4-methylphenyl)isonicotinamide | 1HNMR: 1H NMR (400 MHz, Methanol-d4) δ 8.71 (d, J = 5.1 Hz, 1H), 8.28 (d, J = 2.3 Hz, 1H), 8.09 (s, 1H), 8.00 (d, J = 2.2 Hz, 1H), 7.87 (d, J = 5.1 Hz, 1H), 7.62 (dd, J = 8.2, 2.2 Hz, 1H), 7.57 (d, J = 2.1 Hz, 1H), 7.27 (d, J = 8.3 Hz, 1H), 4.59-4.49 (m, 2H), 4.19 (q, J = 8.5 Hz, 1H), 4.09 (q, J = 8.2 Hz, 1H), 3.96 (dd, J = 11.2, 3.8 Hz, 1H), 3.88-3.71 (m, 2H), 3.60 (d, J = 11.9 Hz, 1H), 3.51 (td, J = 11.9, 1.9 Hz, 1H), 3.18 (d, J = 3.7 Hz, 1H), 2.30 (qd, J = 12.8, 4.6 Hz, 1H), 2.22 (s, 3H), 1.94 (t, J = 18.7 Hz, 3H), 1.46 (d, J = 12.9 Hz, 1H). LCMS (m/z) (M + H) = 539.2130, Rt = 2.66 min |
| 333 | (structure shown) | (R)-N-(3-(7-(2-hydroxyethyl)-6-oxo-2,4,4a,5,6,7-hexahydro-1H-[1,4]oxazino[4,3-d]pyrido[2,3-b][1,4]diazepin-10-yl)-4-methylphenyl)-2-(trifluoromethyl)isonicotinamide | $^1$H NMR (400 MHz, Methanol-d$_4$) δ 8.90 (d, J = 5.0 Hz, 1H), 8.30 (s, 1H), 8.18 (d, J = 2.0 Hz, 1H), 8.12 (dd, J = 5.0, 1.2 Hz, 1H), 7.72 (d, J = 22.2 Hz, 1H), 7.66 (dd, J = 8.2, 2.3 Hz, 1H), 7.59 (d, J = 2.0 Hz, 1H), 7.36 (d, J = 8.3 Hz, 1H), 4.40-4.29 (m, 1H), 3.94 (dd, J = 11.1, 2.2 Hz, 1H), 3.91-3.79 (m, 3H), 3.74-3.61 (m, 3H), 3.43 (d, J = 7.5 Hz, 2H), 3.01 (d, J = 11.5 Hz, 1H), 2.79 (dd, J = 13.8, 7.5 Hz, 1H), 2.31 (s, 3H), 2.22 (d, J = 13.8 Hz, 1H). LCMS (m/z) (M + H) = 542.3, Rt = 0.94 min |

Synthesis of 9-(5-amino-2-methylphenyl)-5,5-dimethyl-1,2,4,4a,5,6-hexahydro-[1,4]oxazino[4,3-a][1,5]naphthyridin-6-ol (from Peak 1)

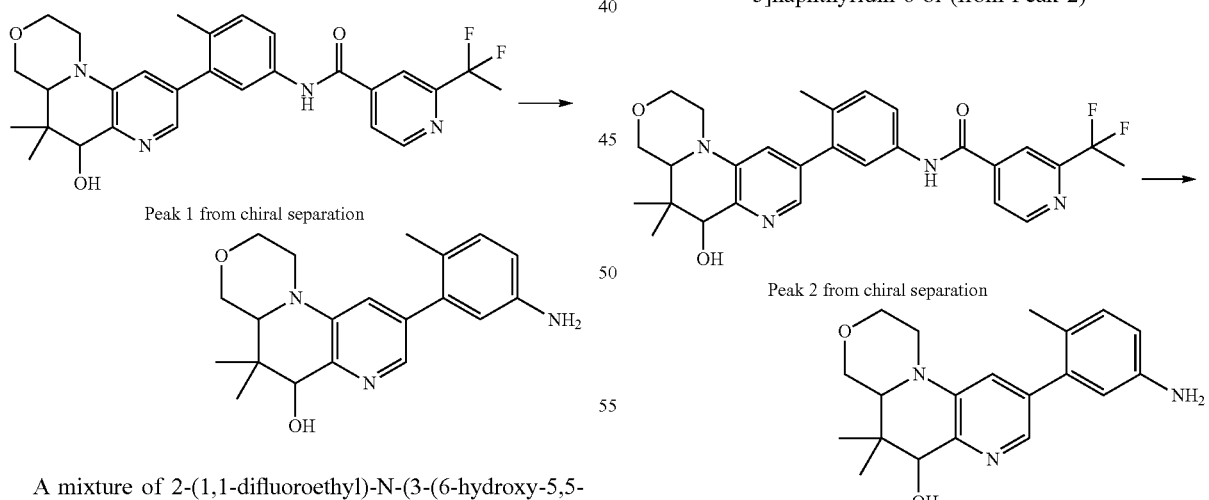

A mixture of 2-(1,1-difluoroethyl)-N-(3-(6-hydroxy-5,5-dimethyl-1,2,4,4a,5,6-hexahydro-[1,4]oxazino[4,3-a][1,5]naphthyridin-9-yl)-4-methylphenyl)isonicotinamide (1.0 equiv: see Ex. 160) in 1:1 THF/MeOH (0.051 M) and NaOH (1 M aq, 10 equiv) was heated to 75° C. and stirred for 4 h. The mixture was poured onto water and extracted three times with ethyl acetate. LCMS The combined organics were washed with brine, dried over magnesium sulfate, filtered, and concentrated to 9-(5-amino-2-methylphenyl)-5,5-dimethyl-1,2,4,4a,5,6-hexahydro-[1,4]oxazino[4,3-a][1,5]naphthyridin-6-ol which was used without further purification. LCMS (m/z) (M+H)=340.3, Rt=0.57 min.

Synthesis of 9-(5-amino-2-methylphenyl)-5,5-dimethyl-1,2,4,4a,5,6-hexahydro-[1,4]oxazino[4,3-a][1,5]naphthyridin-6-ol (from Peak 2)

A mixture of 2-(1,1-difluoroethyl)-N-(3-(6-hydroxy-5,5-dimethyl-1,2,4,4a,5,6-hexahydro-[1,4]oxazino[4,3-a][1,5]naphthyridin-9-yl)-4-methylphenyl)isonicotinamide (1.0 equiv: see Ex. 160) in 1:1 THF/MeOH (0.051 M) and NaOH (1 M aq, 10 equiv) was heated to 75° C. and stirred for overnight. The mixture was poured onto water and extracted three times with ethyl acetate. LCMS The combined organics were washed with brine, dried over magnesium sulfate, filtered, and concentrated to 9-(5-amino-2-methylphenyl)-5,5-dimethyl-1,2,4,4a,5,6-hexahydro-[1,4]oxazino[4,3-a][1,5]naphthyridin-6-ol which was used without further purification. LCMS (m/z) (M+H)=340.3, Rt=0.56 min.

Example 334: N-(3-(6-hydroxy-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide (Single Enantiomer from Peak 1 Intermediate)

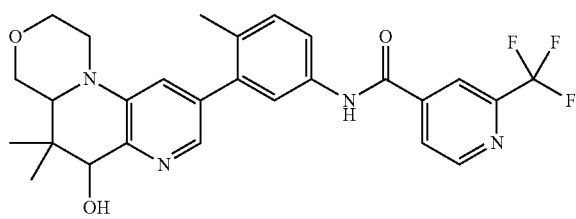

single enantiomer, from Peak 1 intermediate 9-(5-amino-2-methylphenyl)-5,5-dimethyl-1,2,4,4a,5,6-hexahydro-[1,4]oxazino[4,3-a][1,5]naphthyridin-6-ol (from Peak 1 chiral intermediate) (1.0 equiv) and 2-(trifluoromethyl)isonicotinic acid (1.1 equiv) were taken up in DMA (0.05 M) at 25° C. HOAT (1.3 equiv), iPr$_2$EtN (3 equiv), and EDC (1.3 equiv) were added and the mixture was stirred overnight at 25° C. The mixture was poured onto water and extracted three times with ethyl acetate. The combined organics were washed with water and brine, dried over magnesium sulfate, filtered, and concentrated. The residue was purified by flash column chromatography over silica gel (heptane and 0-100% EtOAc gradient) to provide. N-(3-(6-hydroxy-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide in 63% yield. LCMS (m/z) (M+H)=513.3, Rt=0.87 min. $^1$H NMR (400 MHz, Methanol-d4) δ 8.90 (d, J=5.0 Hz, 1H), 8.30 (s, 1H), 8.12 (dd, J=5.0, 1.2 Hz, 1H), 7.90 (d, J=1.6 Hz, 1H), 7.66 (dd, J=8.2, 2.3 Hz, 1H), 7.63 (d, J=2.2 Hz, 1H), 7.33 (d, J=8.3 Hz, 1H), 7.23 (d, J=1.6 Hz, 1H), 4.40 (s, 1H), 4.04 (dd, J=11.3, 3.0 Hz, 1H), 3.93 (dd, J=11.5, 3.4 Hz, 1H), 3.81 (d, J=12.5 Hz, 1H), 3.63 (td, J=11.5, 2.8 Hz, 2H), 3.12 (dd, J=10.7, 3.2 Hz, 1H), 2.96 (td, J=12.2, 3.6 Hz, 1H), 2.27 (s, 3H), 1.14 (s, 3H), 0.93 (s, 3H).

The following were prepared using the same methods as described for Example 334 using the appropriate starting materials:

| # | Structure | Name | Data |
|---|---|---|---|
| 335 | 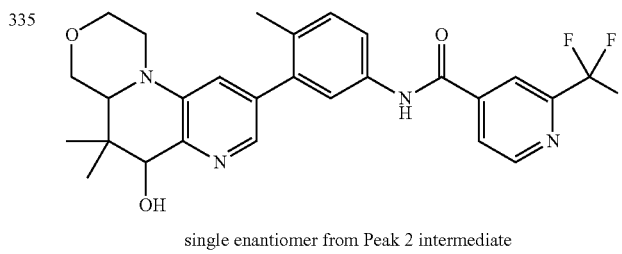<br>single enantiomer from Peak 2 intermediate | N-(3-(6-hydroxy-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.30 (s, 1H), 8.14-8.08 (m, 1H), 7.90 (d, J = 1.5 Hz, 1H), 7.66 (dd, J = 8.2, 2.2 Hz, 1H), 7.63 (d, J = 2.2 Hz, 1H), 7.32 (d, J = 8.3 Hz, 1H), 7.22 (d, J = 1.4 Hz, 1H), 4.40 (s, 1H), 4.04 (dd, J = 11.3, 3.0 Hz, 1H), 3.93 (dd, J = 11.5, 3.3 Hz, 1H), 3.81 (d, J = 12.3 Hz, 1H), 3.63 (td, J = 11.5, 3.0 Hz, 2H), 3.11 (dd, J = 10.7, 3.1 Hz, 1H), 2.96 (td, J = 12.2, 3.6 Hz, 1H), 2.27 (s, 3H), 1.14 (s, 3H), 0.93 (s, 3H), LCMS (m/z) (M + H) = 513.3, Rt = 0.88 min |
| 336 | 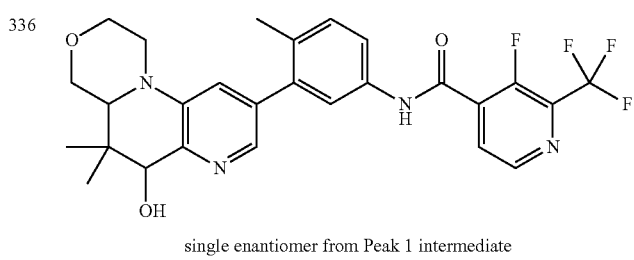<br>single enantiomer from Peak 1 intermediate | 3-fluoro-N-(3-(6-hydroxy-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.65 (d, J = 4.7 Hz, 1H), 7.95 (t, J = 4.8 Hz, 1H), 7.89 (d, J = 1.6 Hz, 1H), 7.61 (dd, J = 8.2, 2.3 Hz, 1H), 7.58 (d, J = 2.2 Hz, 1H), 7.32 (d, J = 8.2 Hz, 1H), 7.22 (d, J = 1.6 Hz, 1H), 4.40 (s, 1H), 4.04 (dd, J = 11.3, 3.0 Hz, 1H), 3.93 (dd, J = 11.5, 3.4 Hz, 1H), 3.85-3.76 (m, 1H), 3.62 (td, J = 11.5, 2.9 Hz, 2H), 3.11 (dd, J = 10.7, 3.2 Hz, 1H), 2.96 (td, J = 12.2, 3.6 Hz, 1H), 2.26 (s, 3H), 1.14 (s, 3H), 0.93 (s, 3H). LCMS (m/z) (M + H) = 531.5, Rt = 0.90 min |
| 337 | 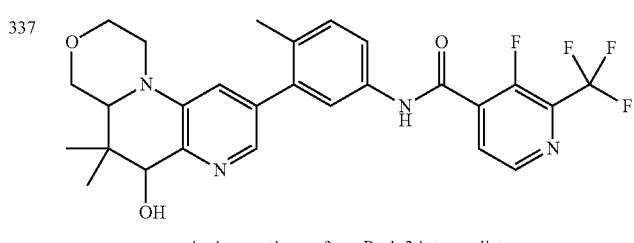<br>single enantiomer from Peak 2 intermediate | 3-fluoro-N-(3-(6-hydroxy-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.65 (d, J = 4.7 Hz, 1H), 7.95 (t, J = 4.8 Hz, 1H), 7.89 (d, J = 1.6 Hz, 1H), 7.61 (dd, J = 8.2, 2.3 Hz, 1H), 7.58 (d, J = 2.2 Hz, 1H), 7.32 (d, J = 8.2 Hz, 1H), 7.22 (d, J = 1.6 Hz, 1H), 4.40 (s, 1H), 4.04 (dd, J = 11.3, 3.1 Hz, 1H), 3.93 (dd, J = 11.5, 3.4 Hz, 1H), 3.85-3.76 (m, 1H), 3.63 (td, J = 11.5, 2.7 Hz, 2H), 3.47-3.32 (m, 2H), 3.10 (d, J = 3.2 Hz, 1H), 2.96 (td, J = 12.2, 3.6 Hz, 1H), 2.26 (s, 3H), 1.14 (s, 3H), 0.93 (s, 3H), LCMS (m/z) (M + H) = 531.3, Rt = 0.90 min |

297
Synthesis of (10bR)-9-bromo-6-ethyl-4a-fluoro-4,4a,6,10b-tetrahydro-1H-pyrano[3,4-c][1,8]naphthyridin-5(2H)-one

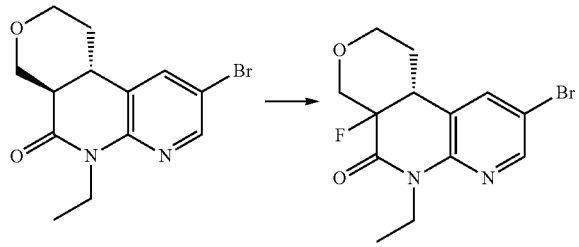

To a stirred solution of (4aR, 10bS)-9-bromo-6-ethyl-4,4a,6,10b-tetrahydro-1H-pyrano[3,4-c][1,8]naphthyridin-5(2H)-one (1.0 equiv) in THF (0.1 M) at −78° C. was added LDA (2 M in THF/heptane/ethyl benzene, 1.3 equiv) and the mixture was stirred for 30 min. N-fluorobenzenesulfonimide (1.3 equiv) was then added, and the mixture was stirred for 30 min and the allowed to warm to RT over 1 h. The reaction was quenched with saturated aqueous NaHCO$_3$ and extracted twice with EtOAc The combined organics were washed with brine, dried over MgSO$_4$, filtered, and concentrated. The residue was purified by flash column chromatography over silica gel (heptane and 0-50% EtOAc gradient) to provide (10bR)-9-bromo-6-ethyl-4a-fluoro-4,4a,6,10b-tetrahydro-1H-pyrano[3,4-c][1,8]naphthyridin-5(2H)-one as a colorless oil in 82% yield. LCMS (m/z) (M+H)=329.0/331.0, Rt=1.06 min.

298
Example 338: 2-(1,1-difluoroethyl)-N-(3-((10bR)-6-ethyl-4a-fluoro-5-oxo-2,4,4a,5,6,10b-hexahydro-1H-pyrano[3,4-c][1,8]naphthyridin-9-yl)-4-methylphenyl)isonicotinamide

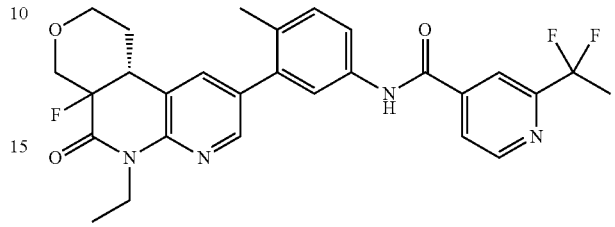

A vial was charged with (10bR)-9-bromo-6-ethyl-4a-fluoro-4,4a,6,10b-tetrahydro-1H-pyrano[3,4-c][1,8]naphthyridin-5(2H)-one (1.0 equiv) and 2-(1,1-difluoroethyl)-N-(4-methyl-3-(4,4,5,5-tetramethyl-1,3,2-dioxaborolan-2-yl)phenyl)isonicotinamide (1.05 equiv). THF (0.1 M) and K$_3$PO$_4$ (0.5 M aq, 2 equiv) were added, and the flask was purged with N$_2$. XPhos Pd G2 (0.05 equiv) and XPhos (0.05 equiv) were added, and the reaction was heated at 45° C. for 1 h. The reaction was diluted with DCM, dried over MgSO$_4$, filtered, and concentrated. The residue was taken up in MeOH/DMSO with a bit of water, filtered, and purified by basic prep HPLC. Pure product fractions were lyophilized to 2-(1,1-difluoroethyl)-N-(3-((10bR)-6-ethyl-4a-fluoro-5-oxo-2,4,4a,5,6,10b-hexahydro-1H-pyrano[3,4-c][1,8]naphthyridin-9-yl)-4-methylphenyl)isonicotinamide as a fluffy white solid in 51% yield. The compound was a single diastereomer, but the relative configuration of the fluoride was not determined. LCMS (m/z) (M+H)=525.3, Rt=1.22 min. $^1$H NMR (400 MHz, DMSO-d6) δ 10.68 (s, 1H), 8.89 (d, J=5.0 Hz, 1H), 8.38 (d, J=2.2 Hz, 1H), 8.19 (s, 1H), 8.04 (d, J=4.9 Hz, 1H), 7.92 (d, J=2.1 Hz, 1H), 7.73 (s, 2H), 7.37 (d, J=8.1 Hz, 1H), 4.42 (dd, J=10.9, 5.4 Hz, 1H), 4.19 (ddq, J=26.9, 13.8, 6.9 Hz, 2H), 3.85-3.74 (m, 1H), 3.62 (td, J=10.9, 5.6 Hz, 1H), 3.56-3.48 (m, 1H), 3.46 (dd, J=10.9, 5.5 Hz, 1H), 2.27 (s, 3H), 2.12-1.96 (m, 4H), 1.69-1.55 (m, 1H), 1.21 (t, J=7.0 Hz, 3H).

The following were prepared using the same methods as described above using the appropriate starting materials:

| | | |
|---|---|---|
| 339 | N-(3-((10bR)-6-ethyl-4a-fluoro-5-oxo-2,4,4a,5,6,10b-hexahydro-1H-pyrano[3,4-c][1,8]naphthyridin-9-yl)-4-methylphenyl)-2-(trifluoromethyl)isonicotinamide | $^1$H NMR (400 MHz, Methanol-d4) δ 8.91 (d, J = 5.0 Hz, 1H), 8.33 (d, J = 2.2 Hz, 1H), 8.30 (s, 1H), 8.12 (dd, J = 5.0, 1.2 Hz, 1H), 7.80 (d, J = 2.1 Hz, 1H), 7.67 (dd, J = 6.2, 2.3 Hz, 2H), 7.38-7.30 (m, 1H), 4.57 (dd, J = 11.0, 4.4 Hz, 1H), 4.36 (dq, J = 13.8, 6.9 Hz, 1H), 4.26 (dd, J = 13.0, 7.0 Hz, 1H), 3.88 (dq, J = 11.2, 4.0 Hz, 1H), 3.65-3.56 (m, 1H), 3.55-3.42 (m, 2H), 2.30 (s, 3H), 2.12-2.04 (m, 1H), 1.69 (qd, J = 11.5, 4.3 Hz, 1H), 1.28 (t, J = 7.0 Hz, 3H). LCMS (m/z) (M + H) = 529.3, Rt = 1.25 min |
| 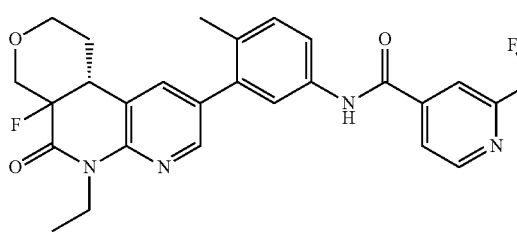 | | |

| | | |
|---|---|---|
| 340 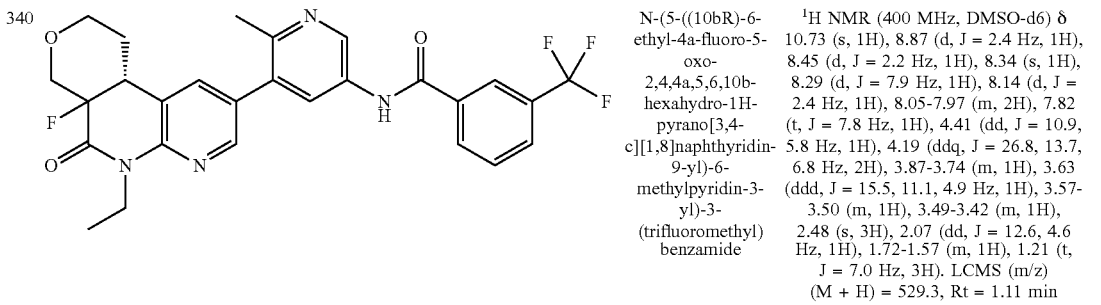 | N-(5-((10bR)-6-ethyl-4a-fluoro-5-oxo-2,4,4a,5,6,10b-hexahydro-1H-pyrano[3,4-c][1,8]naphthyridin-9-yl)-6-methylpyridin-3-yl)-3-(trifluoromethyl)benzamide | $^1$H NMR (400 MHz, DMSO-d6) δ 10.73 (s, 1H), 8.87 (d, J = 2.4 Hz, 1H), 8.45 (d, J = 2.2 Hz, 1H), 8.34 (s, 1H), 8.29 (d, J = 7.9 Hz, 1H), 8.14 (d, J = 2.4 Hz, 1H), 8.05-7.97 (m, 2H), 7.82 (t, J = 7.8 Hz, 1H), 4.41 (dd, J = 10.9, 5.8 Hz, 1H), 4.19 (ddq, J = 26.8, 13.7, 6.8 Hz, 2H), 3.87-3.74 (m, 1H), 3.63 (ddd, J = 15.5, 11.1, 4.9 Hz, 1H), 3.57-3.50 (m, 1H), 3.49-3.42 (m, 1H), 2.48 (s, 3H), 2.07 (dd, J = 12.6, 4.6 Hz, 1H), 1.72-1.57 (m, 1H), 1.21 (t, J = 7.0 Hz, 3H). LCMS (m/z) (M + H) = 529.3, Rt = 1.11 min |

Examples 341: (N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-2-(trifluoromethyl)isonicotinamide (Single Enantiomer, "Peak 1") and Example 342: N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-2-(trifluoromethyl)isonicotinamide (Single Enantiomer, "Peak 2")

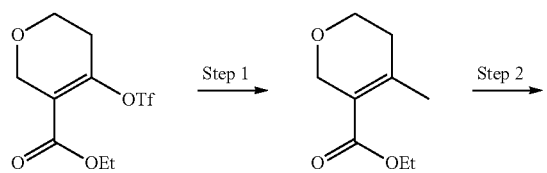

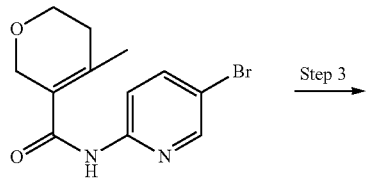

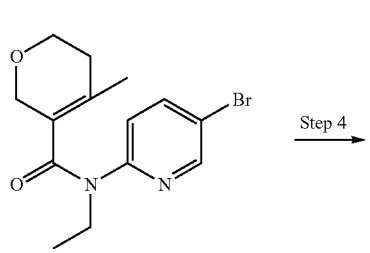

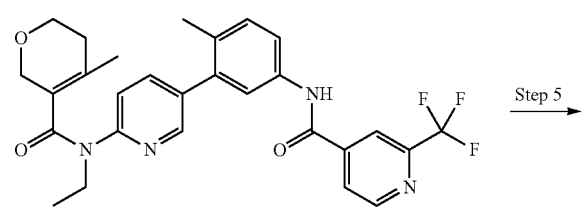

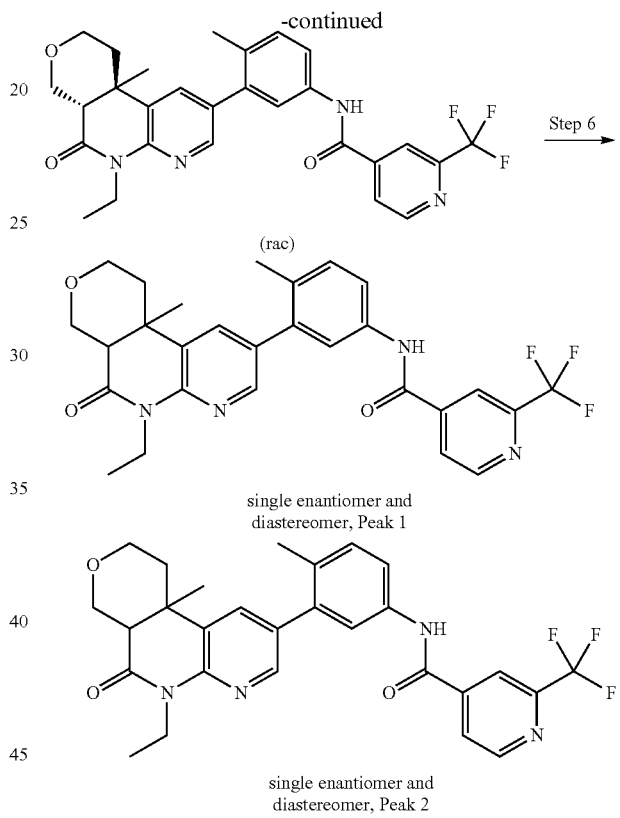

Step 1:

A stirred solution of ethyl 4-(((trifluoromethyl)sulfonyl)oxy)-5,6-dihydro-2H-pyran-3-carboxylate (1.0 equiv) in THF (0.1 M) was degassed with $N_2$; Pd(PPh$_3$)$_4$ (0.05 equiv) was then added, and the mixture was cooled to 0° C. Me$_2$Zn (2 M in heptane, 2.0 equiv) was subsequently added, and the reaction was allowed to warm to RT and stirred for 1 h. The reaction was quenched with brine, and the biphasic mixture was filtered through a pad of Celite. The layers of the filtrate were separated, and the organic layer was dried over sodium sulfate, filtered, and concentrated. The residue was purified by flash column chromatography over silica gel (heptane and 0-10% EtOAc gradient) to give ethyl 4-methyl-5,6-dihydro-2H-pyran-3-carboxylate as a colorless oil in 83% yield. LCMS (m/z) Rt=0.82 min. $^1$H NMR (400 MHz, Chloroform-d) δ 4.31 (h, J=2.1 Hz, 2H), 4.21 (q, J=7.1 Hz, 2H), 3.77 (t, J=5.6 Hz, 2H), 2.31-2.23 (m, 2H), 2.16 (dt, J=1.9, 1.1 Hz, 3H), 1.31 (t, J=7.1 Hz, 3H)

Step 2:

A syringe was charged with a solution "Feed A", prepared of ethyl 4-methyl-5,6-dihydro-2H-pyran-3-carboxylate (1.0 equiv) and 2-amino-5-bromopyridine (1.5 equiv) in THF (0.3 M). A second syringe "Feed B" was charged with LiHMDS (1 M in THF, 1.8 equiv). These syringes were loaded onto separate syringe pumps and simultaneously injected through a 500 ∞L PFA flow reactor submerged in a 65° C. oil bath at a flow rate of 65 μL/min for Feed A and 35 μL/min for Feed B. The eluting reaction mixture was directly quenched into saturated aqueous NH$_4$Cl. The biphasic mixture was extracted three times with ethyl acetate. The combined organics were sequentially washed with 1 M aq HCl, water, saturated aqueous NaHCO$_3$ and brine, dried over magnesium sulfate, filtered, and concentrated. The residue was adsorbed purified by flash column chromatography over silica gel (heptane and 0-50% EtOAc) to provide N-(5-bromopyridin-2-yl)-4-methyl-5,6-dihydro-2H-pyran-3-carboxamide as a pale yellow solid in 45% yield. LCMS (m/z) (M+H)=296.9/238.9, Rt=0.87 min. $^1$H NMR (400 MHz, Chloroform-d) δ 8.36-8.33 (m, 1H), 8.30 (s, 1H), 8.26-8.21 (m, 1H), 7.84 (dd, J=8.9, 2.4 Hz, 1H), 4.38 (h, J=2.0 Hz, 2H), 3.84 (t, J=5.6 Hz, 2H), 2.20 (dq, J=4.8, 2.6 Hz, 2H), 1.97 (s, 3H).

Step 3:

To a stirred solution of N-(5-bromopyridin-2-yl)-4-methyl-5,6-dihydro-2H-pyran-3-carboxamide (1.0 equiv) in DMF (0.16 M) at 25° C. was added NaH (60% in mineral oil, 1.15 equiv). The mixture was stirred for 10 min followed by the addition of iodoethane (1.1 equiv) and the reaction was stirred for 30 min. The mixture was poured onto water and extracted three times with ethyl acetate. The combined organics were washed with water and brine, dried over magnesium sulfate, filtered, and concentrated. The residue was and purified by flash column chromatography over silica gel (heptane and 0-70% EtOAc gradient) to give N-(5-bromopyridin-2-yl)-N-ethyl-4-methyl-5,6-dihydro-2H-pyran-3-carboxamide as a colorless oil in 79% yield. LCMS (m/z) (M+H)=325.0/327.0, Rt=0.92 min.

Step 4:

A vial was charged with N-(5-bromopyridin-2-yl)-N-ethyl-4-methyl-5,6-dihydro-2H-pyran-3-carboxamide (1.0 equiv) and N-(4-methyl-3-(4,4,5,5-tetramethyl-1,3,2-dioxaborolan-2-yl)phenyl)-2-(trifluoromethyl)isonicotinamide (1.05 equiv). THF (0.1 M) and K$_3$PO$_4$ (0.5 M aq, 2.0 equiv) were added, and the vial was purged with N$_2$. XPhos Pd G2 (0.05 equiv) and XPhos (0.05 equiv) were added, and the reaction was heated at 50° C. for 1 h. The reaction was poured onto water and extracted twice with EtOAc The combined organics were washed with brine, dried over MgSO$_4$, filtered, and concentrated. The residue was purified by flash column chromatography over silica gel (heptane and 0-100% EtOAc gradient) to give N-(3-(6-(N-ethyl-4-methyl-5,6-dihydro-2H-pyran-3-carboxamido)pyridin-3-yl)-4-methylphenyl)-2-(trifluoromethyl)isonicotinamide as a white solid in 100% yield. LCMS (m/z) (M+H)=525.2, Rt=1.15 min Step 5:

A solution of N-(3-(6-(N-ethyl-4-methyl-5,6-dihydro-2H-pyran-3-carboxamido)pyridin-3-yl)-4-methylphenyl)-2-(trifluoromethyl)isonicotinamide (1.0 equiv) in DMF (0.03 M) was charged to a quartz vial and irradiated with UVB lamps (Rayonet reactor, RPR3000 A bulbs) at RT overnight. The reaction was poured onto water and extracted twice with EtOAc The combined organics were washed with water and brine, dried over MgSO$_4$, filtered, and concentrated. The residue was purified by flash column chromatography over silica gel (heptane and 0-100% EtOAc gradient) to give (rac)-N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-2-(trifluoromethyl)isonicotinamide as a white solid in 86% yield. LCMS (m/z) (M+H)=525.2, Rt=1.26 min.

Step 6:

(rac)-N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-2-(trifluoromethyl)isonicotinamide was subjected to chiral SFC (IB 21×250 mm column, 30% MeOH in CO$_2$ eluent). The first eluting peak afforded N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-2-(trifluoromethyl)isonicotinamide "Peak 1" as a white solid in 36% yield. The second peak afforded N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-2-(trifluoromethyl)isonicotinamide "Peak 2" as a white solid in 31% yield. LCMS and NMR data for each enantiomer were identical. LCMS (m/z) (M+H)=525.2, Rt=1.26 min. $^1$H NMR (400 MHz, Methanol-d4) δ 8.81 (d, J=5.0 Hz, 1H), 8.21 (s, 1H), 8.18 (d, J=2.2 Hz, 1H), 8.05-8.01 (m, 1H), 7.57 (dd, J=6.5, 2.2 Hz, 2H), 7.53 (d, J=2.2 Hz, 1H), 7.29-7.20 (m, 1H), 4.23 (dq, J=13.9, 7.0 Hz, 1H), 4.11-3.99 (m, 2H), 3.88 (dd, J=12.0, 4.0 Hz, 1H), 3.70 (td, J=12.3, 2.3 Hz, 1H), 3.66-3.55 (m, 1H), 2.69 (dd, J=11.1, 4.5 Hz, 1H), 2.21 (s, 3H), 1.98 (d, J=13.0 Hz, 1H), 1.87 (td, J=12.8, 5.0 Hz, 1H), 1.18-1.07 (m, 6H).

Examples 343: 2-(1,1-difluoroethyl)-N-(3-((4a,10b-trans)6-ethyl-10b-methyl-5-oxo-2,4,4a,5,6,10b-hexahydro-1H-pyrano[3,4-c][1,8]naphthyridin-9-yl)-4-methylphenyl)isonicotinamide (Single Enantiomer, "Peak 1") and 344: 2-(1,1-difluoroethyl)-N-(3-((4a,10b-trans)6-ethyl-10b-methyl-5-oxo-2,4,4a,5,6,10b-hexahydro-1H-pyrano[3,4-c][1,8]naphthyridin-9-yl)-4-methylphenyl)isonicotinamide (Single Enantiomer, "Peak 2")

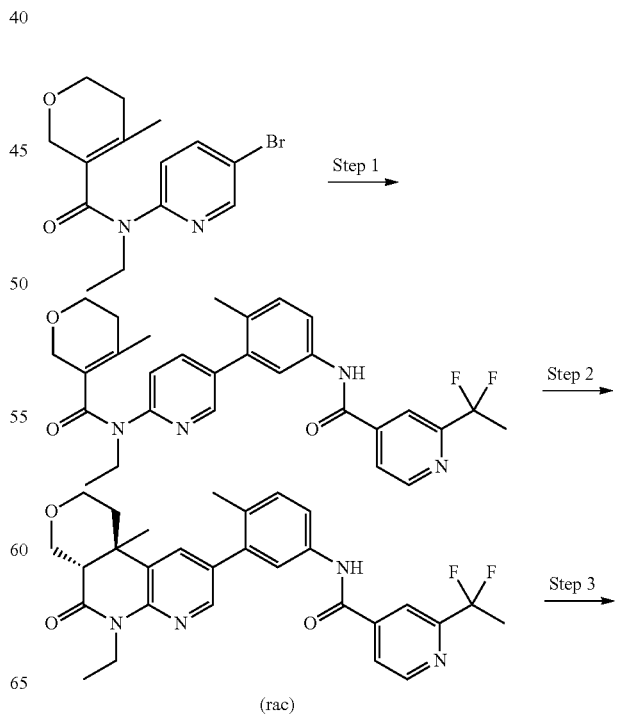

(rac)

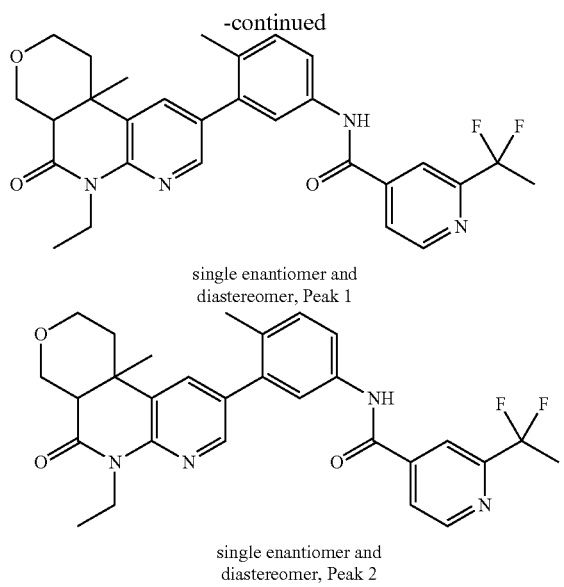

single enantiomer and
diastereomer, Peak 1 single enantiomer and
diastereomer, Peak 2

Step 1:

A vial was charged with N-(5-bromopyridin-2-yl)-N-ethyl-4-methyl-5,6-dihydro-2H-pyran-3-carboxamide (1.0 equiv) and 2-(1,1-difluoroethyl)-N-(4-methyl-3-(4,4,5,5-tetramethyl-1,3,2-dioxaborolan-2-yl)phenyl)isonicotinamide (1.05 equiv). THF (0.1 M) and $K_3PO_4$ (0.5 M aq, 2.0 equiv) were added, and the vial was purged with $N_2$. XPhos Pd G2 (0.05 equiv) and XPhos (0.05 equiv) were added, and the reaction was heated at 50° C. for 1 h. The reaction was poured onto water and extracted twice with EtOAc The combined organics were washed with brine, dried over $MgSO_4$, filtered, and concentrated. The residue was purified by flash column chromatography over silica gel (heptane and 0-100% EtOAc gradient) to give 2-(1,1-difluoroethyl)-N-(3-(6-(N-ethyl-4-methyl-5,6-dihydro-2H-pyran-3-carboxamido)pyridin-3-yl)-4-methylphenyl)isonicotinamide as a white solid in 94% yield. LCMS (m/z) (M+H)=521.3, Rt=1.12 min Step 2:

A solution of 2-(1,1-difluoroethyl)-N-(3-(6-(N-ethyl-4-methyl-5,6-dihydro-2H-pyran-3-carboxamido)pyridin-3-yl)-4-methylphenyl)isonicotinamide (1.0 equiv) in DMF (0.015 M) was irradiated with UVA lamps (Rayonet reactor, RPR3500 A bulbs) at RT for 10 days. The reaction was poured onto water and extracted twice with EtOAc The combined organics were washed with water and brine, dried over $MgSO_4$, filtered, and concentrated. The residue was purified by flash column chromatography over silica gel (heptane and 0-100% EtOAc gradient) to give (rac)-2-(1,1-difluoroethyl)-N-(3-((4a,10b-trans)6-ethyl-10b-methyl-5-oxo-2,4,4a,5,6,10b-hexahydro-1H-pyrano[3,4-c][1,8]naphthyridin-9-yl)-4-methylphenyl)isonicotinamide as a white solid in 38% yield. LCMS (m/z) (M+H)=525.2, Rt=1.21 min.

Step 3:

(rac)-2-(1,1-difluoroethyl)-N-(3-((4a,10b-trans)6-ethyl-10b-methyl-5-oxo-2,4,4a,5,6,10b-hexahydro-1H-pyrano[3,4-c][1,8]naphthyridin-9-yl)-4-methylphenyl)isonicotinamide was subjected to chiral SFC (IA 21×250 mm column, 35% MeOH in $CO_2$ eluent). The first eluting peak afforded 2-(1,1-difluoroethyl)-N-(3-((4a,10b-trans)6-ethyl-10b-methyl-5-oxo-2,4,4a,5,6,10b-hexahydro-1H-pyrano[3,4-c][1,8]naphthyridin-9-yl)-4-methylphenyl)isonicotinamide "Peak 1" as a white solid in 31% yield. The second peak afforded 2-(1,1-difluoroethyl)-N-(3-((4a,10b-trans)6-ethyl-10b-methyl-5-oxo-2,4,4a,5,6,10b-hexahydro-1H-pyrano[3,4-c][1,8]naphthyridin-9-yl)-4-methylphenyl)isonicotinamide "Peak 2" as a white solid in 33% yield. LCMS and NMR data for each enantiomer were identical. LCMS (m/z) (M+H)=525.2, Rt=1.21 min. $^1$H NMR (400 MHz, Methanol-d4) δ 8.86-8.78 (m, 1H), 8.30 (d, J=2.2 Hz, 1H), 8.23-8.15 (m, 1H), 7.99 (dd, J=5.1, 1.5 Hz, 1H), 7.72-7.63 (m, 3H), 7.41-7.34 (m, 1H), 4.35 (dq, J=13.9, 7.0 Hz, 1H), 4.24-4.10 (m, 2H), 4.00 (dd, J=12.0, 4.0 Hz, 1H), 3.82 (td, J=12.3, 2.3 Hz, 1H), 3.78-3.70 (m, 1H), 2.82 (dd, J=11.1, 4.5 Hz, 1H), 2.33 (s, 3H), 2.16-1.93 (m, 5H), 1.29-1.21 (m, 6H).

Examples 345 ("Peak 1") and 346 ("Peak 3")
enantiomers of N-(3-((4a,10b-trans)-6-ethyl-10b-methyl-5-oxo-1,4,4a,5,6,10b-hexahydro-2H-pyrano[3,4-c][1,8]naphthyridin-9-yl)-4-methylphenyl)-5-(trifluoromethyl)nicotinamide

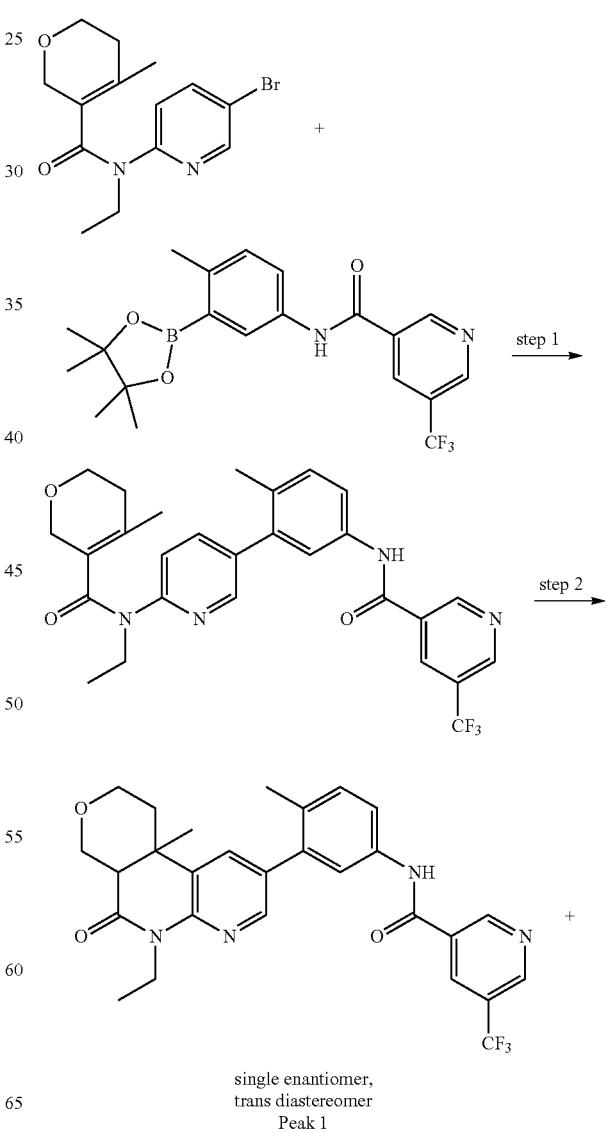

single enantiomer,
trans diastereomer
Peak 1

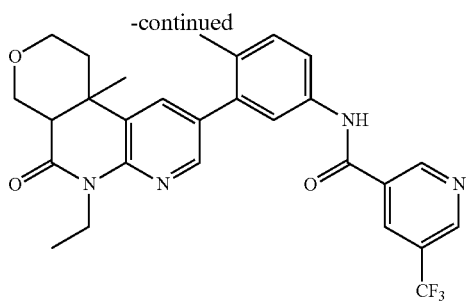

single enantiomer,
trans diastereomer
Peak 3

Step 1:

To a mixture of N-(5-bromopyridin-2-yl)-N-ethyl-4-methyl-5,6-dihydro-2H-pyran-3-carboxamide (1 equiv.), N-(4-methyl-3-(4,4,5,5-tetramethyl-1,3,2-dioxaborolan-2-yl)phenyl)-5-(trifluoromethyl)nicotinamide (1.05 equiv.), XPhos Pd G2 (5 mol %) and XPhos (5 mol %) under an atmosphere of nitrogen was added degassed THF (0.14 M) and 0.5 M aq. $K_3PO_4$ (2 equiv.), and the reaction mixture was heated to 50° C. and stirred for 2 hours. The reaction was poured onto water and extracted twice with EtOAc. The combined organics were washed with brine, dried over MgSO4, filtered, and concentrated in vacuo. The residue was purified by flash column chromatography over silica (heptane with 0-90% ethyl acetate gradient) to afford N-(3-(6-(N-ethyl-4-methyl-5,6-dihydro-2H-pyran-3-carboxamido)pyridin-3-yl)-4-methylphenyl)-5-(trifluoromethyl)nicotinamide as a white solid in 92% yield. LCMS (m/z) (M+H)=525.2, Rt=1.05 min. $^1$H NMR (400 MHz, METHANOL-d4) δ ppm 9.34 (d, J=2.02 Hz, 1H), 9.07 (d, J=1.26 Hz, 1H), 8.66 (s, 1H), 8.47 (d, J=2.53 Hz, 1H), 7.87 (dd, J=8.21, 2.40 Hz, 1H), 7.69 (dq, J=4.42, 2.23 Hz, 2H), 7.41 (d, J=8.34 Hz, 1H), 7.32-7.39 (m, 1H), 4.21 (br d, J=2.02 Hz, 2H), 4.02 (q, J=7.07 Hz, 2H), 3.62 (t, J=5.56 Hz, 2H), 2.26 (s, 3H), 1.89 (br s, 2H), 1.58 (s, 3H), 1.22-1.26 (m, 3H).

Step 2:

A solution of N-(3-(6-ethyl-10b-methyl-5-oxo-2,4,4a,5,6,10b-hexahydro-1H-pyrano[3,4-c][1,8]naphthyridin-9-yl)-4-methylphenyl)-5-(trifluoromethyl)nicotinamide in DMF (0.05 M) was divided between 2 quartz vials and irradiated with a UVB lamp (Rayonet reactor, RPR3000 A bulbs) at room temperature for 17 hours. The reaction was diluted with ethyl acetate, washed with water, brine, dried over MgSO4, filtered, and concentrated in vacuo. The residue was purified by chiral SFC (IX 30×250 mm 5 μM, 40% isopropanol in $CO_2$ eluent). The first eluted peak afforded a single enantiomer of N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-5-(trifluoromethyl)nicotinamide "Peak 1" as a white solid in 30% yield. The third eluted peak afforded a single enantiomer of N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-5-(trifluoromethyl)nicotinamide "Peak 3" as a white solid in 29% yield. The $^1$H NMR and LCMS data matched for the two isolated enantiomers. LCMS (m/z) (M+H)=525.3, Rt=1.14. $^1$H NMR (400 MHz, DMSO-d6) δ ppm 10.65 (s, 1H), 9.38 (d, J=1.52 Hz, 1H), 9.19 (d, J=1.26 Hz, 1H), 8.69 (s, 1H), 8.30 (d, J=2.27 Hz, 1H), 7.67-7.77 (m, 2H), 7.63 (d, J=2.27 Hz, 1H), 7.36 (d, J=8.34 Hz, 1H), 4.21 (dq, J=13.29, 6.85 Hz, 1H), 3.96-4.10 (m, 2H), 3.88 (br dd, J=11.75, 4.17 Hz, 1H), 3.54-3.79 (m, 2H), 2.79 (dd, J=11.12, 4.55 Hz, 1H), 2.28 (s, 3H), 2.11 (br d, J=12.88 Hz, 1H), 1.82 (td, J=12.69, 4.67 Hz, 1H), 1.10-1.19 (m, 6H).

The following were prepared using the same methods as described for Example 346 using the appropriate starting materials.

TABLE XX

| Ex. | Structure | Name | Physical Data |
| --- | --- | --- | --- |
| 347 | single enantiomer Peak 3 | N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-3-fluoro-2-(trifluoromethyl)isonicotinamide | $^1$H NMR (400 MHz, DMSO-d6) δ ppm 10.87 (s, 1 H), 8.76 (d, J = 4.80 Hz, 1 H), 8.29 (d, J = 2.02 Hz, 1 H), 8.10 (t, J = 4.80 Hz, 1 H), 7.57-7.70 (m, 3 H), 7.30-7.42 (m, 1 H), 4.21 (dq, J = 13.29, 6.77 Hz, 1 H), 3.96-4.06 (m, 2 H), 3.87 (br dd, J = 11.62, 4.55 Hz, 1 H), 3.56-3.74 (m, 2 H), 2.79 (dd, J = 10.99, 4.67 Hz, 1 H), 2.27 (s, 3 H), 2.11 (br d, J = 13.14 Hz, 1 H), 1.81 (td, J = 12.82, 4.93 Hz, 1 H), 1.10-1.19 (m, 6 H). LCMS (m/z) (M + H) = 542.8, Rt = 1.17 min. |
| 348 | single enantiomer Peak 1 | N-(3-((4a,10b-trans)-6-ethyl-10b-methyl-5-oxo-2,4,4a,5,6,10b-hexahydro-1H-pyrano[3,4-c][1,8]naphthyridin-9-yl)-4-methylphenyl)-3-fluoro-2-(trifluoromethyl)isonicotinamide | $^1$H NMR (400 MHz, DMSO-d6) δ ppm 10.87 (s, 1 H), 8.76 (d, J = 4.55 Hz, 1 H), 8.29 (d, J = 2.02 Hz, 1 H), 8.10 (t, J = 4.93 Hz, 1H), 7.58-7.67 (m, 3 H), 7.29-7.44 (m, 1 H), 4.21 (dq, J = 13.17, 6.73 Hz, 1 H), 3.96-4.11 (m, 2 H), 3.87 (br dd, J = 12.00, 4.17 Hz, 1 H), 3.55-3.74 (m, 2 H), 2.79 (dd, J = 10.86, 4.55 Hz, 1 H), 2.27 (s, 3 H), 2.11 (br d, J = 12.88 Hz, 1 H), 1.81 (td, J = 12.88, 5.05 Hz, 1 H), 1.10-1.19 (m, 6 H). LCMS (m/z) (M + H) = 543.2, Rt = 1.18 min. |

TABLE XX-continued

| Ex. | Structure | Name | Physical Data |
|---|---|---|---|
| 349 | 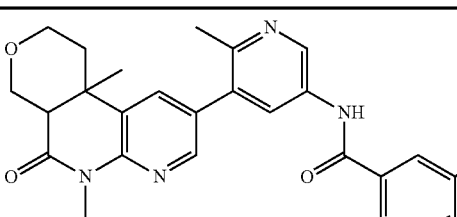<br>single enantiomer<br>Peak 1 | N-(5-((4a,10b-trans)-6-ethyl-10b-methyl-5-oxo-2,4,4a,5,6,10b-hexahydro-1H-pyrano[3,4-c][1,8]naphthyridin-9-yl)-6-methylpyridin-3-yl)-3-(trifluoromethyl)benzamide | $^1$H NMR (400 MHz, Methanol-$d_4$) δ 8.84 (d, J = 2.5 Hz, 1H), 8.34 (d, J = 2.0 Hz, 1H), 8.31-8.29 (m, 1H), 8.24 (d, J = 7.9 Hz, 1H), 8.18 (d, J = 2.5 Hz, 1H), 7.92 (d, J = 7.9 Hz, 1H), 7.77-7.73 (m, 1H), 7.70 (d, J = 2.5 Hz, 1H), 4.39-4.29 (m, 1H), 4.21-4.09 (m, 2H), 3.99 (dd, J = 11.7 Hz, 1H), 3.86-3.69 (m, 2H), 2.80 (dd, J = 11.1, 4.5 Hz, 1H), 2.52 (s, 3H), 2.10 (d, J = 13.0 Hz, 1H), 1.98 (td, J = 12.8, 5.0 Hz, 1H), 1.26-1.14 (m, 6H). LC-MS (m/z) (M + H) = 525.5; Rt = 2.15 min. |

Examples 351: 2-(1,1-difluoroethyl)-N-((5a,11b-trans)-3-(7-(2-hydroxyethyl)-11b-methyl-6-oxo-1,2,4,5,5a,6,7,11b-octahydrooxepino[4,5-c][1,8]naphthyridin-10-yl)-4-methylphenyl) isonicotinamide (Single Enantiomer, "Peak 1") and 352: 2-(1,1-difluoroethyl)-N-((5a,11b-trans)-3-(7-(2-hydroxyethyl)-11b-methyl-6-oxo-1,2,4,5,5a,6,7,11b-octahydrooxepino[4,5-c][1,8]naphthyridin-10-yl)-4-methylphenyl)isonicotinamide (Single Enantiomer, "Peak 2")

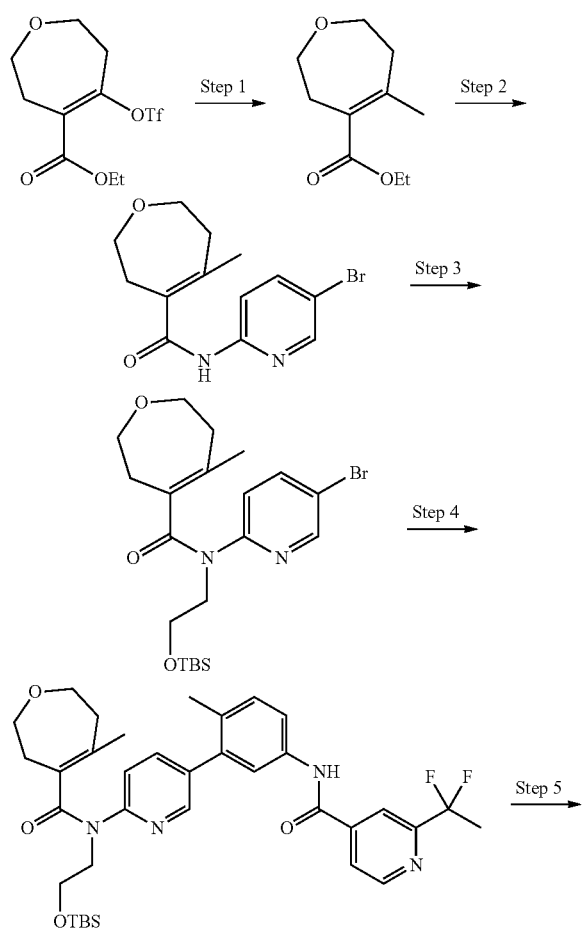

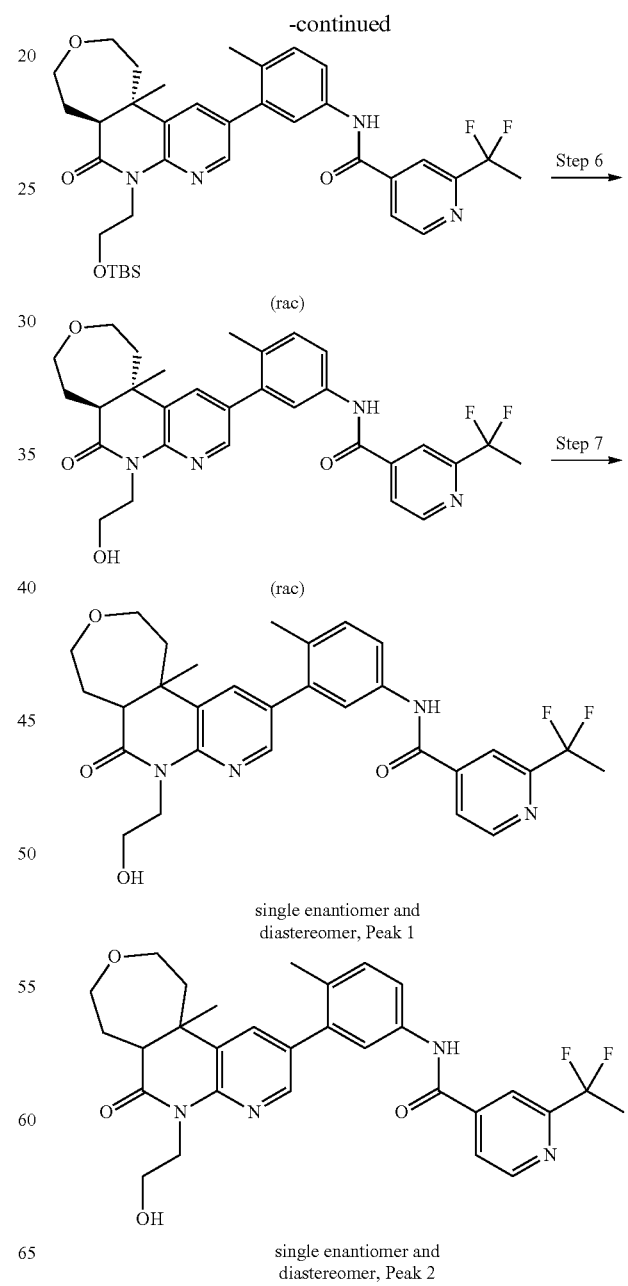

Step 1:

A stirred solution of ethyl 5-(((trifluoromethyl)sulfonyl)oxy)-2,3,6,7-tetrahydrooxepine-4-carboxylate (1.0 equiv) in THF (0.1 M) was degassed with $N_2$; Pd(PPh$_3$)$_4$ (0.05 equiv) was then added, and the mixture was cooled to 0° C. Me$_2$Zn (2 M in heptane, 2.0 equiv) was subsequently added, and the reaction was allowed to warm to RT and stirred for 3 h. The reaction was quenched with brine, stirred vigorously for 5 min, and then extracted twice with ethyl acetate. The combined organics were washed with brine, dried over magnesium sulfate, filtered, and concentrated. The residue was purified by flash column chromatography over silica gel (heptane and 0-30% EtOAc gradient) to give ethyl 5-methyl-2,3,6,7-tetrahydrooxepine-4-carboxylate as a colorless oil in quantitative yield. $^1$H NMR (400 MHz, Chloroform-d) δ 4.21 (q, J=7.1 Hz, 2H), 3.69 (ddd, J=6.4, 3.0, 1.8 Hz, 4H), 2.75-2.63 (m, 2H), 2.54-2.42 (m, 2H), 2.08 (s, 3H), 1.32 (t, J=7.1 Hz, 3H).

Step 2:

A syringe was charged with a solution "Feed A", prepared of ethyl 5-methyl-2,3,6,7-tetrahydrooxepine-4-carboxylate (1.0 equiv) and 2-amino-5-bromopyridine (1.5 equiv) in THF (0.3 M). A second syringe "Feed B" was charged with LiHMDS (1 M in THF, 1.8 equiv). These syringes were loaded onto separate syringe pumps and simultaneously injected through a 500 μL PFA flow reactor submerged in a 65° C. oil bath at a flow rate of 65 μL/min for Feed A and 35 μL/min for Feed B. The eluting reaction mixture was directly quenched into saturated aqueous NH$_4$Cl. The biphasic mixture was extracted three times with ethyl acetate. The combined organics were sequentially washed with 1 M aq HCl, water, saturated aqueous NaHCO$_3$ and brine, dried over magnesium sulfate, filtered, and concentrated. The residue was adsorbed purified by flash column chromatography over silica gel (heptane and 0-75% EtOAc) to provide N-(5-bromopyridin-2-yl)-5-methyl-2,3,6,7-tetrahydrooxepine-4-carboxamide as a white solid in 33% yield. LCMS (m/z) (M+H)=311.0/313.0, Rt=0.88 min min. $^1$H NMR (400 MHz, Chloroform-d) δ 8.36-8.32 (m, 1H), 8.24 (d, J=8.9 Hz, 1H), 7.94 (d, J=9.1 Hz, 1H), 7.85 (dd, J=8.9, 2.4 Hz, 1H), 3.79-3.75 (m, 2H), 3.74-3.70 (m, 2H), 2.70-2.63 (m, 2H), 2.52-2.43 (m, 2H), 1.97 (s, 3H).

Step 3:

To a stirred solution of N-(5-bromopyridin-2-yl)-5-methyl-2,3,6,7-tetrahydrooxepine-4-carboxamide (1.0 equiv) in DMF (0.1 M) at 25° C. was added NaH (60% in mineral oil, 3.5 equiv). The mixture was stirred for 10 min followed by the addition of (2-bromoethoxy)-tert-butyldimethylsilane (3.0 equiv) and NaI (0.3 equiv) and the reaction was stirred overnight at RT. The mixture was poured onto water and extracted three times with ethyl acetate. The combined organics were washed with water and brine, dried over magnesium sulfate, filtered, and concentrated. The residue was and purified by flash column chromatography over silica gel (heptane and 0-70% EtOAc gradient) to give N-(5-bromopyridin-2-yl)-N-(2-((tert-butyldimethylsilyl)oxy)ethyl)-5-methyl-2,3,6,7-tetrahydrooxepine-4-carboxamide as a colorless oil in 46% yield. LCMS (m/z) (M+H)=325.0/327.0, Rt=0.92 min.

Step 4:

A vial was charged with N-(5-bromopyridin-2-yl)-N-(2-((tert-butyldimethylsilyl)oxy)ethyl)-5-methyl-2,3,6,7-tetrahydrooxepine-4-carboxamide (1.0 equiv) and 2-(1,1-difluoroethyl)-N-(4-methyl-3-(4,4,5,5-tetramethyl-1,3,2-dioxaborolan-2-yl)phenyl)isonicotinamide (1.05 equiv). THF (0.1 M) and K$_3$PO$_4$ (0.5 M aq, 2.0 equiv) were added, and the vial was purged with N$_2$. XPhos Pd G2 (0.05 equiv) and XPhos (0.05 equiv) were added, and the reaction was heated at 50° C. for 1 h. The reaction was poured onto water and extracted twice with EtOAc The combined organics were washed with brine, dried over MgSO$_4$, filtered, and concentrated. The residue was purified by flash column chromatography over silica gel (heptane and 0-80% EtOAc gradient) to give N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-2-(1,1-difluoroethyl)isonicotinamide as a white foam in 72% yield. LCMS (m/z) (M+H)=665.3, Rt=1.50 min.

Step 5:

A solution of N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-2-(1,1-difluoroethyl)isonicotinamide (1.0 equiv) in DMF (0.03 M) was charged to a quartz vial and irradiated with UVB lamps (Rayonet reactor, RPR3000 A bulbs) at RT overnight. The reaction was poured onto water and extracted twice with EtOAc The combined organics were washed with water and brine, dried over MgSO$_4$, filtered, and concentrated. The so-obtained residue was used as (rac)-N-(3-(7-((5a,11b-trans)-2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-4-methylphenyl)-2-(1,1-difluoroethyl)isonicotinamide without further purification. LCMS (m/z) (M+H)=665.3, Rt=1.61 min.

Step 6:

To a stirred solution of (rac)-N-(3-(7-((5a,11b-trans)-2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-4-methylphenyl)-2-(1,1-difluoroethyl)isonicotinamide (1.0 equiv) in DCM (0.2 M) at 25° C. was added TfOH (1.5 equiv) and the reaction was stirred for 1 h. The mixture was partitioned between DCM and saturated aqueous NaHCO$_3$ and extracted three times with DCM. The combined organics were dried over magnesium sulfate, filtered, and concentrated. The residue was purified by flash column chromatography over silica gel (heptane and 0-100% EtOAc gradient) to give (rac)-N-(3-(7-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)isonicotinamide as a white foam in 94% yield. LCMS (m/z) (M+H)=551.2, Rt=1.06 min.

Step 7:

(rac)-N-(3-(7-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)isonicotinamide was subjected to chiral SFC (IA 21×250 mm column, 30% MeOH in CO$_2$ eluent). The first eluting peak afforded N-(3-(7-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)isonicotinamide "Peak 1" as a white solid in 31% yield. The second peak afforded N-(3-(7-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)isonicotinamide "Peak 2" as a white solid in 35% yield. LCMS and NMR data for each enantiomer were identical. LCMS (m/z) (M+H)=551.2, Rt=1.06 min. $^1$H NMR (400 MHz, Methanol-d4) δ 8.80 (d, J=5.0 Hz, 1H), 8.25 (d, J=2.0 Hz, 1H), 8.18 (s, 1H), 7.96 (d, J=3.8 Hz, 1H), 7.76 (d, J=2.0 Hz, 1H), 7.66 (dd, J=6.0, 2.3 Hz, 2H), 7.38-7.29 (m, 1H), 4.54 (dt, J=12.2, 6.0 Hz, 1H), 4.23 (dt, J=13.2, 6.5 Hz, 1H), 3.99-3.93 (m, 1H), 3.90 (dt, J=8.3, 4.5 Hz, 1H), 3.81 (ddt, J=12.6, 6.2, 3.5 Hz, 3H), 3.68 (td, J=12.0, 3.2 Hz, 1H), 2.87 (dd, J=10.7, 1.7 Hz, 1H), 2.62-2.53 (m, 1H), 2.28 (d, J=6.0 Hz, 5H), 2.03 (t, J=18.7 Hz, 4H), 1.18 (s, 3H).

Example 353: 3-fluoro-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide (Single Enantiomer, "Peak 1") and Example 354: 3-fluoro-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide (Single Enantiomer, "Peak 2")

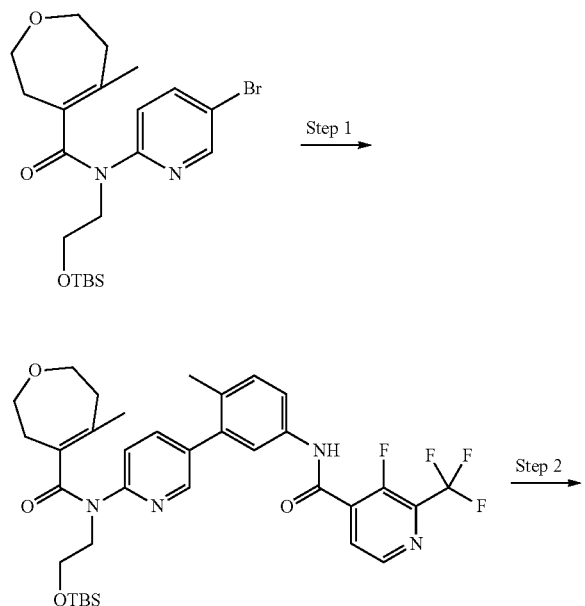

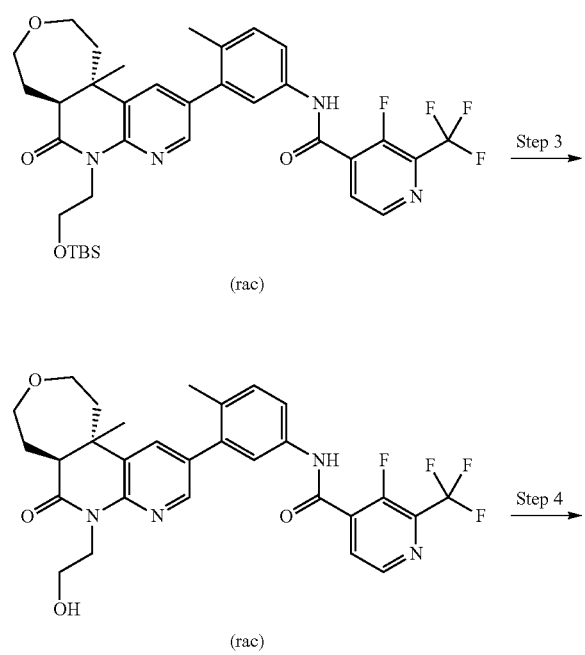

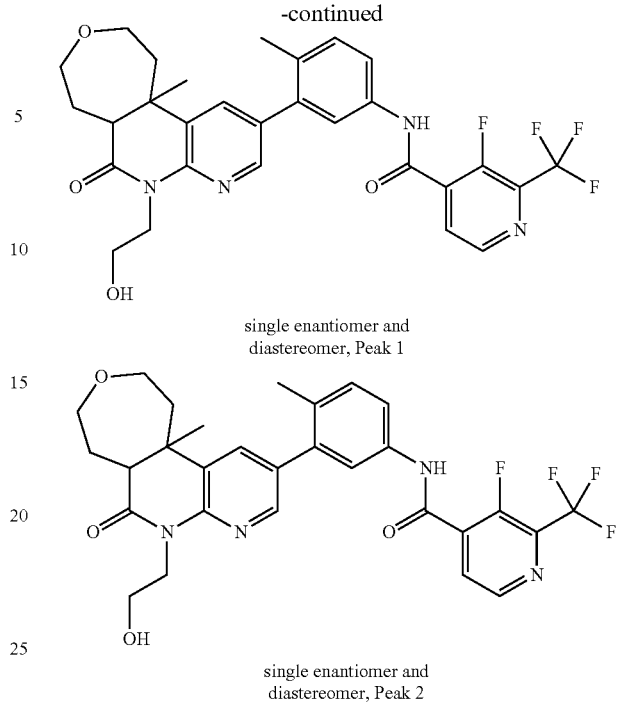

single enantiomer and diastereomer, Peak 1 single enantiomer and diastereomer, Peak 2

Step 1:

A vial was charged with N-(5-bromopyridin-2-yl)-N-(2-((tert-butyldimethylsilyl)oxy)ethyl)-5-methyl-2,3,6,7-tetrahydrooxepine-4-carboxamide (1.0 equiv) and N-(5-bromopyridin-2-yl)-N-(2-((tert-butyldimethylsilyl)oxy)ethyl)-5-methyl-2,3,6,7-tetrahydrooxepine-4-carboxamide (1.05 equiv). THF (0.1 M) and K$_3$PO$_4$ (0.5 M aq, 2.0 equiv) were added, and the vial was purged with N$_2$. XPhos Pd G2 (0.05 equiv) and XPhos (0.05 equiv) were added, and the reaction was heated at 50° C. for 1 h. The reaction was poured onto water and extracted twice with EtOAc The combined organics were washed with brine, dried over MgSO$_4$, filtered, and concentrated. The residue was purified by flash column chromatography over silica gel (heptane and 0-100% EtOAc gradient) to give N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-3-fluoro-2-(trifluoromethyl)isonicotinamide as a pale yellow foam in 80% yield. LCMS (m/z) (M+H)=687.3, Rt=1.42 min.

Step 2:

A solution of N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-3-fluoro-2-(trifluoromethyl)isonicotinamide (1.0 equiv) in DMF (0.03 M) was charged to a quartz vial and irradiated with UVB lamps (Rayonet reactor, RPR3000 A bulbs) at RT overnight. The reaction was poured onto water and extracted twice with EtOAc The combined organics were washed with water and brine, dried over MgSO$_4$, filtered, and concentrated. The so-obtained residue was used as (rac)-N-(3-(7-((5a,10b-trans)-2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-4-methylphenyl)-3-fluoro-2-(trifluoromethyl)isonicotinamide without further purification. LCMS (m/z) (M+H)=687.2, Rt=1.42 min.

Step 3:

To a stirred solution of (rac)-N-(3-(7-((5a,10b-trans)-2-((tert-butyldimethylsilyl)oxy)ethyl)-11b-methyl-6-oxo-1,2, 4,5,5a,6,7,11b-octahydrooxepino[4,5-c][1,8]naphthyridin-10-yl)-4-methylphenyl)-3-fluoro-2-(trifluoromethyl)isonicotinamide (1.0 equiv) in DCM (0.1 M) at 25° C. was added TfOH (1.5 equiv) and the reaction was stirred for 1 h. The mixture was partitioned between DCM and saturated aqueous NaHCO₃ and extracted three times with DCM. The combined organics were dried over magnesium sulfate, filtered, and concentrated. The residue was purified by flash column chromatography over silica gel (heptane and 0-100% EtOAc gradient) to give (rac)-3-fluoro-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide as a pale yellow foam in 73% yield. LCMS (m/z) (M+H)=573.2, Rt=1.04 min.

Step 4:
(rac)-3-fluoro-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide was subjected to chiral SFC (LC-2 21×250 mm column, 45% MeOH in CO₂ eluent). The first eluting peak afforded 3-fluoro-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide "Peak 1" as a white solid in 36% yield. The second peak afforded 3-fluoro-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide "Peak 2" as a white solid in 34% yield. LCMS and NMR data for each enantiomer were identical. LCMS (m/z) (M+H)=573.2, Rt=1.04 min. ¹H NMR (400 MHz, Methanol-d4) δ 8.65 (d, J=4.7 Hz, 1H), 8.24 (d, J=2.1 Hz, 1H), 7.96 (t, J=4.8 Hz, 1H), 7.75 (d, J=2.1 Hz, 1H), 7.61 (dd, J=5.6, 2.3 Hz, 2H), 7.37-7.30 (m, 1H), 4.54 (dt, J=13.0, 6.0 Hz, 1H), 4.23 (dt, J=13.2, 6.6 Hz, 1H), 3.96 (ddd, J=11.6, 4.6, 2.5 Hz, 1H), 3.90 (dt, J=8.3, 4.5 Hz, 1H), 3.81 (ddt, J=12.6, 6.2, 3.6 Hz, 3H), 3.68 (td, J=12.0, 3.3 Hz, 1H), 2.87 (dd, J=10.7, 1.9 Hz, 1H), 2.58 (dt, J=13.1, 2.3 Hz, 1H), 2.28 (d, J=5.7 Hz, 5H), 2.10-1.94 (m, 1H), 1.18 (s, 3H).

Examples 355 and 356: N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide (single enantiomer, "Peak 1") (355) and N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide (Single Enantiomer, "Peak 2") (356)

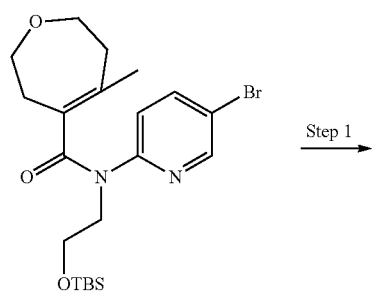

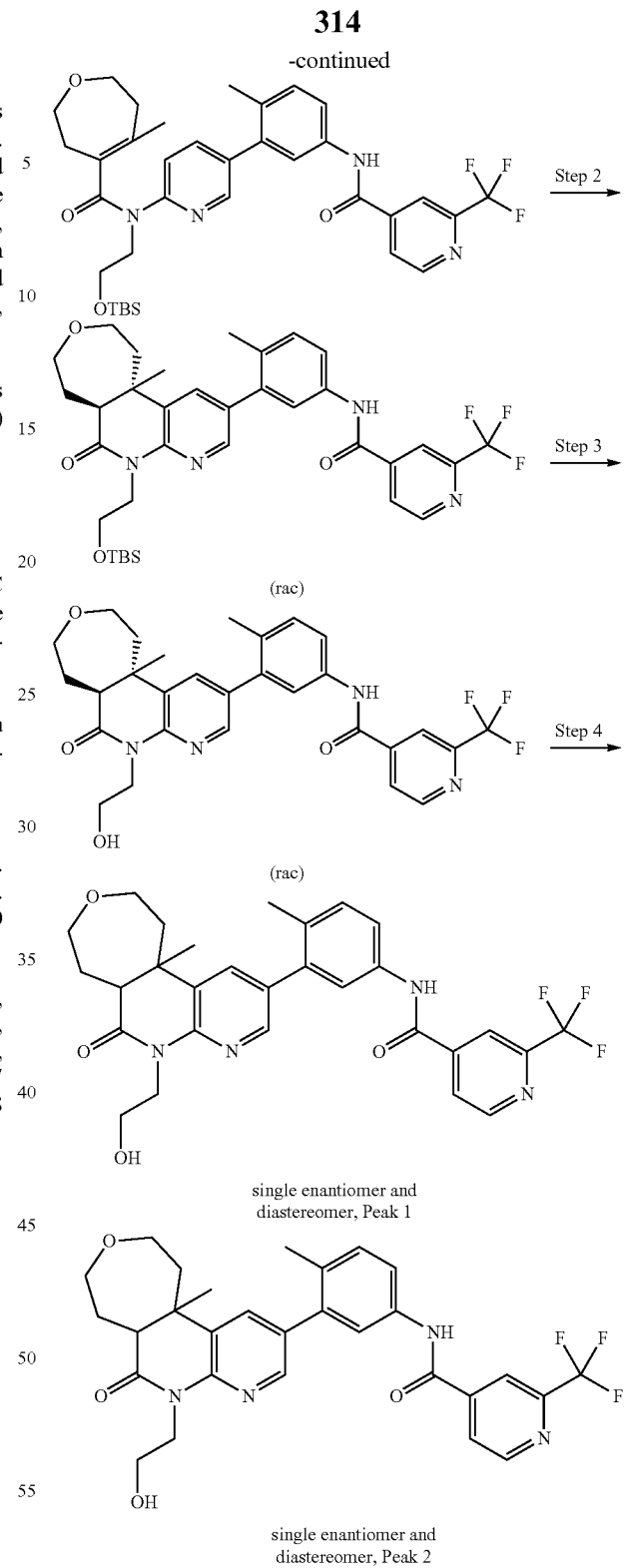

Step 1:
N-(5-bromopyridin-2-yl)-N-(2-((tert-butyldimethylsilyl)oxy)ethyl)-5-methyl-2,3,6,7-tetrahydrooxepine-4-carboxamide (1 equiv) and N-(4-methyl-3-(4,4,5,5-tetramethyl-1,3,2-dioxaborolan-2-yl)phenyl)-2-(trifluoromethyl)isonicotinamide (1.1 equiv) were dissolved into degassed dioxane (0.089 M) along with degassed potassium phosphate (0.5M aq, 2 equiv) in a vial with a pressure relieve screw cap. To this was added XPhos Pd G2 (0.05 equiv) and XPhos (0.05 equiv) and then the reaction was heated closed to 80° C. with stirring. After 16 hr the reaction was diluted with EtOAc and treated with granular anhydrous Na$_2$SO$_4$. After decantation volatiles were removed and the residue was purified by flash column chromatography over silica gel (heptane with 0-80% ethyl acetate gradient) to yield a light amber oily N-(3-(6-(N-(2-((tert-butyldimethylsilyl)oxy) ethyl)-5-methyl-2,3,6,7-tetrahydrooxepine-4-carboxamido) pyridin-3-yl)-4-methylphenyl)-2-(trifluoromethyl)isonicotinamide in 84% yield. LCMS (m/z) (M+H)=669.4, R$_t$=1.87 min.

Step 2:
N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-2-(trifluoromethyl)isonicotinamide (1 equiv) was dissolved into anhydrous DMF in a quartz test tube capped with a rubber septa. The reaction was irradiated with UVB lamps (Rayonet reactor, RPR3000 A bulbs) at RT overnight. After 16 hr the reaction was poured into H$_2$O and extracted three times with EtOAc. Organics were combined, washed with brine and dried over anhydrous granular Na$_2$SO$_4$. After filtration and evaporation the residue (rac)-N-(3-((5a,11b-trans)-7-(2-((tert-butyldimethylsilyl)oxy) ethyl)-11b-methyl-6-oxo-1,2,4,5,5a,6,7,11b-octahydrooxepino[4,5-c][1,8]naphthyridin-10-yl)-4-methylphenyl)-2-(trifluoromethyl) isonicotinamide was obtained in 95% yield. LCMS (m/z) (M+H)=669.5, R$_t$=1.99 min.

Step 3:
(rac)-N-(3-((5 a,11b-trans)-7-(2-((tert-butyldimethylsilyl) oxy)ethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide (1 equiv) was dissolved into MeOH (0.031M) with HCl in methanol (1.25M, 5 equiv). After 30 minutes stirring at RT the reaction was pH adjusted to ~8 with saturated aqueous NaHCO$_3$ and the volatiles removed. The residue was partitioned between DCM and H2O. Organics were separated, washed with brine, and dried over solid granular Na$_2$SO$_4$. After filtration the volatiles were removed to yield (rac)-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl)isonicotinamide in 83% yield. LCMS (m/z) (M+H)=555.1, R$_t$=1.03 min.

Step 4:
(rac)-N-(3-((5a,11b-trans)-7-(2-hydroxyethyl)-11b-methyl-6-oxo-1,2,4,5,5a,6,7,11b-octahydrooxepino[4,5-c] [1,8]naphthyridin-10-yl)-4-methylphenyl)-2-(trifluoromethyl) isonicotinamide was subjected to chiral SFC (Chiralpak AD-H 21×250 mm column, 25% MeOH in CO$_2$ eluent). The first eluting peak afforded N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-2-(trifluoromethyl) isonicotinamide "Peak 1" as a white powder in 29.3% yield. The second eluting peak afforded N-(3-((5a,11b-trans)-7-(2-hydroxyethyl)-11b-methyl-6-oxo-1,2,4,5,5a,6,7,11b-octahydrooxepino[4,5-c] [1,8]naphthyridin-10-yl)-4-methylphenyl)-2-(trifluoromethyl) isonicotinamide "Peak 2" as a white powder in 25.7% yield. LCMS and NMR data for each enantiomer were identical. LCMS (m/z) (M+H)=555.2202, Rt=3.43 min. $^1$H NMR (400 MHz, Methanol-d4) δ 8.85 (d, J=5.0 Hz, 1H), 8.25 (s, 1H), 8.19 (d, J=1.9 Hz, 1H), 8.07 (d, J=4.7 Hz, 1H), 7.70 (d, J=1.9 Hz, 1H), 7.60 (dd, J=5.8, 2.2 Hz, 2H), 7.28 (d, J=9.0 Hz, 1H), 4.48 (dt, J=12.4, 5.9 Hz, 1H), 4.18 (dt, J=13.1, 6.5 Hz, 1H), 3.95-3.80 (m, 2H), 3.75 (dtt, J=10.8, 7.6, 4.1 Hz, 3H), 3.62 (td, J=11.9, 3.2 Hz, 1H), 2.82-2.79 (m, 1H), 2.58-2.48 (m, 1H), 2.27-2.10 (m, 5H), 1.98 (dtd, J=15.8, 11.9, 4.8 Hz, 1H), 1.14 (s, 3H).

Examples 357 and 358: N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-5-(trifluoromethyl)nicotinamide (single enantiomer, "Peak 1") (357) and N-(3-((5a, 11b-trans)-7-(2-hydroxyethyl)-11b-methyl-6-oxo-1, 2,4,5,5a,6,7,11b-octahydrooxepino[4,5-c][1,8]naphthyridin-10-yl)-4-methylphenyl)-5-(trifluoromethyl) nicotinamide (Single Enantiomer, "Peak 2") (358)

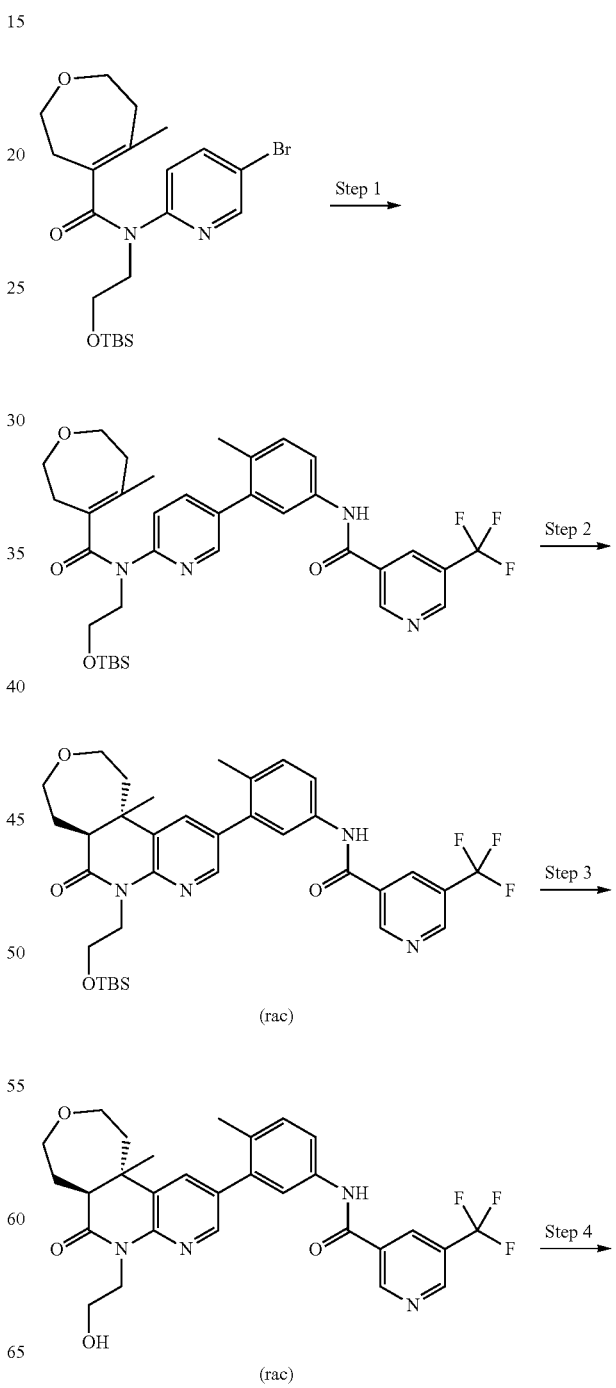

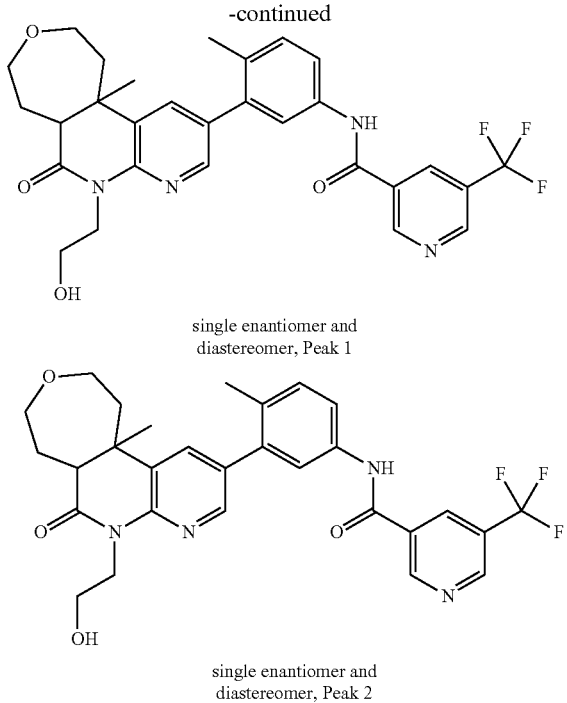

single enantiomer and diastereomer, Peak 1 single enantiomer and diastereomer, Peak 2

Step 1:

N-(5-bromopyridin-2-yl)-N-(2-((tert-butyldimethylsilyl)oxy)ethyl)-5-methyl-2,3,6,7-tetrahydrooxepine-4-carboxamide (105 mg, 0.224 mmol) and N-(4-methyl-3-(4,4,5,5-tetramethyl-1,3,2-dioxaborolan-2-yl)phenyl)-5-(trifluoromethyl)nicotinamide (1 equiv) were dissolved into pre-degassed dioxane (0.089 M) along with degassed potassium phosphate (0.5M aq, 2 equiv) in a vial with a pressure relieve screw cap. To this was added XPhos Pd G2 (0.05 equiv) and XPhos (0.05 equiv) and then the reaction was heated closed to 80° C. with stirring. After 16 hr the reaction was diluted with EtOAc and treated with granular anhydrous Na$_2$SO$_4$. After decantation volatiles were removed the residue was purified by flash column chromatography over silica gel (heptane with 0-80% ethyl acetate gradient). Fractions containing product were combined and evaporated to yield a light amber oily N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-5-(trifluoromethyl)nicotinamide in 79% yield. LCMS (m/z) (M+H)=669.3, R$_t$=1.39 min.

Step 2:

N-(3-(6-(N-(2-((tert-butyldimethylsilyl)oxy)ethyl)-5-methyl-2,3,6,7-tetrahydrooxepine-4-carboxamido)pyridin-3-yl)-4-methylphenyl)-5-(trifluoromethyl)nicotinamide (1 equiv) was dissolved into anhydrous DMF in a quartz test tube capped with a rubber septa. The reaction was irradiated with UVB lamps (Rayonet reactor, RPR3000 A bulbs) at RT overnight. After 16 hr the reaction was poured into H$_2$O and extracted three times with EtOAc. Organics were combined, washed with brine and dried over anhydrous granular Na$_2$SO$_4$. After filtration and evaporation the residue (rac)-N-(3-((5a,11b-trans)-7-(2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-4-methylphenyl)-5-(trifluoromethyl)nicotinamide was obtained in 92% yield. LCMS (m/z) (M+H)=669.1, R$_t$=1.49 min.

Step 3:

(rac)-N-(3-((5a,11b-trans)-7-(2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-4-methylphenyl)-5-(trifluoromethyl)nicotinamide (1 equiv) was dissolved into MeOH (0.031M) with HCl in methanol (1.25M, 5 equiv). After 30 minutes stirring at RT the reaction was pH adjusted to ~8 with saturated aqueous NaHCO$_3$ and the volatiles were removed. The residue was partitioned between DCM and H$_2$O. The organics were separated, washed with brine and dried over solid granular Na$_2$SO$_4$. After filtration the volatiles were removed to yield (rac)-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-5-(trifluoromethyl) nicotinamide in 89% yield. LCMS (m/z) (M+H)=555.1, R$_t$=1.01 min.

Step 4:

(rac)-N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-5-(trifluoromethyl) nicotinamide was subjected to chiral SFC (IC 30×250 mm column, 20% MeOH and 20% isopropanol in CO$_2$ eluent). The first eluting peak afforded N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-5-(trifluoromethyl) nicotinamide "Peak 1" as a white powder in 16.5% yield. The second eluting peak afforded N-(3-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-4-methylphenyl)-5-(trifluoromethyl) nicotinamide "Peak 2" as a white powder in 14.67% yield. LCMS and NMR data for each enantiomer were identical. LCMS (m/z) (M+H)=555.2182, R$_t$=3.35 min. $^1$H NMR (400 MHz, Methanol-d4) δ 9.25 (d, J=1.7 Hz, 1H), 8.99-8.95 (m, 1H), 8.57 (s, 1H), 8.18-8.14 (m, 1H), 7.65 (dd, J=8.1, 2.1 Hz, 1H), 7.56 (dq, J=4.3, 2.2 Hz, 2H), 7.27-7.22 (m, 1H), 4.44 (dt, J=12.1, 6.0 Hz, 1H), 4.14 (dt, J=13.2, 6.5 Hz, 1H), 3.90-3.77 (m, 2H), 3.70 (dddd, J=17.3, 14.1, 6.8, 3.7 Hz, 3H), 3.63-3.53 (m, 1H), 2.77 (dd, J=10.7, 1.8 Hz, 1H), 2.49 (dd, J=15.7, 2.2 Hz, 1H), 2.23-2.14 (m, 5H), 1.94 (dq, J=8.7, 3.8 Hz, 1H), 1.09 (s, 3H).

Examples 359 and 360: N-(5-((5a,11b-trans)-7-(2-hydroxyethyl)-11b-methyl-6-oxo-1,2,4,5,5 a,6,7,11b-octahydrooxepino[4,5-c][1,8]naphthyridin-10-yl)-6-methylpyridin-3-yl)-3-(trifluoromethyl)benzamide (single enantiomer, "Peak 1") (359) and N-(5-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl)benzamide (Single enantiomer, "Peak 2") (360)

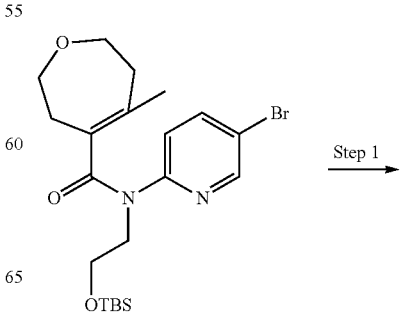

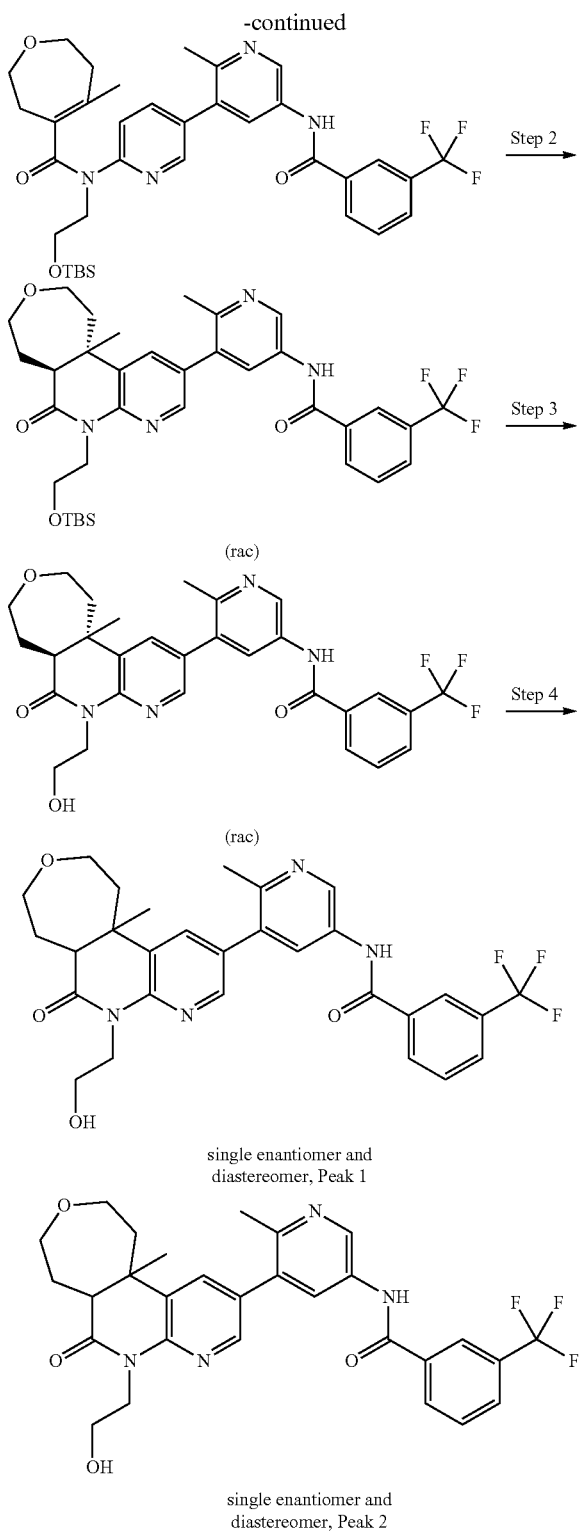

single enantiomer and diastereomer, Peak 1 single enantiomer and diastereomer, Peak 2

Step 1:
N-(5-bromopyridin-2-yl)-N-(2-((tert-butyldimethylsilyl)oxy)ethyl)-5-methyl-2,3,6,7-tetrahydrooxepine-4-carboxamide (105 mg, 0.224 mmol) and N-(6-methyl-5-(4,4,5,5-tetramethyl-1,3,2-dioxaborolan-2-yl)pyridin-3-yl)-3-(trifluoromethyl)benzamide (1 equiv) were dissolved into pre-degassed dioxane (0.089 M) along with degassed potassium phosphate (0.5M aqueous, 2 equiv) in a vial with a pressure relieve screw cap. To this was added XPhos Pd G2 (0.05 equiv) and XPhos (0.05 equiv) and then the reaction was heated closed to 80° C. with stirring. After 16 hr the reaction was diluted with EtOAc and treated with granular anhydrous Na$_2$SO$_4$. After decantation volatiles were removed the residue was purified by flash column chromatography over silica gel (heptane with 0-100% ethyl acetate gradient) to provide a light amber oily N-(2-((tert-butyldimethylsilyl)oxy)ethyl)-5-methyl-N-(2'-methyl-5'-(3-(trifluoromethyl)benzamido)-[3,3'-bipyridin]-6-yl)-2,3,6,7-tetrahydrooxepine-4-carboxamide in 66.7% yield. LCMS (m/z) (M+H)=669.2, R$_t$=1.28 min.

Step 2:
N-(2-((tert-butyldimethylsilyl)oxy)ethyl)-5-methyl-N-(2'-methyl-5'-(3-(trifluoromethyl)benzamido)-[3,3'-bipyridin]-6-yl)-2,3,6,7-tetrahydrooxepine-4-carboxamide (1 equiv) was dissolved into anhydrous DMF in a quartz test tube capped with a rubber septa. The reaction was irradiated with UVB lamps (Rayonet reactor, RPR3000 A bulbs) at RT overnight. After 16 hr the reaction was poured into H$_2$O and extracted three times with EtOAc. The organics were combined, washed with brine and dried over anhydrous granular Na$_2$SO$_4$. After filtration and evaporation the residue (rac)-N-(5-((5a,11b-trans)-7-(2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl) benzamide was obtained in 89% yield. LCMS (m/z) (M+H)=669.2, R$_t$=1.37 min.

Step 3:
N-(5-((rac)-N-(5-((5a,11b-trans)-7-(2-((tert-butyldimethylsilyl)oxy)ethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl) benzamide (1 equiv) was dissolved into MeOH (0.031M) with HCl in methanol (1.25M, 5 equiv). After 30 minutes stirring at RT the reaction was pH adjusted to ~8 with saturated aqueous NaHCO$_3$ and the volatiles removed. The residue was partitioned between DCM and H$_2$O. The organics were separated, washed with brine and dried over solid granular Na$_2$SO$_4$. After filtration the volatiles were removed to yield (rac)-N-(5-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl)benzamide in 82% yield. LCMS (m/z) (M+H)=555.07, R$_t$=0.86 min.

Step 4:
(rac)-N-(5-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl)benzamide was subjected to chiral SFC (AS-H 21×250 mm column, 20% MeOH in CO$_2$ eluent). The first eluting peak afforded N-(5-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl)benzamide "Peak 1" as a white powder in 32.1% yield. The second eluting peak afforded N-(5-((5a,11b-trans)-7-(2-hydroxyethyl)-11b-methyl-6-oxo-1,2,4,5,5a,6,7,11b-octahydrooxepino[4,5-c][1,8]naphthyridin-10-yl)-6-methylpyridin-3-yl)-3-(trifluoromethyl)benzamide "Peak 2" as a white powder in 30.6% yield. LCMS and NMR data for each enantiomer were identical. LCMS (m/z) (M+H)=555.2, R$_t$=0.87 min. $^1$H NMR (400 MHz, Methanol-d4) δ 8.84 (d, J=2.5 Hz, 1H), 8.31 (d, J=2.2 Hz, 2H), 8.24 (d, J=7.9 Hz, 1H), 8.16 (d, J=2.4 Hz, 1H), 7.92 (d, J=7.8 Hz, 1H), 7.83 (d, J=2.1 Hz, 1H), 7.75 (t, J=7.8 Hz, 1H), 4.60-4.50 (m, 1H), 4.24 (dt, J=13.1, 6.5 Hz, 1H), 4.02-3.87 (m, 2H), 3.87-3.76 (m, 3H), 3.68 (td, J=12.0, 3.4

Hz, 1H), 2.92-2.85 (m, 1H), 2.59 (dd, J=15.7, 2.2 Hz, 1H), 2.51 (s, 3H), 2.34-2.24 (m, 2H), 2.10-1.97 (m, 1H), 1.19 (s, 3H).

Example 361: N-(3-((4a'R,10b'R)-6'-ethyl-1',2',4',4a',6',10b'-hexahydrospiro[cyclopropane-1,5'-pyrano[3,4-c][1,8]naphthyridin]-9'-yl)-4-methylphenyl)-2-(trifluoromethyl)isonicotinamide

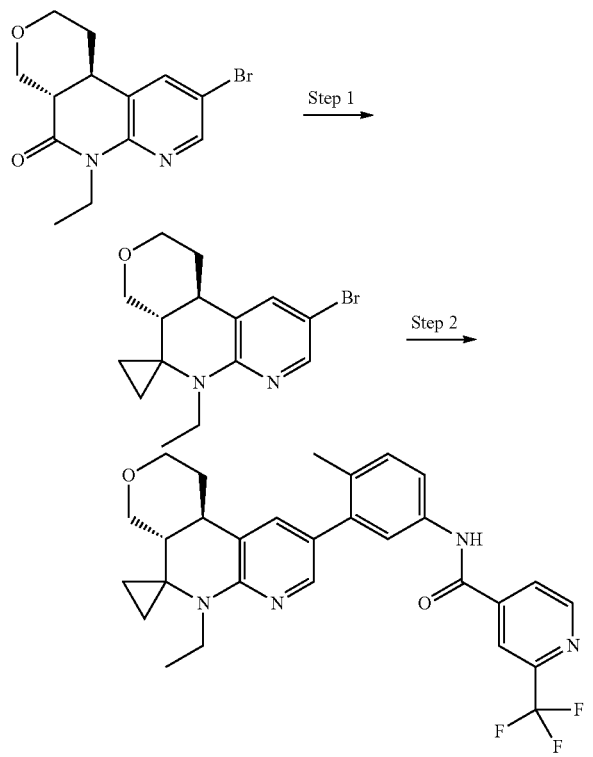

Step 1:
To a stirred solution of (4aS,10bR)-9-bromo-6-ethyl-4,4a,6,10b-tetrahydro-1H-pyrano[3,4-c][1,8]naphthyridin-5(2H)-one (1.0 equiv) in THF (0.2 M) at 10° C. was added methyltitanium(IV)triisopropoxide (1 M in THF, 1.05 equiv) followed by dropwise addition of EtMgBr (1 M in THF, 2 equiv) and the mixture was allowed to warm to RT and stirred overnight. The mixture was quenched with saturated aqueous NH$_4$Cl, stirred for 5 min, and then filtered through Celite, washing with EtOAc. The filtrate was partitioned between EtOAc and more saturated aqueous NH$_4$Cl and extracted three times with EtOAc. The combined organics were washed with brine, dried over magnesium sulfate, filtered, and concentrated. The residue was purified by flash column chromatography over silica gel (heptane and 0-60% EtOAc gradient) to give (4a'R,10b'R)-9'-bromo-6'-ethyl-1',2',4',4a',6',10b'-hexahydrospiro[cyclopropane-1,5'-pyrano[3,4-c][1,8]naphthyridine] as a yellow oil in 32% yield. LCMS indicated about 70% purity; the material was used without further purification. LCMS (m/z) (M+H)=323.1/325.1, Rt=1.02 min.

Step 2:
A vial was charged with (4a'R,10b'R)-9'-bromo-6'-ethyl-1',2',4',4a',6',10b'-hexahydrospiro[cyclopropane-1,5'-pyrano[3,4-c][1,8]naphthyridine] (1.0 equiv) and N-(4-methyl-3-(4,4,5,5-tetramethyl-1,3,2-dioxaborolan-2-yl)phenyl)-2-(trifluoromethyl)isonicotinamide (1.05 equiv). THF (0.05 M) and K$_3$PO$_4$ (0.5 M aq, 2.0 equiv) were added, and the vial was purged with N$_2$. XPhos Pd G2 (0.05 equiv) and XPhos (0.05 equiv) were added, and the reaction was heated at 50° C. for 1 h. The reaction was poured onto water and extracted twice with EtOAc The combined organics were washed with brine, dried over MgSO$_4$, filtered, and concentrated. The residue was purified by flash column chromatography over silica gel (heptane and 0-100% EtOAc gradient). Product-containing fractions were concentrated and further purified by SFC (biphenyl 21×150 mm column, 10-20%% MeOH in CO$_2$ gradient eluent) to give N-(3-((4a'R,10b'R)-6'-ethyl-1',2',4',4a',6',10b'-hexahydrospiro[cyclopropane-1,5'-pyrano[3,4-c][1,8]naphthyridin]-9'-yl)-4-methylphenyl)-2-(trifluoromethyl)isonicotinamide as a white solid in 33% yield. LCMS (m/z) (M+H)=523.3, Rt=1.07 min. $^1$H NMR (400 MHz, Methanol-d4) δ 8.90 (d, J=5.0 Hz, 1H), 8.30 (s, 1H), 8.15-8.10 (m, 1H), 7.63 (dd, J=8.2, 2.3 Hz, 1H), 7.57 (d, J=2.3 Hz, 1H), 7.50-7.46 (m, 1H), 7.30 (d, J=8.3 Hz, 1H), 4.09-3.94 (m, 2H), 3.91 (dd, J=10.8, 4.2 Hz, 1H), 3.50 (td, J=12.3, 2.1 Hz, 1H), 3.27-3.21 (m, 1H), 2.96-2.80 (m, 2H), 2.37-2.27 (m, 4H), 1.93 (td, J=11.2, 4.2 Hz, 1H), 1.52 (qd, J=12.6, 4.6 Hz, 1H), 1.38-1.26 (m, 1H), 1.12 (t, J=7.0 Hz, 3H), 1.01 (dt, J=10.6, 7.1 Hz, 1H), 0.58 (tq, J=11.4, 5.2 Hz, 2H).

Methodology Example (R)-6'-ethyl-1',2',4',4a',6',10b'-hexahydrospiro[cyclopropane-1,5'-pyrano[3,4-c][1,8]naphthyridin]-9'-yl)-4-methylphenyl)-2-(trifluoromethyl)isonicotinamide

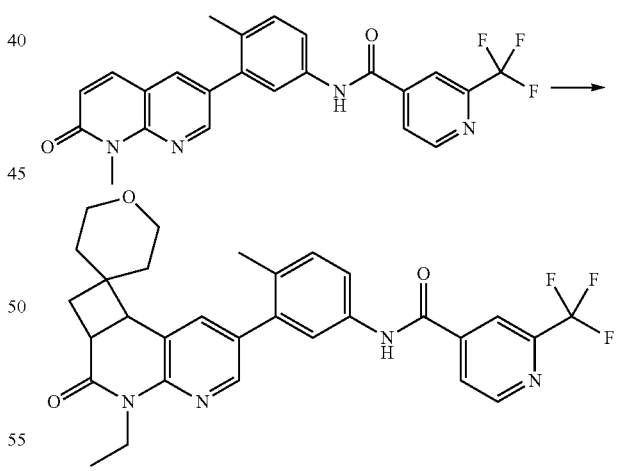

To a solution of N-(3-(8-ethyl-7-oxo-7,8-dihydro-1,8-naphthyridin-3-yl)-4-methylphenyl)-2-(trifluoromethyl)isonicotinamide (1 equiv) in DMF (0.033 M) was added 4-methylenetetrahydro-2H-pyran (10 equiv). The solution was then irradiated in RPR 200 Rayonet Reactor fitted with 3500A (UVA) lamps over a period of 72 hours. The reaction mixture was evaporated to a solid, dissolved in MeOH and purified by basic reverse phase prep HPLC to give N-(3-(4-ethyl-3-oxo-2a,2',3,3',4,5',6',8b-octahydro-2H-spiro[cyclobuta[c][1,8]naphthyridine-1,4'-pyran]-7-yl)-4-methylphenyl)-2-(trifluoromethyl)isonicotinamide as a white solid in 9% yield. LCMS (m/z) (M+H)=551.3, Rt=1.22 min. $^1$H NMR (400 MHz, Methanol-$d_4$) δ 8.90 (d, J=5.0 Hz, 1H), 8.30 (s, 1H), 8.25 (d, J=2.3 Hz, 1H), 8.12 (dd, J=5.0, 1.3 Hz, 1H), 7.70-7.62 (m, 2H), 7.52-7.47 (m, 1H), 7.35 (d, J=8.2 Hz, 1H), 4.38-4.18 (m, 2H), 3.77 (dt, J=11.7, 3.6 Hz, 1H), 3.67-3.54 (m, 2H), 3.53-3.38 (m, 3H), 3.34-3.32 (m, 1H, overlap with solvent), 2.70-2.59 (m, 1H), 2.31 (s, 3H), 1.93-1.69 (m, 2H), 1.39 (td, J=12.4, 11.3, 3.7 Hz, 1H), 1.28 (dd, J=13.4, 2.1 Hz, 1H), 1.22 (t, J=7.0 Hz, 3H).

The following were prepared using the same methods as described for this methodology example, using the appropriate starting materials. Products were purified by flash column chromatography over silica gel, HPLC, and/or SFC methods as appropriate:

Step 1:

(9-bromo-1,2,4,4a,5,6-hexahydro-[1,4]oxazino[4,3-a]quinolin-5-yl)methanol (224 mg, 0.751 mmol) was charged into a vial and Et$_3$N (312 μl, 2.254 mmol) and DCM (3.7 mL). The mixture was cooled to 0° C. and MsCl (64.4 μl, 0.826 mmol) was added. The mixture agitated for 30 min and then quenched by addition of water and Sat'd NH$_4$Cl. The product was extracted with DCM. The organic layer was separated and dried (MgSO$_4$), filtered and concentrated in vacuo. The residue was dissolved in DMF (4.0 mL) and treated with NaSMe (79 mg, 1.127 mmol). The mixture was agitated at room temperature for 30 min and then quenched by addition of Sat'd NaHCO$_3$ and water. The product was extracted with EtOAc and the combined organic extract was washed with water twice and dried (MgSO$_4$), filtered and concentrated in vacuo. The residue was dissolved in DMF

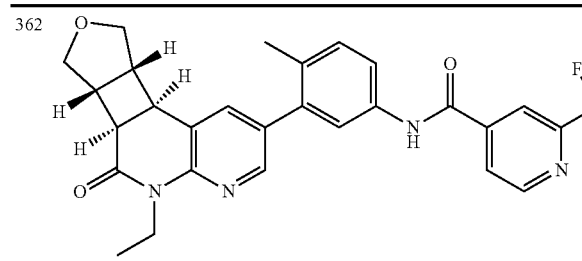

362

(rac)-N-(3-(5-ethyl-6-oxo-5,6,6a,6b,7,9,9a,9b-octahydrofuro[3',4':3,4]cyclobuta[1,2-c][1,8]naphthyridin-2-yl)-4-methylphenyl)-2-(trifluoromethyl)isonicotinamide $^1$H NMR (400 MHz, Methanol-$d_4$) δ ppm 8.90 (d, J = 5.0 Hz, 1H); 8.29 (m, 1H); 8.25 (d, J = 8.5 Hz, 1H); 8.12 (m, 1H); 7.75-7.63 (m; 2H); 7.57 (d; J = 2.3 Hz, 1H); 7.34 (d, J = 9.1 Hz, 1H); 4.30 (q, J = 7.0 Hz, 2H); 4.16 (dd, J = 14.2, 9.7 Hz, 2H); 3.58-3.46 (m; 3H); 3.22-3.15 (m; 2H) 2.94-2.90 (m, 1H); 2.29 (s, 3H); 1.26 (t, J = 7.0 Hz, 3H).; LCMS (m/z) (M + H) = 523.2, Rt = 2.55 min.

(rac)
Relative stereochemistry as drawn

Example 363: (rac)-2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide

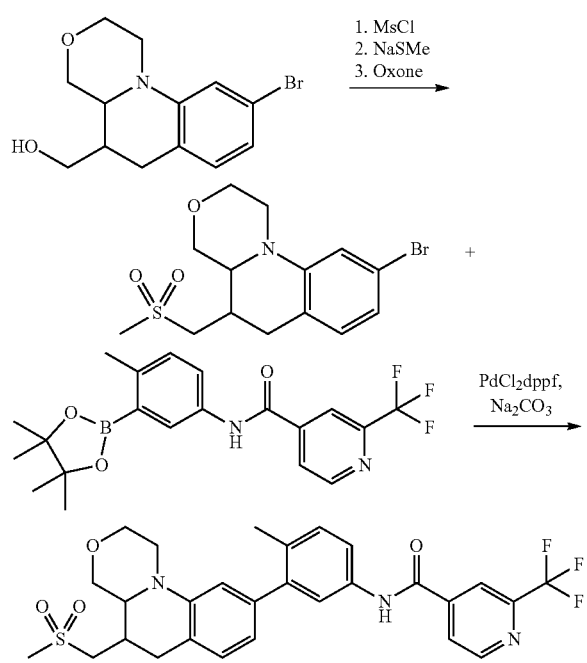

(3.0 mL) and oxone (1385 mg, 2.254 mmol) was added in one portion. The mixture was agitated at room temperature for 45 min after which Sodium bisulfite (1.00 gram) was added in portions and the dark green mixture was agitated vigorously. Immediately, desired product is observed as the major species. The mixture was diluted with EtOAc and filtered through celite. The filtrate was washed twice with water and dried (MgSO$_4$), filtered and concentrated in vacuo to afford 258 mg of 9-bromo-5-((methylsulfonyl)methyl)-1,2,4,4a,5,6-hexahydro-[1,4]oxazino[4,3-a]quinoline, which was taken to the next step as such without any further purification. LCMS: (m/z) (M+H)=362.2, Rt=1.29 min.

Step 2:

9-bromo-5-((methylsulfonyl)methyl)-1,2,4,4a,5,6-hexahydro-[1,4]oxazino[4,3-a]quinoline (60 mg, 0.167 mmol), PdCl$_2$(dppf).CH$_2$Cl$_2$ adduct (13.60 mg, 0.017 mmol), N-(4-methyl-3-(4,4,5,5-tetramethyl-1,3,2-dioxaborolan-2-yl)phenyl)-2-(trifluoromethyl)isonicotinamide (67.0 mg, 0.167 mmol) were combined in Dioxane (833 μl) and then 2M Na$_2$CO$_3$ (210 uL) was added. The mixture was agitated in MW at 130° C. for 40 min and then the product extracted with EtOAc. The organic layer was passed through a plug of anhydrous Na$_2$SO$_4$, and the filtrate concentrated in vacuo. The residue was purified by reverse-phase HPLC to afford the desired product N-(4-methyl-3-(5-((methylsulfonyl)methyl)-1,2,4,4a,5,6-hexahydro-[1,4]oxazino[4,3-a]quinolin-9-yl)phenyl)-2-(trifluoromethyl)isonicotinamide as freebase.

| No. | Structure | Name | Physical Data |
|---|---|---|---|
| 363 | 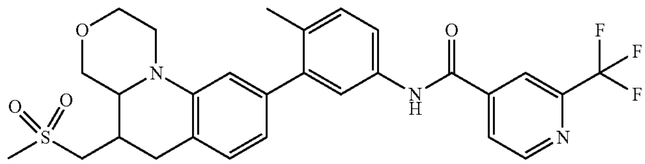 [SMILES: Cc1ccc(NC(=O)c2ccnc(C(F)(F)F)c2)cc1-c1ccc2c(c1)N1CCOCC1C(CS(C)(=O)=O)C2] | (rac)-N-(4-methyl-3-(5-((methylsulfonyl)methyl)-1,2,4,4a,5,6-hexahydro-[1,4]oxazino[4,3-a]quinolin-9-yl)phenyl)-2-(trifluoromethyl)isonicotinamide | $^1$H NMR (400 MHz, DMSO-d6) δ ppm 10.63 (s, 1 H) 8.99 (d, J = 4.89 Hz, 1 H) 8.36 (s, 1 H) 8.19 (dd, J = 5.01, 0.86 Hz, 1 H) 7.56-7.71 (m, 2 H) 7.29 (d, J = 8.31 Hz, 1 H) 7.06 (d, J = 7.58 Hz, 1 H) 6.73-6.85 (m, 1 H) 6.67 (dd, J = 7.46, 1.34 Hz, 1 H) 3.95 (dd, J = 11.07, 2.87 Hz, 1 H) 3.66-3.89 (m, 2 H) 3.38-3.59 (m, 1 H) 3.27 (br d, J = 1.47 Hz, 1 H) 2.84-3.13 (m, 5 H) 2.75 (dd, J = 15.47, 7.27 Hz, 1 H) 2.29-2.41 (m, 1 H) 2.15-2.26 (m, 3 H); LCMS (m/z) (M + H—H$_2$O) = 560.4, Rt = 1.38 min. |
| 364 | 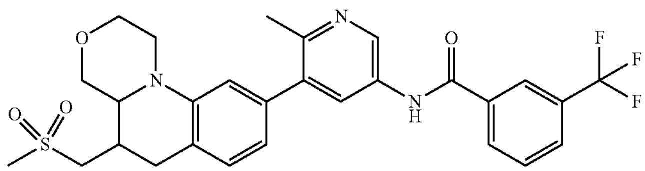 [SMILES: Cc1ncc(NC(=O)c2cccc(C(F)(F)F)c2)cc1-c1ccc2c(c1)N1CCOCC1C(CS(C)(=O)=O)C2] | (rac)-N-(6-methyl-5-(5-((methylsulfonyl)methyl)-1,2,4,4a,5,6-hexahydro-[1,4]oxazino[4,3-a]quinolin-9-yl)pyridin-3-yl)-3-(trifluoromethyl)benzamide | $^1$H NMR (400 MHz, DMSO-d6) δ ppm 10.63 (s, 1 H) 8.66-9.00 (m, 1 H) 8.22-8.41 (m, 2 H) 7.93-8.10 (m, 2 H) 7.81 (t, J = 7.83 Hz, 1 H) 6.99-7.16 (m, 1 H) 6.79-6.97 (m, 1 H) 6.64-6.78 (m, 1 H) 3.72-4.02 (m, 3 H) 3.21-3.65 (m, 11 H) 2.68-2.98 (m, 3 H) 2.43 (s, 3 H) 2.36 (br d, J = 6.72 Hz, 1 H).; LCMS (m/z) (M + H—H$_2$O) = 560.4, Rt = 1.28 min. |
| 365 | 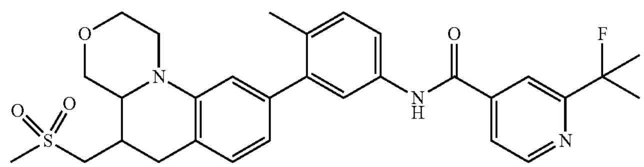 [SMILES: Cc1ccc(NC(=O)c2ccnc(C(C)(C)F)c2)cc1-c1ccc2c(c1)N1CCOCC1C(CS(C)(=O)=O)C2] | (rac)-2-(2-fluoropropan-2-yl)-N-(4-methyl-3-(5-((methylsulfonyl)methyl)-1,2,4,4a,5,6-hexahydro-[1,4]oxazino[4,3-a]quinolin-9-yl)phenyl)isonicotinamide | 1H NMR (400 MHz, DMSO-d6) δ ppm 10.50 (s, 1 H) 8.75 (d, J = 5.14 Hz, 1 H) 8.01 (s, 1 H) 7.81 (dd, J = 5.14, 1.59 Hz, 1 H) 7.58-7.72 (m, 2 H), 7.27 (d, J = 8.31 Hz, 1 H) 7.03-7.12 (m, 1 H) 6.73-6.88 (m, 1 H) 6.59-6.72 (m, 1 H) 3.68-4.04 (m, 3 H) 3.40-3.62 (m, 2 H) 2.85-3.14 (m, 5 H) 2.75 (dd, J = 15.41, 7.34 Hz, 1 H) 2.28-2.39 (m, 1 H) 2.17-2.26 (m, 3 H) 1.73 (s, 2 H) 1.70-1.77 (m, 1 H) 1.68 (s, 3 H); LCMS (m/z) (M + H) = 552.3. Rt = 1.36 min. |

Example 366: (rac)-2-(1,1-difluoroethyl)-N-(3-(5-fluoro-5-(hydroxymethyl)-1,2,4,4a,5,6-hexahydro-[1,4]oxazino[4,3-a]quinolin-9-yl)-4-methylphenyl)isonicotinamide

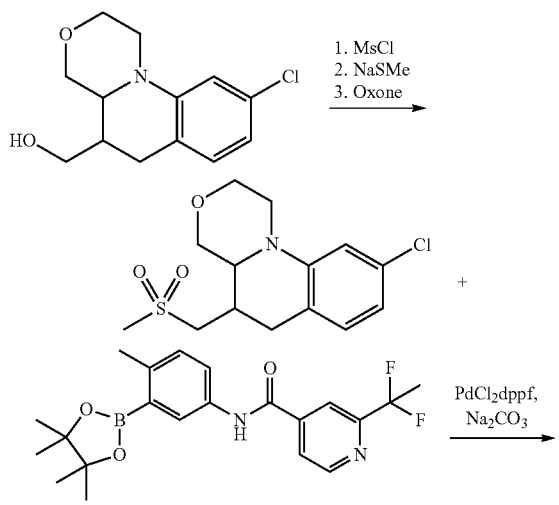

Step 1:
(9-chloro-1,2,4,4a,5,6-hexahydro-[1,4]oxazino[4,3-a]quinolin-5-yl)methanol (85 mg, 0.751 mmol) was charged into a vial and Et$_3$N (119 µl, 0.855 mmol) was added. To the mixture was then added MsCl (24.44 µl, 0.314 mmol) and the mixture agitated for 30 min and then quenched by addition of water and Sat'd NH$_4$Cl. The product was extracted with DCM. The organic layer was separated and dried (MgSO$_4$), filtered and concentrated in vacuo. The residue was dissolved in DMF (4.0 mL) and treated with NaSMe (30.0 mg, 0.428 mmol). The mixture was agitated at room temperature. The mixture was agitated at room temperature for 30 min after which the mixture was quenched with sat'd NaHCO$_3$ and water and the product extracted with EtOAc. The organic layer was dried (MgSO₄), filtered and concentrated in vacuo. The residue was dissolved in DMF (2.0 mL) and treated with oxone (526 mg, 0.855 mmol). The mixture was agitated at room temperature for 45 min upon which LCMS indicated complete formation of desired product. The mixture was diluted with EtOAc and filtered through celite. The filtrate was washed with water twice and then dried (MgSO₄), filtered and concentrated in vacuo to afford 30.0 mg of the desired product 9-chloro-5-((methylsulfonyl)methyl)-1,2,4,4a,5,6-hexahydro-[1,4]oxazino[4,3-a][1,5]naphthyridine, which was taken to the next step as such without any further purification. LCMS: (m/z) (M+H)=317.3, Rt=0.74 min.

Step 2:

9-chloro-5-((methylsulfonyl)methyl)-1,2,4,4a,5,6-hexahydro-[1,4]oxazino[4,3-a][1,5]naphthyridine (15 mg, 0.047 mmol), X-Phos-Pd-G2 (3.72 mg, 4.73 μmol), 2-(1,1-difluoroethyl)-N-(4-methyl-3-(4,4,5,5-tetramethyl-1,3,2-dioxaborolan-2-yl)phenyl)isonicotinamide (19.05 mg, 0.047 mmol) and K₃PO₄ (30.2 mg, 0.142 mmol) were combined in Dioxane (1 mL) and then water 150 uL was added. The mixture was agitated in MW at 130° C. for 40 min and then the product extracted with EtOAc. The organic layer was passed through a plug of anhydrous Na₂SO₄, and the filtrate concentrated in vacuo. The residue was purified by reverse-phase HPLC to afford the desired product as a free-base.

Peak 1

Peak 2

Peak 3

| 366 | 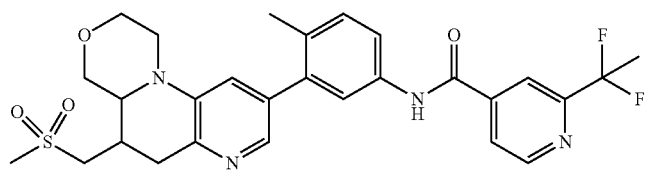 [SMILES: Cc1ccc(NC(=O)c2ccnc(C(C)(F)F)c2)cc1-c1cnc2c(c1)N1CCOCC1C(CS(C)(=O)=O)C2]  (rac)-2-(1,1-difluoroethyl)-N-(4-methyl-3-(5-((methylsulfonyl)methyl)-1,2,4,4a,5,6-hexahydro-[1,4]oxazino[4,3-a][1,5]naphthyridin-9-yl)phenyl)isonicotinamide | ¹H NMR (400 MHz, DMSO-d6) δ ppm 10.63 (s, 1 H) 8.88 (dd, J = 5.01, 0.61 Hz, 1 H) 8.18 (d, J = 0.61 Hz, 1 H) 7.98-8.07 (m, 1 H) 7.83 (d, J = 1.22 Hz, 1 H) 7.73 (dd, J = 8.25, 2.26 Hz, 1 H) 7.66 (d, J = 2.20 Hz, 1 H) 7.32 (d, J = 8.44 Hz, 1 H) 7.21 (br s, 1 H) 4.05 (dd, J = 11.13. 2.69 Hz, 1 H) 3.76-3.90 (m, 2 H) 3.41-3.69 (m, 2 H) 3.10-3.28 (m, 5 H) 3.06 (s, 3 H) 2.79- 2.96 (m, 2 H) 2.23 (s, 3 H) 2.05 (t, J = 19.13 Hz, 3 H); LCMS (m/z) (M + H) = 557.4, Rt = 1.19 min. |

Chiral Resolution of Intermediate X: the mixture of diastereomers of this tricyclic intermediate was separated by chiral SFC and was used to make compounds in the tables below.

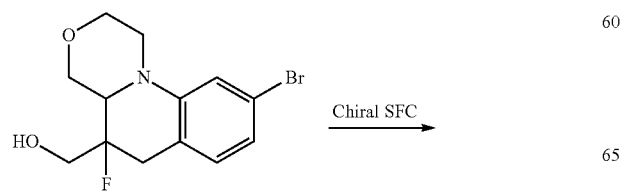

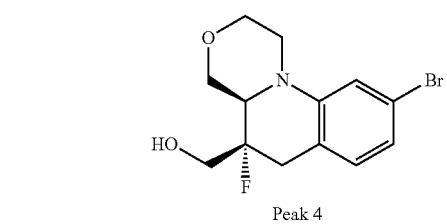

Peak 4

| Ex. No. | Structure | Name | Physical Data |
|---|---|---|---|
| 367 | 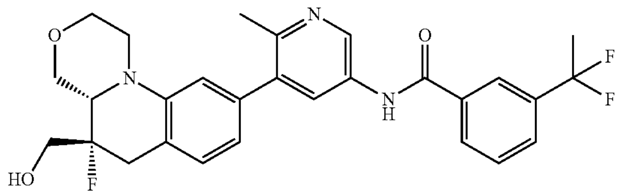 [SMILES: Cc1ncc(NC(=O)c2cccc(C(C)(F)F)c2)cc1-c1ccc2c(c1)N1CCOC[C@H]1[C@](F)(CO)C2] | 3-(1,1-difluoroethyl)-N-(5-((4aS,5S)-5-fluoro-5-(hydroxymethyl)-1,2,4,4a,5,6-hexahydro-[1,4]oxazino[4,3-a]quinolin-9-yl)-6-methylpyridin-3-yl)benzamide | $^1$H NMR (400 MHz, DMSO-d6) δ ppm 10.80 (s, 1 H) 8.90 (d, J = 5.01 Hz, 1 H) 8.83 (d, J = 2.32 Hz, 1 H) 8.20 (s, 1 H) 7.95-8.08 (m, 2 H) 7.13 (d, J = 7.58 Hz, 1 H) 6.84-6.93 (m, 1 H) 6.73-6.79 (m, 1 H) 5.30 (t, J = 5.81 Hz, 1 H) 4.03 (dd, J = 11.13, 2.69 Hz, 1 H) 3.67-3.96 (m, 3 H) 3.37-3.66 (m. 4 H) 2.78-3.25 (m, 4 H) 2.44 (s, 3 H) 2.06 (t, J = 19.13 Hz, 3 H); LCMS (m/z) (M + H) = 513.2, Rt = 1.16 min. |
| 368 | 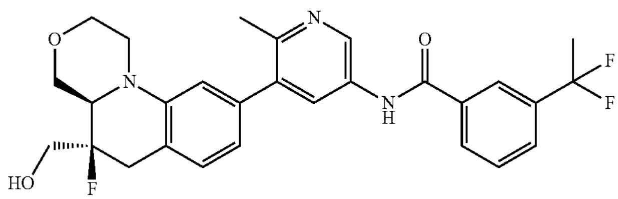 [SMILES: Cc1ncc(NC(=O)c2cccc(C(C)(F)F)c2)cc1-c1ccc2c(c1)N1CCOC[C@@H]1[C@@](F)(CO)C2] | 3-(1,1-difluoroethyl)-N-(5-((4aR,5R)-5-fluoro-5-(hydroxymethyl)-1,2,4,4a,5,6-hexahydro-[1,4]oxazino[4,3-a]quinolin-9-yl)-6-methylpyridin-3-yl)benzamide | $^1$H NMR (400 MHz, DMSO-d6) δ ppm 10.80 (s, 1 H) 8.90 (d, J = 5.01 Hz, 1 H) 8.83 (d, J = 2.32 Hz, 1 H) 8.20 (s, 1 H) 7.86-8.10 (m, 2 H) 7.13 (d, J = 7.58 Hz, 1 H) 6.86 (s, 1 H) 6.75 (d, J = 7.58 Hz, 1 H) 5.75 (s, 1 H) 5.30 (t, J = 5.75 Hz, 1 H) 4.03 (dd, J = 11.13, 2.69 Hz, 1 H) 3.78-3.93 (m, 2 H) 3.41-3.63 (m, 4 H) 2.99-3.30 (m, 2 H) 2.78-2.95 (m, 2 H) 2.44 (s, 3 H) 2.06 (t, J = 19.13 Hz, 3 H).; LCMS (m/z) (M + H) = 513.2, Rt = 1.16 min. |
| 369 | 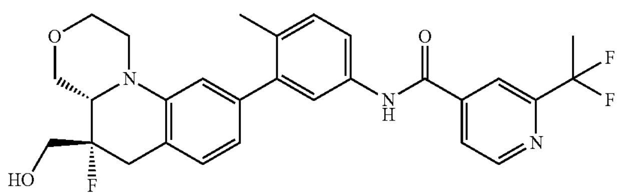 [SMILES: Cc1ccc(NC(=O)c2ccnc(C(C)(F)F)c2)cc1-c1ccc2c(c1)N1CCOC[C@H]1[C@](F)(CO)C2] | 2-(1,1-difluoroethyl)-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.58 (s, 1 H) 8.87 (d, J = 5.01 Hz, 1 H) 8.18 (s, 1 H) 8.03 (br d, J = 4.65 Hz, 1 H) 7.56-7.73 (m, 2 H) 7.28 (d, J = 8.31 Hz, 1 H) 7.09 (d, J = 7.58 Hz, 1 H) 6.78 (s. 1 H) 6.70 (d, J = 7.58 Hz, 1 H) 5.29 (t, J = 5.75 Hz, 1 H) 4.03 (dd, J = 11.19, 2.75 Hz, 1 H) 3.73-3.92 (m, 2 H) 3.43-3.64 (m, 4 H) 3.01-3.29 (m, 2 H) 2.73-2.92 (m, 2 H) 2.23 (s, 3 H) 2.05 (t, J = 19.07 Hz, 3 H).; LCMS (m/z) (M + H) = 512.2, 1.44 min. |
| 370 | 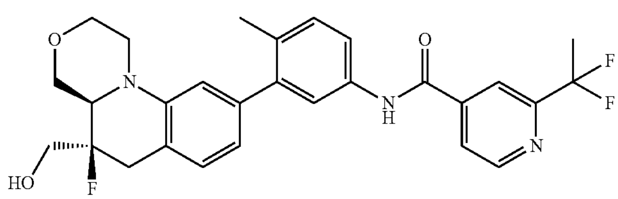 [SMILES: Cc1ccc(NC(=O)c2ccnc(C(C)(F)F)c2)cc1-c1ccc2c(c1)N1CCOC[C@@H]1[C@@](F)(CO)C2] | 2-(1,1-difluoroethyl)-N-(3-((4aR,5R)-5-fluoro-5-(hydroxymethyl)-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.58 (s, 1 H) 8.87 (d, J = 5.01 Hz, 1 H) 8.18 (s, 1 H) 8.03 (br d, J = 4.65 Hz, 1 H) 7.56-7.73 (m, 2 H) 7.28 (d, J = 8.31 Hz, 1 H) 7.09 (d, J = 7.58 Hz, 1 H) 6.78 (s. 1 H) 6.70 (d, J = 7.58 Hz, 1 H) 5.29 (t, J = 5.75 Hz, 1 H) 4.03 (dd, J = 11.19, 2.75 Hz, 1 H) 3.73-3.92 (m, 2 H) 3.43-3.64 (m, 4 H) 3.01-3.29 (m, 2 H) 2.73-2.92 (m, 2 H) 2.23 (s, 3 H) 2.05 (t, J = 19.07 Hz, 3 H).; LCMS (m/z) (M + H) = 512.2. 1.44 min. |
| 371 | 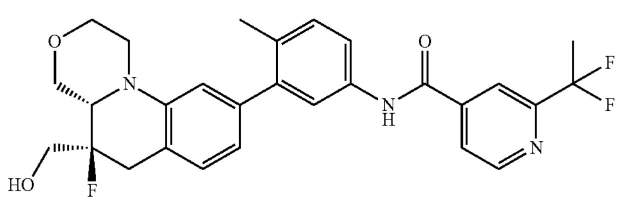 [SMILES: Cc1ccc(NC(=O)c2ccnc(C(C)(F)F)c2)cc1-c1ccc2c(c1)N1CCOC[C@H]1[C@@](F)(CO)C2] | 2-(1,1-difluoroethyl)-N-(3-((4aS,5R)-5-fluoro-5-(hydroxymethyl)-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.58 (s, 1 H) 8.87 (br d, J = 4.89 Hz, 1 H) 8.17 (s, 1 H) 8.02 (br d, J = 4.52 Hz, 1 H) 7.49-7.73 (m, 2 H) 7.28 (br d, J = 8.19 Hz, 1 H) 7.07 (br d, J = 7.58 Hz, 1 H) 6.80 (s, 1 H) 6.66 (br d, J = 7.46 Hz, 1 H) 5.19 (br t, J = 5.44 Hz, 1 H) 3.78-4.04 (m, 3 H) 3.39-3.76 (m, 6 H) 2.77-3.15 (m, 3 H) 2.23 (s, 3 H) 2.05 (br t, J = 19.13 Hz, 3 H).; LCMS (m/z) (M + H) = 512.2, 1.44 min. |

-continued

| Ex. No. | Structure | Name | Physical Data |
|---|---|---|---|
| 372 | 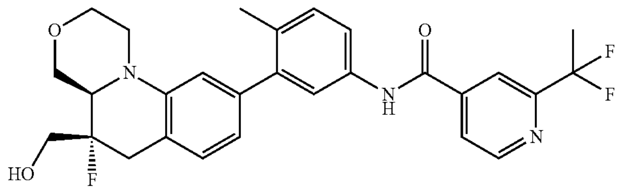 [SMILES: Cc1ccc(NC(=O)c2ccnc(C(C)(F)F)c2)cc1-c1ccc2c(c1)N1CCOC[C@@H]1[C@](F)(CO)C2] | 2-(1,1-difluoroethyl)-N-(3-((4aR,5S)-5-fluoro-5-(hydroxymethyl)-1,2,4,4a,5,6-hexahydro-[1,4]oxazino[4,3-a]quinolin-9-yl)-4-methylphenyl)isonicotinamide | $^1$H NMR (400 MHz, DMSO-d6) δ ppm 10.58 (s, 1 H) 8.87 (br d, J = 4.89 Hz, 1 H) 8.17 (s, 1 H) 8.02 (br d, J = 4.52 Hz, 1 H) 7.49-7.73 (m, 2 H) 7.28 (br d, J = 8.19 Hz, 1 H) 7.07 (br d, J = 7.58 Hz, 1 H) 6.80 (s, 1 H) 6.66 (br d, J = 7.46 Hz, 1 H) 5.19 (br t, J = 5.44 Hz, 1 H) 3.78-4.04 (m, 3 H) 3.39-3.76 (m, 6 H) 2.77-3.15 (m, 3 H) 2.23 (s, 3 H) 2.05 (br t, J = 19.13 Hz, 3 H).; LCMS (m/z) (M + H) = 512.2, 1.44 min. |
| 373 | 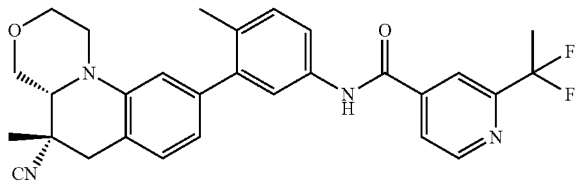 | N-(3-((4aR,5S)-5-cyano-5-methyl-1,2,4,4a,5,6-hexahydro-[1,4]oxazino[4,3-a]quinolin-9-yl)-4-methylphenyl)-2-(1,1-difluoroethyl)isonicotinamide | $^1$H NMR (400 MHz, DMSO-d6) δ ppm 8.74-9.02 (m, 1 H) 8.18 (s, 1 H) 8.03 (dd, J = 5.01, 1.34 Hz, 1 H) 7.71 (dd, J = 8.25, 2.26 Hz, 1H) 7.64 (d, J = 2.20 Hz, 1 H) 7.29 (d, J = 8.44 Hz, 1 H) 7.08 (d, J = 7.70 Hz, 1 H) 6.89 (d, J = 1.10 Hz, 1 H) 6.74 (dd, J = 7.64, 1.28 Hz, 1 H) 4.19 (dd, J = 11.19, 3.12 Hz, 1 H) 3.79-4.03 (m, 2 H) 3.58 (td, J = 11.74, 2.57 Hz, 1 H) 3.39 (t, J = 10.94 Hz, 1 H) 3.03-3.15 (m, 3 H) 2.77 (td, J = 12.10, 3.67 Hz, 1 H) 2.24 (s, 3 H) 2.05 (t, J = 19.13 Hz, 3 H) 1.43 (s, 3 H).; LCMS (m/z) (M + H) = 503.2, 1.47 min. |
| 374 | 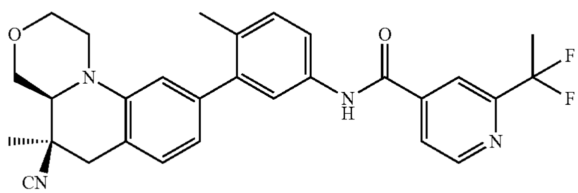 | N-(3-((4aS,5R)-5-cyano-5-methyl-1,2,4,4a,5,6-hexahydro-[1,4]oxazino[4,3-a]quinolin-9-yl)-4-methylphenyl)-2-(1,1-difluoroethyl)isonicotinamide | $^1$H NMR (400 MHz, DMSO-d6) δ ppm 8.74-9.02 (m, 1 H) 8.18 (s, 1 H) 8.03 (dd, J = 5.01, 1.34 Hz, 1 H) 7.71 (dd, J = 8.25, 2.26 Hz, 1H) 7.64 (d, J = 2.20 Hz, 1 H) 7.29 (d, J = 8.44 Hz, 1 H) 7.08 (d, J = 7.70 Hz, 1 H) 6.89 (d, J = 1.10 Hz, 1 H) 6.74 (dd, J = 7.64, 1.28 Hz, 1 H) 4.19 (dd, J = 11.19, 3.12 Hz, 1 H) 3.79-4.03 (m, 2 H) 3.58 (td, J = 11.74, 2.57 Hz, 1 H) 3.39 (t, J = 10.94 Hz, 1 H) 3.03-3.15 (m, 3 H) 2.77 (td, J = 12.10, 3.67 Hz, 1 H) 2.24 (s, 3 H) 2.05 (t, J = 19.13 Hz, 3 H) 1.43 (s, 3 H).; LCMS (m/z) (M + H) = 503.2, 1.47 min. |
| 375 | 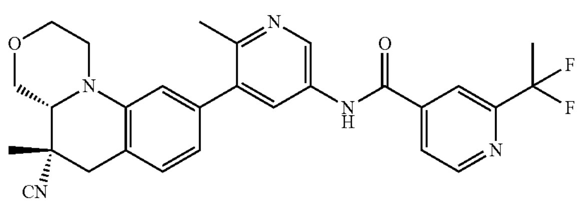 | N-(5-((4aR,5S)-5-cyano-5-methyl-1,2,4,4a,5,6-hexahydro-[1,4]oxazino[4,3-a]quinolin-9-yl)-6-methylpyridin-3-yl)-2-(1,1-difluoroethyl)isonicotinamide | $^1$H NMR (400 MHz, DMSO-d6) δ ppm 10.80 (s, 1 H) 8.90 (dd, J = 5.01, 0.61 Hz, 1 H) 8.84 (d, J = 2.45 Hz, 1 H) 8.21 (d, J = 0.61 Hz, 1 H) 7.96-8.08 (m, 2 H) 7.12 (d, J = 7.70 Hz, 1 H) 6.97 (d, J = 1.22 Hz, 1 H) 6.79 (dd, J = 7.58, 1.47 Hz, 1 H) 4.20 (dd, J = 11.19, 3.12 Hz, 1 H) 3.84-4.04 (m, 2 H) 3.58 (td, J = 11.74, 2.69 Hz, 1 H) 3.36-3.46 (m, 1 H) 3.02-3.19 (m, 3 H) 2.79 (td, J = 12.10, 3.67 Hz, 1 H) 2.44 (s, 3 H) 2.06 (t, J = 19.13 Hz, 3 H) 1.44 (s, 3 H).; LCMS (m/z) (M + H) = 504.1, 1.29 min. |
| 376 | 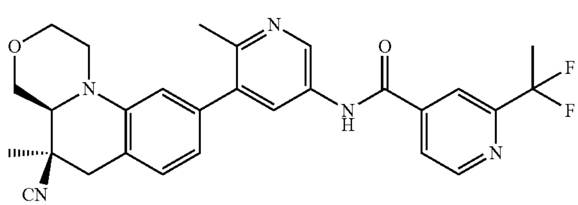 | N-(5-((4aS,5R)-5-cyano-5-methyl-1,2,4,4a,5,6-hexahydro-[1,4]oxazino[4,3-a]quinolin-9-yl)-6-methylpyridin-3-yl)-2-(1,1-difluoroethyl)isonicotinamide | $^1$H NMR (400 MHz, DMSO-d6) δ ppm 10.80 (s, 1 H) 8.90 (dd, J = 5.01, 0.61 Hz, 1 H) 8.84 (d, J = 2.45 Hz, 1 H) 8.21 (d, J = 0.61 Hz, 1 H) 7.96-8.08 (m, 2 H) 7.12 (d, J = 7.70 Hz, 1 H) 6.97 (d, J = 1.22 Hz, 1 H) 6.79 (dd, J = 7.58, 1.47 Hz, 1 H) 4.20 (dd, J = 11.19, 3.12 Hz, 1 H) 3.84-4.04 (m, 2 H) 3.58 (td, J = 11.74, 2.69 Hz, 1 H) 3.36-3.46 (m, 1 H) 3.02-3.19 (m, 3 H) 2.79 (td, J = 12.10, 3.67 Hz, 1 H) 2.44 (s, 3 H) 2.06 (t, J = 19.13 Hz, 3 H) 1.44 (s, 3 H).; LCMS (m/z) (M + H) = 504.1, 1.29 min. |

The following compounds were prepared using same procedure used for examples 367-376, except that 3,5-dichloropicolinaldehyde was used in the first step.

| Ex. No. | Structure | Name | Physical Data |
|---|---|---|---|
| 377 | 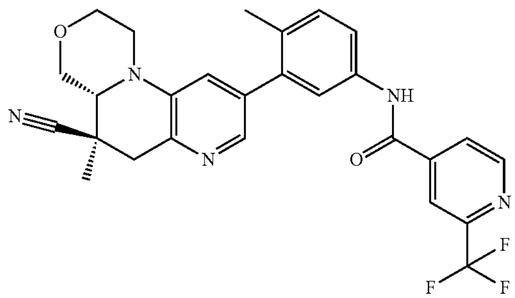 [SMILES: Cc1ccc(NC(=O)c2ccnc(C(F)(F)F)c2)cc1-c1cnc2c(c1)N1CCOC[C@H]1[C@](C)(C#N)C2] | N-(3-((4aR,5R)-5-cyano-5-methyl-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.92 (d, J = 1.6 Hz, 1H), 7.68 (dd, J = 8.2, 2.3 Hz, 1H), 7.63 (d, J = 2.3 Hz, 1H), 7.36 (d, J = 1.6 Hz, 1H), 7.34 (d, J = 8.3 Hz, 1H), 4.30-4.24 (m, 1H), 4.04 (dd, J = 11.5, 3.7 Hz, 1H), 3.80 (dd, J = 12.2, 2.0 Hz, 1H), 3.72 (td, J = 11.8, 2.9 Hz, 1H), 3.60 (t, J = 11.0 Hz, 1H), 3.29-3.15 (m, 3H), 2.93 (td, J = 12.0, 3.8 Hz, 1H), 2.28 (s, 3H), 1.53 (s, 3H). LCMS (m/z) (M + H) = 508.1, Rt = 1.15 min. |
| 378 | 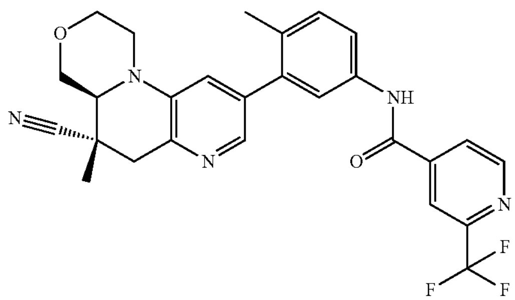 [SMILES: Cc1ccc(NC(=O)c2ccnc(C(F)(F)F)c2)cc1-c1cnc2c(c1)N1CCOC[C@@H]1[C@@](C)(C#N)C2] | N-(3-((4aS,5S)-5-cyano-5-methyl-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.92 (d, J = 1.6 Hz, 1H), 7.68 (dd, J = 8.2, 2.3 Hz, 1H), 7.63 (d, J = 2.3 Hz, 1H), 7.36 (d, J = 1.6 Hz, 1H), 7.34 (d, J = 8.3 Hz, 1H), 4.27 (dd, J = 11.4. 3.0 Hz, 1H), 4.04 (dd, J = 11.5, 3.7 Hz, 1H), 3.84-3.77 (m, 1H), 3.72 (td, J = 11.8, 2.9 Hz, 1H), 3.60 (t, J = 11.0 Hz, 1H), 3.28-3.15 (m, 3H), 2.93 (td, J = 12.0, .3.8 Hz, 1H), 2.28 (s, 3H), 1.53 (s, 3H). CMS (m/z) (M + H) = 508.1, Rt = 1.15 min. |

The following compounds are derived from Peak 1 of the resolved chiral intermediate above:

| Ex. No. | Structure | Name | Physical Data |
|---|---|---|---|
| 379 | 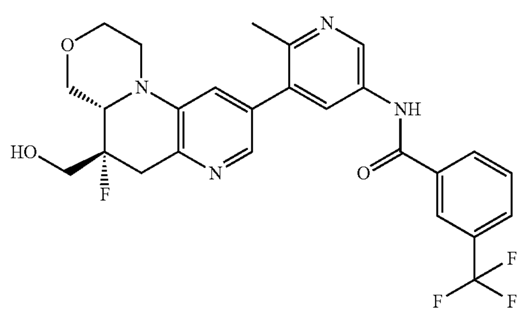 [SMILES: Cc1ncc(NC(=O)c2cccc(C(F)(F)F)c2)cc1-c1cnc2c(c1)N1CCOC[C@H]1[C@](F)(CO)C2] | N-(5-((4aS,5S)-5-fluoro-5-(hydroxymethyl)-1,2,4,4a,5,6-hexahydro-[1,4]oxazino[4,3-a]quinolin-9-yl)-6-methylpyridin-3-yl)-3(trifluoromethyl)benzamide | $^1$H NMR (400 MHz, Methanol-d4) δ 8.79 (s, 1H), 8.29 (s, 1H), 8.23 (d, J = 7.8 Hz, 1H), 8.07 (s, 1H), 7.91 (d, J = 7.6 Hz, 1H), 7.74 (t, J = 7.8 Hz, 1H), 7.16 (d, J = 7.5 Hz, 1H), 6.85 (s, 1H), 6.80 (d, J = 7.5 Hz, 1H), 4.07 (d, J = 11.2 Hz, 1H), 3.92 (d, J = 10.8 Hz, 1H), 3.77-3.54 (m, 5H), 3.28-3.08 (m, 2H), 3.07-2.87 (m, 2H), 2.47 (s, 3H). LCMS (m/z) (M + H) = 516.2, Rt = 1.08 min. |
| 380 | 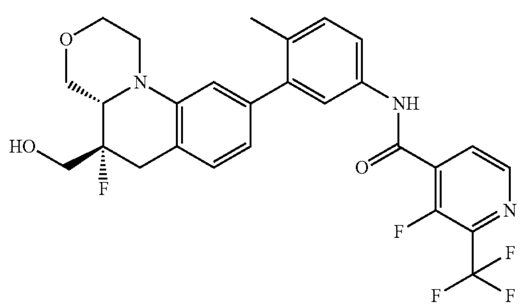 [SMILES: Cc1ccc(NC(=O)c2ccnc(C(F)(F)F)c2F)cc1-c1ccc2c(c1)N1CCOC[C@H]1[C@](F)(CO)C2] | 3-fluoro-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, Methanol-d4) δ 8.63 (d, J = 4.7 Hz, 1H), 7.93 (t, J = 4.8 Hz, 1H), 7.56 (dd, J = 8.2, 2.2 Hz, 1H), 7.52 (d, J = 2.2 Hz, 1H), 7.27 (d, J = 8.3 Hz, 1H), 7.12 (d, J = 7.5 Hz, 1H), 6.84-6.70 (m, 2H), 4.06 (dd, J = 11.4, 2.9 Hz, 1H), 3.91 (dd, J = 11.2, 3.2 Hz, 1H), 3.74-3.52 (m, 5H), 3.25-3.07 (m, 2H), 3.04-2.86 (m, 2H), 2.24 (s, 3H), LCMS (m/z) (M + H) = 534.1. Rt = 1.51 min. |

| | | | |
|---|---|---|---|
| 381 | 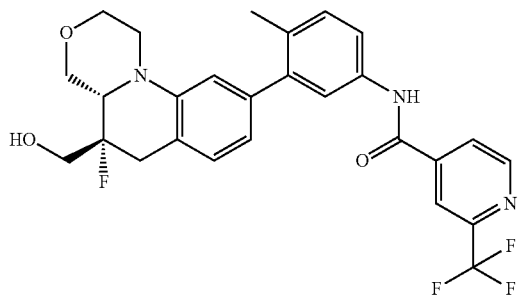 [SMILES: Cc1ccc(NC(=O)c2ccnc(C(F)(F)F)c2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | ¹H NMR (400 MHz, Methanol-d4) δ 8.89 (d, J = 5.0 Hz, 1H), 8.29 (s, 1H), 8.11 (dd, J = 5.0, 1.2 Hz, 1H), 7.61 (dd, J = 8.2, 2.3 Hz, 1H), 7.57 (d, J = 2.3 Hz, 1H), 7.27 (d, J = 8.3 Hz, 1H), 7.12 (d, J = 7.5 Hz, 1H), 6.80 (s, 1H), 6.76 (dd, J = 7.5, 1.4 Hz, 1H), 4.06 (dd, J = 11.4, 3.2 Hz, 1H), 3.92 (dd, J = 11.2, 3.5 Hz, 1H) 3.74-3.53 (m, 5H), 3.25-3.07 (m, 2H), 3.05-2.86 (m, 2H), 2.25 (s, 3H). LCMS (m/z) (M + H) = 516.2, Rt = 1.49 min. |
| 382 | 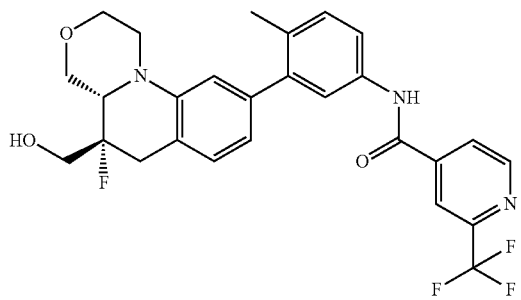 [SMILES: Cc1ccc(NC(=O)c2ccnc(C(F)(F)F)c2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | ¹H NMR (400 MHz, Methanol-d4) δ 8.89 (d, J = 5.0 Hz, 1H), 8.29 (s, 1H), 8.11 (dd, J = 5.0, 1.2 Hz, 1H), 7.61 (dd, J = 8.2, 2.3 Hz, 1H), 7.57 (d, J = 2.3 Hz, 1H), 7.27 (d, J = 8.3 Hz, 1H), 7.12 (d, J = 7.5 Hz, 1H), 6.80 (s, 1H), 6.76 (dd, J =7.5, 1.4 Hz, 1H), 4.06 (dd, J = 11.4, 3.2 Hz, 1H), 3.91 (dd, J = 11.2, 3.5 Hz, 1H), 3.74-3.55 (m, 5H), 3.25-3.07 (m, 2H), 3.05-2.86 (m, 2H), 2.25 (s, 3H). LCMS (m/z) (M + H) = 516.2, Rt = 1.48 min. |
| 383 | 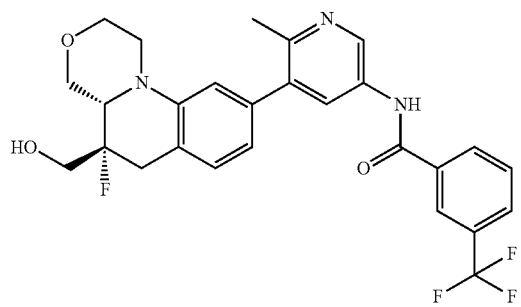 [SMILES: Cc1ncc(NC(=O)c2cccc(C(F)(F)F)c2)cc1-c1ccc2c(c1)N1CCOC[C@H]1[C@](F)(CO)C2] | N-(5-((4aS,5S)-5-fluoro-5-(hydroxymethyl)-1,2,4,4a,5,6-hexahydro-[1,4]oxazino[4,3-a]quinolin-9-yl)-6-methylpyridin-3-yl)-3(trifluoromethyl)benzamide | ¹H NMR (400 MHz, Methanol-d4) δ 8.79 (d, J = 2.5 Hz, 1H), 8.29 (s, 1H), 8.23 (d, J = 7.9 Hz, 1H), 8.07 (d, J = 2.5 Hz, 1H), 7.94-7.87 (m, 1H), 7.74 (t, J = 7.8 Hz, 1H), 7.17 (d, J = 7.6 Hz, 1H), 6.85 (d, J = 1.3 Hz, 1H), 6.81 (dd, J = 7.5, 1.5 Hz, 1H), 4.07 (dd, J = 11.4, 3.2 Hz, 1H), 3.97-3.88 (m, 1H), 3.76-3.56 (m, 5H), 3.28-3.09 (m, 2H), 3.07-2.89 (m, 2H), 2.47 (s, 3H). LCMS (m/z) (M + H) = 516.1, Rt = 1.08 min. |
| 384 | 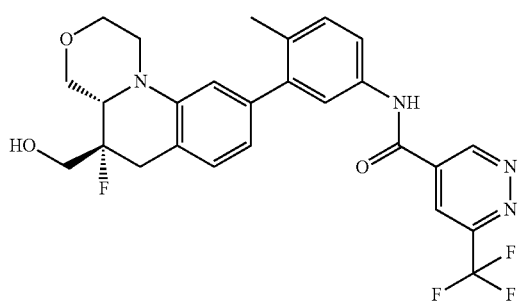 [SMILES: Cc1ccc(NC(=O)c2cnnc(C(F)(F)F)c2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | ¹H NMR (400 MHz, Methanol-d4) δ 9.86 (d, J = 2.0 Hz, 1H), 8.57 (d, J = 2.0 Hz, 1H), 7.64 (dd, J = 8.2, 2.3 Hz, 1H), 7.59 (d, J = 2.3 Hz, 1H), 7.28 (d, J = 8.3 Hz, 1H), 7.12 (d, J = 7.6 Hz, 1H), 6.79 (s, 1H), 6.76 (dd, J = 7.5, 1.5 Hz, 1H), 4.06 (dd, J = 11.4, 3.2 Hz, 1H), 3.92 (dd, J = 11.2, 3.5 Hz, 1H), 3.73-3.53 (m, 5H), 3.24-3.08 (m, 2H), 3.05-2.86 (m, 2H), 2.25 (s, 3H). LCMS (m/z) (M + H) = 517.1, Rt = 1.42 min. |
| 385 | 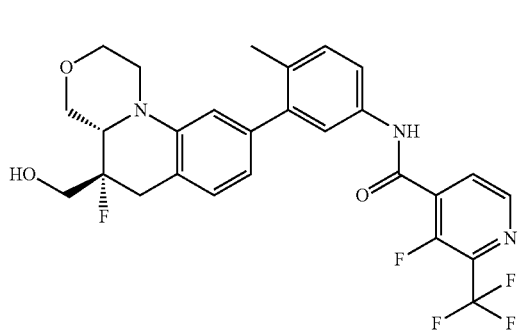 [SMILES: Cc1ccc(NC(=O)c2ccnc(C(F)(F)F)c2F)cc1-c1ccc2c(c1)N1CCOC[C@H]1[C@](F)(CO)C2] | 3-fluoro-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | ¹H NMR (400 MHz, Methanol-d4) δ 8.63 (d, J = 4.7 Hz, 1H), 7.93 (t, J = 4.8 Hz, 1H), 7.56 (dd, J = 8.2, 2.3 Hz, 1H), 7.52 (d, J = 2.3 Hz, 1H), 7.27 (d, J = 8.3 Hz, 1H), 7.12 (d, J = 7.5 Hz, 1H), 6.79 (d, J = 1.2 Hz, 1H), 6.75 (dd, J = 7.5, 1.5 Hz, 1H), 4.06 (dd, J = 11.4, 3.2 Hz, 1H), 3.91 (dd, J = 11.2, 3.5 Hz, 1H), 3.73-3.54 (m, 5H), 3.24-3.08 (m, 2H), 3.04-2.86 (m, 2H), 2.24 (s, 3H). LCMS (m/z) (M + H) = 534.1, Rt = 1.50 min. |

| # | | Name | NMR / LCMS |
|---|---|---|---|
| 386 | 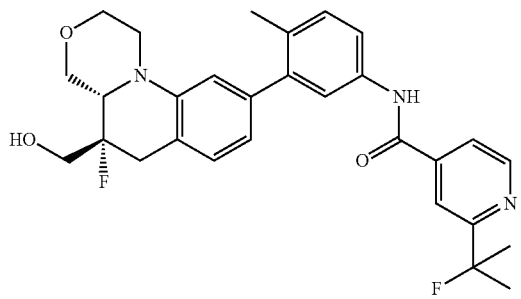 [SMILES: Cc1ccc(NC(=O)c2ccnc(C(C)(C)F)c2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | ¹H NMR (400 MHz, Methanol-d4) δ 8.68 (d, J = 5.1 Hz, 1H), 8.05 (s, 1H), 7.75 (dd, J = 5.1, 1.7 Hz, 1H), 7.63-7.52 (m, 2H), 7.26 (d, J = 8.2 Hz, 1H), 7.11 (d, J = 7.5 Hz, 1H), 6.80 (s, 1H), 6.77 (dd, J = 7.5, 1.3 Hz, 1H), 4.06 (dd, J = 11.4, 3.1 Hz, 1H), 3.91 (dd, J = 11.2, 3.5 Hz, 1H), 3.75-3.52 (m, 5H), 3.24-3.08 (m, 2H), 3.05-2.86 (m, 2H), 2.25 (s, 3H), 1.75 (s, 3H), 1.69 (s, 3H). LCMS (m/z) (M + H) = 508.2, Rt = 1.45 min. |
| 387 | 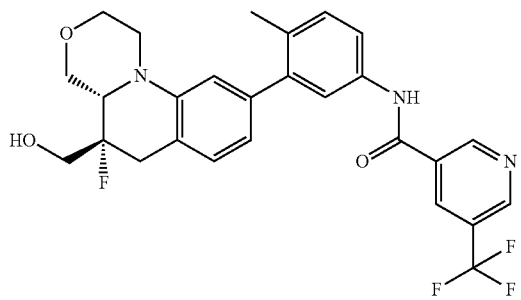 [SMILES: Cc1ccc(NC(=O)c2cncc(C(F)(F)F)c2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | ¹H NMR (400 MHz, Methanol-d4) δ 9.33 (d, J = 1.7 Hz, 1H), 9.06 (s, 1H), 8.65 (s, 1H), 7.65-7.50 (m, 2H), 7.27 (d, J = 8.2 Hz, 1H), 7.12 (d, J = 7.5 Hz, 1H), 6.85-6.71 (m, 2H), 4.06 (dd, J = 11.4, 3.2 Hz, 1H), 3.92 (dd, J = 11.2, 3.5 Hz, 1H), 3.75-3.55 (m, 5H), 3.24-3.12 (m, 2H), 3.09-2.87 (m, 2H), 2.25 (s, 3H). LCMS (m/z) (M + H) = 516.1, Rt = 1.45 min. |
| 388 | 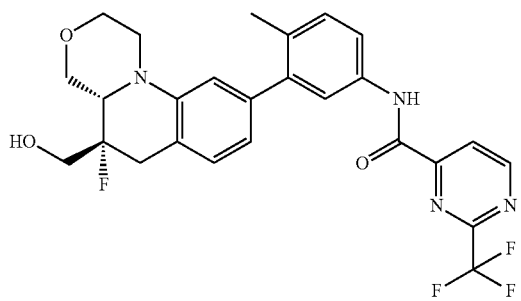 [SMILES: Cc1ccc(NC(=O)c2ccnc(C(F)(F)F)n2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)pyrimidine-4-carboxamide | ¹H NMR (400 MHz, Methanol-d4) δ 9.25 (d, J = 5.0 Hz, 1H), 8.37 (d, J = 5.0 Hz, 1H), 7.72-7.62 (m, 2H), 7.13 (d, J = 7.5 Hz, 1H), 6.81 (d, J = 1.2 Hz, 1H), 6.78 (dd, J = 7.5, 1.5 Hz, 1H), 4.07 (dd, J = 11.4, 3.2 Hz, 1H), 3.92 (dd, J = 11.2, 3.5 Hz, 1H), 3.75-3.53 (m, 5H), 3.24-3.09 (m, 2H), 3.06-2.87 (m, 2H), 2.26 (s, 3H). LCMS (m/z) (M + H) = 517.9, Rt = 1.52 min. |
| 389 | 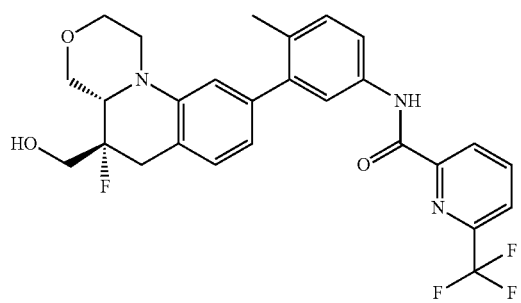 [SMILES: Cc1ccc(NC(=O)c2cccc(C(F)(F)F)n2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazido[4,3-a]quinolin-9-yl)-4-methylphenyl)-6-(trifluoromethyl)picolinamide | ¹H NMR (400 MHz, Methanol-d4) δ 8.44 (d, J = 7.6 Hz, 1H), 8.28 (t, J = 8.0 Hz, 1H), 8.03 (dd, J = 7.8, 0.9 Hz, 1H), 7.67-7.56 (m, 2H), 7.28 (d, J = 8.1 Hz, 1H), 7.12 (d, J = 7.5 Hz, 1H), 6.82 (d, J = 1.2 Hz, 1H), 6.78 (dd, J = 7.5, 1.5 Hz, 1H), 4.06 (dd, J = 11.4, 3.2 Hz, 1H), 3.92 (dd, J = 11.1, 3.5 Hz, 1H), 3.74-3.52 (m, 5H), 3.25-3.08 (m, 2H), 3.05-2.86 (m, 2H), 2.25 (s, 3H). LCMS (m/z) (M + H) = 517.0, Rt = 1.58 min. |
| 390 | 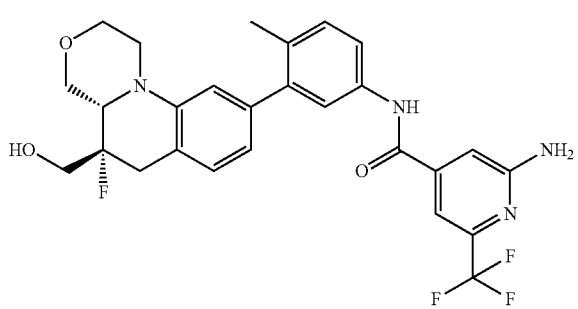 [SMILES: Cc1ccc(NC(=O)c2cc(N)nc(C(F)(F)F)c2)cc1-c1ccc2c(c1)N1CCOC[C@H]1[C@](F)(CO)C2] | 2-amino-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-6-(trifluoromethyl)isonicotinamide | ¹H NMR (400 MHz, Methanol-d4) δ 7.58-7.50 (m, 2H), 7.35 (d, J = 1.1 Hz, 1H), 7.25 (d, J = 8.2 Hz, 1H), 7.15 (s, 1H), 7.11 (d, J = 7.5 Hz, 1H), 6.79 (s, 1H), 6.76 (dd, J = 7.5, 1.4 Hz, 1H), 4.06 (dd, J = 11.4, 3.2 Hz, 1H), 3.92 (dd, J = 11.2, 3.5 Hz, 1H), 3.74-3.53 (m, 5H), 3.24-3.08 (m, 2H), 3.05-2.86 (m, 2H), 2.24 (s, 3H). LCMS (m/z) (M + H) = 531.2, Rt = 1.42 min. |

| | | | |
|---|---|---|---|
| 391 | 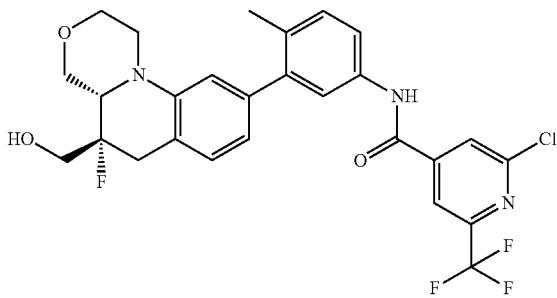 [SMILES: Cc1ccc(NC(=O)c2cc(Cl)nc(C(F)(F)F)c2)cc1-c1ccc2c(c1)N1CCOC[C@H]1[C@](F)(CO)C2] | 2-chloro-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-6-(trifluoromethyl)isonicotinamide | $^1$H NMR (400 MHz, Methanol-d4) δ 8.25 (d, J = 1.1 Hz, 1H), 8.19 (s, 1H), 7.61 (dd, J = 8.2, 2.3 Hz, 1H), 7.57 (d, J = 2.3 Hz, 1H), 7.27 (d, J = 8.3 Hz, 1H), 7.12 (d, J = 7.5 Hz, 1H), 6.79 (s, 1H), 6.76 (dd, J = 7.5, 1.5 Hz, 1H), 4.06 (dd, J = 11.4, 3.2 Hz, 1H), 3.92 (dd, J = 11.2, 3.5 Hz, 1H), 3.74-3.53 (m, 5H), 3.24-3.08 (m, 2H), 3.04-2.87 (m, 2H), 2.25 (s, 3H). LCMS (m/z) (M + H) = 550.1. Rt = 1.62 min. |
| 392 | 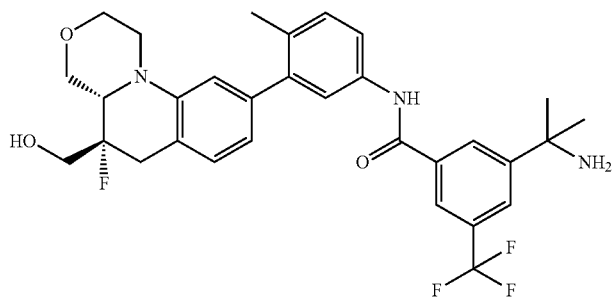 [SMILES: Cc1ccc(NC(=O)c2cc(C(C)(C)N)cc(C(F)(F)F)c2)cc1-c1ccc2c(c1)N1CCOC[C@H]1[C@](F)(CO)C2] | 3-(2-aminopropan-2-yl)-N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-5-(trifluoromethyl)benzamide | $^1$H NMR (400 MHz, Methanol-d4) δ 8.33 (s, 1H), 8.11 (s, 1H), 8.04 (s, 1H), 7.59 (dd, J = 8.2, 2.3 Hz, 1H), 7.55 (d, J = 2.2 Hz, 1H), 7.26 (d, J = 8.2 Hz, 1H), 7.12 (d, J = 7.5 Hz, 1H), 6.81 (s, 1H), 6.77 (dd, J = 7.5, 1.4 Hz, 1H), 4.06 (dd, J = 11.4, 3.2 Hz, 1H), 3.92 (dd, J = 11.1, 3.5 Hz, 1H), 3.73-3.53 (m, 5H), 3.24-3.08 (m, 2H), 3.04-2.85 (m, 2H), 2.25 (s, 3H), 1.57 (s, 6H). LCMS (m/z) (M + H) = 572.2, Rt = 1.14 min. |
| 393 | 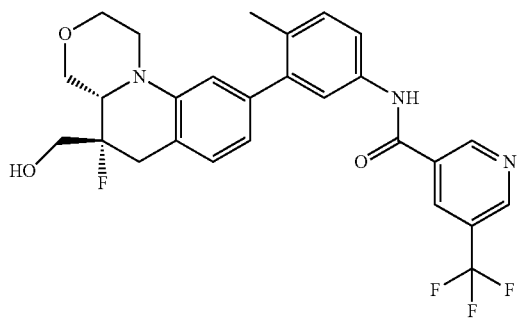 [SMILES: Cc1ccc(NC(=O)c2cncc(C(F)(F)F)c2)cc1-c1ccc2c(c1)N1CCOC[C@H]1[C@](F)(CO)C2] | N-(3-((4aS,5S)-5-fluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, DMSO-d6) δ 10.29-10.82 (m, 1 H) 9.37 (d, J = 1.83 Hz, 1 H) 9.18 (d, J = 1.22 Hz, 1 H) 7.54-7.85 (m, 2 H) 7.28 (d, J = 8.31 Hz, 1 H) 7.10 (d, J = 7.58 Hz, 1 H) 6.79 (s, 1 H) 6.70 (dd, J = 7.52. 1.41 Hz, 1 H) 5.29 (t, J = 5.81 Hz, 1 H) 4.03 (dd, J = 11.13, 3.06 Hz, 1H) 3.73-3.91 (m, 2 H) 3.44-3.62 (m, 4 H) 3.19-3.29 (m, 1 H) 3.01-3.17 (m, 1 H) 2.77-2.93 (m, 2 H) 2.23 (s, 3 H);.; LCMS (m/z) (M + H) = 516.2, 1.43 min. |

The following compounds were derived from Peak 2 of the above resolved intermediate.

| | | | |
|---|---|---|---|
| 394 | 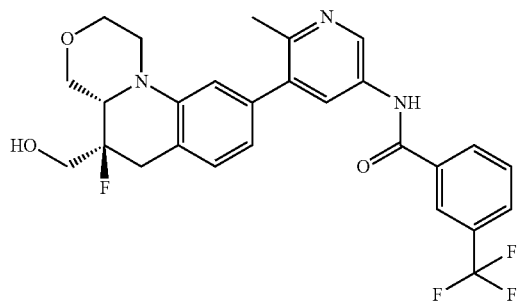 [SMILES: Cc1ncc(NC(=O)c2cccc(C(F)(F)F)c2)cc1-c1ccc2c(c1)N1CCOC[C@H]1[C@@](F)(CO)C2] | N-(5-((4aS,5R)-5-fluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, Methanol-d4) δ 8.80 (d, J = 2.5 Hz, 1H), 8.29 (s, 1H), 8.23 (d, J = 7.9 Hz, 1H), 8.07 (d, J = 2.5 Hz, 1H), 7.91 (d, J = 7.8 Hz, 1H), 7.74 (t, J = 7.8 Hz, 1H), 7.17 (d, J = 7.6 Hz, 1H). 6.85 (d, J = 1.3 Hz, 1H), 6.81 (dd, 7.5, 1.5 Hz, 1H), 4.07 (dd, J = 11.4, 3.2 Hz, 1H), 3.92 (dd, J = 10.7, 3.0 Hz, 1H), 3.77-3.54 (m, 5H), 3.26-3.10 (m, 2H), 3.07-2.88 (m, 2H), 2.47 (s, 3H). LCMS (m/z) (M + H) = 516.1, Rt = 1.08 min. |

| | | | |
|---|---|---|---|
| 395 | 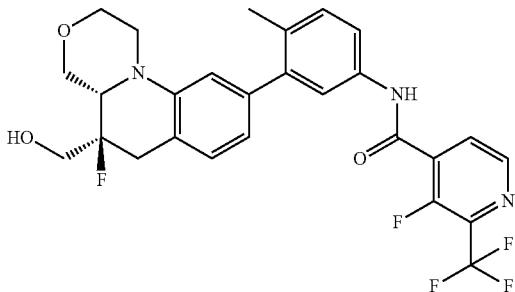 [SMILES: Cc1ccc(NC(=O)c2ccnc(C(F)(F)F)c2F)cc1-c1ccc2c(c1)N1CCOC[C@H]1[C@@](F)(CO)C2] | 3-fluoro-N-(3-((4aS,5R)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, Methanol-d4) δ 8.64 (d, J = 4.7 Hz, 1H), 7.94 (t, J = 4.8 Hz, 1H), 7.56 (dd, J = 8.2, 2.3 Hz, 1H), 7.52 (d, J = 2.3 Hz, 1H), 7.27 (d, J = 8.3 Hz, 1H), 7.12 (d, J = 7.5 Hz, 1H), 6.79 (d, J = 1.2 Hz, 1H), 6.76 (dd, J = 7.5, 1.5 Hz, 1H), 4.06 (dd, J = 11.4, 3.2 Hz, 1H), 3.91 (dd, J = 11.2, 3.5 Hz, 1H), 3.73-3.53 (m, 5H), 3.24-3.08 (m, 2H), 3.04-2.86 (m, 2H), 2.24 (s, 3H). LCMS (m/z) (M + H) = 534.1, Rt = 1.51 min. |
| 396 | 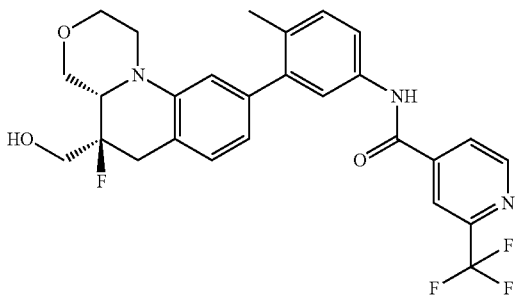 [SMILES: Cc1ccc(NC(=O)c2ccnc(C(F)(F)F)c2)cc1-c1ccc2c(c1)N1CCOC[C@H]1[C@@](F)(CO)C2] | N-(3-((4aS,5R)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, Methanol-d4) δ 8.89 (d, J = 5.0 Hz, 1H), 8.29 (s, 1H), 8.11 (dd, J = 5.0, 1.2 Hz, 1H), 7.61 (dd, J = 8.2, 2.3 Hz, 1H), 7.57 (d, J = 2.3 Hz, 1H), 7.27 (d, J = 8.2 Hz, 1H), 7.12 (d, J = 7.5 Hz, 1H), 6.79 (s, 1H), 6.76 (dd, J = 7.5, 1.4 Hz, 1H), 4.06 (dd, J = 11.4, 3.2 Hz, 1H), 3.91 (dd, J = 11.2, 3.5 Hz, 1H), 3.73-3.53 (m, 5H), 3.24-3.08 (m, 2H), 3.04-2.86 (m, 2H), 2.25 (s, 3H). LCMS (m/z) (M + H) = 516.2, Rt = 1.51 min. |
| 397 | 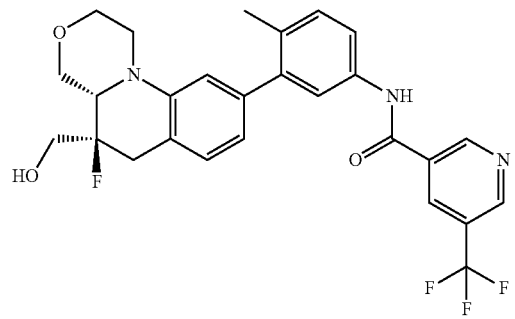 [SMILES: Cc1ccc(NC(=O)c2cncc(C(F)(F)F)c2)cc1-c1ccc2c(c1)N1CCOC[C@H]1[C@@](F)(CO)C2] | N-(3-((4aS,5R)-5-fluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, DMSO-d6) δ 10.32-10.75 (m, 1 H) 9.37 (d, J = 1.71 Hz, 1 H) 9.18 (d, J = 1.22 Hz, 1 H) 8.68 (s, 1 H) 7.57-7.76 (m, 2 H) 7.28 (d, J = 8.31 Hz, 1 H) 7.03-7.15 (m, 1 H) 6.76-6.85 (m, 1 H) 6.58-6.73 (m, 1 H) 5.19 (br s, 1 H) 2.80-4.11 (m, 13 H) 2.23 (s, 3 H).; LCMS (m/z) (M + H) = 516.2, 1.43 min. |

The following Compounds were derived from Peak 3 of the above resolved intermediate.

| | | | |
|---|---|---|---|
| 398 | 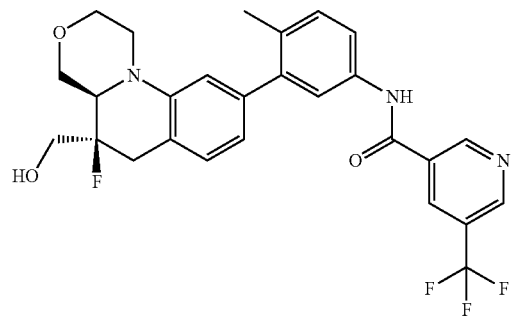 [SMILES: Cc1ccc(NC(=O)c2cncc(C(F)(F)F)c2)cc1-c1ccc2c(c1)N1CCOC[C@@H]1[C@@](F)(CO)C2] | N-(3-((4aR,5R)-5-fluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, DMSO-d6) δ ppm 10.57 (s, 1 H) 9.34-9.40 (m, 1 H) 9.18 (s, 1 H) 8.68 (s, 1 H) 7.68 (dd, J = 8.25, 2.14 Hz, 1 H) 7.63 (d, J = 2.08 Hz, 1 H) 7.28 (d, J = 8.44 Hz, 1 H) 7.10 (d, J = 7.58 Hz, 1 H) 6.76-6.99 (m, 1 H) 6.70 (dd, J = 7.52, 1.16 Hz, 1 H) 5.29 (t, J = 5.81 Hz, 1 H) 4.03 (dd, J = 11.13, 2.93 Hz, 1 H) 3.69-3.90 (m, 2 H) 3.39-3.61 (m, 4 H) 3.17-3.29 (m, 1 H) 3.01-3.17 (m, 1 H) 2.80-2.97 (m, 2 H) 2.23 (s, 3 H).; LCMS (m/z) (M + H) = 516.2, 1.43 min. |

The following Compounds were derived from Peak 4 of the above resolved intermediate.

| | | | |
|---|---|---|---|
| 399 | 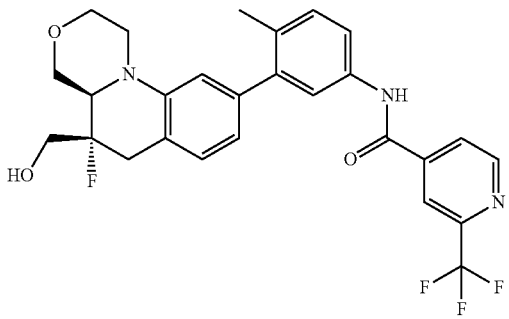 [SMILES: Cc1ccc(NC(=O)c2ccnc(C(F)(F)F)c2)cc1-c1ccc2c(c1)N1CCOC[C@@H]1[C@](F)(CO)C2] | N-(3-((4aR,5S)-5-fluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, DMSO-d6) δ 1H NMR (400 MHz, DMSO-d6) ä ppm 10.62 (s, 1 H) 8.99 (d, J = 5.01 Hz, 1 H) 8.36 (s, 1 H) 8.19 (dd, J = 4.95, 1.04 Hz, 1 H) 7.68 (d, J = 8.44 Hz, 1H) 7.62 (s, 1 H) 7.29 (d, J = 8.31 Hz, 1 H) 7.07 (d, J = 7.70 Hz, 1 H) 6.77-6.83 (m, 1 H) 6.66 (dd, J = 7.52, 1.28 Hz, 1 H) 5.19 (t, J = 5.75 Hz, 1H) 3.73-4.00 (m, 3 H) 3.37-3.70 (m, 5 H) 2.82-3.13 (m, 3 H) 2.23 (s, 3 H).; LCMS (m/z) (M + H) = 516.1, 1.48 min. |
| 400 | 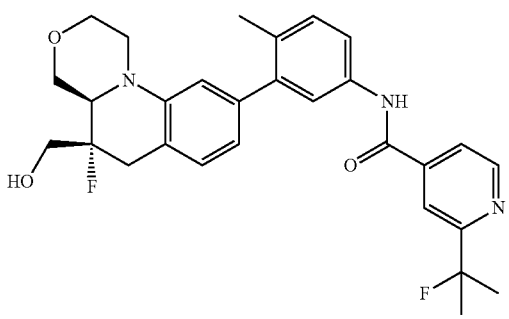 [SMILES: Cc1ccc(NC(=O)c2ccnc(C(C)(C)F)c2)cc1-c1ccc2c(c1)N1CCOC[C@@H]1[C@](F)(CO)C2] | N-(3-((4aR,5S)-5-fluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | $^1$H NMR (400 MHz, DMSO-d6) δ 1H NMR (400 MHz, DMSO-d6) ä ppm 10.50 (s, 1 H) 8.75 (d, J = 5.01 Hz, 1 H) 8.02 (s, 1 H) 7.81 (dd, J = 5.01, 1.59 Hz, 1 H) 7.58-7.73 (m, 2 H) 7.27 (d, J = 8.31 Hz, 1 H) 7.07 (d, J = 7.58 Hz, 1 H) 6.80 (s, 1 H) 6.66 (dd, J = 7.52, 1.28 Hz, 1 H) 5.19 (t, J = 5.69 Hz, 1 H) 3.74-4.01 (m, 3 H) 3.38-3.70 (m, 5 H) 2.83-3.11 (m, 3 H) 2.22 (s, 3 H) 1.63-1.80 (m, 6 H).; LCMS (m/z) (M + H) = 508.2, 1.44 min. |
| 401 | 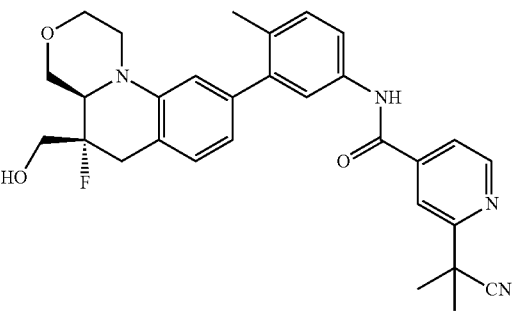 [SMILES: Cc1ccc(NC(=O)c2ccnc(C(C)(C)C#N)c2)cc1-c1ccc2c(c1)N1CCOC[C@@H]1[C@](F)(CO)C2] | 2-(2-cyanopropan-2-yl)-N-(3-((4aR,5S)-5-fluoro-5-(hydroxymethyl)-1,2,4,4a,5,6-hexahydro-[1,4]oxazino[4,3-a]quinolin-9-yl)-4-methylphenyl)isonicotinamide | $^1$H NMR (400 MHz, DMSO-d6) δ 1H NMR (400 MHz, DMSO-d6) ä ppm 10.49 (s, 1 H) 8.80 (dd, J = 5.07, 0.67 Hz, 1 H) 8.00 (s, 1 H) 7.86 (dd, J = 5.01, 1.47 Hz, 1 H) 7.67 (dd, J = 8.25, 2.14 Hz, 1 H) 7.60 (d, J = 2.20 Hz, 1 H) 7.28 (d, J = 8.44 Hz, 1 H) 7.07 (d, J = 7.70 Hz, 1 H) 6.80 (s, 1 H) 6.66 (dd, J = 7.52, 1.28 Hz, 1 H) 5.19 (t, J = 5.69 Hz, 1 H) 3.75-3.98 (m, 3 H) 3.40-3.72 (m, 5 H) 2.81-3.08 (m, 3 H) 2.20-2.33 (m, 3 H) 1.75-1.93 (m, 7 H).; LCMS (m/z) (M + H) = 515.1, 1.41 min. |
| 403 | 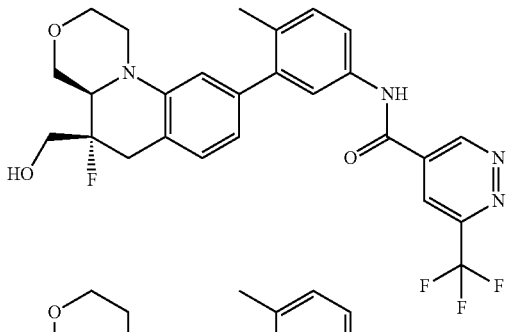 | N-(3-((4aR,5S)-5-fluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, DMSO-d6) δ 10.80 (s, 1 H) 9.91 (d, J = 1.96 Hz, 1 H) 8.67 (d, J = 2.08 Hz, 1 H) 7.67 (d, J = 8.53 Hz, 1 H) 7.62 (s, 1 H) 7.27-7.39 (m, 1 H) 7.03-7.12 (m, 1 H) 6.80 (s, 1 H) 6.66 (dd, J = 7.58, 1.34 Hz, 1 H) 6.23-6.24 (m, 1 H) 5.19 (t, J = 5.75 Hz, 1 H) 3.76-3.97 (m, 3 H) 3.39-3.72 (m, 5 H) 2.83-3.10 (m, 3 H) 2.24 (s, 3 H).; LCMS (m/z) (M + H) = 517.1, 1.42 min. |
| 404 | 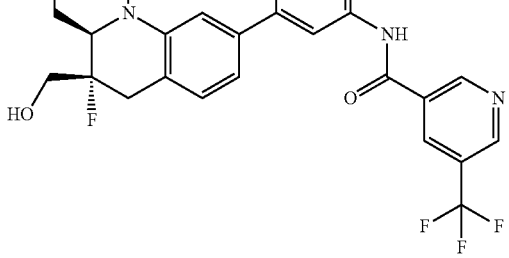 | N-(3-((4aR,5S)-5-fluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, DMSO-d6) δ 10.57 (s, 1 H) 9.37 (d, J = 1.59 Hz, 1 H) 9.18 (s, 1 H) 8.68 (s, 1 H) 7.62-7.71 (m, 1 H) 7.61 (s, 1 H) 7.28 (d, J = 8.44 Hz, 1 H) 7.07 (d, J = 7.58 Hz, 1 H) 6.80 (s, 1 H) 6.67 (dd, J = 7.64, 1.28 Hz, 1 H) 5.19 (br s, 1 H) 3.78-3.99 (m, 3 H) 3.37-3.73 (m, 6 H) 2.82-3.13 (m, 4 H) 2.23 (s, 3 H).; LCMS (m/z) (M + H) = 516.2, 1.43 min. |

345

Intermediate for Example 405: (rac)-(9-chloro-5-(fluoromethyl)-1,2,4,4a,5,6-hexahydro-[1,4]oxazino[4,3-a][1,5]naphthyridin-5-yl)methanol

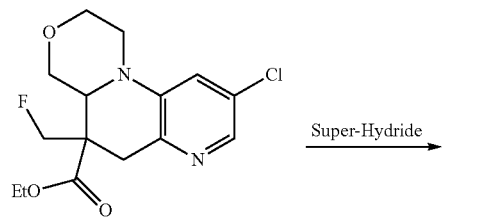

Super-Hydride →

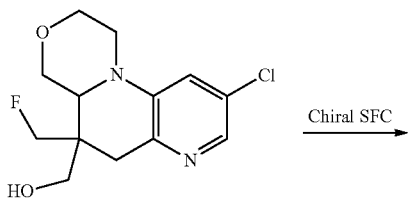

Chiral SFC →

346

-continued

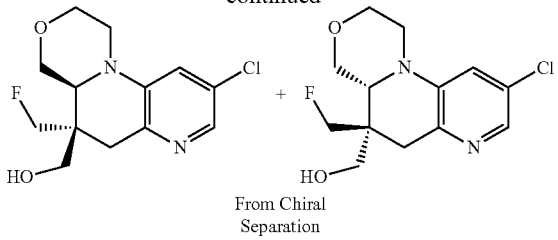

From Chiral Separation ethyl 9-chloro-5-(fluoromethyl)-1,2,4,4a,5,6-hexahydro[1,4]oxazino[4,3-a][1,5]naphthyridine-5-carboxylate (350 mg, 1.065 mmol) was dissolved in THF (10 mL) and then cooled in ice-bath. super hydride (1.0 M in THF) (3.19 mL, 3.19 mmol) was added dropwise and the mixture agitated in ice-bath for 60 min and then quenched by addition of water and then sat'd Na₂CO₃. The product was extracted with EtOAc and the organic layer was washed with Sat'd NH₄Cl and then dried (MgSO₄), filtered and concentrated in vacuo. The residue was purified by flash chromatography (0-70% EtOAc/heptane) to afford the desired product as a white solid in a 80:20 diastereomeric ratio. This material was submitted for chiral separation, which afforded appreciable quantities of only the enantiomeric pairs from major diastereomer. LCMS (m/z) (M+H)=287.2, 0.64 min.

| | | | |
|---|---|---|---|
| 405 | 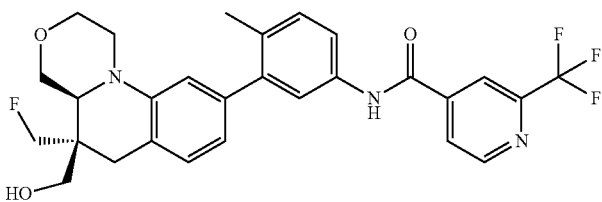 [SMILES: Cc1ccc(NC(=O)c2ccnc(C(F)(F)F)c2)cc1-c1ccc2c(c1)N1CCOC[C@@H]1[C@@](CO)(CF)C2] | N-(3-((4aS,5S)-5-(fluoromethyl)-5-(hydroxymethyl)-1,2,4,4a,5,6-hexahydro-[1,4]oxazino[4,3-a]quinolin-9-yl)-4-methylphenyl)-2-(trifluoromethyl) isonicotinamide | ¹H NMR (400 MHz, DMSO-d6) δ ppm 10.67 (s, 1 H) 8.99 (d, J = 5.01 Hz, 1 H) 8.36 (s, 1 H) 8.19 (dd, J = 4.95, 1.16 Hz, 1 H) 7.85 (d, J = 1.71 Hz, 1H) 7.72 (dd, J = 8.25, 2.26 Hz, 1 H) 7.65 (d, J = 2.20 Hz, 1 H) 7.33 (d, J = 8.44 Hz, 1 H) 7.25 (d, J = 1.59 Hz, 1 H) 5.04 (t, J = 5.14 Hz, 1 H) 4.30-4.65 (m, 2 H) 3.74-4.06 (m, 3 H) 3.41-3.54 (m, 4 H) 3.29 (br s, 1 H) 2.83-2.98 (m, 2 H) 2.68 (d, J = 17.24 Hz, 1 H) 2.24 (s, 3 H); LCMS (m/z) (M + H) = 531.2, 0.89 min. |
| 406 | 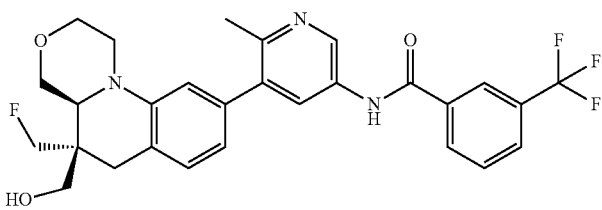 [SMILES: Cc1ncc(NC(=O)c2cccc(C(F)(F)F)c2)cc1-c1ccc2c(c1)N1CCOC[C@@H]1[C@@](CO)(CF)C2] | N-(5-((4aS,5S)-5-(fluoromethyl)-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | ¹H NMR (400 MHz, DMSO-d6) δ ppm 10.66 (s, 1 H) 8.86 (d, J = 2.44 Hz, 1 H) 8.24-8.39 (m, 2 H) 8.05 (d, J = 2.45 Hz, 1 H) 8.00 (d, J = 7.83 Hz, 1H) 7.90 (d, J = 1.59 Hz, 1 H) 7.76-7.85 (m, 1 H) 7.33 (d, J = 1.59 Hz, 1 H) 5.05 (t, J = 5.14 Hz, 1 H) 4.30-4.65 (m, 2 H) 3.80-4.08 (m, 3 H) 3.42-3.57 (m, 4 H) 2.84-3.05 (m, 2 H) 2.69 (d, J = 17.24 Hz, 1 H) 2.44 (s, 3 H).; LCMS (m/z) (M + H) = 531.2, 0.83 min. |
| 407 | 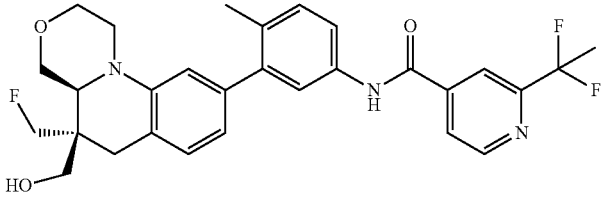 [SMILES: Cc1ccc(NC(=O)c2ccnc(C(C)(F)F)c2)cc1-c1ccc2c(c1)N1CCOC[C@@H]1[C@@](CO)(CF)C2] | 2-(1,1-difluoroethyl)-N-(3-((4aS,5S)-5-(fluoromethyl)-5-(hydroxymethyl)-1,2,4,4a,5,6-hexahydro-[1,4]oxazino[4,3-a]quinolin-9-yl)-4-methylphenyl) isonicotinamide | ¹H NMR (400 MHz, DMSO-d6) δ ppm 10.62 (s, 1 H) 8.88 (d, J = 5.01 Hz, 1 H) 8.18 (s, 1 H) 8.03 (dd, J = 5.01, 1.34 Hz, 1 H) 7.86 (d, J = 1.59 Hz, 1H) 7.73 (dd, J = 8.31, 2.20 Hz, 1 H) 7.66 (d, J = 2.20 Hz, 1 H) 7.32 (d, J = 8.44 Hz, 1 H) 7.26 (d, J = 1.34 Hz, 1 H) 5.04 (br t, J = 4.71 Hz, 1 H) 4.25-4.68 (m, 2 H) 3.77-4.10 (m, 3 H) 3.43-3.62 (m, 4 H) 2.86-3.03 (m, 2 H) 2.68 (d, J = 17.36 Hz, 1 H) 2.24 (s, 3 H) 2.05 (t, J = 19.13 Hz, 3 H).; LCMS (m/z) (M + H) = 527.2, 0.83 min. |

| | | | |
|---|---|---|---|
| 408 | 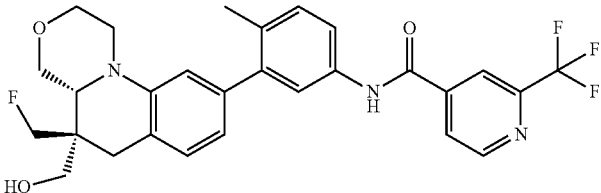 [SMILES: Cc1ccc(NC(=O)c2ccnc(C(F)(F)F)c2)cc1-c1ccc2c(c1)N1CCOC[C@H]1[C@](CO)(CF)C2] | N-(3-((4aR,5R)-5-(fluoromethyl)-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | ¹H NMR (400 MHz, DMSO-d6) δ ppm 10.62 (s, 1 H) 8.88 (d, J = 5.01 Hz, 1 H) 8.18 (s, 1 H) 8.03 (dd, J = 5.01, 1.34 Hz, 1H) 7.86 (d, J = 1.59 Hz, 1H) 7.73 (dd, J = 8.31, 2.20 Hz, 1 H) 7.66 (d, J = 2.20 Hz, 1 H) 7.32 (d, J = 8.44 Hz, 1 H) 7.26 (d, J = 1.34 Hz, 1 H) 5.04 (br t, J = 4.71 Hz, 1 H) 4.25-4.68 (m, 2 H) 3.77-4.10 (m, 3 H) 3.43-3.62 (m, 4 H) 2.86-3.03 (m, 2 H) 2.68 (d, J = 17.36 Hz, 1 H) 2.24 (s, 3 H) 2.05 (t, J = 19.13 Hz, 3 H); LCMS (m/z) (M + H) = 531.2, 0.86 min. |
| 409 | 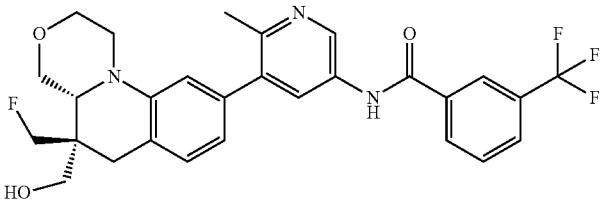 [SMILES: Cc1ncc(NC(=O)c2cccc(C(F)(F)F)c2)cc1-c1ccc2c(c1)N1CCOC[C@H]1[C@](CO)(CF)C2] | N-(5-((4aR,5R)-5-(fluoromethyl)-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | ¹H NMR (400 MHz, DMSO-d6) δ ppm 10.62 (s, 1 H) 8.88 (d, J = 5.01 Hz, 1 H) 8.18 (s, 1 H) 8.03 (dd, J = 5.01, 1.34 Hz, 1H) 7.86 (d, J = 1.59 Hz, 1H) 7.73 (dd, J = 8.31, 2.20 Hz, 1 H) 7.66 (d, J = 2.20 Hz, 1 H) 7.32 (d, J = 8.44 Hz, 1 H) 7.26 (d, J = 1.34 Hz, 1 H) 5.04 (br t, J = 4.71 Hz, 1 H) 4.25-4.68 (m, 2 H) 3.77-4.10 (m, 3 H) 3.43-3.62 (m, 4 H) 2.86-3.03 (m, 2 H) 2.68 (d, J = 17.36 Hz, 1 H) 2.24 (s, 3 H) 2.05 (t, J = 19.13 Hz, 3 H).; LCMS (m/z) (M + H) = 31.2, 0.81 min. |
| 410 | 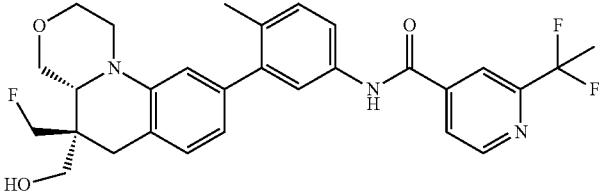 [SMILES: Cc1ccc(NC(=O)c2ccnc(C(C)(F)F)c2)cc1-c1ccc2c(c1)N1CCOC[C@H]1[C@](CO)(CF)C2] | 2-(1,1-difluoroethyl)-N-(3-((4aR,5R)-5-(fluoromethyl)-5-(hydroxymethyl)-1,2,4,4a,5,6-hexahydro-[1,4]oxazino[4,3-a]quinolin-9-yl)-4-methylphenyl)isonicotinamide | ¹H NMR (400 MHz, DMSO-d6) δ ppm 10.66 (s, 1 H) 8.86 (d, J = 2.44 Hz, 1 H) 8.24-8.39 (m, 2 H) 8.05 (d, J = 2.45 Hz, 1 H) 8.00 (d, J = 7.83 Hz, 1H) 7.90 (d, J = 1.59 Hz, 1 H) 7.76-7.85 (m, 1 H) 7.33 (d, J = 1.59 Hz, 1 H) 5.05 (t, J = 5.14 Hz, 1 H) 4.30-4.65 (m, 2 H) 3.80-4.08 (m, 3 H) 3.42-3.57 (m, 4 H) 2.84-3.05 (m, 2 H) 2.69 (d, J = 17.24 Hz, 1 H) 2.44 (s, 3 H).; LCMS (m/z) (M + H) = 527.2, 0.83 min. |
| 411 | 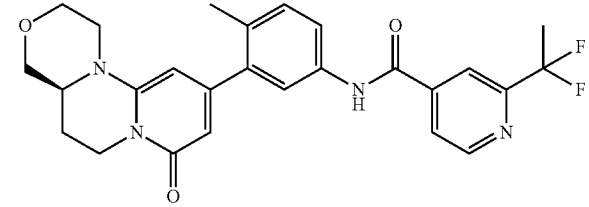 [SMILES: Cc1ccc(NC(=O)c2ccnc(C(C)(F)F)c2)cc1-c1cc2n(c(=O)c1)CC[C@H]1COCCN21] | (S)-2-(1,1-difluoroethyl)-N-(4-methyl-3-(8-oxo-1,2,4,4a,5,6-hexahydro-8H-pyrido[2',1':2,3]pyrimido[6,1-c][1,4]oxazin-10-yl)phenyl)isonicotinamide | ¹H NMR (400 MHz, DMSO-d6) δ ppm 10.62 (s, 1 H) 8.88 (d, J = 5.01 Hz, 1 H) 8.18 (s, 1 H) 8.03 (d, J = 4.89 Hz, 1 H) 7.61-7.77 (m, 2 H) 7.28 (d, J = 8.31 Hz, 1 H) 5.63 (d, J = 1.47 Hz, 1 H) 5.55 (d, J = 1.47 Hz, 1 H) 3.90-4.07 (m, 2 H) 3.74-3.89 (m, 2 H) 3.63 (br d, J = 12.96 Hz, 1 H) 3.53 (td, J = 11.68, 2.57 Hz, 1 H) 3.35 (br dd, J = 6.85, 3.18 Hz, 1 H) 3.23-3.30 (m, 1 H) 3.07 (td, J = 12.32, 3.48 Hz, 1 H) 2.27 (s, 3 H) 2.18-2.19 (m, 1 H) 1.91-2.12 (m, 4 H) 1.51-1.72 (m, 1 H).; LCMS (m/z) (M + H) = 481.0, 0.94 min. |
| 412 | 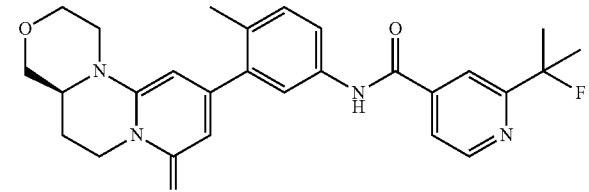 | (S)-2-(2-fluoropropan-2-yl)-N-(4-methyl-3-(8-oxo-1,2,4,4a,5,6-hexahydro-8H-pyrido[2',1':2,3]pyrimido[6,1-c][1,4]oxazin-10-yl)phenyl)isonicotinamide | ¹H NMR (400 MHz, DMSO-d6) δ ppm 10.53 (s, 1 H) 8.75 (d, J = 5.14 Hz, 1 H) 8.01 (s, 1 H) 7.81 (dd, J = 5.07, 1.65 Hz, 1 H) 7.62-7.75 (m, 2 H) 7.27 (d, J = 8.44 Hz, 1 H) 5.63 (d, J = 1.59 Hz, 1 H) 5.54 (d, J = 1.59 Hz, 1 H) 3.92-4.02 (m, 2 H) 3.75-3.91 (m, 2 H) 3.63 (br d, J = 12.96 Hz, 1 H), 3.53 (td, J = 11.68, 2.57 Hz, 1 H) 3.33-3.43 (m, 1 H) 3.20-3.29 (m, 1 H) 3.07 (td, J = 12.32, 3.36 Hz, 1 H) 2.26 (s, 3 H) 1.95-2.11 (m, 1 H) 1.73 (s, 3 H) 1.57-1.70 (m, 4 H).; LCMS (m/z) (M + H) = 477.1, 0.95 min. |

-continued

| Ex. No. | Structure | Name (NVP #) | Physical Data |
|---|---|---|---|
| 413 | 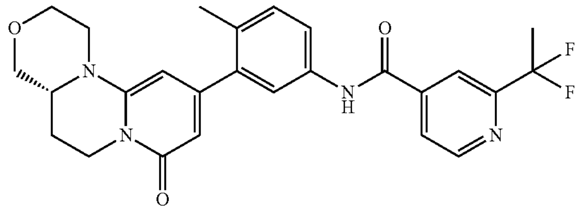 [SMILES: Cc1ccc(NC(=O)c2ccnc(C(C)(F)F)c2)cc1-c1cc2n(c(=O)c1)CC[C@@H]1COCCN21] | (R)-2-(1,1-difluoroethyl)-N-(4-methyl-3-(8-oxo-1,2,4,4a,5,6-hexahydro-8H-pyrido[2',1':2,3]pyrimido[6,1-c][1,4]oxazin-10-yl)phenyl)isonicotinamide | $^1$H NMR (400 MHz, DMSO-d6) δ ppm 10.61 (s, 1 H) 8.76-9.01 (m, 1 H) 8.18 (s, 1 H) 8.02 (dd, J = 4.95, 1.41 Hz, 1 H) 7.59-7.80 (m, 2 H) 7.28 (d, J = 8.31 Hz, 1 H) 5.63 (d, J = 1.59 Hz, 1 H) 5.54 (d, J = 1.59 Hz, 1 H) 3.91-4.05 (m, 2 H) 3.76-3.90 (m, 2 H) 3.63 (br d, J = 12.96 Hz, 1 H) 3.53 (td, J = 11.68, 2.69 Hz, 1 H) 3.33-3.45 (m, 1 H) 3.17-3.29 (m, 1 H) 3.07 (td, J = 12.32, 3.48 Hz, 1 H) 2.27 (s, 3 H) 1.93-2.13 (m, 4 H) 1.43-1.68 (m, 1H).; LCMS (m/z) (M + H) = 481.0, 0.94 min. |
| 414 | 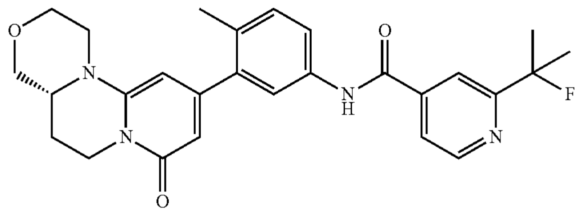 [SMILES: Cc1ccc(NC(=O)c2ccnc(C(C)(C)F)c2)cc1-c1cc2n(c(=O)c1)CC[C@@H]1COCCN21] | (R)-2-(2-fluoropropan-2-yl)-N-(4-methyl-3-(8-oxo-1,2,4,4a,5,6-hexahydro-8H-pyrido[2',1':2,3]pyrimido[6,1-c][1,4]oxazin-10-yl)phenyl)isonicotinamide | $^1$H NMR (400 MHz, DMSO-d6) δ ppm 10.31-10.60 (m, 1 H) 8.75 (d, J = 5.01 Hz, 1 H) 8.02 (s, 1 H) 7.82 (dd, J = 5.01, 1.59 Hz, 1 H) 7.54-7.74 (m, 2 H) 7.27 (d, J = 8.31 Hz, 1 H) 5.63 (d, J = 1.59 Hz, 1 H) 5.54 (d, J = 1.47 Hz, 1 H) 3.95 (t, J = 5.81 Hz, 2 H) 3.76-3.89 (m, 2 H) 3.63 (br d, J = 12.96 Hz, 1 H) 3.53 (td, J = 11.68, 2.57 Hz, 1 H) 3.33-3.40 (m, 1 H) 3.21-3.29 (m, 1 H) 3.07 (td, J = 12.35, 3.42 Hz, 1 H) 2.26 (s, 3 H) 1.93-2.13 (m, 1H) 1.74 (s, 3 H) 1.68 (s, 3 H) 1.56-1.66 (m, 1 H)..; LCMS (m/z) (M + H) = 477.1, 0.95 min. |
| Ex. No. | Structure | Name (NVP #) | Physical Data |
| 415 | 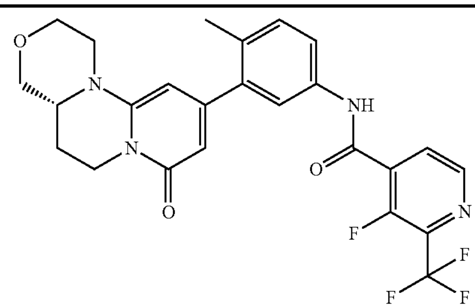 | (R)-3-fluoro-N-(4-methyl-3-(8-oxo-1,2,4,4a,5,6-hexahydro-8H-pyrido[2',1':2,3]pyrimido[6,1-c][1,4]oxazin-10-yl)phenyl)-2-(trifluoromethyl)isonicotinamide | $^1$H NMR (400 MHz, Methanol-d4) δ 8.64 (d, J = 4.7 Hz, 1H), 7.94 (t, J = 4.8 Hz, 1H), 7.61-7.56 (m, 2H), 7.31-7.27 (m, 1H), 5.87 (d, J = 1.6 Hz, 1H), 5.77 (d, J = 1.6 Hz, 1H), 4.27-4.14 (m, 1H), 4.07-3.97 (m, 1H), 3.97-3.90 (m, 1H), 3.85 (d, J = 8.8 Hz, 1H), 3.73-3.58 (m, 2H), 3.45-3.34 (m, 2H), 3.26-3.16 (m, 1H), 2.30 (s, 3H), 2.21-2.07 (m, 1H), 1.82-1.69 (m, 1H). LCMS (m/z) (M + H) = 503.1, Rt = 1.31 min. |
| 416 | 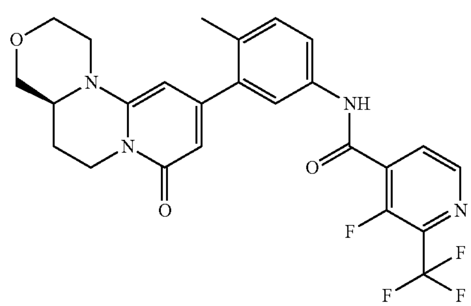 [SMILES: Cc1ccc(NC(=O)c2ccnc(C(F)(F)F)c2F)cc1-c1cc2n(c(=O)c1)CC[C@H]1COCCN21] | (S)-3-fluoro-N-(4-methyl-3-(8-oxo-1,2,4,4a,5,6-hexahydro-8H-pyrido[2',1':2,3]pyrimido[6,1-c][1,4]oxazin-10-yl)phenyl)-2-(trifluoromethyl)isonicotinamide | $^1$H NMR (400 MHz, Methanol-d4) δ 8.64 (d, J = 4.7 Hz, 1H), 7.94 (t, J = 4.8 Hz, 1H), 7.63-7.53 (m, 2H), 7.29 (d, J = 7.8 Hz, 1H), 5.87 (d, J = 1.6 Hz, 1H), 5.77 (d, J = 1.6 Hz, 1H), 4.26-4.13 (m, 1H), 4.08-3.98 (m, 1H), 3.98-3.90 (m, 1H), 3.85 (d, J = 8.9 Hz, 1H), 3.72-3.59 (m, 2H), 3.45-3.36 (m, 2H), 3.26-3.16 (m, 1H), 2.30 (s, 3H), 2.21-2.09 (m, 1H), 1.81-1.70 (m, 1H). LCMS (m/z) (M + H) = 503.1, Rt = 1.30 min. |

Example 417

11-(5-amino-2-methylphenyl)-1,2,5,5a,6,7-hexahydro-4H,9H-pyrido[2',1':2,3]pyrimido[1,6-d][1,4]oxazepin-9-one

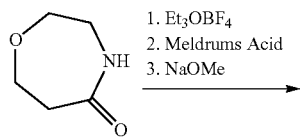

1. Et$_3$OBF$_4$
2. Meldrums Acid
3. NaOMe

-continued

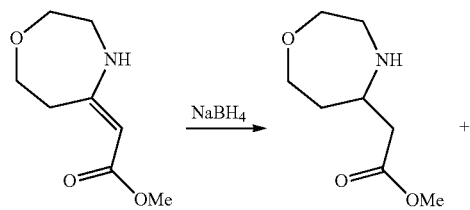

NaBH$_4$

+

-continued

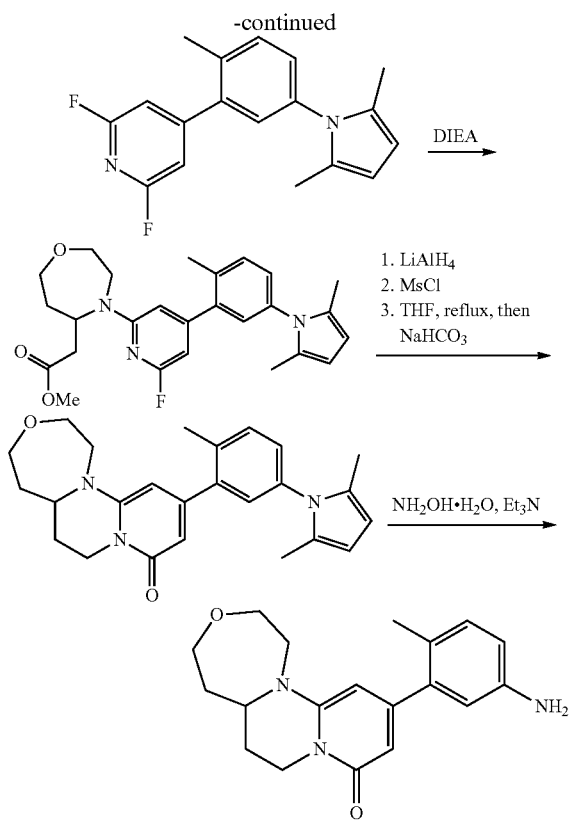

Step 1:

Into a 250 mL RB flask were charged 1,4-oxazepan-5-one (5 g, 43.4 mmol) and DCM (43.4 ml). To the mixture at room temperature under nitrogen was added triethyloxonium tetrafluoroborate (9.08 g, 47.8 mmol). The mixture was agitated at room temperature overnight and the next morning, the reaction mixture was quenched by addition of Sat'd NaHCO₃. The organic layer was separated and dried (MgSO₄), filtered and concentrated in vacuo (30° C., 250 mmHg) to afford the crude 5-ethoxy-2,3,6,7-tetrahydro-1,4-oxazepine (5.76 g, 40.2 mmol, 93% yield). The crude product 5-ethoxy-2,3,6,7-tetrahydro-1,4-oxazepine from above and 2,2-dimethyl-1,3-dioxane-4,6-dione (5.80 g, 40.2 mmol) were suspended in benzene (40.2 ml) and then Et₃N (1.115 ml, 8.05 mmol) was added. The mixture was refluxed overnight. The next morning, the mixture was concentrated in vacuo and the orange-brown syrup residue was azeotroped with toluene (2×20 mL) and the residue 2,2-dimethyl-5-(1,4-oxazepan-5-ylidene)-1,3-dioxane-4,6-dione was taken to the next step as such without any further purification. The crude 2,2-dimethyl-5-(1,4-oxazepan-5-ylidene)-1,3-dioxane-4,6-dione from above was dissolved in MeOH (108 ml) and then NaOMe (5.26 g, 97 mmol) was added in one portion. The mixture was agitated at reflux for overnight and then concentrated in vacuo and the residue neutralized with ammonium chloride (Sa'td) and then with 6N HCl. The product was extracted with EtOAc and the organic layer was dried (MgSO₄), filtered and concentrated in vacuo and the residue (E)-methyl 2-(1,4-oxazepan-5-ylidene)acetate taken to the next step as such without any further purification. LCMS (m/z) (M+H)=172.2, 0.57 min.

Step 2:

(E)-methyl 2-(1,4-oxazepan-5-ylidene)acetate (2.82 g, 16.47 mmol) was suspended in Dioxane (43.9 ml) and Acetic Acid (10.98 ml) and then at room temperature was added NaBH₄ (0.623 g, 16.47 mmol) portionwise. The mixture was then agitated at room temperature for 30 min and then concentrated in vacuo. The residue was basified with Na₂CO₃ (Sat'd) and dissolved in EtOAc and washed with water. The organic layer was dried (MgSO4), filtered and concentrated in vacuo to afford 1.31 gram of methyl 2-(1,4-oxazepan-5-yl)acetate taken to the next step as such. LCMS (m/z) (M+H)=174.0, 0.12 min.

Step 3:

methyl 2-(1,4-oxazepan-5-yl)acetate (600 mg, 3.46 mmol), 4-(5-(2,5-dimethyl-1H-pyrrol-1-yl)-2-methylphenyl)-2,6-difluoropyridine (909 mg, 3.05 mmol), DIEA (1815 µl, 10.39 mmol) were combined in NMP (3464 µl) and the mixture heated in MW at 200 for 60 min. After the elapsed time, the reaction mixture was diluted with EtOAc and washed with water (thrice) and brine and dried (MgSO₄), filtered and concentrated in vacuo. The residue was purified by flash chromatography (0-20% EtOAc/heptane) to afford 733 mg of the desired product methyl 2-(4-(4-(5-(2,5-dimethyl-1H-pyrrol-1-yl)-2-methylphenyl)-6-fluoropyridin-2-yl)-1,4-oxazepan-5-yl)acetate as a faint yellow solid. LCMS (m/z) (M+H)=452.2, 1.83 min.

Step 4:

methyl 2-(4-(4-(5-(2,5-dimethyl-1H-pyrrol-1-yl)-2-methylphenyl)-6-fluoropyridin-2-yl)-1,4-oxazepan-5-yl)acetate (733 mg, 1.623 mmol) was dissolved in THF (16.2 ml) and cooled to 0° C. To the mixture was then added LiAlH₄ (1.0 M in THF) (3.25 ml, 3.25 mmol) dropwise. After 30 min, the reaction mixture was quenched by addition of water (66 uL) and then 15% NaOH (132 uL) and then water (198 uL). The mixture was agitated vigorously for 5 min and then diluted with EtOAc and MgSO₄ was added. The entire mixture was filtered and the filtrate concentrated in vacuo to afford crude product 2-(4-(4-(5-(2,5-dimethyl-1H-pyrrol-1-yl)-2-methylphenyl)-6-fluoropyridin-2-yl)-1,4-oxazepan-5-yl)ethanol. LCMS (m/z) (M+H)=424.2, 1.34 min. The crude product from above was dissolved in DCM (Volume: 1.62E+04 µl) and then Et3N (1125 µl, 8.12 mmol) was added. The mixture was cooled to 0° C. and then MsCl (139 µl, 1.785 mmol) was added. The mixture was agitated at 0° C. for 10 min and then concentrated in vacuo. The residue was dissolved in THF (35 mL) and heated to reflux for 48 h. Accordingly, after a total of 48 h of reflux, Sat'd NaHCO₃ (30 mL) was added and the mixture refluxed for another 2 h and then cooled to room temperature and extracted with EtOAc. The combined organic layer was dried (MgSO₄), filtered and concentrated in vacuo. the residue was purified by flash chromatography (0-10% MeOH/DCM) to afford the desired product 11-(5-(2,5-dimethyl-1H-pyrrol-1-yl)-2-methylphenyl)-1,2,5,5a,6,7-hexahydropyrido[2',1':2,3]pyrimido[1,6-d][1,4]oxazepin-9(4H)-one. LCMS (m/z) (M+H)=404.2, 1.09 min.

Step 5:

11-(5-(2,5-dimethyl-1H-pyrrol-1-yl)-2-methylphenyl)-1,2,5,5a,6,7-hexahydropyrido[2',1':2,3]pyrimido[1,6-d][1,4]oxazepin-9(4H)-one (34 mg, 0.084 mmol), hydroxylamine hydrochloride (70.3 mg, 1.011 mmol) were suspended in EtOH (1.8 mL) and Water (0.600 mL) and then triethylamine (0.070 mL, 0.506 mmol) was added. The mixture was agitated at 95° C. (bath temperature) overnight. The next afternoon (ca~18 h) the mixture was concentrated in vacuo and the residue was extracted twice with EtOAc. The organic layer was dried (MgSO₄), filtered and concentrated in vacuo. The residue was taken to the next step without any further purification. LCMS(m/z) (M+H)=326.1, 0.53 min.

| # | Structure | Name | Data |
|---|---|---|---|
| 417 | 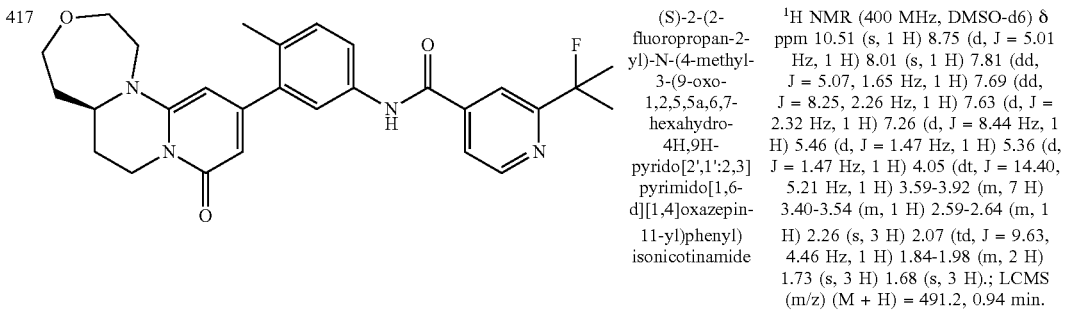 | (S)-2-(2-fluoropropan-2-yl)-N-(4-methyl-3-(9-oxo-1,2,5,5a,6,7-hexahydro-4H,9H-pyrido[2',1':2,3]pyrimido[1,6-d][1,4]oxazepin-11-yl)phenyl)isonicotinamide | ¹H NMR (400 MHz, DMSO-d6) δ ppm 10.51 (s, 1 H) 8.75 (d, J = 5.01 Hz, 1 H) 8.01 (s, 1 H) 7.81 (dd, J = 5.07, 1.65 Hz, 1 H) 7.69 (dd, J = 8.25, 2.26 Hz, 1 H) 7.63 (d, J = 2.32 Hz, 1 H) 7.26 (d, J = 8.44 Hz, 1 H) 5.46 (d, J = 1.47 Hz, 1 H) 5.36 (d, J = 1.47 Hz, 1 H) 4.05 (dt, J = 14.40, 5.21 Hz, 1 H) 3.59-3.92 (m, 7 H) 3.40-3.54 (m, 1 H) 2.59-2.64 (m, 1 H) 2.26 (s, 3 H) 2.07 (td, J = 9.63, 4.46 Hz, 1 H) 1.84-1.98 (m, 2 H) 1.73 (s, 3 H) 1.68 (s, 3 H).; LCMS (m/z) (M + H) = 491.2, 0.94 min. |
| 418 | 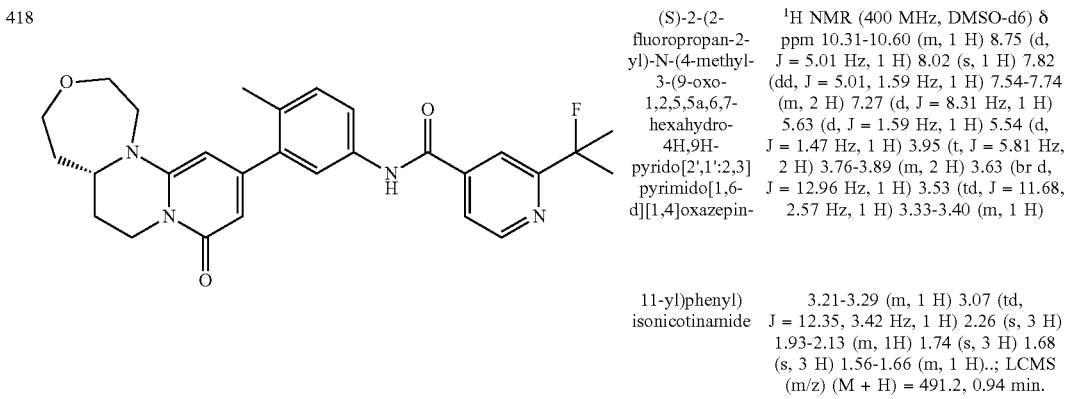 | (S)-2-(2-fluoropropan-2-yl)-N-(4-methyl-3-(9-oxo-1,2,5,5a,6,7-hexahydro-4H,9H-pyrido[2',1':2,3]pyrimido[1,6-d][1,4]oxazepin-11-yl)phenyl)isonicotinamide | ¹H NMR (400 MHz, DMSO-d6) δ ppm 10.31-10.60 (m, 1 H) 8.75 (d, J = 5.01 Hz, 1 H) 8.02 (s, 1 H) 7.82 (dd, J = 5.01, 1.59 Hz, 1 H) 7.54-7.74 (m, 2 H) 7.27 (d, J = 8.31 Hz, 1 H) 5.63 (d, J = 1.59 Hz, 1 H) 5.54 (d, J = 1.47 Hz, 1 H) 3.95 (t, J = 5.81 Hz, 2 H) 3.76-3.89 (m, 2 H) 3.63 (br d, J = 12.96 Hz, 1 H) 3.53 (td, J = 11.68, 2.57 Hz, 1 H) 3.33-3.40 (m, 1 H) 3.21-3.29 (m, 1 H) 3.07 (td, J = 12.35, 3.42 Hz, 1 H) 2.26 (s, 3 H) 1.93-2.13 (m, 1H) 1.74 (s, 3 H) 1.68 (s, 3 H) 1.56-1.66 (m, 1 H)..; LCMS (m/z) (M + H) = 491.2, 0.94 min. |

The following compounds were made in a similar fashion as Example 418 except for using 4-bromo-2,6-difluorobenzaldehyde in the first step and using chiral SFC of intermediate.

Compounds Derived from Peak 2

| # | Structure | Name | Data |
|---|---|---|---|
| 419 | 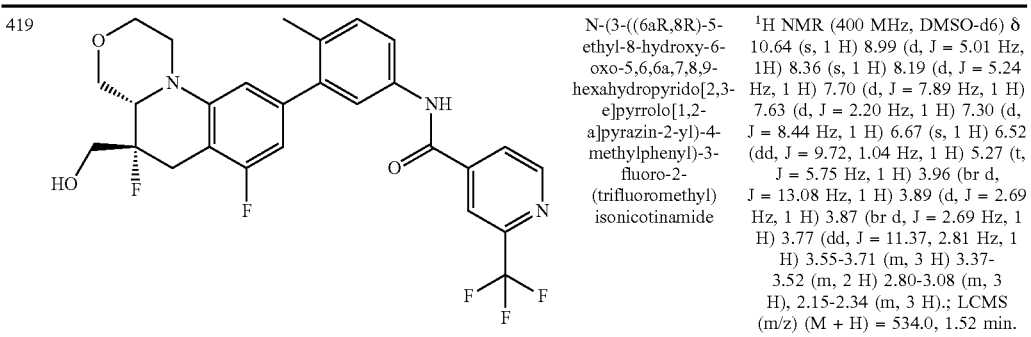 | N-(3-((6aR,8R)-5-ethyl-8-hydroxy-6-oxo-5,6,6a,7,8,9-hexahydropyrido[2,3-e]pyrrolo[1,2-a]pyrazin-2-yl)-4-methylphenyl)-3-fluoro-2-(trifluoromethyl)isonicotinamide | ¹H NMR (400 MHz, DMSO-d6) δ 10.64 (s, 1 H) 8.99 (d, J = 5.01 Hz, 1H) 8.36 (s, 1 H) 8.19 (d, J = 5.24 Hz, 1 H) 7.70 (d, J = 7.89 Hz, 1 H) 7.63 (d, J = 2.20 Hz, 1 H) 7.30 (d, J = 8.44 Hz, 1 H) 6.67 (s, 1 H) 6.52 (dd, J = 9.72, 1.04 Hz, 1 H) 5.27 (t, J = 5.75 Hz, 1 H) 3.96 (br d, J = 13.08 Hz, 1 H) 3.89 (d, J = 2.69 Hz, 1 H) 3.87 (br d, J = 2.69 Hz, 1 H) 3.77 (dd, J = 11.37, 2.81 Hz, 1 H) 3.55-3.71 (m, 3 H) 3.37-3.52 (m, 2 H) 2.80-3.08 (m, 3 H), 2.15-2.34 (m, 3 H).; LCMS (m/z) (M + H) = 534.0, 1.52 min. |
| 420 | 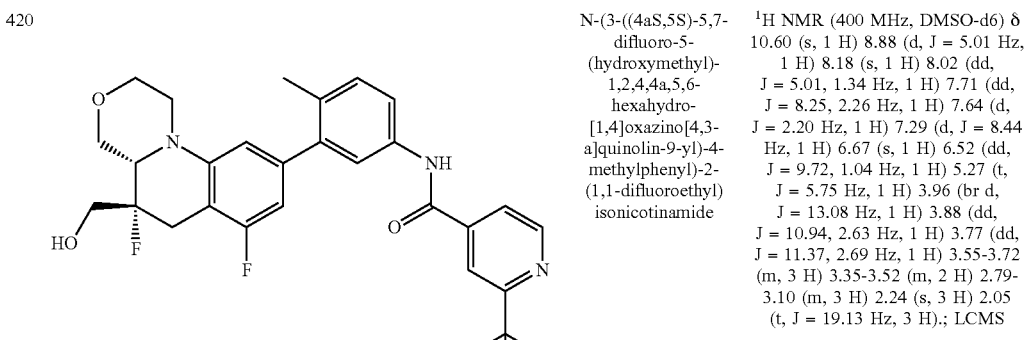 | N-(3-((4aS,5S)-5,7-difluoro-5-(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | ¹H NMR (400 MHz, DMSO-d6) δ 10.60 (s, 1 H) 8.88 (d, J = 5.01 Hz, 1 H) 8.18 (s, 1 H) 8.02 (dd, J = 5.01, 1.34 Hz, 1 H) 7.71 (dd, J = 8.25, 2.26 Hz, 1 H) 7.64 (d, J = 2.20 Hz, 1 H) 7.29 (d, J = 8.44 Hz, 1 H) 6.67 (s, 1 H) 6.52 (dd, J = 9.72, 1.04 Hz, 1 H) 5.27 (t, J = 5.75 Hz, 1 H) 3.96 (br d, J = 13.08 Hz, 1 H) 3.88 (dd, J = 10.94, 2.63 Hz, 1 H) 3.77 (dd, J = 11.37, 2.69 Hz, 1 H) 3.55-3.72 (m, 3 H) 3.35-3.52 (m, 2 H) 2.79-3.10 (m, 3 H) 2.24 (s, 3 H) 2.05 (t, J = 19.13 Hz, 3 H).; LCMS (m/z) (M + H) = 530.1, 1.48 min. |

| | | | |
|---|---|---|---|
| 421 | 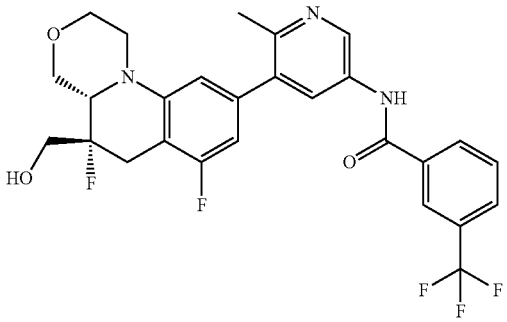 [SMILES: Cc1ncc(NC(=O)c2cccc(C(F)(F)F)c2)cc1-c1cc(F)c2c(c1)N1CCOC[C@H]1[C@](F)(CO)C2] | N-(5-((4aS,5S)-5,7-difluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, DMSO-d6) δ 10.64 (s, 1 H) 8.85 (d, J = 2.45 Hz, 1 H) 8.23-8.44 (m, 2 H) 7.94-8.14 (m, 2 H) 7.81 (t, J = 7.76 Hz, 1 H) 6.75 (s, 1 H) 6.60 (dd, J = 9.72, 1.16 Hz, 1 H) 5.28 (t, J = 5.75 Hz, 1 H) 4.00 (br d, J = 12.96 Hz, 1 H) 3.88 (dd, J = 11.00, 2.69 Hz, 1 H) 3.77 (dd, J = 11.37, 2.69 Hz, 1 H) 3.55-3.70 (m, 3 H) 3.37-3.52 (m, 2 H) 2.76-3.14 (m, 3 H) 2.44 (s, 3 H);.; LCMS (m/z) (M + H) = 534.1, 1.13 min. |
| 422 | 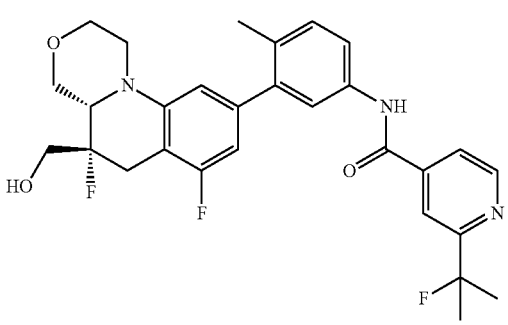 [SMILES: Cc1ccc(NC(=O)c2ccnc(C(C)(C)F)c2)cc1-c1cc(F)c2c(c1)N1CCOC[C@H]1[C@](F)(CO)C2] | N-(3-((4aS,5S)-5,7-difluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | $^1$H NMR (400 MHz, DMSO-d6) δ 10.52 (s, 1 H) 8.65-9.01 (m, 1 H) 8.01 (s, 1 H) 7.81 (dd, J = 5.07, 1.65 Hz, 1 H) 7.70 (dd, J = 8.19, 2.20 Hz, 1H) 7.63 (d, J = 2.20 Hz, 1 H) 7.28 (d, J = 8.44 Hz, 1 H) 6.67 (s, 1 H) 6.52 (dd, J = 9.72, 1.04 Hz, 1 H) 5.26 (br s, 1 H) 3.96 (br d, J = 12.96 Hz, 1 H) 3.88 (dd, J = 11.00, 2.69 Hz, 1 H) 3.76 (dd, J = 11.31, 2.75 Hz, 1 H) 3.55-3.70 (m, 3 H) 3.37-3.52 (m, 2 H) 2.77-3.09 (m, 3 H) 2.23 (s, 3 H) 1.73 (s, 3H) 1.68 (s, 3 H).; LCMS (m/z) (M + H) = 526.1, 1.49 min. |
| 423 | 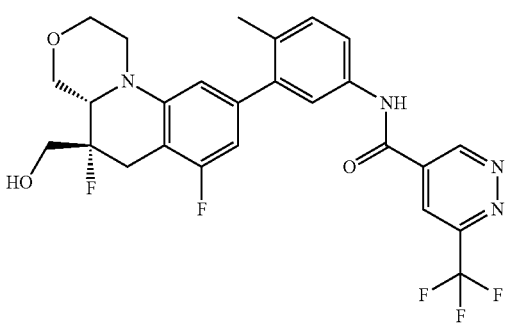 [SMILES: Cc1ccc(NC(=O)c2cnnc(C(F)(F)F)c2)cc1-c1cc(F)c2c(c1)N1CCOC[C@H]1[C@](F)(CO)C2] | N-(3-((4aS,5S)-5,7-difluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, DMSO-d6) δ 10.82 (br s, 1 H) 9.91 (d, J = 1.96 Hz, 1 H) 8.67 (d, J = 1.96 Hz, 1 H) 7.69 (dd, J = 8.19, 2.32 Hz, 1 H) 7.62 (d, J = 2.20 Hz, 1 H) 7.32 (d, J = 8.31 Hz, 1 H) 6.67 (s, 1 H) 6.52 (dd, J = 9.78, 1.10 Hz, 1 H) 5.27 (t, J = 5.75 Hz, 1 H) 3.96 (br d, J = 13.08 Hz, 1 H) 3.88 (dd, J = 11.00, 2.69 Hz, 1 H) 3.77 (dd, J = 11.31, 2.75 Hz, 1H) 3.55-3.72 (m, 3 H) 3.38-3.52 (m, 2 H) 2.78-3.11 (m, 3 H) 2.24 (s, 3 H).; LCMS (m/z) (M + H) = 535.0, 1.45 min. |

Compounds Derived from Peak 4

| | | | |
|---|---|---|---|
| 424 | 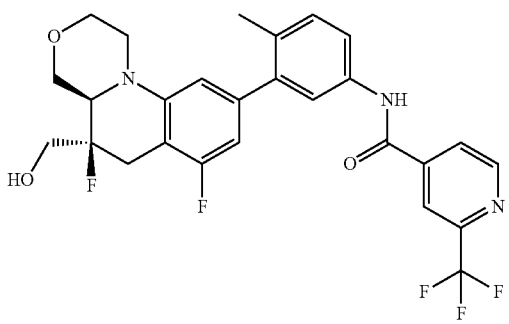 [SMILES: Cc1ccc(NC(=O)c2ccnc(C(F)(F)F)c2)cc1-c1cc(F)c2c(c1)N1CCOC[C@@H]1[C@@](F)(CO)C2] | N-(3-((4aR,5R)-5,7-difluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, DMSO-d6) δ 10.64 (s, 1 H) 8.99 (d, J = 4.89 Hz, 1 H) 8.36 (s, 1 H) 8.19 (dd, J = 4.95, 1.16 Hz, 1 H) 7.70 (d, J = 8.47 Hz, 1H) 7.63 (d, J = 2.32 Hz, 1 H) 7.30 (d, J = 8.44 Hz, 1 H) 6.67 (s, 1 H) 6.52 (dd, J = 9.78, 1.10 Hz, 1 H) 5.27 (t, J = 5.75 Hz, 1 H) 3.96 (br d, J = 13.08 Hz, 1 H) 3.88 (dd, J = 11.00, 2.69 Hz, 1 H) 3.77 (dd, J = 11.43, 2.75 Hz, 1 H) 3.55-3.72 (m, 3 H) 3.37-3.52 (m, 2 H) 2.74-3.12 (m, 3 H) 2.24 (s, 3 H.; LCMS (m/z) (M + H) = 534.1, 1.52 min. |

| | | | |
|---|---|---|---|
| 425 | 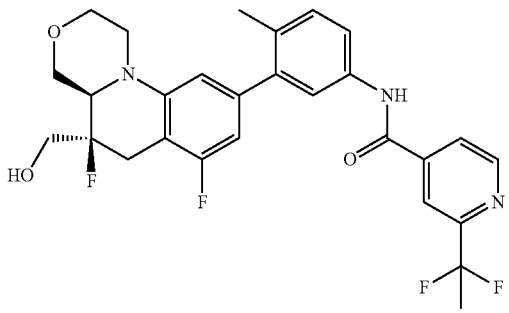 [SMILES: Cc1ccc(NC(=O)c2ccnc(C(C)(F)F)c2)cc1-c1cc(F)c2c(c1)N1CCOC[C@@H]1[C@@](F)(CO)C2] | N-(3-((4aR,5R)-5,7-difluoro-5-(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | $^1$H NMR (400 MHz, DMSO-d6) δ 10.60 (s, 1 H) 8.88 (br d, J = 4.77 Hz, 1 H) 8.18 (s, 1 H) 8.03 (br d, J = 4.77 Hz, 1 H) 7.71 (br d, J = 8.31 Hz, 1H) 7.61-7.67 (m, 1 H) 7.29 (br d, J = 8.19 Hz, 1 H) 6.68 (s, 1 H) 6.53 (br d, J = 9.66 Hz, 1 H) 5.27 (t, J = 5.44 Hz, 1 H) 3.97 (br d, J = 13.08 Hz, 1 H) 3.88 (br d, J = 10.64 Hz, 1 H) 3.77 (br d, J = 11.25 Hz, 1 H) 3.57-3.72 (m, 3 H) 3.39-3.53 (m, 2 H) 2.77-3.12 (m, 3 H) 2.24 (s, 3 H) 1.86-2.14 (m, 3 H).; LCMS (m/z) (M + H) = 530.1, 1.48 min. |
| 426 | 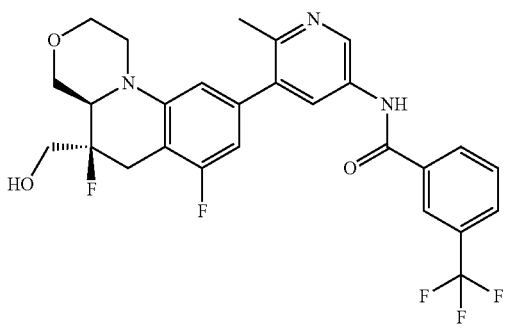 [SMILES: Cc1ncc(NC(=O)c2cccc(C(F)(F)F)c2)cc1-c1cc(F)c2c(c1)N1CCOC[C@@H]1[C@@](F)(CO)C2] | N-(5-((4aR,5R)-5,7-difluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, DMSO-d6) δ 10.64 (s, 1 H) 8.85 (d, J = 2.45 Hz, 1 H) 8.25-8.35 (m, 2 H) 7.96-8.05 (m, 2 H) 7.81 (t, J = 7.82 Hz, 1 H) 6.75 (s, 1 H) 6.60 (dd, J = 9.72, 1.16 Hz, 1 H) 5.28 (t, J = 5.75 Hz, 1 H) 4.00 (br d, J = 12.96 Hz, 1 H) 3.88 (dd, J = 10.94, 2.63 Hz, 1 H) 3.77 (dd, J = 11.43, 2.75 Hz, 1 H) 3.55-3.73 (m, 3 H) 3.37-3.52 (m, 2 H) 2.82-3.13 (m, 3 H) 2.44 (s, 3 H);.; LCMS (m/z) (M + H) = 534.1, 1.13 min. |
| 427 | 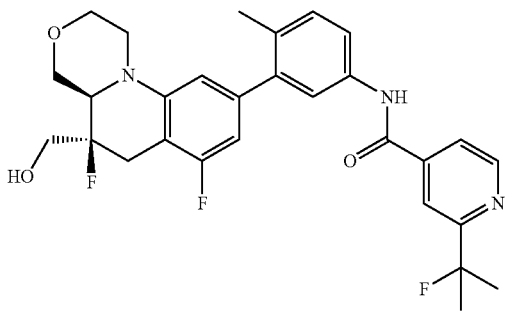 [SMILES: Cc1ccc(NC(=O)c2ccnc(C(C)(C)F)c2)cc1-c1cc(F)c2c(c1)N1CCOC[C@@H]1[C@@](F)(CO)C2] | N-(3-((4aR,5R)-5,7-difluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | $^1$H NMR (400 MHz, DMSO-d6) δ 10.52 (s, 1 H) 8.75 (d, J = 5.15 Hz, 1 H) 8.01 (s, 1 H) 7.81 (dd, J = 5.01, 1.59 Hz, 1 H) 7.71 (dd, J = 8.25, 2.26 Hz, 1 H) 7.63 (d, J = 2.20 Hz, 1 H) 7.28 (d, J = 8.56 Hz, 1 H) 6.67 (s, 1 H) 6.52 (dd, J = 9.78, 1.10 Hz, 1 H) 5.23-5.30 (m, 1 H) 3.96 (br d, J = 13.08 Hz, 1 H) 3.88 (dd, J = 10.94, 2.63 Hz, 1 H) 3.55-3.79 (m, 4 H) 3.45-3.51 (m, 1 H) 3.38-3.52 (m, 1 H) 3.26-3.45 (m, 5 H) 2.81-3.07 (m, 3 H) 2.21-2.34 (m, 3 H) 1.73 (s, 3 H) 1.68 (s, 3 H).; LCMS (m/z) (M + H) = 526.1, 1.49 min. |
| 428 | 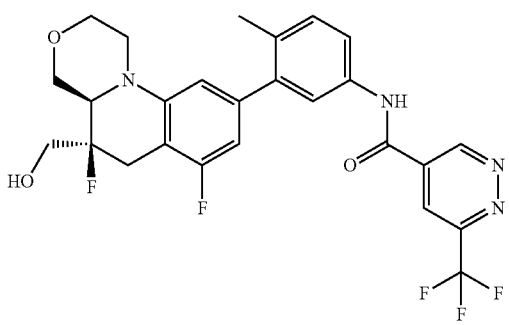 [SMILES: Cc1ccc(NC(=O)c2cnnc(C(F)(F)F)c2)cc1-c1cc(F)c2c(c1)N1CCOC[C@@H]1[C@@](F)(CO)C2] | N-(3-((4aR,5R)-5,7-difluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, DMSO-d6) δ 10.82 (br s, 1 H) 9.91 (d, J = 1.96 Hz, 1 H) 8.67 (d, J = 2.08 Hz, 1 H) 7.69 (dd, J = 8.19, 2.32 Hz, 1 H) 7.62 (d, J = 2.20 Hz, 1 H) 7.32 (d, J = 8.44 Hz, 1 H) 6.67 (s, 1 H) 6.52 (dd, J = 9.78, 1.10 Hz, 1 H) 5.27 (t, J = 5.75 Hz, 1 H) 3.96 (br d, J = 12.84 Hz, 1 H) 3.88 (dd, J = 11.00, 2.69 Hz, 1 H) 3.77 (dd, J = 11.31, 2.75 Hz, 1 H) 3.54-3.72 (m, 3 H) 3.37-3.53 (m, 2 H) 2.79-3.11 (m, 3 H) 2.24 (s, 3 H).; LCMS (m/z) (M + H) = 535.0, 1.45 min. |

Compounds Derived from Peak 1

| | | | |
|---|---|---|---|
| 429 | | N-(3-((4aS,5R)-5,7-difluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | ¹H NMR (400 MHz, DMSO-d6) δ 10.65 (s, 1 H) 8.99 (d, J = 5.01 Hz, 1 H) 8.36 (s, 1 H) 8.19 (dd, J = 4.95, 1.16 Hz, 1 H) 7.70 (d, J = 7.88 Hz, 1H) 7.64 (s, 1 H) 7.30 (d, J = 8.44 Hz, 1 H) 6.66 (s, 1 H) 6.56 (dd, J = 9.72, 1.04 Hz, 1 H) 5.35 (t, J = 5.87 Hz, 1 H) 4.07 (dd, J = 11.13, 3.06 Hz, 1H) 3.81-3.92 (m, 2 H) 3.44-3.71 (m, 4 H) 3.38-3.38 (m, 1 H) 3.26-3.32 (m, 1 H) 2.80-3.07 (m, 3 H) 2.19-2.34 (m, 3 H).; LCMS (m/z) (M + H) = 534.1, 1.52 min.. |
| 430 | | N-(3-((4aS,5R)-5,7-difluoro-5-(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | ¹H NMR (400 MHz, DMSO-d6) δ 10.60 (s, 1 H) 8.88 (d, J = 5.20 Hz, 1 H) 8.18 (s, 1 H) 8.03 (dd, J = 5.01, 1.47 Hz, 1 H) 7.71 (d, J = 7.92 Hz, 1H) 7.65 (s, 1 H) 7.29 (d, J = 8.44 Hz, 1 H) 6.66 (s, 1 H) 6.56 (dd, J = 9.66, 1.10 Hz, 1 H) 5.35 (t, J = 5.81 Hz, 1 H) 4.07 (dd, J = 11.07, 3.12 Hz, 1 H) 3.79-3.92 (m, 2 H) 3.44-3.76 (m, 4 H) 3.35 (dd, J = 10.70, 3.12 Hz, 1 H) 2.79-3.08 (m, 3 H) 2.24 (s, 3 H) 2.05 (t, J = 19.13 Hz, 3 H).; LCMS (m/z) (M + H) = 530.1, 1.48 min. |
| 431 | | N-(5-((4aS,5R)-5,7-difluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | ¹H NMR (400 MHz, DMSO-d6) δ 10.64 (s, 1 H) 8.85 (d, J = 2.45 Hz, 1 H) 8.25-8.35 (m, 2 H) 8.03 (s, 1 H) 7.99 (d, J = 7.57 Hz, 1 H) 7.81 (t, J = 7.82 Hz, 1 H) 6.73 (s, 1 H) 6.64 (dd, J = 9.60, 1.16 Hz, 1 H) 5.36 (t, J = 5.87 Hz, 1 H) 4.07 (dd, J = 11.13, 3.06 Hz, 1 H) 3.81-3.94 (m, 2 H) 3.45-3.77 (m, 4 H) 3.33-3.41 (m, 1 H) 2.82-3.06 (m, 3 H) 2.44 (s, 3 H).; LCMS (m/z) (M + H) = 534.1, 1.134 min. |
| 432 | | N-(3-((4aS,5R)-5,7-difluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | ¹H NMR (400 MHz, DMSO-d6) δ 10.52 (s, 1 H) 8.75 (d, J = 5.01 Hz, 1 H) 8.02 (s, 1 H) 7.82 (dd, J = 5.07, 1.65 Hz, 1 H) 7.70 (d, J = 8.49 Hz, 1H) 7.64 (d, J = 2.20 Hz, 1 H) 7.28 (d, J = 8.44 Hz, 1 H) 6.66 (s, 1 H) 6.56 (dd, J = 9.78, 1.10 Hz, 1 H) 5.35 (s, 1 H) 4.06 (dd, J = 11.19, 3.12 Hz, 1 H) 3.80-3.91 (m, 2 H) 3.44-3.70 (m, 4 H) 3.34 (dd, J = 10.64, 3.06 Hz, 1 H) 2.81-3.08 (m, 3 H) 2.21-2.34 (m, 3 H) 1.72-1.78 (m, 3 H) 1.68 (s, 3H).; LCMS (m/z) (M + H) = 526.1, 1.49 min. |
| 433 | | N-(3-((4aS,5R)-5,7-difluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | ¹H NMR (400 MHz, DMSO-d6) δ 10.82 (br s, 1 H) 9.91 (d, J = 1.96 Hz, 1 H) 8.67 (d, J = 1.96 Hz, 1 H) 7.69 (dd, J = 8.25, 2.26 Hz, 1 H) 7.63 (d, J = 2.32 Hz, 1 H) 7.32 (d, J = 8.44 Hz, 1 H) 6.66 (s, 1 H) 6.56 (dd, J = 9.72, 1.04 Hz, 1 H) 5.35 (t, J = 5.81 Hz, 1 H) 4.07 (dd, J = 11.13, 3.18 Hz, 1 H) 3.77-3.90 (m, 2 H) 3.42-3.69 (m, 4 H) 3.32-3.39 (m, 1 H) 2.80-3.06 (m, 3 H) 2.25 (s, 3 H).; LCMS (m/z) (M + H) = 535.0, 1.45 min. |

| | | | |
|---|---|---|---|
| 434 | 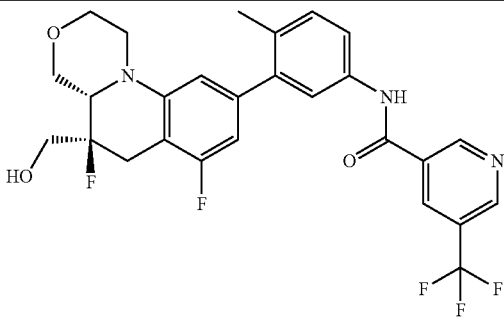 | N-(3-((4aS,5R)-5,7-difluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, DMSO-d6) δ 10.59 (s, 1 H) 9.37 (d, J = 1.83 Hz, 1 H) 9.18 (d, J = 1.22 Hz, 1 H) 8.55-8.75 (m, 1 H) 7.70 (d, J = 8.48 Hz, 1H) 7.62-7.68 (m, 1 H) 7.30 (d, J = 8.44 Hz, 1 H) 6.66 (s, 1 H) 6.56 (dd, J = 9.78, 1.10 Hz, 1 H) 5.35 (t, J = 5.81 Hz, 1 H) 4.07 (dd, J = 11.13, 3.06 Hz, 1H) 3.78-3.93 (m, 2 H) 3.44-3.68 (m, 4 H) 3.32-3.38 (m, 1 H) 2.79-3.11 (m, 3 H) 2.24 (s, 3 H).; LCMS (m/z) (M + H) = 534.1, 1.41 min. |

Compounds Derived from Peak 3

| | | | |
|---|---|---|---|
| 436 | 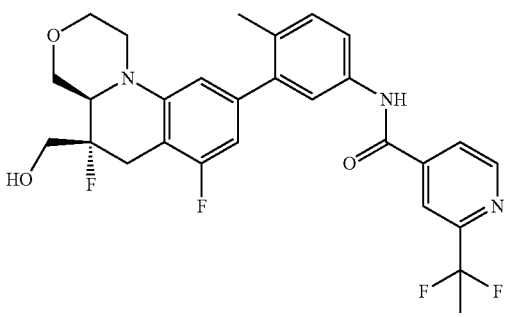 [SMILES: Cc1ccc(NC(=O)c2ccnc(C(C)(F)F)c2)cc1-c1cc(F)c2c(c1)N1CCOC[C@@H]1[C@](F)(CO)C2] | N-(3-((4aR,5S)-5,7-difluoro-5-(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | $^1$H NMR (400 MHz, DMSO-d6) δ 10.60 (s, 1 H) 8.88 (d, J = 5.11 Hz, 1 H) 8.18 (s, 1 H) 8.03 (dd, J = 5.01, 1.47 Hz, 1 H) 7.71 (d, J = 7.92 Hz, 1H) 7.65 (s, 1 H) 7.29 (d, J = 8.44 Hz, 1 H) 6.66 (s, 1 H) 6.56 (dd, J = 9.72, 1.04 Hz, 1 H) 5.35 (t, J = 5.81 Hz, 1 H) 4.07 (dd, J = 11.07, 3.12 Hz, 1 H) 3.81-3.93 (m, 2 H) 3.42-3.72 (m, 4 H) 3.35 (dd, J = 10.70, 3.12 Hz, 1 H) 2.80-3.07 (m, 3 H) 2.24 (s, 3 H) 2.05 (t, J = 19.13 Hz, 3 H).; LCMS (m/z) (M + H) = 530.1, 1.49 min. |
| 437 | 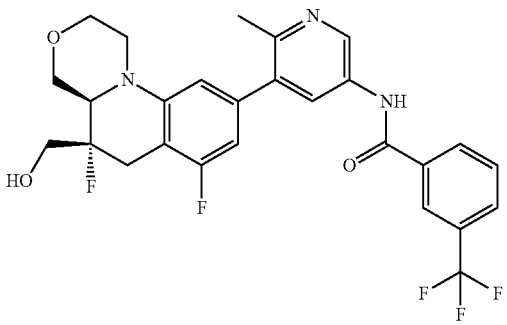 [SMILES: Cc1ncc(NC(=O)c2cccc(C(F)(F)F)c2)cc1-c1cc(F)c2c(c1)N1CCOC[C@@H]1[C@](F)(CO)C2] | N-(5-((4aR,5S)-5,7-difluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, DMSO-d6) δ 10.51-10.72 (m, 1 H) 8.85 (d, J = 2.45 Hz, 1 H) 8.21-8.39 (m, 2 H) 7.94-8.11 (m, 2 H) 7.81 (t, J = 7.83 Hz, 1 H) 6.74 (s, 1 H) 6.64 (dd, J = 9.60, 1.16 Hz, 1 H) 5.36 (t, J = 5.87 Hz, 1 H) 4.07 (dd, J = 11.13, 3.06 Hz, 1 H) 3.81-3.94 (m, 2 H) 3.42-3.78 (m, 4H) 3.37 (br dd, J = 10.64, 2.93 Hz, 1 H) 2.81-3.10 (m, 3 H) 2.44 (s, 3 H).; LCMS (m/z) (M + H) = 534.1. 1.14 min. |
| 438 | 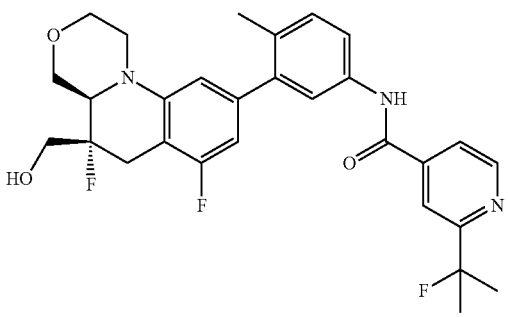 [SMILES: Cc1ccc(NC(=O)c2ccnc(C(C)(C)F)c2)cc1-c1cc(F)c2c(c1)N1CCOC[C@@H]1[C@](F)(CO)C2] | N-(3-((4aR,5S)-5,7-difluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | $^1$H NMR (400 MHz, DMSO-d6) δ 10.52 (s, 1 H) 8.67-8.83 (m, 1 H) 8.02 (s, 1 H) 7.82 (dd, J = 5.07, 1.65 Hz, 1 H) 7.70 (dd, J = 8.19, 2.20 Hz, 1H) 7.64 (d, J = 2.20 Hz, 1 H) 7.28 (d, J = 8.56 Hz, 1 H) 6.66 (s, 1 H) 6.56 (dd, J = 9.78, 1.10 Hz, 1 H) 5.35 (br s, 1 H) 4.06 (dd, J = 11.13, 3.18 Hz, 1 H) 3.76-3.92 (m, 2 H) 3.44-3.67 (m, 4 H) 3.32-3.38 (m, 1 H) 2.82-3.07 (m, 3 H) 2.23 (s, 3 H) 1.60-1.77 (m, 6 H).; LCMS (m/z) (M + H) = 526.1, 1.49 min. |

| | | | |
|---|---|---|---|
| 439 | 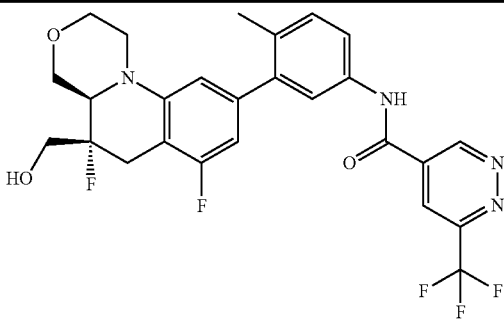 | N-(3-((4aR,5S)-5,7-difluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, DMSO-d6) δ 10.82 (br s, 1 H) 9.91 (d, J = 1.83 Hz, 1 H) 8.67 (d, J = 2.08 Hz, 1 H) 7.58-7.78 (m, 2 H) 7.32 (d, J = 8.44 Hz, 1 H) 6.66 (s, 1 H) 6.56 (dd, J = 9.78, 1.10 Hz, 1 H) 5.35 (t, J = 5.87 Hz, 1 H) 4.07 (dd, J = 11.13, 3.18 Hz, 1 H) 3.76-3.91 (m, 2 H) 3.44-3.70 (m, 4 H) 3.35 (dd, J = 10.64, 3.06 Hz, 1 H) 2.81-3.07 (m, 3 H) 2.25 (s, 3 H).; LCMS (m/z) (M + H) = 535.0, 1.46 min. |
| 440 | 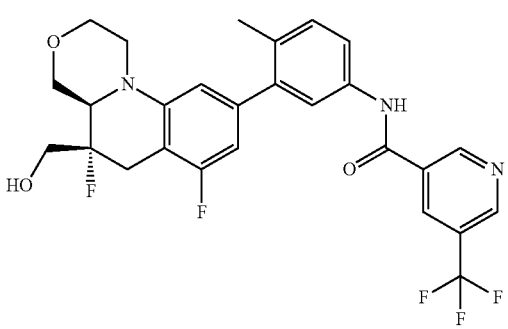 [SMILES: Cc1ccc(NC(=O)c2cncc(C(F)(F)F)c2)cc1-c1cc(F)c2c(c1)N1CCOC[C@@H]1[C@](F)(CO)C2] | N-(3-((4aR,5S)-5,7-difluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, DMSO-d6) δ 10.59 (s, 1 H) 9.37 (d, J = 1.83 Hz, 1 H) 9.18 (s, 1 H) 8.68 (s, 1 H) 7.52-7.90 (m, 2 H) 7.30 (d, J = 8.44 Hz, 1H) 6.66 (s, 1 H) 6.56 (dd, J = 9.72, 1.16 Hz, 1 H) 5.35 (t, J = 5.87 Hz, 1 H) 4.06 (dd, J = 11.13, 3.06 Hz, 1 H) 3.78-3.93 (m, 2 H) 3.44-3.68 (m, 4 H) 3.35 (dd, J = 10.51, 2.93 Hz, 1 H) 2.79-3.07 (m, 3 H) 2.19-2.34 (m, 3 H).; LCMS (m/z) (M + H) = 534.1, 1.41 min. |

Example 441

(rac)-N-(5-(7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide

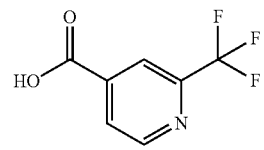

2-(trifluoromethyl)isonicotinic acid

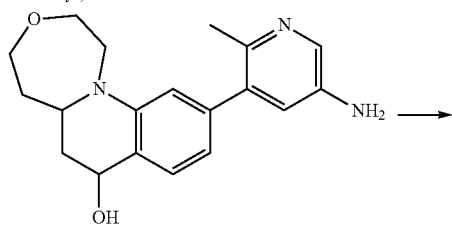

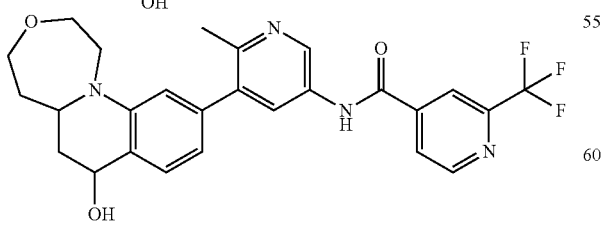

N-(5-(7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide 2-(trifluoromethyl)isonicotinic acid (1 equiv.), 10-(5-amino-2-methylpyridin-3-yl)-1,2,5,5a,6,7-hexahydro-4H-[1,4]oxazepino[4,5-a]quinolin-7-ol (1.0 equiv.), EDC.HCl (1.2 equiv.), HOAT (1.2 equiv.) in DMF (0.1 M) were stirred at inert atmosphere for 1 h. The reaction mixture was purified via reverse phase BASIC prep-HPLC to give the desired racemate and diastereomeric product N-(5-(7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide (4%). $^1$H NMR (400 MHz, Methanol-d4) δ 8.92 (d, J=5.0 Hz, 1H), 8.82 (d, J=2.5 Hz, 1H), 8.33 (s, 1H), 8.14 (dd, J=5.0, 1.3 Hz, 1H), 8.06 (d, J=2.5 Hz, 1H), 7.39 (dd, J=7.7, 0.8 Hz, 1H), 6.63 (dd, J=7.6, 1.5 Hz, 1H), 6.56 (d, J=1.4 Hz, 1H), 4.81-4.78 (m, 1H), 3.99-3.67 (m, 6H), 3.51-3.44 (m, 1H), 2.48 (s, 3H), 2.34-2.15 (m, 2H), 2.09-1.89 (m, 2H). LCMS (m/z) (M+H)=499.1, Rt=0.99 min.

Examples 442 and 443. N-(5-(7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide The following compounds were obtained from chiral SFC of N-(5-(7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide (NIQ120).

| | | | |
|---|---|---|---|
| 442 | 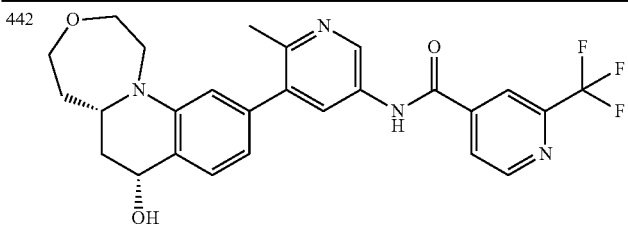 | N-(5-((5aS,7R)-7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide | $^1$H NMR (400 MHz, Methanol-d4) δ 8.92 (d, J = 5.0 Hz, 1H), 8.82 (d, J = 2.5 Hz, 1H), 8.33 (s, 1H), 8.17-8.13 (m, 1H), 8.06 (d, J = 2.5 Hz, 1H), 7.39 (dd, J = 7.7, 0.8 Hz, 1H), 6.63 (dd, J = 7.6, 1.5 Hz, 1H), 6.56 (d, J = 1.4 Hz, 1H), 4.82-4.80 (m, 1H), 3.97-3.68 (m, 6H), 3.52-3.43 (m, 1H), 2.48 (s, 3H), 2.33-2.15 (m, 2H), 2.08-1.94 (m, 2H). LCMS (m/z) (M + H) = 499.1, Rt = 0.98 min. |
| 443 | 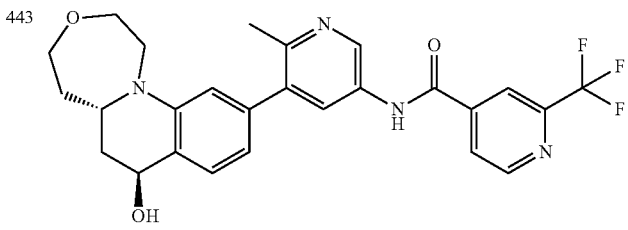 | N-(5-((5aS,7S)-7-hydroxy-1,2,5,5a,6,7-hexahydro-4H-[1,4]oxazepino[4,5-a]quinolin-10-yl)-6-methylpyridin-3-yl)-2-(trifluoromethyl)isonicotinamide | $^1$H NMR (400 MHz, Methanol-d4) δ 8.92 (d, J = 5.0 Hz, 1H), 8.82 (d, J = 2.5 Hz, 1H), 8.33 (s, 1H), 8.16-8.13 (m, 1H), 8.06 (d, J = 2.5 Hz, 1H), 7.39 (dd, J = 7.7, 0.8 Hz, 1H), 6.63 (dd, J = 7.6, 1.5 Hz, 1H), 6.56 (d, J = 1.4 Hz, 1H), 4.82-4.79 (m, 1H), 3.95-3.69 (m, 6H), 3.51-3.42 (m, 1H), 2.48 (s, 3H), 2.34-2.16 (m, 2H), 2.07-1.94 (m, 2H). LCMS (m/z) (M + H) = 499.1, Rt = 0.98 min. |

The compounds listed in the table below, were prepared using methods similar to those described for the preparation of Example 441 above, using the appropriate starting materials:

| | | | |
|---|---|---|---|
| 444 | 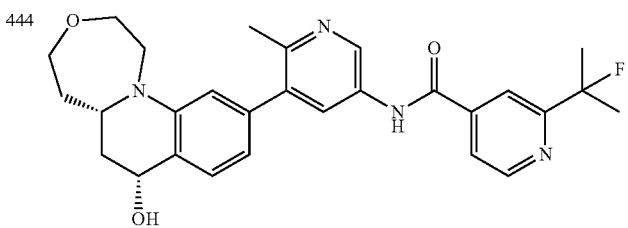 | 2-(2-fluoropropan-2-yl)-N-(5-((5aS,7R)-7-hydroxy-1,2,5,5a,6,7-hexahydro-4H-[1,4]oxazepino[4,5-a]quinolin-10-yl)-6-methylpyridin-3-yl)isonicotinamide | $^1$H NMR (400 MHz, Methanol-d4) δ 8.80 (d, J = 2.5 Hz, 1H), 8.71 (dt, J = 5.1, 0.9 Hz, 1H), 8.09 (s, 1H), 8.05 (d, J = 2.5 Hz, 1H), 7.79 (dd, J = 5.1, 1.7 Hz, 1H), 7.38 (dd, J = 7.7, 0.7 Hz, 1H), 6.63 (dd, J = 7.6, 1.5 Hz, 1H), 6.56 (d, J = 1.4 Hz, 1H), 4.83-4.78 (m, 1H), 3.94-3.71 (m, 6H), 3.52-3.40 (m, 1H), 2.47 (s, 3H), 2.33-2.15 (m, 2H), 2.07-1.94 (m, 2H), 1.76 (s, 3H), 1.70 (s, 3H). LCMS (m/z) (M + H) = 491.3, Rt = 1.45 min. |
| 445 | 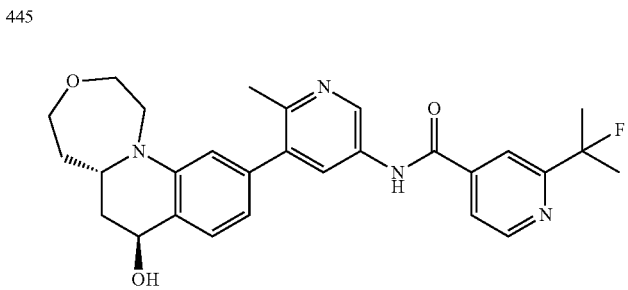 | 2-(2-fluoropropan-2-yl)-N-(5-((5aS,7S)-7-hydroxy-1,2,5,5a,6,7-hexahydro-4H-[1,4]oxazepino[4,5-a]quinolin-10-yl)-6-methylpyridin-3-yl)isonicotinamide | $^1$H NMR (400 MHz, Methanol-d4) δ 8.80 (d, J = 2.5 Hz, 1H), 8.70 (dt, J = 5.1, 0.8 Hz, 1H), 8.09 (s, 1H), 8.05 (d, J = 2.4 Hz, 1H), 7.79 (dd, J = 5.1, 1.7 Hz, 1H), 7.38 (dd, J = 7.7, 0.7 Hz, 1H), 6.62 (dd, J = 7.6, 1.5 Hz, 1H), 6.56 (d, J = 1.3 Hz, 1H), 4.83-4.79 (m, 1H), 3.93-3.74 (m, 6H), 3.52-3.40 (m, 1H), 2.47 (s, 3H), 2.34-2.14 (m, 2H), 2.07-1.93 (m, 2H), 1.75 (s, 3H), 1.70 (s, 3H). LCMS (m/z) (M + H) = 491.3, Rt = 1.45 min. |
| 446 | 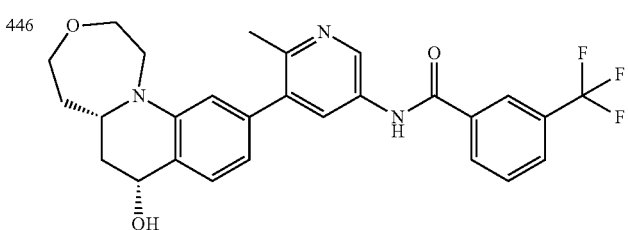 | N-(5-((5aS,7R)-7-hydroxy-1,2,5,5a,6,7-hexahydro-4H-[1,4]oxazepino[4,5-a]quinolin-10-yl)-6-methylpyridin-3-yl)-3-(trifluoromethyl)benzamide | $^1$H NMR (400 MHz, Methanol-d4) δ 8.80 (d, J = 2.5 Hz, 1H), 8.29 (s, 1H), 8.23 (d, J = 7.9 Hz, 1H), 8.05 (d, J = 2.5 Hz, 1H), 7.94-7.87 (m, 1H), 7.74 (t, J = 7.8 Hz, 1H), 7.38 (dd, J = 7.7, 0.8 Hz, 1H), 6.63 (dd, J = 7.6, 1.5 Hz, 1H), 6.56 (d, J = 1.4 Hz, 1H), 4.83-4.79 (m, 1H), 3.94-3.71 (m, 6H), 3.52-3.42 (m, 1H), 2.47 (s, 3H), 2.34-2.14 (m, 2H), 2.08-1.91 (m, 2H). LCMS (m/z) (M + H) = 498.1, Rt = 1.05 min. |

| 447 | 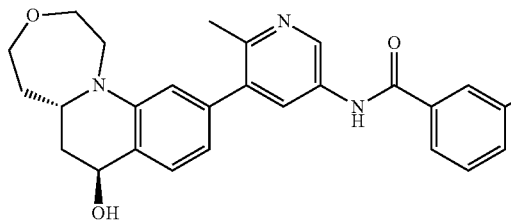 | N-(5-((5aS,7S)-7-hydroxy-1,2,5,5a,6,7-hexahydro-4H-[1,4]oxazepino[4,5-a]quinolin-10-yl)-6-methylpyridin-3-yl)-3-(trifluoromethyl)benzamide | ¹H NMR (400 MHz, Methanol-d4) δ 8.80 (d, J = 2.5 Hz, 1H), 8.29 (s, 1H), 8.23 (d, J = 7.9 Hz, 1H), 8.05 (d, J = 2.5 Hz, 1H), 7.94-7.88 (m, 1H), 7.74 (t, J = 7.8 Hz, 1H), 7.38 (dd, J = 7.7, 0.8 Hz, 1H), 6.63 (dd, J = 7.6, 1.5 Hz, 1H), 6.56 (d, J = 1.4 Hz, 1H), 4.83-4.80 (m, 1H), 3.93-3.74 (m, 6H), 3.53-3.42 (m, 1H), 2.47 (s, 3H), 2.35-2.15 (m, 2H), 2.08-1.92 (m, 2H). LCMS (m/z) (M + H) = 498.1, Rt = 1.05 min. |

Example 448

N-(3-((4aS,5R)-5-(2-hydroxypropan-2-yl)-1,2,4,4a,5,6-hexahydro-[1,4]oxazino[4,3-a][1,5]naphthyridin-9-yl)-4-methylphenyl)-2-(trifluoromethyl)isonicotinamide

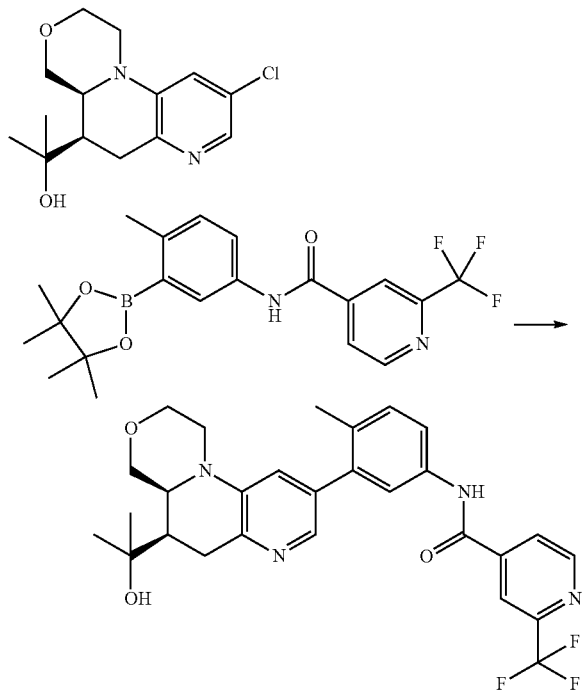

A mixture of 2-((4aS,5R)-9-chloro-1,2,4,4a,5,6-hexahydro-[1,4]oxazino[4,3-a][1,5]naphthyridin-5-yl)propan-2-ol (1 equiv.), N-(4-methyl-3-(4,4,5,5-tetramethyl-1,3,2-dioxaborolan-2-yl)phenyl)-2-(trifluoromethyl) isonicotinamide (1.1 equiv.), Xphos G2-Pd-Cy (0.05 equiv.), Xphos (0.05 equiv.) and $K_3PO_4$ (2 equiv., 0.5 M) in dioxane (0.13 M) was stirred at 70° C. block temperature for 1 hr. The reaction mixture was poured onto water and extracted with EtOAc. Organic phase was washed with brine, dried over sodium sulfate, filtered, and concentrated. The crude product was purified by flash chromatography over silica gel (DCM with 0-30% MeOH) to give the desired final product, N-(3-((4aS,5R)-5-(2-hydroxypropan-2-yl)-1,2,4,4a,5,6-hexahydro-[1,4]oxazino[4,3-a][1,5]naphthyridin-9-yl)-4-methylphenyl)-2-(trifluoromethyl)isonicotinamide (74%). 1H NMR (400 MHz, Methanol-d4) δ 8.90 (d, J=5.0 Hz, 1H), 8.29 (s, 1H), 8.11 (dd, J=5.0, 1.2 Hz, 1H), 7.73 (d, J=1.6 Hz, 1H), 7.66 (dd, J=8.2, 2.3 Hz, 1H), 7.61 (d, J=2.3 Hz, 1H), 7.32 (d, J=8.3 Hz, 1H), 7.23 (d, J=1.6 Hz, 1H), 4.20 (dd, J=11.8, 2.6 Hz, 1H), 4.03 (d, J=14.0 Hz, 1H), 3.91 (dt, J=10.7, 3.1 Hz, 1H), 3.69-3.62 (m, 1H), 3.59-3.49 (m, 2H), 3.46-3.37 (m, 1H), 3.03-2.94 (m, 2H), 2.27 (s, 3H), 2.15-2.05 (m, 1H), 1.40 (s, 3H), 1.34 (s, 3H). LCMS (m/z) (M+H)=527.2, Rt=1.04 min.

The compounds listed in the table below, were prepared using methods similar to those described for the preparation of example 448 using the appropriate starting materials:

| 449 | 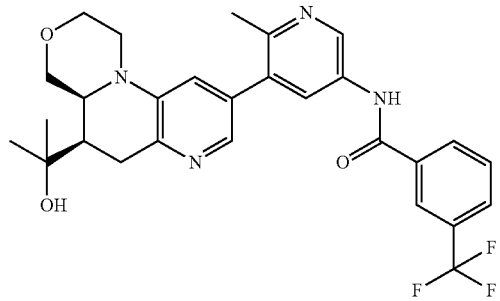 [SMILES: Cc1ncc(NC(=O)c2cccc(C(F)(F)F)c2)cc1-c1cnc2c(c1)N1CCOC[C@@H]1[C@H](C(C)(C)O)C2] | N-(5-((4aS,5R)-5-(2-hydroxypropan-2-yl)-1,2,4,4a,5,6-hexahydro-[1,4]oxazino[4,3-a][1,5]naphthyridin-9-yl)-6-methylpyridin-3-yl)-3-(trifluoromethyl)benzamide | ¹H NMR (400 MHz, Methanol-d4) δ 8.83 (d, J = 2.5 Hz, 1H), 8.30 (s, 1H), 8.23 (d, J = 7.9 Hz, 1H), 8.11 (d, J = 2.4 Hz, 1H), 7.91 (d, J = 7.8 Hz, 1H), 7.82-7.70 (m, 2H), 7.29 (d, J = 1.6 Hz, 1H), 4.21 (dd, J = 11.8, 2.5 Hz, 1H), 4.05 (d, J = 14.0 Hz, 1H), 3.92 (dt, J = 10.7, 3.1 Hz, 1H), 3.66 (dd, J = 11.1, 2.2 Hz, 1H), 3.61-3.48 (m, 2H), 3.49-3.37 (m, 1H), 3.07-2.94 (m, 2H), 2.49 (s, 3H), 2.17-2.04 (m, 1H), 1.40 (s, 3H), 1.35 (s, 3H). LCMS (m/z) (M + H) = 527.2, Rt = 0.95 min. |

| | | | |
|---|---|---|---|
| 450 | 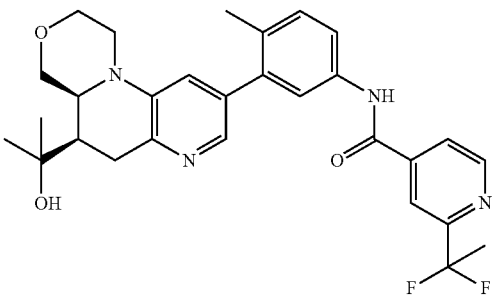 [SMILES: Cc1ccc(NC(=O)c2ccnc(C(C)(F)F)c2)cc1-c1cnc2c(c1)N1CCOC[C@@H]1[C@H](C(C)(C)O)C2] | 2-(1,1-difluoroethyl)-N-(3-((4aS,5R)-5-(2-hydroxypropan-2-yl)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4) δ 8.84-8.74 (m, 1H), 8.17 (s, 1H), 8.00-7.92 (m, 1H), 7.73 (d, J = 1.6 Hz, 1H), 7.65 (dd, J = 8.2, 2.3 Hz, 1H), 7.61 (d, J = 2.2 Hz, 1H), 7.31 (d, J = 8.3 Hz, 1H), 7.23 (d, J = 1.5 Hz, 1H), 4.20 (dd, J = 11.7, 2.5 Hz, 1H), 4.03 (d, J = 14.0 Hz, 1H), 3.91 (dt, J = 10.7, 3.0 Hz, 1H), 3.65 (dd, J = 11.1, 2.3 Hz, 1H), 3.60-3.49 (m, 2H), 3.46-3.36 (m, 1H), 3.06-2.92 (m, 2H), 2.27 (s, 3H), 2.15-1.97 (m, 4H), 1.40 (s, 3H), 1.34 (s, 3H). LCMS (m/z) (M + H) = 523.2, Rt = 1.03 min. |
| 451 | 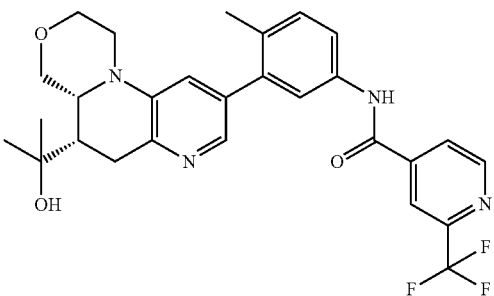 [SMILES: Cc1ccc(NC(=O)c2ccnc(C(F)(F)F)c2)cc1-c1cnc2c(c1)N1CCOC[C@H]1[C@@H](C(C)(C)O)C2] | N-(3-((4aR,5S)-5-(2-hydroxypropan-2-yl)-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.73 (d, J = 1.7 Hz, 1H), 7.66 (dd, J = 8.2, 2.3 Hz, 1H), 7.61 (d, J = 2.3 Hz, 1H), 7.32 (d, J = 8.3 Hz, 1H), 7.23 (d, J = 1.6 Hz, 1H), 4.20 (dd, J = 11.8, 2.6 Hz, 1H), 4.03 (d, J = 14.0 Hz, 1H), 3.91 (dt, J = 10.7, 3.1 Hz, 1H), 3.65 (dd, J = 11.1, 2.3 Hz, 1H), 3.59-3.48 (m, 2H), 3.47-3.36 (m, 1H), 3.06-2.93 (m, 2H), 2.27 (s, 3H), 2.16-2.05 (m, 1H), 1.40 (s, 3H), 1.34 (s, 3H). LCMS (m/z) (M + H) = 527.2, Rt = 1.05 min. |
| 452 | 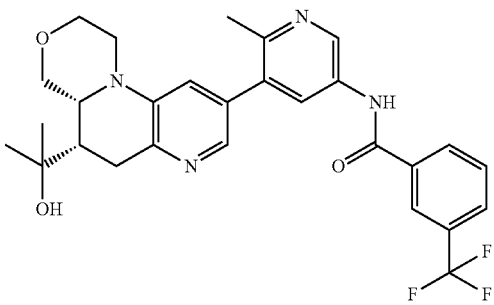 [SMILES: Cc1ncc(NC(=O)c2cccc(C(F)(F)F)c2)cc1-c1cnc2c(c1)N1CCOC[C@H]1[C@@H](C(C)(C)O)C2] | N-(5-((4aR,5S)-5-(2-hydroxypropan-2-yl)-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, Methanol-d4) δ 8.83 (d, J = 2.5 Hz, 1H), 8.30 (s, 1H), 8.23 (d, J = 7.9 Hz, 1H), 8.12 (d, J = 2.5 Hz, 1H), 7.91 (d, J = 7.8 Hz, 1H), 7.81-7.70 (m, 2H), 7.29 (d, J = 1.7 Hz, 1H), 4.21 (dd, J = 11.8, 2.6 Hz, 1H), 4.05 (d, J = 14.0 Hz, 1H), 3.92 (dt, J = 10.7, 3.1 Hz, 1H), 3.66 (dd, J = 11.1, 2.2 Hz, 1H), 3.60-3.49 (m, 2H), 3.48-3.37 (m, 1H), 3.07-2.94 (m, 2H), 2.49 (s, 3H), 2.16-2.05 (m, 1H), 1.40 (s, 3H), 1.35 (s, 3H). LCMS (m/z) (M + H) = 527.2 , Rt = 0.95 min. |
| 453 | 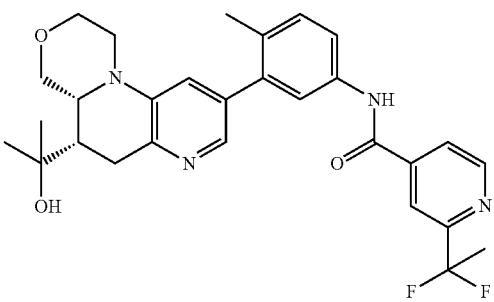 [SMILES: Cc1ccc(NC(=O)c2ccnc(C(C)(F)F)c2)cc1-c1cnc2c(c1)N1CCOC[C@H]1[C@@H](C(C)(C)O)C2] | 2-(1,1-difluoroethyl)-N-(3-((4aR,5S)-5-(2-hydroxypropan-2-yl)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4) δ 8.83-8.76 (m, 1H), 8.21-8.14 (m, 1H), 7.99-7.91 (m, 1H), 7.73 (d, J = 1.7 Hz, 1H), 7.65 (dd, J = 8.2, 2.3 Hz, 1H), 7.60 (d, J = 2.2 Hz, 1H), 7.31 (d, J = 8.3 Hz, 1H), 7.22 (d, J = 1.6 Hz, 1H), 4.20 (dd, J = 11.7, 2.6 Hz, 1H), 4.03 (d, J = 14.0 Hz, 1H), 3.90 (dt, J = 10.7, 3.1 Hz, 1H), 3.65 (dd, J = 11.2, 2.3 Hz, 1H), 3.60-3.48 (m, 2H), 3.47-3.35 (m, 1H), 3.07-2.92 (m, 2H), 2.26 (s, 3H), 2.13-1.97 (m, 4H), 1.40 (s, 3H), 1.34 (s, 3H). LCMS (m/z) (M + H) = 523.2, Rt = 1.03 min. |
| 454 | 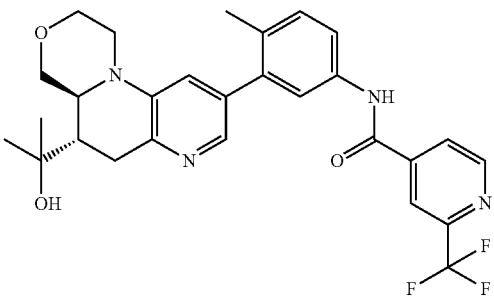 [SMILES: Cc1ccc(NC(=O)c2ccnc(C(F)(F)F)c2)cc1-c1cnc2c(c1)N1CCOC[C@@H]1[C@@H](C(C)(C)O)C2] | N-(3-((4aS,5S)-5-(2-hydroxypropan-2-yl)-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.80 (d, J = 1.7 Hz, 1H), 7.70-7.59 (m, 2H), 7.33 (d, J = 8.2 Hz, 1H), 7.12 (d, J = 1.6 Hz, 1H), 3.93 (dd, J = 11.1, 2.4 Hz, 2H), 3.76 (td, J = 11.7, 2.5 Hz, 1H), 3.57 (d, J = 11.9 Hz, 1H), 3.47-3.39 (m, 1H), 3.26-3.18 (m, 1H), 3.13 (td, J = 12.3, 3.5 Hz, 1H), 2.94-2.82 (m, 2H), 2.25 (s, 3H), 1.88 (q, J = 5.3 Hz, 1H), 1.22 (s, 3H), 0.95 (s, 3H). LCMS (m/z) (M + H) = 527.2, Rt = 1.03 min. |

| | | | |
|---|---|---|---|
| 455 | | N-(5-((4aS,5S)-5-(2-hydroxypropan-2-yl)-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, Methanol-d4) δ 8.83 (d, J = 2.5 Hz, 1H), 8.30 (s, 1H), 8.24 (d, J = 7.9 Hz, 1H), 8.14 (d, J = 2.5 Hz, 1H), 7.94-7.89 (m, 1H), 7.86 (d, J = 1.7 Hz, 1H), 7.75 (t, J = 7.8 Hz, 1H), 7.19 (d, J = 1.7 Hz, 1H), 3.93 (dd, J = 11.2, 2.2 Hz, 2H), 3.76 (td, J = 11.7, 2.5 Hz, 1H), 3.61 (d, J = 11.7 Hz, 1H), 3.43 (t, J = 10.8 Hz, 1H), 3.28-3.22 (m, 1H), 3.17 (dd, J = 12.3, 3.4 Hz, 1H), 2.90 (t, J = 5.7 Hz, 2H), 2.47 (s, 3H), 1.95-1.82 (m, 1H), 1.22 (s, 3H), 0.97 (s, 3H). LCMS (m/z) (M + H) = 527.2, Rt = 0.93 min. |
| 456 | | 2-(1,1-difluoroethyl)-N-(3-((4aS,5S)-5-(2-hydroxypropan-2-yl)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4) δ 8.79 (d, 1H), 8.17 (s, 1H), 8.01-7.90 (m, 1H), 7.81 (d, J = 1.7 Hz, 1H), 7.69-7.60 (m, 2H), 7.32 (d, J = 8.1 Hz, 1H), 7.12 (d, J = 1.6 Hz, 1H), 3.93 (dd, J = 11.2, 2.8 Hz, 2H), 3.75 (td, J = 11.7, 2.5 Hz, 1H), 3.58 (d, J = 11.8 Hz, 1H), 3.43 (t, J = 10.8 Hz, 1H), 3.26-3.19 (m, 1H), 3.13 (td, J = 12.4, 3.4 Hz, 1H), 2.95-2.80 (m, 2H), 2.25 (s, 3H), 2.03 (t, J = 18.7 Hz, 3H), 1.88 (q, J = 5.3 Hz, 1H), 1.22 (s, 3H), 0.95 (s, 3H). LCMS (m/z) (M + H) = 523.2, Rt = 1.01 min. |
| 457 | | N-(3-((4aR,5R)-5-(2-hydroxypropan-2-yl)-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.80 (d, J = 1.7 Hz, 1H), 7.70-7.59 (m, 2H), 7.32 (d, J = 8.2 Hz, 1H), 7.12 (d, J = 1.6 Hz, 1H), 3.93 (dd, J = 11.2, 2.8 Hz, 2H), 3.75 (td, J = 11.7, 2.5 Hz, 1H), 3.57 (d, J = 11.8 Hz, 1H), 3.43 (t, J = 10.8 Hz, 1H), 3.25-3.18 (m, 1H), 3.13 (td, 12.3, 3.4 Hz, 1H), 2.94-2.81 (m, 2H), 2.25 (s, 3H), 1.88 (q, J = 5.3 Hz, 1H), 1.22 (s, 3H), 0.95 (s, 3H). LCMS (m/z) (M + H) = 527.2, Rt = 1.03 min. |
| 458 | | N-(5-((4aR,5R)-5-(2-hydroxypropan-2-yl)-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, Methanol-d4) δ 8.83 (d, J = 2.5 Hz, 1H), 8.30 (s, 1H), 8.23 (d, J = 7.9 Hz, 1H), 8.14 (d, J = 2.5 Hz, 1H), 7.93-7.90 (m, 1H), 7.85 (d, J = 1.7 Hz, 1H), 7.74 (t, J = 7.8 Hz, 1H), 7.18 (d, J = 1.7 Hz, 1H), 3.93 (dd, J = 11.1, 2.3 Hz, 2H), 3.76 (td, J = 11.7, 2.5 Hz, 1H), 3.60 (d, J = 11.8 Hz, 1H), 3.43 (t, J = 10.8 Hz, 1H), 3.28-3.21 (m, 1H), 3.20-3.10 (m, 1H), 2.96-2.83 (m, 2H), 2.47 (s, 3H), 1.88 (q, J = 5.2 Hz, 1H), 1.22 (s, 3H), 0.97 (s, 3H). LCMS (m/z) (M + H) = 527.2, Rt = 0.94 min. |
| 459 | | 2-(1,1-difluoroethyl)-N-(3-((4aS,5S)-5-(2-hydroxypropan-2-yl)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4) δ 8.84-8.74 (m, 1H), 8.17 (s, 1H), 8.00-7.91 (m, 1H), 7.80 (d, J = 1.7 Hz, 1H), 7.70-7.56 (m, 2H), 7.32 (d, J = 8.1 Hz, 1H), 7.12 (d, J = 1.6 Hz, 1H), 3.93 (dd, J = 11.3, 2.8 Hz, 2H), 3.75 (td, J = 11.7, 2.5 Hz, 1H), 3.57 (d, J = 11.9 Hz, 1H), 3.47-3.38 (m, 1H), 3.25-3.18 (m, 1H), 3.13 (td, J = 12.3, 3.4 Hz, 1H), 2.94-2.82 (m, 2H), 2.25 (s, 3H), 2.03 (t, J = 18.7 Hz, 3H), 1.87 (q, J = 5.3 Hz, 1H), 1.22 (s, 3H), 0.95 (s, 3H). LCMS (m/z) (M + H) = 523.2, Rt = 1.01 min. |

373

Intermediate for Example 467. 5-(5-fluoro-5-(fluoromethyl)-1,2,4,4a,5,6-hexahydro-[1,4]oxazino[4,3-a]quinolin-9-yl)-6-methylpyridin-3-amine

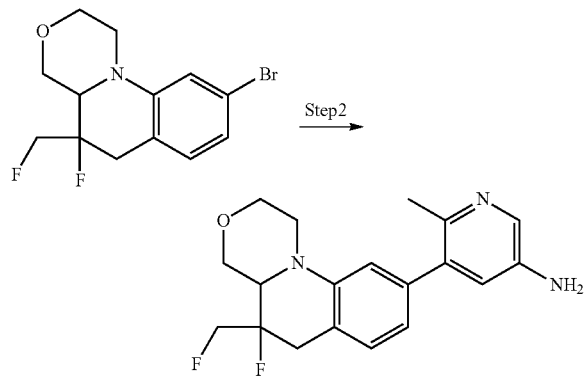

A mixture of 9-bromo-5-fluoro-5-(fluoromethyl)-1,2,4,4a,5,6-hexahydro-[1,4]oxazino[4,3-a]quinoline (1 equiv.), 6-methyl-5-(4,4,5,5-tetramethyl-1,3,2-dioxaborolan-2-yl)pyridin-3-amine (1.1 equiv.), Xphos G2-Pd-Cy (0.05 equiv.), Xphos (0.05 equiv.) and $K_3PO_4$ (2 equiv., 0.5 M) in dioxane (0.16 M) was stirred at 70° C. block temperature for 1 hr. The reaction mixture was poured onto water and extracted with EtOAc. Organic phase was washed with brine, dried over sodium sulfate, filtered, and concentrated. The crude product was purified by flash chromatography over silica gel (heptane with 0-60% ethyl acetate) to give the desired product, 3-(5-fluoro-5-(fluoromethyl)-1,2,4,4a,5,6-hexahydro-[1,4]oxazino[4,3-a]quinolin-9-yl)-4-methylaniline (98%). LCMS (m/z) (M+H)=346.1, Rt=0.91 min.

Intermediate for Example 469. 3-(5-fluoro-5-(fluoromethyl)-1,2,4,4a,5,6-hexahydro-[1,4]oxazino[4,3-a]quinolin-9-yl)-4-methylaniline

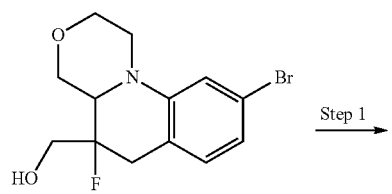

374

Step 1:
To a solution of (9-bromo-5-fluoro-1,2,4,4a,5,6-hexahydro-[1,4]oxazino[4,3-a]quinolin-5-yl)methanol (1.0 equiv.) in THF (0.12 M) was added triethylamine (12 equiv.) followed by perfluorobutanesulfonyl fluoride (4 equiv.) and triethylamine trihydrofluoride (4 equiv.). The reaction mixture was stirred at 60° C. block temperature for 18 hr. The reaction mixture was poured onto water and extracted with EtOAc. Organic phase was washed with brine, dried over sodium sulfate, filtered, and concentrated. The crude product was purified by flash chromatography over silica gel (heptane with 0 to 100% ethyl acetate) to give the desired product, 9-bromo-5-fluoro-5-(fluoromethyl)-1,2,4,4a,5,6-hexahydro-[1,4]oxazino[4,3-a]quinoline (98%). LCMS (m/z) (M+H)=319.9, Rt=1.51 min.

Step 2:
A mixture of 9-bromo-5-fluoro-5-(fluoromethyl)-1,2,4,4a,5,6-hexahydro-[1,4]oxazino[4,3-a]quinoline (1 equiv.), 4-methyl-3-(4,4,5,5-tetramethyl-1,3,2-dioxaborolan-2-yl)aniline (1.1 equiv.), Xphos G2-Pd-Cy (0.05 equiv.), Xphos (0.05 equiv.) and $K_3PO_4$ (2 equiv., 0.5 M) in dioxane (0.16 M) was stirred at 70° C. block temperature for 1 hr. The reaction mixture was poured onto water and extracted with EtOAc. Organic phase was washed with brine, dried over sodium sulfate, filtered, and concentrated. The crude product was purified by flash chromatography over silica gel (heptane with 0-60% ethyl acetate) to give the desired product, 3-(5-fluoro-5-(fluoromethyl)-1,2,4,4a,5,6-hexahydro-[1,4]oxazino[4,3-a]quinolin-9-yl)-4-methylaniline (100%). LCMS (m/z) (M+H)=345.1, Rt=1.03 min.

The compounds listed in the table below, were prepared using the intermediates described above and appropriate starting materials:

| | | |
|---|---|---|
| 467 | 2-(1,1-difluoromethyl)-N-(5-((4aS,5S)-5-fluoro-5-(fluoromethyl)-1,2,4,4a,5,6-hexahydro-[1,4]oxazino[4,3-a]quinolin-9-yl)-6-methylpyridin-3-yl)isonicotinamide | $^1$H NMR (400 MHz, Methanol-d6) δ 8.85-8.79 (m, 2H), 8.24-8.19 (m, 1H), 8.09 (d, J = 2.5 Hz, 1H), 8.02-7.93 (m, 1H), 7.19 (d, J = 7.6 Hz, 1H), 6.88 (d, J = 1.3 Hz, 1H), 6.83 (dd, J = 7.6, 1.5 Hz, 1H), 4.62-4.34 (m, 2H), 4.01 (dd, J = 11.5, 3.1 Hz, 1H), 3.97-3.88 (m, 1H), 3.79-3.61 (m, 3H), 3.26-3.19 (m, 1H), 3.16-2.95 (m, 3H), 2.48 (s, 3H), 2.04 (t, J = 18.7 Hz, 3H). LCMS (m/z) (M + H) = 515.3, Rt = 1.33 min |
| | 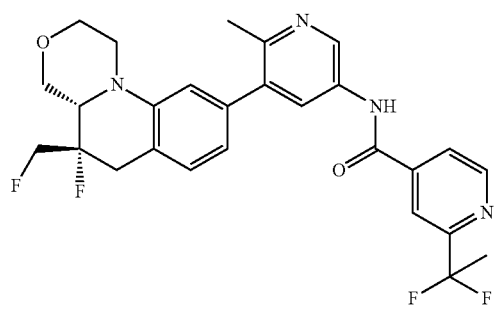 [SMILES: Cc1ncc(NC(=O)c2ccnc(C(C)(F)F)c2)cc1-c1ccc2c(c1)N1CCOC[C@H]1[C@](F)(CF)C2] | |

| # | Structure | Name | Data |
|---|---|---|---|
| 468 | 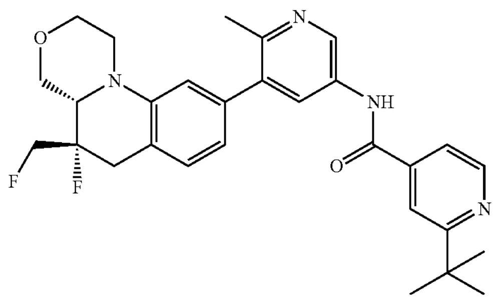 [SMILES: Cc1ncc(NC(=O)c2ccnc(C(C)(C)C)c2)cc1-c1ccc2c(c1)N1CCOC[C@H]1[C@](F)(CF)C2] | 2-(tert-butyl)-N-(5-((4aS,5S)-5-fluoro-5-(fluoromethyl)-1,2,4,4a,5,6-hexahydro-[1,4]oxazino[4,3-a]quinolin-9-yl)-6-methylpyridin-3-yl)isonicotinamide | ¹H NMR (400 MHz, Methanol-d4) δ 8.80 (d, J = 2.5 Hz, 1H), 8.67 (dd, J = 5.1, 0.8 Hz, 1H), 8.08 (d, J = 2.5 Hz, 1H), 7.94 (dd, J = 1.5, 0.8 Hz, 1H), 7.68 (dd, J = 5.1, 1.6 Hz, 1H), 7.19 (d, J = 7.6 Hz, 1H), 6.88 (d, J = 1.2 Hz, 1H), 6.83 (dd, J = 7.5, 1.5 Hz, 1H), 4.63-4.30 (m, 2H), 4.01 (dd, J = 11.5, 3.1 Hz, 1H), 3.97-3.90 (m, 1H), 3.78-3.62 (m, 3H), 3.26-3.19 (m, 1H), 3.16-2.95 (m, 3H), 2.48 (s, 3H), 1.42 (s, 9H). LCMS (m/z) (M + H) = 507.1, Rt = 1.10 min. |
| 469 | 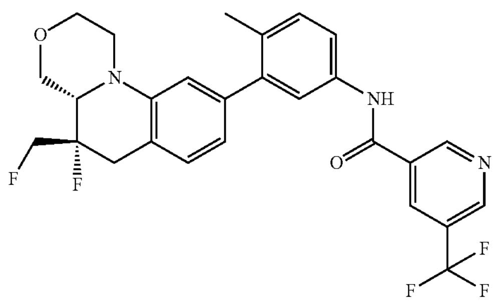 [SMILES: Cc1ccc(NC(=O)c2cncc(C(F)(F)F)c2)cc1-c1ccc2c(c1)N1CCOC[C@H]1[C@](F)(CF)C2] | N-(3-((4aS,5S)-5-fluoro-5-(fluoromethyl)-1,2,4,4a,5,6-hexahydro-[1,4]oxazino[4,3-a]quinolin-9-yl)-4-methylphenyl)-5-(trifluoromethyl)nicotinamide | ¹H NMR (400 MHz, Methanol-d4) δ 9.33 (d, J = 1.9 Hz, 1H), 9.06 (d, J = 1.2 Hz, 1H), 8.64 (s, 1H), 7.67-7.52 (m, 2H), 7.27 (d, J = 8.1 Hz, 1H), 7.13 (d, J = 7.6 Hz, 1H), 6.82 (s, 1H), 6.79 (dd, J = 7.5, 1.5 Hz, 1H), 4.59-4.31 (m, 2H), 4.00 (dd, J = 11.5, 3.1 Hz, 1H), 3.92 (dd, J = 11.2, 3.5 Hz, 1H), 3.74-3.61 (m, 3H), 3.23-2.93 (m, 4H), 2.25 (s, 3H). LCMS (m/z) (M + H) = 518.1, Rt = 1.65 min. |
| 470 | 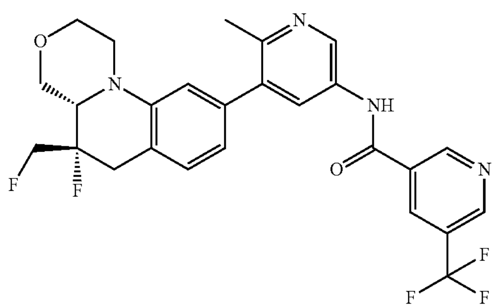 [SMILES: Cc1ncc(NC(=O)c2cncc(C(F)(F)F)c2)cc1-c1ccc2c(c1)N1CCOC[C@H]1[C@](F)(CF)C2] | N-(5-((4aS,5S)-5-fluoro-5-(fluoromethyl)-1,2,4,4a,5,6-hexahydro-[1,4]oxazino[4,3-a]quinolin-9-yl)-6-methylpyridin-3-yl)-5-(trifluoromethyl)nicotinamide | ¹H NMR (400 MHz, Methanol-d4) δ 9.36 (d, J = 2.0 Hz, 1H), 9.12-9.02 (m, 1H), 8.80 (d, J = 2.5 Hz, 1H), 8.68 (td, J = 2.1, 0.7 Hz, 1H), 8.09 (d, J = 2.5 Hz, 1H), 7.19 (d, J = 7.6 Hz, 1H), 6.87 (d, J = 1.3 Hz, 1H), 6.83 (dd, J = 7.6, 1.5 Hz, 1H), 4.62-4.33 (m, 2H), 4.01 (dd, J = 11.5, 3.1 Hz, 1H), 3.97-3.88 (m, 1H), 3.77-3.62 (m, 3H), 3.28-2.96 (m, 4H), 2.47 (s, 3H). LCMS (m/z) (M + H) = 519.1, Rt = 1.13 min. |
| 471 | 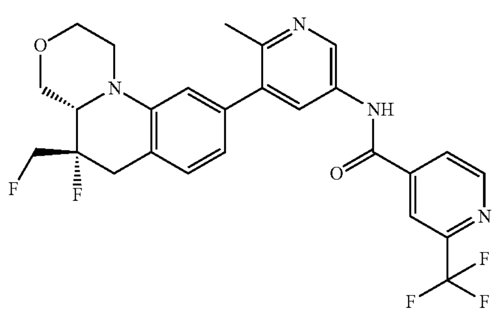 [SMILES: Cc1ncc(NC(=O)c2ccnc(C(F)(F)F)c2)cc1-c1ccc2c(c1)N1CCOC[C@H]1[C@](F)(CF)C2] | N-(5-((4aS,5S)-5-fluoro-5-(fluoromethyl)-1,2,4,4a,5,6-hexahydro-[1,4]oxazino[4,3-a]quinolin-9-yl)-6-methylpyridin-3-yl)-2-(trifluoromethyl)isonictonamide | ¹H NMR (400 MHz, Methanol-d4) δ 8.92 (d, J = 5.0 Hz, 1H), 8.82 (d, J = 2.5 Hz, 1H), 8.32 (s, 1H), 8.14 (dd, J = 5.0, 1.2 Hz, 1H), 8.09 (d, J = 2.5 Hz, 1H), 7.19 (d, J = 7.6 Hz, 1H), 6.87 (s, 1H), 6.83 (dd, J = 7.6, 1.5 Hz, 1H), 4.62-4.32 (m, 2H), 4.01 (dd, J = 11.5, 3.1 Hz, 1H), 3.97-3.87 (m, 1H), 3.77-3.61 (m, 3H), 3.28-2.95 (m, 4H), 2.48 (s, 3H). LCMS (m/z) (M + H) = 519.0, Rt = 1.16 min. |
| 472 | 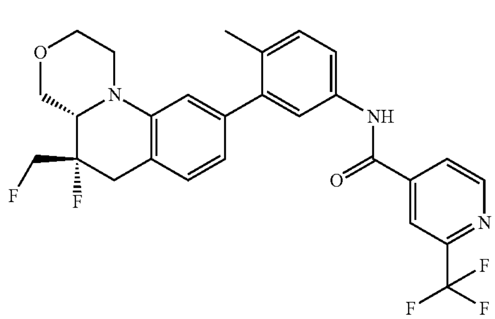 [SMILES: Cc1ccc(NC(=O)c2ccnc(C(F)(F)F)c2)cc1-c1ccc2c(c1)N1CCOC[C@H]1[C@](F)(CF)C2] | N-(3-((4aS,5S)-5-fluoro-5-(fluoromethyl)-1,2,4,4a,5,6-hexahydro-[1,4]oxazino[4,3-a]quinolin-9-yl)-4-methylphenyl)-2-(trifluoromethyl)isonicotinamide | ¹H NMR (400 MHz, Methanol-d4) δ 8.89 (d, J = 5.0 Hz, 1H), 8.28 (s, 1H), 8.11 (dd, J = 5.0, 1.2 Hz, 1H), 7.67-7.52 (m, 2H), 7.27 (d, J = 8.2 Hz, 1H), 7.13 (d, J = 7.6 Hz, 1H), 6.82 (s, 1H), 6.79 (dd, J = 7.5, 1.5 Hz, 1H), 4.62-4.29 (m, 2H), 4.00 (dd, J = 11.5, 3.1 Hz, 1H), 3.92 (dd, J = 11.2, 3.5 Hz, 1H), 3.77-3.61 (m, 3H), 3.24-2.93 (m, 4H), 2.25 (s, 3H). LCMS (m/z) (M + H) = 518.1, Rt = 1.66 min. |

| | | | |
|---|---|---|---|
| 473 | (structure) | 2-(1,1-difluoromethyl)-N-(3-((4aS,5S)-5-fluoro-5-(fluoromethyl)-1,2,4,4a,5,6-hexahydro-[1,4]oxazino[4,3-a]quinolin-9-yl)-4-methylphenyl)isonicotinamide | ¹H NMR (400 MHz, Methanol-d4) δ 8.82-8.73 (m, 1H), 8.16 (s, 1H), 7.97-7.91 (m, 1H), 7.67-7.52 (m, 2H), 7.32 (d, J = 7.5 Hz, 1H), 7.26 (d, J = 8.1 Hz, 1H), 7.12 (d, J = 7.6 Hz, 1H), 7.07 (s, 1H), 6.82 (s, 1H), 6.78 (dd, J = 7.5, 1.4 Hz, 1H), 4.61-4.27 (m, 2H), 4.00 (dd, J = 11.5, 3.1 Hz, 1H), 3.91 (dd, J = 11.2, 3.5 Hz, 1H), 3.75-3.62 (m, 3H), 3.23-2.92 (m, 4H), 2.24 (s, 3H), 2.02 (t, J = 18.7 Hz, 3H). LCMS (m/z) (M + H) = 514.1, Rt = 1.63 min. |
| 474 | (structure) | 2-(tert-butyl)-N-(3-((4aS,5S)-5-fluoro-5-(fluoromethyl)-1,2,4,4a,5,6-hexahydro-[1,4]oxazino[4,3-a]quinolin-9-yl)-4-methylphenyl)isonicotinamide | ¹H NMR (400 MHz, Methanol-d4) δ 8.63 (dd, J = 5.1, 0.8 Hz, 1H), 7.90 (s, 1H), 7.64 (dd, J = 5.1, 1.6 Hz, 1H), 7.61-7.51 (m, 2H), 7.26 (d, J = 8.2 Hz, 1H), 7.12 (d, J = 7.6 Hz, 1H), 6.82 (s, 1H), 6.79 (dd, J = 7.5, 1.4 Hz, 1H), 4.60-4.27 (m, 2H), 4.00 (dd, J = 11.5, 3.1 Hz, 1H), 3.91 (dd, J = 11.2, 3.5 Hz, 1H), 3.75-3.61 (m, 3H), 3.23-2.92 (m, 4H), 2.24 (s, 3H), 1.41 (s, 9H). LCMS (m/z) (M + H) = 506.3, Rt = 1.47 min. |
| 475 | (structure) | N-(3-((4aS,5S)-5-fluoro-5-(fluoromethyl)-1,2,4,4a,5,6-hexahydro-[1,4]oxazino[4,3-a]quinolin-9-yl)-4-methylphenyl)-6-(trifluoromethyl)pyridazine-4-carboxamide | ¹H NMR (400 MHz, Methanol-d4) δ 9.85 (d, J = 2.0 Hz, 1H), 8.57 (s, 1H), 7.69-7.54 (m, 2H), 7.28 (d, J = 8.2 Hz, 1H), 7.14 (d, J = 7.6 Hz, 1H), 6.82 (s, 1H), 6.78 (dd, J = 7.5, 1.5 Hz, 1H), 4.59-4.32 (m, 2H), 4.00 (dd, J = 11.5, 3.1 Hz, 1H), 3.92 (dd, J = 11.2, 3.5 Hz, 1H), 3.75-3.62 (m, 3H), 3.25-2.93 (m, 4H), 2.25 (s, 3H). LCMS (m/z) (M + H) = 519.1, Rt = 1.60 min. |

Intermediate for Ex. 476. (9-bromo-5,8-difluoro-1,2,4,4a,5,6-hexahydro-[1,4]oxazino[4,3-a]quinolin-5-yl)methanol

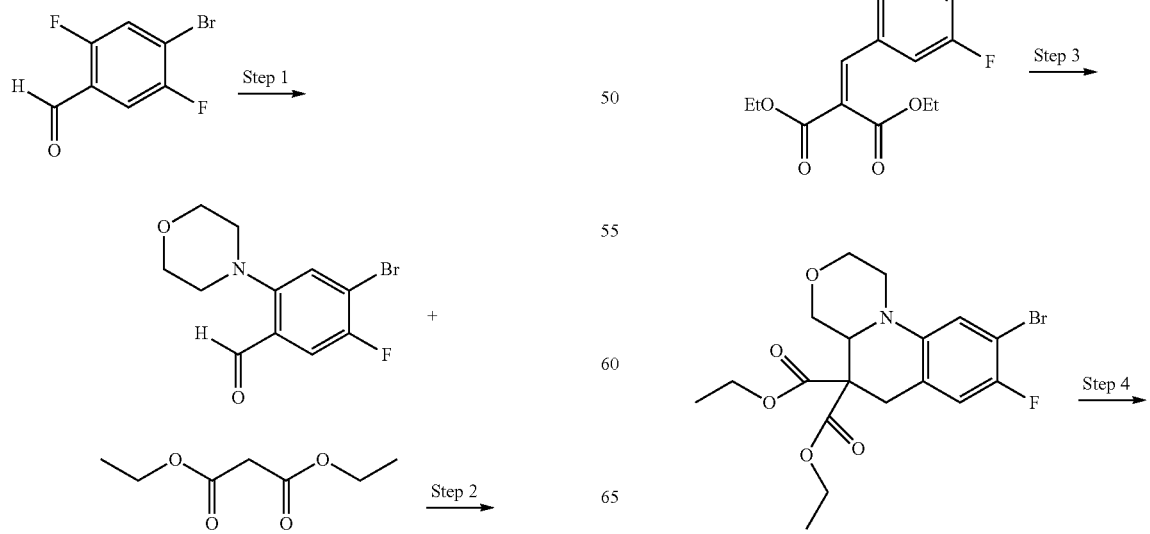

379

-continued

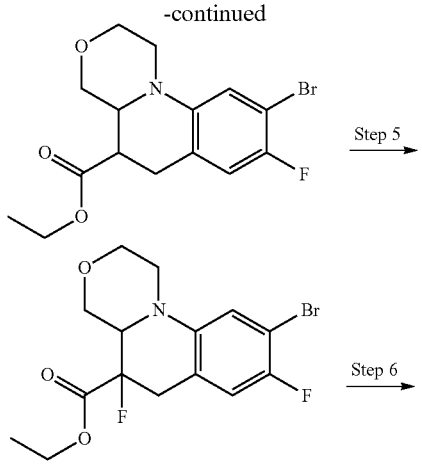

Step 5

Step 6

380

-continued

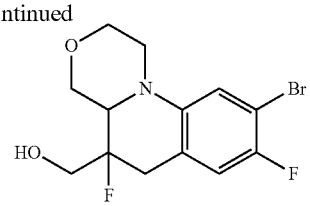

(9-bromo-5,8-difluoro-1,2,4,4a,5,6-hexahydro-[1,4]oxazino[4,3-a]quinolin-5-yl)methanol was synthesized using the same procedure as for synthesis of Example 369, starting with 4-bromo-2,5-difluorobenzaldehyde staring material. The desired final intermediate was used after its chiral separation to 4 pure single enantiomers and diastereomers.

The compounds listed in the table below were prepared using the above intermediate and the appropriate starting materials:

| 476 | 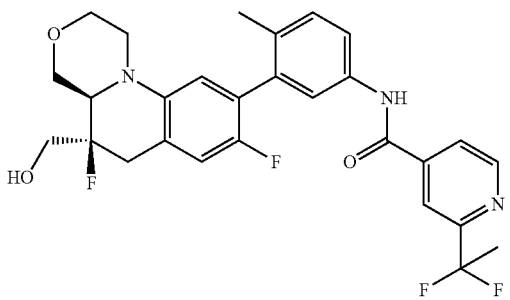 | N-(3-((4aR,5R)-5,8-difluoro-5-(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | $^1$H NMR (400 MHz, Methanol-d4) δ 8.83-8.74 (m, 1H), 8.17 (s, 1H), 7.99-7.90 (m, 1H), 7.64 (dd, J = 8.2, 2.3 Hz, 1H), 7.58 (d, J = 2.2 Hz, 1H), 7.29 (d, J = 8.3 Hz, 1H), 6.93 (d, J = 9.6 Hz, 1H), 6.72 (d, J = 6.3 Hz, 1H), 4.06 (dd, J = 11.5, 3.2 Hz, 1H), 3.91 (dd, J = 11.4, 3.4 Hz, 1H), 3.74-3.53 (m, 5H), 3.23-3.08 (m, 2H), 3.02-2.84 (m, 2H), 2.18 (s, 3H), 2.03 (t, J = 18.7 Hz, 3H). LCMS (m/z) (M + H) = 530.1, Rt = 1.45 min. |
| --- | --- | --- | --- |
| 477 | 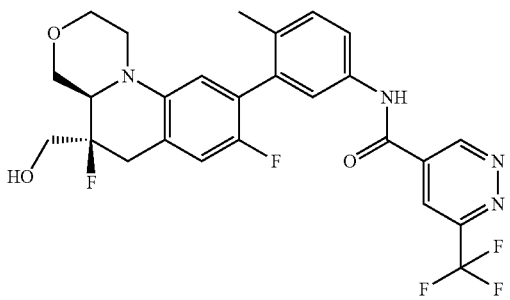 [SMILES: Cc1ccc(NC(=O)c2cnnc(C(F)(F)F)c2)cc1-c1cc2c(cc1F)C[C@](F)(CO)[C@H]1COCCN21] | N-(3-((4aR,5R)-5,8-difluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, Methanol-d4) δ 9.86 (d, J = 2.0 Hz, 1H), 8.57 (d, J = 2.0 Hz, 1H), 7.67 (dd, J = 8.2, 2.3 Hz, 1H), 7.61 (d, J = 2.3 Hz, 1H), 7.30 (d, J = 8.3 Hz, 1H), 6.94 (d, J = 9.6 Hz, 1H), 6.71 (d, J = 6.3 Hz, 1H), 4.06 (dd, J = 11.5, 3.2 Hz, 1H), 3.91 (dd, J = 11.4, 3.4 Hz, 1H), 3.73-3.53 (m, 5H), 3.22-3.09 (m, 2H), 3.02-2.86 (m, 2H), 2.18 (s, 3H). LCMS (m/z) (M + H) = 535.1, Rt = 1.42 min. |
| 478 | 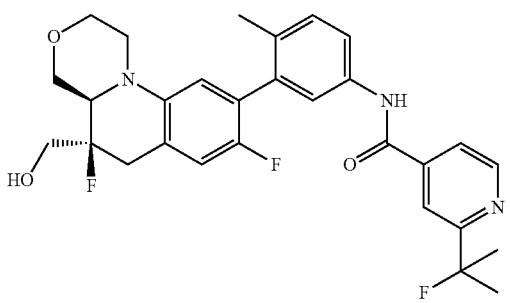 [SMILES: Cc1ccc(NC(=O)c2ccnc(C(C)(C)F)c2)cc1-c1cc2c(cc1F)C[C@](F)(CO)[C@H]1COCCN21] | N-(3-((4aR,5R)-5,8-difluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | $^1$H NMR (400 MHz, Methanol-d4) δ 8.68 (d, J = 5.1 Hz, 1H), 8.05 (s, 1H), 7.75 (dd, J = 5.1, 1.7 Hz, 1H), 7.63 (dd, J = 8.2, 2.3 Hz, 1H), 7.58 (d, J = 2.2 Hz, 1H), 7.28 (d, J = 8.3 Hz, 1H), 6.93 (d, J = 9.6 Hz, 1H), 6.72 (d, J = 6.3 Hz, 1H), 4.06 (dd, J = 11.5, 3.2 Hz, 1H), 3.91 (dd, J = 11.4, 3.4 Hz, 1H), 3.75-3.51 (m, 5H), 3.22-3.07 (m, 2H), 3.01-2.85 (m, 2H), 2.17 (s, 3H), 1.75 (s, 3H), 1.69 (s, 3H). LCMS (m/z) (M + H) = 526.2, Rt = 1.45 min. |

| | | | |
|---|---|---|---|
| 479 | 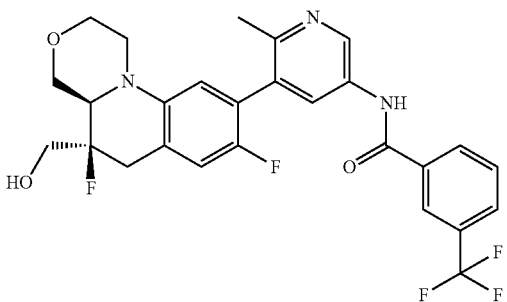 [SMILES: Cc1ncc(NC(=O)c2cccc(C(F)(F)F)c2)cc1-c1cc2c(cc1F)C[C@](F)(CO)[C@H]1COCCN21] | N-(5-((4aR,5R)-5,8-difluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, Methanol-d4) δ 8.83 (d, J = 2.5 Hz, 1H), 8.29 (s, 1H), 8.23 (d, J = 7.9 Hz, 1H), 8.10 (d, J = 2.5 Hz, 1H), 7.91 (d, J = 7.8 Hz, 1H), 7.74 (t, J = 7.8 Hz, 1H), 6.99 (d, J = 9.6 Hz, 1H), 6.78 (d, J = 6.3 Hz, 1H), 4.07 (dd, J = 11.4, 3.2 Hz, 1H), 3.96-3.87 (m, 1H), 3.73-3.55 (m, 5H), 3.24-3.12 (m, 2H), 3.03-2.89 (m, 2H), 2.40 (s, 3H). LCMS (m/z) (M + H) = 534.0, Rt = 1.13 min. |
| 480 | 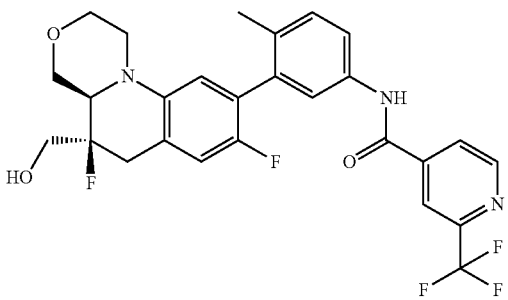 | N-(3-((4aR,5R)-5,8-difluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, Methanol-d4) δ 8.89 (d, J = 5.0 Hz, 1H), 8.29 (s, 1H), 8.11 (dd, J = 5.0, 1.2 Hz, 1H), 7.65 (dd, J = 8.2, 2.3 Hz, 1H), 7.59 (d, J = 2.3 Hz, 1H), 7.29 (d, J = 8.3 Hz, 1H), 6.93 (d, J = 9.6 Hz, 1H), 6.72 (d, J = 6.3 Hz, 1H), 4.06 (dd, J = 11.5, 3.2 Hz, 1H), 3.91 (dd, J = 11.4, 3.4 Hz, 1H), 3.75-3.51 (m, 5H), 3.23-3.08 (m, 2H), 3.02-2.86 (m, 2H), 2.18 (s, 3H). LCMS (m/z) (M + H) = 534.1, Rt = 1.48 min. |
| 481 | 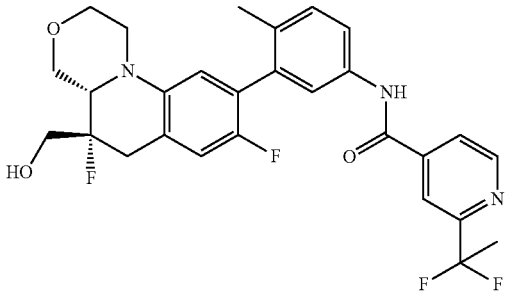 [SMILES: Cc1ccc(NC(=O)c2ccnc(C(C)(F)F)c2)cc1-c1cc2c(cc1F)C[C@@](F)(CO)[C@@H]1COCCN21] | N-(3-((4aS,5S)-5,8-difluoro-5-(hydroxymethyl)-1,2,4,4a,5,6-hexahydro-[1,4]oxazino[4,3-a]quinolin-9-yl)-4-methylphenyl)-2-(1,1-difluoroethyl)isonicotinamide | 1H NMR (400 MHz, Methanol-d4) δ 8.85-8.69 (m, 1H), 8.17 (s, 1H), 8.02-7.89 (m, 1H), 7.64 (dd, J = 8.2, 2.3 Hz, 1H), 7.58 (d, J = 2.2 Hz, 1H), 7.29 (d, J = 8.3 Hz, 1H), 6.93 (d, J = 9.6 Hz, 1H), 6.72 (d, J = 6.3 Hz, 1H), 4.06 (dd, J = 11.4, 3.2 Hz, 1H), 3.91 (dd, J = 11.2, 3.6 Hz, 1H), 3.73-3.53 (m, 5H), 3.22-3.08 (m, 2H), 3.01-2.86 (m, 2H), 2.18 (s, 3H), 2.03 (t, J = 18.7 Hz, 3H). LCMS (m/z) (M + H) = 530.1 Rt = 1.45 min. |
| 482 | 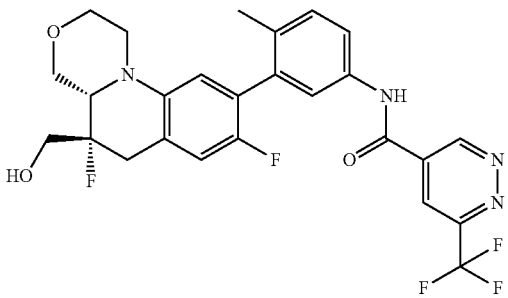 [SMILES: Cc1ccc(NC(=O)c2cnnc(C(F)(F)F)c2)cc1-c1cc2c(cc1F)C[C@@](F)(CO)[C@@H]1COCCN21] | N-(3-((4aS,5S)-5,8-difluoro-5-(hydroxymethyl)-1,2,4,4a,5,6-hexahydro-[1,4]oxazino[4,3-a]quinolin-9-yl)-4-methylphenyl)-6-(trifluoromethyl)pyridazine-4-carboxamide | $^1$H NMR (400 MHz, Methanol-d4) δ 9.86 (d, J = 2.0 Hz, 1H), 8.57 (d, J = 2.0 Hz, 1H), 7.67 (dd, J = 8.2, 2.3 Hz, 1H), 7.61 (d, J = 2.3 Hz, 1H), 7.31 (d, J = 8.3 Hz, 1H), 6.94 (d, J = 9.6 Hz, 1H), 6.71 (d, J = 6.3 Hz, 1H), 4.06 (dd, J = 11.5, 3.2 Hz, 1H), 3.91 (dd, J = 11.4, 3.4 Hz, 1H), 3.74-3.53 (m, 5H), 3.22-3.10 (m, 2H), 3.01-2.87 (m, 2H), 2.18 (s, 3H). LCMS (m/z) (M + H) = 535.1, Rt = 1.42 min. |
| 483 | 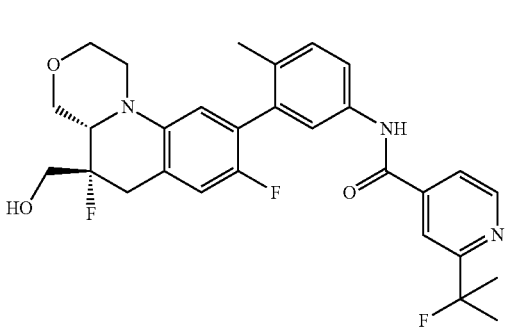 [SMILES: Cc1ccc(NC(=O)c2ccnc(C(C)(C)F)c2)cc1-c1cc2c(cc1F)C[C@@](F)(CO)[C@@H]1COCCN21] | N-(3-((4aS,5S)-5,8-difluoro-5-(hydroxymethyl)-1,2,4,4a,5,6-hexahydro-[1,4]oxazino[4,3-a]quinolin-9-yl)-4-methylphenyl)-2-(2-fluoropropan-2-yl)isonicotinamide | $^1$H NMR (400 MHz, Methanol-d4) δ 8.68 (d, J = 5.1 Hz, 1H), 8.05 (s, 1H), 7.76 (dd, J = 5.1, 1.6 Hz, 1H), 7.63 (dd, J = 8.2, 2.2 Hz, 1H), 7.58 (d, J = 2.2 Hz, 1H), 7.28 (d, J = 8.3 Hz, 1H), 6.93 (d, J = 9.6 Hz, 1H), 6.72 (d, J = 6.3 Hz, 1H), 4.06 (dd, J = 11.2, 3.4 Hz, 1H), 3.91 (dd, J = 11.4, 3.3 Hz, 1H), 3.74-3.54 (m, 5H), 3.23-3.08 (m, 2H), 3.00-2.86 (m, 2H), 2.17 (s, 3H), 1.75 (s, 3H), 1.70 (s, 3H). LCMS (m/z) (M + H) = 526.2, Rt = 1.45 min. |

| | | | |
|---|---|---|---|
| 484 | 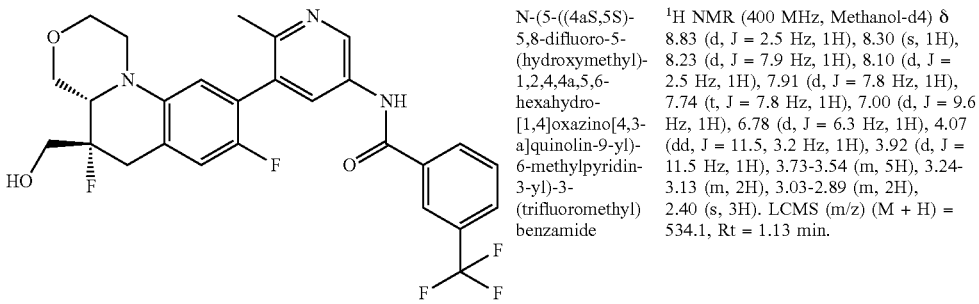 | N-(5-((4aS,5S)-5,8-difluoro-5-(hydroxymethyl)-1,2,4,4a,5,6-hexahydro-[1,4]oxazino[4,3-a]quinolin-9-yl)-6-methylpyridin-3-yl)-3-(trifluoromethyl)benzamide | $^1$H NMR (400 MHz, Methanol-d4) δ 8.83 (d, J = 2.5 Hz, 1H), 8.30 (s, 1H), 8.23 (d, J = 7.9 Hz, 1H), 8.10 (d, J = 2.5 Hz, 1H), 7.91 (d, J = 7.8 Hz, 1H), 7.74 (t, J = 7.8 Hz, 1H), 7.00 (d, J = 9.6 Hz, 1H), 6.78 (d, J = 6.3 Hz, 1H), 4.07 (dd, J = 11.5, 3.2 Hz, 1H), 3.92 (d, J = 11.5 Hz, 1H), 3.73-3.54 (m, 5H), 3.24-3.13 (m, 2H), 3.03-2.89 (m, 2H), 2.40 (s, 3H). LCMS (m/z) (M + H) = 534.1, Rt = 1.13 min. |
| 485 | 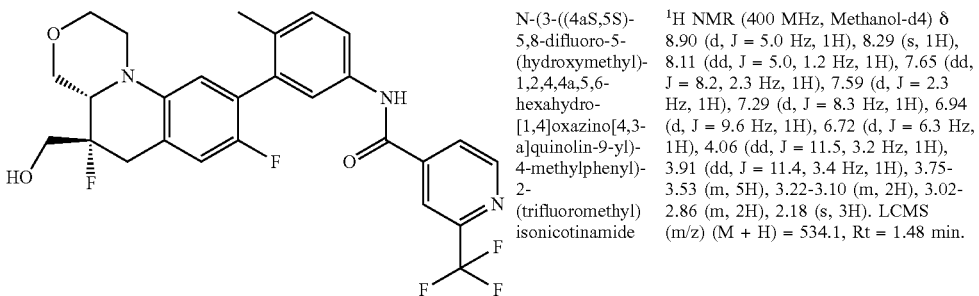 | N-(3-((4aS,5S)-5,8-difluoro-5-(hydroxymethyl)-1,2,4,4a,5,6-hexahydro-[1,4]oxazino[4,3-a]quinolin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.65 (dd, J = 8.2, 2.3 Hz, 1H), 7.59 (d, J = 2.3 Hz, 1H), 7.29 (d, J = 8.3 Hz, 1H), 6.94 (d, J = 9.6 Hz, 1H), 6.72 (d, J = 6.3 Hz, 1H), 4.06 (dd, J = 11.5, 3.2 Hz, 1H), 3.91 (dd, J = 11.4, 3.4 Hz, 1H), 3.75-3.53 (m, 5H), 3.22-3.10 (m, 2H), 3.02-2.86 (m, 2H), 2.18 (s, 3H). LCMS (m/z) (M + H) = 534.1, Rt = 1.48 min. |
| 486 | 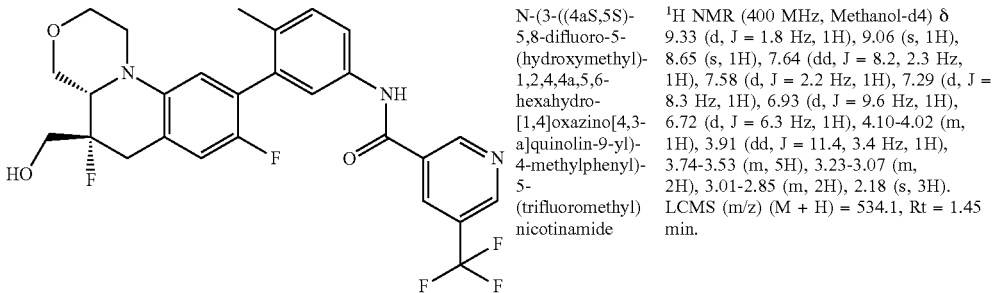 | N-(3-((4aS,5S)-5,8-difluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, Methanol-d4) δ 9.33 (d, J = 1.8 Hz, 1H), 9.06 (s, 1H), 8.65 (s, 1H), 7.64 (dd, J = 8.2, 2.3 Hz, 1H), 7.58 (d, J = 2.2 Hz, 1H), 7.29 (d, J = 8.3 Hz, 1H), 6.93 (d, J = 9.6 Hz, 1H), 6.72 (d, J = 6.3 Hz, 1H), 4.10-4.02 (m, 1H), 3.91 (dd, J = 11.4, 3.4 Hz, 1H), 3.74-3.53 (m, 5H), 3.23-3.07 (m, 2H), 3.01-2.85 (m, 2H), 2.18 (s, 3H). LCMS (m/z) (M + H) = 534.1, Rt = 1.45 min. |
| 487 | 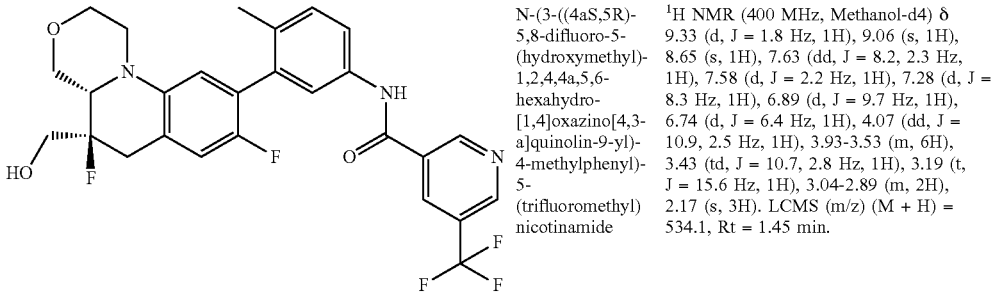 | N-(3-((4aS,5R)-5,8-difluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, Methanol-d4) δ 9.33 (d, J = 1.8 Hz, 1H), 9.06 (s, 1H), 8.65 (s, 1H), 7.63 (dd, J = 8.2, 2.3 Hz, 1H), 7.58 (d, J = 2.2 Hz, 1H), 7.28 (d, J = 8.3 Hz, 1H), 6.89 (d, J = 9.7 Hz, 1H), 6.74 (d, J = 6.4 Hz, 1H), 4.07 (dd, J = 10.9, 2.5 Hz, 1H), 3.93-3.53 (m, 6H), 3.43 (td, J = 10.7, 2.8 Hz, 1H), 3.19 (t, J = 15.6 Hz, 1H), 3.04-2.89 (m, 2H), 2.17 (s, 3H). LCMS (m/z) (M + H) = 534.1, Rt = 1.45 min. |
| 488 | 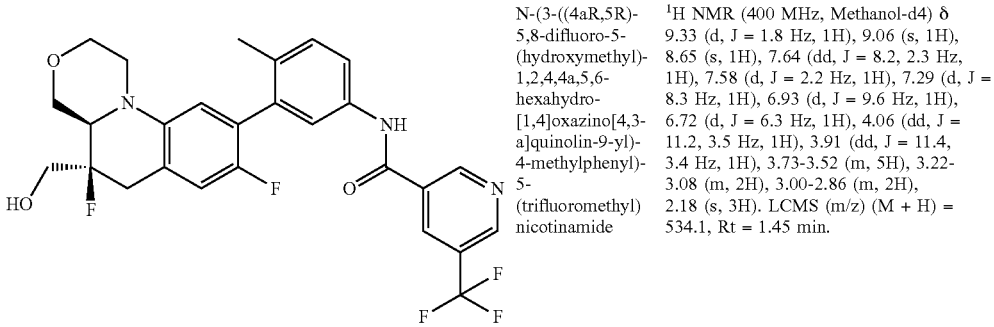 | N-(3-((4aR,5R)-5,8-difluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, Methanol-d4) δ 9.33 (d, J = 1.8 Hz, 1H), 9.06 (s, 1H), 8.65 (s, 1H), 7.64 (dd, J = 8.2, 2.3 Hz, 1H), 7.58 (d, J = 2.2 Hz, 1H), 7.29 (d, J = 8.3 Hz, 1H), 6.93 (d, J = 9.6 Hz, 1H), 6.72 (d, J = 6.3 Hz, 1H), 4.06 (dd, J = 11.2, 3.5 Hz, 1H), 3.91 (dd, J = 11.4, 3.4 Hz, 1H), 3.73-3.52 (m, 5H), 3.22-3.08 (m, 2H), 3.00-2.86 (m, 2H), 2.18 (s, 3H). LCMS (m/z) (M + H) = 534.1, Rt = 1.45 min. |

| | | | |
|---|---|---|---|
| 489 | 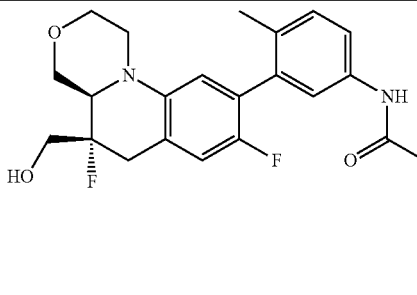 | N-(3-((4aR,5S)-5,8-difluoro-5-(hydroxymethyl)-1,2,4,4a,5,6-hexahydro-[1,4]oxazino[4,3-a]quinolin-9-yl)-4-methylphenyl)-5-(trifluoromethyl)nicotinamide | $^1$H NMR (400 MHz, Methanol-d4) δ 9.33 (d, J = 1.8 Hz, 1H), 9.06 (s, 1H), 8.64 (s, 1H), 7.63 (dd, J = 8.2, 2.3 Hz, 1H), 7.58 (d, J = 2.2 Hz, 1H), 7.28 (d, J = 8.3 Hz, 1H), 6.89 (d, J = 9.7 Hz, 1H), 6.74 (d, J = 6.3 Hz, 1H), 4.07 (dd, J = 11.0, 2.7 Hz, 1H), 3.89 (dd, J = 11.3, 3.4 Hz, 1H), 3.87-3.54 (m, 5H), 3.43 (td, J = 10.7, 2.9 Hz, 1H), 3.19 (t, J = 15.6 Hz, 1H), 3.04-2.91 (m, 2H), 2.17 (s, 3H). LCMS (m/z) (M + H) = 534.1, Rt = 1.45 min. |

15

The compounds listed in the table below, were prepared using intermediates described above and the appropriate starting materials:

| | | | |
|---|---|---|---|
| 490 | 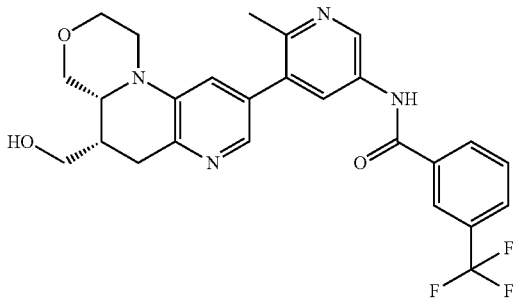 [SMILES: Cc1ncc(NC(=O)c2cccc(C(F)(F)F)c2)cc1-c1cnc2c(c1)N1CCOC[C@H]1[C@@H](CO)C2] | N-(5-((4aR,5S)-5-(hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, Methanol-d4) δ 8.84 (d, J = 2.4 Hz, 1H), 8.30 (s, 1H), 8.24 (d, J = 7.9 Hz, 1H), 8.12 (d, J = 2.4 Hz, 1H), 7.91 (d, J = 7.8 Hz, 1H), 7.85 (d, J = 1.6 Hz, 1H), 7.75 (t, J = 7.8 Hz, 1H), 7.32 (d, J = 1.6 Hz, 1H), 3.96-3.87 (m, 2H), 3.83-3.76 (m, 2H), 3.73-3.62 (m, 2H), 3.55-3.46 (m, 2H), 3.14-2.96 (m, 3H), 2.48 (s, 3H), 2.32-2.25 (m, 1H). LCMS (m/z) (M + H) = 499.1, Rt = 0.90 min. |
| 491 | 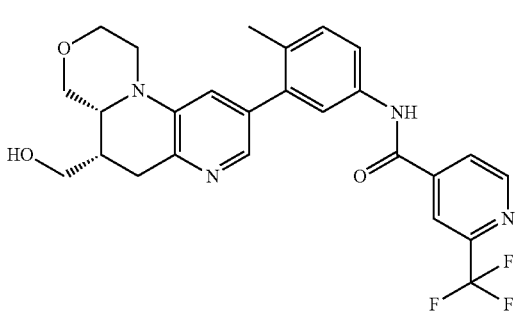 [SMILES: Cc1ccc(NC(=O)c2ccnc(C(F)(F)F)c2)cc1-c1cnc2c(c1)N1CCOC[C@H]1[C@@H](CO)C2] | N-(3-((4aR,5S)-5-(hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.80 (d, J = 1.7 Hz, 1H), 7.66 (dd, J = 8.2, 2.3 Hz, 1H), 7.62 (d, J = 2.2 Hz, 1H), 7.32 (d, J = 8.3 Hz, 1H), 7.25 (d, J = 1.6 Hz, 1H), 3.91 (td, J = 11.6, 11.1, 3.2 Hz, 2H), 3.81-3.75 (m, 2H), 3.73-3.61 (m, 2H), 3.54-3.43 (m, 2H), 3.11-2.94 (m, 3H), 2.32-2.23 (m, 4H). LCMS (m/z) (M + H) = 499.1, Rt = 1.00 min. |
| 492 | 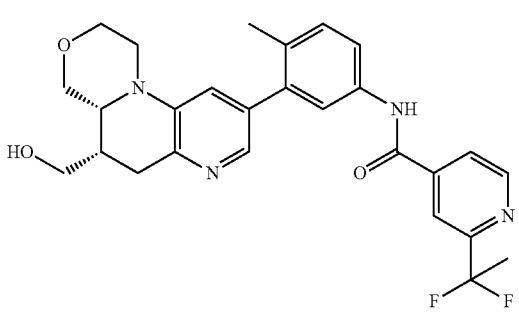 [SMILES: Cc1ccc(NC(=O)c2ccnc(C(C)(F)F)c2)cc1-c1cnc2c(c1)N1CCOC[C@H]1[C@@H](CO)C2] | 2-(1,1-difluoroethyl)-N-(3-((4aR,5S)-5-(hydroxymethyl)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4) δ 8.79 (d, 1H), 8.17 (d, J = 5.0 Hz 1H), 7.95 (s, 1H), 7.81 (d, J = 1.7 Hz, 1H), 7.65 (dd, J = 8.2, 2.3 Hz, 1H), 7.61 (d, J = 2.2 Hz, 1H), 7.32 (d, J = 8.3 Hz, 1H), 7.25 (d, J = 1.6 Hz, 1H), 3.91 (td, J = 10.8, 3.2 Hz, 2H), 3.82-3.76 (m, 2H), 3.74-3.61 (m, 2H), 3.55-3.43 (m, 2H), 3.11-2.93 (m, 3H), 2.32-2.24 (m, 4H), 2.03 (t, J = 18.7 Hz, 3H). LCMS (m/z) (M + H) = 495.2, Rt = 0.97 min. |

| | | | |
|---|---|---|---|
| 493 | 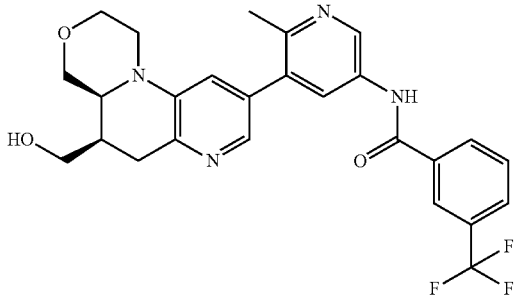 [SMILES: Cc1ncc(NC(=O)c2cccc(C(F)(F)F)c2)cc1-c1cnc2c(c1)N1CCOC[C@@H]1[C@H](CO)C2] | N-(5-((4aS,5R)-5-(hydroxymethyl)-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, Methanol-d4) δ 8.83 (d, J = 2.5 Hz, 1H), 8.30 (s, 1H), 8.23 (d, J = 7.9 Hz, 1H), 8.12 (d, J = 2.5 Hz, 1H), 7.91 (d, J = 7.8 Hz, 1H), 7.85 (dd, J = 1.7 Hz, 1H), 7.74 (t, J = 7.8 Hz, 1H), 7.32 (d, J = 1.7 Hz, 1H), 3.95-3.88 (m, 2H), 3.84-3.76 (m, 2H), 3.73-3.62 (m, 2H), 3.55-3.45 (m, 2H), 3.13-2.96 (m, 3H), 2.48 (s, 3H), 2.33-2.24 (m, 1H). LCMS (m/z) (M + H) = 499.1, Rt = 0.89 min. |
| 494 | 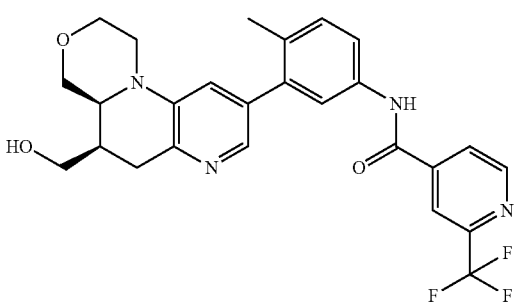 [SMILES: Cc1ccc(NC(=O)c2ccnc(C(F)(F)F)c2)cc1-c1cnc2c(c1)N1CCOC[C@@H]1[C@H](CO)C2] | N-(3-((4aS,5R)-5-(hydroxymethyl)-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.90 (d, J = 5.0 Hz, 1H), 8.29 (s, 1H), 8.11 (dd, J = 5.0, 1.2 Hz, 1H), 7.80 (d, J = 1.7 Hz, 1H), 7.66 (dd, J = 8.2, 2.3 Hz, 1H), 7.62 (d, J = 2.2 Hz, 1H), 7.32 (d, J = 8.3 Hz, 1H), 7.25 (d, J = 1.6 Hz, 1H), 3.91 (td, J = 11.6, 11.1, 3.2 Hz, 2H), 3.82-3.76 (m, 2H), 3.74-3.61 (m, 2H), 3.55-3.43 (m, 2H), 3.11-2.94 (m, 3H), 2.32-2.23 (m, 4H). LCMS (m/z) (M + H) = 499.1, Rt = 0.99 min. |
| 495 | 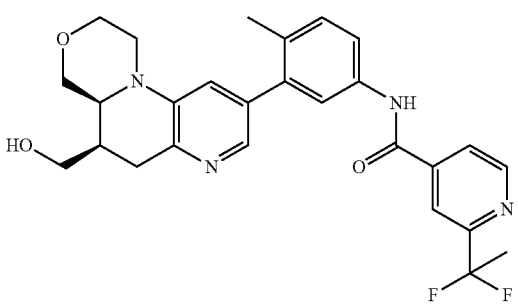 [SMILES: Cc1ccc(NC(=O)c2ccnc(C(C)(F)F)c2)cc1-c1cnc2c(c1)N1CCOC[C@@H]1[C@H](CO)C2] | 2-(1,1-difluoroethyl)-N-(3-((4aS,5R)-5-(hydroxymethyl)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4, δ 8.79 (d, J = 5.0 Hz, 1H), 8.17 (s, 1H), 7.95 (dd, J = 5.1, 1.5 Hz, 1H), 7.81 (d, J = 1.7 Hz, 1H), 7.65 (dd, J = 8.2, 2.3 Hz, 1H), 7.61 (d, J = 2.2 Hz, 1H), 7.31 (d, J = 8.3 Hz, 1H), 7.25 (d, J = 1.6 Hz, 1H), 3.90 (td, J = 11.6, 11.1, 3.3 Hz, 2H), 3.82-3.75 (m, 2H), 3.74-3.60 (m, 2H), 3.55-3.42 (m, 2H), 3.11-2.93 (m, 3H), 2.32-2.22 (m, 4H), 2.03 (t, J = 18.7 Hz, 3H). LCMS (m/z) (M + H) = 495.2, Rt = 0.97 min. |

Intermediate for Example 496

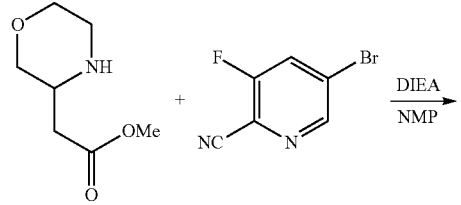

DIEA / NMP →

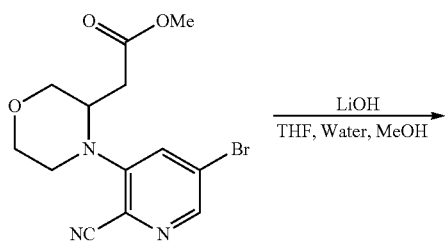

LiOH / THF, Water, MeOH →

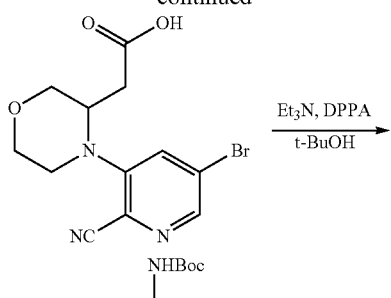

Et$_3$N, DPPA / t-BuOH →

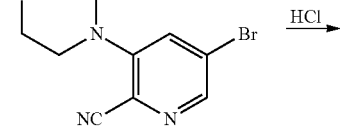

HCl →

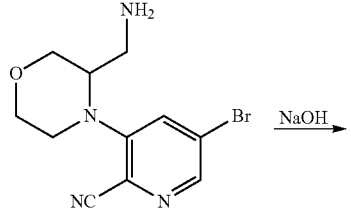

NaOH →

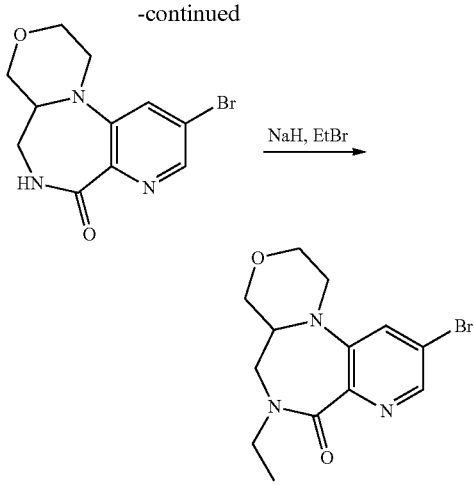

Step 1:

Methyl 2-(morpholin-3-yl)acetate (1.034 g, 6.50 mmol), 4-bromo-2-fluorobenzonitrile (1.186 g, 5.9 mmol), DIEA (3.09 ml, 17.70 mmol) were combined in NMP (Volume: 5 ml) and the mixture heated in a heating block maintained at 110° C. for 24 h. After the elapsed time, the reaction mixture was diluted with EtOAc and washed with water twice and then dried ($MgSO_4$), filtered and concentrated in vacuo. The residue was purified by flash chromatography (0-50% EtOAc/heptane) to afford the desired product methyl 2-(4-(5-bromo-2-cyanopyridin-3-yl)morpholin-3-yl)acetate in 36% isolated yield. LCMS (m/z) (M+H) 342.1; Rt.=0.0.92 min.

Step 2:

methyl 2-(4-(5-bromo-2-cyanopyridin-3-yl)morpholin-3-yl)acetate (715 mg, 2.102 mmol) was dissolved in THF (5.2 mL), MeOH (3.5 mL) and then $LiOH \cdot H_2O$ (441 mg, 10.51 mmol) dissolved in Water (1.7 mL)) was added. The mixture was agitated at room temperature for 1 h and then concentrated in vacuo. The residue was acidified to pH 4 and then extracted with EtOAc. The combined organic layer was dried ($MgSO_4$), filtered and concentrated in vacuo. The residue 2-(4-(5-bromo-2-cyanopyridin-3-yl)morpholin-3-yl)acetic acid was taken to the next step as such without any further purification. LCMS (m/z) (M+H) 325.9; Rt.=0.73 min.

Step 3: 2-(4-(5-bromo-2-cyanopyridin-3-yl)morpholin-3-yl)acetic acid (686 mg, 2.102 mmol) was dissolved in t-BuOH (21 mL)) and then triethylamine (586 µl, 4.20 mmol) followed by DPPA (578 mg, 2.102 mmol) were added. The mixture was agitated at 90° C. overnight. The next morning, the reaction mixture was concentrated in vacuo and the residue was purified by flash chromatography (0-40% EtOAc/heptane) to afford tert-butyl ((4-(5-bromo-2-cyanopyridin-3-yl)morpholin-3-yl)methyl)carbamate in 45% isolated yield. LCMS (m/z) (M+H) 398.9; Rt.=1.04 min.

Step 4:

Tert-butyl ((4-(5-bromo-2-cyanopyridin-3-yl)morpholin-3-yl)methyl)carbamate (374 mg, 0.941 mmol) was dissolved in DCM (4.7 mL) and at room temperature was treated with 4 N HCl in dioxane (4.7 mL). The mixture was agitated at room temperature for 1 h upon the reaction mixture was concentrated in vacuo and the residue 3-(3-(aminomethyl) morpholino)-5-bromopicolinonitrile was taken to the next step as such. LCMS (m/z) (M+H) 299.2; Rt.=0.70 min.

Step 5:

3-(3-(aminomethyl)morpholino)-5-bromopicolinonitrile (3.26 g, 9.77 mmol) was dissolved in EtOH (26 mL) and then NaOH (3.91 g, 98 mmol) was added. The mixture was placed in a preheated oil bath maintained at 100° C. After 10 min, the reaction mixture was cooled to room temperature and quenched by addition of 4N HCl (aq) until pH=1. The entire mixture was extracted with EtOAc. The aq. acidic layer was then directly loaded onto reverse-phase column and the product eluted with (0-30% ACN/water) and the product fractions were collected and frozen and lyophilized to afford 530 mg of the desired product 10-bromo-4,4a,5,6-tetrahydro-1H-[1,4]oxazino[4,3-a]pyrido[2,3-f][1,4]diazepin-7(2H)-one. LCMS (m/z) (M+H) 299.5; Rt.=0.55 min.

Step 6:

To an ice cold solution of 10-bromo-1,2,4,4a,5,6-hexahydro-7H-[1,4]oxazino[4,3-a]pyrido[2,3-f][1,4]diazepin-7-one (1.0 equiv.) in DMF (0.34 M) was added NaH (2.5 equiv.) and stirred for 1 hr. Bromoethane (2.5 equiv.) was then added and allowed the reaction mixture to come to ambient temperature. The reaction mixture was stirred for 3 hr, quenched with water and extracted with EtOAc. The organic phase was washed with sat. $NaHCO_3$. The combined aqueous layer was back extracted with EtOAc. The combined organic phase was washed with brine, dried over sodium sulfate, filtered, and concentrated. The crude product was purified by flash chromatography over silica gel (DCM with 0-10% MeOH) to give 10-bromo-6-ethyl-1,2,4,4a,5,6-hexahydro-7H-[1,4]oxazino[4,3-a]pyrido[2,3-f][1,4]diazepin-7-one in 26% yield and the racemate material was resolved by chiral SFC. Two peaks were isolated after chiral separation. LCMS (m/z) (M+H)=328.0, Rt=0.91 min.

The compounds listed in the table below were prepared using the above intermediate and the appropriate starting materials:

| 496 | 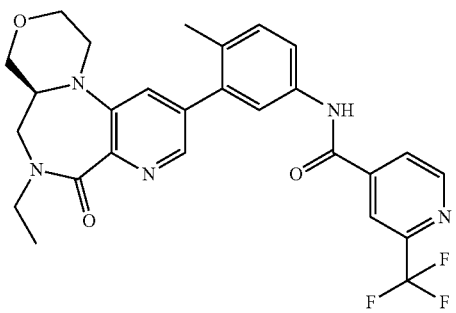 | (S)-N-(3-(6-ethyl-7-oxo-1,2,4a,5,6,7-hexahydro-4H-[1,4]oxazino[4,3-a]pyrido[2,3-f][1,4]diazepin-10-yl)-4-methylphenyl)-2-(trifluoromethyl)isonicotinamide | $^1$H NMR (400 MHz, Methanol-d4) δ 8.90 (d, J = 5.0 Hz, 1H), 8.30 (s, 1H), 8.26 (s, 1H), 8.12 (dd, J = 5.0, 1.2 Hz, 1H), 7.73-7.66 (m, 2H), 7.50 (d, J = 1.6 Hz, 1H), 7.36 (d, J = 7.9 Hz, 1H), 4.11 (dq, J = 14.2, 7.1 Hz, 1H), 3.92 (ddd, J = 18.5, 11.0, 2.4 Hz, 2H), 3.76-3.63 (m, 3H), 3.39-3.33 (m, 2H), 3.23-3.12 (m, 2H), 2.30 (s, 3H), 1.26 (t, J = 7.1 Hz, 3H). LCMS (m/z) (M + H) = 526.1, Rt = 1.21 min. |
|---|---|---|---|

| | | | |
|---|---|---|---|
| 497 | 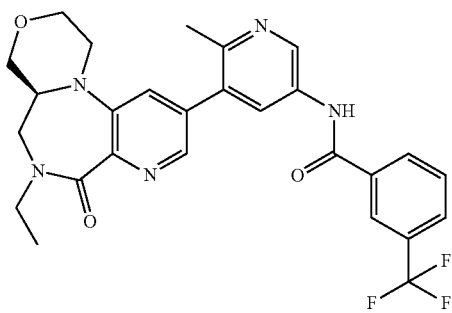 [SMILES: CCN1C[C@H]2COCCN2c2cc(-c3cc(NC(=O)c4cccc(C(F)(F)F)c4)cnc3C)cnc2C1=O] | (S)-N-(5-(6-ethyl-7-oxo-1,2,4a,5,6,7-hexahydro-4H-[1,4]oxazino[4,3-a]pyrido[2,3-f][1,4]diazepin-10-yl)-6-methylpyridin-3-yl)-3-(trifluoromethyl)benzamide | ¹H NMR (400 MHz, Methanol-d4) δ 8.86 (d, J = 2.5 Hz, 1H), 8.35-8.28 (m, 2H), 8.24 (d, J = 7.9 Hz, 1H), 8.21 (d, J = 2.4 Hz, 1H), 7.92 (d, J = 7.8 Hz, 1H), 7.75 (t, J = 7.8 Hz, 1H), 7.58 (d, J = 1.7 Hz, 1H), 4.11 (dq, J = 14.2, 7.1 Hz, 1H), 3.92 (ddd, J = 18.4, 11.0, 2.3 Hz, 2H), 3.77-3.63 (m, 3H), 3.40-3.32 (m, 3H), 3.25-3.14 (m, 2H), 2.51 (s, 3H), 1.27 (t, J = 7.1 Hz, 3H). LCMS (m/z) (M + H) = 526.1, Rt = 1.02 min. |
| 498 | 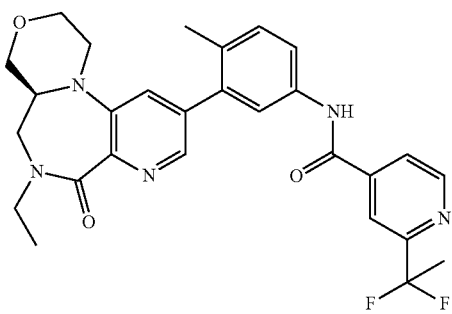 [SMILES: CCN1C[C@H]2COCCN2c2cc(-c3cc(NC(=O)c4ccnc(C(C)(F)F)c4)ccc3C)cnc2C1=O] | (S)-2-(1,1-difluoroethyl)-N-(3-(6-ethyl-7-oxo-1,2,4a,5,6,7-hexahydro-4H-[1,4]oxazino[4,3-a]pyrido[2,3-f][1,4]diazepin-10-yl)-4-methylphenyl)isonicotinamide | ¹H NMR (400 MHz, Methanol-d4) δ 8.80 (d, J = 5.0 Hz, 1H), 8.26 (s, 1H), 8.21-8.15 (m, 1H), 7.96 (d, J = 5.0 Hz, 1H), 7.74-7.64 (m, 2H), 7.51 (d, J = 1.6 Hz, 1H), 7.36 (d, J = 7.9 Hz, 1H), 4.11 (dq, J = 14.2, 7.2 Hz, 1H), 3.92 (ddd, J = 18.9, 10.9, 2.4 Hz, 2H), 3.76-3.63 (m, 3H), 3.40-3.32 (m, 3H), 3.23-3.12 (m, 2H), 2.30 (s, 3H), 2.03 (t, J = 18.7 Hz, 3H), 1.27 (t, J = 7.1 Hz, 3H). LCMS (m/z) (M + H) = 522.1, Rt = 1.17 min. |
| 499 | 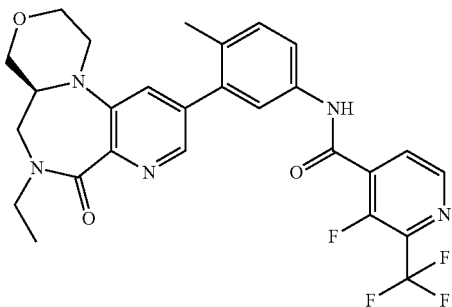 [SMILES: CCN1C[C@H]2COCCN2c2cc(-c3cc(NC(=O)c4ccnc(C(F)(F)F)c4F)ccc3C)cnc2C1=O] | (S)-N-(3-(6-ethyl-7-oxo-1,2,4a,5,6,7-hexahydro-4H-[1,4]oxazino[4,3-a]pyrido[2,3-f][1,4]diazepin-10-yl)-4-methylphenyl)-3-fluoro-2-(trifluoromethyl)isonicotinamide | ¹H NMR (400 MHz, Methanol-d4) δ 8.65 (d, J = 4.7 Hz, 1H), 8.25 (d, J = 1.4 Hz, 1H), 7.95 (t, J = 4.8 Hz, 1H), 7.66 (d, J = 2.3 Hz, 1H), 7.63 (dd, J = 8.2, 2.3 Hz, 1H), 7.50 (d, J = 1.7 Hz, 1H), 7.37 (d, J = 8.3 Hz, 1H), 4.11 (dq, J = 14.1, 7.1 Hz, 1H), 3.92 (ddd, J = 18.8, 11.0, 2.5 Hz, 2H), 3.76-3.63 (m, 3H), 3.38-3.32 (m, 3H), 3.22-3.14 (m, 2H), 2.29 (s, 3H), 1.26 (t, J = 7.1 Hz, 3H). LCMS (m/z) (M + H) = 544.1, Rt = 1.23 min. |
| 500 | 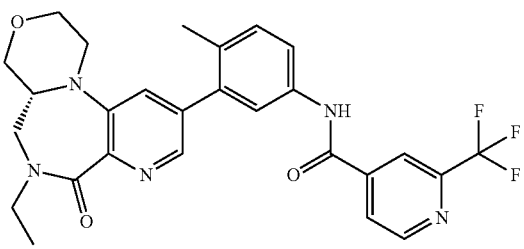 [SMILES: CCN1C[C@@H]2COCCN2c2cc(-c3cc(NC(=O)c4ccnc(C(F)(F)F)c4)ccc3C)cnc2C1=O] | (R)-N-(3-(6-ethyl-7-oxo-1,2,4a,5,6,7-hexahydro-4H-[1,4]oxazino[4,3-a]pyrido[2,3-f][1,4]diazepin-10-yl)-4-methylphenyl)-2-(trifluoromethyl)isonicotinamide | ¹H NMR (400 MHz, MeOH-d4) δ ppm 10.73 (s, 1 H) 9.00 (d, J = 5.01 Hz, 1 H) 8.37 (s, 1 H) 8.25 (d, J = 1.83 Hz, 1 H) 8.20 (dd, J = 5.01, 1.10 Hz, 1H) 7.76 (dd, J = 8.25, 2.26 Hz, 1 H) 7.72 (d, J = 2.20 Hz, 1 H) 7.36-7.43 (m, 2 H) 3.78-4.11 (m, 3 H) 3.44-3.70 (m, 3 H) 3.02-3.30 (m, 4 H) 2.26 (s, 3 H) 1.14 (t, J = 7.09 Hz, 3 H) LCMS (m/z) (M + H) = 526.1, 1.21 min. |
| 501 | 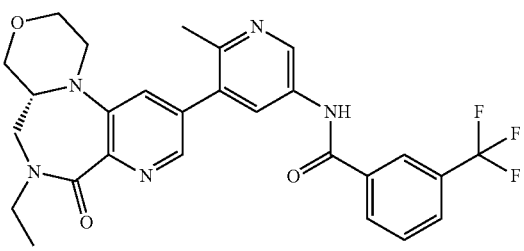 [SMILES: CCN1C[C@@H]2COCCN2c2cc(-c3cc(NC(=O)c4cccc(C(F)(F)F)c4)cnc3C)cnc2C1=O] | (R)-N-(5-(6-ethyl-7-oxo-1,2,4a,5,6,7-hexahydro-4H-[1,4]oxazino[4,3-a]pyrido[2,3-f][1,4]diazepin-10-yl)-6-methypyridin-3-yl)-3-(trifluoromethyl)benzamide | ¹H NMR (400 MHz, MeOH-d4) δ ppm 10.31-10.60 (m, 1 H) 8.75 (d, J = 5.01 Hz, 1 H) 8.02 (s, 1 H) 7.82 (dd, J = 5.01, 1.59 Hz, 1 H) 7.54-7.74 (m, 2 H) 7.27 (d, J = 8.31 Hz, 1 H) 5.63 (d, J = 1.59 Hz, 1 H) 5.54 (d, J = 1.47 Hz, 1 H) 3.95 (t, J = 5.81 Hz, 2 H) 3.76-3.89 (m, 2 H) 3.63 (br d, J = 12.96 Hz, 1 H) 3.53 (td, J = 11.68, 2.57 Hz, 1 H) 3.33-3.40 (m, 1 H) 3.21-3.29 (m, 1 H) 3.07 (td, J = 12.35, 3.42 Hz, 1 H) 2.26 (s, 3 H) 1.93-2.13 (m, 1H) 1.74 (s, 3 H) 1.68 (s, 3 H) 1.56-1.66 (m, 1 H).; LCMS (m/z) (M + H) = 526.1, 1.01 min. |

| | | | |
|---|---|---|---|
| 502 | 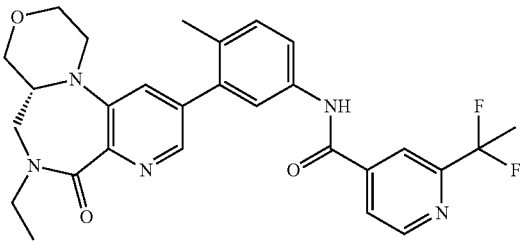 [SMILES: CCN1C[C@@H]2COCCN2c2cc(-c3cc(NC(=O)c4ccnc(C(C)(F)F)c4)ccc3C)cnc2C1=O] | (R)-2-(1,1-difluoroethyl)-N-(3-(6-ethyl-7-oxo-1,2,4a,5,6,7-hexahydro-4H-[1,4]oxazino[4,3-a]pyrido[2,3-f][1,4]diazepin-10-yl)-4-methylphenyl)isonicotinamide | $^1$H NMR (400 MHz, MeOH-d4) δ ppm 8.80 (d, J = 5.0 Hz, 1 H), 8.26 (s, 1H), 8.21-8.15 (m, 1H), 7.96 (d, J = 5.0 Hz, 1H), 7.74-7.64 (m, 2H), 7.51 (d, J = 1.6 Hz, 1H), 7.36 (d, J = 7.9 Hz, 1H), 4.11 (dq, J = 14.2, 7.2 Hz, 1H), 3.92 (ddd, J = 18.9, 10.9, 2.4 Hz, 2H), 3.76-3.63 (m, 3H), 3.40-3.32 (m, 3H), 3.23-3.12 (m, 2H), 2.30 (s, 3H), 2.03 (t, J = 18.7 Hz, 3H), 1.27 (t, J = 7.1 Hz, 3H).; LCMS (m/z) (M + H) = 522.2, 1.17 min. |
| 503 | 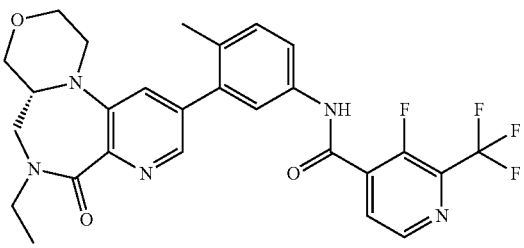 [SMILES: CCN1C[C@@H]2COCCN2c2cc(-c3cc(NC(=O)c4ccnc(C(F)(F)F)c4F)ccc3C)cnc2C1=O] | (R)-2-(1,1-difluoroethyl)-N-(3-(6-ethyl-7-oxo-1,2,4a,5,6,7-hexahydro-4H-[1,4]oxazino[4,3-a]pyrido[2,3-f][1,4]diazepin-10-yl)-4-methylphenyl)isonicotinamide | $^1$H NMR (400 MHz, MeOH-d4) δ ppm 8.65 (d, J = 4.7 Hz, 1H), 8.25 (d, J = 1.4 Hz, 1H), 7.95 (t, J = 4.8 Hz, 1H), 7.66 (d, J = 2.3 Hz, 1H), 7.63 (dd, J = 8.2, 2.3 Hz, 1H), 7.50 (d, J = 1.7 Hz, 1H), 7.37 (d, J = 8.3 Hz, 1H), 4.11 (dq, J = 14.1, 7.1 Hz, 1H), 3.92 (ddd, J = 18.8, 11.0, 2.5 Hz, 2H), 3.76-3.63 (m, 3H), 3.38-3.32 (m, 3H), 3.22-3.14 (m, 2H), 2.29 (s, 3H), 1.26 (t, J = 7.1 Hz, 3H).; LCMS (m/z) (M + H) = 544.1, 1.23 min. |

The compounds listed in the table below were prepared using methods similar to those described for the preparation of Example 496 using the appropriate starting materials:

| | | | |
|---|---|---|---|
| 504 | 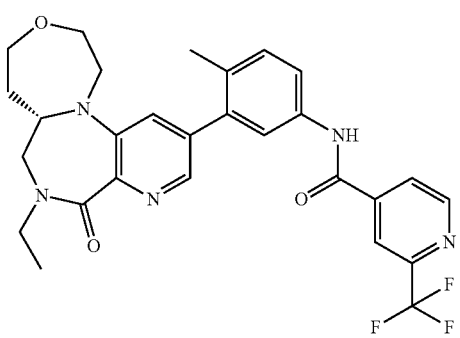 [SMILES: CCN1C[C@@H]2CCOCCN2c2cc(-c3cc(NC(=O)c4ccnc(C(F)(F)F)c4)ccc3C)cnc2C1=O] | (S)-N-(3-(7-ethyl-8-oxo-1,2,4,5,5a,6,7,8-octahydropyrido[2',3':6,7][1,4]diazepino[1,2-d][1,4]oxazepin-11-yl)-4-methylphenyl)-2-(trifluoromethyl)isonicotinamide | $^1$H NMR (400 MHz, Methanol-d4) δ 8.90 (d, J = 5.0 Hz, 1H), 8.30 (s, 1H), 8.20 (d, J = 1.4 Hz, 1H), 8.12 (dd, J = 5.0, 1.2 Hz, 1H), 7.74-7.65 (m, 2H), 7.37 (d, J = 9.1 Hz, 1H), 4.52 (dd, J = 14.0, 3.7 Hz, 1H), 4.13-4.00 (m, 3H), 3.59 (t, J = 11.3 Hz, 1H), 3.53-3.38 (m, 4H), 3.19-3.07 (m, 2H), 2.30 (s, 3H), 2.19-1.97 (m, 2H), 1.21 (t, J = 7.1 Hz, 3H). LCMS (m/z) (M + H) = 540.1, Rt = 1.09 min. |
| 505 | 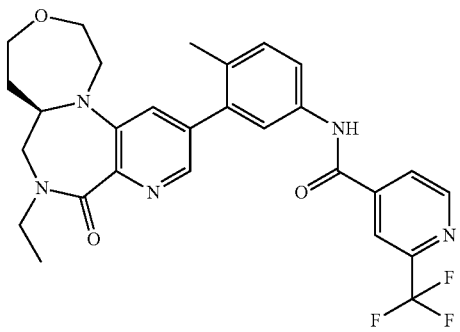 [SMILES: CCN1C[C@H]2CCOCCN2c2cc(-c3cc(NC(=O)c4ccnc(C(F)(F)F)c4)ccc3C)cnc2C1=O] | (R)-N-(3-(7-ethyl-8-oxo-1,2,4,5,5a,6,7,8-octahydropyrido[2',3':6,7][1,4]diazepino[1,2-d][1,4]oxazepin-11-yl)-4-methylphenyl)-2-(trifluoromethyl)isonicotinamide | $^1$H NMR (400 MHz, Methanol-d4) δ 8.90 (d, J = 5.0 Hz, 1H), 8.30 (s, 1H), 8.20 (d, J = 1.7 Hz, 1H), 8.12 (dd, J = 5.0, 1.2 Hz, 1H), 7.73-7.66 (m, 2H), 7.45 (d, J = 1.7 Hz, 1H), 7.40-7.35 (m, 1H), 4.52 (dd, J = 14.1, 3.8 Hz, 1H), 4.13-3.99 (m, 3H), 3.59 (t, J = 11.3 Hz, 1H), 3.51-3.38 (m, 4H), 3.19-3.07 (m, 2H), 2.30 (s, 3H), 2.19-1.98 (m, 2H), 1.21 (t, J = 7.1 Hz, 3H). LCMS (m/z) (M + H) = 540.1, Rt = 1.10 min. |

| 506 | 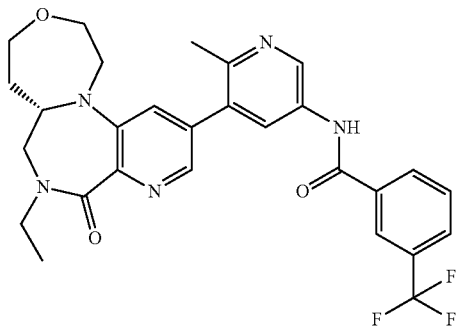 [SMILES: CCN1C[C@@H]2CCOCCN2c2cc(-c3cc(NC(=O)c4cccc(C(F)(F)F)c4)cnc3C)cnc2C1=O] | (S)-N-(5-(7-ethyl-8-oxo-1,2,4,5,5a,6,7,8-octahydropyrido[2',3':6,7][1,4]diazepino[1,2-d][1,4]oxazepin-11-yl)-6-methylpyridin-3-yl)-3-(trifluoromethyl)benzamide | $^1$H NMR (400 MHz, Methanol-d4) δ 8.87 (d, J = 2.5 Hz, 1H), 8.30 (s, 1H), 8.28-8.22 (m, 2H), 8.19 (d, J = 2.4 Hz, 1H), 7.95-7.89 (m, 1H), 7.75 (t, J = 7.8 Hz, 1H), 7.52 (d, J = 1.7 Hz, 1H), 4.52 (dd, J = 14.0, 3.8 Hz, 1H), 4.14-4.00 (m, 3H), 3.60 (t, J = 11.3 Hz, 1H), 3.53-3.39 (m, 4H), 3.21-3.07 (m, 2H), 2.51 (s, 3H), 2.22-1.96 (m, 2H), 1.22 (t, J = 7.1 Hz, 3H). LCMS (m/z) (M + H) = 540.1, Rt = 1.01 min. |
| 507 | 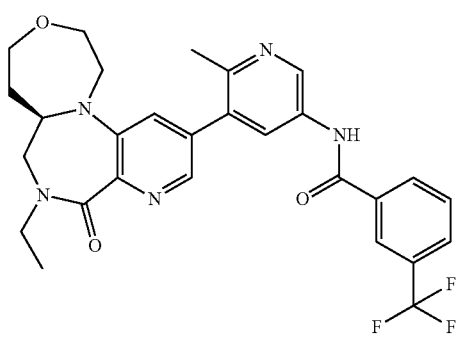 [SMILES: CCN1C[C@H]2CCOCCN2c2cc(-c3cc(NC(=O)c4cccc(C(F)(F)F)c4)cnc3C)cnc2C1=O] | (R)-N-(5-(7-ethyl-8-oxo-1,2,4,5,5a,6,7,8-octahydropyrido[2',3':6,7][1,4]diazepino[1,2-d][1,4]oxazepin-11-yl)-6-methylpyridin-3-yl)-3-(trifluoromethyl)benzamide | $^1$H NMR (400 MHz, Methanol-d4) δ 8.87 (d, J = 2.5 Hz, 1H), 8.30 (s, 1H), 8.27-8.22 (m, 2H), 8.19 (d, J = 2.4 Hz, 1H), 7.92 (d, J = 7.8 Hz, 1H), 7.75 (t, J = 7.8 Hz, 1H), 7.52 (d, J = 1.7 Hz, 1H), 4.52 (dd, J = 14.0, 3.8 Hz, 1H), 4.14-4.01 (m, 3H), 3.60 (t, J = 11.3 Hz, 1H), 3.53-3.39 (m, 4H), 3.21-3.08 (m, 2H), 2.51 (s, 3H), 2.19-1.99 (m, 2H), 1.22 (t, J = 7.1 Hz, 3H). LCMS (m/z) (M + H) = 540.2, Rt = 1.01 min. |

Examples 508 and 509

N-(3-(6-(2-hydroxyethoxy)-1,2,4,4a,5,6-hexahydro-[1,4]oxazino[4,3-a][1,5]naphthyridin-9-yl)-4-methylphenyl)-2-(trifluoromethyl)isonicotinamide

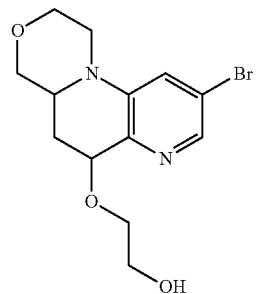

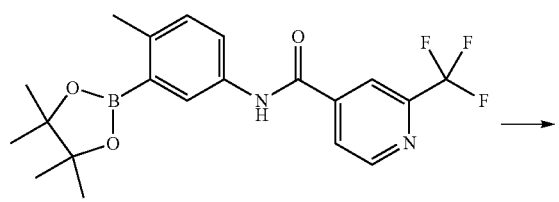

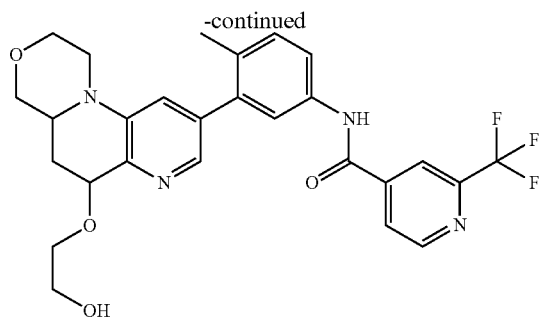

A mixture of 2-((9-bromo-1,2,4,4a,5,6-hexahydro-[1,4]oxazino[4,3-a][1,5]naphthyridin-6-yl)oxy)ethan-1-ol (1 equiv.), N-(4-methyl-3-(4,4,5,5-tetramethyl-1,3,2-dioxaborolan-2-yl)phenyl)-2-(trifluoromethyl)isonicotinamide (1.1 equiv.), Xphos G2-Pd-Cy (0.05 equiv.), Xphos (0.05 equiv.) and K$_3$PO$_4$ (2 equiv., 0.5 M) in dioxane (0.06 M) was stirred at 70° C. block temperature for 1 hr. The reaction mixture was poured onto water and extracted with EtOAc. Organic phase was washed with brine, dried over sodium sulfate, filtered, and concentrated. The crude product was purified by flash chromatography over silica gel (DCM with 0-100% MeOH) to give the desired final product, N-(3-(6-(2-hydroxyethoxy)-1,2,4,4a,5,6-hexahydro-[1,4]oxazino[4,3-a][1,5]naphthyridin-9-yl)-4-methylphenyl)-2-(trifluoromethyl)isonicotinamide (55%). The following two compounds were isolated after chiral separation as outlined in the table below. LCMS (m/z) (M+H)=328.0, Rt=0.91 min.

| # | Structure | Name | Data |
|---|---|---|---|
| 508 | 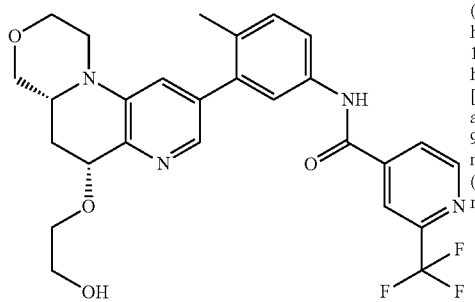 | N-(3-((4aR,6R)-6-(2-hydroxyethoxy)-1,2,4,4a,5,6-hexahydro-[1,4]oxazino[4,3-a][1,5]naphthyridin-9-yl)-4-methylphenyl)-2-(trifluoromethyl)iso-nicotinamide | $^1$H NMR (400 MHz, Methanol-d4) δ 8.90 (d, J = 5.0 Hz, 1H), 8.29 (s, 1H), 8.16-8.08 (m, 1H), 7.91 (d, J = 1.6 Hz, 1H), 7.68 (dd, J = 8.2, 2.3 Hz, 1H), 7.63 (d, J = 2.2 Hz, 1H), 7.34 (d, J = 8.3 Hz, 1H), 7.25 (d, J = 1.5 Hz, 1H), 4.77 (dd, J = 10.3, 6.4 Hz, 1H), 3.99 (dd, J = 11.3, 3.5 Hz, 1H), 3.93-3.85 (m, 2H), 3.78-3.65 (m, 5H), 3.46-3.40 (m, 1H), 2.84 (td, J = 12.6, 3.6 Hz, 1H), 2.39 (ddt, J = 12.6, 6.3, 3.4 Hz, 1H), 2.27 (s, 3H), 1.78 (dt, J = 12.6, 10.8 Hz, 1H). LCMS (m/z) (M + H) = 529.1, Rt = 1.03 min. |
| 509 | 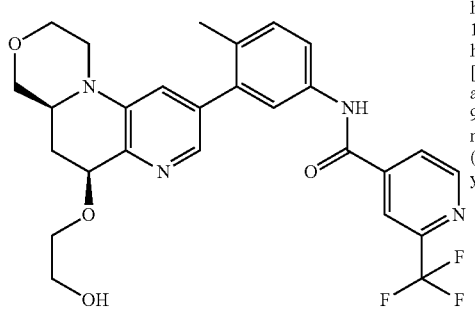 | N-(3-((4aS,6S)-6-(2-hydroxyethoxy)-1,2,4,4a,5,6-hexahydro-[1,4]oxazino[4,3-a][1,5]naphthyridin-9-yl)-4-methylphenyl)-2-(trifluorometh-yl)isonicotinamide | $^1$H NMR (400 MHz, Methanol-d4) δ 8.90 (d, J = 5.0 Hz, 1H), 8.29 (s, 1H), 8.12 (d, J = 4.9 Hz, 1H), 7.91 (d, J = 1.3 Hz, 1H), 7.67 (dd, J = 8.2, 2.2 Hz, 1H), 7.63 (d, J = 2.2 Hz, 1H), 7.33 (d, J = 8.3 Hz, 1H), 7.25 (d, J = 1.3 Hz, 1H), 4.77 (dd, J = 10.3, 6.4 Hz, 1H), 3.99 (dd, J = 11.3, 3.4 Hz, 1H), 3.94-3.84 (m, 2H), 3.80-3.64 (m, 5H), 3.43 (t, J = 10.8 Hz, 1H), 2.83 (td, J = 12.6, 3.6 Hz, 1H), 2.39 (ddt, J = 12.6, 6.3, 3.3 Hz, 1H), 2.27 (s, 3H), 1.83-1.73 (m, 1H). LCMS (m/z) (M + H) = 529.1, Rt = 1.03 min. |

The compounds below were prepared using methods similar to those described for the preparation of examples 508-9 using the appropriate active reduced ketone and other starting materials:

| # | Structure | Name | Data |
|---|---|---|---|
| 510 | 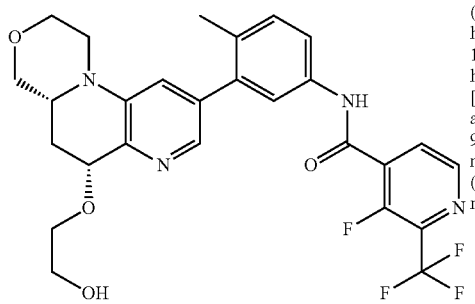 | 3-fluoro-N-(3-((4aR,6R)-6-(2-hydroxyethoxy)-1,2,4,4a,5,6-hexahydro-[1,4]oxazino[4,3-a][1,5]naphthyridin-9-yl)-4-methylphenyl)-2-(trifluoromethyl)iso-nicotinamide | $^1$H NMR (400 MHz, Methanol-d4) δ 8.64 (d, J = 4.7 Hz, 1H), 7.94 (t, J = 4.8 Hz, 1H), 7.90 (d, J = 1.7 Hz, 1H), 7.61 (dd, J = 8.2, 2.3 Hz, 1H), 7.58 (d, J = 2.3 Hz, 1H), 7.33 (d, J = 8.3 Hz, 1H), 7.24 (d, J = 1.7 Hz, 1H), 4.77 (dd, J = 10.3, 6.4 Hz, 1H), 4.03-3.81 (m, 3H), 3.79-3.63 (m, 5H), 3.42 (t, J = 10.8 Hz, 1H), 3.37-3.32-3.23 (m, 1H), 2.94-2.77 (m, 1H), 2.38 (ddd, J = 12.6, 6.4, 2.6 Hz, 1H), 2.26 (s, 3H), 1.77 (dt, J = 12.6, 10.8 Hz, 1H). LCMS (m/z) (M + H) = 547.0, Rt = 1.06 min. |
| 511 | 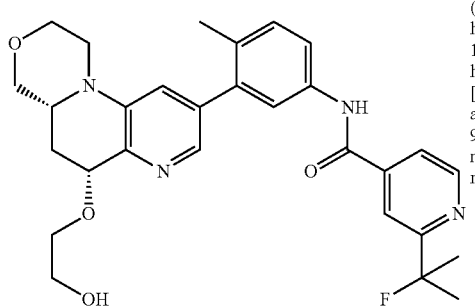 | 2-(2-fluoropropan-2-yl)-N-(3-((4aR,6R)-6-(2-hydroxyethoxy)-1,2,4,4a,5,6-hexahydro-[1,4]oxazino[4,3-a][1,5]naphthyridin-9-yl)-4-methylphenyl)iso-nicotinamide | $^1$H NMR (400 MHz, Methanol-d4) δ 8.69 (dt, J = 5.1, 0.8 Hz, 1H), 8.05 (s, 1H), 7.91 (d, J = 1.7 Hz, 1H), 7.76 (dd, J = 5.1, 1.7 Hz, 1H), 7.66 (dd, J = 8.2, 2.3 Hz, 1H), 7.62 (d, J = 2.2 Hz, 1H), 7.32 (d, J = 8.3 Hz, 1H), 7.25 (d, J = 1.6 Hz, 1H), 4.77 (dd, J = 10.3, 6.4 Hz, 1H), 4.05-3.80 (m, 3H), 3.80-3.64 (m, 5H), 3.43 (t, J = 10.8 Hz, 1H), 3.38-3.24 (m, 1H), 2.94-2.76 (m, 1H), 2.39 (ddt, J = 12.6, 6.4, 3.3 Hz, 1H), 2.27 (s, 3H), 1.84-1.73 (m, 4H), 1.70 (s, 3H). LCMS (m/z) (M + H) = 521.1, Rt = 1.03 min. |

-continued

| | | | |
|---|---|---|---|
| 512 | 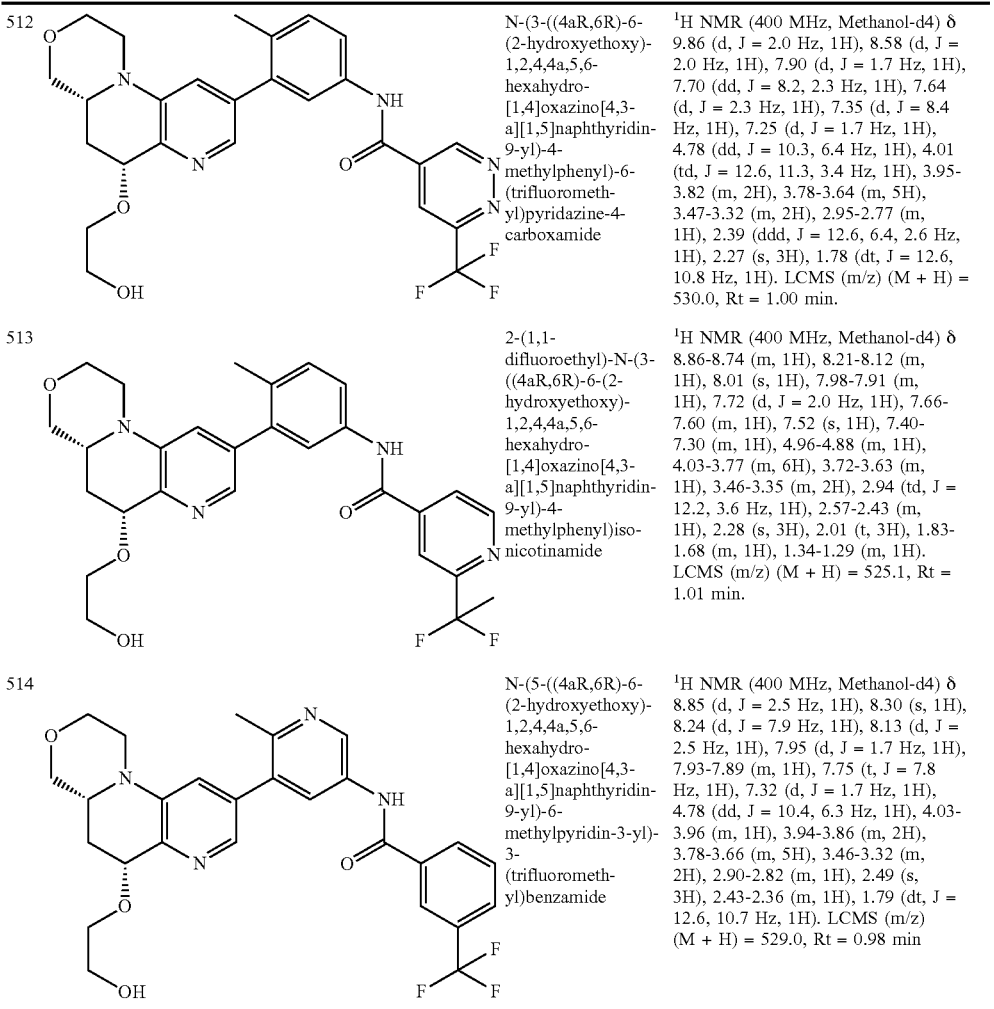 | N-(3-((4aR,6R)-6-(2-hydroxyethoxy)-1,2,4,4a,5,6-hexahydro-[1,4]oxazino[4,3-a][1,5]naphthyridin-9-yl)-4-methylphenyl)-6-(trifluoromethyl)pyridazine-4-carboxamide | $^1$H NMR (400 MHz, Methanol-d4) δ 9.86 (d, J = 2.0 Hz, 1H), 8.58 (d, J = 2.0 Hz, 1H), 7.90 (d, J = 1.7 Hz, 1H), 7.70 (dd, J = 8.2, 2.3 Hz, 1H), 7.64 (d, J = 2.3 Hz, 1H), 7.35 (d, J = 8.4 Hz, 1H), 7.25 (d, J = 1.7 Hz, 1H), 4.78 (dd, J = 10.3, 6.4 Hz, 1H), 4.01 (td, J = 12.6, 11.3, 3.4 Hz, 1H), 3.95-3.82 (m, 2H), 3.78-3.64 (m, 5H), 3.47-3.32 (m, 2H), 2.95-2.77 (m, 1H), 2.39 (ddd, J = 12.6, 6.4, 2.6 Hz, 1H), 2.27 (s, 3H), 1.78 (dt, J = 12.6, 10.8 Hz, 1H). LCMS (m/z) (M + H) = 530.0, Rt = 1.00 min. |
| 513 | | 2-(1,1-difluoroethyl)-N-(3-((4aR,6R)-6-(2-hydroxyethoxy)-1,2,4,4a,5,6-hexahydro-[1,4]oxazino[4,3-a][1,5]naphthyridin-9-yl)-4-methylphenyl)isonicotinamide | $^1$H NMR (400 MHz, Methanol-d4) δ 8.86-8.74 (m, 1H), 8.21-8.12 (m, 1H), 8.01 (s, 1H), 7.98-7.91 (m, 1H), 7.72 (d, J = 2.0 Hz, 1H), 7.66-7.60 (m, 1H), 7.52 (s, 1H), 7.40-7.30 (m, 1H), 4.96-4.88 (m, 1H), 4.03-3.77 (m, 6H), 3.72-3.63 (m, 1H), 3.46-3.35 (m, 2H), 2.94 (td, J = 12.2, 3.6 Hz, 1H), 2.57-2.43 (m, 1H), 2.28 (s, 3H), 2.01 (t, 3H), 1.83-1.68 (m, 1H), 1.34-1.29 (m, 1H). LCMS (m/z) (M + H) = 525.1, Rt = 1.01 min. |
| 514 | | N-(5-((4aR,6R)-6-(2-hydroxyethoxy)-1,2,4,4a,5,6-hexahydro-[1,4]oxazino[4,3-a][1,5]naphthyridin-9-yl)-6-methylpyridin-3-yl)-3-(trifluoromethyl)benzamide | $^1$H NMR (400 MHz, Methanol-d4) δ 8.85 (d, J = 2.5 Hz, 1H), 8.30 (s, 1H), 8.24 (d, J = 7.9 Hz, 1H), 8.13 (d, J = 2.5 Hz, 1H), 7.95 (d, J = 1.7 Hz, 1H), 7.93-7.89 (m, 1H), 7.75 (t, J = 7.8 Hz, 1H), 7.32 (d, J = 1.7 Hz, 1H), 4.78 (dd, J = 10.4, 6.3 Hz, 1H), 4.03-3.96 (m, 1H), 3.94-3.86 (m, 2H), 3.78-3.66 (m, 5H), 3.46-3.32 (m, 2H), 2.90-2.82 (m, 1H), 2.49 (s, 3H), 2.43-2.36 (m, 1H), 1.79 (dt, J = 12.6, 10.7 Hz, 1H). LCMS (m/z) (M + H) = 529.0, Rt = 0.98 min |

Intermediates for Examples 515-520. 9-chloro-5-(fluoromethyl)-1,2,4,4a,5,6-hexahydro-[1,4]oxazino[4,3-a][1,5]naphthyridine-5-carbonitrile

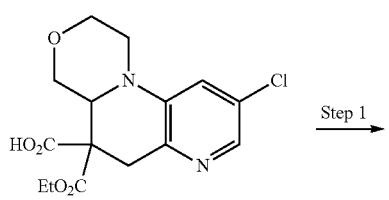

Step 1 →

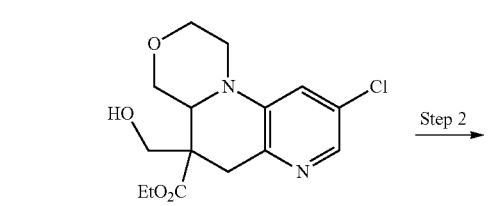

Step 2 →

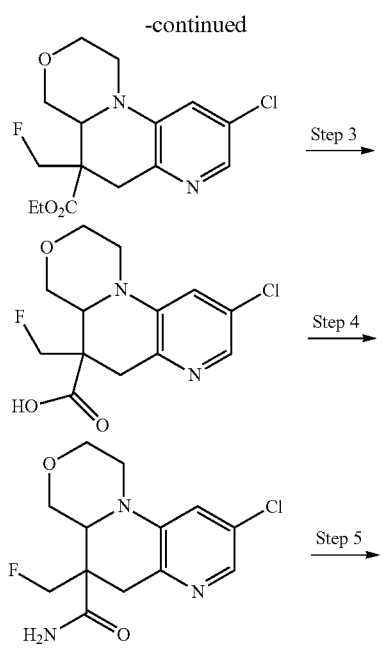

Step 3 →

Step 4 →

Step 5 →

-continued

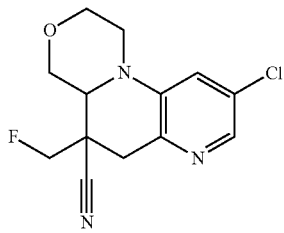

Step 1:

To a solution of 9-chloro-5-(ethoxycarbonyl)-1,2,4,4a,5,6-hexahydro-[1,4]oxazino[4,3-a][1,5]naphthyridine-5-carboxylic acid (1.0 equiv.) in DME (0.15 M) at −15° C. was added 4-methylmorpholine (1.2 equiv.) followed by isobutyl chloroformate (1.2 equiv.) and stirred for 10 min. NaBH$_4$ (2 equiv.) dissolved in H$_2$O (1 mL) was added and allowed the reaction mixture to come to ambient temperature upon which additional NaBH$_4$ (1.2 equiv.) was added. The reaction mixture was quenched with acetone and volatiles were evaporated in vacuo. The reaction mixture was diluted with EtOAc and washed with 1 N NaOH. Organic phase was washed with brine, dried over magnesium sulfate, filtered, and concentrated. The crude product was purified by flash chromatography over silica gel (heptane with 0-100% ethyl acetate) to give the desired product, ethyl 9-chloro-5-(hydroxymethyl)-1,2,4,4a,5,6-hexahydro-[1,4]oxazino[4,3-a][1,5]naphthyridine-5-carboxylate. LCMS (m/z) (M+H)=327.0, Rt=0.90 min.

Step 2:

To a solution of ethyl 9-chloro-5-(hydroxymethyl)-1,2,4,4a,5,6-hexahydro-[1,4]oxazino[4,3-a][1,5]naphthyridine-5-carboxylate (1.0 equiv.) in THF (0.11 M) was added triethylamine (12 equiv.) followed by perfluorobutanesulfonyl fluoride (4 equiv.) and triethylamine trihydrofluoride (4 equiv.). The reaction mixture was stirred at 60° C. block temperature for 18 hr. The reaction mixture was poured onto sat. Na$_2$CO$_3$ and extracted with EtOAc. Organic phase was washed with brine, dried over magnesium sulfate, filtered, and concentrated. The crude product was purified by flash chromatography over silica gel (heptane with 0 to 100% ethyl acetate) to give the product, ethyl 9-chloro-5-(fluoromethyl)-1,2,4,4a,5,6-hexahydro-[1,4]oxazino[4,3-a][1,5]naphthyridine-5-carboxylate (100%). LCMS (m/z) (M+H)=329.0, Rt=1.15 min.

Step 3:

To a solution of ethyl 9-chloro-5-(fluoromethyl)-1,2,4,4a,5,6-hexahydro-[1,4]oxazino[4,3-a][1,5]naphthyridine-5-carboxylate (1 equiv.) in THF:MeOH (0.1 M, 6 mL:4 mL) was added LiOH (5 equiv.) dissolved in H$_2$O (2 mL). The reaction mixture was stirred at 70° C. block temperature for 1 hr and concentrated under reduced pressure. The residue was acidified with 6 N HCl and extracted with EtOAc, dried over magnesium sulfate, filtered, and concentrated to give crude product, 9-chloro-5-(fluoromethyl)-1,2,4,4a,5,6-hexahydro-[1,4]oxazino[4,3-a][1,5]naphthyridine-5-carboxylic acid. LCMS (m/z) (M+H)=301.0, Rt=0.89 min.

Step 4:

To a reaction mixture of 9-chloro-5-(fluoromethyl)-1,2,4,4a,5,6-hexahydro-[1,4]oxazino[4,3-a][1,5]naphthyridine-5-carboxylic acid (1 equiv.), NH$_4$Cl (4 equiv.), HATU (1.3 equiv.) in DMF (0.17 M) was added DIPEA (4 equiv.) and stirred for 30 min at ambient temperature. The reaction mixture was diluted in EtOAc after concentrated under reduced pressure and washed with Na$_2$CO$_3$. Organic phase was washed with brine, dried over magnesium sulfate, filtered, and concentrated to give the crude product, 9-chloro-5-(fluoromethyl)-1,2,4,4a,5,6-hexahydro-[1,4]oxazino[4,3-a][1,5]naphthyridine-5-carboxamide. LCMS (m/z) (M+H)=300.0, Rt=0.80 min.

Step 5:

To a solution of 9-chloro-5-(fluoromethyl)-1,2,4,4a,5,6-hexahydro-[1,4]oxazino[4,3-a][1,5]naphthyridine-5-carboxamide (1 equiv.) in DCM (0.2 M) was added TEA (6 equiv.) followed by TFAA (4.5 equiv.). The reaction mixture was stirred at ambient temperature for 2 hrs. The reaction mixture was diluted in EtOAc and washed with NH$_4$Cl, Na$_2$CO$_3$, brine, dried over magnesium sulfate, filtered, and concentrated. The crude product was purified by flash chromatography over silica gel (heptane with 0 to 100% ethyl acetate) to give the product, 9-chloro-5-(fluoromethyl)-1,2,4,4a,5,6-hexahydro-[1,4]oxazino[4,3-a][1,5]naphthyridine-5-carbonitrile (65%). LCMS (m/z) (M+H)=282.0, Rt=1.13 and 1.17 min.

The compounds listed in the table below were prepared using the intermediates described above and the appropriate starting materials, followed by chiral purification to provide a single enantiomer and diastereomer.

| 515 | 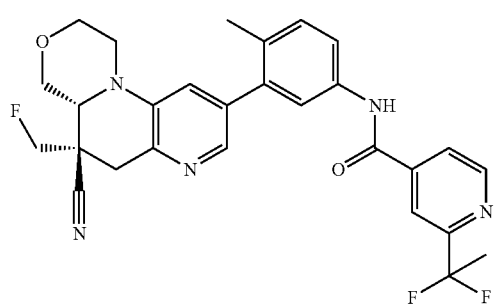 [SMILES: Cc1ccc(NC(=O)c2ccnc(C(C)(F)F)c2)cc1-c1cnc2c(c1)N1CCOC[C@H]1[C@@](C#N)(CF)C2] | N-(3-((4aR,5S)-5-cyano-5-(fluoromethyl)-1,2,4,4a,5,6-hexahydro-[1,4]oxazino[4,3-a][1,5]naphthyridin-9-yl)-4-methylphenyl)-2-(1,1-difluoroethyl)isonicotinamide | $^1$H NMR (400 MHz, Methanol-d4) δ 8.84-8.71 (m, 1H), 8.23-8.11 (m, 1H), 7.94 (dd, J = 3.7, 1.5 Hz, 2H), 7.65 (dd, J = 5.5, 2.3 Hz, 2H), 7.40 (d, J = 1.6 Hz, 1H), 7.36-7.27 (m, 1H), 4.89 (d, J = 9.7 Hz, 1H), 4.77 (d, J = 9.7 Hz, 1H), 4.60 (dd, J = 46.4, 9.7 Hz, 1H), 4.21-4.12 (m, 1H), 3.98 (dd, J = 11.7, 3.6 Hz, 1H), 3.92-3.82 (m, 1H), 3.79-3.61 (m, 3H), 3.50 (dd, J = 17.0, 2.9 Hz, 1H), 3.35 (s, 1H), 3.04 (td, J = 12.2, 3.8 Hz, 1H), 2.26 (s, 3H), 2.03 (t, J = 18.7 Hz, 3H). LCMS (m/z) (M + H) = 522.1, Rt = 1.32 min. |

| | | | |
|---|---|---|---|
| 516 | | N-(3-((4aS,5R)-5-cyano-5-(fluoromethyl)-1,2,4,4a,5,6-hexahydro-[1,4]oxazino[4,3-a][1,5]naphthyridin-9-yl)-4-methylphenyl)-2-(1,1-difluoroethyl)isonicotinamide | 1H NMR (400 MHz, Methanol-d4) δ 8.79 (d, J = 5.0 Hz, 1H), 8.16 (s, 1H), 7.98-7.89 (m, 2H), 7.65 (dd, J = 5.2, 2.2 Hz, 2H), 7.40 (d, J = 1.5 Hz, 1H), 7.37-7.28 (m, 1H), 4.89 (d, J = 9.7 Hz, 0H), 4.78 (dd, J = 9.5, 5.2 Hz, 1H), 4.60 (dd, J = 46.4, 9.7 Hz, 1H), 4.17 (d, J = 9.1 Hz, 1H), 3.98 (dd, J = 11.7, 3.5 Hz, 1H), 3.87 (d, J = 12.3 Hz, 1H), 3.77-3.61 (m, 3H), 3.50 (dd, J = 17.0, 2.9 Hz, 1H), 3.35 (s, 1H), 3.04 (td, J = 12.2, 3.8 Hz, 1H), 2.26 (s, 3H), 2.03 (t, J = 18.7 Hz, 3H). LCMS (m/z) (M + H) = 522.1, Rt = 1.32 min. |
| 517 | | N-(3-((4aS,5S)-5-cyano-5-(fluoromethyl)-1,2,4,4a,5,6-hexahydro-[1,4]oxazino[4,3-a][1,5]naphthyridin-9-yl)-4-methyphenyl)-2-(1,1-difluoroethyl)isonicotinamide | ¹H NMR (400 MHz, Methanol-d4) δ 8.85-8.74 (m, 1H), 8.17 (s, 1H), 7.96 (d, J = 1.7 Hz, 2H), 7.68 (dd, J = 8.2, 2.3 Hz, 1H), 7.64 (d, J = 2.2 Hz, 1H), 7.40 (d, J = 1.5 Hz, 1H), 7.34 (d, J = 8.3 Hz, 1H), 4.80-4.73 (m, 1H), 4.66 (q, J = 9.7 Hz, 1H), 4.22 (d, J = 11.5 Hz, 1H), 4.04 (dd, J = 11.6, 3.7 Hz, 1H), 3.82 (d, J = 12.4 Hz, 1H), 3.74 (td, J = 11.8, 2.8 Hz, 1H), 3.69-3.61 (m, 1H), 3.38 (dd, J = 10.7, 3.6 Hz, 1H), 3.26 (s, 2H), 2.97 (td, J = 12.0, 3.9 Hz, 1H), 2.28 (s, 3H), 2.03 (t, J = 18.7 Hz, 3H). LCMS (m/z) (M + H) = 522.1, Rt = 1.32 min. |
| 518 | | N-(3-((4aR,5R)-5-cyano-5-(fluoromethyl)-1,2,4,4a,5,6-hexahydro-[1,4]oxazino[4,3-a][1,5]naphthyridin-9-yl)-4-methyphenyl)-2-(1,1-difluoroethyl)isonicotinamide | ¹H NMR (400 MHz, Methanol-d4) δ 8.86-8.74 (m, 1H), 8.22-8.14 (m, 1H), 8.02-7.92 (m, 2H), 7.68 (dd, J = 8.2, 2.3 Hz, 1H), 7.64 (d, J = 2.2 Hz, 1H), 7.40 (d, J = 1.6 Hz, 1H), 7.34 (d, J = 8.3 Hz, 1H), 4.81-4.74 (m, 1H), 4.66 (q, J = 9.7 Hz, 1H), 4.22 (d, J = 11.5 Hz, 1H), 4.04 (dd, J = 11.6, 3.7 Hz, 1H), 3.82 (d, J = 12.3 Hz, 1H), 3.74 (td, J = 11.8, 2.8 Hz, 1H), 3.69-3.61 (m, 1H), 3.38 (dd, J = 10.7, 3.7 Hz, 1H), 3.26 (s, 2H), 2.97 (td, J = 12.0, 3.8 Hz, 1H), 2.28 (s, 3H), 2.03 (t, J = 18.7 Hz, 3H). LCMS (m/z) (M + H) = 522.1, Rt = 1.32 min. |
| 519 | | N-(3-((4aR,5R)-5-cyano-5-(fluoromethyl)-1,2,4,4a,5,6-hexahydro-[1,4]oxazino[4,3-a][1,5]naphthyridin-9-yl)-4-methylphenyl)-2-(trifluoromethyl)isonicotinamide | ¹H NMR (400 MHz, Methanol-d4) δ 8.90 (d, J = 5.0 Hz, 1H), 8.29 (s, 1H), 8.15-8.05 (m, 1H), 7.95 (d, J = 1.6 Hz, 1H), 7.71-7.60 (m, 2H), 7.40 (d, J = 1.6 Hz, 1H), 7.38-7.29 (m, 1H), 4.89 (d, J = 9.7 Hz, 1H), 4.77 (d, J = 9.7 Hz, 1H), 4.61 (dd, J = 46.4, 9.7 Hz, 1H), 4.22-4.14 (m, 1H), 3.98 (dd, J = 11.7, 3.6 Hz, 1H), 3.91-3.84 (m, 1H), 3.77-3.62 (m, 3H), 3.51 (dd, J = 17.0, 2.9 Hz, 1H), 3.35 (d, J = 3.7 Hz, 1H), 3.04 (td, J = 12.2, 3.8 Hz, 1H), 2.27 (s, 3H). LCMS (m/z) (M + H) = 526.1, Rt = 1.27 min. |
| 520 | | N-(3-((4aR,5S)-5-cyano-5-(fluoromethyl)-1,2,4,4a,5,6-hexahydro-[1,4]oxazino[4,3-a][1,5]naphthyridin-9-yl)-4-methyphenyl)-2-(trifluoromethyl-isonicotinamide | ¹H NMR (400 MHz, Methanol-d4) δ 8.90 (d, J = 5.0 Hz, 1H), 8.29 (s, 1H), 8.11 (dd, J = 5.0, 1.2 Hz, 1H), 7.95 (d, J = 1.7 Hz, 1H), 7.65 (dd, J = 6.2, 2.3 Hz, 2H), 7.40 (d, J = 1.6 Hz, 1H), 7.37-7.30 (m, 1H), 4.89 (d, J = 9.7 Hz, 1H), 4.77 (d, J = 9.7 Hz, 1H), 4.61 (dd, J = 46.4, 9.7 Hz, 1H), 4.21-4.14 (m, 1H), 3.98 (dd, J = 11.7, 3.6 Hz, 1H), 3.91-3.84 (m, 1H), 3.77-3.62 (m, 3H), 3.51 (dd, J = 17.0, 2.9 Hz, 1H), 3.35 (d, J = 3.6 Hz, 1H), 3.04 (td, J = 12.2, 3.8 Hz, 1H), 2.27 (s, 3H). LCMS (m/z) (M + H) = 526.1, Rt = 1.27 min. |

405

Intermediate for Examples 521-2. 4-methyl-3-(6-methyl-1,2,4,4a,5,6-hexahydro-[1,4]oxazino[4,3-a][1,5]naphthyridin-9-yl)aniline

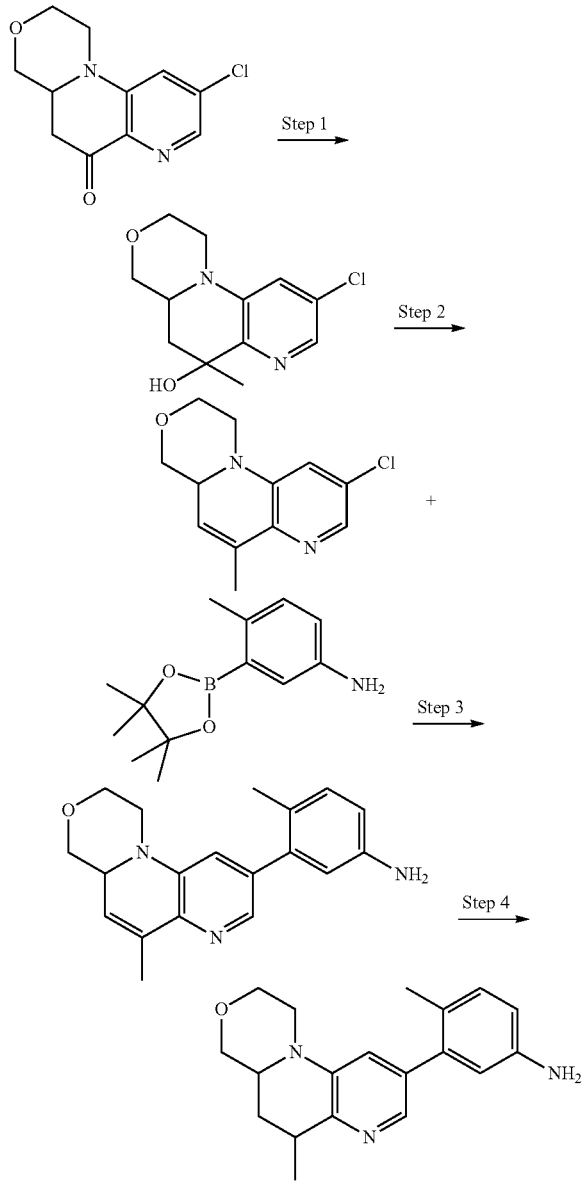

406

Step 1:

To an ice cold solution of 9-chloro-1,2,4a,5-tetrahydro-[1,4]oxazino[4,3-a][1,5]naphthyridin-6(4H)-one (1.0 equiv.) in THF (0.1 M) was added 3 M MeMgI in ether (7 equiv.) and allowed the reaction mixture to come to ambient temperature and stirred for 48 hr. The reaction mixture was cooled down and quenched with $NH_4Cl$ solution. It was extracted with DCM and organic phase was washed with brine, dried over sodium sulfate, filtered, and concentrated. The crude product was purified by flash chromatography over silica gel (heptane with 50-100% ethyl acetate) to give the product, 9-chloro-6-methyl-1,2,4,4a,5,6-hexahydro-[1,4]oxazino[4,3-a][1,5]naphthyridin-6-ol (35%). LCMS (m/z) (M+H)=255.0, Rt=0.72 min.

Step 2:

9-chloro-6-methyl-1,2,4,4a,5,6-hexahydro-[1,4]oxazino[4,3-a][1,5]naphthyridin-6-ol (1.0 equiv.) and p-toluenesulfonic acid monohydrate (0.5 equiv.) in toluene (0.1 M) was heated to reflux for 1.5 hr. The reaction mixture was allowed to come to room temperature and quenched with solid $K_2CO_3$. It was then concentrated to dryness. The crude product was purified by flash chromatography over silica gel (heptane with 0 to 100% ethyl acetate) to give the product, 9-chloro-6-methyl-1,2,4,4a-tetrahydro-[1,4]oxazino[4,3-a][1,5]naphthyridine (58.8%). LCMS (m/z) (M+H)=237.2, Rt=1.19 min.

Step 3:

Using the standard Suzuki coupling method as in Example 1, step 3, isolated product 4-methyl-3-(6-methyl-1,2,4,4a-tetrahydro-[1,4]oxazino[4,3-a][1,5]naphthyridin-9-yl)aniline (100%). LCMS (m/z) (M+H)=308.1, Rt=0.71 min.

Step 4:

To a nitrogen purged solution of 4-methyl-3-(6-methyl-1,2,4,4a-tetrahydro-[1,4]oxazino[4,3-a][1,5]naphthyridin-9-yl)aniline (1.0 equiv.) in MeOH (0.11 M) was added 10% Pd—C (0.15 equiv.). The reaction mixture was purged with hydrogen and hydrogenated with a hydrogen balloon overnight. The reaction mixture was filtered through a celite pad, and the pad was rinsed with MeOH. Filtrate was concentrated to dryness under reduced pressure to give product 4-methyl-3-(6-methyl-1,2,4,4a,5,6-hexahydro-[1,4]oxazino[4,3-a][1,5]naphthyridin-9-yl)aniline 100% yield. LCMS (m/z) (M+H)=310.1, Rt=1.12 min.

The compounds listed in the table below were prepared using the intermediates above and the appropriate starting materials, followed by chiral purification to provide single enantiomer and diastereomer.

| 521 | | |
|---|---|---|
| 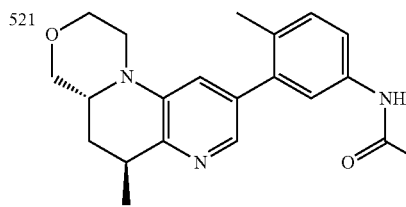 | N-(4-methyl-3-((4aR,6S)-6-methyl-1,2,4,4a,5,6-hexahydro-[1,4]oxazino[4,3-a][1,5]naphthyridin-9-yl)phenyl)-2-(trifluoromethyl)iso-nicotinamide 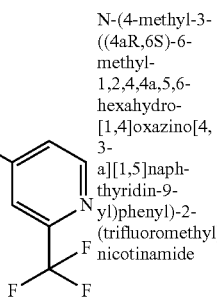 | $^1$H NMR (400 MHz, Methanol-d4) δ 8.90 (d, J = 5.0 Hz, 1H), 8.29 (s, 1H), 8.12 (dd, J = 5.0, 1.2 Hz, 1H), 7.82 (d, J = 1.7 Hz, 1H), 7.66 (dd, J = 8.2, 2.3 Hz, 1H), 7.61 (d, J = 2.3 Hz, 1H), 7.33 (d, J = 8.3 Hz, 1H), 7.23 (d, J = 1.6 Hz, 1H), 4.02 (dd, J = 11.1, 2.3 Hz, 1H), 3.89 (dd, J = 11.1, 2.3 Hz, 1H), 3.75-3.63 (m, 2H), 3.37-3.32 (m, 1H), 3.22-3.06 (m, 2H), 2.86 (td, J = 12.6, 3.7 Hz, 1H), 2.27 (s, 3H), 1.91-1.81 (m, 1H), 1.73 (dt, J = 13.3, 2.5 Hz, 1H), 1.37 (d, J = 7.2 Hz, 3H). LCMS (m/z) (M + H) = 483.1, Rt = 1.10 min. |

-continued

| | | |
|---|---|---|
| 522 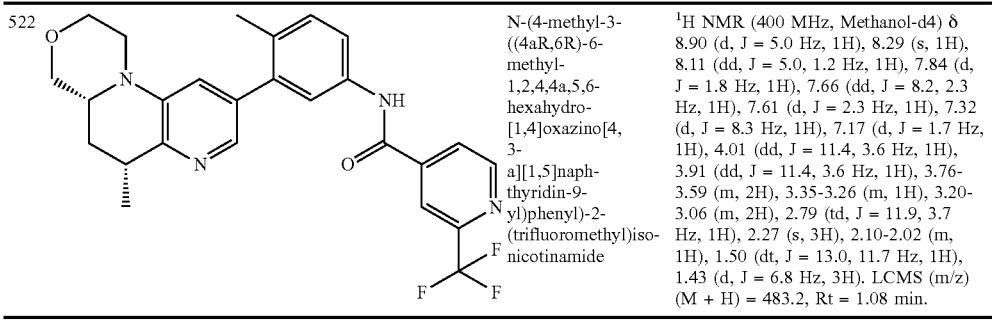 | N-(4-methyl-3-((4aR,6R)-6-methyl-1,2,4,4a,5,6-hexahydro-[1,4]oxazino[4,3-a][1,5]naphthyridin-9-yl)phenyl)-2-(trifluoromethyl)isonicotinamide | ¹H NMR (400 MHz, Methanol-d4) δ 8.90 (d, J = 5.0 Hz, 1H), 8.29 (s, 1H), 8.11 (dd, J = 5.0, 1.2 Hz, 1H), 7.84 (d, J = 1.8 Hz, 1H), 7.66 (dd, J = 8.2, 2.3 Hz, 1H), 7.61 (d, J = 2.3 Hz, 1H), 7.32 (d, J = 8.3 Hz, 1H), 7.17 (d, J = 1.7 Hz, 1H), 4.01 (dd, J = 11.4, 3.6 Hz, 1H), 3.91 (dd, J = 11.4, 3.6 Hz, 1H), 3.76-3.59 (m, 2H), 3.35-3.26 (m, 1H), 3.20-3.06 (m, 2H), 2.79 (td, J = 11.9, 3.7 Hz, 1H), 2.27 (s, 3H), 2.10-2.02 (m, 1H), 1.50 (dt, J = 13.0, 11.7 Hz, 1H), 1.43 (d, J = 6.8 Hz, 3H). LCMS (m/z) (M + H) = 483.2, Rt = 1.08 min. |

Intermediate for Ex. 525. 3-(5-(azidomethyl)-5-fluoro-1,2,4,4a,5,6-hexahydro-[1,4]oxazino[4,3-a]quinolin-9-yl)-4-methylaniline

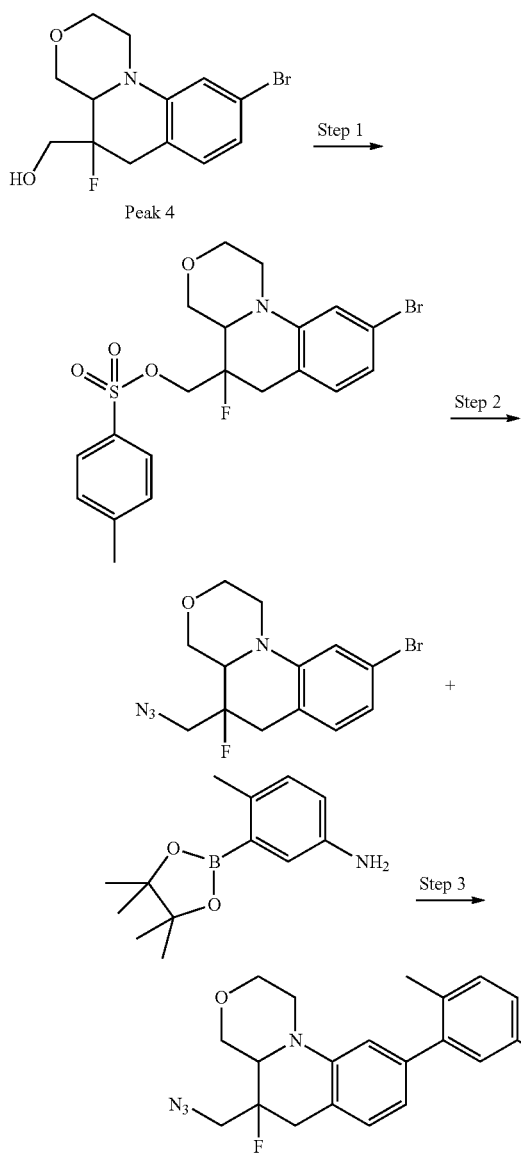

Step 1:

To a reaction mixture of (9-bromo-5-fluoro-1,2,4,4a,5,6-hexahydro-[1,4]oxazino[4,3-a]quinolin-5-yl)methanol 91 equiv.), 4-methylbenzenesulfonyl chloride (1.05 equiv.) and DMAP (0.1 equiv.) in DCM (0.42 M) was added TEA (1.5 equiv.) and stirred at ambient temperature for 2 hr. The reaction mixture was then directly purified by flash chromatography over silica gel (heptane with 0-100% ethyl acetate) to give the product, (9-bromo-5-fluoro-1,2,4,4a,5,6-hexahydro-[1,4]oxazino[4,3-a]quinolin-5-yl)methyl 4-methylbenzenesulfonate (97%) LCMS (m/z) (M+H)=471.9, Rt=1.69 min.

Step 2:

To a solution of (9-bromo-5-fluoro-1,2,4,4a,5,6-hexahydro-[1,4]oxazino[4,3-a]quinolin-5-yl)methyl 4-methylbenzenesulfonate (1 equiv.) in DMF (0.18 M) was added sodium azide (4 equiv.) and stirred at 105° C. block temperature for 24 hr. It was diluted with EtOAc and washed with water, brine, dried over sodium sulfate, filtered, and concentrated. The crude product was purified by flash chromatography over silica gel (heptane with 0-20% ethyl acetate) to give the product, 5-(azidomethyl)-9-bromo-5-fluoro-1,2,4,4a,5,6-hexahydro-[1,4]oxazino[4,3-a]quinoline (92%). LCMS (m/z) (M+H)=342.9, Rt=1.60 min.

Step 3:

Using the standard Suzuki coupling method as in example 116, isolated product 3-(5-(azidomethyl)-5-fluoro-1,2,4,4a,5,6-hexahydro-[1,4]oxazino[4,3-a]quinolin-9-yl)-4-methylaniline (100%). LCMS (m/z) (M+H)=368.1, Rt=1.10 min.

Example 525: N-(3-((4aS,5R)-5-(aminomethyl)-5-fluoro-1,2,4,4a,5,6-hexahydro-[1,4]oxazino[4,3-a]quinolin-9-yl)-4-methylphenyl)-2-(2-fluoropropan-2-yl)isonicotinamide

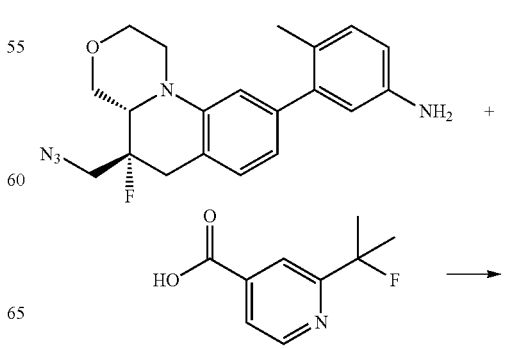

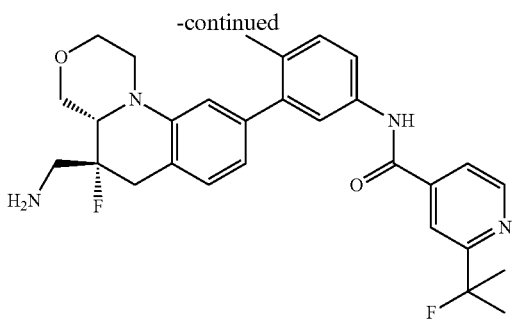

2-(2-fluoropropan-2-yl)isonicotinic acid (1 equiv.), 3-((4aS,5R)-5-(azidomethyl)-5-fluoro-1,2,4,4a,5,6-hexahydro-[1,4]oxazino[4,3-a]quinolin-9-yl)-4-methylaniline (1.0 equiv.), EDC.HCl (1.2 equiv.), HOAT (1.2 equiv.) in DMF (0.08 M) were stirred at inert atmosphere for 1 h. It was diluted with EtOAc and washed with water, brine, dried over sodium sulfate, filtered, and concentrated. It was further dried under high vac for 14 hrs. The residue was then dissolved in THF (2 mL) and triphenylphosphine (polymer bound, 12 equiv.) was added dropwise and the reaction mixture stirred at 70° C. block temperature for 2 hr. Water (2 mL) and THF (2 mL) were added then the reaction was further heated and stirred at 80° C. block temperature for 2 hr. The reaction mixture was allowed to come to room temperature and filtered. The filtrate cake was washed with DCM and concentrated to dryness. It was redissolved in DCM and washed with water, brine, dried over magnesium sulfate, filtered, and concentrated. The crude product was purified by reverse phase ISCO flash chromatography (no modifier) to give the desired product, N-(3-((4aS,5R)-5-(aminomethyl)-5-fluoro-1,2,4,4a,5,6-hexahydro-[1,4]oxazino[4,3-a]quinolin-9-yl)-4-methylphenyl)-2-(2-fluoropropan-2-yl)isonicotinamide (8.7%). 1H NMR (400 MHz, Methanol-d4) δ 8.68 (d, J=5.1 Hz, 1H), 8.05 (s, 1H), 7.75 (dd, J=5.1, 1.7 Hz, 1H), 7.63-7.54 (m, 2H), 7.26 (d, J=8.0 Hz, 1H), 7.14 (d, J=7.6 Hz, 1H), 6.85-6.72 (m, 2H), 4.03 (dd, J=11.4, 3.0 Hz, 1H), 3.95-3.85 (m, 1H), 3.79-3.56 (m, 3H), 3.25-3.14 (m, 1H), 3.12-2.98 (m, 2H), 2.96-2.85 (m, 1H), 2.83-2.70 (m, 1H), 2.24 (s, 3H), 1.75 (s, 3H), 1.70 (s, 3H). LCMS (m/z) (M+H)=507.1, Rt=1.11 min.

Example 526: N-(5-((4aS,5R)-5-(aminomethyl)-5-fluoro-1,2,4,4a,5,6-hexahydro-[1,4]oxazino[4,3-a]quinolin-9-yl)-6-methylpyridin-3-yl)-3-(trifluoromethyl)benzamide

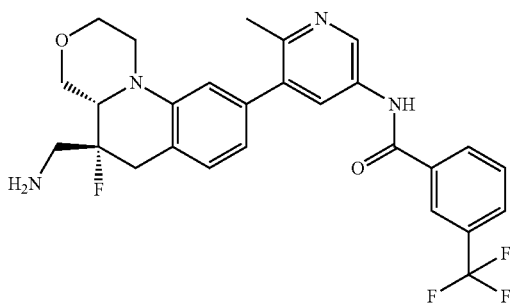 [SMILES: Cc1ncc(NC(=O)c2cccc(C(F)(F)F)c2)cc1-c1ccc2c(c1)N1CCOC[C@H]1[C@](F)(CN)C2]

This compound was synthesized using the same method as Example 525 using appropriate starting material in the Suzuki-cross coupling reaction. 1H NMR (400 MHz, Methanol-d4) δ 8.79 (d, J=2.5 Hz, 1H), 8.29 (s, 1H), 8.23 (d, J=7.9 Hz, 1H), 8.07 (d, J=2.5 Hz, 1H), 7.91 (d, J=7.8 Hz, 1H), 7.74 (t, J=7.8 Hz, 1H), 7.20 (d, J=7.6 Hz, 1H), 6.85 (d, J=1.3 Hz, 1H), 6.81 (dd, J=7.5, 1.5 Hz, 1H), 4.04 (dd, J=11.4, 3.0 Hz, 1H), 3.91 (dd, J=11.2, 3.3 Hz, 1H), 3.77-3.60 (m, 3H), 3.38 (ddt, J=20.0, 3.3, 1.7 Hz, 1H), 3.25-3.15 (m, 1H), 3.11-2.69 (m, 4H), 2.47 (s, 3H). LCMS (m/z) (M+H)=515.2, Rt=1.34 min.

Intermediate for Example 527. 9-bromo-5,5-dimethyl-1,2,4,4a,5,6-hexahydro-[1,4]oxazino[4,3-a][1,5]naphthyridin-6-amine

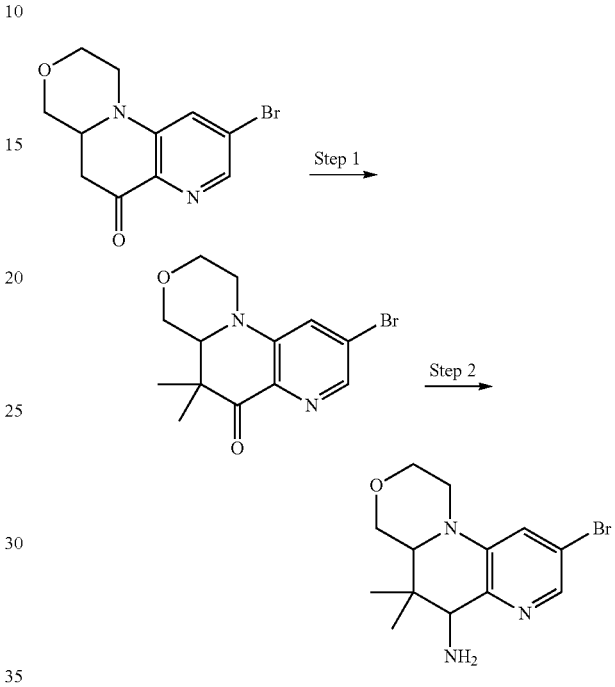

Step 1:
To an ice cold solution of 9-bromo-1,2,4a,5-tetrahydro-[1,4]oxazino[4,3-a][1,5]naphthyridin-6(4H)-one (1.0 equiv.) in THF (0.12 M) was added NaH (3 equiv.) and stirred for 30 min. Iodomethane (3 equiv.) was then added and allowed the reaction mixture to come to ambient temperature. It was stirred for 45 min, poured onto saturated aqueous NH4Cl and extracted with EtOAc. The organic phase was washed with sat. NaHCO3. The combined aqueous layer was back extracted with EtOAc. The combined organic phase was washed with brine, dried over magnesium sulfate, filtered, and concentrated. The crude product was purified by flash chromatography over silica gel (hept with 0-100% ethyl acetate) to give 9-bromo-5,5-dimethyl-1,2,4a,5-tetrahydro-[1,4]oxazino[4,3-a][1,5]naphthyridin-6(4H)-one in 39% yield. LCMS (m/z) (M+H)=313.1, Rt=1.00 min.

Step 2:
A mixture of 9-bromo-5,5-dimethyl-1,2,4a,5-tetrahydro-[1,4]oxazino[4,3-a][1,5]naphthyridin-6(4H)-one (1 equiv.), hydroxylamine hydrochloride (6 equiv.) and sodium acetate (6 equiv.) in EtOH (0.046 M) was heated to reflux for 4.5 hr. The reaction mixture was concentrated to dryness and re-dissolved in EtOAc. It was washed with water, brine, dried over sodium sulfate, filtered, and concentrated. To this was added acetic acid (55 equiv.) and Zn dust (8 equiv.). The reaction mixture was filtered through a pad of celite after stirring for 1 hr. The filter pad was rinsed with EtOH and concentrated. To this solid residue was added NH4OH (1 mL) and DCM (10 mL) and stirred for 10 min. Organic layer was separated. Aqueous layer was extracted with DCM twice. The combined organic phase was washed with brine, dried over sodium sulfate, filtered, and concentrated to dryness to give 9-bromo-5,5-dimethyl-1,2,4,4a,5,6-hexahydro-[1,4]oxazino[4,3-a][1,5]naphthyridin-6-amine (100%). LCMS (m/z) (M+H)=313.9, Rt=0.78 min.

| 527 | 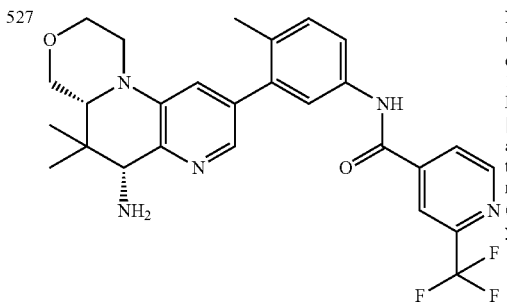 | N-(3-((4aR,6R)-6-amino-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide | $^1$H NMR (400 MHz, Methanol-d4) δ 8.91 (d, J = 5.0 Hz, 1H), 8.28 (s, 1H), 8.11 (dd, J = 5.0, 1.2 Hz, 1H), 8.06 (d, J = 1.6 Hz, 1H), 7.74 (t, J = 2.5 Hz, 1H), 7.58 (dt, J = 8.2, 2.2 Hz, 1H), 7.42 (d, J = 1.6 Hz, 1H), 7.35 (d, J = 8.4 Hz, 1H), 4.09 (s, 1H), 4.02 (dd, J = 11.3, 3.2 Hz, 1H), 3.98-3.89 (m, 2H), 3.66 (td, J = 11.9, 2.7 Hz, 1H), 3.58 (t, J = 11.0 Hz, 1H), 3.19 (dd, J = 10.6, 3.3 Hz, 1H), 3.13-3.04 (m, 1H), 2.27 (s, 3H), 1.19 (s, 3H), 1.14 (s, 3H). LCMS (m/z) (M + H) = 512.2, Rt = 1.07 min. |

Intermediate for Example 528. 10-bromo-6,6-difluoro-1,2,5,5a,6,7-hexahydro-4H-[1,4]oxazepino[4,5-a]quinolin-7-ol

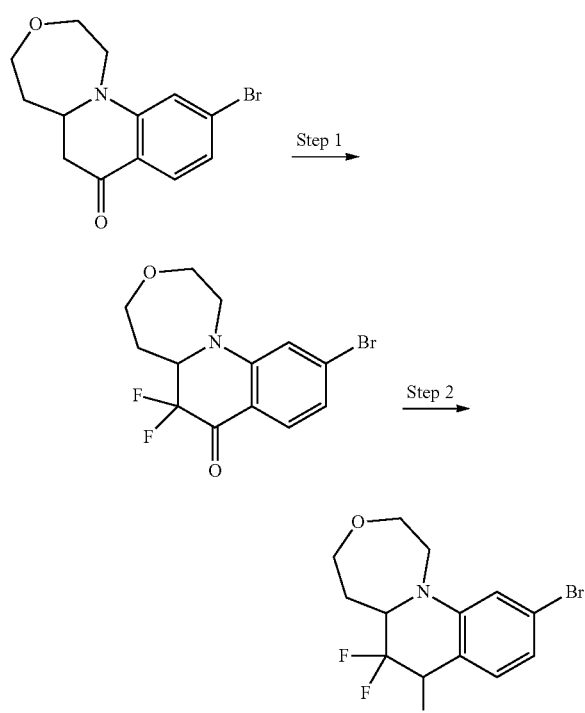

Step 1:

To a solution 10-bromo-1,2,4,5,5a,6-hexahydro-7H-[1,4]oxazepino[4,5-a]quinolin-7-one (0.1 equiv.) in THF (0.16 M) was added NaH (6 equiv.) and stirred for 20 min. at an ambient temperature. To this was added N-fluorobenzenesulfonimide (4 equiv.) and stirred for 2 hr. The reaction mixture was quenched with sat. NH$_4$Cl solution and extracted with EtoAc. Organic layer was washed with sat. NaHCO$_3$ solution, brine, dried over sodium sulfate, filtered and concentrated. It was purified by flash chromatography over silica gel (Heptane with 0-50% EtOAc) to give 10-bromo-6,6-difluoro-1,2,4,5,5a,6-hexahydro-7H-[1,4]oxazepino[4,5-a]quinolin-7-one in 5.8% yield. LCMS (m/z) (M+H)=334.1, Rt=1.42 min.

Step 2:

To a cooled mixture of 10-bromo-6,6-difluoro-1,2,4,5,5a,6-hexahydro-7H-[1,4]oxazepino[4,5-a]quinolin-7-one (1 equiv.) at −20° C. in THF (0.08 M), was d added L-selectride (4 equiv.), and the reaction mixture was allowed to come to ambient temperature over 1 hr. The reaction mixture was quenched with dropwise addition of H$_2$O. The reaction mixture was concentrated under reduced pressure, diluted with EtOAc, washed with sat. NH$_4$Cl solution. The organic extracts were dried over magnesium sulfate, filtered, and concentrated to give 10-bromo-6,6-difluoro-1,2,5,5a,6,7-hexahydro-4H-[1,4]oxazepino[4,5-a]quinolin-7-ol in 100% yield. LCMS (m/z) (M+H)=336.3, Rt=1.26 min.

| 528 | 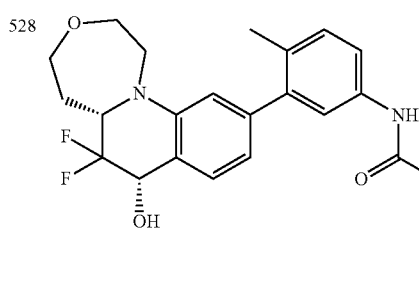 | N-(3-((5aS,7S)-6,6-difluoro-7-hydroxy-1,2,5,5a,6,7-hexahydro-4H-[1,4]oxazepino[4,5-a]quinolin-10-yl)-4-methyl)phenyl)-2-(trifluoromethyl)isonicotinamide | $^1$H NMR (400 MHz, Methanol-d4) δ 8.89 (d, J = 5.0 Hz, 1H), 8.29 (s, 1H), 8.11 (dd, J = 5.0, 1.2 Hz, 1H), 7.63 (dd, J = 8.2, 2.3 Hz, 1H), 7.57 (d, J = 2.3 Hz, 1H), 7.37 (d, J = 8.2 Hz, 1H), 7.28 (d, J = 8.3 Hz, 1H), 6.72 (dd, J = 7.7, 1.4 Hz, 1H), 6.64 (d, J = 1.1 Hz, 1H), 4.81-4.74 (m, 1H), 4.01-3.86 (m, 3H), 3.86-3.71 (m, 3H), 3.50-3.39 (m, 1H), 2.66-2.53 (m, 1H), 2.26 (s, 3H), 2.17-2.06 (m, 1H). LCMS (m/z) (M + H) = 534.1, Rt = 1.52 min. |

Example 529: N-(3-((4aR,6R)-6-acetamido-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide

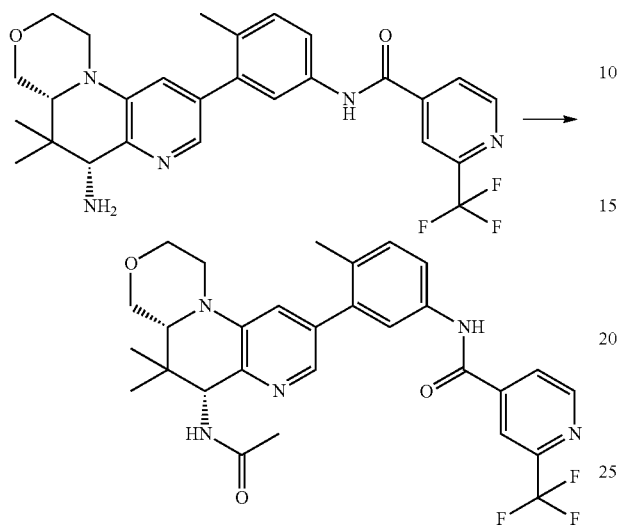

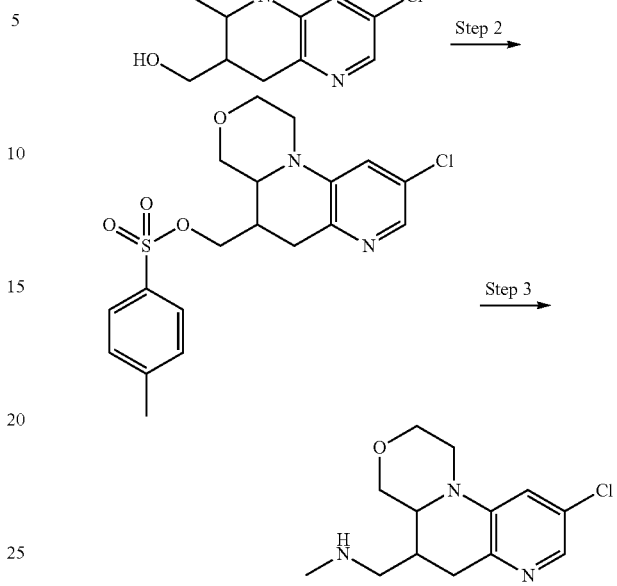

To a solution of N-(3-((4aR,6R)-6-amino-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide (1.0 equiv.) in pyridine (0.26 M) was added acetic anhydride (50 equiv.) and stirred for 30 min at ambient temperature. It was diluted with EtOAc and washed with sat. NH$_4$Cl solution, brine, dried over sodium sulfate, filtered, and concentrated. The crude product was purified by flash chromatography over silica gel (DCM with 0-50% MeOH) to give the desired product N-(3-((4aR,6R)-6-acetamido-5,5-dimethyl-1,2,4,4a,5,6-hexahydro-[1,4]oxazino[4,3-a][1,5]naphthyridin-9-yl)-4-methylphenyl)-2-(trifluoromethyl)isonicotinamide (35.7%). 1H NMR (400 MHz, Methanol-d4) δ 8.90 (d, J=5.0 Hz, 1H), 8.29 (s, 1H), 8.11 (dd, J=5.0, 1.2 Hz, 1H), 7.89 (d, J=1.7 Hz, 1H), 7.69-7.60 (m, 2H), 7.36-7.31 (m, 1H), 7.28 (d, J=1.7 Hz, 1H), 5.13 (s, 1H), 4.07 (dd, J=11.4, 3.1 Hz, 1H), 3.98 (dd, J=11.5, 3.5 Hz, 1H), 3.78 (d, J=12.2 Hz, 1H), 3.66 (td, J=11.8, 2.9 Hz, 1H), 3.55 (t, J=11.0 Hz, 1H), 3.22 (dd, J=10.7, 3.4 Hz, 1H), 2.93 (td, J=12.0, 3.8 Hz, 1H), 2.26 (s, 3H), 1.93 (s, 3H), 1.03 (s, 3H), 0.94 (s, 3H). LCMS (m/z) (M+H)=554.2, Rt=1.06 min.

Intermediate for Examples 530-531. 1-(9-chloro-1,2,4,4a,5,6-hexahydro-[1,4]oxazino[4,3-a][1,5]naphthyridin-5-yl)-N-methylmethanamine

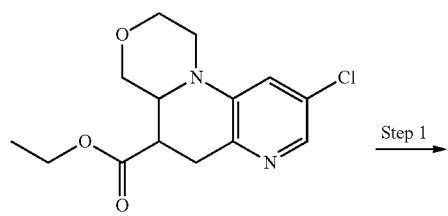

Step 1:
To an ice cold solution ethyl 9-chloro-1,2,4,4a,5,6-hexahydro-[1,4]oxazino[4,3-a][1,5]naphthyridine-5-carboxylate (0.1 equiv.) in THF (0.2 M) was drop-wise added lithium aluminum hydride in THF (1.1 equiv., 1M) and stirred for 10 min. To this was added sodium sulfate decahydrate (1 equiv.) and allowed the reaction mixture to come to ambient temperature. The reaction mixture was diluted with EtOAc and filtered through a celite pad. The combined filtrate after washing the pad were concentrated to give (9-chloro-1,2,4,4a,5,6-hexahydro-[1,4]oxazino[4,3-a][1,5]naphthyridin-5-yl)methanol in 98% yield. LCMS (m/z) (M+H)=255.1, Rt=0.66 min.

Step 2:
To a vial containing mixture of (9-chloro-1,2,4,4a,5,6-hexahydro-[1,4]oxazino[4,3-a][1,5]naphthyridin-5-yl)methanol (1 equiv.), 4-methylbenzenesulfonyl chloride (1.05 equiv.), DMAP (0.1 equiv.) and DCM (0.2 M) was added TEA (1.4 equiv.) and stirred for 2 hr. The reaction mixture was directly purified via flash chromatography over silica gel (Heptane with 0-100% EtOAc) to give (9-chloro-1,2,4,4a,5,6-hexahydro-[1,4]oxazino[4,3-a][1,5]naphthyridin-5-yl)methyl 4-methylbenzenesulfonate in 94% yield. LCMS (m/z) (M+H)=409.4, Rt=1.27 min.

Step 3:
To a solution of (9-chloro-1,2,4,4a,5,6-hexahydro-[1,4]oxazino[4,3-a][1,5]naphthyridin-5-yl)methyl 4-methylbenzenesulfonate (1 equiv.) in DMSO (0.6 M) was added methyl amine in THF (10 equiv., 2 M) and stirred at 60° C. for 48 hr. It was allowed to come to ambient temperature. It was diluted with EtOAc, washed with sat. NaHCO$_3$ solution, water, brine, dried over sodium sulfate, filtered, and concentrated. This crude material was purified via chiral separation to give two chirally pure compounds, 1-(9-chloro-1,2,4,4a,5,6-hexahydro-[1,4]oxazino[4,3-a][1,5]naphthyridin-5-yl)-N-methylmethanamine. LCMS (m/z) (M+H)=268.1, Rt=0.61 min.

The compounds listed in the following table were prepared using the above intermediate and the appropriate starting materials:

| | | | |
|---|---|---|---|
| 530 | 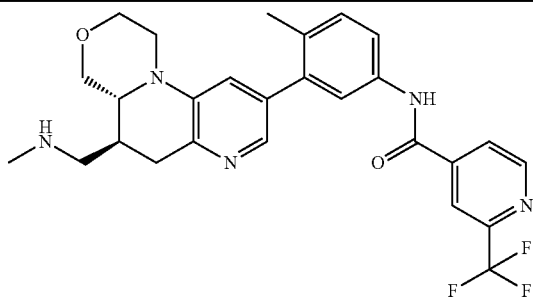 | N-(4-methyl-3-((4aR,5S)-5-((methylamino)methyl)-1,2,4,4a,5,6-hexahydro-[1,4]oxazino[4,3-a][1,5]naphthyridin-9-yl)phenyl)-2-(trifluoromethyl)isonicotinamide | $^1$H NMR (400 MHz, Methanol-d4) δ 8.89 (d, J = 5.0 Hz, 1H), 8.29 (s, 1H), 8.11 (dd, J = 5.0, 1.2 Hz, 1H), 7.79 (d, J = 1.7 Hz, 1H), 7.69-7.59 (m, 2H), 7.32 (d, J = 8.3 Hz, 1H), 7.19 (d, J = 1.6 Hz, 1H), 4.01 (dd, J = 11.2, 3.1 Hz, 1H), 3.94 (dd, J = 10.9, 3.2 Hz, 1H), 3.74-3.62 (m, 2H), 3.42 (t, J = 10.9 Hz, 1H), 3.07-2.95 (m, 3H), 2.77 (dd, J = 16.4, 8.9 Hz, 1H), 2.63 (dd, J = 12.0, 5.5 Hz, 1H), 2.52 (dd, J = 12.0, 7.8 Hz, 1H), 2.41 (s, 3H), 2.26 (s, 3H), 2.13-2.04 (m, 1H). LCMS (m/z) (M + H) = 512.2, Rt = 0.88 min. |
| 531 | 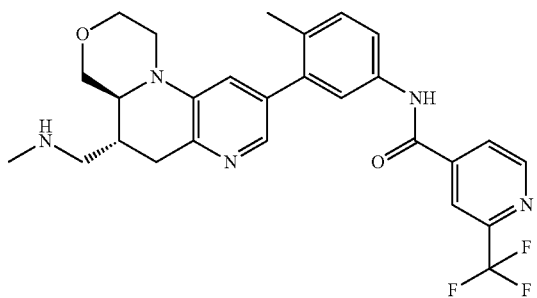 [SMILES: CNC[C@H]1Cc2ncc(-c3cc(NC(=O)c4ccnc(C(F)(F)F)c4)ccc3C)cc2N2CCOC[C@H]12] | N-(4-methyl-3-((4aS,5R)-5-((methylamino)methyl)-1,2,4,4a,5,6-hexahydro-[1,4]oxazino[4,3-a][1,5]naphthyridin-9-yl)phenyl)-2-(trifluoromethyl)isonicotinamide | $^1$H NMR (400 MHz, Methanol-d4) δ 8.91 (d, J = 5.0 Hz, 1H), 8.28 (s, 1H), 8.11 (dd, J = 5.0, 1.2 Hz, 1H), 8.03 (d, J = 1.5 Hz, 1H), 7.83 (d, J = 2.3 Hz, 1H), 7.80 (d, J = 1.4 Hz, 1H), 7.61 (dd, J = 8.3, 2.3 Hz, 1H), 7.39 (d, J = 8.4 Hz, 1H), 4.09-3.93 (m, 3H), 3.66 (td, J = 11.9, 2.7 Hz, 1H), 3.49 (t, J = 10.8 Hz, 1H), 3.42-3.32 (m, 2H), 3.28-3.19 (m, 2H), 3.13-3.02 (m, 2H), 2.80 (s, 3H), 2.51-2.38 (m, 1H), 2.30 (s, 3H). LCMS (m/z) (M + H) = 512.2, Rt = 0.88 min. |

2-(1,1-Difluoroethyl)-N-(3-((6S,6aR)-6-ethyl-6a,7,9,10-tetrahydro-6H-[1,4]oxazino[4,3-d]pyridazino[3,4-b][1,4]oxazin-2-yl)-4-methylphenyl)isonicotinamide (Ex. 532), 2-(1,1-difluoroethyl)-N-(3-((6R,6aR)-6-ethyl-6a,7,9,10-tetrahydro-6H-[1,4]oxazino[4,3-d]pyridazino[3,4-b][1,4]oxazin-2-yl)-4-methylphenyl)isonicotinamide (Ex. 533), and 2-(1,1-difluoroethyl)-N-(3-((6S,6aS)-6-ethyl-6a,7,9,10-tetrahydro-6H-[1,4]oxazino[4,3-d]pyridazino[3,4-b][1,4]oxazin-2-yl)-4-methylphenyl)isonicotinamide (Ex. 534)

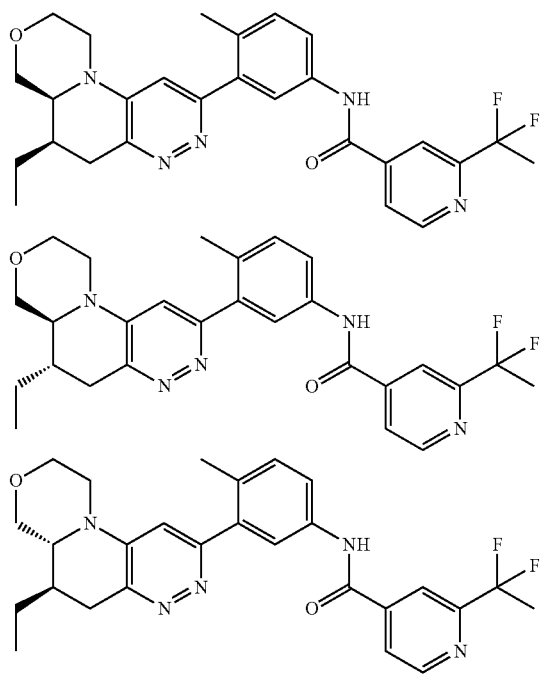

A vial was charged with 2-chloro-6-ethyl-6a,7,9,10-tetrahydro-6H-[1,4]oxazino[4,3-d]pyridazino[3,4-b][1,4]oxazine (1 equiv), 2-(1,1-difluoroethyl)-N-(4-methyl-3-(4,4,5,5-tetramethyl-1,3,2-dioxaborolan-2-yl)phenyl) isonicotinamide (1.2 equiv), XPhos 2nd Gen Precatalyst (5 mol %), potassium phosphate (3 equiv), and a 4:1 mixture of 1,4-dioxane and water (0.1 M). The vial was sealed and heated to 120° C. for 1 h in a Biotage Initiator microwave reactor. The mixture was extracted with EtOAc (3×), and the combined organic extracts were concentrated. The residue was purified by chromatography on silica gel (24-g RediSep Gold column, 75-100% EtOAc/heptane) to give 2-(1,1-difluoroethyl)-N-(3-(6-ethyl-6a,7,9,10-tetrahydro-6H-[1,4]oxazino[4,3-d]pyridazino[3,4-b][1,4]oxazin-2-yl)-4-methylphenyl)isonicotinamide (78% yield) as a light-yellow foam as a mixture of stereoisomers. The mixture was purified by chiral SFC, and the resulting pure stereoisomers were lyophilized from acetonitrile/water to afford white solids. The first eluting peak afforded 2-(1,1-Difluoroethyl)-N-(3-((6S,6aR)-6-ethyl-6a,7,9,10-tetrahydro-6H-[1,4]oxazino[4,3-d]pyridazino[3,4-b][1,4]oxazin-2-yl)-4-methylphenyl)isonicotinamide (Ex. 532): $^1$H NMR (400 MHz, DMSO-d6) δ ppm 10.66 (s, 1H) 8.88 (d, J=5.01 Hz, 1H) 8.19 (s, 1H) 8.04 (d, J=4.89 Hz, 1H) 7.76-7.81 (m, 2H) 7.30-7.38 (m, 1H) 7.10 (s, 1H) 4.34-4.39 (m, 1H) 3.89-4.01 (m, 2H) 3.84 (dd, J=11.49, 3.06 Hz, 1H) 3.64 (dt, J=10.82, 3.03 Hz, 1H) 3.48 (td, J=11.77, 2.26 Hz, 1H) 3.33-3.40 (m, 1H) 3.06-3.27 (m, 1H) 2.28 (s, 3H) 2.05 (t, J=19.13 Hz, 3H) 1.48-1.71 (m, 2H) 0.97-1.14 (m, 3H). LMCS (m/z) (M+H)=496.0, Rt=1.21 min. The second peak afforded 2-(1,1-difluoroethyl)-N-(3-((6R,6aR)-6-ethyl-6a,7,9,10-tetrahydro-6H-[1,4]oxazino[4,3-d]pyridazino[3,4-b][1,4]oxazin-2-yl)-4-methylphenyl)isonicotinamide (Ex. 533): $^1$H NMR (400 MHz, DMSO-d6) δ ppm 10.67 (s, 1H) 8.88 (d, J=5.01 Hz, 1H) 8.19 (s, 1H) 8.04 (d, J=4.65 Hz, 1H) 7.78 (d, J=6.43 Hz, 2H) 7.77 (s, 1H) 7.32 (d, J=9.05 Hz, 1H) 7.02 (s, 1H) 4.11 (td, J=7.73, 2.87 Hz, 1H) 3.93-4.05 (m, 2H) 3.81 (br d, J=11.37 Hz, 1H) 3.34-3.59 (m, 1H) 3.21-3.29 (m, 2H) 2.93 (td, J=12.38, 3.73 Hz, 1H) 2.27 (s, 3H) 2.05 (t, J=19.13 Hz, 3H) 1.73-1.89 (m, 1H) 1.63 (dt, J=14.70, 7.50 Hz, 1H) 1.01-1.15 (m, 3H). LMCS (m/z) (M+H)=496.0, Rt=1.21 min. The third eluting peak afforded 2-(1,1-difluoroethyl)-N-(3S,6aS)-6-ethyl-6a,7,9,10-tetrahydro-6H-[1,4]oxazino[4,3-d]pyridazino[3,4-b][1,4]oxazin-2-yl)-4-methylphenyl)isonicotinamide (Ex. 534): $^1$H NMR (400 MHz, DMSO-d6) δ ppm 10.67 (s, 1H) 8.88 (d, J=5.01 Hz, 1H) 8.19 (s, 1H) 8.04 (d, J=4.65 Hz, 1H) 7.78 (d, J=6.43 Hz, 2H) 7.77 (s, 1H) 7.32 (d, J=9.05 Hz, 1H) 7.02 (s, 1H) 4.11 (td, J=7.73, 2.87 Hz, 1H) 3.93-4.05 (m, 2H) 3.81 (br d, J=11.37 Hz, 1H) 3.34-3.59 (m, 1H) 3.21-3.29 (m, 2H) 2.93 (td, J=12.38, 3.73 Hz, 1H) 2.27 (s, 3H) 2.05 (t, J=19.13 Hz, 3H) 1.73-1.89 (m, 1H) 1.63 (dt, J=14.70, 7.50 Hz, 1H) 1.01-1.15 (m, 3H). LMCS (m/z) (M+H)=496.0, Rt=1.21 min.

Biological Assays

The activity of a compound according to the present invention can be assessed by well-known in vitro & in vivo methods. Raf inhibition data provided herein was obtained using the following procedures.

In Vitro Raf Activity Determination: The RAF enzymes and the catalytically inactive MEK1 protein substrate were all made in-house using conventional methods. CRAF cDNA was subcloned as full length protein, with Y340E and Y341E activating mutations, into a baculovirus expression vector for Sf9 insect cell expression. h14-3-3 zeta cDNA was subcloned into a baculovirus expression vector for SF9 insect cell expression. Sf9 cells co-expressing both proteins were lysed and subjected to immobilized nickel chromatography and eluted with Imidazole. A second column (StrepII binding column) was used and eluted with desthiobiotin. Protein Tags were removed using Prescission enzyme and the protein was further purified using a flowthrough step to remove tags.

C-Raf TR refers to a truncated C-Raf protein, a Δ1-324 deletion mutant. C-Raf FL refers to the full-length C-Raf protein.

Full length MEK1 with an inactivating K97R ATP binding site mutation is utilized as a RAF substrate. The MEK1 cDNA was subcloned with an N-terminal (his)$_6$ tag into a vector for E. Coli expression. The MEK1 substrate was purified from E. Coli lysate by nickel affinity chromatography followed by anion exchange. The final MEK1 preparation was biotinylated (Pierce EZ-Link Sulfo-NHS-LC-Biotin) and concentrated.

Assay Materials: Assay buffer is 50 mM Tris, pH 7.5, 15 mM MgCl$_2$, 0.01% Bovine Serum Albumin (BSA) and 1 mM dithiothreitol (DTT); Stop buffer is 60 mM ethylenediaminetetraacetic acid (EDTA) and 0.01% Tween® 20; b-Raf (V600E), active; biotinylated Mek, kinase dead; Alpha Screen detection kit (available from PerkinElmer™, #6760617R); Anti phospho-MEK1/2 (available from Cell Signaling Technology, Inc. #9121); 384 well low volume assay plates (White Greiner® plates).

Assay conditions: b-Raf (V600E) approximately 4 pM; c-Raf approximately 4 nM; biotinylated Mek, kinase dead approximately 10 nM; ATP 10 μM for BRAF (V600E) and 1 μM for CRAF; Pre-incubation time with compounds 60 minutes at room temperature; Reaction time 1 or 3 hours at room temperature.

Assay protocol: Raf and biotinylated Mek (kinase dead) were combined at 2× final concentrations in assay buffer (50 mM Tris, pH 7.5, 15 mM MgCl$_2$, 0.01% BSA and 1 mM DTT) and dispensed 5 ml per well in assay plates (Greiner white 384 well assay plates #781207) containing 0.25 ml of 40× of a Raf kinase inhibitor test compound diluted in 100% DMSO. The plate was incubated for 60 minutes at room temperature. The Raf kinase activity reaction was started by the addition of 5 mL per well of 2×ATP diluted in assay buffer. After 3 hours (b-Raf(V600E)) or 1 hour (c-Raf). The reactions were stopped and the phosphorylated product was measured using a rabbit anti-p-MEK (Cell Signaling, #9121) antibody and the Alpha Screen IgG (ProteinA) detection Kit (PerkinElmer #6760617R), by the addition of 10 mL to the well of a mixture of the antibody (1:2000 dilution) and detection beads (1:2000 dilution of both beads) in Stop/bead buffer (25 mM EDTA, 50 mM Tris, pH 7.5, 0.01% Tween20). The additions were carried out under dark conditions to protect the detection beads from light. A lid was placed on top of the plate and incubated for 1 hour at room temperature, after which the luminescence was read on a PerkinElmer Envision instrument. The concentration of each compound for 50% inhibition (IC$_{50}$) was calculated by non-linear regression using XL Fit data analysis software.

Using the assays described above, compounds of the invention exhibit inhibitory efficacy for C-Raf. The Bioactivity Table below summarizes IC50 data for compounds of the Examples.

BIOACTIVITY TABLE

| Example | C-RAF IC50 μM |
|---|---|
| 1 | 0.000045 |
| 2 | 0.000136 |
| 3 | 0.000031 |
| 4 | 0.0000062 |
| 5 | 0.000036 |
| 6 | 0.000076 |
| 7 | 0.000033 |
| 8 | 0.00019 |
| 9 | 0.000051 |
| 10 | 0.000036 |
| 11 | 0.0000098 |
| 12 | 0.0000072 |
| 13 | 0.0000055 |
| 14 | 0.000034 |
| 15 | 0.000084 |
| 16 | 0.000055 |
| 17 | 0.000046 |
| 18 | NA |
| 19 | 0.000019 |
| 20 | 0.000025 |
| 21 | 0.0000012 |
| 22 | 0.00023 |
| 23 | 0.000046 |
| 24 | 0.000049 |
| 25 | 0.00052 |
| 26 | 0.000014 |
| 27 | 0.000017 |
| 28 | 0.000059 |
| 29 | 0.00017 |
| 30 | 0.00018 |
| 31 | 0.000033 |
| 32 | 0.000023 |
| 33 | 0.0000082 |
| 34 | 0.0000087 |
| 35 | 0.000018 |
| 36 | 0.000013 |
| 37 | 0.0000081 |
| 38 | 0.000030 |
| 39 | 0.0000023 |
| 40 | 0.000066 |
| 41 | 0.0000099 |
| 42 | 0.000015 |
| 43 | 0.0000082 |
| 44 | 0.000037 |
| 45 | 0.00017 |
| 46 | 0.000014 |
| 47 | 0.000073 |
| 48 | 0.000049 |
| 49 | 0.000021 |
| 50 | 0.000013 |
| 51 | 0.000036 |
| 52 | 0.00016 |
| 53 | 0.0000062 |
| 54 | 0.000013 |

BIOACTIVITY TABLE-continued

| Example | C-RAF IC50 μM |
|---|---|
| 55 | 0.000022 |
| 56 | 0.000071 |
| 57 | 0.000011 |
| 58 | 0.000010 |
| 59 | 0.0000089 |
| 60 | 0.000019 |
| 61 | 0.000033 |
| 62 | 0.000015 |
| 63 | 0.000020 |
| 64 | 0.000013 |
| 65 | 0.0000060 |
| 66 | 0.00011 |
| 67 | 0.00013 |
| 68 | 0.00034 |
| 69 | 0.000028 |
| 70 | 0.000032 |
| 71 | 0.000027 |
| 72 | 0.000014 |
| 73 | 0.00020 |
| 74 | 0.00028 |
| 75 | 0.00048 |
| 76 | 0.000 |
| 77 | |
| 78 | 0.000020 |
| 79 | 0.000038 |
| 80 | 0.00042 |
| 81 | 0.000081 |
| 82 | 0.00017 |
| 83 | 0.00085 |
| 84 | 0.0010 |
| 85 | 0.000070 |
| 86 | 0.000027 |
| 87 | 0.000022 |
| 88 | 0.000032 |
| 89 | 0.000036 |
| 90 | 0.000023 |
| 91 | 0.000076 |
| 92 | 0.00061 |
| 93 | 0.000025 |
| 94 | 0.000019 |
| 95 | 0.000030 |
| 96 | 0.000053 |
| 97 | 0.000014 |
| 98 | 0.00056 |
| 99 | 0.000038 |
| 100 | 0.000037 |
| 101 | 0.000026 |
| 102 | <0.0000017 |
| 103 | 0.000013 |
| 104 | 0.000044 |
| 105 | 0.000045 |
| 106 | 0.000012 |
| 107 | 0.000019 |
| 108 | 0.000013 |
| 109 | 0.0000057 |
| 110 | 0.0000020 |
| 111 | 0.0000054 |
| 112 | <0.0000017 |
| 113 | 0.0000084 |
| 114 | 0.000070 |
| 115 | 0.000011 |
| 116 | <0.0000017 |
| 117 | 0.0000047 |
| 118 | 0.0000046 |
| 119 | 0.000010 |
| 120 | 0.000011 |
| 121 | 0.0000095 |
| 122 | 0.0000050 |
| 123 | 0.0000052 |
| 124 | 0.0000094 |
| 125 | 0.000034 |
| 126 | 0.000016 |
| 127 | 0.000048 |
| 128 | 0.000023 |
| 129 | 0.00018 |
| 130 | 0.00037 |
| 131 | 0.000060 |
| 132 | 0.00014 |
| 133 | 0.000011 |
| 134 | 0.000016 |
| 135 | 0.000019 |
| 136 | 0.000018 |
| 137 | 0.00024 |
| 138 | 0.00059 |
| 139 | 0.000057 |
| 140 | 0.0000085 |
| 141 | 0.0000042 |
| 142 | 0.000021 |
| 143 | 0.0000088 |
| 144 | 0.0000023 |
| 145 | 0.000017 |
| 146 | 0.000012 |
| 147 | 0.0000026 |
| 148 | 0.000046 |
| 149 | 0.000013 |
| 150 | 0.000079 |
| 151 | 0.000014 |
| 152 | 0.000011 |
| 153 | 0.0000048 |
| 154 | 0.000063 |
| 155 | 0.00036 |
| 156 | 0.000048 |
| 157 | 0.00016 |
| 158 | 0.000010 |
| 159 | 0.0000068 |
| 160 | 0.000027 |
| 161 | 0.00008 |
| 162 | 0.000093 |
| 163 | 0.000020 |
| 164 | 0.00043 |
| 165 | 0.00062 |
| 166 | 0.000011 |
| 167 | 0.000077 |
| 168 | 0.00077 |
| 169 | 0.000032 |
| 170 | 0.000025 |
| 171 | 0.000019 |
| 172 | 0.000034 |
| 173 | 0.000012 |
| 234 | 0.0013 |
| 235 | 0.0009 |
| 236 | 0.0003 |
| 237 | 0.0013 |
| 238 | 0.0027 |
| 239 | 0.0047 |
| 240 | 0.0106 |
| 241 | 0.0095 |
| 242 | 0.0003 |
| 243 | 0.0006 |
| 244 | 0.0001 |
| 245 | 0.0002 |
| 246 | 0.0002 |
| 247 | 0.0003 |
| 248 | 0.0005 |
| 249 | 0.0001 |
| 250 | 0.0003 |
| 251 | 0.0002 |
| 252 | 0.0001 |
| 253 | 0.0032 |
| 254 | 0.0002 |
| 255 | 0.0008 |
| 256 | 0.0001 |
| 257 | 0.0000 |
| 258 | 0.0000 |
| 259 | 0.0006 |
| 260 | 0.0001 |
| 261 | 0.0002 |
| 262 | 0.0007 |
| 263 | 0.0003 |
| 265 | 0.0001 |
| 266 | 0.0003 |
| 267 | 0.0000 |
| 268 | 0.0003 |
| 269 | 0.0003 |
| 270 | 0.0002 |
| 271 | 0.0002 |

BIOACTIVITY TABLE-continued

| Example | C-RAF IC50 μM |
| --- | --- |
| 272 | 0.0005 |
| 273 | 0.0002 |
| 274 | 0.0005 |
| 275 | 0.0008 |
| 276 | 0.0005 |
| 277 | 0.0001 |
| 278 | 0.0003 |
| 279 | 0.0004 |
| 280 | 0.0005 |
| 281 | 0.0002 |
| 283 | 0.0002 |
| 284 | 0.0000 |
| 285 | 0.0001 |
| 286 | 0.0000 |
| 287 | 0.0002 |
| 288 | 0.0009 |
| 289 | 0.0009 |
| 290 | 0.0010 |
| 291 | 0.0001 |
| 292 | 0.0001 |
| 293 | 0.0001 |
| 294 | 0.0001 |
| 295 | 0.0001 |
| 296 | 0.0018 |
| 297 | 0.0002 |
| 298 | 0.0003 |
| 299 | 0.0001 |
| 300 | 0.0002 |
| 301 | 0.0000 |
| 302 | 0.0001 |
| 303 | 0.0001 |
| 304 | 0.0005 |
| 305 | 0.0003 |
| 306 | 0.0001 |
| 307 | 0.0001 |
| 308 | 0.0007 |
| 309 | 0.0003 |
| 310 | 0.0001 |
| 311 | 0.0001 |
| 312 | 0.0001 |
| 313 | 0.0005 |
| 314 | 0.0006 |
| 315 | 0.0017 |
| 316 | 0.0008 |
| 317 | 0.0017 |
| 318 | 0.0014 |
| 319 | 0.0022 |
| 320 | 0.0008 |
| 322 | 0.0003 |
| 323 | 0.0002 |
| 324 | 0.0008 |
| 325 | 0.0001 |
| 326 | 0.0005 |
| 327 | 0.0003 |
| 328 | 0.0001 |
| 329 | 0.0002 |
| 330 | 0.0031 |
| 331 | 0.0066 |
| 332 | 0.0021 |
| 333 | 0.0000 |
| 334 | 0.0004 |
| 335 | 0.0001 |
| 336 | 0.0002 |
| 337 | 0.0003 |
| 338 | 0.0005 |
| 339 | 0.0005 |
| 340 | 0.0013 |
| 341 | 0.0006 |
| 342 | 0.0001 |
| 343 | 0.0002 |
| 344 | 0.0001 |
| 345 | 0.0008 |
| 346 | 0.0001 |
| 347 | 0.0003 |
| 348 | 0.0007 |
| 349 | 0.0030 |
| 351 | 0.0011 |
| 352 | 0.0001 |
| 353 | 0.0000 |
| 354 | 0.0003 |
| 355 | 0.0012 |
| 356 | 0.0001 |
| 357 | 0.0000 |
| 358 | 0.0001 |
| 359 | 0.0003 |
| 360 | 0.0000 |
| 361 | 0.0009 |
| 362 | 0.0002 |
| 363 | 0.0001 |
| 364 | 0.0008 |
| 365 | 0.0002 |
| 366 | 0.0000 |
| 367 | 0.0010 |
| 368 | 0.0001 |
| 369 | 0.0003 |
| 370 | 0.0001 |
| 371 | 0.0002 |
| 372 | 0.0003 |
| 373 | 0.0004 |
| 374 | 0.0002 |
| 375 | 0.0004 |
| 376 | 0.0005 |
| 377 | 0.0009 |
| 378 | 0.0002 |
| 379 | 0.0011 |
| 380 | 0.0004 |
| 381 | 0.0003 |
| 382 | 0.0002 |
| 383 | 0.0010 |
| 384 | 0.0002 |
| 385 | 0.0006 |
| 386 | 0.0003 |
| 387 | 0.0003 |
| 388 | 0.0004 |
| 389 | 0.0005 |
| 390 | 0.0017 |
| 391 | 0.0068 |
| 392 | 0.0034 |
| 393 | 0.0001 |
| 394 | 0.0003 |
| 395 | 0.0002 |
| 396 | 0.0002 |
| 397 | 0.0000 |
| 398 | 0.0000 |
| 399 | 0.0003 |
| 400 | 0.0001 |
| 401 | 0.0003 |
| 403 | 0.0001 |
| 404 | 0.0000 |
| 405 | 0.0002 |
| 406 | 0.0004 |
| 407 | 0.0001 |
| 408 | 0.0007 |
| 409 | 0.0004 |
| 410 | 0.0005 |
| 411 | 0.0002 |
| 412 | 0.0004 |
| 413 | 0.0002 |
| 414 | 0.0005 |
| 415 | 0.0008 |
| 416 | 0.0004 |
| 417 | 0.0005 |
| 418 | 0.0021 |
| 419 | 0.0005 |
| 420 | 0.0006 |
| 421 | 0.0008 |
| 422 | 0.0010 |
| 423 | 0.0007 |
| 424 | 0.0002 |
| 425 | 0.0004 |
| 426 | 0.0004 |
| 427 | 0.0006 |
| 428 | 0.0001 |
| 429 | 0.0008 |
| 430 | 0.0006 |
| 431 | 0.0044 |

BIOACTIVITY TABLE-continued

| Example | C-RAF IC50 μM |
|---|---|
| 432 | 0.0007 |
| 433 | 0.0001 |
| 434 | 0.0013 |
| 436 | 0.0003 |
| 437 | 0.0006 |
| 438 | 0.0008 |
| 439 | 0.0001 |
| 440 | 0.0003 |
| 441 | 0.0000 |
| 442 | 0.0007 |
| 443 | 0.0006 |
| 444 | 0.0004 |
| 445 | 0.0007 |
| 446 | 0.0007 |
| 447 | 0.0005 |
| 448 | 0.0002 |
| 449 | 0.0007 |
| 450 | 0.0002 |
| 451 | 0.0006 |
| 452 | 0.0005 |
| 453 | 0.0007 |
| 454 | 0.0008 |
| 455 | 0.0013 |
| 456 | 0.0007 |
| 457 | 0.0004 |
| 458 | 0.0007 |
| 459 | 0.0004 |
| 460 | 0.0002 |
| 461 | 0.0022 |
| 462 | 0.0007 |
| 463 | 0.0021 |
| 464 | 0.0007 |
| 465 | 0.0020 |
| 466 | 0.0009 |
| 467 | 0.0019 |
| 468 | 0.0080 |
| 469 | 0.0018 |
| 470 | 0.0022 |
| 471 | 0.0012 |
| 472 | 0.0020 |
| 473 | 0.0015 |
| 474 | 0.0055 |
| 475 | 0.0004 |
| 476 | 0.0002 |
| 477 | 0.0001 |
| 478 | 0.0002 |
| 479 | 0.0004 |
| 480 | 0.0002 |
| 481 | 0.0011 |
| 482 | 0.0003 |
| 483 | 0.0010 |
| 484 | 0.0041 |
| 485 | 0.0003 |
| 486 | 0.0016 |
| 487 | 0.0007 |
| 488 | 0.0003 |
| 489 | 0.0004 |
| 490 | 0.0005 |
| 491 | 0.0000 |
| 492 | 0.0002 |
| 493 | 0.0001 |
| 494 | 0.0001 |
| 495 | 0.0001 |
| 496 | 0.0007 |
| 497 | 0.0014 |
| 498 | 0.0006 |
| 499 | 0.0004 |
| 500 | 0.0001 |
| 501 | 0.0002 |
| 502 | 0.0002 |
| 503 | 0.0001 |
| 504 | 0.0154 |
| 505 | 0.0036 |
| 506 | 0.0803 |
| 507 | 0.0269 |
| 508 | 0.0002 |
| 509 | 0.0002 |
| 510 | 0.0001 |

BIOACTIVITY TABLE-continued

| Example | C-RAF IC50 μM |
|---|---|
| 511 | 0.0002 |
| 512 | 0.0004 |
| 513 | 0.0001 |
| 514 | 0.0004 |
| 515 | 0.0001 |
| 516 | 0.0001 |
| 517 | 0.0001 |
| 518 | 0.0001 |
| 519 | 0.0000 |
| 520 | 0.0001 |
| 521 | 0.0005 |
| 522 | 0.0001 |
| 525 | 0.0015 |
| 526 | 0.0026 |
| 527 | 0.0009 |
| 528 | 0.0007 |
| 529 | 0.0023 |
| 530 | 0.0004 |
| 531 | 0.0002 |
| 532 | 0.0002 |
| 533 | 0.0001 |
| 534 | 0.0001 |

We claim:

1. A compound of formula (A):

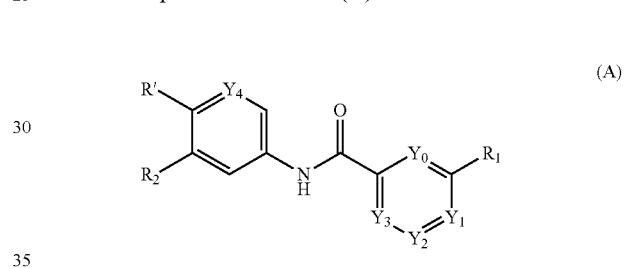

in which:

R' is selected from the group consisting of H and methyl;

$R_1$ is $C_{1-3}$alkyl substituted by CN or by one or more halogens;

$R_2$ is selected from the group consisting of:

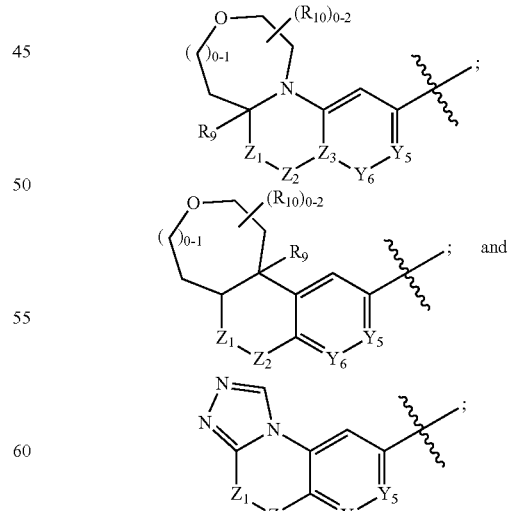

wherein $Z_1$ is $CR_3R_4$, —O—, a bond, or $CR_7$; provided that when $Z_1$ is $CR_7$, $Z_1$ is attached to the carbon atom bonded to $R_9$ by a double bond and $R_9$ is absent;

$Z_2$ is $CR_5R_6$, O, —C(O)$NR_8$—[$Y_6$], —$NR_8$C(O)—[$Y_6$], or —$(CR_7)_{0-1}$—C(O)—[$Y_6$], where [$Y_6$] indicates which atom of $Z_2$ is attached to the ring containing $Y_6$; provided $Z_1$ and $Z_2$ are not both simultaneously O;

$Z_3$ is a carbon atom bonded to $Y_6$ by an aromatic bond, or $Z_3$ is a nitrogen atom bonded to $Y_6$ by a single bond;

$R_3$ is selected from the group consisting of hydrogen, $C_{1-3}$alkyl, halo, $C_{1-3}$alkyl-amino-carbonyl, $C_{1-3}$alkyl-S$(O)_{0-2}$—$C_{1-2}$alkyl, carboxyl and hydroxy-substituted-$C_{1-3}$alkyl;

$R_4$ is selected from the group consisting of hydrogen, amino, $C_{1-3}$alkyl, cyano, hydroxy-ethyl and halo; or $R_3$ and $R_4$ together with the carbon atom to which $R_3$ and $R_4$ are attached form a 4 member saturated cyclic ring containing an oxygen molecule;

$R_5$ is selected from the group consisting of hydrogen, halo, amino, $C_{1-3}$alkyl-amino-carbonyl, $C_{1-3}$alkyl-carbonyl, hydroxy and $C_{1-3}$alkoxy;

$R_6$ is selected from the group consisting of hydrogen, $C_{1-3}$alkyl, halo, halo-substituted-$C_{1-3}$alkyl; or $R_4$ and $R_6$ together with the carbon atom to which $R_4$ and $R_6$ are attached form 5-6 member unsaturated ring containing up to 2 heteroatoms selected from O, S and N; wherein said ring is optionally substituted with $C_{1-2}$alkyl;

$R_7$ is selected from the group consisting of hydrogen, hydroxy-carbonyl and $C_{1-3}$alkoxy-carbonyl;

$R_8$ is selected from the group consisting of hydrogen, $C_{1-3}$alkyl-amino-carbonyl, $C_{1-3}$alkyl-carbonyl, $C_{1-3}$alkoxy and hydroxy-substituted-$C_{1-4}$alkoxy, hydroxy-substituted-$C_{1-3}$alkyl, and $C_{1-3}$alkyl;

$R_9$ is independently selected at each occurrence from the group consisting of hydrogen, fluorine, and methyl;

each $R_{10}$ represents an optional substituent selected from the group consisting of $C_{1-3}$ alkyl and $C_{1-3}$ alkoxy, or two $R_{10}$ on non-adjacent ring atoms can be taken together to form a bond or a $(CH_2)_{1-2}$ bridge linking the two non-adjacent ring atoms to form a fused or bridged ring;

$Y_0$ is selected from the group consisting of N, CH and CF;
$Y_1$ is selected from the group consisting of N and CH;
$Y_2$ is selected from the group consisting of N, CH, CF, CCl, C—$NH_2$, and C—$C(R_9)_2NH_2$;
$Y_3$ is selected from the group consisting of N and CH;
$Y_4$ is selected from the group consisting of N and CH;
$Y_5$ is selected from the group consisting of N and CH; and
$Y_6$ is selected from the group consisting of N and CH when $Z_3$ is carbon, and $Y_6$ is C(=O) when $Z_3$ is nitrogen;

or a pharmaceutically acceptable salt thereof.

2. The compound of claim 1, wherein R' is methyl.
3. The compound of claim 1, wherein $Y_4$ is CH.
4. The compound of claim 1, wherein $Y_4$ is N.
5. The compound of claim 1, wherein $Y_0$ is CH.
6. The compound of claim 1, wherein $Y_1$ is N.
7. The compound of claim 1, wherein $Y_2$ is CH.
8. The compound of claim 1, wherein $Y_3$ is CH.
9. The compound of claim 1, wherein $Y_5$ is CH.
10. The compound of claim 1, wherein $Y_6$ is CH.
11. The compound of claim 1, wherein $R_9$ is H.
12. The compound of claim 1, wherein $Z_1$ is $CH_2$ or a bond.
13. The compound of claim 1, wherein $R_2$ is selected from the group consisting of:

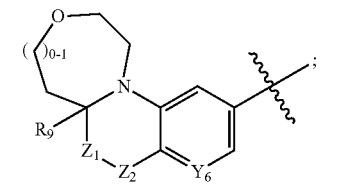

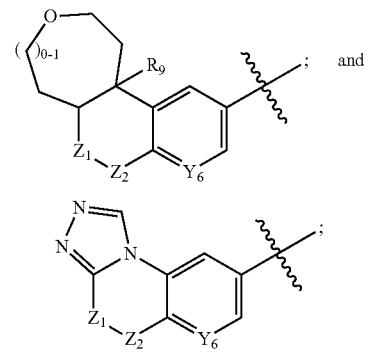

wherein $Y_6$ is selected from the group consisting of N and CH;

$Z_1$ is $CR_3R_4$ or a bond; and $Z_2$ is $CR_5R_6$, —C(O)$NR_8$—[$Y_6$] or —$NR_8$C(O)—[$Y_6$], where [$Y_6$] indicates which atom of $Z_2$ is attached to the ring containing $Y_6$.

14. The compound of claim 1, which is of the formula (I):

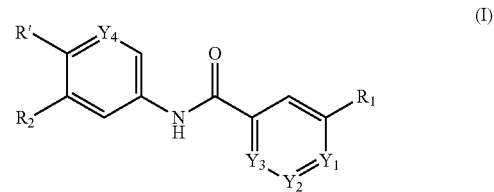

in which:

R' is selected from the group consisting of H and methyl;

$R_1$ is halo-substituted $C_{1-3}$alkyl;

$R_2$ is selected from the group consisting of:

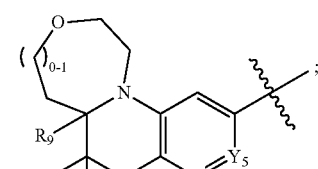

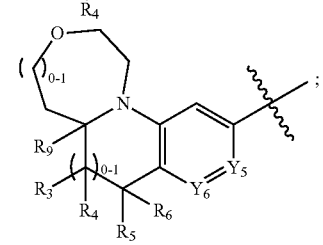

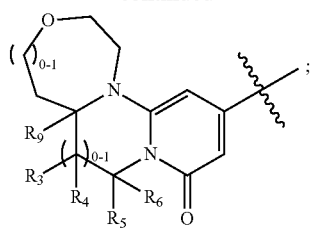
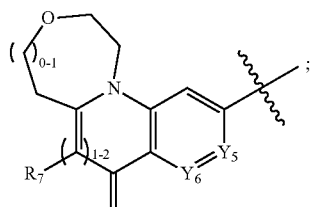
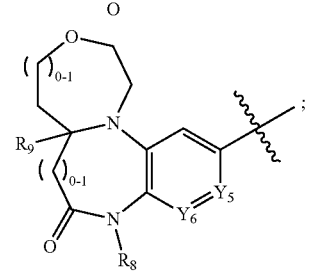
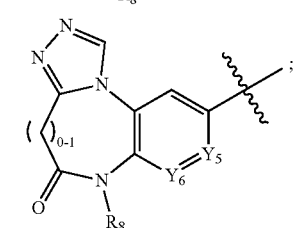
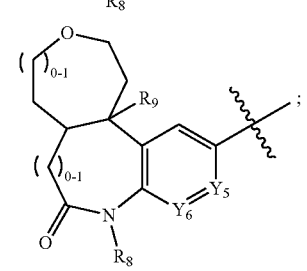
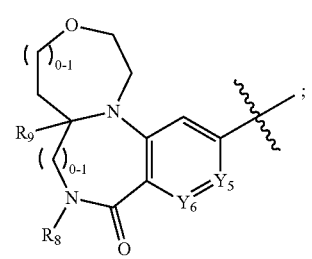
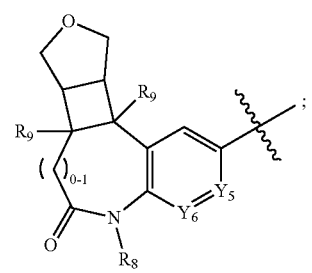

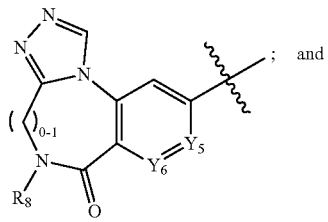
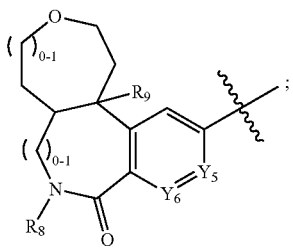

$R_3$ is selected from the group consisting of hydrogen, $C_{1-3}$alkyl, halo, $C_{1-3}$alkyl-amino-carbonyl, $C_{1-3}$alkyl-S$(O)_{0-2}$—$C_{1-2}$alkyl, carboxyl and hydroxy-substituted-$C_{1-3}$alkyl;

$R_4$ is selected from the group consisting of hydrogen, amino, $C_{1-3}$alkyl, cyano, hydroxy-ethyl and halo; or $R_3$ and $R_4$ together with the carbon atom to which $R_3$ and $R_4$ are attached form a 4 member saturated cyclic ring containing an oxygen molecule;

$R_5$ is selected from the group consisting of hydrogen, halo, amino, $C_{1-3}$alkyl-amino-carbonyl, $C_{1-3}$alkyl-carbonyl, hydroxy and $C_{1-3}$alkoxy;

$R_6$ is selected from the group consisting of hydrogen, $C_{1-3}$alkyl, halo, halo-substituted-$C_{1-3}$alkyl; or $R_4$ and $R_6$ together with the carbon atom to which $R_4$ and $R_6$ are attached form 5-6 member unsaturated ring containing up to 2 heteroatoms selected from O, S and N; wherein said ring is optionally substituted with $C_{1-2}$alkyl; each $R_7$ is selected from the group consisting of hydrogen, hydroxy-carbonyl and $C_{1-3}$alkoxy-carbonyl;

$R_8$ is selected from the group consisting of hydrogen, $C_{1-3}$alkyl-amino-carbonyl, $C_{1-3}$alkyl-carbonyl, $C_{1-3}$alkoxy and hydroxy-substituted-$C_{1-4}$alkoxy and $C_{1-3}$alkyl;

$R_9$ is selected from the group consisting of hydrogen and methyl;

$Y_1$ is selected from the group consisting of N and CH;

$Y_2$ is selected from the group consisting of N and CH;

$Y_3$ is selected from the group consisting of N and CH;

$Y_4$ is selected from the group consisting of N and CH;

$Y_5$ is selected from the group consisting of N and CH; and $Y_6$ is selected from the group consisting of N and CH; or the pharmaceutically acceptable salt thereof.

15. The compound of claim 1 which is a compound of formula (Ia):

(Ia)

in which:
R₁ is halo-substituted C₁₋₃alkyl;
R₈ is selected from the group consisting of hydrogen and C₁₋₃alkyl;
R₉ is selected from the group consisting of hydrogen and methyl;
Y₁ is selected from the group consisting of N and CH;
Y₂ is CH;
Y₃ is CH;
Y₄ is selected from the group consisting of N and CH;
Y₅ is selected from the group consisting of N and CH; and
Y₆ is selected from the group consisting of N and CH; or the pharmaceutically acceptable salt thereof.

16. The compound of claim 1, in which:
R₁ is selected from the group consisting of trifluoromethyl, 2-fluoropropan-2-yl, 2-cyanopropan-2-yl and 1,1-difluoroethyl;
R₈ is selected from the group consisting of hydrogen and ethyl;
Y₁ is selected from the group consisting of N and CH;
Y₄ is selected from the group consisting of N and CH;
Y₅ is selected from the group consisting of N and CH; and
Y₆ is selected from the group consisting of N and CH; or the pharmaceutically acceptable salt thereof.

17. The compound of claim 1, which is a compound of formula (Ib):

(Ib)

in which:
R₁ is halo-substituted C₁₋₃alkyl;
R₃ is selected from the group consisting of hydrogen, C₁₋₃alkyl, halo, C₁₋₃alkyl-amino-carbonyl, C₁₋₃alkyl-S(O)₀₋₂—C₁₋₂alkyl, carboxyl and hydroxy-substituted-C₁₋₃alkyl;
R₄ is selected from the group consisting of hydrogen, amino, C₁₋₃alkyl, cyano, hydroxy-ethyl and halo; or R₃ and R₄ together with the carbon atom to which R₃ and R₄ are attached form a 4 member saturated cyclic ring containing an oxygen molecule;
R₅ is selected from the group consisting of hydrogen, halo, amino, C₁₋₃alkyl-amino-carbonyl, hydroxy and C₁₋₃alkoxy;

R₆ is selected from the group consisting of hydrogen, C₁₋₃alkyl, halo, halo-substituted-C₁₋₃alkyl; or R₄ and R₆ together with the carbon atom to which R₄ and R₆ are attached form 5-6 member unsaturated ring containing up to 2 heteroatoms selected from O, S and N; wherein said ring is optionally substituted with C₁₋₂alkyl;
R₉ is selected from the group consisting of hydrogen and methyl;
Y₁ is selected from the group consisting of N and CH;
Y₂ is selected from the group consisting of N and CH;
Y₃ is selected from the group consisting of N and CH;
Y₄ is selected from the group consisting of N and CH;
Y₅ is selected from the group consisting of N and CH; and
Y₆ is selected from the group consisting of N and CH; or the pharmaceutically acceptable salt thereof.

18. The compound of claim 17 in which:
R₁ is selected from the group consisting of trifluoromethyl, 2-fluoropropan-2-yl, 2-cyanopropan-2-yl and 1,1-difluoroethyl;
R₃ is selected from the group consisting of hydrogen and methyl, fluoro, methyl-amino-carbonyl, ethyl-amino-carbonyl, methyl-sulfonyl-methyl, carboxyl and hydroxy-ethyl;
R₄ is selected from the group consisting of hydrogen, methyl, cyano, amino, hydroxy-ethyl and fluoro; or R₃ and R₄ together with the carbon atom to which R₃ and R₄ are attached form oxetan-3-yl;
R₅ is selected from the group consisting of hydrogen, fluoro, amino, methyl-carbonyl-amino, ethyl-carbonyl-amino, hydroxy and methoxy;
R₆ is selected from the group consisting of hydrogen, methyl, fluoro and trifluoromethyl; or R₄ and R₆ together with the carbon atom to which R₄ and R₆ are attached form pyrazolyl optionally substituted with methyl;
R₉ is selected from the group consisting of hydrogen and methyl;
Y₁ is selected from the group consisting of N and CH;
Y₂ is CH;
Y₃ is CH;
Y₄ is selected from the group consisting of N and CH;
Y₅ is selected from the group consisting of N and CH; and
Y₆ is selected from the group consisting of N and CH; or the pharmaceutically acceptable salt thereof.

19. The compound of claim 1, which is a compound of formula (Ic):

(Ic)

in which:
R₁ is halo-substituted C₁₋₃alkyl;
R₈ is selected from the group consisting of hydrogen and C₁₋₃alkyl;
R₉ is selected from the group consisting of hydrogen and methyl;

$Y_1$ is selected from the group consisting of N and CH;
$Y_2$ is selected from the group consisting of N and CH;
$Y_3$ is selected from the group consisting of N and CH;
$Y_4$ is selected from the group consisting of N and CH;
$Y_5$ is selected from the group consisting of N and CH; and
$Y_6$ is selected from the group consisting of N and CH; or the pharmaceutically acceptable salt thereof.

20. The compound of claim 19 in which:
$R_1$ is selected from the group consisting of trifluoromethyl, 2-fluoropropan-2-yl, 2-cyanopropan-2-yl and 1,1-difluoroethyl;
$R_8$ is selected from the group consisting of hydrogen and ethyl;
$R_9$ is selected from the group consisting of hydrogen and methyl;
$Y_1$ is selected from the group consisting of N and CH;
$Y_2$ is CH;
$Y_3$ is CH;
$Y_4$ is selected from the group consisting of N and CH;
$Y_5$ is selected from the group consisting of N and CH; and
$Y_6$ is selected from the group consisting of N and CH; or the pharmaceutically acceptable salt thereof.

21. The compound of claim 1, which is a compound of formula (Id):

(Id)

in which:
$R_1$ is halo-substituted $C_{1-3}$alkyl; each
$R_7$ is selected from the group consisting of hydrogen, $C_{1-2}$alkoxy-carbonyl and hydroxy-carbonyl;
$Y_1$ is selected from the group consisting of N and CH;
$Y_2$ is CH;
$Y_3$ is CH; and
$Y_4$ is selected from the group consisting of N and CH; or the pharmaceutically acceptable salt thereof.

22. The compound of claim 21 in which:
$R_1$ is selected from the group consisting of trifluoromethyl, 2-fluoropropan-2-yl, 2-cyanopropan-2-yl and 1,1-difluoroethyl; each
$R_7$ is selected from the group consisting of hydrogen, ethoxy-carbonyl and hydroxy-carbonyl;
$Y_1$ is selected from the group consisting of N and CH;
$Y_2$ is CH;
$Y_3$ is CH; and
$Y_4$ is selected from the group consisting of N and CH; or the pharmaceutically acceptable salt thereof.

23. The compound of claim 1, which is a compound of formula (Ie):

(Ie)

in which:
$R_1$ is halo-substituted $C_{1-3}$alkyl;
$R_3$ is selected from the group consisting of hydrogen and $C_{1-3}$alkyl;
$R_4$ is selected from the group consisting of hydrogen and $C_{1-3}$alkyl;
$Y_1$ is selected from the group consisting of N and CH;
$Y_2$ is selected from the group consisting of N and CH;
$Y_3$ is selected from the group consisting of N and CH;
$Y_4$ is selected from the group consisting of N and CH;
$Y_5$ is selected from the group consisting of N and CH; and
$Y_6$ is selected from the group consisting of N and CH; or the pharmaceutically acceptable salt thereof.

24. The compound of claim 23 in which:
$R_1$ is selected from the group consisting of trifluoromethyl, 2-fluoropropan-2-yl, 2-cyanopropan-2-yl and 1,1-difluoroethyl;
$R_3$ is selected from the group consisting of hydrogen, methyl and ethyl;
$R_4$ is selected from the group consisting of hydrogen, methyl and ethyl;
$Y_1$ is N;
$Y_2$ is CH;
$Y_3$ is CH;
$Y_4$ is CH;
$Y_5$ is N; and
$Y_6$ is N; or the pharmaceutically acceptable salt thereof.

25. The compound of claim 1, which is a compound of formula (If):

(If)

in which:
$R_1$ is selected from the group consisting of trifluoromethyl, 2-fluoropropan-2-yl, 2-cyanopropan-2-yl and 1,1-difluoroethyl;
$R_3$ is selected from the group consisting of hydrogen and $C_{1-3}$alkyl;
$R_4$ is selected from the group consisting of hydrogen and $C_{1-3}$alkyl;
$R_5$ is selected from the group consisting of hydrogen, halo, amino, $C_{1-3}$alkyl-amino-carbonyl, hydroxy and $C_{1-3}$alkoxy;
$R_6$ is selected from the group consisting of hydrogen, $C_{1-3}$alkyl, halo and halo-substituted-$C_{1-3}$alkyl;

Y₁ is selected from the group consisting of N and CH;
Y₂ is selected from the group consisting of N and CH;
Y₃ is selected from the group consisting of N and CH; and
Y₄ is selected from the group consisting of N and CH; or the pharmaceutically acceptable salt thereof.

26. The compound of claim 1, which is a compound of formula (Ig):

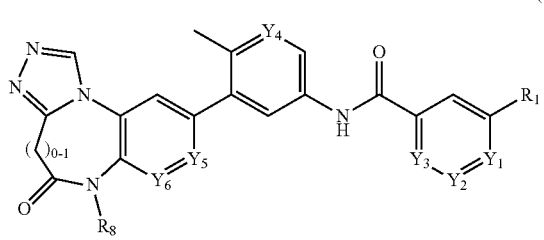

in which:
R₁ is selected from the group consisting of trifluoromethyl, 2-fluoropropan-2-yl, 2-cyanopropan-2-yl and 1,1-difluoroethyl;
R₈ is selected from the group consisting of hydrogen and C₁₋₃alkyl;
Y₁ is selected from the group consisting of N and CH;
Y₂ is selected from the group consisting of N and CH;
Y₃ is selected from the group consisting of N and CH;
Y₄ is selected from the group consisting of N and CH;
Y₅ is selected from the group consisting of N and CH; and
Y₆ is selected from the group consisting of N and CH; or the pharmaceutically acceptable salt thereof.

27. The compound of claim 1, or a pharmaceutically acceptable salt thereof, selected from the compound of any of Examples 1-534.

28. A pharmaceutical composition comprising a compound of claim 1, or a pharmaceutically acceptable salt thereof, and one or more pharmaceutically acceptable carriers.

29. A combination comprising a therapeutically effective amount of a compound according to claim 1, or a pharmaceutically acceptable salt thereof, and one or more therapeutically active co-agents.

30. A method of treating a cancer, comprising administering to a subject in need thereof a therapeutically effective amount of a compound of claim 1, or a pharmaceutically acceptable salt thereof, wherein the cancer is selected from melanoma, breast cancer, non-small cell lung cancer, lung adenocarcinoma, sarcoma, gastrointestinal stromal tumors, ovarian cancer, colorectal cancer, thyroid cancer and pancreatic cancer.

* * * * *